US011099176B2

(12) United States Patent
Hellinga et al.

(10) Patent No.: US 11,099,176 B2
(45) Date of Patent: Aug. 24, 2021

(54) LACTATE BIOSENSORS AND USES THEREOF

(71) Applicant: Duke University, Durham, NC (US)

(72) Inventors: Homme W. Hellinga, Durham, NC (US); Malin J. Allert, Raleigh, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 15/777,061

(22) PCT Filed: Nov. 19, 2016

(86) PCT No.: PCT/US2016/062961
§ 371 (c)(1),
(2) Date: May 17, 2018

(87) PCT Pub. No.: WO2017/087915
PCT Pub. Date: May 26, 2017

(65) Prior Publication Data

US 2018/0364217 A1 Dec. 20, 2018

Related U.S. Application Data

(60) Provisional application No. 62/257,856, filed on Nov. 20, 2015, provisional application No. 62/257,796, filed on Nov. 20, 2015.

(51) Int. Cl.

| | |
|---|---|
| ***G01N 33/53*** | (2006.01) |
| ***G01N 33/542*** | (2006.01) |
| ***G01N 21/64*** | (2006.01) |
| ***C07K 14/00*** | (2006.01) |
| ***G01N 33/566*** | (2006.01) |

(52) U.S. Cl.
CPC ......... *G01N 33/5308* (2013.01); *C07K 14/00* (2013.01); *G01N 21/6428* (2013.01); *G01N 33/542* (2013.01); *G01N 33/566* (2013.01)

(58) Field of Classification Search
None
See application file for complete search history.

(56) References Cited

U.S. PATENT DOCUMENTS

| | | | |
|---|---|---|---|
| 6,428,797 | B2 | 8/2002 | Fishman |
| 8,608,310 | B2 | 12/2013 | Otis et al. |
| 2004/0118681 | A1 | 6/2004 | Hellinga et al. |
| 2004/0229290 | A1 | 11/2004 | Hellinga et al. |
| 2008/0166747 | A1 | 7/2008 | Hellinga et al. |
| 2009/0325221 | A1 | 12/2009 | Long et al. |
| 2011/0171737 | A1 | 7/2011 | Hellinga et al. |
| 2016/0220686 | A1 | 8/2016 | Brudno et al. |

FOREIGN PATENT DOCUMENTS

| | | | |
|---|---|---|---|
| WO | 2013/154587 | A1 | 10/2013 |
| WO | 2017/087912 | A2 | 5/2017 |
| WO | 2017/087915 | A1 | 5/2017 |

OTHER PUBLICATIONS

RCSB 2ZZV. RCSB.org. 2009. p. 1-3 (Year: 2009).*
Database Uniprot (May 1, 2013) "2,3-Diketo-L-Gulonate-Binding Periplasmic Protein Yiao", Accession No. M1FFZ1, 6 pages.
Ejima et al. (Oct. 15, 2010) "Biological Identification of Peptides that Specifically Bind to Poly(phenylene vinylene) Surfaces: Recognition of the Branched or Linear Structure of the Conjugated Polymer", Langmuir, 26(22):17278-17285.
George et al. (Aug. 30, 2005) "Effective Function Annotation Through Catalytic Residue Conservation", PNAS, 102(35):12299-12304.
Gill et al. (Nov. 1, 1989) "Calculation of Protein Extinction Coefficients from Amino Acid Sequence Data", Analytical Biochemistry, 182(2):319-326.
Gough et al. (Sep. 1995) "Development of the Implantable Glucose Sensor: What Are the Prospects and Why Is It Taking So Long?", Diabetes, 44(9):1005-1009.
Groarke et al. (Nov. 1983) "The Amino Acid Sequence of D-Ribose-binding Protein from *Escherichia coli* K12", Journal of Biological Chemistry, 258(21):12952-12956.
Group (Sep. 30, 1993) "The Effect of Intensive Treatment of Diabetes on the Development and Progression of Long-Term Complications in Insulin-Dependent Diabetes Mellitus", The New England Journal of Medicine, 329:977-986.
Gunay et al. (Oct. 21, 2015) "Identification of Soft Matter Binding Peptide Ligands Using Phage Display", Bioconjugate Chemistry, 26(10):2002-2015.
Guo et al. (Jun. 10, 2013) "Identification and Characterization of a Cellulose Binding Heptapeptide Revealed by Phage Display", Biomacromolecules, 14(6):1795-1805.
Guyer et al. (Nov. 1986) "Binding Specificity of the Periplasmic Oligopeptide-Binding Protein from *Escherichia coli*", Journal of Bacteriology, 168(2):775-779.
He et al. (1993) "Dominant Role of Local Dipoles in Stabilizing Uncompensated Charges on a Sulfate Sequestered in a Periplasmic Active Transport Protein", Protein Science, 2:1643-1647.
Hellinga et al. (Jul. 1985) "Nucleotide Sequence and High-Level Expression of the Major *Escherichia coli* Phosphofructokinase", European Journal of Biochemistry, 149(2)363-373.
Heo et al. (Jan. 2013) "Toward Smart Tattoos: Implantable Biosensor for Continuous Glucose Monitoring", Advanced Healthcare Materials, 2(1):43-56.
Hnilova et al. (2012) "Peptide-Directed Co-Assembly of Nanoprobes on Multimaterial Patterned Solid Surfaces", Soft Matter, 8(16):4327-4334.
Hsiao et al. (Sep. 20, 1996) "The Crystal Structure of Glutamine-binding Protein from *Escherichia coli*", Journal of Molecular Biology, 262(2):225-242.
Jacobson et al. (Dec. 5, 1998) "Sulfate-Binding Protein Dislikes Protonated Oxyacids. A Molecular Explanation", Journal of Molecular Biology, 204(3):783-787.

(Continued)

*Primary Examiner* — Paul J Holland
(74) *Attorney, Agent, or Firm* — Mintz Levin Cohn Ferris Glovsky and Popeo, P.C.; Ingrid A. Beattie

(57) ABSTRACT

The present subject matter provides lactate biosensors as well as compositions, devices, and methods comprising such biosensors.

17 Claims, 111 Drawing Sheets

Specification includes a Sequence Listing.

(56) References Cited

OTHER PUBLICATIONS

Jansen et al. (Sep. 15, 2010) "Early Lactate-Guided Therapy in Intensive Care Unit Patients", American Journal of Respiratory and Critical Care Medicine, 182(6):752-761.
Joshi et al. (Jan. 29, 1998) "*Escherichia coli* Lysine-Arginine-Ornithine(LAO)-Binding Periplasmic Protein Argt (Argt) Gene, Partial Cds, Histidine-Binding Periplasmic Protein Hisj (Hisj) and Histidine Transport System Permease Protein Hisq (Hisq) Genes, Complete Cds, and Histidine Iran", GenBank: U47027.1, 2 pages.
Judge et al. (Feb. 27, 2011) "Continuous Glucose Monitoring Using a Novel Glucose/Galactose Binding Protein: Results of a 12-Hour Feasibility Study with the Becton Dickinson Glucose/Galactose Binding Protein Sensor", Diabetes Technology & Therapeutics, 13(3):309-317.
Kim et al. (2013) "Protein Immobilization Techniques for Microfluidic Assays", Biomicrofluidics, 7:48 pages.
Klymchenko et al. (Jan. 1, 2013) "Fluorescent Environment-Sensitive Dyes as Reporters of Biomolecular Interactions", Progress in Molecular Biology and Translational Science, 113:35-58.
Kolb et al. (Jun. 1, 2001) "Click Chemistry: Diverse Chemical Function from a Few Good Reactions", Angewandte Chemie International Edition, 40(11):2004-2021.
Koo et al. (Nov. 19, 2012) "Bioorthogonal Copper-Free Click Chemistry in Vivo for Tumor-Targeted Delivery of Nanoparticles", Angewandte Chemie, 51(47):11836-11840.
Kucherak et al. (Jan. 12, 2010) "Fluorene Analogues of Prodan with Superior Fluorescence Brightness and Solvatochromism", The Journal of Physical Chemistry Letters, 1(3):616-620.
Kumada et al. (Dec. 14, 2009) "Characterization of Polystyrene-Binding Peptides (PS-tags) for Site-Specific Immobilization of Proteins", Journal of Bioscience and Bioengineering, 109(6):583-587.
Kumada et al. (Aug. 31, 2012) "Screening of PC and PMMA-Binding Peptides for Site-Specific Immobilization of Proteins", Journal of Biotechnology, 160(3-4):222-228.
Kumada (Nov. 2014) "Site-Specific Immobilization of Recombinant Antibody Fragments Through Material-Binding Peptides for the Sensitive Detection of Antigens in Enzyme Immunoassays", Biochimica et Biophysica Acta (BBA)—Proteins and Proteomics, 1844(11):1960-1969.
Layton et al. (Nov. 4, 2010) "Thermodynamic Analysis of Ligand-Induced Changes in Protein Thermal Unfolding Applied to High-Throughput Determination of Ligand Affinities with Extrinsic Fluorescent Dyes", Biochemistry, 49(51):10831-10841.
Ledvina et al. (Jun. 1996) "Negative Electrostatic Surface Potential of Protein Sites Specific for Anionic Ligands", Proceedings of the National Academy of Sciences, 93:6786-6791.
Lee et al. (Jun. 2002) "Ordering of Quantum Dots Using Genetically Engineered Viruses", Science, 296(5569):892-895.
Lu et al. (Nov. 23, 2006) "Long-Wavelength Analogue of PRODAN: Synthesis and Properties of Anthradan, a Fluorophore with a 2,6-Donor-Acceptor Anthracene Structure", The Journal of Organic Chemistry, 71(26):9651-9657.
Luecke et al. (Sep. 27, 1990) "High Specificity of a Phosphate Transport Protein Determined by Hydrogen Bonds", Nature, 347:402-406.
Magota et al. (Mar. 1984) "Nucleotide Sequence of the phoS Gene, the Structural Gene for the Phosphate-Binding Protein of *Escherichia coli*", Journal of Bacteriology, 157(3):909-917.
Marvin et al. (1998) "Engineering Biosensors by Introducing Fluorescent Allosteric Signal Transducers: Construction of a Novel Glucose Sensor", Journal of the American Chemical Society, 120:7-11.
Marvin et al. (Apr. 1997) "The Rational Design of Allosteric Interactions in a Monomeric Protein and its Applications to the Construction of Biosensors", Proceedings of the National Academy of Sciences, 94:4366-4371.
Matsuno et al. (May 24, 2008) "Biological Selection of Peptides for Poly(l-lactide) Substrates", Langmuir, 24(13):6399-6403.
McDonagh et al. (Jan. 30, 2008) "Optical Chemical Sensors", Chemical Reviews, 108(2):400-422.
Medintz et al. (Jun. 1, 2005) "Quantum Dot Bioconjugates for Imaging, Labelling and Sensing", Nature Materials, 4:435-446.
Medveczky et al. (Nov. 18, 1969) "The Binding and Release of Phosphate by a Protein Isolated from *Escherichia coli*", Biochimica et Biophysica Acta (BBA)—General Subjects, 192(2):369-371.
Meyerhoff et al. (1966) "Current Status of the Glucose Sensor", Endricon, 6(1):51-58.
Miller et al. (Nov. 25, 1983) "Rates of Ligand Binding to Periplasmic Proteins Involved in Bacterial Transport and Chemotaxis", The Journal of Biological Chemistry, 258(22)13665-13672.
Monosik et al. (Jan. 2012) "A Rapid Method for Determination of L-lactic Acid in Real Samples by Amperometric Biosensor Utilizing Nanocomposite", Food Control, 23(1):238-24.
Mowbray et al. (May 5, 1992) "1.7 A X-Ray Structure of the Periplasmic Ribose Receptor from *Escherichia coli*", Journal of Molecular Biology, 225(1):155-175.
Neves et al. (Jun. 19, 2013) "Imaging Cell Surface Glycosylation in Vivo Using "Double Click" Chemistry", Bioconjugate chemistry, 24(6):934-941.
Nickitenko (Dec. 1995) "2 A Resolution Structure of DppA, a Periplasmic Dipeptide Transport/Chemosensory Receptor", Biochemistry, 34(51):16585-16595.
Niko et al. (Jul. 22, 2013) "Solvatochromic Pyrene Analogues of Prodan Exhibiting Extremely High Fluorescence Quantum Yields in Apolar and Polar Solvents", Chemistry, 19(30):9760-9765.
Nohno et al. (1986) "Cloning and Complete Nucleotide Sequence of the *Escherichia coli* Glutamine Permease Operon (Glnhpq)", Molecular Genetics and Genomics, 205:260-269.
Nwe et al. (2009) "Growing Applications of "Click Chemistry" for Bioconjugation in Contemporary Biomedical Research", Cancer Biotherapy and Radiopharmaceuticals, 24(3):289-302.
Oliveira et al. (Aug. 2015) "Recombinant CBM-Fusion Technology—Applications Overview", Biotechnology Advances, May-33(3-4):358-369.
Oneto et al. (2014) "Implantable Biomaterial Based on Click Chemistry for Targeting Small Molecules", Acta Biomaterilia, 10:5099-5105.
Parra et al. (Jan. 2006) "Design and Characterization of a Lactate Biosensor Based on Immobilized Lactate Oxidase Onto Gold Surfaces", Analytica Chimica Acta, 555(2):308-315.
Pflugrath et al. (Mar. 21, 1985) "Sulphate Sequestered in the Sulphate-Binding Protein of *Salmonella typhimurium* is Bound Solely by Hydrogen Bonds", Nature, 314:257-260.
Pickup (1993) "Developing Glucose Sensors for In Vivo Use", Tibtech, 11:285-291.
Quiocho et al. (Aug. 15, 1997) "Extensive Features of Tight Oligosaccharide Binding Revealed in High-Resolution Structures of the Maltodextrin Transport/Chemosensory Receptor", Structure, 5(8):997-1015.
Quiocho et al. (Aug. 2, 1984) "Novel Stereospecificity of the L-Arabinose-Binding Protein", Nature, 310:381-386.
Resch-Genger et al. (Oct. 2008) "Quantum Dots Versus Organic Dyes as Fluorescent Labels", Nature Methods, 5(9):763-775.
Riklin et al. (Aug. 24, 1995) "Improving Enzyme—Electrode Contacts by Redox Modification of Cofactors", Nature, 376:672-675.
Romero et al. (Jun. 2, 2010) "Amperometric Biosensor for Direct Blood Lactate Detection", Analytical Chemistry, 82(13):5568-5572.
Rossin et al. (Apr. 10, 2010) "In Vivo Chemistry for Pretargeted Tumor Imaging in Live Mice", Angewandte Chemie, 49(19):3375-3378.
Sanders et al. (Oct. 1994) "Identification of a Locus Involved in the Utilization of Iron by Haemophilus Influenzae", Infection and Immunity, 62(10):4515-4525.
Sapsford et al. (Jul. 10, 2006) "Materials for Fluorescence Resonance Energy Transfer Analysis: Beyond Traditional Donor—Acceptor Combinations", Angew Chern Int Ed Engl, 45(28):4562-4589.
Sartain et al. (Jul. 15, 2006) "Holographic Lactate Sensor", Analytical Chemistry, 78(16):5664-5670.

(56) References Cited

OTHER PUBLICATIONS

Scholle et al. (Jun. 1987) "Sequence of the Mglb Gene from *Escherichia coli* K12: Comparison of Wild-Type and Mutant Galactose Chemoreceptors", Molecular and General Genetics MGG, 208(1-2):247-253.
Schwartz et al. (1976) "Further Studies on the Binding of Maltose to the Maltose-Binding Protein of *Escherichia coli*", European Journal of Biochemistry, 71:167-170.
Scripture et al. (Sep. 5, 1987) "High-Affinity L-Arabinose Transport Operon. Nucleotide Sequence and Analysis of Gene Products", Journal of Molecular Biology, 197(1):37-46.
Serizawa et al. (Sep. 15, 2005) "A Peptide Motif Recognizing a Polymer Stereoregularity", Journal of the American Chemical Society, 127(40):13780-13781.
Serizawa et al. (Oct. 23, 2007) "Highly Specific Affinities of Short Peptides Against Synthetic Polymers", Langmuir, 23(22):11127-11133.
Serizawa et al. (Jun. 18, 2007) "Isolation of Peptides that Can Recognize Syndiotactic Polystyrene", Chembiochem, 8(9):989-993.
Serizawa et al. (2007) "Peptide Motifs that Recognize Differences in Polymer-Film Surfaces", Angew Chem Int Ed Engl, 46(5):723-726.
Sharff et al. (Nov. 10, 1992) "Crystallographic Evidence of a Large Ligand-Induced Hinge-Twist Motion between the two Domains of the Maltodextrin Binding Protein Involved in Active Transport and Chemotaxis", Biochemistry, 31(44):10657-10663.
Shen et al. (Dec. 21, 2015) "Fluorescence Enhancement on Silver Nanoplates at the Single- and Sub-Nanoparticle Level", Nanoscale, 7(47):20132-20141.
Shin et al. (2005) "Chemical Structure and Physical Properties of Cyclic Olefin Copolymers (IUPAC Technical Report)", Pure and Applied Chemistry, 77(5):801-814.
Shoseyov et al. (Jun. 2006) "Carbohydrate Binding Modules: Biochemical Properties and Novel Applications", Microbiology and Molecular Biology Reviews, 70(2):283-295.
Smith et al. (2005) "Orthogonal Site-Specific Protein Modification by Engineering Reversible Thiol Protection Mechanisms", Protein Science, 14:64-73.
Smith et al. (1999) "Substrate Specificity of the Periplasmic Dipeptide-Binding Protein from *Escherichia coli*: Experimental Basis for the Design of Peptide Prodrugs", Microbiology, 145:2891-2901.
Spurlino et al. (Mar. 15, 1991) "The 2.3-A Resolution Structure of the Maltose- or Maltodextrinbinding Protein, A Primary Receptor of Bacterial Active Transport and Chemotaxis", Journal of Biological Chemistry, 266(8):5202-5219.
Sriram (Aug. 19, 2009) "BIOT 348—Optical Sensing of Lactate Using a Fluorescently Labeled Lactate Binding Protein", American Chemical Society, 1 page.
Suleiman et al. (Oct. 23, 1992) "Biosensors for Food Analysis", Biosensor Design and Application, 511:26-40.
Suman et al. (Jun. 29, 2005) "Development of a Lactate Biosensor Based on Conducting Copolymer Bound Lactate Oxidase", Sensors and Actuators B: Chemical, 107(2):768-772.
Sun et al. (Apr. 24, 1998) "The Structure of Glutamine-Binding Protein Complexed With Glutamine at 1.94 A Resolution: Comparisons with other Amino Acid Binding Proteins", Journal of Molecular Biology, 278(1):219-229.
Tian et al. (Oct. 1, 2003) "How Well is Enzyme Function Conserved as a Function of Pairwise Sequence Identity?", Journal of Molecular Biology, 333(4):863-882.
Todd (Apr. 1, 2001) "Evolution of Function in Protein Superfamilies, from a Structural Perspective", Journal of Molecular Biology, 307(4):1113-1143.
Vodnik et al. (May 15, 2012) "HWGMWSY, An Unanticipated Polystyrene Binding Peptide from Random Phage Display Libraries", Analytical Biochemistry, 424(2):83-86.
Vyas et al. (Apr. 26, 1994) "Crystallographic Analysis of the Epimeric and Anomeric Specificity of the Periplasmic Transport/Chemosensory Protein Receptor for D-Glucose and D-Galactose", Biochemistry, 33(16):4762-4768.
Vyas et al. (Dec. 2, 1988) "Sugar and Signal-Transducer Binding Sites of the *Escherichia coli* Galactose Chemoreceptor Protein", Science, 242(4883):1290-1295.
Weidemaier et al. (Jun. 15, 2011) "Multi-Day Pre-Clinical Demonstration of Glucose/Galactose Binding Protein-Based Fiber Optic Sensor", Biosensors and Bioelectronics, 26(10):4117-4123.
Weiner et al. (1971) "A Binding Protein for L-Glutamine and its Relation to Active Transport in *E. coli*", Archives of Biochemistry and Biophysics, 124:715-717.
Wilkins et al. (Jun. 1996) "Glucose Monitoring: State of Art and Future Possibilities", Medical Engineering & Physics, 18:273-288.
Willis et al. (Apr. 10, 1975) "Purification and Properties of a Periplasmic Glutamate—Aspartate Binding Protein from *Escherichkz coli* K12 Strain W3092", The Journal of Biological Chemistry, 250(7):2574-2580.
Willis et al. (Nov. 10, 1974) "Purification and Properties of a Ribose-binding Protein from *Escherichia coli*", Journal of Biological Chemistry, 249(21):6926-6929.
Willner et al. (Oct. 23, 1996) "Electrical Wiring of Glucose Oxidase by Reconstitution of Fad-Modified Monolayers Assembled onto AU-Electrodes", Journal of the American Chemical Society, 118(42):10321-10322.
Yao et al. (Apr. 26, 1994) "Refined 1.89-A Structure of the Histidine-Binding Protein Complexed with Histidine and its Relationship with Many Other Active Transport/Chemosensory Proteins", Biochemistry, 33(16):4769-4779.
Zeng et al. (2014) "Nanomaterials Enhanced Surface Plasmon Resonance for Biological and Chemical Sensing Applications", Chemical Society Reviews, 43(10):3426-3452.
Akiyama et al., Crystal Structure of a Periplasmic Substrate-Binding Protein in Complex with Calcium Lactate, J. Mo. Biol., Sep. 25, 2009, vol. 392 No. 3 pp. 559-565.
GenBank Accession WP_014515914.1, ABC Transporter Substrate-Binding Protein [*Thermus* sp. CCB_US3_UF1] [online] May 19, 2013 [retrieved Feb. 2, 2017], Available on the internet: <www.ncbi.nlm.nih.gov/protein/504328812?report-genbank&log$=protalign&blast_&RID-97UNB61E016 >.
Abouhamad et al. (Jun. 1991) "Peptide Transport and Chemotaxis in *Escherichia coli* and *Salmonella typhimurium*: Characterization of the Dipeptide Permease (Dpp) and the Dipeptide-Binding Protein", Molecular Microbiology, 5(5):1035-1047.
Adey et al. (Apr. 14, 1995) "Characterization of Phage that Bind Plastic from Phage-Displayed Random Peptide Libraries", Gene, 156(1):27-31.
Adhikari et al. (Oct. 20, 1995) "Biochemical Characterization of a Haemophilus influenzae Periplasmic Iron Transport Operon", The Journal of Biological Chemistry, 270(42):25142-25149.
Allert et al. (Oct. 8, 2010) "Multifactorial Determinants of Protein Expression in Prokaryotic Open Reading Frames", Journal of Molecular Biology, 402(5):905-918.
Altschul et al. (Oct. 1990) "Basic Local Alignment Search Tool", Journal of Molecular Biology, 215(3):403-410.
Andersen et al. (2003) "Secondary Structure Assignment", Structural Bioinformatics, 341-363.
Anraku (Jun. 10, 1968) "Transport of Sugars and Amino Acids in Bacteria", Journal of Biological Chemistry, 243(11):3116-3122.
Artimo et al. (May 2012) "ExPASy: SIB Bioinformatics Resource Portal", Nucleic Acids Research, 40:W597-W603.
Avvakumova et al. (Jan. 2014) "Biotechnological Approaches Toward Nanoparticle Biofunctionalization", Trends in Biotechnology, 32(1):11-20.
Bakker et al. (Feb. 1996) "Serial Blood Lactate Levels can Predict the Development of Multiple Organ Failure Following Septic Shock", The American Journal of Surgery, 171(2):221-226.
Baneyx et al. (Jul. 5, 2007) "Selection and Analysis of Solid-Binding Peptides", Current Opinion in Biotechnology, 18(4):312-317.

(56) References Cited

OTHER PUBLICATIONS

Barash et al. (Mar. 28, 1975) "Purification and Properties of Glutamate Binding Protein from the Periplasmic Space of *Escherichia coli* K-12", Biochimica et Biophysica Acta (BBA)—Protein Structure, 386(1)168-180.
Baskin et al. (Oct. 23, 2007) "Copper-Free Click Chemistry for Dynamic in Vivo Imaging", PNAS, 104(43):16793-16797.
Benedetti et al. (Jul. 13, 2012) "Synthesis and Photophysical Properties of a Series of Cyclopenta[b]naphthalene Solvatochromic Fluorophores", Journal of the American Chemical Society, 134(30):12418-12421.
Berman et al. (2000) "The Protein Data Bank", Nucleic Acids Research, 28(1):235-242.
Biju et al. (Feb. 7, 2014) "Chemical Modifications and Bioconjugate Reactions of Nanomaterials for Sensing, Imaging, Drug Delivery and Therapy", Chemical Society Reviews, 43(3):744-764.
Bjorkman et al. (Jun. 12, 1998) "Multiple Open Forms of Ribose-Binding Protein Trace the Path of its Conformational Change", Journal of Molecular Biology, 279(3):651-664.
Borisov et al. (Jan. 30, 2008) "Optical Biosensors", Chemical Reviews, 108(2):423-461.
Bruns et al. (2001) "Crystallographic and Biochemical Analyses of the Metal-Free Haemophilus influenzae Fe3+-Binding Protein", Biochemistry, 40(51):15631-15637.
Bruns et al.(Nov. 1997) "Structure of Haemophilus Infuenzae Fe+3-Binding Protein Reveals Convergent Evolution within a Superfamily", Nature Structural Biology, 4(11):919-924.
Care et al. (May 2015) "Solid-Binding Peptides: Smart Tools for Nanobiotechnology", Trends in Biotechnology, 33(5):259-268.
Then et al. (Feb. 2011) "Binding Analysis of Peptides That Recognize Preferentially Cis-Azobenzene Groups of Synthetic Polymers", Journal of Peptide Science, 17(2):163-168.
Chenna et al. (Jul. 2003) "Multiple Sequence Alignment with the Clustal Series of Programs", Nucleic Acids Research, 31(13):3497-3500.
Cheung (1991) "Resonance Energy Transfer", Topics in Fluorescence Spectroscopy, 2:127-176.
Chothia et al. (1986) "The Relation Between the Divergence of Sequence and Structure in Proteins", The EMBO Journal, 5(4):823-826.
Clark et al. (1982) Proton Nuclear Magnetic Resonance Spectroscopy and Ligand Binding Dynamics of the *Escherichia coli* L-Arabinose Binding Protein, Biochemistry, 21:2227-2233.
Clegg (1995) "Fluorescence Resonance Energy Transfer", Current Opinion in Biotechnology, 6(1):103-110.
Cox et al. (Mar. 2007) "Protein Fabrication Automation", Protein Science, 16(3):379-390.
Database Genbank "Anaeromyxobacter dehalogenans 2CP-C, Complete Genome", NCBI Reference Sequence: NC_007760.1.
Database Genbank "Flexistipes sinusarabici DSM 4947, Complete Genome", NCBI Reference Sequence: NC_015672.1.
Database Genbank "Marinobacter adhaerens HP15, Complete Genome", NCBI Reference Sequence: NC_017506.1.
Database Genbank "*Marinobacter* sp. BSs20148, Complete Genome", NCBI Reference Sequence: NC_018268.1.
Database Genbank "Polymorphum gilvum SL003B-26A1, Complete Genome", NCBI Reference Sequence: NC_015259.1.
Database Genbank "Pseudomonas stutzeri DSM 10701, Complete Genome", NCBI Reference Sequence: NC_018177.1.
Database Genbank "Rhodobacter sphaeroides 2.4.1 Chromosome 2, Complete Sequence", NCBI Reference Sequence: NC_007494.2.
Database Genbank "Roseobacter denitrificans OCh 114, Complete Genome", NCBI Reference Sequence: NC_008209.1.
Database Genbank "Thermanaerovibrio acidaminovorans DSM 6589 Chromosome, Complete Genome", NCBI Reference Sequence: NC_013522.1.
Database Genbank "Thermus oshimai JL-2, Complete Genome", NCBI Reference Sequence: NC_019386.1.
Database Genbank "Thermus Scotoductus SA-01, Complete Genome", Accession No. NC_014974.1.
Database Genbank "*Thermus* sp. CCB_US3_UF1, complete genome", NCBI Reference Sequence: NC_017278.1.
Database Genbank "Thermus thermophilus HB8 Chromosome, Complete Genome", NCBI Reference Sequence: NC_006461.1.
Database Genbank "Thioalkalivibrio sulfidiphilus HL-EbGr7, complete sequence", NCBI Reference Sequence: NC_011901.1.
Date et al. (Feb. 2, 2011) "Polymer-Binding Peptides for the Noncovalent Modification of Polymer Surfaces: Effects of Peptide Density on the Subsequent Immobilization of Functional Proteins", ACS Applied Materials & Interfaces, 3(2):351-359.
D'Auria et al. (Jul. 15, 2000) "A Protein Biosensor for Lactate", Analytical Biochemistry, 283(1):83-88.
De Lorimier et al. (2002) "Construction of a Fluorescent Biosensor Family", Protein Science, 11:2655-2575.
Demchenko (Dec. 5, 2014) "Practical Aspects of Wavelength Ratiometry in the Studies of Intermolecular Interactions", Journal of Molecular Structure, 1077:51-67.
Demchenko (Sep. 2010) "The Concept of λ-Ratiometry in Fluorescence Sensing and Imaging", Journal of Fluorescence, 20(5):1099-1128.
Dunten (Nov. 1995) "Crystal Structure of the Dipeptide Binding Protein From *Escherichia coli* Involved in Active Transport and Chemotaxis", Protein Science, 4(11):2327-2334.
Duplay et al. (Aug. 25, 1984) "Sequences of the malE Gene and of its Product, the Maltose-binding Protein of *Escherichia coli* K12", The Journal of Biological Chemistry, 259(16):10606-10613.
Dwyer et al. (2004) "Periplasmic Binding Proteins: A Versatile Superfamily for Protein Engineering", Current Opinion in Structural Biology, 14:495-504.

* cited by examiner

| Position | Allowed residues |
|---|---|
| 98 | F, W, Y |
| 101 | Y, N, Q, H, E, D |
| 158 | N, D, E, Q, H |
| 178 | R |
| 180 | P, A, V, L, I, G |
| 216 | D, N , Q, E |
| 247 | Q, E, N, D |
| 250 | D, N, E, Q, S, T, H |

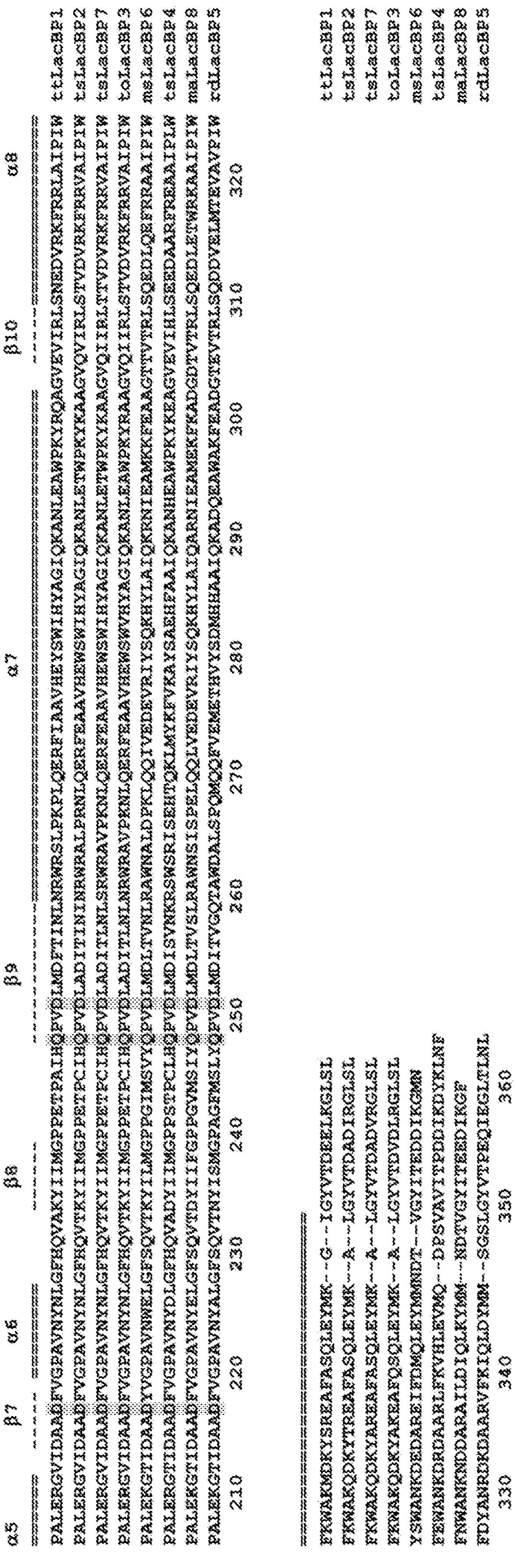

FIG. 4 (Continued)

```
     α5                 β7       α6             β8                              β9                                   α7                                    β10              α8
     ────────────────────────    ──────────    ─────                ──────────────    ──────────────────────────────────────────          ──────────    ─────────
PALERGVIDAADFVGPAVNYNLGFHQYAKYIIMGPPETPAIHQPVDLMDFTINLNRWRSLPKPLQERFIAAVHEYSWIHYAGIQKANLEAWPKIYRQAGVEVIRLSMEDVRKFRRLAIPIW    ttLacBP1
PALERGVIDAADFVGPAVNYNLGFHQYTKYIIMGPPETPCIHQPVDLADITININRWRALPRNLQERFEAAVHEWSWIHYAGIQKANLETWPKIYKAAGVQVIRLSTVDVRKFRRVAIPIW    tsLacBP2
PALERGVIDAADFVGPAVNYNLGFHQYTKYIIMGPPETPCIHQPVDLADITINLSRWRAAVHEWSWIHYAGIQKANLETWPKIYKAAGVQIIRLTTVDVRKFRRVAIPIW               tsLacBP7
PALERGVIDAADFVGPAVNYNLGFHQYTKYIIMGPPETPCIHQPVDLADITILNLNRRAVPKNLQERFEAAVHEWSWVHYAGIQKANLEAWPKIYKAAGVQIIRLSTVDVRKFRRVAIPIW    toLacBP3
PALERGTIDAADFVGPAVNWELGFSSQVTKYILMGPPGIMSVYQPVDLMDLTVMLRAWNALDPKLQQIVEDEVRIYSQKHYLAIQKRNIEAMKKFEAAGTTVTRLSQEDLQEFRRAAIPIW    msLacBP6
PALERGTIDAADFVGPAVNYDLGFHQVADYIIMGPPSTPCLHQPVDLMDISVNKRSWSRISEHTQKLMYKFVKAYSAEHFAAIQKANHEAWPKIYKEAGVEVIHLSEEDAARFREAAIPIW    tsLacBP4
PALERGTIDAADFVGPAVNYELGFSQVDYIIFGPPGVMSIYQPVDLMDLTVSLRAWNSISPELQQIVEDEVRIYSQKHYLAIQARNIEAMEKFKADGDTVTRLSQEDLETWRKAAIPIW     maLacBP8
PALERGTIDAADFVGPAVNYALGFSQVTNYISMGPAGFMSLYQPVDLMDITVGQTAWDALSPQMCQFVEMETHVYSDMHHAAIQKADQEAWAKFEADGIEVTRLSQDDVELMTEVAVPIW    rdLacBP5
         210       220       230       240       250       260       270       280       290       300       310       320

FKWAKMDKYSREAFASQLEYMK--G---LGYVTDEELKGLSL                                       ttLacBP1
FKWAKQDKYTREAFASQLEYMK---A--LGYVTDADIRGLSL                                       tsLacBP2
FKWAKQDKYAREAFASQLEYMK--A---LGYVTDADVRGLSL                                       tsLacBP7
FKWAKQDKYAKEAFQSQLEYMK--A---LGYVTDVDLRGLSL                                       toLacBP3
YSWANKDEDAREIFDMQLEYMANYT---VGYITEDDIKGMN                                        msLacBP6
FEWABNKDRDAARLFKVHLEVMQ---DPSVAITPDDIKDYKLNF                                     tsLacBP4
FNWARKMDDARAILDIQLKIMM----NDTVGYITEEDIKGF                                        maLacBP8
FDYANRDKDAARVFKIQLDYMM---SGSLGYVTPEQIEGLITINL                                    rdLacBP5
         330       340       350       360
```

FIG. 10 - Exemplary Expression Construct for ttLacBP1

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                        10
                                                              M  F  S  P  L  A  V  A  Q  A  R  R  Y  R  W  R  I  Q  T  A
GGAGACCACAACGGTTTCCCTCTAGAAATAATTTTGTTTAACTTTAAGAAGGAGATATACCATGTTTAGTCCTTTAGCAGTAGCACAAGCTCGTCGCTATCGTTGGCGTATTCAGACAGC
CCTCTGGTGTTGCCAAAGGGAGATCTTTATTAAAACAAATTGAAATTCTTCCTCTATATGGTACAAATCAGGAAATCGTCATCGTGTTCGAGCAGCGATAGCAACCGCATAAGTCTGTCG
       130       140       150       160       170       180       190       200       210       220       230       240

                           30                            40                            50
 W  D  A  G  T  V  G  Y  S  L  F  Q  K  F  T  E  R  V  K  E  L  T  D  G  Q  L  E  V  Q  P  F  P  A  G  A  V  V  G  T  F
ATGGGACGCAGGGACCGTGGGGTACTCTCTTTTTCAAAAGTTTACCGAGCGCGTAAAAGAACTCACAGACGGGCAGTTAGAGGTACAACCGTTCCCGGCTGGTGCGGTAGTAGGGACCTT
TACCCTGCGTCCCTGGCACCCCATGAGAGAAAAAGTTTTCAAATGGCTCGCGCATTTTCTTGAGTGTCTGCCCGTCAATCTCCATGTTGGCAAGGGCCGACCACGCCATCATCCCTGGAA
       250       260       270       280       290       300       310       320       330       340       350       360

                           70                            80                            90
 D  M  F  D  A  V  K  T  G  V  L  D  G  M  N  P  F  T  L  Y  W  A  G  R  M  P  V  T  A  F  L  S  S  Y  A  L  G  L  D  R
TGACATGTTCGACGCCGTCAAGACAGGTGTATTAGACGGGATGAATCCTTTCACACTCTATTGGGCCGGTCGTATGCCAGTCACCGCATTTTTGAGCAGTTACGCGCTGGGTCTCGATCG
ACTGTACAAGCTGCGGCAGTTCTGTCCACATAATCTGCCCTACTTAGGAAAGTGTGAGATAACCCGGCCAGCATACGGTCAGTGGCGTAAAAACTCGTCAATGCGCGACCCAGAGCTAGC
       370       380       390       400       410       420       430       440       450       460       470       480

                           110                           120                           130
 P  D  Q  W  E  T  W  F  Y  S  L  G  G  L  D  I  A  R  R  A  F  A  E  Q  G  L  F  Y  V  G  P  V  Q  H  D  L  N  I  I  H
GCCAGACCAATGGGAAACGTGGTTCTACAGTCTCGGCGGTTTAGATATCGCACGCCGTGCGTTCGCGGAGCAGGGTCTCTTTTACGTAGGGCCAGTACAACACGATCTCAATATTATTCA
CGGTCTGGTTACCCTTTGCACCAAGATGTCAGAGCCGCCAAATCTATAGCGTGCGGCACGCAAGCGCCTCGTCCCAGAGAAAATGCATCCCGGTCATGTTGTGCTAGAGTTATAATAAGT
       490       500       510       520       530       540       550       560       570       580       590       600

                           150                           160                           170
 S  K  K  P  I  R  R  F  E  D  F  K  G  V  K  L  R  V  P  G  G  M  I  A  E  V  F  A  A  A  G  A  S  T  V  L  L  P  G  G
TTCAAAGAAGCCAATCCGCCGTTTCGAAGACTTCAAGGGTGTAAAGTTACGGGTACCGGGTGGCATGATTGCTGAAGTCTTCGCAGCTGCAGGTGCCTCAACAGTGCTCCTCCCTGGCGG
AAGTTTCTTCGGTTAGGCGGCAAAGCTTCTGAAGTTCCCACATTTCAATGCCCATGGCCCACCGTACTAACGACTTCAGAAGCGTCGACGTCCACGGAGTTGTCACGAGGAGGGACCGCC
       610       620       630       640       650       660       670       680       690       700       710       720

                           190                           200                           210
 E  V  Y  P  A  L  E  R  G  V  I  D  A  A  D  F  V  G  P  A  V  N  Y  N  L  G  F  H  Q  V  A  K  Y  I  I  M  G  P  P  E
GGAAGTATATCCGGCCTTAGAGCGTGGTGTCATCGACGCAGCCGATTTCGTAGGTCCAGCCGTTAATTACAACTTAGGTTTCCACCAGGTAGCCAAATACATCATCATGGGTCCACCAGA
CCTTCATATAGGCCGGAATCTCGCACCACAGTAGCTGCGTCGGCTAAAGCATCCAGGTCGGCAATTAATGTTGAATCCAAAGGTGGTCCATCGGTTTATGTAGTAGTACCCAGGTGGTCT
       730       740       750       760       770       780       790       800       810       820       830       840

                           230                           240                           250
 T  P  A  I  H  Q  P  V  D  L  M  D  F  T  I  N  L  N  R  W  R  S  L  P  K  P  L  Q  E  R  F  I  A  A  V  H  E  Y  S  W
AACACCGGCAATTCATCAACCAGTAGACCTCATGGACTTTACGATCAATCTGAATCGTTGGCGTAGTTTGCCAAAACCATTACAAGAACGCTTCATTGCAGCTGTCCATGAGTATTCCTG
TTGTGGCCGTTAAGTAGTTGGTCATCTGGAGTACCTGAAATGCTAGTTAGACTTAGCAACCGCATCAAACGGTTTTGGTAATGTTCTTGCGAAGTAACGTCGACAGGTACTCATAAGGAC
       850       860       870       880       890       900       910       920       930       940       950       960
```

```
                    270                           280                           290
 I  H  Y  A  G  I  Q  K  A  N  L  E  A  W  P  K  Y  R  Q  A  G  V  E  V  I  R  L  S  N  E  D  V  R  K  F  R  R  L  A  I
GATCCATTACGCTGGCATTCAAAAGGCGAATCTGGAAGCCTGGCCAAAATACCGGCAAGCAGGTGTCGAAGTCATCCGGTTATCCAATGAAGACGTGCGTAAATTCCGTCGTCTCGCCAT
CTAGGTAATGCGACCGTAAGTTTTCCGCTTAGACCTTCGGACCGGTTTTATGGCCGTTCGTCCACAGCTTCAGTAGGCCAATAGGTTACTTCTGCACGCATTTAAGGCAGCAGAGCGGTA
       970       980       990      1000      1010      1020      1030      1040      1050      1060      1070      1080

                    310                           320                           330
 P  I  W  F  K  W  A  K  M  D  K  Y  S  R  E  A  F  A  S  Q  L  E  Y  M  K  G  I  G  Y  V  T  D  E  E  L  K  G  L  S  L
TCCTATCTGGTTTAAGTGGGCAAAAATGGACAAATATAGCCGTGAGGCATTCGCCAGTCAATTGGAATACATGAAGGGCATTGGGTACGTAACCGACGAGGAATTAAAGGGTTTGTCCTT
AGGATAGACCAAATTCACCCGTTTTTACCTGTTTATATCGGCACTCCGTAAGCGGTCAGTTAACCTTATGTACTTCCCGTAACCCATGCATTGGCTGCTCCTTAATTTCCCAAACAGGAA
      1090      1100      1110      1120      1130      1140      1150      1160      1170      1180      1190      1200

                    350
 G  G  S  H  H  H  H  H  H  *  *
AGGTGGTTCACATCATCATCATCATCATTAATGAAAGGGCGATATCCAGCACACTGGCGGCCGTTACTAGTGGATCCGGCTGCTAACAAAGCCCGAAAGGAAGCTGAGTTGGCTGCTGCC
TCCACCAAGTGTAGTAGTAGTAGTAGTAATTACTTTCCCGCTATAGGTCGTGTGACCGCCGGCAATGATCACCTAGGCCGACGATTGTTTCGGGCTTTCCTTCGACTCAACCGACGACGG
      1210      1220      1230      1240      1250      1260      1270      1280      1290      1300      1310      1320


ACCGCTGAGCAATAACTAGCATAACCCCTTGGGGCCTCTAAACGGGTCTTGAGGGGTTTTTTGCTGAAAGGAGGAACTATATCCGGAGCGACTCCCACGGCACGTTGGCAAGCTCGGAAT
TGGCGACTCGTTATTGATCGTATTGGGGAACCCCGGAGATTTGCCCAGAACTCCCCAAAAAACGACTTTCCTCCTTGATATAGGCCTCGCTGAGGGTGCCGTGCAACCGTTCGAGCCTTA
      1330      1340      1350      1360      1370      1380      1390      1400      1410      1420      1430      1440


TCGGCGTAATC
AGCCGCATTAG
      1450
```

FIG. 10 (Continued)

FIG. 11 ~ Exemplary Expression Construct for tscLacBP2

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                                 10
                                                                              M  F  S  P  L  A  V  A  Q  A  P  R  F  R  W  R  I  Q  S  A
GGAGACCACAACGGTTTCCCTCTAGAAATAATTTTGTTTAACTTTAAGAAGGAGATATACCATGTTTAGTCCATTAGCAGTAGCACAAGCACCACGTTTTCGTTGGCGTATCCAATCTGC
CCTCTGGTGTTGCCAAAGGGAGATCTTTATTAAAACAAATTGAAATTCTTCCTCTATATGGTACAAATCAGGTAATCGTCATCGTGTTCGTGGTGCAAAAGCAACCGCATAGGTTAGACG
       130       140       150       160       170       180       190       200       210       220       230       240

                                          30                            40                            50
 W  D  A  G  T  V  G  Y  S  L  F  Q  K  F  A  E  R  V  K  E  L  T  D  G  Q  I  E  I  Q  T  F  P  A  G  A  V  V  G  T  F
CTGGGACGCAGGGACAGTGGGCTATTCCCTTTTTCAAAAATTTGCCGAACGGGTCAAGGAACTCACGGACGGTCAAATTGAAATCCAGACATTCCCAGCAGGCGCGGTCGTTGGTACTTT
GACCCTGCGTCCCTGTCACCCGATAAGGGAAAAAGTTTTTAAACGGCTTGCCCAGTTCCTTGAGTGCCTGCCAGTTTAACTTTAGGTCTGTAAGGGTCGTCCGCGCCAGCAACCATGAAA
       250       260       270       280       290       300       310       320       330       340       350       360

                                          70                            80                            90
 D  M  F  D  A  V  K  T  G  V  L  D  G  M  H  P  F  T  L  Y  W  A  G  R  M  P  V  T  A  F  L  S  S  Y  P  L  G  L  D  R
CGATATGTTTGACGCAGTAAAAACCGGGGTCCTCGATGGGATGCACCCGTTTACCCTCTACTGGGCCGGCCGGATGCCAGTCACTGCTTTTTTGTCATCATATCCACTTGGCCTCGACCG
GCTATACAAACTGCGTCATTTTTGGCCCCAGGAGCTACCCTACGTGGGCAAATGGGAGATGACCCGGCCGGCCTACGGTCAGTGACGAAAAAACAGTAGTATAGGTGAACCGGAGCTGGC
       370       380       390       400       410       420       430       440       450       460       470       480

                                         110                           120                           130
 P  D  Q  W  E  T  W  Y  Y  G  L  G  G  L  E  L  A  R  K  A  Y  E  E  Q  G  L  F  F  V  G  P  V  Q  H  D  Y  N  L  I  H
GCCTGATCAATGGGAGACGTGGTATTACGGCCTCGGTGGTCTGGAATTAGCACGTAAAGCATATGAAGAACAAGGCCTCTTTTTTGTCGGCCCGGTTCAACACGATTACAACTTAATTCA
CGGACTAGTTACCCTCTGCACCATAATGCCGGAGCCACCAGACCTTAATCGTGCATTTCGTATACTTCTTGTTCCGGAGAAAAAACAGCCGGGCCAAGTTGTGCTAATGTTGAATTAAGT
       490       500       510       520       530       540       550       560       570       580       590       600

                                         150                           160                           170
 S  K  K  P  I  K  S  F  E  D  F  K  G  V  K  L  R  V  P  G  G  M  I  A  E  I  F  A  A  A  G  A  A  T  V  L  L  P  G  G
TTCCAAAAAGCCAATCAAATCATTCGAGGATTTTAAGGGTGTCAAACTCCGCGTCCCAGGCGGCATGATTGCCGAGATTTTCGCCGCAGCAGGGGCCGCAACAGTACTCCTCCCAGGCGG
AAGGTTTTTCGGTTAGTTTAGTAAGCTCCTAAAATTCCCACAGTTTGAGGCGCAGGGTCCGCCGTACTAACGGCTCTAAAAGCGGCGTCGTCCCCGGCGTTGTCATGAGGAGGGTCCGCC
       610       620       630       640       650       660       670       680       690       700       710       720

                                         190                           200                           210
 E  V  Y  P  A  L  E  R  G  V  I  D  A  A  D  F  V  G  P  A  V  N  Y  N  L  G  F  H  Q  V  T  K  Y  I  I  M  G  P  P  E
GGAAGTCTATCCGGCCCTTGAGCGTGGTGTCATCGACGCGGCCGACTTCGTAGGTCCAGCCGTAAACTACAATTTAGGTTTTCATCAAGTCACCAAATACATCATCATGGGCCCGCCTGA
CCTTCAGATAGGCCGGGAACTCGCACCACAGTAGCTGCGCCGGCTGAAGCATCCAGGTCGGCATTTGATGTTAAATCCAAAAGTAGTTCAGTGGTTTATGTAGTAGTACCCGGGCGGACT
       730       740       750       760       770       780       790       800       810       820       830       840

                                         230                           240                           250
```

```
 T  P  A  I  H  Q  P  V  D  L  A  D  I  T  I  N  I  N  R  W  R  A  L  P  R  N  L  Q  E  R  F  E  A  A  V  H  E  W  S  W
AACACCGGCCATTCACCAGCCAGTCGACTTAGCCGACATTACCATTAATATCAATCGCTGGCGGGCGCTTCCACGTAACCTGCAAGAACGCTTTGAGGCTGCCGTGCACGAGTGGTCCTG
TTGTGGCCGGTAAGTGGTCGGTCAGCTGAATCGGCTGTAATGGTAATTATAGTTAGCGACCGCCCGCGAAGGTGCATTGGACGTTCTTGCGAAACTCCGACGGCACGTGCTCACCAGGAC
       850       860       870       880       890       900       910       920       930       940       950       960

                                      270                                       280                                       290
 I  H  Y  A  G  I  Q  K  A  N  L  E  T  W  P  K  Y  K  A  A  G  V  Q  V  I  R  L  S  T  V  D  V  R  K  F  R  R  V  A  I
GATTCACTATGCCGGTATTCAAAAGGCGAACCTTGAGACCTGGCCGAAGTACAAAGCCGCCGGCGTGCAAGTGATTCGCTTATCCACCGTAGACGTCCGTAAATTTCGCCGTGTCGCGAT
CTAAGTGATACGGCCATAAGTTTTCCGCTTGGAACTCTGGACCGGCTTCATGTTTCGGCGGCCGCACGTTCACTAAGCGAATAGGTGGCATCTGCAGGCATTTAAAGCGGCACAGCGCTA
       970       980       990      1000      1010      1020      1030      1040      1050      1060      1070      1080

                                      310                                       320                                       330
 P  I  W  F  K  W  A  K  Q  D  K  Y  T  R  E  A  F  A  S  Q  L  E  Y  M  K  A  L  G  Y  V  T  D  A  D  I  R  G  L  S  L
CCCAATTTGGTTCAAGTGGGCGAAACAGGACAAATATACACGCGAGGCATTCGCAAGTCAATTGGAGTATATGAAAGCATTAGGTTATGTAACAGACGCAGACATCCGGGGGCTGAGCTT
GGGTTAAACCAAGTTCACCCGCTTTGTCCTGTTTATATGTGCGCTCCGTAAGCGTTCAGTTAACCTCATATACTTTCGTAATCCAATACATTGTCTGCGTCTGTAGGCCCCCGACTCGAA
      1090      1100      1110      1120      1130      1140      1150      1160      1170      1180      1190      1200

                                      350
 G  G  S  H  H  H  H  H  H  *  *
AGGTGGTTCTCATCATCATCATCATCATTAATGAAAGGGCGATATCCAGCACACTGGCGGCCGTTACTAGTGGATCCGGCTGCTAACAAAGCCCGAAAGGAAGCTGAGTTGGCTGCTGCC
TCCACCAAGAGTAGTAGTAGTAGTAGTAATTACTTTCCCGCTATAGGTCGTGTGACCGCCGGCAATGATCACCTAGGCCGACGATTGTTTCGGGCTTTCCTTCGACTCAACCGACGACGG
      1210      1220      1230      1240      1250      1260      1270      1280      1290      1300      1310      1320

ACCGCTGAGCAATAACTAGCATAACCCCTTGGGGCCTCTAAACGGGTCTTGAGGGGTTTTTTGCTGAAAGGAGGAACTATATCCGGAGCGACTCCCACGGCACGTTGGCAAGCTCGGAAT
TGGCGACTCGTTATTGATCGTATTGGGGAACCCCGGAGATTTGCCCAGAACTCCCCAAAAAACGACTTTCCTCCTTGATATAGGCCTCGCTGAGGGTGCCGTGCAACCGTTCGAGCCTTA
      1330      1340      1350      1360      1370      1380      1390      1400      1410      1420      1430      1440

TCGGCGTAATC
AGCCGCATTAG
      1450
```

FIG. 11 (Continued)

FIG. 12 - Exemplary Expression Construct for toLacBP3

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                          10
                                                                 M  K  S  T  R  R  Q  F  L  K  K  A  A  I  G  V  A  A  S  S
GGAGACCACAACGGTTTCCCTCTAGAAATAATTTTGTTTAACTTTAAGAAGGAGATATACCATGAAATCAACACGGCGTCAATTTTTAAAAAAAGCAGCAATCGGTGTGGCCGCCTCCTC
CCTCTGGTGTTGCCAAAGGGAGATCTTTATTAAAACAAATTGAAATTCTTCCTCTATATGGTACTTTAGTTGTGCCGCAGTTAAAAATTTTTTTCGTCGTTAGCCACACCGGCGGAGGAG
       130       140       150       160       170       180       190       200       210       220       230       240

                                    30                            40                            50
 A  F  S  P  L  A  I  A  Q  A  P  R  F  R  W  R  I  Q  S  A  W  D  A  G  T  V  G  Y  T  L  F  Q  R  F  A  E  R  V  K  E
AGCATTTTCACCTCTCGCAATCGCGCAGGCTCCACGGTTCCGTTGGCGTATCCAATCGGCATGGGACGCAGGCACAGTAGGTTACACGTTATTTCAACGCTTCGCCGAACGCGTCAAAGA
TCGTAAAAGTGGAGAGCGTTAGCGCGTCCGAGGTGCCAAGGCAACCGCATAGGTTAGCCGTACCCTGCGTCCGTGTCATCCAATGTGCAATAAAGTTGCGAAGCGGCTTGCGCAGTTTCT
       250       260       270       280       290       300       310       320       330       340       350       360

                                    70                            80                            90
 L  T  D  G  Q  I  E  I  Q  P  F  P  A  G  A  V  V  G  T  F  D  M  F  D  A  V  K  T  G  V  L  D  G  M  H  P  F  T  L  Y
GCTTACAGACGGCCAGATTGAAATTCAGCCTTTTCCGGCAGGCGCAGTCGTAGGCACCTTCGATATGTTCGACGCGGTGAAAACAGGGGTCCTCGATGGGATGCACCCATTTACCCTGTA
CGAATGTCTGCCGGTCTAACTTTAAGTCGGAAAAGGCCGTCCGCGTCAGCATCCGTGGAAGCTATACAAGCTGCGCCACTTTTGTCCCCAGGAGCTACCCTACGTGGGTAAATGGGACAT
       370       380       390       400       410       420       430       440       450       460       470       480

                                   110                           120                           130
 W  A  G  R  M  P  V  T  A  F  L  S  S  Y  P  L  G  L  D  R  P  D  Q  W  E  T  W  Y  Y  G  L  G  G  L  E  L  A  R  K  A
CTGGGCTGGCCGTATGCCTGTCACCGCATTCTTATCATCCTACCCGCTTGGCTTAGATCGCCCAGATCAATGGGAAACCTGGTACTACGGCTTAGGGGGCTTGGAGTTAGCCCGTAAAGC
GACCCGACCGGCATACGGACAGTGGCGTAAGAATAGTAGGATGGGCGAACCGAATCTAGCGGGTCTAGTTACCCTTTGGACCATGATGCCGAATCCCCCGAACCTCAATCGGGCATTTCG
       490       500       510       520       530       540       550       560       570       580       590       600

                                   150                           160                           170
 Y  E  E  Q  G  L  A  Y  I  G  P  V  Q  H  D  Y  N  L  I  H  S  K  K  P  I  K  S  F  E  E  F  K  G  V  K  L  R  V  P  G
ATATGAGGAGCAGGGTTTGGCATATATTGGCCCAGTACAACACGATTATAACCTCATCCATTCAAAGAAACCTATTAAGTCGTTCGAAGAGTTCAAAGGCGTCAAGTTACGCGTGCCAGG
TATACTCCTCGTCCCAAACCGTATATAACCGGGTCATGTTGTGCTAATATTGGAGTAGGTAAGTTTCTTTGGATAATTCAGCAAGCTTCTCAAGTTTCCGCAGTTCAATGCGCACGGTCC
       610       620       630       640       650       660       670       680       690       700       710       720

                                   190                           200                           210
 G  M  I  A  E  I  F  A  A  A  G  A  A  T  V  L  L  P  G  G  E  V  Y  P  A  L  E  R  G  V  I  D  A  A  D  F  V  G  P  A
TGGGATGATCGCTGAAATCTTCGCAGCAGCAGGTGCGGCTACTGTCTTATTACCAGGGGGGGAAGTCTACCCGGCTCTCGAGCGTGGCGTCATTGATGCAGCTGATTTCGTAGGCCCAGC
ACCCTACTAGCGACTTTAGAAGCGTCGTCGTCCACGCCGATGACAGAATAATGGTCCCCCCCTTCAGATGGGCCGAGAGCTCGCACCGCAGTAACTACGTCGACTAAAGCATCCGGGTCG
       730       740       750       760       770       780       790       800       810       820       830       840

                                   230                           240                           250
 V  N  Y  N  L  G  F  H  Q  V  T  K  Y  I  I  M  G  P  P  E  T  P  A  I  H  Q  P  V  D  L  A  D  I  T  L  N  L  N  R  W
TGTCAATTACAATTTAGGCTTTCATCAAGTAACAAAGTATATCATTATGGGCCCGCCAGAAACACCGGCCATTCACCAACCAGTAGACCTCGCGGATATCACCTTGAACTTAAATCGTTG
ACAGTTAATGTTAAATCCGAAAGTAGTTCATTGTTTCATATAGTAATACCCGGGCGGTCTTTGTGGCCGGTAAGTGGTTGGTCATCTGGAGCGCCTATAGTGGAACTTGAATTTAGCAAC
       850       860       870       880       890       900       910       920       930       940       950       960
```

```
                   270                                     280                                     290
 R   A   V   P   K   N   L   Q   E   R   F   E   A   A   V   H   E   W   S   W   V   H   Y   A   G   I   Q   K   A   N   L   E   A   W   P   K   Y   R   A   A
GCGGGCAGTACCTAAGAATTTGCAAGAGCGCTTCGAAGCCGCTGTACACGAATGGTCATGGGTCCATTACGCAGGCATCCAAAAAGCCAACCTCGAAGCCTGGCCAAAATATCGGGCTGC
CGCCCGTCATGGATTCTTAAACGTTCTCGCGAAGCTTCGGCGACATGTGCTTACCAGTACCCAGGTAATGCGTCCGTAGGTTTTTCGGTTGGAGCTTCGGACCGGTTTTATAGCCCGACG
        970       980       990      1000      1010      1020      1030      1040      1050      1060      1070      1080

                   310                                     320                                     330
 G   V   Q   I   I   R   L   S   T   V   D   V   R   K   F   R   R   V   A   I   P   I   W   F   K   W   A   K   Q   D   K   Y   A   K   E   A   F   Q   S   Q
AGGTGTGCAGATCATCCGCTTAAGTACAGTTGACGTCCGCAAGTTTCGTCGTGTGGCAATTCCGATTTGGTTCAAATGGGCAAAGCAAGACAAGTATGCAAAAGAAGCCTTTCAATCACA
TCCACACGTCTAGTAGGCGAATTCATGTCAACTGCAGGCGTTCAAAGCAGCACACCGTTAAGGCTAAACCAAGTTTACCCGTTTCGTTCTGTTCATACGTTTTCTTCGGAAAGTTAGTGT
       1090      1100      1110      1120      1130      1140      1150      1160      1170      1180      1190      1200

                   350                                     360                                     370
 L   E   Y   M   K   A   L   G   Y   V   T   D   V   D   L   R   G   L   S   L   G   G   S   H   H   H   H   H   H   *   *
GCTGGAATACATGAAGGCGTTAGGGTATGTTACCGACGTCGACCTGCGGGGTTTGTCCTTAGGTGGTTCACATCATCATCATCATCATTAATGAAAGGGCGATATCCAGCACACTGGCGG
CGACCTTATGTACTTCCGCAATCCCATACAATGGCTGCAGCTGGACGCCCCAAACAGGAATCCACCAAGTGTAGTAGTAGTAGTAGTAATTACTTTCCCGCTATAGGTCGTGTGACCGCC
       1210      1220      1230      1240      1250      1260      1270      1280      1290      1300      1310      1320


CCGTTACTAGTGGATCCGGCTGCTAACAAAGCCCGAAAGGAAGCTGAGTTGGCTGCTGCCACCGCTGAGCAATAACTAGCATAACCCCTTGGGGCCTCTAAACGGGTCTTGAGGGGTTTT
GGCAATGATCACCTAGGCCGACGATTGTTTCGGGCTTTCCTTCGACTCAACCGACGACGGTGGCGACTCGTTATTGATCGTATTGGGGAACCCCGGAGATTTGCCCAGAACTCCCCAAAA
       1330      1340      1350      1360      1370      1380      1390      1400      1410      1420      1430      1440


TTGCTGAAAGGAGGAACTATATCCGGAGCGACTCCCACGGCACGTTGGCAAGCTCGGAATTCGGCGTAATC
AACGACTTTCCTCCTTGATATAGGCCTCGCTGAGGGTGCCGTGCAACCGTTCGAGCCTTAAGCCGCATTAG
       1450      1460      1470      1480      1490      1500      1510
```

FIG. 12 (Continued)

FIG. 13 - Exemplary Expression Construct for tsuLacBP4

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                                     10
                                                                              M  T  A  R  G  V  R  W  R  M  Q  S  A  W  Q  P  G  T  I  G
GGAGACCACAACGGTTTCCCTCTAGAAATAATTTTGTTTAACTTTAAGAAGGAGATATACCATGACAGCACGTGGTGTTCGTTGGCGTATGCAATCAGCATGGCAACCAGGCACAATCGG
CCTCTGGTGTTGCCAAAGGGAGATCTTTATTAAAACAAATTGAAATTCTTCCTCTATATGGTACTGTCGTGCACCACAAGCAACCGCATACGTTAGTCGTACCGTTGGTCCGTGTTAGCC
       130       140       150       160       170       180       190       200       210       220       230       240

                              30                            40                            50
 Y  R  T  F  E  T  W  A  R  S  I  Q  E  L  T  S  G  E  L  S  I  E  P  F  P  A  G  A  V  A  G  T  F  E  M  A  D  A  V  R
TTATCGTACATTCGAAACTTGGGCACGTTCCATTCAAGAGCTCACCAGTGGTGAATTGTCGATCGAACCTTTTCCGGCCGGGGCAGTAGCCGGTACCTTCGAAATGGCAGACGCGGTCCG
AATAGCATGTAAGCTTTGAACCCGTGCAAGGTAAGTTCTCGAGTGGTCACCACTTAACAGCTAGCTTGGAAAAGGCCGGCCCCGTCATCGGCCATGGAAGCTTTACCGTCTGCGCCAGGC
       250       260       270       280       290       300       310       320       330       340       350       360

                              70                            80                            90
 S  G  V  L  D  G  M  N  W  F  T  V  Y  W  P  G  K  M  P  A  G  V  F  M  S  A  Y  P  M  A  L  S  L  P  H  H  W  D  M  M
GTCTGGGGTCCTCGACGGCATGAATTGGTTCACTGTCTATTGGCCGGGGAAAATGCCAGCAGGTGTCTTTATGTCGGCGTACCCTATGGCGCTCTCCCTGCCACACCACTGGGATATGAT
CAGACCCCAGGAGCTGCCGTACTTAACCAAGTGACAGATAACCGGCCCCTTTTACGGTCGTCCACAGAAATACAGCCGCATGGGATACCGCGAGAGGGACGGTGTGGTGACCCTATACTA
       370       380       390       400       410       420       430       440       450       460       470       480

                             110                           120                           130
 F  D  S  F  G  G  R  Q  I  V  D  E  L  Y  D  R  Q  G  L  V  F  L  G  H  V  Q  H  D  L  N  L  I  H  S  K  V  P  L  R  S
GTTCGATTCTTTTGGGGGCCGTCAGATCGTCGACGAGCTCTACGACCGTCAGGGGCTTGTATTTCTCGGCCATGTACAACACGATCTCAATTTAATTCACTCAAAAGTTCCTTTGCGTTC
CAAGCTAAGAAAACCCCCGGCAGTCTAGCAGCTGCTCGAGATGCTGGCAGTCCCCGAACATAAAGAGCCGGTACATGTTGTGCTAGAGTTAAATTAAGTGAGTTTTCAAGGAAACGCAAG
       490       500       510       520       530       540       550       560       570       580       590       600

                             150                           160                           170
 F  D  D  F  R  G  K  R  I  R  F  P  G  G  I  I  A  E  T  F  A  K  V  G  V  R  T  T  L  L  P  G  G  D  V  Y  P  A  L  E
CTTCGACGACTTTCGGGGTAAGCGTATTCGTTTTCCAGGTGGTATTATCGCAGAAACATTTGCCAAGGTCGGCGTACGTACAACATTATTACCGGGGGGTGACGTATATCCGGCCTTAGA
GAAGCTGCTGAAAGCCCCATTCGCATAAGCAAAAGGTCCACCATAATAGCGTCTTTGTAAACGGTTCCAGCCGCATGCATGTTGTAATAATGGCCCCCCACTGCATATAGGCCGGAATCT
       610       620       630       640       650       660       670       680       690       700       710       720

                             190                           200                           210
 R  G  T  I  D  A  A  D  F  V  G  P  A  V  N  Y  D  L  G  F  H  Q  V  A  D  Y  I  I  M  G  P  P  S  T  P  A  L  H  Q  P
GCGTGGTACCATTGACGCAGCAGACTTTGTAGGCCCAGCGGTAAACTACGATTTAGGTTTTCATCAGGTGGCCGATTATATCATCATGGGCCCTCCAAGTACCCCAGCGTTACACCAACC
CGCACCATGGTAACTGCGTCGTCTGAAACATCCGGGTCGCCATTTGATGCTAAATCCAAAAGTAGTCCACCGGCTAATATAGTAGTACCCGGGAGGTTCATGGGGTCGCAATGTGGTTGG
       730       740       750       760       770       780       790       800       810       820       830       840

                             230                           240                           250
```

```
 V  D  L  M  D  I  S  V  N  K  R  S  W  S  R  I  S  E  H  T  Q  K  L  M  Y  K  F  V  K  A  Y  S  A  E  H  F  A  A  I  Q
AGTTGATCTCATGGACATCTCTGTAAACAAGCGTAGCTGGTCGCGTATCTCGGAGCACACCCAGAAATTAATGTATAAATTCGTCAAAGCATATTCCGCAGAGCACTTTGCAGCCATCCA
TCAACTAGAGTACCTGTAGAGACATTTGTTCGCATCGACCAGCGCATAGAGCCTCGTGTGGGTCTTTAATTACATATTTAAGCAGTTTCGTATAAGGCGTCTCGTGAAACGTCGGTAGGT
        850       860       870       880       890       900       910       920       930       940       950       960

                          270                           280                           290
 K  A  N  H  E  A  W  P  K  Y  K  E  A  G  V  E  V  I  H  L  S  E  E  D  A  A  R  F  R  E  A  A  I  P  L  W  F  E  W  A
AAAAGCCAACCATGAGGCATGGCCGAAATACAAGGAGGCCGGTGTCGAAGTCATCCACTTAAGTGAAGAGGATGCAGCACGTTTCCGGGAGGCAGCAATCCCGCTCTGGTTCGAATGGGC
TTTTCGGTTGGTACTCCGTACCGGCTTTATGTTCCTCCGGCCACAGCTTCAGTAGGTGAATTCACTTCTCCTACGTCGTGCAAAGGCCCTCCGTCGTTAGGGCGAGACCAAGCTTACCCG
        970       980       990      1000      1010      1020      1030      1040      1050      1060      1070      1080

                          310                           320                           330
 N  K  D  R  D  A  A  R  L  F  K  V  H  L  E  V  M  Q  D  P  S  V  A  V  I  T  P  D  D  I  K  D  Y  K  L  N  F  G  G  S
AAACAAAGACCGTGATGCGGCCCGGCTCTTTAAGGTTCATTTAGAAGTCATGCAAGACCCATCGGTAGCGGTCATCACCCCAGATGACATTAAAGATTACAAATTGAACTTTGGCGGTTC
TTTGTTTCTGGCACTACGCCGGGCCGAGAAATTCCAAGTAAATCTTCAGTACGTTCTGGGTAGCCATCGCCAGTAGTGGGGTCTACTGTAATTTCTAATGTTTAACTTGAAACCGCCAAG
       1090      1100      1110      1120      1130      1140      1150      1160      1170      1180      1190      1200

 H  H  H  H  H  H  *  *
TCATCATCATCATCATCATTAATGAAAGGGCGATATCCAGCACACTGGCGGCCGTTACTAGTGGATCCGGCTGCTAACAAAGCCCGAAAGGAAGCTGAGTTGGCTGCTGCCACCGCTGAG
AGTAGTAGTAGTAGTAGTAATTACTTTCCCGCTATAGGTCGTGTGACCGCCGGCAATGATCACCTAGGCCGACGATTGTTTCGGGCTTTCCTTCGACTCAACCGACGACGGTGGCGACTC
       1210      1220      1230      1240      1250      1260      1270      1280      1290      1300      1310      1320

CAATAACTAGCATAACCCCTTGGGGCCTCTAAACGGGTCTTGAGGGGTTTTTTGCTGAAAGGAGGAACTATATCCGGAGCGACTCCCACGGCACGTTGGCAAGCTCGGAATTCGGCGTAA
GTTATTGATCGTATTGGGGAACCCCGGAGATTTGCCCAGAACTCCCCAAAAAACGACTTTCCTCCTTGATATAGGCCTCGCTGAGGGTGCCGTGCAACCGTTCGAGCCTTAAGCCGCATT
       1330      1340      1350      1360      1370      1380      1390      1400      1410      1420      1430      1440

TC
AG
```

FIG. 14 - Exemplary Expression Construct for rdLacBP5

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                            10
                                                                               M  A  A  G  E  G  T  T  W  K  I  Q  T  S  H  T  G  G  I  G
GGAGACCACAACGGTTTCCCTCTAGAAATAATTTTGTTTAACTTTAAGAAGGAGATATACCATGGCAGCTGGTGAAGGTACAACTTGGAAAATTCAGACAAGTCATACCGGTGGTATTGG
CCTCTGGTGTTGCCAAAGGGAGATCTTTATTAAAACAAATTGAAATTCTTCCTCTATATGGTACCGTCGACCACTTCCATGTTGAACCTTTTAAGTCTGTTCAGTATGGCCACCATAACC
       130       140       150       160       170       180       190       200       210       220       230       240

                                           30                            40                            50
 L  A  T  F  K  D  W  A  S  S  I  E  E  K  T  G  G  E  L  A  F  T  A  F  G  A  N  D  V  V  G  D  F  Q  L  Y  D  A  V  K
CCTCGCGACTTTTAAAGACTGGGCGTCCTCTATCGAGGAGAAGACGGGTGGTGAGTTAGCCTTTACAGCTTTTGGTGCCAATGATGTGGTAGGTGACTTTCAACTTTACGACGCAGTCAA
GGAGCGCTGAAAATTTCTGACCCGCAGGAGATAGCTCCTCTTCTGCCCACCACTCAATCGGAAATGTCGAAAACCACGGTTACTACACCATCCACTGAAAGTTGAAATGCTGCGTCAGTT
       250       260       270       280       290       300       310       320       330       340       350       360

                                           70                            80                            90
 N  G  V  L  D  A  V  N  P  F  T  I  Y  A  Q  G  I  I  P  A  A  T  F  L  T  S  Y  P  L  G  L  R  N  P  H  E  W  D  V  F
AAACGGTGTTTTAGATGCGGTCAACCCATTCACAATTTATGCACAAGGTATCATCCCGGCTGCAACATTTCTGACTTCATACCCACTCGGTCTCCGCAATCCGCACGAATGGGACGTCTT
TTTGCCACAAAATCTACGCCAGTTGGGTAAGTGTTAAATACGTGTTCCATAGTAGGGCCGACGTTGTAAAGACTGAAGTATGGGTGAGCCAGAGGCGTTAGGCGTGCTTACCCTGCAGAA
       370       380       390       400       410       420       430       440       450       460       470       480

                                          110                           120                           130
 F  Y  S  L  G  G  L  E  I  A  R  E  L  Y  A  A  Q  G  M  K  F  V  G  P  V  H  H  G  P  N  I  I  H  S  K  V  P  I  R  S
CTTTTACAGCCTTGGCGGCCTCGAAATTGCCCGTGAACTCTACGCCGCACAAGGTATGAAATTCGTCGGGCCTGTCCATCATGGTCCAAATATCATTCATTCGAAGGTGCCTATTCGTTC
GAAAATGTCGGAACCGCCGGAGCTTTAACGGGCACTTGAGATGCGGCGTGTTCCATACTTTAAGCAGCCCGGACAGGTAGTACCAGGTTTATAGTAAGTAAGCTTCCACGGATAAGCAAG
       490       500       510       520       530       540       550       560       570       580       590       600

                                          150                           160                           170
 I  D  D  F  A  G  L  K  M  R  M  P  G  G  M  V  A  E  V  F  S  E  I  G  A  E  T  T  V  L  P  G  S  E  I  F  P  A  L  E
CATCGATGACTTCGCGGGTCTCAAAATGCGTATGCCAGGCGGCATGGTCGCAGAAGTCTTCAGTGAAATCGGTGCCGAGACAACCGTCTTACCTGGTAGCGAGATTTTCCCGGCGCTTGA
GTAGCTACTGAAGCGCCCAGAGTTTTACGCATACGGTCCGCCGTACCAGCGTCTTCAGAAGTCACTTTAGCCACGGCTCTGTTGGCAGAATGGACCATCGCTCTAAAAGGGCCGCGAACT
       610       620       630       640       650       660       670       680       690       700       710       720

                                          190                           200                           210
 K  G  T  I  D  A  A  D  F  V  G  P  A  V  N  Y  A  L  G  F  S  Q  V  T  N  Y  I  S  M  G  P  A  G  F  M  S  L  Y  Q  P
AAAAGGTACAATCGACGCCGCTGACTTCGTTGGCCCAGCAGTAAATTATGCGTTAGGCTTCAGCCAGGTCACCAACTATATTTCCATGGGTCCAGCCGGTTTCATGTCCTTGTACCAACC
TTTTCCATGTTAGCTGCGGCGACTGAAGCAACCGGGTCGTCATTTAATACGCAATCCGAAGTCGGTCCAGTGGTTGATATAAAGGTACCCAGGTCGGCCAAAGTACAGGAACATGGTTGG
       730       740       750       760       770       780       790       800       810       820       830       840

                                          230                           240                           250
 V  D  L  M  D  I  T  V  G  Q  T  A  W  D  A  L  S  P  Q  M  Q  Q  F  V  E  M  E  T  H  V  Y  S  D  M  H  H  A  A  I  Q
AGTAGATTTAATGGATATTACGGTAGGCCAAACCGCATGGGACGCACTCTCACCGCAGATGCAACAGTTTGTAGAGATGGAAACCCACGTATACAGCGACATGCATCACGCCGCCATTCA
TCATCTAAATTACCTATAATGCCATCCGGTTTGGCGTACCCTGCGTGAGAGTGGCGTCTACGTTGTCAAACATCTCTACCTTTGGGTGCATATGTCGCTGTACGTAGTGCGGCGGTAAGT
       850       860       870       880       890       900       910       920       930       940       950       960
```

```
                                   270                                     280                                     290
 K   A   D   Q   E   A   W   A   K   F   E   A   D   G   T   E   V   T   R   L   S   Q   D   D   V   E   L   M   T   E   V   A   V   P   I   W   F   D   Y   A
AAAAGCAGACCAAGAGGCATGGGCTAAATTCGAGGCCGACGGTACTGAGGTTACCCGTTTGTCCCAAGATGATGTAGAATTAATGACCGAAGTCGCCGTTCCAATCTGGTTCGACTATGC
TTTTCGTCTGGTTCTCCGTACCCGATTTAAGCTCCGGCTGCCATGACTCCAATGGGCAAACAGGGTTCTACTACATCTTAATTACTGGCTTCAGCGGCAAGGTTAGACCAAGCTGATACG
         970         980         990        1000        1010        1020        1030        1040        1050        1060        1070        1080

                                   310                                     320                                     330
 N   R   D   K   D   A   A   R   V   F   K   I   Q   L   D   Y   M   M   S   G   S   L   G   Y   V   T   P   E   Q   I   E   G   L   T   L   N   L   G   G   S
AAACCGTGATAAGGACGCAGCACGGGTCTTCAAAATCCAATTAGACTACATGATGTCAGGCAGTCTCGGGTATGTGACACCAGAACAAATTGAAGGCTTGACCTTGAATTTAGGTGGTTC
TTTGGCACTATTCCTGCGTCGTGCCCAGAAGTTTTAGGTTAATCTGATGTACTACAGTCCGTCAGAGCCCATACACTGTGGTCTTGTTTAACTTCCGAACTGGAACTTAAATCCACCAAG
        1090        1100        1110        1120        1130        1140        1150        1160        1170        1180        1190        1200

 H   H   H   H   H   H   *   *
ACATCATCATCATCATCATTAATGAAAGGGCGATATCCAGCACACTGGCGGCCGTTACTAGTGGATCCGGCTGCTAACAAAGCCCGAAAGGAAGCTGAGTTGGCTGCTGCCACCGCTGAG
TGTAGTAGTAGTAGTAGTAATTACTTTCCCGCTATAGGTCGTGTGACCGCCGGCAATGATCACCTAGGCCGACGATTGTTTCGGGCTTTCCTTCGACTCAACCGACGACGGTGGCGACTC
        1210        1220        1230        1240        1250        1260        1270        1280        1290        1300        1310        1320

CAATAACTAGCATAACCCCTTGGGGCCTCTAAACGGGTCTTGAGGGGTTTTTTGCTGAAAGGAGGAACTATATCCGGAGCGACTCCCACGGCACGTTGGCAAGCTCGGAATTCGGCGTAA
GTTATTGATCGTATTGGGGAACCCCGGAGATTTGCCCAGAACTCCCCAAAAAACGACTTTCCTCCTTGATATAGGCCTCGCTGAGGGTGCCGTGCAACCGTTCGAGCCTTAAGCCGCATT
        1330        1340        1350        1360        1370        1380        1390        1400        1410        1420        1430        1440

TC
AG
```

FIG. 15 - Exemplary Expression Construct for msLacBP6

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAACGGTTTCCCTCTAGAAATAATTTTGT
TTAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTGCCAAAGGGAGATCTTTATTAAAACA
AATTG
        10        20        30        40        50        60        70        80        90       100       110       120       130       140
150

                                    10                                      20                                      30                                      40
                 M  A  T  T  W  K  I  Q  S  V  W  D  A  G  T  V  G  Y  D  L  F  K  E  W  C  D  G  M  E  E  K  T  G  G  E  L  K  F  T  C  F  P
A  K
TTTAAGAAGGAGATATACCATGGCAACAACTTGGAAAATTCAAAGTGTATGGGATGCAGGGACGGTGGGCTATGACCTCTTCAAGGAGTGGTGCGACGGTATGGAAGAAAAGACGGGCGGTGAACTCAAATTCACGTGCTTCCCA
GCCAA
AAATTCTTCCTCTATATGGTACCGTTGTTGAACCTTTTAAGTTTCACATACCCTACGTCCCTGCCACCCGATACTGGAGAAGTTCCTCACCACGCTGCCATACCTTCTTTTCTGCCCGCCACTTGAGTTTAAGTGCACGAAGGGT
CGGTT
       160       170       180       190       200       210       220       230       240       250       260       270       280       290
300

            50                                      60                                      70                                      80                                      90
 A  V  A  A  D  N  N  G  L  F  D  A  V  R  N  G  V  L  Q  G  M  N  P  F  T  L  Y  W  S  G  K  I  P  A  S  V  F  L  S  S  Y  P  A  G  P  D  Q  P
H  Q
AGCCGTCGCCGCAGATAATAATGGTCTTTTTGATGCAGTACGGAATGGCGTCTTGCAAGGTATGAATCCTTTCACCCTCTACTGGTCAGGTAAGATTCCGGCCTCCGTATTTCTCTCGTCGTACCCAGCCGGTCCAGATCAACCA
CATCA
TCGGCAGCGGCGTCTATTATTACCAGAAAAACTACGTCATGCCTTACCGCAGAACGTTCCATACTTAGGAAAGTGGGAGATGACCAGTCCATTCTAAGGCCGGAGGCATAAAGAGAGCAGCATGGGTCGGCCAGGTCTAGTTGGT
GTAGT
       310       320       330       340       350       360       370       380       390       400       410       420       430       440
450

           100                                     110                                     120                                     130                                     140
 W  D  T  M  F  Y  S  L  G  M  L  E  K  T  R  E  I  Y  K  K  F  G  L  F  Y  V  G  P  I  Q  H  D  A  N  I  I  H  S  K  Q  P  I  N  S  L  D  D  L
K  G
ATGGGATACAATGTTCTACAGCCTTGGTATGTTAGAAAAAACACGTGAAATTTACAAAAAGTTCGGCCTCTTCTACGTCGGCCCAATTCAGCACGACGCAAACATTATCCACAGTAAACAGCCGATTAATTCCCTGGACGACCTT
AAGGG
TACCCTATGTTACAAGATGTCGGAACCATACAATCTTTTTTGTGCACTTTAAATGTTTTTCAAGCCGGAGAAGATGCAGCCGGGTTAAGTCGTGCTGCGTTTGTAATAGGTGTCATTTGTCGGCTAATTAAGGGACCTGCTGGAA
TTCCC
       460       470       480       490       500       510       520       530       540       550       560       570       580       590
600

           150                                     160                                     170                                     180                                     190
 L  K  M  R  L  P  G  G  M  V  A  E  V  F  A  K  F  G  V  A  A  V  S  L  P  G  S  D  I  F  P  A  L  E  K  G  T  I  D  A  A  D  Y  V  G  P  A  V
N  W
TCTCAAAATGCGCTTACCTGGCGGGATGGTAGCGGAAGTCTTTGCAAAGTTTGGCGTCGCAGCGGTCAGTCTCCCAGGCAGCGACATCTTTCCAGCCTTAGAAAAAGGCACAATCGACGCTGCTGATTACGTGGGTCCGGCTGTA
AACTG
AGAGTTTTACGCGAATGGACCGCCCTACCATCGCCTTCAGAAACGTTTCAAACCGCAGCGTCGCCAGTCAGAGGGTCCGTCGCTGTAGAAAGGTCGGAATCTTTTTCCGTGTTAGCTGCGACGACTAATGCACCCAGGCCGACAT
TTGAC
       610       620       630       640       650       660       670       680       690       700       710       720       730       740
750
```

```
                200                                     210                                     220                                     230                                     240
 E  L  G  F  S  Q  V  T  K  Y  I  L  M  G  P  P  G  I  M  S  V  Y  Q  P  V  D  L  M  D  L  T  V  N  L  R  A  W  N  A  L  D  P  K  L  Q  Q  I  V
E  D
GGAGCTCGGCTTCAGCCAAGTAACAAAGTACATCTTAATGGGTCCACCAGGCATCATGTCAGTCTACCAACCGGTCGACCTTATGGACCTCACTGTCAATCTGCGGGCCTGGAACGCATTAGATCCAAAGTTACAGCAAATCGTT
GAAGA
CCTCGAGCCGAAGTCGGTTCATTGTTTCATGTAGAATTACCCAGGTGGTCCGTAGTACAGTCAGATGGTTGGCCAGCTGGAATACCTGGAGTGACAGTTAGACGCCCGGACCTTGCGTAATCTAGGTTTCAATGTCGTTTAGCAA
CTTCT
       760       770       780       790       800       810       820       830       840       850       860       870       880       890
900

                250                                     260                                     270                                     280                                     290
 E  V  R  I  Y  S  Q  K  H  Y  L  A  I  Q  K  R  N  I  E  A  M  K  K  F  E  A  A  G  T  T  V  T  R  L  S  Q  E  D  L  Q  E  F  R  R  A  A  I  P
I  W
TGAAGTACGCATCTACTCTCAGAAGCATTACCTCGCAATTCAGAAACGGAATATTGAAGCTATGAAGAAGTTCGAGGCCGCTGGTACAACCGTAACCCGTCTGTCACAAGAGGACCTCCAGGAGTTTCGTCGTGCAGCTATCCCA
ATTTG
ACTTCATGCGTAGATGAGAGTCTTCGTAATGGAGCGTTAAGTCTTTGCCTTATAACTTCGATACTTCTTCAAGCTCCGGCGACCATGTTGGCATTGGGCAGACAGTGTTCTCCTGGAGGTCCTCAAAGCAGCACGTCGATAGGGT
TAAAC
       910       920       930       940       950       960       970       980       990      1000      1010      1020      1030      1040
1050

                300                                     310                                     320                                     330                                     340
 Y  S  W  A  N  K  D  E  D  A  R  E  I  F  D  M  Q  L  E  Y  M  M  N  D  T  V  G  Y  I  T  E  D  D  I  K  G  M  N  G  G  S  H  H  H  H  H  H  *
*
GTATTCATGGGCAAACAAAGATGAAGACGCACGGGAGATTTTCGACATGCAATTAGAGTACATGATGAACGACACTGTAGGTTACATCACTGAAGATGACATTAAGGGCATGAATGGCGGTTCACATCATCATCATCATCATTAA
TGAAA
CATAAGTACCCGTTTGTTTCTACTTCTGCGTGCCCTCTAAAAGCTGTACGTTAATCTCATGTACTACTTGCTGTGACATCCAATGTAGTGACTTCTACTGTAATTCCCGTACTTACCGCCAAGTGTAGTAGTAGTAGTAGTAATT
ACTTT
      1060      1070      1080      1090      1100      1110      1120      1130      1140      1150      1160      1170      1180      1190
1200


GGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCCTCTAAACGGGTCTTGAGGGGTTTTT
TGCTG
CCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGGAGATTTGCCCAGAACTCCCCAAAAA
ACGAC
      1210      1220      1230      1240      1250      1260      1270      1280      1290      1300      1310      1320      1330      1340
1350


AAAGGAGGAACTATATCCGGAGCGACTCCCACGGCACGTTGGCAAGCTCG
TTTCCTCCTTGATATAGGCCTCGCTGAGGGTGCCGTGCAACCGTTCGAGC
      1360      1370      1380      1390      1400
```

FIG. 15 (Continued)

FIG. 16 - Exemplary Expression Construct for tspLacBP7

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                     10                            20
                                                      M  Q  A  P  R  F  R  W  R  I  Q  S  A  W  D  A  G  T  V  G  Y  T  L  F
GGTTTCCCTCTAGAAATAATTTTGTTTAACTTTAAGAAGGAGATATACCATGCAAGCACCACGTTTTCGTTGGCGTATTCAAAGTGCATGGGATGCAGGAACAGTGGGTTACACCCTCTT
CCAAAGGGAGATCTTTATTAAAACAAATTGAAATTCTTCCTCTATATGGTACGTTCGTGGTGCAAAAGCAACCGCATAAGTTTCACGTACCCTACGTCCTTGTCACCCAATGTGGGAGAA
       130       140       150       160       170       180       190       200       210       220       230       240

              30                            40                            50                            60
 Q  R  F  A  E  R  V  K  E  L  T  D  G  Q  I  E  I  Q  T  F  P  A  G  A  V  V  G  T  F  D  M  F  D  A  V  K  T  G  V  L
TCAGCGCTTTGCAGAACGCGTCAAAGAGCTGACCGATGGACAGATCGAGATCCAGACCTTTCCAGCGGGTGCAGTCGTGGGTACCTTCGACATGTTCGACGCAGTCAAAACCGGAGTGCT
AGTCGCGAAACGTCTTGCGCAGTTTCTCGACTGGCTACCTGTCTAGCTCTAGGTCTGGAAAGGTCGCCCACGTCAGCACCCATGGAAGCTGTACAAGCTGCGTCAGTTTTGGCCTCACGA
       250       260       270       280       290       300       310       320       330       340       350       360

              70                            80                            90                           100
 D  G  M  H  P  F  T  L  Y  W  A  G  R  M  P  V  T  A  F  L  S  S  Y  P  L  G  L  D  R  P  D  Q  W  E  T  W  Y  Y  A  L
GGATGGCATGCATCCCTTTACCCTCTATTGGGCAGGTCGAATGCCGGTTACCGCCTTTCTCAGCAGCTACCCGTTAGGCCTGGATCGACCAGATCAGTGGGAAACGTGGTACTACGCACT
CCTACCGTACGTAGGGAAATGGGAGATAACCCGTCCAGCTTACGGCCAATGGCGGAAAGAGTCGTCGATGGGCAATCCGGACCTAGCTGGTCTAGTCACCCTTTGCACCATGATGCGTGA
       370       380       390       400       410       420       430       440       450       460       470       480

             110                           120                           130                           140
 G  G  L  D  L  A  R  R  A  F  E  E  Q  G  L  F  Y  V  G  P  V  Q  H  D  Y  N  L  I  H  S  K  K  P  I  K  S  F  E  D  F
TGGCGGTCTGGATCTGGCGAGACGTGCATTCGAGGAACAGGGTCTGTTCTACGTTGGTCCAGTGCAGCATGACTACAACCTGATCCACAGCAAAAAGCCGATCAAGTCCTTCGAGGACTT
ACCGCCAGACCTAGACCGCTCTGCACGTAAGCTCCTTGTCCCAGACAAGATGCAACCAGGTCACGTCGTACTGATGTTGGACTAGGTGTCGTTTTTCGGCTAGTTCAGGAAGCTCCTGAA
       490       500       510       520       530       540       550       560       570       580       590       600

             150                           160                           170                           180
 K  G  V  K  L  R  V  P  G  G  M  I  A  D  V  F  S  A  A  G  A  A  T  V  L  L  P  G  G  E  V  Y  P  A  L  E  R  G  V  I
CAAAGGCGTGAAGCTGAGAGTGCCTGGTGGCATGATAGCAGACGTCTTCTCAGCAGCTGGAGCAGCAACAGTCCTCTTGCCTGGTGGTGAGGTCTATCCGGCTCTGGAACGTGGTGTGAT
GTTTCCGCACTTCGACTCTCACGGACCACCGTACTATCGTCTGCAGAAGAGTCGTCGACCTCGTCGTTGTCAGGAGAACGGACCACCACTCCAGATAGGCCGAGACCTTGCACCACACTA
       610       620       630       640       650       660       670       680       690       700       710       720

             190                           200                           210                           220
 D  A  A  D  F  V  G  P  A  V  N  Y  N  L  G  F  H  Q  V  T  K  Y  I  I  M  G  P  P  E  T  P  A  I  H  Q  P  V  D  L  A
CGATGCAGCAGACTTCGTGGGTCCTGCAGTGAACTACAACCTTGGCTTCCATCAGGTGACCAAGTACATCATCATGGGTCCTCCAGAAACCCCTGCGATCCATCAGCCAGTGGATCTGGC
GCTACGTCGTCTGAAGCACCCAGGACGTCACTTGATGTTGGAACCGAAGGTAGTCCACTGGTTCATGTAGTAGTACCCAGGAGGTCTTTGGGGACGCTAGGTAGTCGGTCACCTAGACCG
       730       740       750       760       770       780       790       800       810       820       830       840

             230                           240                           250                           260
 D  I  T  L  N  L  S  R  W  R  A  V  P  K  N  L  Q  E  R  F  E  A  A  V  H  E  W  S  W  I  H  Y  A  G  I  Q  K  A  N  L
AGACATCACCCTGAACCTCAGCCGTTGGCGTGCAGTGCCCAAAAACCTGCAGGAACGATTCGAAGCAGCGGTTCACGAATGGAGCTGGATCCACTATGCCGGTATCCAGAAAGCCAACCT
TCTGTAGTGGGACTTGGAGTCGGCAACCGCACGTCACGGGTTTTTGGACGTCCTTGCTAAGCTTCGTCGCCAAGTGCTTACCTCGACCTAGGTGATACGGCCATAGGTCTTTCGGTTGGA
```

```
        850       860       870       880       890       900       910       920       930       940       950       960

              270                           280                           290                           300
 E  T  W  P  K  Y  K  A  A  G  V  Q  I  I  R  L  T  T  V  D  V  R  K  F  R  R  V  A  I  P  I  W  F  K  W  A  K  Q  D  K
GGAGACCTGGCCGAAGTACAAAGCGGCAGGTGTGCAGATCATCAGGCTGACTACCGTGGATGTGCGCAAGTTTCGTCGTGTTGCGATTCCGATCTGGTTCAAATGGGCGAAACAGGACAA
CCTCTGGACCGGCTTCATGTTTCGCCGTCCACACGTCTAGTAGTCCGACTGATGGCACCTACACGCGTTCAAAGCAGCACAACGCTAAGGCTAGACCAAGTTTACCCGCTTTGTCCTGTT
        970       980       990      1000      1010      1020      1030      1040      1050      1060      1070      1080

              310                           320                           330                           340
 Y  A  R  E  A  F  A  S  Q  L  E  Y  M  K  A  L  G  Y  V  T  D  A  D  V  R  G  L  S  L  G  G  S  H  H  H  H  H  H  *  *
GTATGCCCGTGAAGCCTTTGCAAGCCAGCTGGAGTACATGAAAGCACTGGGCTATGTGACAGATGCAGATGTTCGTGGTTTAAGCTTAGGCGGCAGCCATCATCATCATCATCATTAATA
CATACGGGCACTTCGGAAACGTTCGGTCGACCTCATGTACTTTCGTGACCCGATACACTGTCTACGTCTACAAGCACCAAATTCGAATCCGCCGTCGGTAGTAGTAGTAGTAGTAATTAT
       1090      1100      1110      1120      1130      1140      1150      1160      1170      1180      1190      1200

 *
ATGAAAGGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTT
TACTTTCCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAA
       1210      1220      1230      1240      1250      1260      1270      1280      1290      1300      1310      1320

GGGGCCTCTAAACGGGTCTTGAGGGGTTTTTTGCTGAAAGGAGGAACTATATCCGGAGCGACTCCCACGGCACGTTGGCAAGCTCG
CCCCGGAGATTTGCCCAGAACTCCCCAAAAAACGACTTTCCTCCTTGATATAGGCCTCGCTGAGGGTGCCGTGCAACCGTTCGAGC
       1330      1340      1350      1360      1370      1380      1390      1400
```

FIG. 16 (Continued)

FIG. 17 - Exemplary Expression Construct for maLacBP8

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                            10                            20
                                                  M  Q  A  A  T  T  W  K  I  Q  S  T  W  D  A  G  T  V  G  Y  T  L  F  E
GGTTTCCCTCTAGAAATAATTTTGTTTAACTTTAAGAAGGAGATATACCATGCAAGCAGCAACTACTTGGAAAATTCAAAGTACCTGGGATGCTGGTACGGTTGGCTACACCCTCTTCGA
CCAAAGGGAGATCTTTATTAAAACAAATTGAAATTCTTCCTCTATATGGTACGTTCGTCGTTGATGAACCTTTTAAGTTTCATGGACCCTACGACCATGCCAACCGATGTGGGAGAAGCT
       130       140       150       160       170       180       190       200       210       220       230       240

                30                            40                            50                            60
  E  W  A  K  S  I  E  A  K  S  G  G  E  L  K  F  Q  A  F  P  A  K  A  V  A  A  D  N  N  A  L  F  D  A  V  R  N  G  V  L
AGAGTGGGCGAAGAGCATCGAAGCCAAATCCGGTGGTGAACTGAAGTTCCAGGCGTTTCCGGCAAAAGCCGTTGCTGCTGACAACAACGCGCTCTTTGACGCTGTTCGCAACGGTGTGCT
TCTCACCCGCTTCTCGTAGCTTCGGTTTAGGCCACCACTTGACTTCAAGGTCCGCAAAGGCCGTTTTCGGCAACGACGACTGTTGTTGCGCGAGAAACTGCGACAAGCGTTGCCACACGA
       250       260       270       280       290       300       310       320       330       340       350       360

                70                            80                            90                           100
  Q  G  M  N  P  F  T  L  Y  W  A  G  K  I  P  A  S  V  F  L  S  S  Y  P  A  G  P  D  Q  P  H  Q  W  D  T  M  F  Y  S  M
TCAGGGCATGAACCCGTTCACCCTGTACTGGGCGGGCAAAATCCCTGCCTCTGTGTTCCTGTCGAGCTACCCAGCAGGTCCGGATCAACCCCATCAGTGGGATACCATGTTCTACTCGAT
AGTCCCGTACTTGGGCAAGTGGGACATGACCCGCCCGTTTTAGGGACGGAGACACAAGGACAGCTCGATGGGTCGTCCAGGCCTAGTTGGGGTAGTCACCCTATGGTACAAGATGAGCTA
       370       380       390       400       410       420       430       440       450       460       470       480

               110                           120                           130                           140
  G  M  L  E  K  T  R  E  I  Y  K  K  F  G  L  F  Y  V  G  P  I  Q  H  D  A  N  I  I  H  S  K  Q  P  V  N  S  L  D  D  L
GGGTATGCTGGAGAAAACCCGCGAAATCTACAAGAAATTTGGCCTGTTCTACGTTGGTCCGATCCAGCATGATGCGAACATCATCCACAGCAAACAGCCAGTCAACTCTCTGGACGACCT
CCCATACGACCTCTTTTGGGCGCTTTAGATGTTCTTTAAACCGGACAAGATGCAACCAGGCTAGGTCGTACTACGCTTGTAGTAGGTGTCGTTTGTCGGTCAGTTGAGAGACCTGCTGGA
       490       500       510       520       530       540       550       560       570       580       590       600

               150                           160                           170                           180
  K  G  M  K  I  R  V  P  G  G  M  V  A  E  V  F  Q  Q  F  G  V  S  T  V  S  L  P  G  S  D  I  F  P  A  L  E  K  G  T  I
GAAAGGGATGAAGATCCGTGTACCTGGTGGCATGGTTGCCGAAGTCTTCCAGCAGTTTGGCGTTTCCACCGTCAGTCTGCCGGGTAGCGACATCTTCCCGGCATTGGAGAAAGGCACGAT
CTTTCCCTACTTCTAGGCACATGGACCACCGTACCAACGGCTTCAGAAGGTCGTCAAACCGCAAAGGTGGCAGTCAGACGGCCCATCGCTGTAGAAGGGCCGTAACCTCTTTCCGTGCTA
       610       620       630       640       650       660       670       680       690       700       710       720

               190                           200                           210                           220
  D  A  A  D  F  V  G  P  A  V  N  Y  E  L  G  F  S  Q  V  T  D  Y  I  I  F  G  P  P  G  V  M  S  I  Y  Q  P  V  D  L  M
TGACGCTGCAGACTTCGTAGGTCCAGCAGTCAACTACGAACTGGGCTTTAGCCAGGTTACGGACTACATCATCTTCGGACCACCTGGCGTCATGAGCATCTATCAACCGGTGGACCTGAT
ACTGCGACGTCTGAAGCATCCAGGTCGTCAGTTGATGCTTGACCCGAAATCGGTCCAATGCCTGATGTAGTAGAAGCCTGGTGGACCGCAGTACTCGTAGATAGTTGGCCACCTGGACTA
       730       740       750       760       770       780       790       800       810       820       830       840

               230                           240                           250                           260
  D  L  T  V  S  L  R  A  W  N  S  I  S  P  E  L  Q  Q  L  V  E  D  E  V  R  I  Y  S  Q  K  H  Y  L  A  I  Q  A  R  N  I
GGATCTGACCGTCAGTCTGCGTGCTTGGAACTCGATCTCACCAGAGCTGCAGCAGCTGGTTGAGGATGAAGTGCGCATCTACTCGCAGAAACACTATCTGGCGATTCAGGCTCGCAACAT
CCTAGACTGGCAGTCAGACGCACGAACCTTGAGCTAGAGTGGTCTCGACGTCGTCGACCAACTCCTACTTCACGCGTAGATGAGCGTCTTTGTGATAGACCGCTAAGTCCGAGCGTTGTA
       850       860       870       880       890       900       910       920       930       940       950       960
```

```
                    270                                     280                                     290                                     300
 E   A   M   E   K   F   K   A   D   G   D   T   V   T   R   L   S   Q   E   D   L   E   T   W   R   K   A   A   I   P   I   W   F   N   W   A   N   K   N   D
CGAAGCGATGGAGAAATTCAAAGCCGATGGTGACACGGTAACCCGTCTGAGCCAGGAAGACCTGGAAACCTGGCGTAAGGCTGCAATCCCGATCTGGTTCAACTGGGCGAACAAGAACGA
GCTTCGCTACCTCTTTAAGTTTCGGCTACCACTGTGCCATTGGGCAGACTCGGTCCTTCTGGACCTTTGGACCGCATTCCGACGTTAGGGCTAGACCAAGTTGACCCGCTTGTTCTTGCT
        970       980       990      1000      1010      1020      1030      1040      1050      1060      1070      1080

                    310                                     320                                     330                                     340
 D   A   R   A   I   L   D   I   Q   L   K   Y   M   M   N   D   T   V   G   Y   I   T   E   E   D   I   K   G   F   G   G   S   H   H   H   H   H   H   *   *
TGATGCTCGTGCGATCCTGGATATCCAGCTGAAATACATGATGAACGACACTGTGGGCTACATTACTGAAGAAGATATTAAAGGATTTGGCGGCAGCCATCATCATCATCATCATTAATG
ACTACGAGCACGCTAGGACCTATAGGTCGACTTTATGTACTACTTGCTGTGACACCCGATGTAATGACTTCTTCTATAATTTCCTAAACCGCCGTCGGTAGTAGTAGTAGTAGTAATTAC
      1090      1100      1110      1120      1130      1140      1150      1160      1170      1180      1190      1200

 *
ATAAAAGGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTT
TATTTTCCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAA
      1210      1220      1230      1240      1250      1260      1270      1280      1290      1300      1310      1320

GGGGCCTCTAAACGGGTCTTGAGGGGTTTTTTGCTGAAAGGAGGAACTATATCCGGAGCGACTCCCACGGCACGTTGGCAAGCTCG
CCCCGGAGATTTGCCCAGAACTCCCCAAAAAACGACTTTCCTCCTTGATATAGGCCTCGCTGAGGGTGCCGTGCAACCGTTCGAGC
      1330      1340      1350      1360      1370      1380      1390      1400
```

FIG. 17 (Continued)

FIG. 18 - Exemplary Expression Construct for adLacBP9

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                  10                  20
                                                            M  Q  A  P  I  T  L  R  F  Q  S  T  W  P  Q  K  D  I  F  H  E  F  A  L
GGTTTCCCTCTAGAAATAATTTTGTTTAACTTTAAGAAGGAGATATACCATGCAAGCACCAATTACTCTGAGATTTCAGAGTACTTGGCCGCAGAAAGACATCTTCCACGAGTTTGCCCT
CCAAAGGGAGATCTTTATTAAAACAAATTGAAATTCTTCCTCTATATGGTACGTTCGTGGTTAATGAGACTCTAAAGTCTCATGAACCGGCGTCTTTCTGTAGAAGGTGCTCAAACGGGA
       130       140       150       160       170       180       190       200       210       220       230       240

      30                  40                  50                  60
D  Y  A  K  K  V  N  E  M  S  G  G  R  L  K  I  E  V  L  A  A  G  S  V  V  K  A  F  D  L  L  D  A  V  S  K  G  T  L  D
GGATTACGCCAAAAAGGTCAACGAGATGAGCGGTGGACGTCTGAAGATCGAGGTTCTGGCAGCAGGCAGTGTGGTGAAGGCGTTCGATCTCCTGGATGCAGTGAGCAAGGGTACGCTGGA
CCTAATGCGGTTTTTCCAGTTGCTCTACTCGCCACCTGCAGACTTCTAGCTCCAAGACCGTCGTCCGTCACACCACTTCCGCAAGCTAGAGGACCTACGTCACTCGTTCCCATGCGACCT
       250       260       270       280       290       300       310       320       330       340       350       360

      70                  80                  90                 100
G  G  H  G  V  V  A  Y  W  Y  G  K  N  T  A  L  A  L  W  G  S  G  P  A  F  G  M  D  P  N  M  V  L  A  W  H  H  Y  G  G
TGGAGGTCATGGCGTAGTCGCCTACTGGTACGGCAAGAACACCGCATTAGCGCTGTGGGGCTCTGGACCTGCATTCGGCATGGACCCAAACATGGTGCTTGCATGGCACCATTACGGCGG
ACCTCCAGTACCGCATCAGCGGATGACCATGCCGTTCTTGTGGCGTAATCGCGACACCCCGAGACCTGGACGTAAGCCGTACCTGGGTTTGTACCACGAACGTACCGTGGTAATGCCGCC
       370       380       390       400       410       420       430       440       450       460       470       480

     110                 120                 130                 140
G  R  Q  L  L  E  E  I  Y  R  S  L  N  L  D  V  V  S  L  M  Y  G  P  M  P  T  Q  P  L  G  W  F  K  Q  K  P  I  A  K  P
AGGTCGTCAGCTCCTGGAAGAGATCTACCGAAGCCTCAACCTGGATGTCGTCAGCCTCATGTACGGACCAATGCCGACTCAGCCGTTAGGCTGGTTCAAGCAGAAACCCATTGCGAAACC
TCCAGCAGTCGAGGACCTTCTCTAGATGGCTTCGGAGTTGGACCTACAGCAGTCGGAGTACATGCCTGGTTACGGCTGAGTCGGCAATCCGACCAAGTTCGTCTTTGGGTAACGCTTTGG
       490       500       510       520       530       540       550       560       570       580       590       600

     150                 160                 170                 180
D  D  M  K  G  L  K  F  R  T  V  G  L  S  I  D  I  F  N  G  L  G  A  A  V  N  A  L  P  G  A  E  I  V  P  A  M  D  R  G
TGACGACATGAAAGGGCTGAAGTTCCGTACGGTAGGTCTGAGCATCGACATCTTCAACGGACTGGGTGCTGCAGTGAACGCGTTACCAGGTGCCGAAATCGTTCCGGCTATGGATCGAGG
ACTGCTGTACTTTCCCGACTTCAAGGCATGCCATCCAGACTCGTAGCTGTAGAAGTTGCCTGACCCACGACGTCACTTGCGCAATGGTCCACGGCTTTAGCAAGGCCGATACCTAGCTCC
       610       620       630       640       650       660       670       680       690       700       710       720

     190                 200                 210                 220
L  L  D  A  A  E  F  N  N  A  S  S  D  R  V  L  G  F  P  D  V  S  K  I  A  M  L  Q  S  F  H  Q  A  S  E  Q  F  E  I  L
TCTGCTCGATGCGGCAGAGTTCAACAACGCTTCTTCCGATCGTGTGCTAGGGTTTCCGGATGTCTCGAAGATCGCGATGCTGCAATCGTTCCATCAGGCGTCAGAGCAGTTCGAGATCCT
AGACGAGCTACGCCGTCTCAAGTTGTTGCGAAGAAGGCTAGCACACGATCCCAAAGGCCTACAGAGCTTCTAGCGCTACGACGTTAGCAAGGTAGTCCGCAGTCTCGTCAAGCTCTAGGA
       730       740       750       760       770       780       790       800       810       820       830       840

     230                 240                 250                 260
F  N  G  K  R  F  Q  A  L  P  A  D  L  K  S  I  I  S  I  A  A  Q  A  A  S  A  D  M  S  W  K  A  I  D  R  Y  S  S  D  Y
GTTCAACGGCAAGCGTTTCCAGGCGTTACCGGCTGATCTGAAGAGCATCATCTCCATTGCTGCGCAAGCTGCAAGCGCCGACATGTCCTGGAAGGCCATCGATCGCTACTCTAGCGACTA
CAAGTTGCCGTTCGCAAAGGTCCGCAATGGCCGACTAGACTTCTCGTAGTAGAGGTAACGACGCGTTCGACGTTCGCGGCTGTACAGGACCTTCCGGTAGCTAGCGATGAGATCGCTGAT
       850       860       870       880       890       900       910       920       930       940       950       960
```

```
                270                                     280                                     290                                     300
 F   E   M   R   D   K   Q   G   V   K   F   Y   S   T   R   P   E   I   L   K   R   Q   L   E   I   W   D   Q   V   M   E   K   R   A   A   E   N   P   T   F
CTTCGAGATGCGTGACAAGCAGGGCGTGAAGTTCTACAGCACCAGACCGGAAATCCTGAAACGGCAACTGGAGATCTGGGACCAGGTGATGGAGAAGCGTGCAGCCGAAAACCCGACGTT
GAAGCTCTACGCACTGTTCGTCCCGCACTTCAAGATGTCGTGGTCTGGCCTTTAGGACTTTGCCGTTGACCTCTAGACCCTGGTCCACTACCTCTTCGCACGTCGGCTTTTGGGCTGCAA
        970         980         990        1000        1010        1020        1030        1040        1050        1060        1070        1080

                310                                     320                                     330                                     340
 K   K   V   L   E   S   Q   R   R   F   A   Q   R   A   A   R   W   Q   N   D   T   N   V   D   F   K   M   A   Y   N   H   F   F   G   G   K   K   K   A   T
CAAAAAGGTCCTGGAGAGCCAACGCAGGTTTGCACAGCGTGCTGCGAGATGGCAGAACGACACCAACGTGGACTTCAAGATGGCCTACAACCACTTCTTTGGTGGTAAGAAAAAAGCTAC
GTTTTTCCAGGACCTCTCGGTTGCGTCCAAACGTGTCGCACGACGCTCTACCGTCTTGCTGTGGTTGCACCTGAAGTTCTACCGGATGTTGGTGAAGAAACCACCATTCTTTTTTCGATG
       1090        1100        1110        1120        1130        1140        1150        1160        1170        1180        1190        1200

                350
 G   G   S   H   H   H   H   H   H   *   *   *
TGGCGGCAGCCATCATCATCATCATCATTAATAATGAAAGGGCGATATCCAGCACACTGGCGGCCGTTACTAGTGGATCCGGCTGCTAACAAAGCCCGAAAGGAAGCTGAGTTGGCTGCT
ACCGCCGTCGGTAGTAGTAGTAGTAGTAATTATTACTTTCCCGCTATAGGTCGTGTGACCGCCGGCAATGATCACCTAGGCCGACGATTGTTTCGGGCTTTCCTTCGACTCAACCGACGA
       1210        1220        1230        1240        1250        1260        1270        1280        1290        1300        1310        1320


GCCACCGCTGAGCAATAACTAGCATAACCCCTTGGGGCCTCTAAACGGGTCTTGAGGGGTTTTTTGCTGAAAGGAGGAACTATATCCGGAGCGACTCCCACGGCACGTTGGCAAGCTCG
CGGTGGCGACTCGTTATTGATCGTATTGGGGAACCCCGGAGATTTGCCCAGAACTCCCCAAAAAACGACTTTCCTCCTTGATATAGGCCTCGCTGAGGGTGCCGTGCAACCGTTCGAGC
       1330        1340        1350        1360        1370        1380        1390        1400        1410        1420        1430
```

FIG. 18 (Continued)

FIG. 19 - Exemplary Expression Construct for pgLacBP10

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                            10                            20
                                                                    M  Q  E  A  V  E  W  R  M  Q  A  L  W  D  A  G  T  T  P  F  E  F  E  K
GGTTTCCCTCTAGAAATAATTTTGTTTAACTTTAAGAAGGAGATATACCATGCAAGAAGCAGTTGAATGGAGAATGCAAGCATTGTGGGATGCAGGTACGACCCCATTCGAATTCGAAAA
CCAAAGGGAGATCTTTATTAAAACAAATTGAAATTCTTCCTCTATATGGTACGTTCTTCGTCAACTTACCTCTTACGTTCGTAACACCCTACGTCCATGCTGGGGTAAGCTTAAGCTTTT
       130       140       150       160       170       180       190       200       210       220       230       240

                30                            40                            50                            60
K  F  V  E  R  V  G  E  L  T  E  G  R  F  K  I  T  L  Y  S  A  G  Q  I  V  P  A  N  Q  A  F  D  A  V  R  S  G  A  F  E
GAAGTTCGTGGAACGTGTAGGCGAGTTGACGGAAGGTCGCTTCAAGATCACGCTGTACAGCGCAGGTCAGATAGTGCCGGCAAACCAGGCCTTCGATGCTGTGCGTTCTGGTGCCTTCGA
CTTCAAGCACCTTGCACATCCGCTCAACTGCCTTCCAGCGAAGTTCTAGTGCGACATGTCGCGTCCAGTCTATCACGGCCGTTTGGTCCGGAAGCTACGACACGCAAGACCACGGAAGCT
       250       260       270       280       290       300       310       320       330       340       350       360

                70                            80                            90                           100
M  M  K  T  F  D  G  Y  E  A  G  K  I  P  A  F  A  F  T  S  T  I  P  F  G  F  P  Q  S  D  Q  Y  E  A  W  F  Y  E  L  G
GATGATGAAAACCTTCGATGGCTATGAGGCAGGCAAAATCCCGGCATTCGCCTTCACCTCGACCATTCCGTTCGGTTTCCCGCAGTCTGACCAGTACGAGGCATGGTTCTACGAACTGGG
CTACTACTTTTGGAAGCTACCGATACTCCGTCCGTTTTAGGGCCGTAAGCGGAAGTGGAGCTGGTAAGGCAAGCCAAAGGGCGTCAGACTGGTCATGCTCCGTACCAAGATGCTTGACCC
       370       380       390       400       410       420       430       440       450       460       470       480

               110                           120                           130                           140
G  L  D  L  A  R  E  A  Y  A  K  G  G  L  F  Y  I  A  P  T  V  Y  G  E  E  P  M  H  S  T  V  K  I  E  S  I  A  D  M  A
TGGTCTGGATCTTGCTCGCGAAGCTTACGCCAAAGGTGGCCTGTTCTACATCGCACCGACCGTCTATGGCGAAGAACCCATGCACAGCACCGTGAAGATCGAATCCATCGCGGATATGGC
ACCAGACCTAGAACGAGCGCTTCGAATGCGGTTTCCACCGGACAAGATGTAGCGTGGCTGGCAGATACCGCTTCTTGGGTACGTGTCGTGGCACTTCTAGCTTAGGTAGCGCCTATACCG
       490       500       510       520       530       540       550       560       570       580       590       600

               150                           160                           170                           180
G  K  K  G  R  F  V  G  L  A  S  A  V  M  A  D  L  G  V  A  V  S  P  L  A  T  A  E  V  Y  T  A  L  E  K  G  L  I  D  F
GGGGAAGAAAGGCCGTTTTGTCGGTTTGGCATCTGCGGTGATGGCAGATCTCGGTGTAGCGGTGTCGCCGTTAGCGACTGCCGAAGTGTACACTGCGCTCGAAAAAGGCCTGATCGACTT
CCCCTTCTTTCCGGCAAAACAGCCAAACCGTAGACGCCACTACCGTCTAGAGCCACATCGCCACAGCGGCAATCGCTGACGGCTTCACATGTGACGCGAGCTTTTTCCGGACTAGCTGAA
       610       620       630       640       650       660       670       680       690       700       710       720

               190                           200                           210                           220
A  D  R  G  D  L  T  A  N  Y  E  A  G  L  G  E  V  A  K  F  I  I  L  P  G  V  H  Q  P  T  T  A  T  S  Y  V  A  N  Q  A
TGCGGATCGTGGTGATCTGACAGCCAACTACGAAGCAGGACTTGGCGAAGTGGCGAAATTCATCATCCTTCCGGGTGTGCATCAACCGACCACTGCAACCAGCTATGTCGCGAATCAGGC
ACGCCTAGCACCACTAGACTGTCGGTTGATGCTTCGTCCTGAACCGCTTCACCGCTTTAAGTAGTAGGAAGGCCCACACGTAGTTGGCTGGTGACGTTGGTCGATACAGCGCTTAGTCCG
       730       740       750       760       770       780       790       800       810       820       830       840

               230                           240                           250                           260
A  Y  Q  K  L  P  D  G  F  K  A  A  L  A  V  A  A  R  E  I  S  G  S  L  R  Q  H  I  L  V  Q  D  M  E  V  L  T  K  Y  K
AGCGTACCAGAAGCTTCCGGATGGCTTCAAAGCGGCGTTAGCGGTTGCTGCACGTGAGATCTCCGGTTCACTGCGTCAGCACATCCTGGTTCAGGACATGGAAGTGCTCACCAAGTACAA
TCGCATGGTCTTCGAAGGCCTACCGAAGTTTCGCCGCAATCGCCAACGACGTGCACTCTAGAGGCCAAGTGACGCAGTCGTGTAGGACCAAGTCCTGTACCTTCACGAGTGGTTCATGTT
       850       860       870       880       890       900       910       920       930       940       950       960
```

270 280 290 300
D Q G V E V V R L D A A D I A A A R A K A V E S W E K A T K G D E L A T R V L K
GGATCAGGGTGTGGAAGTGGTACGTCTCGATGCAGCGGATATTGCTGCGGCAAGAGCGAAAGCGGTCGAATCCTGGGAAAAGGCGACCAAAGGGGATGAACTGGCGACCAGAGTGCTGAA
CCTAGTCCCACACCTTCACCATGCAGAGCTACGTCGCCTATAACGACGCCGTTCTCGCTTTCGCCAGCTTAGGACCCTTTTCCGCTGGTTTCCCCTACTTGACCGCTGGTCTCACGACTT
970 980 990 1000 1010 1020 1030 1040 1050 1060 1070 1080

310 320
G Q V D F M T S L G L L G G S H H H H H H * * *
GGGACAGGTGGATTTTATGACTTCTTTAGGTTTACTGGGCGGCAGCCATCATCATCATCATCATTAATAATGAAAGGGCGATATCCAGCACACTGGCGGCCGTTACTAGTGGATCCGGCT
CCCTGTCCACCTAAAATACTGAAGAAATCCAAATGACCCGCCGTCGGTAGTAGTAGTAGTAGTAATTATTACTTTCCCGCTATAGGTCGTGTGACCGCCGGCAATGATCACCTAGGCCGA
1090 1100 1110 1120 1130 1140 1150 1160 1170 1180 1190 1200

GCTAACAAAGCCCGAAAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATA
CGATTGTTTCGGGCTTTCCTTCGACTCAACCGACGACGGTGGCGACTCGTTATTGATCGTATTGGGGAACCCCGGAGATTTGCCCAGAACTCCCCAAAAAACGACTTTCCTCCTTGATAT
1210 1220 1230 1240 1250 1260 1270 1280 1290 1300 1310 1320

TCCGGAGCGACTCCCACGGCACGTTGGCAAGCTCG
AGGCCTCGCTGAGGGTGCCGTGCAACCGTTCGAGC
1330 1340 1350

FIG. 19 (Continued)

FIG. 20 - Exemplary Expression Construct for psLacBP11

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                   10                            20
                                                  M  Q  Q  A  A  G  E  P  A  K  T  Y  H  W  K  M  V  T  A  W  P  K  N  Y
GGTTTCCCTCTAGAAATAATTTTGTTTAACTTTAAGAAGGAGATATACCATGCAACAAGCAGCAGGTGAACCAGCAAAAACCTATCACTGGAAGATGGTGACCGCTTGGCCGAAGAACTA
CCAAAGGGAGATCTTTATTAAAACAAATTGAAATTCTTCCTCTATATGGTACGTTGTTCGTCGTCCACTTGGTCGTTTTTGGATAGTGACCTTCTACCACTGGCGAACCGGCTTCTTGAT
       130       140       150       160       170       180       190       200       210       220       230       240

              30                            40                            50                            60
P  G  L  G  T  S  A  E  R  L  A  E  R  V  N  A  M  S  G  G  R  L  T  I  K  V  Y  A  A  G  E  L  V  P  A  L  E  V  F  D
TCCGGGTTTAGGCACCAGTGCGGAACGACTGGCAGAACGTGTGAACGCGATGAGTGGTGGACGTCTGACCATCAAGGTGTATGCAGCAGGAGAACTGGTTCCAGCTCTGGAAGTGTTCGA
AGGCCCAAATCCGTGGTCACGCCTTGCTGACCGTCTTGCACACTTGCGCTACTCACCACCTGCAGACTGGTAGTTCCACATACGTCGTCCTCTTGACCAAGGTCGAGACCTTCACAAGCT
       250       260       270       280       290       300       310       320       330       340       350       360

              70                            80                            90                           100
A  V  S  R  G  T  A  E  L  G  H  G  A  S  Y  Y  W  K  G  K  V  P  T  A  Q  F  F  T  S  V  P  F  G  L  S  T  S  E  M  N
TGCAGTCTCTCGTGGTACCGCAGAACTGGGTCATGGAGCAAGCTACTACTGGAAAGGCAAGGTTCCGACTGCGCAGTTCTTCACCAGTGTACCGTTTGGTCTGTCAACCAGCGAGATGAA
ACGTCAGAGAGCACCATGGCGTCTTGACCCAGTACCTCGTTCGATGATGACCTTTCCGTTCCAAGGCTGACGCGTCAAGAAGTGGTCACATGGCAAACCAGACAGTTGGTCGCTCTACTT
       370       380       390       400       410       420       430       440       450       460       470       480

             110                           120                           130                           140
A  W  L  S  K  G  G  G  Q  A  F  W  D  E  A  Y  A  P  F  G  V  K  P  L  V  I  G  N  T  G  M  Q  M  G  G  W  Y  N  K  E
CGCATGGCTGAGCAAAGGTGGTGGACAGGCGTTCTGGGACGAAGCCTACGCTCCTTTCGGCGTGAAACCGCTTGTGATCGGCAATACCGGCATGCAGATGGGTGGATGGTACAACAAAGA
GCGTACCGACTCGTTTCCACCACCTGTCCGCAAGACCCTGCTTCGGATGCGAGGAAAGCCGCACTTTGGCGAACACTAGCCGTTATGGCCGTACGTCTACCCACCTACCATGTTGTTTCT
       490       500       510       520       530       540       550       560       570       580       590       600

             150                           160                           170                           180
I  N  S  L  T  D  L  K  G  L  K  I  R  M  P  G  L  G  G  E  V  L  S  R  L  G  A  T  T  V  N  L  P  G  G  E  V  F  T  A
GATCAACAGCCTGACTGACCTCAAAGGCCTGAAAATCCGCATGCCAGGTCTGGGTGGTGAAGTGCTAAGCAGACTGGGTGCAACCACCGTGAACCTTCCAGGTGGTGAAGTCTTTACCGC
CTAGTTGTCGGACTGACTGGAGTTTCCGGACTTTTAGGCGTACGGTCCAGACCCACCACTTCACGATTCGTCTGACCCACGTTGGTGGCACTTGGAAGGTCCACCACTTCAGAAATGGCG
       610       620       630       640       650       660       670       680       690       700       710       720

             190                           200                           210                           220
L  Q  T  G  A  I  D  A  T  D  W  V  S  P  Y  N  D  L  A  F  G  L  H  K  A  A  R  Y  Y  Y  Y  P  G  W  Q  E  P  Q  A  V
ACTGCAGACAGGAGCGATCGATGCAACCGATTGGGTGAGTCCCTACAACGATCTGGCCTTTGGTCTGCACAAAGCAGCACGCTACTACTACTACCCGGGTTGGCAGGAACCACAGGCTGT
TGACGTCTGTCCTCGCTAGCTACGTTGGCTAACCCACTCAGGGATGTTGCTAGACCGGAAACCAGACGTGTTTCGTCGTGCGATGATGATGATGGGCCCAACCGTCCTTGGTGTCCGACA
       730       740       750       760       770       780       790       800       810       820       830       840

             230                           240                           250                           260
L  E  L  L  I  N  Q  K  A  F  D  S  L  P  A  D  L  Q  A  I  V  T  E  A  S  L  A  A  S  R  D  M  H  D  D  Y  V  Y  N  N
ACTGGAACTGCTGATCAACCAGAAGGCGTTCGATAGCTTACCGGCAGATCTGCAGGCGATCGTGACCGAAGCAAGCCTGGCAGCAAGCCGCGATATGCATGACGATTACGTCTACAACAA
TGACCTTGACGACTAGTTGGTCTTCCGCAAGCTATCGAATGGCCGTCTAGACGTCCGCTAGCACTGGCTTCGTTCGGACCGTCGTTCGGCGCTATACGTACTGCTAATGCAGATGTTGTT
       850       860       870       880       890       900       910       920       930       940       950       960
```

```
                270                                     280                                     290                                     300
 A   L   A   L   E   Q   L   K   Q   Q   G   T   E   L   K   R   F   P   D   E   V   L   A   A   M   R   E   Q   S   D   L   I   L   G   E   L   A   A   Q   S
CGCTCTGGCTCTGGAACAGCTCAAACAGCAGGGAACCGAACTGAAGCGCTTTCCGGACGAAGTGCTGGCAGCAATGCGCGAACAGTCTGACCTGATCCTCGGTGAACTGGCTGCACAGAG
GCGAGACCGAGACCTTGTCGAGTTTGTCGTCCCTTGGCTTGACTTCGCGAAAGGCCTGCTTCACGACCGTCGTTACGCGCTTGTCAGACTGGACTAGGAGCCACTTGACCGACGTGTCTC
         970          980          990         1000         1010         1020         1030         1040         1050         1060         1070         1080

                310                                     320                                     330                                     340
 E   L   N   G   R   I   W   A   S   M   K   A   F   Q   A   Q   V   E   P   M   H   E   I   S   E   K   E   L   Y   N   W   R   G   G   S   H   H   H   H   H
CGAACTGAACGGTCGTATCTGGGCAAGCATGAAGGCCTTTCAGGCTCAGGTCGAACCGATGCACGAGATTAGCGAAAAAGAATTGTATAATTGGAGAGGCGGCAGCCATCATCATCATCA
GCTTGACTTGCCAGCATAGACCCGTTCGTACTTCCGGAAAGTCCGAGTCCAGCTTGGCTACGTGCTCTAATCGCTTTTTCTTAACATATTAACCTCTCCGCCGTCGGTAGTAGTAGTAGT
        1090         1100         1110         1120         1130         1140         1150         1160         1170         1180         1190         1200

 H   *   *   *
TCATTAATAATGAAAGGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCA
AGTAATTATTACTTTCCCGCTATAGGTCGTGTGACCGCCGGCAATGATCACCTAGGCCGACGATTGTTTCGGGCTTTCCTTCGACTCAACCGACGACGGTGGCGACTCGTTATTGATCGT
        1210         1220         1230         1240         1250         1260         1270         1280         1290         1300         1310         1320

TAACCCCTTGGGGCCTCTAAACGGGTCTTGAGGGGTTTTTTGCTGAAAGGAGGAACTATATCCGGAGCGACTCCCACGGCACGTTGGCAAGCTCG
ATTGGGGAACCCCGGAGATTTGCCCAGAACTCCCCAAAAAACGACTTTCCTCCTTGATATAGGCCTCGCTGAGGGTGCCGTGCAACCGTTCGAGC
        1330         1340         1350         1360         1370         1380         1390         1400         1410
```

FIG. 20 (Continued)

FIG. 21 - Exemplary Expression Construct for fsLacBP13

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10         20         30         40         50         60         70         80         90        100        110        120

                                                                                      10                            20
                                                                  M  E  K  K  I  R  W  K  L  A  M  T  W  G  P  T  L  H  P  L  S  D  T  A
GGTTTCCCTCTAGAAATAATTTTGTTTAACTTTAAGAAGGAGATATACCATGGAAAAAAAAATTCGTTGGAAATTAGCAATGACTTGGGGTCCGACCTTGCATCCGTTGTCCGACACAGC
CCAAAGGGAGATCTTTATTAAAACAAATTGAAATTCTTCCTCTATATGGTACCTTTTTTTTTAAGCAACCTTTAATCGTTACTGAACCCCAGGCTGGAACGTAGGCAACAGGCTGTGTCG
       130        140        150        160        170        180        190        200        210        220        230        240

             30                            40                            50                            60
 E  H  M  A  E  I  V  K  E  L  S  D  G  N  F  V  I  N  I  D  A  S  N  V  H  K  A  P  F  G  I  F  D  M  V  K  L  G  Q  Y
AGAGCATATGGCGGAAATCGTGAAGGAGTTGAGCGATGGCAACTTCGTGATCAACATCGATGCGTCGAACGTGCACAAAGCGCCGTTTGGCATCTTCGATATGGTGAAACTCGGTCAGTA
TCTCGTATACCGCCTTTAGCACTTCCTCAACTCGCTACCGTTGAAGCACTAGTTGTAGCTACGCAGCTTGCACGTGTTTCGCGGCAAACCGTAGAAGCTATACCACTTTGAGCCAGTCAT
       250        260        270        280        290        300        310        320        330        340        350        360

             70                            80                            90                           100
 E  M  G  H  T  A  S  Y  Y  Y  K  G  K  N  I  A  F  L  P  L  T  T  M  P  F  G  M  T  A  P  E  Q  Y  A  W  F  Y  Y  G  G
CGAGATGGGCCATACTGCGAGCTACTACTACAAAGGCAAAAACATCGCGTTTTTACCGCTGACGACCATGCCTTTCGGTATGACCGCACCGGAACAGTATGCGTGGTTCTACTATGGTGG
GCTCTACCCGGTATGACGCTCGATGATGATGTTTCCGTTTTTGTAGCGCAAAAATGGCGACTGCTGGTACGGAAAGCCATACTGGCGTGGCCTTGTCATACGCACCAAGATGATACCACC
       370        380        390        400        410        420        430        440        450        460        470        480

            110                           120                           130                           140
 G  L  E  L  M  Q  E  A  Y  T  K  H  G  M  L  A  F  P  G  G  N  T  G  N  Q  M  G  G  W  F  T  K  E  I  N  S  L  D  D  L
CGGTCTGGAGCTGATGCAGGAAGCGTACACCAAGCATGGCATGCTGGCGTTTCCTGGTGGTAACACCGGTAACCAGATGGGAGGTTGGTTCACCAAGGAGATCAACAGCCTGGATGACCT
GCCAGACCTCGACTACGTCCTTCGCATGTGGTTCGTACCGTACGACCGCAAAGGACCACCATTGTGGCCATTGGTCTACCCTCCAACCAAGTGGTTCCTCTAGTTGTCGGACCTACTGGA
       490        500        510        520        530        540        550        560        570        580        590        600

            150                           160                           170                           180
 K  G  L  K  M  R  I  P  G  F  A  G  Q  I  M  S  K  L  G  V  T  V  T  N  I  P  P  G  E  L  Y  T  A  L  E  R  G  T  V  D
CAAGGGTCTCAAGATGAGGATCCCAGGCTTTGCGGGCCAGATCATGTCCAAACTGGGTGTGACCGTGACCAACATCCCTCCAGGTGAGCTGTACACCGCACTGGAACGTGGTACCGTGGA
GTTCCCAGAGTTCTACTCCTAGGGTCCGAAACGCCCGGTCTAGTACAGGTTTGACCCACACTGGCACTGGTTGTAGGGAGGTCCACTCGACATGTGGCGTGACCTTGCACCATGGCACCT
       610        620        630        640        650        660        670        680        690        700        710        720

            190                           200                           210                           220
 A  V  E  W  T  G  P  G  M  D  I  N  M  G  F  H  K  I  A  K  Y  Y  Y  T  G  W  H  E  P  G  S  E  V  E  F  L  I  N  E  K
TGCGGTGGAATGGACCGGTCCTGGTATGGACATCAACATGGGATTCCACAAGATCGCGAAATACTACTATACCGGTTGGCATGAACCGGGATCCGAAGTGGAGTTCCTGATCAACGAAAA
ACGCCACCTTACCTGGCCAGGACCATACCTGTAGTTGTACCCTAAGGTGTTCTAGCGCTTTATGATGATATGGCCAACCGTACTTGGCCCTAGGCTTCACCTCAAGGACTAGTTGCTTTT
       730        740        750        760        770        780        790        800        810        820        830        840

            230                           240                           250                           260
 E  Y  N  K  L  P  E  K  Y  K  K  I  L  K  I  A  M  K  T  A  A  Y  D  M  Y  I  Q  S  Y  E  M  N  A  E  A  W  Q  Q  M  K
GGAATACAACAAACTGCCGGAAAAATACAAAAAGATCCTGAAAATCGCCATGAAAACCGCAGCGTACGACATGTACATCCAGTCGTACGAGATGAACGCTGAAGCTTGGCAGCAGATGAA
CCTTATGTTGTTTGACGGCCTTTTTATGTTTTTCTAGGACTTTTAGCGGTACTTTTGGCGTCGCATGCTGTACATGTAGGTCAGCATGCTCTACTTGCGACTTCGAACCGTCGTCTACTT
       850        860        870        880        890        900        910        920        930        940        950        960
```

```
               270                                     280                                     290                                     300
 E   K   Y   P   D   I   K   V   K   V   F   P   E   E   V   L   K   E   M   K   T   A   Y   D   N   L   V   A   S   Y   E   K   E   S   P   M   F   K   K   I
AGAGAAATACCCGGATATCAAGGTCAAGGTTTTTCCGGAAGAAGTGCTGAAAGAGATGAAGACCGCGTACGACAACCTTGTGGCGAGCTACGAGAAAGAAAGCCCGATGTTCAAGAAAAT
TCTCTTTATGGGCCTATAGTTCCAGTTCCAAAAAGGCCTTCTTCACGACTTTCTCTACTTCTGGCGCATGCTGTTGGAACACCGCTCGATGCTCTTTCTTTCGGGCTACAAGTTCTTTTA
         970       980       990      1000      1010      1020      1030      1040      1050      1060      1070      1080

               310                                     320                                     330                                     340
 M   E   S   K   R   A   Y   L   D   K   V   R   D   W   T   H   I   S   D   Y   L   Y   L   K   S   T   S   E   S   N   L   N   G   G   S   H   H   H   H   H
CATGGAGAGCAAACGTGCGTATCTGGACAAGGTTCGAGACTGGACCCACATATCGGACTACCTCTACCTGAAAAGTACTTCTGAAAGTAATCTGAATGGCGGCAGCCATCATCATCATCA
GTACCTCTCGTTTGCACGCATAGACCTGTTCCAAGCTCTGACCTGGGTGTATAGCCTGATGGAGATGGACTTTTCATGAAGACTTTCATTAGACTTACCGCCGTCGGTAGTAGTAGTAGT
        1090      1100      1110      1120      1130      1140      1150      1160      1170      1180      1190      1200

 H   *   *   *
TCATTAATGATAAAAGGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCA
AGTAATTACTATTTTCCCGCTATAGGTCGTGTGACCGCCGGCAATGATCACCTAGGCCGACGATTGTTTCGGGCTTTCCTTCGACTCAACCGACGACGGTGGCGACTCGTTATTGATCGT
        1210      1220      1230      1240      1250      1260      1270      1280      1290      1300      1310      1320

TAACCCCTTGGGGCCTCTAAACGGGTCTTGAGGGGTTTTTTGCTGAAAGGAGGAACTATATCCGGAGCGACTCCCACGGCACGTTGGCAAGCTCG
ATTGGGGAACCCCGGAGATTTGCCCAGAACTCCCCAAAAAACGACTTTCCTCCTTGATATAGGCCTCGCTGAGGGTGCCGTGCAACCGTTCGAGC
        1330      1340      1350      1360      1370      1380      1390      1400      1410
```

FIG. 21 (Continued)

FIG. 22 - Exemplary Expression Construct for taLacBP14

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                          10                            20
                                                     M  E  E  Y  K  F  K  M  A  T  F  Y  L  K  G  D  S  A  F  D  V  I  D  H
GGTTTCCCTCTAGAAATAATTTTGTTTAACTTTAAGAAGGAGATATACCATGGAAGAATATAAATTTAAAATGGCAACTTTTTACCTGAAAGGTGATAGCGCCTTTGACGTGATCGACCA
CCAAAGGGAGATCTTTATTAAAACAAATTGAAATTCTTCCTCTATATGGTACCTTCTTATATTTAAATTTTACCGTTGAAAAATGGACTTTCCACTATCGCGGAAACTGCACTAGCTGGT
       130       140       150       160       170       180       190       200       210       220       230       240

         30                            40                            50                            60
 F  R  Q  L  V  W  K  K  T  G  G  K  V  R  I  D  A  F  Q  A  G  E  L  G  F  P  V  T  E  I  L  E  A  T  S  R  G  V  V  E
CTTTCGCCAACTGGTCTGGAAGAAAACCGGTGGTAAGGTACGCATCGATGCGTTCCAAGCTGGGGAACTGGGCTTTCCAGTGACCGAGATCCTGGAAGCGACCAGTCGTGGTGTGGTGGA
GAAAGCGGTTGACCAGACCTTCTTTTGGCCACCATTCCATGCGTAGCTACGCAAGGTTCGACCCCTTGACCCGAAAGGTCACTGGCTCTAGGACCTTCGCTGGTCAGCACCACACCACCT
       250       260       270       280       290       300       310       320       330       340       350       360

         70                            80                            90                           100
 M  S  I  F  Y  P  N  Y  K  A  A  Q  D  P  V  M  A  L  A  G  G  R  P  G  P  M  F  D  L  R  D  Q  K  A  Q  V  D  A  T  K
GATGAGCATCTTCTACCCGAACTACAAAGCGGCACAGGATCCGGTGATGGCCTTAGCGGGAGGACGTCCGGGTCCAATGTTCGACCTGCGTGATCAGAAAGCCCAAGTGGATGCGACCAA
CTACTCGTAGAAGATGGGCTTGATGTTTCGCCGTGTCCTAGGCCACTACCGGAATCGCCCTCCTGCAGGCCCAGGTTACAAGCTGGACGCACTAGTCTTTCGGGTTCACCTACGCTGGTT
       370       380       390       400       410       420       430       440       450       460       470       480

        110                           120                           130                           140
 D  L  L  E  R  S  F  G  R  F  G  V  R  Y  I  A  P  M  V  Y  G  E  P  E  I  L  V  S  R  R  P  M  S  S  L  K  D  L  K  G
AGATCTCCTGGAAAGGTCCTTCGGTCGTTTCGGAGTTCGCTACATTGCGCCTATGGTGTACGGTGAACCGGAGATCCTGGTCTCGAGACGTCCGATGAGTAGCCTCAAAGACCTGAAAGG
TCTAGAGGACCTTTCCAGGAAGCCAGCAAAGCCTCAAGCGATGTAACGCGGATACCACATGCCACTTGGCCTCTAGGACCAGAGCTCTGCAGGCTACTCATCGGAGTTTCTGGACTTTCC
       490       500       510       520       530       540       550       560       570       580       590       600

        150                           160                           170                           180
 R  I  F  R  A  S  G  M  A  A  E  F  Y  T  A  I  G  A  Q  A  M  M  L  P  A  G  E  L  Y  Q  A  L  Q  L  G  T  I  D  G  L
GCGTATCTTCCGTGCGAGTGGTATGGCAGCGGAGTTCTACACCGCAATTGGCGCACAAGCGATGATGCTTCCAGCAGGTGAGCTCTACCAGGCACTGCAGTTAGGCACCATCGATGGTCT
CGCATAGAAGGCACGCTCACCATACCGTCGCCTCAAGATGTGGCGTTAACCGCGTGTTCGCTACTACGAAGGTCGTCCACTCGAGATGGTCCGTGACGTCAATCCGTGGTAGCTACCAGA
       610       620       630       640       650       660       670       680       690       700       710       720

        190                           200                           210                           220
 E  W  T  D  Y  T  A  N  Y  K  L  G  F  H  E  V  A  K  N  V  L  E  P  T  K  G  V  N  L  H  S  E  A  T  V  H  A  F  L  V
GGAGTGGACCGACTATACCGCGAACTACAAGCTTGGCTTCCACGAAGTGGCGAAGAACGTGCTGGAACCGACGAAAGGTGTGAACCTCCATTCGGAAGCTACCGTTCATGCGTTCCTGGT
CCTCACCTGGCTGATATGGCGCTTGATGTTCGAACCGAAGGTGCTTCACCGCTTCTTGCACGACCTTGGCTGCTTTCCACACTTGGAGGTAAGCCTTCGATGGCAAGTACGCAAGGACCA
       730       740       750       760       770       780       790       800       810       820       830       840

        230                           240                           250                           260
 V  N  P  K  V  W  E  K  L  P  K  E  H  Q  K  A  I  Q  E  A  A  D  E  A  Y  K  W  G  A  D  H  L  A  K  L  N  K  T  Y  K
TGTGAACCCGAAAGTCTGGGAGAAACTGCCGAAGGAACACCAGAAAGCGATCCAGGAAGCGGCGGACGAAGCGTACAAATGGGGTGCGGATCACCTTGCGAAACTGAACAAAACCTACAA
ACACTTGGGCTTTCAGACCCTCTTTGACGGCTTCCTTGTGGTCTTTCGCTAGGTCCTTCGCCGCCTGCTTCGCATGTTTACCCCACGCCTAGTGGAACGCTTTGACTTGTTTTGGATGTT
       850       860       870       880       890       900       910       920       930       940       950       960
```

```
              270                      280                      290                      300
 D  K  W  I  K  A  G  A  K  V  T  Q  L  P  K  E  D  Q  D  K  V  I  E  V  S  A  K  I  L  S  G  Y  S  A  K  S  P  D  A  K
GGACAAATGGATCAAAGCGGGTGCGAAGGTGACCCAACTGCCGAAAGAAGACCAGGACAAAGTGATCGAAGTGTCGGCAAAGATCCTGTCTGGCTATAGCGCGAAGAGTCCGGATGCGAA
CCTGTTTACCTAGTTTCGCCCACGCTTCCACTGGGTTGACGGCTTTCTTCTGGTCCTGTTTCACTAGCTTCACAGCCGTTTCTAGGACAGACCGATATCGCGCTTCTCAGGCCTACGCTT
       970       980       990      1000      1010      1020      1030      1040      1050      1060      1070      1080

              310                      320                      330                      340
 E  Y  A  R  R  L  V  E  L  W  K  K  L  G  Y  T  K  W  S  D  A  L  A  K  Q  I  K  G  G  S  H  H  H  H  H  H  *  *  *
AGAGTACGCGCGTCGTCTAGTGGAGCTGTGGAAGAAACTGGGCTACACCAAATGGTCTGATGCATTAGCAAAACAGATTAAAGGCGGCAGCCATCATCATCATCATCATTAATAATGAAA
TCTCATGCGCGCAGCAGATCACCTCGACACCTTCTTTGACCCGATGTGGTTTACCAGACTACGTAATCGTTTTGTCTAATTTCCGCCGTCGGTAGTAGTAGTAGTAGTAATTATTACTTT
      1090      1100      1110      1120      1130      1140      1150      1160      1170      1180      1190      1200


GGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCC
CCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGG
      1210      1220      1230      1240      1250      1260      1270      1280      1290      1300      1310      1320


TCTAAACGGGTCTTGAGGGGTTTTTTGCTGAAAGGAGGAACTATATCCGGAGCGACTCCCACGGCACGTTGGCAAGCTCG
AGATTTGCCCAGAACTCCCCAAAAAACGACTTTCCTCCTTGATATAGGCCTCGCTGAGGGTGCCGTGCAACCGTTCGAGC
      1330      1340      1350      1360      1370      1380      1390      1400
```

FIG. 22 (Continued)

FIG. 23 - Exemplary Expression Construct for msLacBP6.10C

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                  10                            20
                                                    M  A  T  T  W  K  I  Q  S  C  W  D  A  G  T  V  G  Y  D  L  F  K  E  W
GGTTTCCCTCTAGAAATAATTTTGTTTAACTTTAAGAAGGAGATATACCATGGCAACAACTTGGAAAATTCAAAGTTGTTGGGATGCAGGGACGGTGGGCTATGACCTCTTCAAGGAGTG
CCAAAGGGAGATCTTTATTAAAACAAATTGAAATTCTTCCTCTATATGGTACCGTTGTTGAACCTTTTAAGTTTCAACAACCCTACGTCCCTGCCACCCGATACTGGAGAAGTTCCTCAC
       130       140       150       160       170       180       190       200       210       220       230       240

             30                            40                            50                            60
 S  D  G  M  E  E  K  T  G  G  E  L  K  F  T  A  F  P  A  K  A  V  A  A  D  N  N  G  L  F  D  A  V  R  N  G  V  L  Q  G
GAGCGACGGTATGGAAGAAAAGACGGGCGGTGAACTCAAATTCACGGCGTTCCCAGCCAAAGCCGTCGCCGCAGATAATAATGGTCTTTTTGATGCAGTACGGAATGGCGTCTTGCAAGG
CTCGCTGCCATACCTTCTTTTCTGCCCGCCACTTGAGTTTAAGTGCCGCAAGGGTCGGTTTCGGCAGCGGCGTCTATTATTACCAGAAAAACTACGTCATGCCTTACCGCAGAACGTTCC
       250       260       270       280       290       300       310       320       330       340       350       360

             70                            80                            90                           100
 M  N  P  F  T  L  Y  W  S  G  K  I  P  A  S  V  F  L  S  S  Y  P  A  G  P  D  Q  P  H  Q  W  D  T  M  F  Y  S  L  G  M
TATGAATCCTTTCACCCTCTACTGGTCAGGTAAGATTCCGGCCTCCGTATTTCTCTCGTCGTACCCAGCCGGTCCAGATCAACCACATCAATGGGATACAATGTTCTACAGCCTTGGTAT
ATACTTAGGAAAGTGGGAGATGACCAGTCCATTCTAAGGCCGGAGGCATAAAGAGAGCAGCATGGGTCGGCCAGGTCTAGTTGGTGTAGTTACCCTATGTTACAAGATGTCGGAACCATA
       370       380       390       400       410       420       430       440       450       460       470       480

            110                           120                           130                           140
 L  E  K  T  R  E  I  Y  K  K  F  G  L  F  Y  V  G  P  I  Q  H  D  A  N  I  I  H  S  K  Q  P  I  N  S  L  D  D  L  K  G
GTTAGAAAAAAACACGTGAAATTTACAAAAAGTTCGGCCTCTTCTACGTCGGCCCAATTCAGCACGACGCAAACATTATCCACAGTAAACAGCCGATTAATTCCCTGGACGACCTTAAGGG
CAATCTTTTTTTGTGCACTTTAAATGTTTTTCAAGCCGGAGAAGATGCAGCCGGGTTAAGTCGTGCTGCGTTTGTAATAGGTGTCATTTGTCGGCTAATTAAGGGACCTGCTGGAATTCCC
       490       500       510       520       530       540       550       560       570       580       590       600

            150                           160                           170                           180
 L  K  M  R  L  P  G  G  M  V  A  E  V  F  A  K  F  G  V  A  A  V  S  L  P  G  S  D  I  F  P  A  L  E  K  G  T  I  D  A
TCTCAAAATGCGCTTACCTGGCGGGATGGTAGCGGAAGTCTTTGCAAAGTTTGGCGTCGCAGCGGTCAGTCTCCCAGGCAGCGACATCTTTCCAGCCTTAGAAAAAGGCACAATCGACGC
AGAGTTTTACGCGAATGGACCGCCCTACCATCGCCTTCAGAAACGTTTCAAACCGCAGCGTCGCCAGTCAGAGGGTCCGTCGCTGTAGAAAGGTCGGAATCTTTTTCCGTGTTAGCTGCG
       610       620       630       640       650       660       670       680       690       700       710       720

            190                           200                           210                           220
 A  D  Y  V  G  P  A  V  N  W  E  L  G  F  S  Q  V  T  K  Y  I  L  M  G  P  P  G  I  M  S  V  Y  Q  P  V  D  L  M  D  L
TGCTGATTACGTGGGTCCGGCTGTAAACTGGGAGCTCGGCTTCAGCCAAGTAACAAAGTACATCTTAATGGGTCCACCAGGCATCATGTCAGTCTACCAACCGGTCGACCTTATGGACCT
ACGACTAATGCACCCAGGCCGACATTTGACCCTCGAGCCGAAGTCGGTTCATTGTTTCATGTAGAATTACCCAGGTGGTCCGTAGTACAGTCAGATGGTTGGCCAGCTGGAATACCTGGA
       730       740       750       760       770       780       790       800       810       820       830       840

            230                           240                           250                           260
 T  V  N  L  R  A  W  N  A  L  D  P  K  L  Q  Q  I  V  E  D  E  V  R  I  Y  S  Q  K  H  Y  L  A  I  Q  K  R  N  I  E  A
CACTGTCAATCTGCGGGCCTGGAACGCATTAGATCCAAAGTTACAGCAAATCGTTGAAGATGAAGTACGCATCTACTCTCAGAAGCATTACCTCGCAATTCAGAAACGGAATATTGAAGC
GTGACAGTTAGACGCCCGGACCTTGCGTAATCTAGGTTTCAATGTCGTTTAGCAACTTCTACTTCATGCGTAGATGAGAGTCTTCGTAATGGAGCGTTAAGTCTTTGCCTTATAACTTCG
       850       860       870       880       890       900       910       920       930       940       950       960
```

```
              270                                     280                                     290                                     300
 M  K  K  F  E  A  A  G  T  T  V  T  R  L  S  Q  E  D  L  Q  E  F  R  R  A  A  I  P  I  W  Y  S  W  A  N  K  D  E  D  A
TATGAAGAAGTTCGAGGCCGCTGGTACAACCGTAACCCGTCTGTCACAAGAGGACCTCCAGGAGTTTCGTCGTGCAGCTATCCCAATTTGGTATTCATGGCAAACAAAGATGAAGACGC
ATACTTCTTCAAGCTCCGGCGACCATGTTGGCATTGGGCAGACAGTGTTCTCCTGGAGGTCCTCAAAGCAGCACGTCGATAGGGTTAAACCATAAGTACCCGTTTGTTTCTACTTCTGCG
        970       980       990      1000      1010      1020      1030      1040      1050      1060      1070      1080

              310                                     320                                     330                                     340
 R  E  I  F  D  M  Q  L  E  Y  M  M  N  D  T  V  G  Y  I  T  E  D  D  I  K  G  M  N  G  G  S  H  H  H  H  H  H  *  *
ACGGGAGATTTTCGACATGCAATTAGAGTACATGATGAACGACACTGTAGGTTACATCACTGAAGATGACATTAAGGGCATGAATGGCGGTTCACATCATCATCATCATCATTAATGAAA
TGCCCTCTAAAAGCTGTACGTTAATCTCATGTACTACTTGCTGTGACATCCAATGTAGTGACTTCTACTGTAATTCCCGTACTTACCGCCAAGTGTAGTAGTAGTAGTAGTAATTACTTT
       1090      1100      1110      1120      1130      1140      1150      1160      1170      1180      1190      1200

GGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCC
CCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGG
       1210      1220      1230      1240      1250      1260      1270      1280      1290      1300      1310      1320

TCTAAACGGGTCTTGAGGGGTTTTTTGCTGAAAGGAGGAACTATATCCGGAGCGACTCCCACGGCACGTTGGCAAGCTCG
AGATTTGCCCAGAACTCCCCAAAAAACGACTTTCCTCCTTGATATAGGCCTCGCTGAGGGTGCCGTGCAACCGTTCGAGC
       1330      1340      1350      1360      1370      1380      1390      1400
```

FIG. 23 (Continued)

FIG. 24 - Exemplary Expression Construct for msLacBP6.12C

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                       10                            20
                                                  M  A  T  T  W  K  I  Q  S  V  W  C  A  G  T  V  G  Y  D  L  F  K  E  W
GGTTTCCCTCTAGAAATAATTTTGTTTAACTTTAAGAAGGAGATATACCATGGCAACAACTTGGAAAATTCAAAGTGTATGGTGTGCAGGGACGGTGGGCTATGACCTCTTCAAGGAGTG
CCAAAGGGAGATCTTTATTAAAACAAATTGAAATTCTTCCTCTATATGGTACCGTTGTTGAACCTTTTAAGTTTCACATACCACACGTCCCTGCCACCCGATACTGGAGAAGTTCCTCAC
       130       140       150       160       170       180       190       200       210       220       230       240

          30                            40                            50                            60
 S  D  G  M  E  E  K  T  G  G  E  L  K  F  T  A  F  P  A  K  A  V  A  A  D  N  N  G  L  F  D  A  V  R  N  G  V  L  Q  G
GAGCGACGGTATGGAAGAAAAGACGGGCGGTGAACTCAAATTCACGGCGTTCCCAGCCAAAGCCGTCGCCGCAGATAATAATGGTCTTTTTGATGCAGTACGGAATGGCGTCTTGCAAGG
CTCGCTGCCATACCTTCTTTTCTGCCCGCCACTTGAGTTTAAGTGCCGCAAGGGTCGGTTTCGGCAGCGGCGTCTATTATTACCAGAAAAACTACGTCATGCCTTACCGCAGAACGTTCC
       250       260       270       280       290       300       310       320       330       340       350       360

          70                            80                            90                           100
 M  N  P  F  T  L  Y  W  S  G  K  I  P  A  S  V  F  L  S  S  Y  P  A  G  P  D  Q  P  H  Q  W  D  T  M  F  Y  S  L  G  M
TATGAATCCTTTCACCCTCTACTGGTCAGGTAAGATTCCGGCCTCCGTATTTCTCTCGTCGTACCCAGCCGGTCCAGATCAACCACATCAATGGGATACAATGTTCTACAGCCTTGGTAT
ATACTTAGGAAAGTGGGAGATGACCAGTCCATTCTAAGGCCGGAGGCATAAAGAGAGCAGCATGGGTCGGCCAGGTCTAGTTGGTGTAGTTACCCTATGTTACAAGATGTCGGAACCATA
       370       380       390       400       410       420       430       440       450       460       470       480

         110                           120                           130                           140
 L  E  K  T  R  E  I  Y  K  K  F  G  L  F  Y  V  G  P  I  Q  H  D  A  N  I  I  H  S  K  Q  P  I  N  S  L  D  D  L  K  G
GTTAGAAAAAACACGTGAAATTTACAAAAAGTTCGGCCTCTTCTACGTCGGCCCAATTCAGCACGACGCAAACATTATCCACAGTAAACAGCCGATTAATTCCCTGGACGACCTTAAGGG
CAATCTTTTTTGTGCACTTTAAATGTTTTTCAAGCCGGAGAAGATGCAGCCGGGTTAAGTCGTGCTGCGTTTGTAATAGGTGTCATTTGTCGGCTAATTAAGGGACCTGCTGGAATTCCC
       490       500       510       520       530       540       550       560       570       580       590       600

         150                           160                           170                           180
 L  K  M  R  L  P  G  G  M  V  A  E  V  F  A  K  F  G  V  A  A  V  S  L  P  G  S  D  I  F  P  A  L  E  K  G  T  I  D  A
TCTCAAAATGCGCTTACCTGGCGGGATGGTAGCGGAAGTCTTTGCAAAGTTTGGCGTCGCAGCGGTCAGTCTCCCAGGCAGCGACATCTTTCCAGCCTTAGAAAAAGGCACAATCGACGC
AGAGTTTTACGCGAATGGACCGCCCTACCATCGCCTTCAGAAACGTTTCAAACCGCAGCGTCGCCAGTCAGAGGGTCCGTCGCTGTAGAAAGGTCGGAATCTTTTTCCGTGTTAGCTGCG
       610       620       630       640       650       660       670       680       690       700       710       720

         190                           200                           210                           220
 A  D  Y  V  G  P  A  V  N  W  E  L  G  F  S  Q  V  T  K  Y  I  L  M  G  P  P  G  I  M  S  V  Y  Q  P  V  D  L  M  D  L
TGCTGATTACGTGGGTCCGGCTGTAAACTGGGAGCTCGGCTTCAGCCAAGTAACAAAGTACATCTTAATGGGTCCACCAGGCATCATGTCAGTCTACCAACCGGTCGACCTTATGGACCT
ACGACTAATGCACCCAGGCCGACATTTGACCCTCGAGCCGAAGTCGGTTCATTGTTTCATGTAGAATTACCCAGGTGGTCCGTAGTACAGTCAGATGGTTGGCCAGCTGGAATACCTGGA
       730       740       750       760       770       780       790       800       810       820       830       840

         230                           240                           250                           260
 T  V  N  L  R  A  W  N  A  L  D  P  K  L  Q  Q  I  V  E  D  E  V  R  I  Y  S  Q  K  H  Y  L  A  I  Q  K  R  N  I  E  A
CACTGTCAATCTGCGGGCCTGGAACGCATTAGATCCAAAGTTACAGCAAATCGTTGAAGATGAAGTACGCATCTACTCTCAGAAGCATTACCTCGCAATTCAGAAACGGAATATTGAAGC
GTGACAGTTAGACGCCCGGACCTTGCGTAATCTAGGTTTCAATGTCGTTTAGCAACTTCTACTTCATGCGTAGATGAGAGTCTTCGTAATGGAGCGTTAAGTCTTTGCCTTATAACTTCG
       850       860       870       880       890       900       910       920       930       940       950       960
```

```
                270                                     280                                     290                                     300
 M   K   K   F   E   A   A   G   T   T   V   T   R   L   S   Q   E   D   L   Q   E   F   R   R   A   A   I   P   I   W   Y   S   W   A   N   K   D   E   D   A
TATGAAGAAGTTCGAGGCCGCTGGTACAACCGTAACCCGTCTGTCACAAGAGGACCTCCAGGAGTTTCGTCGTGCAGCTATCCCAATTTGGTATTCATGGGCAAACAAAGATGAAGACGC
ATACTTCTTCAAGCTCCGGCGACCATGTTGGCATTGGGCAGACAGTGTTCTCCTGGAGGTCCTCAAAGCAGCACGTCGATAGGGTTAAACCATAAGTACCCGTTTGTTTCTACTTCTGCG
        970          980          990         1000         1010         1020         1030         1040         1050         1060         1070         1080

                310                                     320                                     330                                     340
 R   E   I   F   D   M   Q   L   E   Y   M   M   N   D   T   V   G   Y   I   T   E   D   D   I   K   G   M   N   G   G   S   H   H   H   H   H   H   *   *
ACGGGAGATTTTCGACATGCAATTAGAGTACATGATGAACGACACTGTAGGTTACATCACTGAAGATGACATTAAGGGCATGAATGGCGGTTCACATCATCATCATCATCATTAATGAAA
TGCCCTCTAAAAGCTGTACGTTAATCTCATGTACTACTTGCTGTGACATCCAATGTAGTGACTTCTACTGTAATTCCCGTACTTACCGCCAAGTGTAGTAGTAGTAGTAGTAATTACTTT
       1090         1100         1110         1120         1130         1140         1150         1160         1170         1180         1190         1200

GGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCC
CCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGG
       1210         1220         1230         1240         1250         1260         1270         1280         1290         1300         1310         1320

TCTAAACGGGTCTTGAGGGGTTTTTTGCTGAAAGGAGGAACTATATCCGGAGCGACTCCCACGGCACGTTGGCAAGCTCG
AGATTTGCCCAGAACTCCCCAAAAAACGACTTTCCTCCTTGATATAGGCCTCGCTGAGGGTGCCGTGCAACCGTTCGAGC
       1330         1340         1350         1360         1370         1380         1390         1400
```

FIG. 24 (Continued)

FIG. 25 - Exemplary Expression Construct for msLacBP6.43C

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                       10                            20
                                                            M  A  T  T  W  K  I  Q  S  V  W  D  A  G  T  V  G  Y  D  L  F  K  E  W
GGTTTCCCTCTAGAAATAATTTTGTTTAACTTTAAGAAGGAGATATACCATGGCAACAACTTGGAAAATTCAAAGTGTATGGGATGCAGGGACGGTGGGCTATGACCTCTTCAAGGAGTG
CCAAAGGGAGATCTTTATTAAAACAAATTGAAATTCTTCCTCTATATGGTACCGTTGTTGAACCTTTTAAGTTTCACATACCCTACGTCCCTGCCACCCGATACTGGAGAAGTTCCTCAC
       130       140       150       160       170       180       190       200       210       220       230       240

             30                            40                            50                            60
 S  D  G  M  E  E  K  T  G  G  E  L  K  F  T  A  F  P  C  K  A  V  A  A  D  N  N  G  L  F  D  A  V  R  N  G  V  L  Q  G
GAGCGACGGTATGGAAGAAAAGACGGGCGGTGAACTCAAATTCACGGCGTTCCCATGTAAAGCCGTCGCCGCAGATAATAATGGTCTTTTTGATGCAGTACGGAATGGCGTCTTGCAAGG
CTCGCTGCCATACCTTCTTTTCTGCCCGCCACTTGAGTTTAAGTGCCGCAAGGGTACATTTCGGCAGCGGCGTCTATTATTACCAGAAAAACTACGTCATGCCTTACCGCAGAACGTTCC
       250       260       270       280       290       300       310       320       330       340       350       360

             70                            80                            90                           100
 M  N  P  F  T  L  Y  W  S  G  K  I  P  A  S  V  F  L  S  S  Y  P  A  G  P  D  Q  P  H  Q  W  D  T  M  F  Y  S  L  G  M
TATGAATCCTTTCACCCTCTACTGGTCAGGTAAGATTCCGGCCTCCGTATTTCTCTCGTCGTACCCAGCCGGTCCAGATCAACCACATCAATGGGATACAATGTTCTACAGCCTTGGTAT
ATACTTAGGAAAGTGGGAGATGACCAGTCCATTCTAAGGCCGGAGGCATAAAGAGAGCAGCATGGGTCGGCCAGGTCTAGTTGGTGTAGTTACCCTATGTTACAAGATGTCGGAACCATA
       370       380       390       400       410       420       430       440       450       460       470       480

            110                           120                           130                           140
 L  E  K  T  R  E  I  Y  K  K  F  G  L  F  Y  V  G  P  I  Q  H  D  A  N  I  I  H  S  K  Q  P  I  N  S  L  D  D  L  K  G
GTTAGAAAAAACACGTGAAATTTACAAAAAGTTCGGCCTCTTCTACGTCGGCCCAATTCAGCACGACGCAAACATTATCCACAGTAAACAGCCGATTAATTCCCTGGACGACCTTAAGGG
CAATCTTTTTTGTGCACTTTAAATGTTTTTCAAGCCGGAGAAGATGCAGCCGGGTTAAGTCGTGCTGCGTTTGTAATAGGTGTCATTTGTCGGCTAATTAAGGGACCTGCTGGAATTCCC
       490       500       510       520       530       540       550       560       570       580       590       600

            150                           160                           170                           180
 L  K  M  R  L  P  G  G  M  V  A  E  V  F  A  K  F  G  V  A  A  V  S  L  P  G  S  D  I  F  P  A  L  E  K  G  T  I  D  A
TCTCAAAATGCGCTTACCTGGCGGGATGGTAGCGGAAGTCTTTGCAAAGTTTGGCGTCGCAGCGGTCAGTCTCCCAGGCAGCGACATCTTTCCAGCCTTAGAAAAAGGCACAATCGACGC
AGAGTTTTACGCGAATGGACCGCCCTACCATCGCCTTCAGAAACGTTTCAAACCGCAGCGTCGCCAGTCAGAGGGTCCGTCGCTGTAGAAAGGTCGGAATCTTTTTCCGTGTTAGCTGCG
       610       620       630       640       650       660       670       680       690       700       710       720

            190                           200                           210                           220
 A  D  Y  V  G  P  A  V  N  W  E  L  G  F  S  Q  V  T  K  Y  I  L  M  G  P  P  G  I  M  S  V  Y  Q  P  V  D  L  M  D  L
TGCTGATTACGTGGGTCCGGCTGTAAACTGGGAGCTCGGCTTCAGCCAAGTAACAAAGTACATCTTAATGGGTCCACCAGGCATCATGTCAGTCTACCAACCGGTCGACCTTATGGACCT
ACGACTAATGCACCCAGGCCGACATTTGACCCTCGAGCCGAAGTCGGTTCATTGTTTCATGTAGAATTACCCAGGTGGTCCGTAGTACAGTCAGATGGTTGGCCAGCTGGAATACCTGGA
       730       740       750       760       770       780       790       800       810       820       830       840

            230                           240                           250                           260
 T  V  N  L  R  A  W  N  A  L  D  P  K  L  Q  Q  I  V  E  D  E  V  R  I  Y  S  Q  K  H  Y  L  A  I  Q  K  R  N  I  E  A
CACTGTCAATCTGCGGGCCTGGAACGCATTAGATCCAAAGTTACAGCAAATCGTTGAAGATGAAGTACGCATCTACTCTCAGAAGCATTACCTCGCAATTCAGAAACGGAATATTGAAGC
GTGACAGTTAGACGCCCGGACCTTGCGTAATCTAGGTTTCAATGTCGTTTAGCAACTTCTACTTCATGCGTAGATGAGAGTCTTCGTAATGGAGCGTTAAGTCTTTGCCTTATAACTTCG
       850       860       870       880       890       900       910       920       930       940       950       960
```

```
            270                                280                                290                                300
M  K  K  F  E  A  A  G  T  T  V  T  R  L  S  Q  E  D  L  Q  E  F  R  R  A  A  I  P  I  W  Y  S  W  A  N  K  D  E  D  A
TATGAAGAAGTTCGAGGCCGCTGGTACAACCGTAACCCGTCTGTCACAAGAGGACCTCCAGGAGTTTCGTCGTGCAGCTATCCCAATTTGGTATTCATGGGCAAACAAAGATGAAGACGC
ATACTTCTTCAAGCTCCGGCGACCATGTTGGCATTGGGCAGACAGTGTTCTCCTGGAGGTCCTCAAAGCAGCACGTCGATAGGGTTAAACCATAAGTACCCGTTTGTTTCTACTTCTGCG
       970       980       990      1000      1010      1020      1030      1040      1050      1060      1070      1080

            310                                320                                330                                340
R  E  I  F  D  M  Q  L  E  Y  M  M  N  D  T  V  G  Y  I  T  E  D  D  I  K  G  M  N  G  G  S  H  H  H  H  H  H  *  *
ACGGGAGATTTTCGACATGCAATTAGAGTACATGATGAACGACACTGTAGGTTACATCACTGAAGATGACATTAAGGGCATGAATGGCGGTTCACATCATCATCATCATCATTAATGAAA
TGCCCTCTAAAAGCTGTACGTTAATCTCATGTACTACTTGCTGTGACATCCAATGTAGTGACTTCTACTGTAATTCCCGTACTTACCGCCAAGTGTAGTAGTAGTAGTAGTAATTACTTT
      1090      1100      1110      1120      1130      1140      1150      1160      1170      1180      1190      1200

GGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCC
CCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGG
      1210      1220      1230      1240      1250      1260      1270      1280      1290      1300      1310      1320

TCTAAACGGGTCTTGAGGGGTTTTTTGCTGAAAGGAGGAACTATATCCGGAGCGACTCCCACGGCACGTTGGCAAGCTCG
AGATTTGCCCAGAACTCCCCAAAAAACGACTTTCCTCCTTGATATAGGCCTCGCTGAGGGTGCCGTGCAACCGTTCGAGC
      1330      1340      1350      1360      1370      1380      1390      1400
```

FIG. 25 (Continued)

FIG. 26 - Exemplary Expression Construct for msLacBP6.49C

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                             10                            20
                                                  M  A  T  T  W  K  I  Q  S  V  W  D  A  G  T  V  G  Y  D  L  F  K  E  W
GGTTTCCCTCTAGAAATAATTTTGTTTAACTTTAAGAAGGAGATATACCATGGCAACAACTTGGAAAATTCAAAGTGTATGGGATGCAGGGACGGTGGGCTATGACCTCTTCAAGGAGTG
CCAAAGGGAGATCTTTATTAAAACAAATTGAAATTCTTCCTCTATATGGTACCGTTGTTGAACCTTTTAAGTTTCACATACCCTACGTCCCTGCCACCCGATACTGGAGAAGTTCCTCAC
       130       140       150       160       170       180       190       200       210       220       230       240

          30                            40                            50                            60
 S  D  G  M  E  E  K  T  G  G  E  L  K  F  T  A  F  P  A  K  A  V  A  A  C  N  N  G  L  F  D  A  V  R  N  G  V  L  Q  G
GAGCGACGGTATGGAAGAAAAGACGGGCGGTGAACTCAAATTCACGGCGTTCCCAGCCAAAGCCGTCGCCGCATGTAATAATGGTCTTTTTGATGCAGTACGGAATGGCGTCTTGCAAGG
CTCGCTGCCATACCTTCTTTTCTGCCCGCCACTTGAGTTTAAGTGCCGCAAGGGTCGGTTTCGGCAGCGGCGTACATTATTACCAGAAAAACTACGTCATGCCTTACCGCAGAACGTTCC
       250       260       270       280       290       300       310       320       330       340       350       360

          70                            80                            90                           100
 M  N  P  F  T  L  Y  W  S  G  K  I  P  A  S  V  F  L  S  S  Y  P  A  G  P  D  Q  P  H  Q  W  D  T  M  F  Y  S  L  G  M
TATGAATCCTTTCACCCTCTACTGGTCAGGTAAGATTCCGGCCTCCGTATTTCTCTCGTCGTACCCAGCCGGTCCAGATCAACCACATCAATGGGATACAATGTTCTACAGCCTTGGTAT
ATACTTAGGAAAGTGGGAGATGACCAGTCCATTCTAAGGCCGGAGGCATAAAGAGAGCAGCATGGGTCGGCCAGGTCTAGTTGGTGTAGTTACCCTATGTTACAAGATGTCGGAACCATA
       370       380       390       400       410       420       430       440       450       460       470       480

         110                           120                           130                           140
 L  E  K  T  R  E  I  Y  K  K  F  G  L  F  Y  V  G  P  I  Q  H  D  A  N  I  I  H  S  K  Q  P  I  N  S  L  D  D  L  K  G
GTTAGAAAAAACACGTGAAATTTACAAAAAGTTCGGCCTCTTCTACGTCGGCCCAATTCAGCACGACGCAAACATTATCCACAGTAAACAGCCGATTAATTCCCTGGACGACCTTAAGGG
CAATCTTTTTTGTGCACTTTAAATGTTTTTCAAGCCGGAGAAGATGCAGCCGGGTTAAGTCGTGCTGCGTTTGTAATAGGTGTCATTTGTCGGCTAATTAAGGGACCTGCTGGAATTCCC
       490       500       510       520       530       540       550       560       570       580       590       600

         150                           160                           170                           180
 L  K  M  R  L  P  G  G  M  V  A  E  V  F  A  K  F  G  V  A  A  V  S  L  P  G  S  D  I  F  P  A  L  E  K  G  T  I  D  A
TCTCAAAATGCGCTTACCTGGCGGGATGGTAGCGGAAGTCTTTGCAAAGTTTGGCGTCGCAGCGGTCAGTCTCCCAGGCAGCGACATCTTTCCAGCCTTAGAAAAAGGCACAATCGACGC
AGAGTTTTACGCGAATGGACCGCCCTACCATCGCCTTCAGAAACGTTTCAAACCGCAGCGTCGCCAGTCAGAGGGTCCGTCGCTGTAGAAAGGTCGGAATCTTTTTCCGTGTTAGCTGCG
       610       620       630       640       650       660       670       680       690       700       710       720

         190                           200                           210                           220
 A  D  Y  V  G  P  A  V  N  W  E  L  G  F  S  Q  V  T  K  Y  I  L  M  G  P  P  G  I  M  S  V  Y  Q  P  V  D  L  M  D  L
TGCTGATTACGTGGGTCCGGCTGTAAACTGGGAGCTCGGCTTCAGCCAAGTAACAAAGTACATCTTAATGGGTCCACCAGGCATCATGTCAGTCTACCAACCGGTCGACCTTATGGACCT
ACGACTAATGCACCCAGGCCGACATTTGACCCTCGAGCCGAAGTCGGTTCATTGTTTCATGTAGAATTACCCAGGTGGTCCGTAGTACAGTCAGATGGTTGGCCAGCTGGAATACCTGGA
       730       740       750       760       770       780       790       800       810       820       830       840

         230                           240                           250                           260
 T  V  N  L  R  A  W  N  A  L  D  P  K  L  Q  Q  I  V  E  D  E  V  R  I  Y  S  Q  K  H  Y  L  A  I  Q  K  R  N  I  E  A
CACTGTCAATCTGCGGGCCTGGAACGCATTAGATCCAAAGTTACAGCAAATCGTTGAAGATGAAGTACGCATCTACTCTCAGAAGCATTACCTCGCAATTCAGAAACGGAATATTGAAGC
GTGACAGTTAGACGCCCGGACCTTGCGTAATCTAGGTTTCAATGTCGTTTAGCAACTTCTACTTCATGCGTAGATGAGAGTCTTCGTAATGGAGCGTTAAGTCTTTGCCTTATAACTTCG
       850       860       870       880       890       900       910       920       930       940       950       960
```

```
                 270                                     280                                     290                                     300
 M   K   K   F   E   A   A   G   T   T   V   T   R   L   S   Q   E   D   L   Q   E   F   R   R   A   A   I   P   I   W   Y   S   W   A   N   K   D   E   D   A
TATGAAGAAGTTCGAGGCCGCTGGTACAACCGTAACCCGTCTGTCACAAGAGGACCTCCAGGAGTTTCGTCGTGCAGCTATCCCAATTTGGTATTCATGGGCAAACAAAGATGAAGACGC
ATACTTCTTCAAGCTCCGGCGACCATGTTGGCATTGGGCAGACAGTGTTCTCCTGGAGGTCCTCAAAGCAGCACGTCGATAGGGTTAAACCATAAGTACCCGTTTGTTTCTACTTCTGCG
       970       980       990      1000      1010      1020      1030      1040      1050      1060      1070      1080

                 310                                     320                                     330                                     340
 R   E   I   F   D   M   Q   L   E   Y   M   M   N   D   T   V   G   Y   I   T   E   D   D   I   K   G   M   N   G   G   S   H   H   H   H   H   H   *   *
ACGGGAGATTTTCGACATGCAATTAGAGTACATGATGAACGACACTGTAGGTTACATCACTGAAGATGACATTAAGGGCATGAATGGCGGTTCACATCATCATCATCATCATTAATGAAA
TGCCCTCTAAAAGCTGTACGTTAATCTCATGTACTACTTGCTGTGACATCCAATGTAGTGACTTCTACTGTAATTCCCGTACTTACCGCCAAGTGTAGTAGTAGTAGTAGTAATTACTTT
      1090      1100      1110      1120      1130      1140      1150      1160      1170      1180      1190      1200

GGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCC
CCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGG
      1210      1220      1230      1240      1250      1260      1270      1280      1290      1300      1310      1320

TCTAAACGGGTCTTGAGGGGTTTTTTGCTGAAAGGAGGAACTATATCCGGAGCGACTCCCACGGCACGTTGGCAAGCTCG
AGATTTGCCCAGAACTCCCCAAAAAACGACTTTCCTCCTTGATATAGGCCTCGCTGAGGGTGCCGTGCAACCGTTCGAGC
      1330      1340      1350      1360      1370      1380      1390      1400
```

FIG. 26 (Continued)

FIG. 27 - Exemplary Expression Construct for msLacBP6.50C

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                               10                            20
                                                    M  A  T  T  W  K  I  Q  S  V  W  D  A  G  T  V  G  Y  D  L  F  K  E  W
GGTTTCCCTCTAGAAATAATTTTGTTTAACTTTAAGAAGGAGATATACCATGGCAACAACTTGGAAAATTCAAAGTGTATGGGATGCAGGGACGGTGGGCTATGACCTCTTCAAGGAGTG
CCAAAGGGAGATCTTTATTAAAACAAATTGAAATTCTTCCTCTATATGGTACCGTTGTTGAACCTTTTAAGTTTCACATACCCTACGTCCCTGCCACCCGATACTGGAGAAGTTCCTCAC
       130       140       150       160       170       180       190       200       210       220       230       240

         30                            40                            50                            60
 S  D  G  M  E  E  K  T  G  G  E  L  K  F  T  A  F  P  A  K  A  V  A  A  D  C  N  G  L  F  D  A  V  R  N  G  V  L  Q  G
GAGCGACGGTATGGAAGAAAAGACGGGCGGTGAACTCAAATTCACGGCGTTCCCAGCCAAAGCCGTCGCCGCAGATTGTAATGGTCTTTTTGATGCAGTACGGAATGGCGTCTTGCAAGG
CTCGCTGCCATACCTTCTTTTCTGCCCGCCACTTGAGTTTAAGTGCCGCAAGGGTCGGTTTCGGCAGCGGCGTCTAACATTACCAGAAAAACTACGTCATGCCTTACCGCAGAACGTTCC
       250       260       270       280       290       300       310       320       330       340       350       360

         70                            80                            90                           100
 M  N  P  F  T  L  Y  W  S  G  K  I  P  A  S  V  F  L  S  S  Y  P  A  G  P  D  Q  P  H  Q  W  D  T  M  F  Y  S  L  G  M
TATGAATCCTTTCACCCTCTACTGGTCAGGTAAGATTCCGGCCTCCGTATTTCTCTCGTCGTACCCAGCCGGTCCAGATCAACCACATCAATGGGATACAATGTTCTACAGCCTTGGTAT
ATACTTAGGAAAGTGGGAGATGACCAGTCCATTCTAAGGCCGGAGGCATAAAGAGAGCAGCATGGGTCGGCCAGGTCTAGTTGGTGTAGTTACCCTATGTTACAAGATGTCGGAACCATA
       370       380       390       400       410       420       430       440       450       460       470       480

        110                           120                           130                           140
 L  E  K  T  R  E  I  Y  K  K  F  G  L  F  Y  V  G  P  I  Q  H  D  A  N  I  I  H  S  K  Q  P  I  N  S  L  D  D  L  K  G
GTTAGAAAAAACACGTGAAATTTACAAAAAGTTCGGCCTCTTCTACGTCGGCCCAATTCAGCACGACGCAAACATTATCCACAGTAAACAGCCGATTAATTCCCTGGACGACCTTAAGGG
CAATCTTTTTTGTGCACTTTAAATGTTTTTCAAGCCGGAGAAGATGCAGCCGGGTTAAGTCGTGCTGCGTTTGTAATAGGTGTCATTTGTCGGCTAATTAAGGGACCTGCTGGAATTCCC
       490       500       510       520       530       540       550       560       570       580       590       600

        150                           160                           170                           180
 L  K  M  R  L  P  G  G  M  V  A  E  V  F  A  K  F  G  V  A  A  V  S  L  P  G  S  D  I  F  P  A  L  E  K  G  T  I  D  A
TCTCAAAATGCGCTTACCTGGCGGGATGGTAGCGGAAGTCTTTGCAAAGTTTGGCGTCGCAGCGGTCAGTCTCCCAGGCAGCGACATCTTTCCAGCCTTAGAAAAAGGCACAATCGACGC
AGAGTTTTACGCGAATGGACCGCCCTACCATCGCCTTCAGAAACGTTTCAAACCGCAGCGTCGCCAGTCAGAGGGTCCGTCGCTGTAGAAAGGTCGGAATCTTTTTCCGTGTTAGCTGCG
       610       620       630       640       650       660       670       680       690       700       710       720

        190                           200                           210                           220
 A  D  Y  V  G  P  A  V  N  W  E  L  G  F  S  Q  V  T  K  Y  I  L  M  G  P  P  G  I  M  S  V  Y  Q  P  V  D  L  M  D  L
TGCTGATTACGTGGGTCCGGCTGTAAACTGGGAGCTCGGCTTCAGCCAAGTAACAAAGTACATCTTAATGGGTCCACCAGGCATCATGTCAGTCTACCAACCGGTCGACCTTATGGACCT
ACGACTAATGCACCCAGGCCGACATTTGACCCTCGAGCCGAAGTCGGTTCATTGTTTCATGTAGAATTACCCAGGTGGTCCGTAGTACAGTCAGATGGTTGGCCAGCTGGAATACCTGGA
       730       740       750       760       770       780       790       800       810       820       830       840

        230                           240                           250                           260
 T  V  N  L  R  A  W  N  A  L  D  P  K  L  Q  Q  I  V  E  D  E  V  R  I  Y  S  Q  K  H  Y  L  A  I  Q  K  R  N  I  E  A
CACTGTCAATCTGCGGGCCTGGAACGCATTAGATCCAAAGTTACAGCAAATCGTTGAAGATGAAGTACGCATCTACTCTCAGAAGCATTACCTCGCAATTCAGAAACGGAATATTGAAGC
GTGACAGTTAGACGCCCGGACCTTGCGTAATCTAGGTTTCAATGTCGTTTAGCAACTTCTACTTCATGCGTAGATGAGAGTCTTCGTAATGGAGCGTTAAGTCTTTGCCTTATAACTTCG
       850       860       870       880       890       900       910       920       930       940       950       960
```

```
                  270                                     280                                     290                                     300
 M   K   K   F   E   A   A   G   T   T   V   T   R   L   S   Q   E   D   L   Q   E   F   R   R   A   A   I   P   I   W   Y   S   W   A   N   K   D   E   D   A
TATGAAGAAGTTCGAGGCCGCTGGTACAACCGTAACCCGTCTGTCACAAGAGGACCTCCAGGAGTTTCGTCGTGCAGCTATCCCAATTTGGTATTCATGGCAAACAAAGATGAAGACGC
ATACTTCTTCAAGCTCCGGCGACCATGTTGGCATTGGGCAGACAGTGTTCTCCTGGAGGTCCTCAAAGCAGCACGTCGATAGGGTTAAACCATAAGTACCCGTTTGTTTCTACTTCTGCG
         970          980          990         1000         1010         1020         1030         1040         1050         1060         1070         1080

                  310                                     320                                     330                                     340
 R   E   I   F   D   M   Q   L   E   Y   M   M   N   D   T   V   G   Y   I   T   E   D   D   I   K   G   M   N   G   G   S   H   H   H   H   H   H   *   *
ACGGGAGATTTTCGACATGCAATTAGAGTACATGATGAACGACACTGTAGGTTACATCACTGAAGATGACATTAAGGGCATGAATGGCGGTTCACATCATCATCATCATCATTAATGAAA
TGCCCTCTAAAAGCTGTACGTTAATCTCATGTACTACTTGCTGTGACATCCAATGTAGTGACTTCTACTGTAATTCCCGTACTTACCGCCAAGTGTAGTAGTAGTAGTAGTAATTACTTT
        1090         1100         1110         1120         1130         1140         1150         1160         1170         1180         1190         1200

GGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCC
CCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGG
        1210         1220         1230         1240         1250         1260         1270         1280         1290         1300         1310         1320

TCTAAACGGGTCTTGAGGGGTTTTTTGCTGAAAGGAGGAACTATATCCGGAGCGACTCCCACGGCACGTTGGCAAGCTCG
AGATTTGCCCAGAACTCCCCAAAAAACGACTTTCCTCCTTGATATAGGCCTCGCTGAGGGTGCCGTGCAACCGTTCGAGC
        1330         1340         1350         1360         1370         1380         1390         1400
```

FIG. 27 (Continued)

FIG. 28 - Exemplary Expression Construct for msLacBP6.68C

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                         10                            20
                                                  M  A  T  T  W  K  I  Q  S  V  W  D  A  G  T  V  G  Y  D  L  F  K  E  W
GGTTTCCCTCTAGAAATAATTTTGTTTAACTTTAAGAAGGAGATATACCATGGCAACAACTTGGAAAATTCAAAGTGTATGGGATGCAGGGACGGTGGGCTATGACCTCTTCAAGGAGTG
CCAAAGGGAGATCTTTATTAAAACAAATTGAAATTCTTCCTCTATATGGTACCGTTGTTGAACCTTTTAAGTTTCACATACCCTACGTCCCTGCCACCCGATACTGGAGAAGTTCCTCAC
       130       140       150       160       170       180       190       200       210       220       230       240

              30                            40                            50                            60
 S  D  G  M  E  E  K  T  G  G  E  L  K  F  T  A  F  P  A  K  A  V  A  A  D  N  N  G  L  F  D  A  V  R  N  G  V  L  Q  G
GAGCGACGGTATGGAAGAAAAGACGGGCGGTGAACTCAAATTCACGGCGTTCCCAGCCAAAGCCGTCGCCGCAGATAATAATGGTCTTTTTGATGCAGTACGGAATGGCGTCTTGCAAGG
CTCGCTGCCATACCTTCTTTTCTGCCCGCCACTTGAGTTTAAGTGCCGCAAGGGTCGGTTTCGGCAGCGGCGTCTATTATTACCAGAAAAACTACGTCATGCCTTACCGCAGAACGTTCC
       250       260       270       280       290       300       310       320       330       340       350       360

              70                            80                            90                           100
 M  N  P  C  T  L  Y  W  S  G  K  I  P  A  S  V  F  L  S  S  Y  P  A  G  P  D  Q  P  H  Q  W  D  T  M  F  Y  S  L  G  M
TATGAATCCTTGTACCCTCTACTGGTCAGGTAAGATTCCGGCCTCCGTATTTCTCTCGTCGTACCCAGCCGGTCCAGATCAACCACATCAATGGGATACAATGTTCTACAGCCTTGGTAT
ATACTTAGGAACATGGGAGATGACCAGTCCATTCTAAGGCCGGAGGCATAAAGAGAGCAGCATGGGTCGGCCAGGTCTAGTTGGTGTAGTTACCCTATGTTACAAGATGTCGGAACCATA
       370       380       390       400       410       420       430       440       450       460       470       480

             110                           120                           130                           140
 L  E  K  T  R  E  I  Y  K  K  F  G  L  F  Y  V  G  P  I  Q  H  D  A  N  I  I  H  S  K  Q  P  I  N  S  L  D  D  L  K  G
GTTAGAAAAAACACGTGAAATTTACAAAAAGTTCGGCCTCTTCTACGTCGGCCCAATTCAGCACGACGCAAACATTATCCACAGTAAACAGCCGATTAATTCCCTGGACGACCTTAAGGG
CAATCTTTTTTGTGCACTTTAAATGTTTTTCAAGCCGGAGAAGATGCAGCCGGGTTAAGTCGTGCTGCGTTTGTAATAGGTGTCATTTGTCGGCTAATTAAGGGACCTGCTGGAATTCCC
       490       500       510       520       530       540       550       560       570       580       590       600

             150                           160                           170                           180
 L  K  M  R  L  P  G  G  M  V  A  E  V  F  A  K  F  G  V  A  A  V  S  L  P  G  S  D  I  F  P  A  L  E  K  G  T  I  D  A
TCTCAAAATGCGCTTACCTGGCGGGATGGTAGCGGAAGTCTTTGCAAAGTTTGGCGTCGCAGCGGTCAGTCTCCCAGGCAGCGACATCTTTCCAGCCTTAGAAAAAGGCACAATCGACGC
AGAGTTTTACGCGAATGGACCGCCCTACCATCGCCTTCAGAAACGTTTCAAACCGCAGCGTCGCCAGTCAGAGGGTCCGTCGCTGTAGAAAGGTCGGAATCTTTTTCCGTGTTAGCTGCG
       610       620       630       640       650       660       670       680       690       700       710       720

             190                           200                           210                           220
 A  D  Y  V  G  P  A  V  N  W  E  L  G  F  S  Q  V  T  K  Y  I  L  M  G  P  P  G  I  M  S  V  Y  Q  P  V  D  L  M  D  L
TGCTGATTACGTGGGTCCGGCTGTAAACTGGGAGCTCGGCTTCAGCCAAGTAACAAAGTACATCTTAATGGGTCCACCAGGCATCATGTCAGTCTACCAACCGGTCGACCTTATGGACCT
ACGACTAATGCACCCAGGCCGACATTTGACCCTCGAGCCGAAGTCGGTTCATTGTTTCATGTAGAATTACCCAGGTGGTCCGTAGTACAGTCAGATGGTTGGCCAGCTGGAATACCTGGA
       730       740       750       760       770       780       790       800       810       820       830       840

             230                           240                           250                           260
 T  V  N  L  R  A  W  N  A  L  D  P  K  L  Q  Q  I  V  E  D  E  V  R  I  Y  S  Q  K  H  Y  L  A  I  Q  K  R  N  I  E  A
CACTGTCAATCTGCGGGCCTGGAACGCATTAGATCCAAAGTTACAGCAAATCGTTGAAGATGAAGTACGCATCTACTCTCAGAAGCATTACCTCGCAATTCAGAAACGGAATATTGAAGC
GTGACAGTTAGACGCCCGGACCTTGCGTAATCTAGGTTTCAATGTCGTTTAGCAACTTCTACTTCATGCGTAGATGAGAGTCTTCGTAATGGAGCGTTAAGTCTTTGCCTTATAACTTCG
       850       860       870       880       890       900       910       920       930       940       950       960
```

```
                  270                                     280                                     290                                     300
 M   K   K   F   E   A   A   G   T   T   V   T   R   L   S   Q   E   D   L   Q   E   F   R   R   A   A   I   P   I   W   Y   S   W   A   N   K   D   E   D   A
TATGAAGAAGTTCGAGGCCGCTGGTACAACCGTAACCCGTCTGTCACAAGAGGACCTCCAGGAGTTTCGTCGTGCAGCTATCCCAATTTGGTATTCATGGGCAAACAAAGATGAAGACGC
ATACTTCTTCAAGCTCCGGCGACCATGTTGGCATTGGGCAGACAGTGTTCTCCTGGAGGTCCTCAAAGCAGCACGTCGATAGGGTTAAACCATAAGTACCCGTTTGTTTCTACTTCTGCG
         970       980       990      1000      1010      1020      1030      1040      1050      1060      1070      1080

                  310                                     320                                     330                                     340
 R   E   I   F   D   M   Q   L   E   Y   M   M   N   D   T   V   G   Y   I   T   E   D   D   I   K   G   M   N   G   G   S   H   H   H   H   H   H   *   *
ACGGGAGATTTTCGACATGCAATTAGAGTACATGATGAACGACACTGTAGGTTACATCACTGAAGATGACATTAAGGGCATGAATGGCGGTTCACATCATCATCATCATCATTAATGAAA
TGCCCTCTAAAAGCTGTACGTTAATCTCATGTACTACTTGCTGTGACATCCAATGTAGTGACTTCTACTGTAATTCCCGTACTTACCGCCAAGTGTAGTAGTAGTAGTAGTAATTACTTT
        1090      1100      1110      1120      1130      1140      1150      1160      1170      1180      1190      1200

GGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCC
CCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGG
        1210      1220      1230      1240      1250      1260      1270      1280      1290      1300      1310      1320

TCTAAACGGGTCTTGAGGGGTTTTTTGCTGAAAGGAGGAACTATATCCGGAGCGACTCCCACGGCACGTTGGCAAGCTCG
AGATTTGCCCAGAACTCCCCAAAAAACGACTTTCCTCCTTGATATAGGCCTCGCTGAGGGTGCCGTGCAACCGTTCGAGC
        1330      1340      1350      1360      1370      1380      1390      1400
```

FIG. 28 (Continued)

FIG. 29 - Exemplary Expression Construct for msLacBP6.169C

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10         20         30         40         50         60         70         80         90        100        110        120

                                                                                          10                            20
                                                  M  A  T  T  W  K  I  Q  S  V  W  D  A  G  T  V  G  Y  D  L  F  K  E  W
GGTTTCCCTCTAGAAATAATTTTGTTTAACTTTAAGAAGGAGATATACCATGGCAACAACTTGGAAAATTCAAAGTGTATGGGATGCAGGGACGGTGGGCTATGACCTCTTCAAGGAGTG
CCAAAGGGAGATCTTTATTAAAACAAATTGAAATTCTTCCTCTATATGGTACCGTTGTTGAACCTTTTAAGTTTCACATACCCTACGTCCCTGCCACCCGATACTGGAGAAGTTCCTCAC
       130        140        150        160        170        180        190        200        210        220        230        240

              30                            40                            50                            60
 S  D  G  M  E  E  K  T  G  G  E  L  K  F  T  A  F  P  A  K  A  V  A  A  D  N  N  G  L  F  D  A  V  R  N  G  V  L  Q  G
GAGCGACGGTATGGAAGAAAAGACGGGCGGTGAACTCAAATTCACGGCGTTCCCAGCCAAAGCCGTCGCCGCAGATAATAATGGTCTTTTTGATGCAGTACGGAATGGCGTCTTGCAAGG
CTCGCTGCCATACCTTCTTTTCTGCCCGCCACTTGAGTTTAAGTGCCGCAAGGGTCGGTTTCGGCAGCGGCGTCTATTATTACCAGAAAAACTACGTCATGCCTTACCGCAGAACGTTCC
       250        260        270        280        290        300        310        320        330        340        350        360

              70                            80                            90                           100
 M  N  P  F  T  L  Y  W  S  G  K  I  P  A  S  V  F  L  S  S  Y  P  A  G  P  D  Q  P  H  Q  W  D  T  M  F  Y  S  L  G  M
TATGAATCCTTTCACCCTCTACTGGTCAGGTAAGATTCCGGCCTCCGTATTTCTCTCGTCGTACCCAGCCGGTCCAGATCAACCACATCAATGGGATACAATGTTCTACAGCCTTGGTAT
ATACTTAGGAAAGTGGGAGATGACCAGTCCATTCTAAGGCCGGAGGCATAAAGAGAGCAGCATGGGTCGGCCAGGTCTAGTTGGTGTAGTTACCCTATGTTACAAGATGTCGGAACCATA
       370        380        390        400        410        420        430        440        450        460        470        480

             110                           120                           130                           140
 L  E  K  T  R  E  I  Y  K  K  F  G  L  F  Y  V  G  P  I  Q  H  D  A  N  I  I  H  S  K  Q  P  I  N  S  L  D  D  L  K  G
GTTAGAAAAAACACGTGAAATTTACAAAAAGTTCGGCCTCTTCTACGTCGGCCCAATTCAGCACGACGCAAACATTATCCACAGTAAACAGCCGATTAATTCCCTGGACGACCTTAAGGG
CAATCTTTTTTGTGCACTTTAAATGTTTTTCAAGCCGGAGAAGATGCAGCCGGGTTAAGTCGTGCTGCGTTTGTAATAGGTGTCATTTGTCGGCTAATTAAGGGACCTGCTGGAATTCCC
       490        500        510        520        530        540        550        560        570        580        590        600

             150                           160                           170                           180
 L  K  M  R  L  P  G  G  M  V  A  E  V  F  A  K  F  G  V  A  A  V  S  L  C  G  S  D  I  F  P  A  L  E  K  G  T  I  D  A
TCTCAAAATGCGCTTACCTGGCGGGATGGTAGCGGAAGTCTTTGCAAAGTTTGGCGTCGCAGCGGTCAGTCTCTGTGGCAGCGACATCTTTCCAGCCTTAGAAAAAGGCACAATCGACGC
AGAGTTTTACGCGAATGGACCGCCCTACCATCGCCTTCAGAAACGTTTCAAACCGCAGCGTCGCCAGTCAGAGACACCGTCGCTGTAGAAAGGTCGGAATCTTTTTCCGTGTTAGCTGCG
       610        620        630        640        650        660        670        680        690        700        710        720

             190                           200                           210                           220
 A  D  Y  V  G  P  A  V  N  W  E  L  G  F  S  Q  V  T  K  Y  I  L  M  G  P  P  G  I  M  S  V  Y  Q  P  V  D  L  M  D  L
TGCTGATTACGTGGGTCCGGCTGTAAACTGGGAGCTCGGCTTCAGCCAAGTAACAAAGTACATCTTAATGGGTCCACCAGGCATCATGTCAGTCTACCAACCGGTCGACCTTATGGACCT
ACGACTAATGCACCCAGGCCGACATTTGACCCTCGAGCCGAAGTCGGTTCATTGTTTCATGTAGAATTACCCAGGTGGTCCGTAGTACAGTCAGATGGTTGGCCAGCTGGAATACCTGGA
       730        740        750        760        770        780        790        800        810        820        830        840

             230                           240                           250                           260
 T  V  N  L  R  A  W  N  A  L  D  P  K  L  Q  Q  I  V  E  D  E  V  R  I  Y  S  Q  K  H  Y  L  A  I  Q  K  R  N  I  E  A
CACTGTCAATCTGCGGGCCTGGAACGCATTAGATCCAAAGTTACAGCAAATCGTTGAAGATGAAGTACGCATCTACTCTCAGAAGCATTACCTCGCAATTCAGAAACGGAATATTGAAGC
GTGACAGTTAGACGCCCGGACCTTGCGTAATCTAGGTTTCAATGTCGTTTAGCAACTTCTACTTCATGCGTAGATGAGAGTCTTCGTAATGGAGCGTTAAGTCTTTGCCTTATAACTTCG
       850        860        870        880        890        900        910        920        930        940        950        960
```

```
                 270                                     280                                     290                                     300
 M   K   K   F   E   A   A   G   T   T   V   T   R   L   S   Q   E   D   L   Q   E   F   R   R   A   A   I   P   I   W   Y   S   W   A   N   K   D   E   D   A
TATGAAGAAGTTCGAGGCCGCTGGTACAACCGTAACCCGTCTGTCACAAGAGGACCTCCAGGAGTTTCGTCGTGCAGCTATCCCAATTTGGTATTCATGGCAAACAAAGATGAAGACGC
ATACTTCTTCAAGCTCCGGCGACCATGTTGGCATTGGGCAGACAGTGTTCTCCTGGAGGTCCTCAAAGCAGCACGTCGATAGGGTTAAACCATAAGTACCCGTTTGTTTCTACTTCTGCG
        970       980       990      1000      1010      1020      1030      1040      1050      1060      1070      1080

                 310                                     320                                     330                                     340
 R   E   I   F   D   M   Q   L   E   Y   M   M   N   D   T   V   G   Y   I   T   E   D   D   I   K   G   M   N   G   G   S   H   H   H   H   H   H   *   *
ACGGGAGATTTTCGACATGCAATTAGAGTACATGATGAACGACACTGTAGGTTACATCACTGAAGATGACATTAAGGGCATGAATGGCGGTTCACATCATCATCATCATCATTAATGAAA
TGCCCTCTAAAAGCTGTACGTTAATCTCATGTACTACTTGCTGTGACATCCAATGTAGTGACTTCTACTGTAATTCCCGTACTTACCGCCAAGTGTAGTAGTAGTAGTAGTAATTACTTT
       1090      1100      1110      1120      1130      1140      1150      1160      1170      1180      1190      1200

GGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCC
CCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGG
       1210      1220      1230      1240      1250      1260      1270      1280      1290      1300      1310      1320

TCTAAACGGGTCTTGAGGGGTTTTTTGCTGAAAGGAGGAACTATATCCGGAGCGACTCCCACGGCACGTTGGCAAGCTCG
AGATTTGCCCAGAACTCCCCAAAAAACGACTTTCCTCCTTGATATAGGCCTCGCTGAGGGTGCCGTGCAACCGTTCGAGC
       1330      1340      1350      1360      1370      1380      1390      1400
```

FIG. 29 (Continued)

FIG. 30 - Exemplary Expression Construct for msLacBP6.170C

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                               10                            20
                                                      M  A  T  T  W  K  I  Q  S  V  W  D  A  G  T  V  G  Y  D  L  F  K  E  W
GGTTTCCCTCTAGAAATAATTTTGTTTAACTTTAAGAAGGAGATATACCATGGCAACAACTTGGAAAATTCAAAGTGTATGGGATGCAGGGACGGTGGGCTATGACCTCTTCAAGGAGTG
CCAAAGGGAGATCTTTATTAAAACAAATTGAAATTCTTCCTCTATATGGTACCGTTGTTGAACCTTTTAAGTTTCACATACCCTACGTCCCTGCCACCCGATACTGGAGAAGTTCCTCAC
       130       140       150       160       170       180       190       200       210       220       230       240

                  30                            40                            50                            60
 S  D  G  M  E  E  K  T  G  G  E  L  K  F  T  A  F  P  A  K  A  V  A  A  D  N  N  G  L  F  D  A  V  R  N  G  V  L  Q  G
GAGCGACGGTATGGAAGAAAAGACGGGCGGTGAACTCAAATTCACGGCGTTCCCAGCCAAAGCCGTCGCCGCAGATAATAATGGTCTTTTTGATGCAGTACGGAATGGCGTCTTGCAAGG
CTCGCTGCCATACCTTCTTTTCTGCCCGCCACTTGAGTTTAAGTGCCGCAAGGGTCGGTTTCGGCAGCGGCGTCTATTATTACCAGAAAAACTACGTCATGCCTTACCGCAGAACGTTCC
       250       260       270       280       290       300       310       320       330       340       350       360

                  70                            80                            90                           100
 M  N  P  F  T  L  Y  W  S  G  K  I  P  A  S  V  F  L  S  S  Y  P  A  G  P  D  Q  P  H  Q  W  D  T  M  F  Y  S  L  G  M
TATGAATCCTTTCACCCTCTACTGGTCAGGTAAGATTCCGGCCTCCGTATTTCTCTCGTCGTACCCAGCCGGTCCAGATCAACCACATCAATGGGATACAATGTTCTACAGCCTTGGTAT
ATACTTAGGAAAGTGGGAGATGACCAGTCCATTCTAAGGCCGGAGGCATAAAGAGAGCAGCATGGGTCGGCCAGGTCTAGTTGGTGTAGTTACCCTATGTTACAAGATGTCGGAACCATA
       370       380       390       400       410       420       430       440       450       460       470       480

                 110                           120                           130                           140
 L  E  K  T  R  E  I  Y  K  K  F  G  L  F  Y  V  G  P  I  Q  H  D  A  N  I  I  H  S  K  Q  P  I  N  S  L  D  D  L  K  G
GTTAGAAAAAACACGTGAAATTTACAAAAAGTTCGGCCTCTTCTACGTCGGCCCAATTCAGCACGACGCAAACATTATCCACAGTAAACAGCCGATTAATTCCCTGGACGACCTTAAGGG
CAATCTTTTTTGTGCACTTTAAATGTTTTTCAAGCCGGAGAAGATGCAGCCGGGTTAAGTCGTGCTGCGTTTGTAATAGGTGTCATTTGTCGGCTAATTAAGGGACCTGCTGGAATTCCC
       490       500       510       520       530       540       550       560       570       580       590       600

                 150                           160                           170                           180
 L  K  M  R  L  P  G  G  M  V  A  E  V  F  A  K  F  G  V  A  A  V  S  L  P  C  S  D  I  F  P  A  L  E  K  G  T  I  D  A
TCTCAAAATGCGCTTACCTGGCGGGATGGTAGCGGAAGTCTTTGCAAAGTTTGGCGTCGCAGCGGTCAGTCTCCCATGTAGCGACATCTTTCCAGCCTTAGAAAAAGGCACAATCGACGC
AGAGTTTTACGCGAATGGACCGCCCTACCATCGCCTTCAGAAACGTTTCAAACCGCAGCGTCGCCAGTCAGAGGGTACATCGCTGTAGAAAGGTCGGAATCTTTTTCCGTGTTAGCTGCG
       610       620       630       640       650       660       670       680       690       700       710       720

                 190                           200                           210                           220
 A  D  Y  V  G  P  A  V  N  W  E  L  G  F  S  Q  V  T  K  Y  I  L  M  G  P  P  G  I  M  S  V  Y  Q  P  V  D  L  M  D  L
TGCTGATTACGTGGGTCCGGCTGTAAACTGGGAGCTCGGCTTCAGCCAAGTAACAAAGTACATCTTAATGGGTCCACCAGGCATCATGTCAGTCTACCAACCGGTCGACCTTATGGACCT
ACGACTAATGCACCCAGGCCGACATTTGACCCTCGAGCCGAAGTCGGTTCATTGTTTCATGTAGAATTACCCAGGTGGTCCGTAGTACAGTCAGATGGTTGGCCAGCTGGAATACCTGGA
       730       740       750       760       770       780       790       800       810       820       830       840

                 230                           240                           250                           260
 T  V  N  L  R  A  W  N  A  L  D  P  K  L  Q  Q  I  V  E  D  E  V  R  I  Y  S  Q  K  H  Y  L  A  I  Q  K  R  N  I  E  A
CACTGTCAATCTGCGGGCCTGGAACGCATTAGATCCAAAGTTACAGCAAATCGTTGAAGATGAAGTACGCATCTACTCTCAGAAGCATTACCTCGCAATTCAGAAACGGAATATTGAAGC
GTGACAGTTAGACGCCCGGACCTTGCGTAATCTAGGTTTCAATGTCGTTTAGCAACTTCTACTTCATGCGTAGATGAGAGTCTTCGTAATGGAGCGTTAAGTCTTTGCCTTATAACTTCG
       850       860       870       880       890       900       910       920       930       940       950       960
```

```
               270                                     280                                     290                                     300
 M   K   K   F   E   A   A   G   T   T   V   T   R   L   S   Q   E   D   L   Q   E   F   R   R   A   A   I   P   I   W   Y   S   W   A   N   K   D   E   D   A
TATGAAGAAGTTCGAGGCCGCTGGTACAACCGTAACCCGTCTGTCACAAGAGGACCTCCAGGAGTTTCGTCGTGCAGCTATCCCAATTTGGTATTCATGGGCAAACAAAGATGAAGACGC
ATACTTCTTCAAGCTCCGGCGACCATGTTGGCATTGGGCAGACAGTGTTCTCCTGGAGGTCCTCAAAGCAGCACGTCGATAGGGTTAAACCATAAGTACCCGTTTGTTTCTACTTCTGCG
         970          980          990         1000         1010         1020         1030         1040         1050         1060         1070         1080

               310                                     320                                     330                                     340
 R   E   I   F   D   M   Q   L   E   Y   M   M   N   D   T   V   G   Y   I   T   E   D   D   I   K   G   M   N   G   G   S   H   H   H   H   H   H   *   *
ACGGGAGATTTTCGACATGCAATTAGAGTACATGATGAACGACACTGTAGGTTACATCACTGAAGATGACATTAAGGGCATGAATGGCGGTTCACATCATCATCATCATCATTAATGAAA
TGCCCTCTAAAAGCTGTACGTTAATCTCATGTACTACTTGCTGTGACATCCAATGTAGTGACTTCTACTGTAATTCCCGTACTTACCGCCAAGTGTAGTAGTAGTAGTAGTAATTACTTT
        1090         1100         1110         1120         1130         1140         1150         1160         1170         1180         1190         1200


GGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCC
CCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGG
        1210         1220         1230         1240         1250         1260         1270         1280         1290         1300         1310         1320


TCTAAACGGGTCTTGAGGGGTTTTTTGCTGAAAGGAGGAACTATATCCGGAGCGACTCCCACGGCACGTTGGCAAGCTCG
AGATTTGCCCAGAACTCCCCAAAAAACGACTTTCCTCCTTGATATAGGCCTCGCTGAGGGTGCCGTGCAACCGTTCGAGC
        1330         1340         1350         1360         1370         1380         1390         1400
```

FIG. 30 (Continued)

FIG. 31 - Exemplary Expression Construct for msLacBP6.171C

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                         10                            20
                                                     M  A  T  T  W  K  I  Q  S  V  W  D  A  G  T  V  G  Y  D  L  F  K  E  W
GGTTTCCCTCTAGAAATAATTTTGTTTAACTTTAAGAAGGAGATATACCATGGCAACAACTTGGAAAATTCAAAGTGTATGGGATGCAGGGACGGTGGGCTATGACCTCTTCAAGGAGTG
CCAAAGGGAGATCTTTATTAAAACAAATTGAAATTCTTCCTCTATATGGTACCGTTGTTGAACCTTTTAAGTTTCACATACCCTACGTCCCTGCCACCCGATACTGGAGAAGTTCCTCAC
       130       140       150       160       170       180       190       200       210       220       230       240

             30                            40                            50                            60
 S  D  G  M  E  E  K  T  G  G  E  L  K  F  T  A  F  P  A  K  A  V  A  A  D  N  N  G  L  F  D  A  V  R  N  G  V  L  Q  G
GAGCGACGGTATGGAAGAAAAAGACGGGCGGTGAACTCAAATTCACGGCGTTCCCAGCCAAAGCCGTCGCCGCAGATAATAATGGTCTTTTTGATGCAGTACGGAATGGCGTCTTGCAAGG
CTCGCTGCCATACCTTCTTTTTCTGCCCGCCACTTGAGTTTAAGTGCCGCAAGGGTCGGTTTCGGCAGCGGCGTCTATTATTACCAGAAAAACTACGTCATGCCTTACCGCAGAACGTTCC
       250       260       270       280       290       300       310       320       330       340       350       360

             70                            80                            90                             100
 M  N  P  F  T  L  Y  W  S  G  K  I  P  A  S  V  F  L  S  S  Y  P  A  G  P  D  Q  P  H  Q  W  D  T  M  F  Y  S  L  G  M
TATGAATCCTTTCACCCTCTACTGGTCAGGTAAGATTCCGGCCTCCGTATTTCTCTCGTCGTACCCAGCCGGTCCAGATCAACCACATCAATGGGATACAATGTTCTACAGCCTTGGTAT
ATACTTAGGAAAGTGGGAGATGACCAGTCCATTCTAAGGCCGGAGGCATAAAGAGAGCAGCATGGGTCGGCCAGGTCTAGTTGGTGTAGTTACCCTATGTTACAAGATGTCGGAACCATA
       370       380       390       400       410       420       430       440       450       460       470       480

            110                           120                           130                           140
 L  E  K  T  R  E  I  Y  K  K  F  G  L  F  Y  V  G  P  I  Q  H  D  A  N  I  I  H  S  K  Q  P  I  N  S  L  D  D  L  K  G
GTTAGAAAAAACACGTGAAATTTACAAAAAGTTCGGCCTCTTCTACGTCGGCCCAATTCAGCACGACGCAAACATTATCCACAGTAAACAGCCGATTAATTCCCTGGACGACCTTAAGGG
CAATCTTTTTTGTGCACTTTAAATGTTTTTCAAGCCGGAGAAGATGCAGCCGGGTTAAGTCGTGCTGCGTTTGTAATAGGTGTCATTTGTCGGCTAATTAAGGGACCTGCTGGAATTCCC
       490       500       510       520       530       540       550       560       570       580       590       600

            150                           160                           170                           180
 L  K  M  R  L  P  G  G  M  V  A  E  V  F  A  K  F  G  V  A  A  V  S  L  P  G  C  D  I  F  P  A  L  E  K  G  T  I  D  A
TCTCAAAATGCGCTTACCTGGCGGGATGGTAGCGGAAGTCTTTGCAAAGTTTGGCGTCGCAGCGGTCAGTCTCCCAGGCTGTGACATCTTTCCAGCCTTAGAAAAAGGCACAATCGACGC
AGAGTTTTACGCGAATGGACCGCCCTACCATCGCCTTCAGAAACGTTTCAAACCGCAGCGTCGCCAGTCAGAGGGTCCGACACTGTAGAAAGGTCGGAATCTTTTTCCGTGTTAGCTGCG
       610       620       630       640       650       660       670       680       690       700       710       720

            190                           200                           210                            220
 A  D  Y  V  G  P  A  V  N  W  E  L  G  F  S  Q  V  T  K  Y  I  L  M  G  P  P  G  I  M  S  V  Y  Q  P  V  D  L  M  D  L
TGCTGATTACGTGGGTCCGGCTGTAAACTGGGAGCTCGGCTTCAGCCAAGTAACAAAGTACATCTTAATGGGTCCACCAGGCATCATGTCAGTCTACCAACCGGTCGACCTTATGGACCT
ACGACTAATGCACCCAGGCCGACATTTGACCCTCGAGCCGAAGTCGGTTCATTGTTTCATGTAGAATTACCCAGGTGGTCCGTAGTACAGTCAGATGGTTGGCCAGCTGGAATACCTGGA
       730       740       750       760       770       780       790       800       810       820       830       840

            230                           240                           250                           260
 T  V  N  L  R  A  W  N  A  L  D  P  K  L  Q  Q  I  V  E  D  E  V  R  I  Y  S  Q  K  H  Y  L  A  I  Q  K  R  N  I  E  A
CACTGTCAATCTGCGGGCCTGGAACGCATTAGATCCAAAGTTACAGCAAATCGTTGAAGATGAAGTACGCATCTACTCTCAGAAGCATTACCTCGCAATTCAGAAACGGAATATTGAAGC
GTGACAGTTAGACGCCCGGACCTTGCGTAATCTAGGTTTCAATGTCGTTTAGCAACTTCTACTTCATGCGTAGATGAGAGTCTTCGTAATGGAGCGTTAAGTCTTTGCCTTATAACTTCG
       850       860       870       880       890       900       910       920       930       940       950       960
```

```
              270                           280                           290                           300
 M  K  K  F  E  A  A  G  T  T  V  T  R  L  S  Q  E  D  L  Q  E  F  R  R  A  A  I  P  I  W  Y  S  W  A  N  K  D  E  D  A
TATGAAGAAGTTCGAGGCCGCTGGTACAACCGTAACCCGTCTGTCACAAGAGGACCTCCAGGAGTTTCGTCGTGCAGCTATCCCAATTTGGTATTCATGGGCAAACAAAGATGAAGACGC
ATACTTCTTCAAGCTCCGGCGACCATGTTGGCATTGGGCAGACAGTGTTCTCCTGGAGGTCCTCAAAGCAGCACGTCGATAGGGTTAAACCATAAGTACCCGTTTGTTTCTACTTCTGCG
       970       980       990      1000      1010      1020      1030      1040      1050      1060      1070      1080

              310                           320                           330                           340
 R  E  I  F  D  M  Q  L  E  Y  M  M  N  D  T  V  G  Y  I  T  E  D  D  I  K  G  M  N  G  G  S  H  H  H  H  H  H  *  *
ACGGGAGATTTTCGACATGCAATTAGAGTACATGATGAACGACACTGTAGGTTACATCACTGAAGATGACATTAAGGGCATGAATGGCGGTTCACATCATCATCATCATCATTAATGAAA
TGCCCTCTAAAAGCTGTACGTTAATCTCATGTACTACTTGCTGTGACATCCAATGTAGTGACTTCTACTGTAATTCCCGTACTTACCGCCAAGTGTAGTAGTAGTAGTAGTAATTACTTT
      1090      1100      1110      1120      1130      1140      1150      1160      1170      1180      1190      1200

GGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCC
CCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGG
      1210      1220      1230      1240      1250      1260      1270      1280      1290      1300      1310      1320

TCTAAACGGGTCTTGAGGGGTTTTTTGCTGAAAGGAGGAACTATATCCGGAGCGACTCCCACGGCACGTTGGCAAGCTCG
AGATTTGCCCAGAACTCCCCAAAAAACGACTTTCCTCCTTGATATAGGCCTCGCTGAGGGTGCCGTGCAACCGTTCGAGC
      1330      1340      1350      1360      1370      1380      1390      1400
```

FIG. 31 (Continued)

FIG. 32 - Exemplary Expression Construct for msLacBP6.187C

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                      10                            20
                                                      M  A  T  T  W  K  I  Q  S  V  W  D  A  G  T  V  G  Y  D  L  F  K  E  W
GGTTTCCCTCTAGAAATAATTTTGTTTAACTTTAAGAAGGAGATATACCATGGCAACAACTTGGAAAATTCAAAGTGTATGGGATGCAGGGACGGTGGGCTATGACCTCTTCAAGGAGTG
CCAAAGGGAGATCTTTATTAAAACAAATTGAAATTCTTCCTCTATATGGTACCGTTGTTGAACCTTTTAAGTTTCACATACCCTACGTCCCTGCCACCCGATACTGGAGAAGTTCCTCAC
       130       140       150       160       170       180       190       200       210       220       230       240

          30                            40                            50                            60
 S  D  G  M  E  E  K  T  G  G  E  L  K  F  T  A  F  P  A  K  A  V  A  A  D  N  N  G  L  F  D  A  V  R  N  G  V  L  Q  G
GAGCGACGGTATGGAAGAAAAGACGGGCGGTGAACTCAAATTCACGGCGTTCCCAGCCAAAGCCGTCGCCGCAGATAATAATGGTCTTTTTGATGCAGTACGGAATGGCGTCTTGCAAGG
CTCGCTGCCATACCTTCTTTTCTGCCCGCCACTTGAGTTTAAGTGCCGCAAGGGTCGGTTTCGGCAGCGGCGTCTATTATTACCAGAAAAACTACGTCATGCCTTACCGCAGAACGTTCC
       250       260       270       280       290       300       310       320       330       340       350       360

          70                            80                            90                           100
 M  N  P  F  T  L  Y  W  S  G  K  I  P  A  S  V  F  L  S  S  Y  P  A  G  P  D  Q  P  H  Q  W  D  T  M  F  Y  S  L  G  M
TATGAATCCTTTCACCCTCTACTGGTCAGGTAAGATTCCGGCCTCCGTATTTCTCTCGTCGTACCCAGCCGGTCCAGATCAACCACATCAATGGGATACAATGTTCTACAGCCTTGGTAT
ATACTTAGGAAAGTGGGAGATGACCAGTCCATTCTAAGGCCGGAGGCATAAAGAGAGCAGCATGGGTCGGCCAGGTCTAGTTGGTGTAGTTACCCTATGTTACAAGATGTCGGAACCATA
       370       380       390       400       410       420       430       440       450       460       470       480

         110                           120                           130                           140
 L  E  K  T  R  E  I  Y  K  K  F  G  L  F  Y  V  G  P  I  Q  H  D  A  N  I  I  H  S  K  Q  P  I  N  S  L  D  D  L  K  G
GTTAGAAAAAACACGTGAAATTTACAAAAAGTTCGGCCTCTTCTACGTCGGCCCAATTCAGCACGACGCAAACATTATCCACAGTAAACAGCCGATTAATTCCCTGGACGACCTTAAGGG
CAATCTTTTTTGTGCACTTTAAATGTTTTTCAAGCCGGAGAAGATGCAGCCGGGTTAAGTCGTGCTGCGTTTGTAATAGGTGTCATTTGTCGGCTAATTAAGGGACCTGCTGGAATTCCC
       490       500       510       520       530       540       550       560       570       580       590       600

         150                           160                           170                           180
 L  K  M  R  L  P  G  G  M  V  A  E  V  F  A  K  F  G  V  A  A  V  S  L  P  G  S  D  I  F  P  A  L  E  K  G  T  I  D  A
TCTCAAAATGCGCTTACCTGGCGGGATGGTAGCGGAAGTCTTTGCAAAGTTTGGCGTCGCAGCGGTCAGTCTCCCAGGCAGCGACATCTTTCCAGCCTTAGAAAAAGGCACAATCGACGC
AGAGTTTTACGCGAATGGACCGCCCTACCATCGCCTTCAGAAACGTTTCAAACCGCAGCGTCGCCAGTCAGAGGGTCCGTCGCTGTAGAAAGGTCGGAATCTTTTTCCGTGTTAGCTGCG
       610       620       630       640       650       660       670       680       690       700       710       720

         190                           200                           210                           220
 A  D  C  V  G  P  A  V  N  W  E  L  G  F  S  Q  V  T  K  Y  I  L  M  G  P  P  G  I  M  S  V  Y  Q  P  V  D  L  M  D  L
TGCTGATTGTGTGGGTCCGGCTGTAAACTGGGAGCTCGGCTTCAGCCAAGTAACAAAGTACATCTTAATGGGTCCACCAGGCATCATGTCAGTCTACCAACCGGTCGACCTTATGGACCT
ACGACTAACACACCCAGGCCGACATTTGACCCTCGAGCCGAAGTCGGTTCATTGTTTCATGTAGAATTACCCAGGTGGTCCGTAGTACAGTCAGATGGTTGGCCAGCTGGAATACCTGGA
       730       740       750       760       770       780       790       800       810       820       830       840

         230                           240                           250                           260
 T  V  N  L  R  A  W  N  A  L  D  P  K  L  Q  Q  I  V  E  D  E  V  R  I  Y  S  Q  K  H  Y  L  A  I  Q  K  R  N  I  E  A
CACTGTCAATCTGCGGGCCTGGAACGCATTAGATCCAAAGTTACAGCAAATCGTTGAAGATGAAGTACGCATCTACTCTCAGAAGCATTACCTCGCAATTCAGAAACGGAATATTGAAGC
GTGACAGTTAGACGCCCGGACCTTGCGTAATCTAGGTTTCAATGTCGTTTAGCAACTTCTACTTCATGCGTAGATGAGAGTCTTCGTAATGGAGCGTTAAGTCTTTGCCTTATAACTTCG
       850       860       870       880       890       900       910       920       930       940       950       960
```

```
          270                                     280                                     290                                     300
M  K  K  F  E  A  A  G  T  T  V  T  R  L  S  Q  E  D  L  Q  E  F  R  R  A  A  I  P  I  W  Y  S  W  A  N  K  D  E  D  A
TATGAAGAAGTTCGAGGCCGCTGGTACAACCGTAACCCGTCTGTCACAAGAGGACCTCCAGGAGTTTCGTCGTGCAGCTATCCCAATTTGGTATTCATGGCAAACAAAGATGAAGACGC
ATACTTCTTCAAGCTCCGGCGACCATGTTGGCATTGGGCAGACAGTGTTCTCCTGGAGGTCCTCAAAGCAGCACGTCGATAGGGTTAAACCATAAGTACCCGTTTGTTTCTACTTCTGCG
       970       980       990      1000      1010      1020      1030      1040      1050      1060      1070      1080

          310                                     320                                     330                                     340
R  E  I  F  D  M  Q  L  E  Y  M  M  N  D  T  V  G  Y  I  T  E  D  D  I  K  G  M  N  G  G  S  H  H  H  H  H  H  *  *
ACGGGAGATTTTCGACATGCAATTAGAGTACATGATGAACGACACTGTAGGTTACATCACTGAAGATGACATTAAGGGCATGAATGGCGGTTCACATCATCATCATCATCATTAATGAAA
TGCCCTCTAAAAGCTGTACGTTAATCTCATGTACTACTTGCTGTGACATCCAATGTAGTGACTTCTACTGTAATTCCCGTACTTACCGCCAAGTGTAGTAGTAGTAGTAGTAATTACTTT
      1090      1100      1110      1120      1130      1140      1150      1160      1170      1180      1190      1200

GGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCC
CCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGG
      1210      1220      1230      1240      1250      1260      1270      1280      1290      1300      1310      1320

TCTAAACGGGTCTTGAGGGGTTTTTTGCTGAAAGGAGGAACTATATCCGGAGCGACTCCCACGGCACGTTGGCAAGCTCG
AGATTTGCCCAGAACTCCCCAAAAAACGACTTTCCTCCTTGATATAGGCCTCGCTGAGGGTGCCGTGCAACCGTTCGAGC
      1330      1340      1350      1360      1370      1380      1390      1400
```

FIG. 32 (Continued)

FIG. 33 - Exemplary Expression Construct for msLacBP6.188C

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                 10                            20
                                                 M  A  T  T  W  K  I  Q  S  V  W  D  A  G  T  V  G  Y  D  L  F  K  E  W
GGTTTCCCTCTAGAAATAATTTTGTTTAACTTTAAGAAGGAGATATACCATGGCAACAACTTGGAAAATTCAAAGTGTATGGGATGCAGGGACGGTGGGCTATGACCTCTTCAAGGAGTG
CCAAAGGGAGATCTTTATTAAAACAAATTGAAATTCTTCCTCTATATGGTACCGTTGTTGAACCTTTTAAGTTTCACATACCCTACGTCCCTGCCACCCGATACTGGAGAAGTTCCTCAC
       130       140       150       160       170       180       190       200       210       220       230       240

          30                            40                            50                            60
 S  D  G  M  E  E  K  T  G  G  E  L  K  F  T  A  F  P  A  K  A  V  A  A  D  N  N  G  L  F  D  A  V  R  N  G  V  L  Q  G
GAGCGACGGTATGGAAGAAAAGACGGGCGGTGAACTCAAATTCACGGCGTTCCCAGCCAAAGCCGTCGCCGCAGATAATAATGGTCTTTTTGATGCAGTACGGAATGGCGTCTTGCAAGG
CTCGCTGCCATACCTTCTTTTCTGCCCGCCACTTGAGTTTAAGTGCCGCAAGGGTCGGTTTCGGCAGCGGCGTCTATTATTACCAGAAAAACTACGTCATGCCTTACCGCAGAACGTTCC
       250       260       270       280       290       300       310       320       330       340       350       360

          70                            80                            90                            100
 M  N  P  F  T  L  Y  W  S  G  K  I  P  A  S  V  F  L  S  S  Y  P  A  G  P  D  Q  P  H  Q  W  D  T  M  F  Y  S  L  G  M
TATGAATCCTTTCACCCTCTACTGGTCAGGTAAGATTCCGGCCTCCGTATTTCTCTCGTCGTACCCAGCCGGTCCAGATCAACCACATCAATGGGATACAATGTTCTACAGCCTTGGTAT
ATACTTAGGAAAGTGGGAGATGACCAGTCCATTCTAAGGCCGGAGGCATAAAGAGAGCAGCATGGGTCGGCCAGGTCTAGTTGGTGTAGTTACCCTATGTTACAAGATGTCGGAACCATA
       370       380       390       400       410       420       430       440       450       460       470       480

         110                           120                           130                           140
 L  E  K  T  R  E  I  Y  K  K  F  G  L  F  Y  V  G  P  I  Q  H  D  A  N  I  I  H  S  K  Q  P  I  N  S  L  D  D  L  K  G
GTTAGAAAAAACACGTGAAATTTACAAAAAGTTCGGCCTCTTCTACGTCGGCCCAATTCAGCACGACGCAAACATTATCCACAGTAAACAGCCGATTAATTCCCTGGACGACCTTAAGGG
CAATCTTTTTTGTGCACTTTAAATGTTTTTCAAGCCGGAGAAGATGCAGCCGGGTTAAGTCGTGCTGCGTTTGTAATAGGTGTCATTTGTCGGCTAATTAAGGGACCTGCTGGAATTCCC
       490       500       510       520       530       540       550       560       570       580       590       600

         150                           160                           170                           180
 L  K  M  R  L  P  G  G  M  V  A  E  V  F  A  K  F  G  V  A  A  V  S  L  P  G  S  D  I  F  P  A  L  E  K  G  T  I  D  A
TCTCAAAATGCGCTTACCTGGCGGGATGGTAGCGGAAGTCTTTGCAAAGTTTGGCGTCGCAGCGGTCAGTCTCCCAGGCAGCGACATCTTTCCAGCCTTAGAAAAAGGCACAATCGACGC
AGAGTTTTACGCGAATGGACCGCCCTACCATCGCCTTCAGAAACGTTTCAAACCGCAGCGTCGCCAGTCAGAGGGTCCGTCGCTGTAGAAAGGTCGGAATCTTTTTCCGTGTTAGCTGCG
       610       620       630       640       650       660       670       680       690       700       710       720

         190                           200                           210                           220
 A  D  Y  C  G  P  A  V  N  W  E  L  G  F  S  Q  V  T  K  Y  I  L  M  G  P  P  G  I  M  S  V  Y  Q  P  V  D  L  M  D  L
TGCTGATTACTGTGGTCCGGCTGTAAACTGGGAGCTCGGCTTCAGCCAAGTAACAAAGTACATCTTAATGGGTCCACCAGGCATCATGTCAGTCTACCAACCGGTCGACCTTATGGACCT
ACGACTAATGACACCAGGCCGACATTTGACCCTCGAGCCGAAGTCGGTTCATTGTTTCATGTAGAATTACCCAGGTGGTCCGTAGTACAGTCAGATGGTTGGCCAGCTGGAATACCTGGA
       730       740       750       760       770       780       790       800       810       820       830       840

         230                           240                           250                           260
 T  V  N  L  R  A  W  N  A  L  D  P  K  L  Q  Q  I  V  E  D  E  V  R  I  Y  S  Q  K  H  Y  L  A  I  Q  K  R  N  I  E  A
CACTGTCAATCTGCGGGCCTGGAACGCATTAGATCCAAAGTTACAGCAAATCGTTGAAGATGAAGTACGCATCTACTCTCAGAAGCATTACCTCGCAATTCAGAAACGGAATATTGAAGC
GTGACAGTTAGACGCCCGGACCTTGCGTAATCTAGGTTTCAATGTCGTTTAGCAACTTCTACTTCATGCGTAGATGAGAGTCTTCGTAATGGAGCGTTAAGTCTTTGCCTTATAACTTCG
       850       860       870       880       890       900       910       920       930       940       950       960
```

```
                 270                                     280                                     290                                     300
  M   K   K   F   E   A   A   G   T   T   V   T   R   L   S   Q   E   D   L   Q   E   F   R   R   A   A   I   P   I   W   Y   S   W   A   N   K   D   E   D   A
TATGAAGAAGTTCGAGGCCGCTGGTACAACCGTAACCCGTCTGTCACAAGAGGACCTCCAGGAGTTTCGTCGTGCAGCTATCCCAATTTGGTATTCATGGGCAAACAAAGATGAAGACGC
ATACTTCTTCAAGCTCCGGCGACCATGTTGGCATTGGGCAGACAGTGTTCTCCTGGAGGTCCTCAAAGCAGCACGTCGATAGGGTTAAACCATAAGTACCCGTTTGTTTCTACTTCTGCG
        970       980       990      1000      1010      1020      1030      1040      1050      1060      1070      1080

                 310                                     320                                     330                                     340
  R   E   I   F   D   M   Q   L   E   Y   M   M   N   D   T   V   G   Y   I   T   E   D   D   I   K   G   M   N   G   G   S   H   H   H   H   H   H   *   *
ACGGGAGATTTTCGACATGCAATTAGAGTACATGATGAACGACACTGTAGGTTACATCACTGAAGATGACATTAAGGGCATGAATGGCGGTTCACATCATCATCATCATCATTAATGAAA
TGCCCTCTAAAAGCTGTACGTTAATCTCATGTACTACTTGCTGTGACATCCAATGTAGTGACTTCTACTGTAATTCCCGTACTTACCGCCAAGTGTAGTAGTAGTAGTAGTAATTACTTT
       1090      1100      1110      1120      1130      1140      1150      1160      1170      1180      1190      1200


GGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCC
CCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGG
       1210      1220      1230      1240      1250      1260      1270      1280      1290      1300      1310      1320


TCTAAACGGGTCTTGAGGGGTTTTTTGCTGAAAGGAGGAACTATATCCGGAGCGACTCCCACGGCACGTTGGCAAGCTCG
AGATTTGCCCAGAACTCCCCAAAAAACGACTTTCCTCCTTGATATAGGCCTCGCTGAGGGTGCCGTGCAACCGTTCGAGC
       1330      1340      1350      1360      1370      1380      1390      1400
```

FIG. 33 (Continued)

FIG. 34 - Exemplary Expression Construct for msLacBP6.192C

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                      10                            20
                                                         M  A  T  T  W  K  I  Q  S  V  W  D  A  G  T  V  G  Y  D  L  F  K  E  W
GGTTTCCCTCTAGAAATAATTTTGTTTAACTTTAAGAAGGAGATATACCATGGCAACAACTTGGAAAATTCAAAGTGTATGGGATGCAGGGACGGTGGGCTATGACCTCTTCAAGGAGTG
CCAAAGGGAGATCTTTATTAAAACAAATTGAAATTCTTCCTCTATATGGTACCGTTGTTGAACCTTTTAAGTTTCACATACCCTACGTCCCTGCCACCCGATACTGGAGAAGTTCCTCAC
       130       140       150       160       170       180       190       200       210       220       230       240

        30                            40                            50                            60
S  D  G  M  E  E  K  T  G  G  E  L  K  F  T  A  F  P  A  K  A  V  A  A  D  N  N  G  L  F  D  A  V  R  N  G  V  L  Q  G
GAGCGACGGTATGGAAGAAAAGACGGGCGGTGAACTCAAATTCACGGCGTTCCCAGCCAAAGCCGTCGCCGCAGATAATAATGGTCTTTTTGATGCAGTACGGAATGGCGTCTTGCAAGG
CTCGCTGCCATACCTTCTTTTCTGCCCGCCACTTGAGTTTAAGTGCCGCAAGGGTCGGTTTCGGCAGCGGCGTCTATTATTACCAGAAAAACTACGTCATGCCTTACCGCAGAACGTTCC
       250       260       270       280       290       300       310       320       330       340       350       360

        70                            80                            90                           100
M  N  P  F  T  L  Y  W  S  G  K  I  P  A  S  V  F  L  S  S  Y  P  A  G  P  D  Q  P  H  Q  W  D  T  M  F  Y  S  L  G  M
TATGAATCCTTTCACCCTCTACTGGTCAGGTAAGATTCCGGCCTCCGTATTTCTCTCGTCGTACCCAGCCGGTCCAGATCAACCACATCAATGGGATACAATGTTCTACAGCCTTGGTAT
ATACTTAGGAAAGTGGGAGATGACCAGTCCATTCTAAGGCCGGAGGCATAAAGAGAGCAGCATGGGTCGGCCAGGTCTAGTTGGTGTAGTTACCCTATGTTACAAGATGTCGGAACCATA
       370       380       390       400       410       420       430       440       450       460       470       480

       110                           120                           130                           140
L  E  K  T  R  E  I  Y  K  K  F  G  L  F  Y  V  G  P  I  Q  H  D  A  N  I  I  H  S  K  Q  P  I  N  S  L  D  D  L  K  G
GTTAGAAAAAACACGTGAAATTTACAAAAAGTTCGGCCTCTTCTACGTCGGCCCAATTCAGCACGACGCAAACATTATCCACAGTAAACAGCCGATTAATTCCCTGGACGACCTTAAGGG
CAATCTTTTTTGTGCACTTTAAATGTTTTTCAAGCCGGAGAAGATGCAGCCGGGTTAAGTCGTGCTGCGTTTGTAATAGGTGTCATTTGTCGGCTAATTAAGGGACCTGCTGGAATTCCC
       490       500       510       520       530       540       550       560       570       580       590       600

       150                           160                           170                           180
L  K  M  R  L  P  G  G  M  V  A  E  V  F  A  K  F  G  V  A  A  V  S  L  P  G  S  D  I  F  P  A  L  E  K  G  T  I  D  A
TCTCAAAATGCGCTTACCTGGCGGGATGGTAGCGGAAGTCTTTGCAAAGTTTGGCGTCGCAGCGGTCAGTCTCCCAGGCAGCGACATCTTTCCAGCCTTAGAAAAAGGCACAATCGACGC
AGAGTTTTACGCGAATGGACCGCCCTACCATCGCCTTCAGAAACGTTTCAAACCGCAGCGTCGCCAGTCAGAGGGTCCGTCGCTGTAGAAAGGTCGGAATCTTTTTCCGTGTTAGCTGCG
       610       620       630       640       650       660       670       680       690       700       710       720

       190                           200                           210                           220
A  D  Y  V  G  P  A  C  N  W  E  L  G  F  S  Q  V  T  K  Y  I  L  M  G  P  P  G  I  M  S  V  Y  Q  P  V  D  L  M  D  L
TGCTGATTACGTGGGTCCGGCTTGTAACTGGGAGCTCGGCTTCAGCCAAGTAACAAAGTACATCTTAATGGGTCCACCAGGCATCATGTCAGTCTACCAACCGGTCGACCTTATGGACCT
ACGACTAATGCACCCAGGCCGAACATTGACCCTCGAGCCGAAGTCGGTTCATTGTTTCATGTAGAATTACCCAGGTGGTCCGTAGTACAGTCAGATGGTTGGCCAGCTGGAATACCTGGA
       730       740       750       760       770       780       790       800       810       820       830       840

       230                           240                           250                           260
T  V  N  L  R  A  W  N  A  L  D  P  K  L  Q  Q  I  V  E  D  E  V  R  I  Y  S  Q  K  H  Y  L  A  I  Q  K  R  N  I  E  A
CACTGTCAATCTGCGGGCCTGGAACGCATTAGATCCAAAGTTACAGCAAATCGTTGAAGATGAAGTACGCATCTACTCTCAGAAGCATTACCTCGCAATTCAGAAACGGAATATTGAAGC
GTGACAGTTAGACGCCCGGACCTTGCGTAATCTAGGTTTCAATGTCGTTTAGCAACTTCTACTTCATGCGTAGATGAGAGTCTTCGTAATGGAGCGTTAAGTCTTTGCCTTATAACTTCG
       850       860       870       880       890       900       910       920       930       940       950       960
```

```
              270                                280                                290                                300
 M  K  K  F  E  A  A  G  T  T  V  T  R  L  S  Q  E  D  L  Q  E  F  R  R  A  A  I  P  I  W  Y  S  W  A  N  K  D  E  D  A
TATGAAGAAGTTCGAGGCCGCTGGTACAACCGTAACCCGTCTGTCACAAGAGGACCTCCAGGAGTTTCGTCGTGCAGCTATCCCAATTTGGTATTCATGGGCAAACAAAGATGAAGACGC
ATACTTCTTCAAGCTCCGGCGACCATGTTGGCATTGGGCAGACAGTGTTCTCCTGGAGGTCCTCAAAGCAGCACGTCGATAGGGTTAAACCATAAGTACCCGTTTGTTTCTACTTCTGCG
       970        980        990       1000       1010       1020       1030       1040       1050       1060       1070       1080

              310                                320                                330                                340
 R  E  I  F  D  M  Q  L  E  Y  M  M  N  D  T  V  G  Y  I  T  E  D  D  I  K  G  M  N  G  G  S  H  H  H  H  H  H  *  *
ACGGGAGATTTTCGACATGCAATTAGAGTACATGATGAACGACACTGTAGGTTACATCACTGAAGATGACATTAAGGGCATGAATGGCGGTTCACATCATCATCATCATCATTAATGAAA
TGCCCTCTAAAAGCTGTACGTTAATCTCATGTACTACTTGCTGTGACATCCAATGTAGTGACTTCTACTGTAATTCCCGTACTTACCGCCAAGTGTAGTAGTAGTAGTAGTAATTACTTT
      1090       1100       1110       1120       1130       1140       1150       1160       1170       1180       1190       1200

GGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCC
CCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGG
      1210       1220       1230       1240       1250       1260       1270       1280       1290       1300       1310       1320

TCTAAACGGGTCTTGAGGGGTTTTTTGCTGAAAGGAGGAACTATATCCGGAGCGACTCCCACGGCACGTTGGCAAGCTCG
AGATTTGCCCAGAACTCCCCAAAAAACGACTTTCCTCCTTGATATAGGCCTCGCTGAGGGTGCCGTGCAACCGTTCGAGC
      1330       1340       1350       1360       1370       1380       1390       1400
```

FIG. 34 (Continued)

FIG. 35 - Exemplary Expression Construct for msLacBP6.196C

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10         20         30         40         50         60         70         80         90        100        110        120

                                                                                             10                            20
                                                                   M  A  T  T  W  K  I  Q  S  V  W  D  A  G  T  V  G  Y  D  L  F  K  E  W
GGTTTCCCTCTAGAAATAATTTTGTTTAACTTTAAGAAGGAGATATACCATGGCAACAACTTGGAAAATTCAAAGTGTATGGGATGCAGGGACGGTGGGCTATGACCTCTTCAAGGAGTG
CCAAAGGGAGATCTTTATTAAAACAAATTGAAATTCTTCCTCTATATGGTACCGTTGTTGAACCTTTTAAGTTTCACATACCCTACGTCCCTGCCACCCGATACTGGAGAAGTTCCTCAC
       130        140        150        160        170        180        190        200        210        220        230        240

              30                            40                            50                            60
 S  D  G  M  E  E  K  T  G  G  E  L  K  F  T  A  F  P  A  K  A  V  A  A  D  N  N  G  L  F  D  A  V  R  N  G  V  L  Q  G
GAGCGACGGTATGGAAGAAAAGACGGGCGGTGAACTCAAATTCACGGCGTTCCCAGCCAAAGCCGTCGCCGCAGATAATAATGGTCTTTTTGATGCAGTACGGAATGGCGTCTTGCAAGG
CTCGCTGCCATACCTTCTTTTCTGCCCGCCACTTGAGTTTAAGTGCCGCAAGGGTCGGTTTCGGCAGCGGCGTCTATTATTACCAGAAAAACTACGTCATGCCTTACCGCAGAACGTTCC
       250        260        270        280        290        300        310        320        330        340        350        360

              70                            80                            90                           100
 M  N  P  F  T  L  Y  W  S  G  K  I  P  A  S  V  F  L  S  S  Y  P  A  G  P  D  Q  P  H  Q  W  D  T  M  F  Y  S  L  G  M
TATGAATCCTTTCACCCTCTACTGGTCAGGTAAGATTCCGGCCTCCGTATTTCTCTCGTCGTACCCAGCCGGTCCAGATCAACCACATCAATGGGATACAATGTTCTACAGCCTTGGTAT
ATACTTAGGAAAGTGGGAGATGACCAGTCCATTCTAAGGCCGGAGGCATAAAGAGAGCAGCATGGGTCGGCCAGGTCTAGTTGGTGTAGTTACCCTATGTTACAAGATGTCGGAACCATA
       370        380        390        400        410        420        430        440        450        460        470        480

             110                           120                           130                           140
 L  E  K  T  R  E  I  Y  K  K  F  G  L  F  Y  V  G  P  I  Q  H  D  A  N  I  I  H  S  K  Q  P  I  N  S  L  D  D  L  K  G
GTTAGAAAAAACACGTGAAATTTACAAAAAGTTCGGCCTCTTCTACGTCGGCCCAATTCAGCACGACGCAAACATTATCCACAGTAAACAGCCGATTAATTCCCTGGACGACCTTAAGGG
CAATCTTTTTTGTGCACTTTAAATGTTTTTCAAGCCGGAGAAGATGCAGCCGGGTTAAGTCGTGCTGCGTTTGTAATAGGTGTCATTTGTCGGCTAATTAAGGGACCTGCTGGAATTCCC
       490        500        510        520        530        540        550        560        570        580        590        600

             150                           160                           170                           180
 L  K  M  R  L  P  G  G  M  V  A  E  V  F  A  K  F  G  V  A  A  V  S  L  P  G  S  D  I  F  P  A  L  E  K  G  T  I  D  A
TCTCAAAATGCGCTTACCTGGCGGGATGGTAGCGGAAGTCTTTGCAAAGTTTGGCGTCGCAGCGGTCAGTCTCCCAGGCAGCGACATCTTTCCAGCCTTAGAAAAAGGCACAATCGACGC
AGAGTTTTACGCGAATGGACCGCCCTACCATCGCCTTCAGAAACGTTTCAAACCGCAGCGTCGCCAGTCAGAGGGTCCGTCGCTGTAGAAAGGTCGGAATCTTTTTCCGTGTTAGCTGCG
       610        620        630        640        650        660        670        680        690        700        710        720

             190                           200                           210                           220
 A  D  Y  V  G  P  A  V  N  W  E  C  G  F  S  Q  V  T  K  Y  I  L  M  G  P  P  G  I  M  S  V  Y  Q  P  V  D  L  M  D  L
TGCTGATTACGTGGGTCCGGCTGTAAACTGGGAGTGTGGCTTCAGCCAAGTAACAAAGTACATCTTAATGGGTCCACCAGGCATCATGTCAGTCTACCAACCGGTCGACCTTATGGACCT
ACGACTAATGCACCCAGGCCGACATTTGACCCTCACACCGAAGTCGGTTCATTGTTTCATGTAGAATTACCCAGGTGGTCCGTAGTACAGTCAGATGGTTGGCCAGCTGGAATACCTGGA
       730        740        750        760        770        780        790        800        810        820        830        840

             230                           240                           250                           260
 T  V  N  L  R  A  W  N  A  L  D  P  K  L  Q  Q  I  V  E  D  E  V  R  I  Y  S  Q  K  H  Y  L  A  I  Q  K  R  N  I  E  A
CACTGTCAATCTGCGGGCCTGGAACGCATTAGATCCAAAGTTACAGCAAATCGTTGAAGATGAAGTACGCATCTACTCTCAGAAGCATTACCTCGCAATTCAGAAACGGAATATTGAAGC
GTGACAGTTAGACGCCCGGACCTTGCGTAATCTAGGTTTCAATGTCGTTTAGCAACTTCTACTTCATGCGTAGATGAGAGTCTTCGTAATGGAGCGTTAAGTCTTTGCCTTATAACTTCG
       850        860        870        880        890        900        910        920        930        940        950        960
```

```
                270                                     280                                     290                                     300
 M   K   K   F   E   A   A   G   T   T   V   T   R   L   S   Q   E   D   L   Q   E   F   R   R   A   A   I   P   I   W   Y   S   W   A   N   K   D   E   D   A
TATGAAGAAGTTCGAGGCCGCTGGTACAACCGTAACCCGTCTGTCACAAGAGGACCTCCAGGAGTTTCGTCGTGCAGCTATCCCAATTTGGTATTCATGGGCAAACAAAGATGAAGACGC
ATACTTCTTCAAGCTCCGGCGACCATGTTGGCATTGGGCAGACAGTGTTCTCCTGGAGGTCCTCAAAGCAGCACGTCGATAGGGTTAAACCATAAGTACCCGTTTGTTTCTACTTCTGCG
        970          980          990         1000         1010         1020         1030         1040         1050         1060         1070         1080

                310                                     320                                     330                                     340
 R   E   I   F   D   M   Q   L   E   Y   M   M   N   D   T   V   G   Y   I   T   E   D   D   I   K   G   M   N   G   G   S   H   H   H   H   H   H   *   *
ACGGGAGATTTTCGACATGCAATTAGAGTACATGATGAACGACACTGTAGGTTACATCACTGAAGATGACATTAAGGGCATGAATGGCGGTTCACATCATCATCATCATCATTAATGAAA
TGCCCTCTAAAAGCTGTACGTTAATCTCATGTACTACTTGCTGTGACATCCAATGTAGTGACTTCTACTGTAATTCCCGTACTTACCGCCAAGTGTAGTAGTAGTAGTAGTAATTACTTT
       1090         1100         1110         1120         1130         1140         1150         1160         1170         1180         1190         1200

GGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCC
CCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGG
       1210         1220         1230         1240         1250         1260         1270         1280         1290         1300         1310         1320

TCTAAACGGGTCTTGAGGGGTTTTTTGCTGAAAGGAGGAACTATATCCGGAGCGACTCCCACGGCACGTTGGCAAGCTCG
AGATTTGCCCAGAACTCCCCAAAAAACGACTTTCCTCCTTGATATAGGCCTCGCTGAGGGTGCCGTGCAACCGTTCGAGC
       1330         1340         1350         1360         1370         1380         1390         1400
```

FIG. 35 (Continued)

FIG. 36 - Exemplary Expression Construct for tspLacBP7.189C

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                10                  20
                                                            M  Q  A  P  R  F  R  W  R  I  Q  S  A  W  D  A  G  T  V  G  Y  T  L  F
GGTTTCCCTCTAGAAATAATTTTGTTTAACTTTAAGAAGGAGATATACCATGCAAGCACCACGTTTTCGTTGGCGTATTCAAAGTGCATGGGATGCAGGAACAGTGGGTTACACCCTCTT
CCAAAGGGAGATCTTTATTAAAACAAATTGAAATTCTTCCTCTATATGGTACGTTCGTGGTGCAAAAGCAACCGCATAAGTTTCACGTACCCTACGTCCTTGTCACCCAATGTGGGAGAA
       130       140       150       160       170       180       190       200       210       220       230       240

          30                  40                  50                  60
 Q  R  F  A  E  R  V  K  E  L  T  D  G  Q  I  E  I  Q  T  F  P  A  G  A  V  V  G  T  F  D  M  F  D  A  V  K  T  G  V  L
TCAGCGCTTTGCAGAACGCGTCAAAGAGCTGACCGATGGACAGATCGAGATCCAGACCTTTCCAGCGGGTGCAGTCGTGGGTACCTTCGACATGTTCGACGCAGTCAAAACCGGAGTGCT
AGTCGCGAAACGTCTTGCGCAGTTTCTCGACTGGCTACCTGTCTAGCTCTAGGTCTGGAAAGGTCGCCCACGTCAGCACCCATGGAAGCTGTACAAGCTGCGTCAGTTTTGGCCTCACGA
       250       260       270       280       290       300       310       320       330       340       350       360

          70                  80                  90                 100
 D  G  M  H  P  F  T  L  Y  W  A  G  R  M  P  V  T  A  F  L  S  S  Y  P  L  G  L  D  R  P  D  Q  W  E  T  W  Y  Y  A  L
GGATGGCATGCATCCCTTTACCCTCTATTGGGCAGGTCGAATGCCGGTTACCGCCTTTCTCAGCAGCTACCCGTTAGGCCTGGATCGACCAGATCAGTGGGAAACGTGGTACTACGCACT
CCTACCGTACGTAGGGAAATGGGAGATAACCCGTCCAGCTTACGGCCAATGGCGGAAAGAGTCGTCGATGGGCAATCCGGACCTAGCTGGTCTAGTCACCCTTTGCACCATGATGCGTGA
       370       380       390       400       410       420       430       440       450       460       470       480

         110                 120                 130                 140
 G  G  L  D  L  A  R  R  A  F  E  E  Q  G  L  F  Y  V  G  P  V  Q  H  D  Y  N  L  I  H  S  K  K  P  I  K  S  F  E  D  F
TGGCGGTCTGGATCTGGCGAGACGTGCATTCGAGGAACAGGGTCTGTTCTACGTTGGTCCAGTGCAGCATGACTACAACCTGATCCACAGCAAAAAGCCGATCAAGTCCTTCGAGGACTT
ACCGCCAGACCTAGACCGCTCTGCACGTAAGCTCCTTGTCCCAGACAAGATGCAACCAGGTCACGTCGTACTGATGTTGGACTAGGTGTCGTTTTTCGGCTAGTTCAGGAAGCTCCTGAA
       490       500       510       520       530       540       550       560       570       580       590       600

         150                 160                 170                 180
 K  G  V  K  L  R  V  P  G  G  M  I  A  D  V  F  S  A  A  G  A  A  T  V  L  L  P  G  G  E  V  Y  P  A  L  E  R  G  V  I
CAAAGGCGTGAAGCTGAGAGTGCCTGGTGGCATGATAGCAGACGTCTTCTCAGCAGCTGGAGCAGCAACAGTCCTCTTGCCTGGTGGTGAGGTCTATCCGGCTCTGGAACGTGGTGTGAT
GTTTCCGCACTTCGACTCTCACGGACCACCGTACTATCGTCTGCAGAAGAGTCGTCGACCTCGTCGTTGTCAGGAGAACGGACCACCACTCCAGATAGGCCGAGACCTTGCACCACACTA
       610       620       630       640       650       660       670       680       690       700       710       720

         190                 200                 210                 220
 D  A  A  D  C  V  G  P  A  V  N  Y  N  L  G  F  H  Q  V  T  K  Y  I  I  M  G  P  P  E  T  P  A  I  H  Q  P  V  D  L  A
CGATGCAGCAGACTGCGTGGGTCCTGCAGTGAACTACAACCTTGGCTTCCATCAGGTGACCAAGTACATCATCATGGGTCCTCCAGAAACCCCTGCGATCCATCAGCCAGTGGATCTGGC
GCTACGTCGTCTGACGCACCCAGGACGTCACTTGATGTTGGAACCGAAGGTAGTCCACTGGTTCATGTAGTAGTACCCAGGAGGTCTTTGGGGACGCTAGGTAGTCGGTCACCTAGACCG
       730       740       750       760       770       780       790       800       810       820       830       840

         230                 240                 250                 260
 D  I  T  L  N  L  S  R  W  R  A  V  P  K  N  L  Q  E  R  F  E  A  A  V  H  E  W  S  W  I  H  Y  A  G  I  Q  K  A  N  L
AGACATCACCCTGAACCTCAGCCGTTGGCGTGCAGTGCCCAAAAACCTGCAGGAACGATTCGAAGCAGCGGTTCACGAATGGAGCTGGATCCACTATGCCGGTATCCAGAAAGCCAACCT
TCTGTAGTGGGACTTGGAGTCGGCAACCGCACGTCACGGGTTTTTGGACGTCCTTGCTAAGCTTCGTCGCCAAGTGCTTACCTCGACCTAGGTGATACGGCCATAGGTCTTTCGGTTGGA
       850       860       870       880       890       900       910       920       930       940       950       960
```

```
           270                                280                                290                                300
 E   T   W   P   K   Y   K   A   A   G   V   Q   I   I   R   L   T   T   V   D   V   R   K   F   R   R   V   A   I   P   I   W   F   K   W   A   K   Q   D   K
GGAGACCTGGCCGAAGTACAAAGCGGCAGGTGTGCAGATCATCAGGCTGACTACCGTGGATGTGCGCAAGTTTCGTCGTGTTGCGATTCCGATCTGGTTCAAATGGGCGAAACAGGACAA
CCTCTGGACCGGCTTCATGTTTCGCCGTCCACACGTCTAGTAGTCCGACTGATGGCACCTACACGCGTTCAAAGCAGCACAACGCTAAGGCTAGACCAAGTTTACCCGCTTTGTCCTGTT
        970       980       990      1000      1010      1020      1030      1040      1050      1060      1070      1080

           310                                320                                330                                340
 Y   A   R   E   A   F   A   S   Q   L   E   Y   M   K   A   L   G   Y   V   T   D   A   D   V   R   G   L   S   L   G   G   S   H   H   H   H   H   H   *   *
GTATGCCCGTGAAGCCTTTGCAAGCCAGCTGGAGTACATGAAAGCACTGGGCTATGTGACAGATGCAGATGTTCGTGGTTTAAGCTTAGGCGGCAGCCATCATCATCATCATCATTAATA
CATACGGGCACTTCGGAAACGTTCGGTCGACCTCATGTACTTTCGTGACCCGATACACTGTCTACGTCTACAAGCACCAAATTCGAATCCGCCGTCGGTAGTAGTAGTAGTAGTAATTAT
       1090      1100      1110      1120      1130      1140      1150      1160      1170      1180      1190      1200

 *
ATGAAAGGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTT
TACTTTCCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAA
       1210      1220      1230      1240      1250      1260      1270      1280      1290      1300      1310      1320

GGGGCCTCTAAACGGGTCTTGAGGGGTTTTTTGCTGAAAGGAGGAACTATATCCGGAGCGACTCCCACGGCACGTTGGCAAGCTCG
CCCCGGAGATTTGCCCAGAACTCCCCAAAAAACGACTTTCCTCCTTGATATAGGCCTCGCTGAGGGTGCCGTGCAACCGTTCGAGC
       1330      1340      1350      1360      1370      1380      1390      1400
```

FIG. 36 (Continued)

FIG. 37 - Exemplary Expression Construct for maLacBP8.189C

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                              10                            20
                                                            M  Q  A  A  T  T  W  K  I  Q  S  T  W  D  A  G  T  V  G  Y  T  L  F  E
GGTTTCCCTCTAGAAATAATTTTGTTTAACTTTAAGAAGGAGATATACCATGCAAGCAGCAACTACTTGGAAAATTCAAAGTACCTGGGATGCTGGTACGGTTGGCTACACCCTCTTCGA
CCAAAGGGAGATCTTTATTAAAACAAATTGAAATTCTTCCTCTATATGGTACGTTCGTCGTTGATGAACCTTTTAAGTTTCATGGACCCTACGACCATGCCAACCGATGTGGGAGAAGCT
       130       140       150       160       170       180       190       200       210       220       230       240

              30                            40                            50                            60
 E  W  A  K  S  I  E  A  K  S  G  G  E  L  K  F  Q  A  F  P  A  K  A  V  A  A  D  N  N  A  L  F  D  A  V  R  N  G  V  L
AGAGTGGGCGAAGAGCATCGAAGCCAAATCCGGTGGTGAACTGAAGTTCCAGGCGTTTCCGGCAAAAGCCGTTGCTGCTGACAACAACGCGCTCTTTGACGCTGTTCGCAACGGTGTGCT
TCTCACCCGCTTCTCGTAGCTTCGGTTTAGGCCACCACTTGACTTCAAGGTCCGCAAAGGCCGTTTTCGGCAACGACGACTGTTGTTGCGCGAGAAACTGCGACAAGCGTTGCCACACGA
       250       260       270       280       290       300       310       320       330       340       350       360

              70                            80                            90                            100
 Q  G  M  N  P  F  T  L  Y  W  A  G  K  I  P  A  S  V  F  L  S  S  Y  P  A  G  P  D  Q  P  H  Q  W  D  T  M  F  Y  S  M
TCAGGGCATGAACCCGTTCACCCTGTACTGGGCGGGCAAAATCCCTGCCTCTGTGTTCCTGTCGAGCTACCCAGCAGGTCCGGATCAACCCCATCAGTGGGATACCATGTTCTACTCGAT
AGTCCCGTACTTGGGCAAGTGGGACATGACCCGCCCGTTTTAGGGACGGAGACACAAGGACAGCTCGATGGGTCGTCCAGGCCTAGTTGGGGTAGTCACCCTATGGTACAAGATGAGCTA
       370       380       390       400       410       420       430       440       450       460       470       480

             110                           120                           130                           140
 G  M  L  E  K  T  R  E  I  Y  K  K  F  G  L  F  Y  V  G  P  I  Q  H  D  A  N  I  I  H  S  K  Q  P  V  N  S  L  D  D  L
GGGTATGCTGGAGAAAACCCGCGAAATCTACAAGAAATTTGGCCTGTTCTACGTTGGTCCGATCCAGCATGATGCGAACATCATCCACAGCAAACAGCCAGTCAACTCTCTGGACGACCT
CCCATACGACCTCTTTTGGGCGCTTTAGATGTTCTTTAAACCGGACAAGATGCAACCAGGCTAGGTCGTACTACGCTTGTAGTAGGTGTCGTTTGTCGGTCAGTTGAGAGACCTGCTGGA
       490       500       510       520       530       540       550       560       570       580       590       600

             150                           160                           170                           180
 K  G  M  K  I  R  V  P  G  G  M  V  A  E  V  F  Q  Q  F  G  V  S  T  V  S  L  P  G  S  D  I  F  P  A  L  E  K  G  T  I
GAAAGGGATGAAGATCCGTGTACCTGGTGGCATGGTTGCCGAAGTCTTCCAGCAGTTTGGCGTTTCCACCGTCAGTCTGCCGGGTAGCGACATCTTCCCGGCATTGGAGAAAGGCACGAT
CTTTCCCTACTTCTAGGCACATGGACCACCGTACCAACGGCTTCAGAAGGTCGTCAAACCGCAAAGGTGGCAGTCAGACGGCCCATCGCTGTAGAAGGGCCGTAACCTCTTTCCGTGCTA
       610       620       630       640       650       660       670       680       690       700       710       720

             190                           200                           210                           220
 D  A  A  D  C  V  G  P  A  V  N  Y  E  L  G  F  S  Q  V  T  D  Y  I  I  F  G  P  P  G  V  M  S  I  Y  Q  P  V  D  L  M
TGACGCTGCAGACTGCGTAGGTCCAGCAGTCAACTACGAACTGGGCTTTAGCCAGGTTACGGACTACATCATCTTCGGACCACCTGGCGTCATGAGCATCTATCAACCGGTGGACCTGAT
ACTGCGACGTCTGACGCATCCAGGTCGTCAGTTGATGCTTGACCCGAAATCGGTCCAATGCCTGATGTAGTAGAAGCCTGGTGGACCGCAGTACTCGTAGATAGTTGGCCACCTGGACTA
       730       740       750       760       770       780       790       800       810       820       830       840

             230                           240                           250                           260
 D  L  T  V  S  L  R  A  W  N  S  I  S  P  E  L  Q  Q  L  V  E  D  E  V  R  I  Y  S  Q  K  H  Y  L  A  I  Q  A  R  N  I
GGATCTGACCGTCAGTCTGCGTGCTTGGAACTCGATCTCACCAGAGCTGCAGCAGCTGGTTGAGGATGAAGTGCGCATCTACTCGCAGAAACACTATCTGGCGATTCAGGCTCGCAACAT
CCTAGACTGGCAGTCAGACGCACGAACCTTGAGCTAGAGTGGTCTCGACGTCGTCGACCAACTCCTACTTCACGCGTAGATGAGCGTCTTTGTGATAGACCGCTAAGTCCGAGCGTTGTA
       850       860       870       880       890       900       910       920       930       940       950       960
```

```
                   270                                     280                                     290                                     300
 E   A   M   E   K   F   K   A   D   G   D   T   V   T   R   L   S   Q   E   D   L   E   T   W   R   K   A   A   I   P   I   W   F   N   W   A   N   K   N   D
CGAAGCGATGGAGAAATTCAAAGCCGATGGTGACACGGTAACCCGTCTGAGCCAGGAAGACCTGGAAACCTGGCGTAAGGCTGCAATCCCGATCTGGTTCAACTGGGCGAACAAGAACGA
GCTTCGCTACCTCTTTAAGTTTCGGCTACCACTGTGCCATTGGGCAGACTCGGTCCTTCTGGACCTTTGGACCGCATTCCGACGTTAGGGCTAGACCAAGTTGACCCGCTTGTTCTTGCT
         970       980       990      1000      1010      1020      1030      1040      1050      1060      1070      1080

                   310                                     320                                     330                                     340
 D   A   R   A   I   L   D   I   Q   L   K   Y   M   M   N   D   T   V   G   Y   I   T   E   E   D   I   K   G   F   G   G   S   H   H   H   H   H   H   *   *
TGATGCTCGTGCGATCCTGGATATCCAGCTGAAATACATGATGAACGACACTGTGGGCTACATTACTGAAGAAGATATTAAAGGATTTGGCGGCAGCCATCATCATCATCATCATTAATG
ACTACGAGCACGCTAGGACCTATAGGTCGACTTTATGTACTACTTGCTGTGACACCCGATGTAATGACTTCTTCTATAATTTCCTAAACCGCCGTCGGTAGTAGTAGTAGTAGTAATTAC
        1090      1100      1110      1120      1130      1140      1150      1160      1170      1180      1190      1200

 *
ATAAAAGGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTT
TATTTTCCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAA
        1210      1220      1230      1240      1250      1260      1270      1280      1290      1300      1310      1320

GGGGCCTCTAAACGGGTCTTGAGGGGTTTTTTGCTGAAAGGAGGAACTATATCCGGAGCGACTCCCACGGCACGTTGGCAAGCTCG
CCCCGGAGATTTGCCCAGAACTCCCCAAAAAACGACTTTCCTCCTTGATATAGGCCTCGCTGAGGGTGCCGTGCAACCGTTCGAGC
        1330      1340      1350      1360      1370      1380      1390      1400
```

FIG. 37 (Continued)

FIG. 38 - Exemplary Expression Construct for adLacBP9.C191

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                             10                            20
                                                    M  Q  A  P  I  T  L  R  F  Q  S  T  W  P  Q  K  D  I  F  H  E  F  A  L
GGTTTCCCTCTAGAAATAATTTTGTTTAACTTTAAGAAGGAGATATACCATGCAAGCACCAATTACTCTGAGATTTCAGAGTACTTGGCCGCAGAAAGACATCTTCCACGAGTTTGCCCT
CCAAAGGGAGATCTTTATTAAAACAAATTGAAATTCTTCCTCTATATGGTACGTTCGTGGTTAATGAGACTCTAAAGTCTCATGAACCGGCGTCTTTCTGTAGAAGGTGCTCAAACGGGA
       130       140       150       160       170       180       190       200       210       220       230       240

             30                            40                            50                            60
 D  Y  A  K  K  V  N  E  M  S  G  G  R  L  K  I  E  V  L  A  A  G  S  V  V  K  A  F  D  L  L  D  A  V  S  K  G  T  L  D
GGATTACGCCAAAAAGGTCAACGAGATGAGCGGTGGACGTCTGAAGATCGAGGTTCTGGCAGCAGGCAGTGTGGTGAAGGCGTTCGATCTCCTGGATGCAGTGAGCAAGGGTACGCTGGA
CCTAATGCGGTTTTTCCAGTTGCTCTACTCGCCACCTGCAGACTTCTAGCTCCAAGACCGTCGTCCGTCACACCACTTCCGCAAGCTAGAGGACCTACGTCACTCGTTCCCATGCGACCT
       250       260       270       280       290       300       310       320       330       340       350       360

             70                            80                            90                           100
 G  G  H  G  V  V  A  Y  W  Y  G  K  N  T  A  L  A  L  W  G  S  G  P  A  F  G  M  D  P  N  M  V  L  A  W  H  H  Y  G  G
TGGAGGTCATGGCGTAGTCGCCTACTGGTACGGCAAGAACACCGCATTAGCGCTGTGGGGCTCTGGACCTGCATTCGGCATGGACCCAAACATGGTGCTTGCATGGCACCATTACGGCGG
ACCTCCAGTACCGCATCAGCGGATGACCATGCCGTTCTTGTGGCGTAATCGCGACACCCCGAGACCTGGACGTAAGCCGTACCTGGGTTTGTACCACGAACGTACCGTGGTAATGCCGCC
       370       380       390       400       410       420       430       440       450       460       470       480

            110                           120                           130                           140
 G  R  Q  L  L  E  E  I  Y  R  S  L  N  L  D  V  V  S  L  M  Y  G  P  M  P  T  Q  P  L  G  W  F  K  Q  K  P  I  A  K  P
AGGTCGTCAGCTCCTGGAAGAGATCTACCGAAGCCTCAACCTGGATGTCGTCAGCCTCATGTACGGACCAATGCCGACTCAGCCGTTAGGCTGGTTCAAGCAGAAACCCATTGCGAAACC
TCCAGCAGTCGAGGACCTTCTCTAGATGGCTTCGGAGTTGGACCTACAGCAGTCGGAGTACATGCCTGGTTACGGCTGAGTCGGCAATCCGACCAAGTTCGTCTTTGGGTAACGCTTTGG
       490       500       510       520       530       540       550       560       570       580       590       600

            150                           160                           170                           180
 D  D  M  K  G  L  K  F  R  T  V  G  L  S  I  D  I  F  N  G  L  G  A  A  V  N  A  L  P  G  A  E  I  V  P  A  M  D  R  G
TGACGACATGAAAGGGCTGAAGTTCCGTACGGTAGGTCTGAGCATCGACATCTTCAACGGACTGGGTGCTGCAGTGAACGCGTTACCAGGTGCCGAAATCGTTCCGGCTATGGATCGAGG
ACTGCTGTACTTTCCCGACTTCAAGGCATGCCATCCAGACTCGTAGCTGTAGAAGTTGCCTGACCCACGACGTCACTTGCGCAATGGTCCACGGCTTTAGCAAGGCCGATACCTAGCTCC
       610       620       630       640       650       660       670       680       690       700       710       720

            190                           200                           210                           220
 L  L  D  A  A  E  C  N  N  A  S  S  D  R  V  L  G  F  P  D  V  S  K  I  A  M  L  Q  S  F  H  Q  A  S  E  Q  F  E  I  L
TCTGCTCGATGCGGCAGAGTGCAACAACGCTTCTTCCGATCGTGTGCTAGGGTTTCCGGATGTCTCGAAGATCGCGATGCTGCAATCGTTCCATCAGGCGTCAGAGCAGTTCGAGATCCT
AGACGAGCTACGCCGTCTCACGTTGTTGCGAAGAAGGCTAGCACACGATCCCAAAGGCCTACAGAGCTTCTAGCGCTACGACGTTAGCAAGGTAGTCCGCAGTCTCGTCAAGCTCTAGGA
       730       740       750       760       770       780       790       800       810       820       830       840

            230                           240                           250                           260
 F  N  G  K  R  F  Q  A  L  P  A  D  L  K  S  I  I  S  I  A  A  Q  A  A  S  A  D  M  S  W  K  A  I  D  R  Y  S  S  D  Y
GTTCAACGGCAAGCGTTTCCAGGCGTTACCGGCTGATCTGAAGAGCATCATCTCCATTGCTGCGCAAGCTGCAAGCGCCGACATGTCCTGGAAGGCCATCGATCGCTACTCTAGCGACTA
CAAGTTGCCGTTCGCAAAGGTCCGCAATGGCCGACTAGACTTCTCGTAGTAGAGGTAACGACGCGTTCGACGTTCGCGGCTGTACAGGACCTTCCGGTAGCTAGCGATGAGATCGCTGAT
       850       860       870       880       890       900       910       920       930       940       950       960
```

```
          270                 280                 290                 300
 F E M R D K Q G V K F Y S T R P E I L K R Q L E I W D Q V M E K R A A E N P T F
CTTCGAGATGCGTGACAAGCAGGGCGTGAAGTTCTACAGCACCAGACCGGAAATCCTGAAACGGCAACTGGAGATCTGGGACCAGGTGATGGAGAAGCGTGCAGCCGAAAACCCGACGTT
GAAGCTCTACGCACTGTTCGTCCCGCACTTCAAGATGTCGTGGTCTGGCCTTTAGGACTTTGCCGTTGACCTCTAGACCCTGGTCCACTACCTCTTCGCACGTCGGCTTTTGGGCTGCAA
      970       980       990      1000      1010      1020      1030      1040      1050      1060      1070      1080

          310                 320                 330                 340
 K K V L E S Q R R F A Q R A A R W Q N D T N V D F K M A Y N H F F G G K K K A T
CAAAAAGGTCCTGGAGAGCCAACGCAGGTTTGCACAGCGTGCTGCGAGATGGCAGAACGACACCAACGTGGACTTCAAGATGGCCTACAACCACTTCTTTGGTGGTAAGAAAAAAGCTAC
GTTTTTCCAGGACCTCTCGGTTGCGTCCAAACGTGTCGCACGACGCTCTACCGTCTTGCTGTGGTTGCACCTGAAGTTCTACCGGATGTTGGTGAAGAAACCACCATTCTTTTTTCGATG
     1090      1100      1110      1120      1130      1140      1150      1160      1170      1180      1190      1200

          350
 G G S H H H H H H * * *
TGGCGGCAGCCATCATCATCATCATCATTAATAATGAAAGGGCGATATCCAGCACACTGGCGGCCGTTACTAGTGGATCCGGCTGCTAACAAAGCCCGAAAGGAAGCTGAGTTGGCTGCT
ACCGCCGTCGGTAGTAGTAGTAGTAGTAATTATTACTTTCCCGCTATAGGTCGTGTGACCGCCGGCAATGATCACCTAGGCCGACGATTGTTTCGGGCTTTCCTTCGACTCAACCGACGA
     1210      1220      1230      1240      1250      1260      1270      1280      1290      1300      1310      1320


GCCACCGCTGAGCAATAACTAGCATAACCCCTTGGGGCCTCTAAACGGGTCTTGAGGGGTTTTTTGCTGAAAGGAGGAACTATATCCGGAGCGACTCCCACGGCACGTTGGCAAGCTCG
CGGTGGCGACTCGTTATTGATCGTATTGGGGAACCCCGGAGATTTGCCCAGAACTCCCCAAAAAACGACTTTCCTCCTTGATATAGGCCTCGCTGAGGGTGCCGTGCAACCGTTCGAGC
     1330      1340      1350      1360      1370      1380      1390      1400      1410      1420      1430
```

FIG. 38 (Continued)

Figure 39:
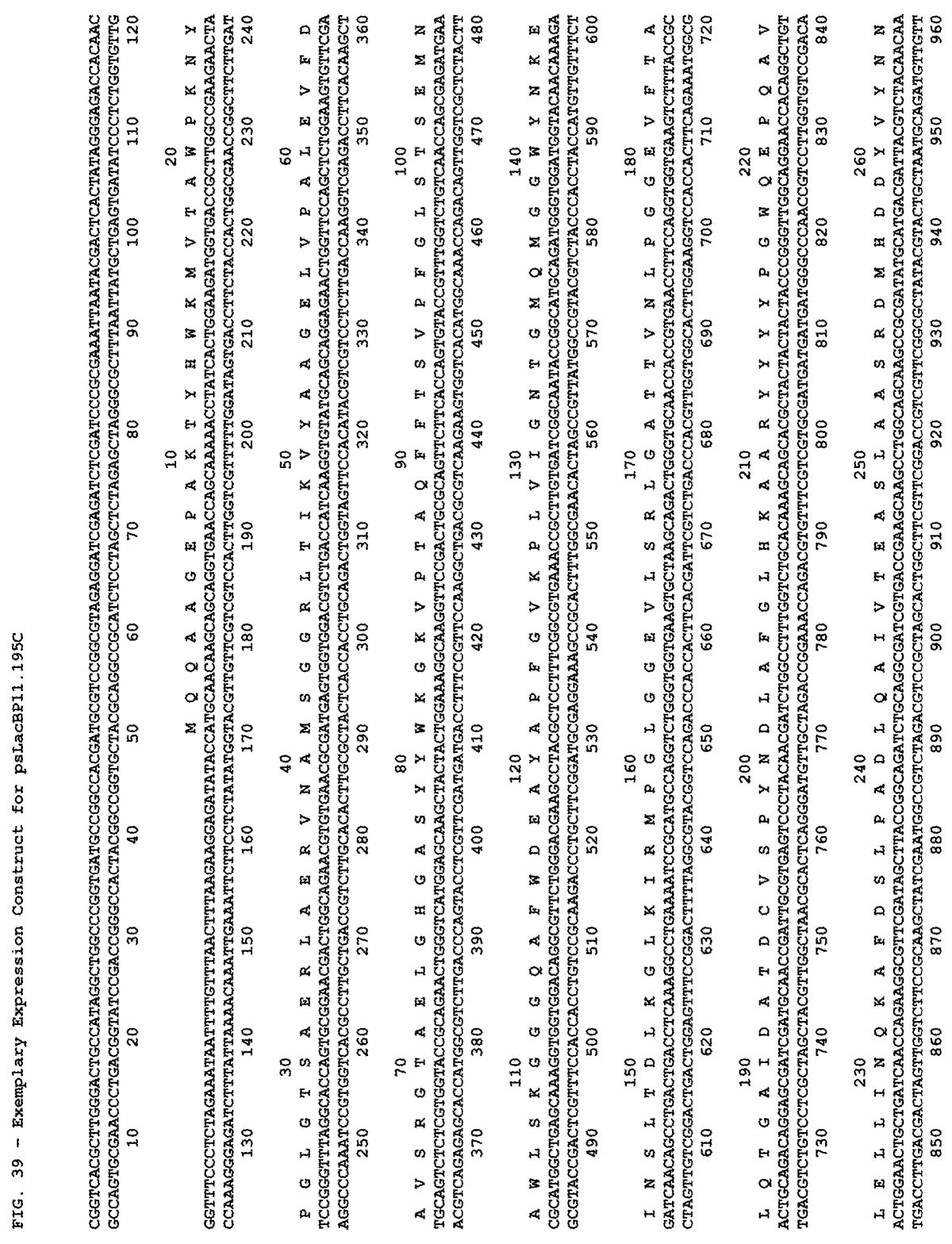

FIG. 39 - Exemplary Expression Construct for psLacBP11.195C

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                          10                            20
                                                  M  Q  Q  A  A  G  E  P  A  K  T  Y  H  W  K  M  V  T  A  W  P  K  N  Y
GGTTTCCCTCTAGAAATAATTTTGTTTAACTTTAAGAAGGAGATATACCATGCAACAAGCAGCAGGTGAACCAGCAAAAACCTATCACTGGAAGATGGTGACCGCTTGGCCGAAGAACTA
CCAAAGGGAGATCTTTATTAAAACAAATTGAAATTCTTCCTCTATATGGTACGTTGTTCGTCGTCCACTTGGTCGTTTTTGGATAGTGACCTTCTACCACTGGCGAACCGGCTTCTTGAT
       130       140       150       160       170       180       190       200       210       220       230       240

         30                            40                            50                            60
 P  G  L  G  T  S  A  E  R  L  A  E  R  V  N  A  M  S  G  G  R  L  T  I  K  V  Y  A  A  G  E  L  V  P  A  L  E  V  F  D
TCCGGGTTTAGGCACCAGTGCGGAACGACTGGCAGAACGTGTGAACGCGATGAGTGGTGGACGTCTGACCATCAAGGTGTATGCAGCAGGAGAACTGGTTCCAGCTCTGGAAGTGTTCGA
AGGCCCAAATCCGTGGTCACGCCTTGCTGACCGTCTTGCACACTTGCGCTACTCACCACCTGCAGACTGGTAGTTCCACATACGTCGTCCTCTTGACCAAGGTCGAGACCTTCACAAGCT
       250       260       270       280       290       300       310       320       330       340       350       360

         70                            80                            90                           100
 A  V  S  R  G  T  A  E  L  G  H  G  A  S  Y  Y  W  K  G  K  V  P  T  A  Q  F  F  T  S  V  P  F  G  L  S  T  S  E  M  N
TGCAGTCTCTCGTGGTACCGCAGAACTGGGTCATGGAGCAAGCTACTACTGGAAAGGCAAGGTTCCGACTGCGCAGTTCTTCACCAGTGTACCGTTTGGTCTGTCAACCAGCGAGATGAA
ACGTCAGAGAGCACCATGGCGTCTTGACCCAGTACCTCGTTCGATGATGACCTTTCCGTTCCAAGGCTGACGCGTCAAGAAGTGGTCACATGGCAAACCAGACAGTTGGTCGCTCTACTT
       370       380       390       400       410       420       430       440       450       460       470       480

        110                           120                           130                           140
 A  W  L  S  K  G  G  G  Q  A  F  W  D  E  A  Y  A  P  F  G  V  K  P  L  V  I  G  N  T  G  M  Q  M  G  G  W  Y  N  K  E
CGCATGGCTGAGCAAAGGTGGTGGACAGGCGTTCTGGGACGAAGCCTACGCTCCTTTCGGCGTGAAACCGCTTGTGATCGGCAATACCGGCATGCAGATGGGTGGATGGTACAACAAAGA
GCGTACCGACTCGTTTCCACCACCTGTCCGCAAGACCCTGCTTCGGATGCGAGGAAAGCCGCACTTTGGCGAACACTAGCCGTTATGGCCGTACGTCTACCCACCTACCATGTTGTTTCT
       490       500       510       520       530       540       550       560       570       580       590       600

        150                           160                           170                           180
 I  N  S  L  T  D  L  K  G  L  K  I  R  M  P  G  L  G  G  E  V  L  S  R  L  G  A  T  T  V  N  L  P  G  G  E  V  F  T  A
GATCAACAGCCTGACTGACCTCAAAGGCCTGAAAATCCGCATGCCAGGTCTGGGTGGTGAAGTGCTAAGCAGACTGGGTGCAACCACCGTGAACCTTCCAGGTGGTGAAGTCTTTACCGC
CTAGTTGTCGGACTGACTGGAGTTTCCGGACTTTTAGGCGTACGGTCCAGACCCACCACTTCACGATTCGTCTGACCCACGTTGGTGGCACTTGGAAGGTCCACCACTTCAGAAATGGCG
       610       620       630       640       650       660       670       680       690       700       710       720

        190                           200                           210                           220
 L  Q  T  G  A  I  D  A  T  D  C  V  S  P  Y  N  D  L  A  F  G  L  H  K  A  A  R  Y  Y  Y  Y  P  G  W  Q  E  P  Q  A  V
ACTGCAGACAGGAGCGATCGATGCAACCGATTGCGTGAGTCCCTACAACGATCTGGCCTTTGGTCTGCACAAAGCAGCACGCTACTACTACTACCCGGGTTGGCAGGAACCACAGGCTGT
TGACGTCTGTCCTCGCTAGCTACGTTGGCTAACGCACTCAGGGATGTTGCTAGACCGGAAACCAGACGTGTTTCGTCGTGCGATGATGATGATGGGCCCAACCGTCCTTGGTGTCCGACA
       730       740       750       760       770       780       790       800       810       820       830       840

        230                           240                           250                           260
 L  E  L  L  I  N  Q  K  A  F  D  S  L  P  A  D  L  Q  A  I  V  T  E  A  S  L  A  A  S  R  D  M  H  D  D  Y  V  Y  N  N
ACTGGAACTGCTGATCAACCAGAAGGCGTTCGATAGCTTACCGGCAGATCTGCAGGCGATCGTGACCGAAGCAAGCCTGGCAGCAAGCCGCGATATGCATGACGATTACGTCTACAACAA
TGACCTTGACGACTAGTTGGTCTTCCGCAAGCTATCGAATGGCCGTCTAGACGTCCGCTAGCACTGGCTTCGTTCGGACCGTCGTTCGGCGCTATACGTACTGCTAATGCAGATGTTGTT
       850       860       870       880       890       900       910       920       930       940       950       960
```

```
                 270                                     280                                     290                                     300
 A   L   A   L   E   Q   L   K   Q   Q   G   T   E   L   K   R   F   P   D   E   V   L   A   A   M   R   E   Q   S   D   L   I   L   G   E   L   A   A   Q   S
CGCTCTGGCTCTGGAACAGCTCAAACAGCAGGGAACCGAACTGAAGCGCTTTCCGGACGAAGTGCTGGCAGCAATGCGCGAACAGTCTGACCTGATCCTCGGTGAACTGGCTGCACAGAG
GCGAGACCGAGACCTTGTCGAGTTTGTCGTCCCTTGGCTTGACTTCGCGAAAGGCCTGCTTCACGACCGTCGTTACGCGCTTGTCAGACTGGACTAGGAGCCACTTGACCGACGTGTCTC
        970       980       990      1000      1010      1020      1030      1040      1050      1060      1070      1080

                 310                                     320                                     330                                     340
 E   L   N   G   R   I   W   A   S   M   K   A   F   Q   A   Q   V   E   P   M   H   E   I   S   E   K   E   L   Y   N   W   R   G   G   S   H   H   H   H   H
CGAACTGAACGGTCGTATCTGGGCAAGCATGAAGGCCTTTCAGGCTCAGGTCGAACCGATGCACGAGATTAGCGAAAAAGAATTGTATAATTGGAGAGGCGGCAGCCATCATCATCATCA
GCTTGACTTGCCAGCATAGACCCGTTCGTACTTCCGGAAAGTCCGAGTCCAGCTTGGCTACGTGCTCTAATCGCTTTTTCTTAACATATTAACCTCTCCGCCGTCGGTAGTAGTAGTAGT
       1090      1100      1110      1120      1130      1140      1150      1160      1170      1180      1190      1200

 H   *   *   *
TCATTAATAATGAAAGGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCA
AGTAATTATTACTTTCCCGCTATAGGTCGTGTGACCGCCGGCAATGATCACCTAGGCCGACGATTGTTTCGGGCTTTCCTTCGACTCAACCGACGACGGTGGCGACTCGTTATTGATCGT
       1210      1220      1230      1240      1250      1260      1270      1280      1290      1300      1310      1320

TAACCCCTTGGGGCCTCTAAACGGGTCTTGAGGGGTTTTTTGCTGAAAGGAGGAACTATATCCGGAGCGACTCCCACGGCACGTTGGCAAGCTCG
ATTGGGGAACCCCGGAGATTTGCCCAGAACTCCCCAAAAAACGACTTTCCTCCTTGATATAGGCCTCGCTGAGGGTGCCGTGCAACCGTTCGAGC
       1330      1340      1350      1360      1370      1380      1390      1400      1410
```

FIG. 39 (Continued)

FIG. 40 - Exemplary Expression Construct for rsLacBP12.191C

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                             10                            20
                                                  M  Q  A  P  L  V  M  K  M  Q  T  S  W  P  A  S  D  I  W  M  D  F  A  R
GGTTTCCCTCTAGAAATAATTTTGTTTAACTTTAAGAAGGAGATATACCATGCAAGCACCGTTAGTTATGAAAATGCAAACTAGTTGGCCAGCTAGCGATATCTGGATGGACTTCGCACG
CCAAAGGGAGATCTTTATTAAAACAAATTGAAATTCTTCCTCTATATGGTACGTTCGTGGCAATCAATACTTTTACGTTTGATCAACCGGTCGATCGCTATAGACCTACCTGAAGCGTGC
       130       140       150       160       170       180       190       200       210       220       230       240

          30                            40                            50                            60
 E  Y  V  T  R  V  E  E  M  S  G  G  R  I  K  V  D  L  L  P  A  G  A  V  V  G  A  F  Q  V  M  D  A  V  H  D  G  V  I  D
TGAGTACGTGACCAGAGTGGAAGAGATGTCAGGTGGACGCATCAAGGTGGATCTGCTGCCAGCAGGTGCGGTAGTTGGTGCGTTCCAGGTGATGGACGCAGTACACGATGGGGTCATCGA
ACTCATGCACTGGTCTCACCTTCTCTACAGTCCACCTGCGTAGTTCCACCTAGACGACGGTCGTCCACGCCATCAACCACGCAAGGTCCACTACCTGCGTCATGTGCTACCCCAGTAGCT
       250       260       270       280       290       300       310       320       330       340       350       360

          70                            80                            90                           100
 A  S  H  S  V  S  A  Y  W  Y  G  K  S  K  A  A  S  F  F  G  T  G  P  V  F  G  G  S  A  T  T  M  L  G  W  F  Y  Q  G  G
TGCTAGCCACTCGGTGAGCGCTTACTGGTATGGCAAGAGCAAAGCGGCTAGCTTCTTTGGCACTGGTCCAGTCTTTGGCGGTAGTGCAACCACGATGCTCGGCTGGTTCTACCAAGGTGG
ACGATCGGTGAGCCACTCGCGAATGACCATACCGTTCTCGTTTCGCCGATCGAAGAAACCGTGACCAGGTCAGAAACCGCCATCACGTTGGTGCTACGAGCCGACCAAGATGGTTCCACC
       370       380       390       400       410       420       430       440       450       460       470       480

         110                           120                           130                           140
 G  Q  D  L  Y  R  E  L  T  Q  D  I  L  G  M  N  I  V  G  F  Y  G  F  P  M  P  A  Q  P  F  G  W  F  K  T  E  V  N  G  V
AGGTCAGGACCTGTACCGTGAACTGACGCAAGACATCCTCGGAATGAACATCGTAGGCTTCTACGGTTTCCCGATGCCGGCACAGCCATTCGGCTGGTTCAAGACGGAAGTGAACGGCGT
TCCAGTCCTGGACATGGCACTTGACTGCGTTCTGTAGGAGCCTTACTTGTAGCATCCGAAGATGCCAAAGGGCTACGGCCGTGTCGGTAAGCCGACCAAGTTCTGCCTTCACTTGCCGCA
       490       500       510       520       530       540       550       560       570       580       590       600

         150                           160                           170                           180
 A  D  I  Q  G  F  K  Y  R  T  V  G  L  A  A  D  L  L  Q  A  M  G  M  S  V  A  Q  L  P  G  G  E  I  V  P  A  M  E  R  G
TGCGGACATCCAAGGCTTCAAGTACCGTACCGTTGGACTGGCAGCAGATCTGCTGCAGGCTATGGGCATGTCAGTGGCACAGCTGCCAGGTGGCGAAATCGTTCCGGCAATGGAGCGTGG
ACGCCTGTAGGTTCCGAAGTTCATGGCATGGCAACCTGACCGTCGTCTAGACGACGTCCGATACCCGTACAGTCACCGTGTCGACGGTCCACCGCTTTAGCAAGGCCGTTACCTCGCACC
       610       620       630       640       650       660       670       680       690       700       710       720

         190                           200                           210                           220
 V  I  D  A  F  E  C  N  N  P  S  S  D  M  R  F  G  A  Q  D  V  A  K  N  Y  Y  L  S  S  Y  H  Q  A  S  E  S  F  E  Y  T
TGTGATCGATGCGTTCGAGTGCAACAACCCTAGCTCGGATATGCGCTTTGGTGCACAAGATGTGGCGAAGAACTACTACCTGTCCTCCTACCATCAGGCATCTGAGAGCTTCGAGTACAC
ACACTAGCTACGCAAGCTCACGTTGTTGGGATCGAGCCTATACGCGAAACCACGTGTTCTACACCGCTTCTTGATGATGGACAGGAGGATGGTAGTCCGTAGACTCTCGAAGCTCATGTG
       730       740       750       760       770       780       790       800       810       820       830       840

         230                           240                           250                           260
 F  N  R  D  F  Y  E  D  L  D  P  D  L  Q  A  I  L  K  Y  A  V  E  A  A  S  T  S  N  T  A  L  A  L  R  Q  Y  S  A  D  L
CTTCAATCGCGACTTCTACGAGGATCTGGATCCTGACCTGCAAGCCATCCTGAAGTACGCTGTGGAAGCAGCGAGTACCAGCAATACCGCGTTAGCGCTGAGGCAGTATAGCGCAGATCT
GAAGTTAGCGCTGAAGATGCTCCTAGACCTAGGACTGGACGTTCGGTAGGACTTCATGCGACACCTTCGTCGCTCATGGTCGTTATGGCGCAATCGCGACTCCGTCATATCGCGTCTAGA
       850       860       870       880       890       900       910       920       930       940       950       960
```

```
               270                                280                                290                                300
 A  T  L  A  A  E  N  G  V  A  V  H  R  T  P  K  D  I  L  S  G  Q  L  E  A  W  D  K  L  I  V  D  L  E  A  D  E  F  F  K
TGCGACGTTAGCGGCTGAAAACGGTGTTGCAGTGCATCGGACTCCGAAAGACATCCTGTCTGGTCAGCTGGAAGCATGGGACAAGCTGATCGTGGATCTCGAAGCGGATGAGTTCTTCAA
ACGCTGCAATCGCCGACTTTTGCCACAACGTCACGTAGCCTGAGGCTTTCTGTAGGACAGACCAGTCGACCTTCGTACCCTGTTCGACTAGCACCTAGAGCTTCGCCTACTCAAGAAGTT
        970       980       990      1000      1010      1020      1030      1040      1050      1060      1070      1080

               310                                320                                330                                340
 K  V  L  D  S  Q  R  A  W  V  E  Q  V  S  Y  Y  E  L  M  N  A  A  D  L  G  L  A  Y  E  H  H  F  P  G  K  L  K  L  G  G
GAAAGTGCTGGATTCCCAACGTGCATGGGTCGAACAGGTCTCCTACTACGAGCTGATGAACGCAGCGGATCTTGGACTGGCATACGAACATCATTTTCCAGGAAAATTAAAACTGGGCGG
CTTTCACGACCTAAGGGTTGCACGTACCCAGCTTGTCCAGAGGATGATGCTCGACTACTTGCGTCGCCTAGAACCTGACCGTATGCTTGTAGTAAAAGGTCCTTTTAATTTTGACCCGCC
      1090      1100      1110      1120      1130      1140      1150      1160      1170      1180      1190      1200

               350
 S  H  H  H  H  H  H  *  *  *
CAGCCATCATCATCATCATCATTAATAATGAAAGGGCGATATCCAGCACACTGGCGGCCGTTACTAGTGGATCCGGCTGCTAACAAAGCCCGAAAGGAAGCTGAGTTGGCTGCTGCCACC
GTCGGTAGTAGTAGTAGTAGTAATTATTACTTTCCCGCTATAGGTCGTGTGACCGCCGGCAATGATCACCTAGGCCGACGATTGTTTCGGGCTTTCCTTCGACTCAACCGACGACGGTGG
      1210      1220      1230      1240      1250      1260      1270      1280      1290      1300      1310      1320


GCTGAGCAATAACTAGCATAACCCCTTGGGGCCTCTAAACGGGTCTTGAGGGGTTTTTTGCTGAAAGGAGGAACTATATCCGGAGCGACTCCCACGGCACGTTGGCAAGCTCG
CGACTCGTTATTGATCGTATTGGGGAACCCCGGAGATTTGCCCAGAACTCCCCAAAAAACGACTTTCCTCCTTGATATAGGCCTCGCTGAGGGTGCCGTGCAACCGTTCGAGC
      1330      1340      1350      1360      1370      1380      1390      1400      1410      1420      1430
```

FIG. 40 (Continued)

FIG. 41 - Exemplary Expression Construct for fsLacBP13.188C

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                              10                  20
                                                            M  E  K  K  I  R  W  K  L  A  M  T  W  G  P  T  L  H  P  L  S  D  T  A
GGTTTCCCTCTAGAAATAATTTTGTTTAACTTTAAGAAGGAGATATACCATGGAAAAAAAAATTCGTTGGAAATTAGCAATGACTTGGGGTCCGACCTTGCATCCGTTGTCCGACACAGC
CCAAAGGGAGATCTTTATTAAAACAAATTGAAATTCTTCCTCTATATGGTACCTTTTTTTTTAAGCAACCTTTAATCGTTACTGAACCCCAGGCTGGAACGTAGGCAACAGGCTGTGTCG
       130       140       150       160       170       180       190       200       210       220       230       240

              30                  40                  50                  60
 E  H  M  A  E  I  V  K  E  L  S  D  G  N  F  V  I  N  I  D  A  S  N  V  H  K  A  P  F  G  I  F  D  M  V  K  L  G  Q  Y
AGAGCATATGGCGGAAATCGTGAAGGAGTTGAGCGATGGCAACTTCGTGATCAACATCGATGCGTCGAACGTGCACAAAGCGCCGTTTGGCATCTTCGATATGGTGAAACTCGGTCAGTA
TCTCGTATACCGCCTTTAGCACTTCCTCAACTCGCTACCGTTGAAGCACTAGTTGTAGCTACGCAGCTTGCACGTGTTTCGCGGCAAACCGTAGAAGCTATACCACTTTGAGCCAGTCAT
       250       260       270       280       290       300       310       320       330       340       350       360

              70                  80                  90                 100
 E  M  G  H  T  A  S  Y  Y  Y  K  G  K  N  I  A  F  L  P  L  T  T  M  P  F  G  M  T  A  P  E  Q  Y  A  W  F  Y  Y  G  G
CGAGATGGGCCATACTGCGAGCTACTACTACAAAGGCAAAAACATCGCGTTTTTACCGCTGACGACCATGCCTTTCGGTATGACCGCACCGGAACAGTATGCGTGGTTCTACTATGGTGG
GCTCTACCCGGTATGACGCTCGATGATGATGTTTCCGTTTTTGTAGCGCAAAAATGGCGACTGCTGGTACGGAAAGCCATACTGGCGTGGCCTTGTCATACGCACCAAGATGATACCACC
       370       380       390       400       410       420       430       440       450       460       470       480

             110                 120                 130                 140
 G  L  E  L  M  Q  E  A  Y  T  K  H  G  M  L  A  F  P  G  G  N  T  G  N  Q  M  G  G  W  F  T  K  E  I  N  S  L  D  D  L
CGGTCTGGAGCTGATGCAGGAAGCGTACACCAAGCATGGCATGCTGGCGTTTCCTGGTGGTAACACCGGTAACCAGATGGGAGGTTGGTTCACCAAGGAGATCAACAGCCTGGATGACCT
GCCAGACCTCGACTACGTCCTTCGCATGTGGTTCGTACCGTACGACCGCAAAGGACCACCATTGTGGCCATTGGTCTACCCTCCAACCAAGTGGTTCCTCTAGTTGTCGGACCTACTGGA
       490       500       510       520       530       540       550       560       570       580       590       600

             150                 160                 170                 180
 K  G  L  K  M  R  I  P  G  F  A  G  Q  I  M  S  K  L  G  V  T  V  T  N  I  P  P  G  E  L  Y  T  A  L  E  R  G  T  V  D
CAAGGGTCTCAAGATGAGGATCCCAGGCTTTGCGGGCCAGATCATGTCCAAACTGGGTGTGACCGTGACCAACATCCCTCCAGGTGAGCTGTACACCGCACTGGAACGTGGTACCGTGGA
GTTCCCAGAGTTCTACTCCTAGGGTCCGAAACGCCCGGTCTAGTACAGGTTTGACCCACACTGGCACTGGTTGTAGGGAGGTCCACTCGACATGTGGCGTGACCTTGCACCATGGCACCT
       610       620       630       640       650       660       670       680       690       700       710       720

             190                 200                 210                 220
 A  V  E  C  T  G  P  G  M  D  I  N  M  G  F  H  K  I  A  K  Y  Y  Y  T  G  W  H  E  P  G  S  E  V  E  F  L  I  N  E  K
TGCGGTGGAATGCACCGGTCCTGGTATGGACATCAACATGGGATTCCACAAGATCGCGAAATACTACTATACCGGTTGGCATGAACCGGGATCCGAAGTGGAGTTCCTGATCAACGAAAA
ACGCCACCTTACGTGGCCAGGACCATACCTGTAGTTGTACCCTAAGGTGTTCTAGCGCTTTATGATGATATGGCCAACCGTACTTGGCCCTAGGCTTCACCTCAAGGACTAGTTGCTTTT
       730       740       750       760       770       780       790       800       810       820       830       840

             230                 240                 250                 260
 E  Y  N  K  L  P  E  K  Y  K  K  I  L  K  I  A  M  K  T  A  A  Y  D  M  Y  I  Q  S  Y  E  M  N  A  E  A  W  Q  Q  M  K
GGAATACAACAAACTGCCGGAAAAATACAAAAAGATCCTGAAAATCGCCATGAAAACCGCAGCGTACGACATGTACATCCAGTCGTACGAGATGAACGCTGAAGCTTGGCAGCAGATGAA
CCTTATGTTGTTTGACGGCCTTTTTATGTTTTTCTAGGACTTTTAGCGGTACTTTTGGCGTCGCATGCTGTACATGTAGGTCAGCATGCTCTACTTGCGACTTCGAACCGTCGTCTACTT
       850       860       870       880       890       900       910       920       930       940       950       960
```

```
                    270                                     280                                     290                                     300
 E   K   Y   P   D   I   K   V   K   V   F   P   E   E   V   L   K   E   M   K   T   A   Y   D   N   L   V   A   S   Y   E   K   E   S   P   M   F   K   K   I
AGAGAAATACCCGGATATCAAGGTCAAGGTTTTTCCGGAAGAAGTGCTGAAAGAGATGAAGACCGCGTACGACAACCTTGTGGCGAGCTACGAGAAAGAAAGCCCGATGTTCAAGAAAAT
TCTCTTTATGGGCCTATAGTTCCAGTTCCAAAAAGGCCTTCTTCACGACTTTCTCTACTTCTGGCGCATGCTGTTGGAACACCGCTCGATGCTCTTTCTTTCGGGCTACAAGTTCTTTTA
       970       980       990      1000      1010      1020      1030      1040      1050      1060      1070      1080

                    310                                     320                                     330                                     340
 M   E   S   K   R   A   Y   L   D   K   V   R   D   W   T   H   I   S   D   Y   L   Y   L   K   S   T   S   E   S   N   L   N   G   G   S   H   H   H   H   H
CATGGAGAGCAAACGTGCGTATCTGGACAAGGTTCGAGACTGGACCCACATATCGGACTACCTCTACCTGAAAAGTACTTCTGAAAGTAATCTGAATGGCGGCAGCCATCATCATCATCA
GTACCTCTCGTTTGCACGCATAGACCTGTTCCAAGCTCTGACCTGGGTGTATAGCCTGATGGAGATGGACTTTTCATGAAGACTTTCATTAGACTTACCGCCGTCGGTAGTAGTAGTAGT
      1090      1100      1110      1120      1130      1140      1150      1160      1170      1180      1190      1200

 H   *   *   *
TCATTAATGATAAAAGGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCA
AGTAATTACTATTTTCCCGCTATAGGTCGTGTGACCGCCGGCAATGATCACCTAGGCCGACGATTGTTTCGGGCTTTCCTTCGACTCAACCGACGACGGTGGCGACTCGTTATTGATCGT
      1210      1220      1230      1240      1250      1260      1270      1280      1290      1300      1310      1320

TAACCCCTTGGGGCCTCTAAACGGGTCTTGAGGGGTTTTTTGCTGAAAGGAGGAACTATATCCGGAGCGACTCCCACGGCACGTTGGCAAGCTCG
ATTGGGGAACCCCGGAGATTTGCCCAGAACTCCCCAAAAAACGACTTTCCTCCTTGATATAGGCCTCGCTGAGGGTGCCGTGCAACCGTTCGAGC
      1330      1340      1350      1360      1370      1380      1390      1400      1410
```

FIG. 41 (Continued)

FIG. 42 - Exemplary Expression Construct for msLacBP6_187C_F68L

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                           10                            20
                                                  M  A  T  T  W  K  I  Q  S  V  W  D  A  G  T  V  G  Y  D  L  F  K  E  W
GGTTTCCCTCTAGAAATAATTTTGTTTAACTTTAAGAAGGAGATATACCATGGCAACAACTTGGAAAATTCAAAGTGTATGGGATGCAGGGACGGTGGGCTATGACCTCTTCAAGGAGTG
CCAAAGGGAGATCTTTATTAAAACAAATTGAAATTCTTCCTCTATATGGTACCGTTGTTGAACCTTTTAAGTTTCACATACCCTACGTCCCTGCCACCCGATACTGGAGAAGTTCCTCAC
       130       140       150       160       170       180       190       200       210       220       230       240

        30                            40                            50                            60
 C  D  G  M  E  E  K  T  G  G  E  L  K  F  T  C  F  P  A  K  A  V  A  A  D  N  N  G  L  F  D  A  V  R  N  G  V  L  Q  G
GTGCGACGGTATGGAAGAAAAAGACGGGCGGTGAACTCAAATTCACGTGCTTCCCAGCCAAAGCCGTCGCCGCAGATAATAATGGTCTTTTTGATGCAGTACGGAATGGCGTCTTGCAAGG
CACGCTGCCATACCTTCTTTTTCTGCCCGCCACTTGAGTTTAAGTGCACGAAGGGTCGGTTTCGGCAGCGGCGTCTATTATTACCAGAAAAACTACGTCATGCCTTACCGCAGAACGTTCC
       250       260       270       280       290       300       310       320       330       340       350       360

        70                            80                            90                            100
 M  N  P  L  T  L  Y  W  S  G  K  I  P  A  S  V  F  L  S  S  Y  P  A  G  P  D  Q  P  H  Q  W  D  T  M  F  Y  S  L  G  M
TATGAATCCTCTGACCCTCTACTGGTCAGGTAAGATTCCGGCCTCCGTATTTCTCTCGTCGTACCCAGCCGGTCCAGATCAACCACATCAATGGGATACAATGTTCTACAGCCTTGGTAT
ATACTTAGGAGACTGGGAGATGACCAGTCCATTCTAAGGCCGGAGGCATAAAGAGAGCAGCATGGGTCGGCCAGGTCTAGTTGGTGTAGTTACCCTATGTTACAAGATGTCGGAACCATA
       370       380       390       400       410       420       430       440       450       460       470       480

       110                           120                           130                           140
 L  E  K  T  R  E  I  Y  K  K  F  G  L  F  Y  V  G  P  I  Q  H  D  A  N  I  I  H  S  K  Q  P  I  N  S  L  D  D  L  K  G
GTTAGAAAAAACACGTGAAATTTACAAAAAGTTCGGCCTCTTCTACGTCGGCCCAATTCAGCACGACGCAAACATTATCCACAGTAAACAGCCGATTAATTCCCTGGACGACCTTAAGGG
CAATCTTTTTTGTGCACTTTAAATGTTTTTCAAGCCGGAGAAGATGCAGCCGGGTTAAGTCGTGCTGCGTTTGTAATAGGTGTCATTTGTCGGCTAATTAAGGGACCTGCTGGAATTCCC
       490       500       510       520       530       540       550       560       570       580       590       600

       150                           160                           170                           180
 L  K  M  R  L  P  G  G  M  V  A  E  V  F  A  K  F  G  V  A  A  V  S  L  P  G  S  D  I  F  P  A  L  E  K  G  T  I  D  A
TCTCAAAATGCGCTTACCTGGCGGGATGGTAGCGGAAGTCTTTGCAAAGTTTGGCGTCGCAGCGGTCAGTCTCCCAGGCAGCGACATCTTTCCAGCCTTAGAAAAAGGCACAATCGACGC
AGAGTTTTACGCGAATGGACCGCCCTACCATCGCCTTCAGAAACGTTTCAAACCGCAGCGTCGCCAGTCAGAGGGTCCGTCGCTGTAGAAAGGTCGGAATCTTTTTCCGTGTTAGCTGCG
       610       620       630       640       650       660       670       680       690       700       710       720

       190                           200                           210                           220
 A  D  C  V  G  P  A  V  N  W  E  L  G  F  S  Q  V  T  K  Y  I  L  M  G  P  P  G  I  M  S  V  Y  Q  P  V  D  L  M  D  L
TGCTGATTGTGTGGGTCCGGCTGTAAACTGGGAGCTCGGCTTCAGCCAAGTAACAAAGTACATCTTAATGGGTCCACCAGGCATCATGTCAGTCTACCAACCGGTCGACCTTATGGACCT
ACGACTAACACACCCAGGCCGACATTTGACCCTCGAGCCGAAGTCGGTTCATTGTTTCATGTAGAATTACCCAGGTGGTCCGTAGTACAGTCAGATGGTTGGCCAGCTGGAATACCTGGA
       730       740       750       760       770       780       790       800       810       820       830       840

       230                           240                           250                           260
 T  V  N  L  R  A  W  N  A  L  D  P  K  L  Q  Q  I  V  E  D  E  V  R  I  Y  S  Q  K  H  Y  L  A  I  Q  K  R  N  I  E  A
CACTGTCAATCTGCGGGCCTGGAACGCATTAGATCCAAAGTTACAGCAAATCGTTGAAGATGAAGTACGCATCTACTCTCAGAAGCATTACCTCGCAATTCAGAAACGGAATATTGAAGC
GTGACAGTTAGACGCCCGGACCTTGCGTAATCTAGGTTTCAATGTCGTTTAGCAACTTCTACTTCATGCGTAGATGAGAGTCTTCGTAATGGAGCGTTAAGTCTTTGCCTTATAACTTCG
       850       860       870       880       890       900       910       920       930       940       950       960
```

```
                 270                                     280                                     290                                     300
  M   K   K   F   E   A   A   G   T   T   V   T   R   L   S   Q   E   D   L   Q   E   F   R   R   A   A   I   P   I   W   Y   S   W   A   N   K   D   E   D   A
TATGAAGAAGTTCGAGGCCGCTGGTACAACCGTAACCCGTCTGTCACAAGAGGACCTCCAGGAGTTTCGTCGTGCAGCTATCCCAATTTGGTATTCATGGGCAAACAAAGATGAAGACGC
ATACTTCTTCAAGCTCCGGCGACCATGTTGGCATTGGGCAGACAGTGTTCTCCTGGAGGTCCTCAAAGCAGCACGTCGATAGGGTTAAACCATAAGTACCCGTTTGTTTCTACTTCTGCG
       970       980       990      1000      1010      1020      1030      1040      1050      1060      1070      1080

                 310                                     320                                     330                                     340
  R   E   I   F   D   M   Q   L   E   Y   M   M   N   D   T   V   G   Y   I   T   E   D   D   I   K   G   M   N   G   G   S   H   H   H   H   H   H   *   *
ACGGGAGATTTTCGACATGCAATTAGAGTACATGATGAACGACACTGTAGGTTACATCACTGAAGATGACATTAAGGGCATGAATGGCGGTTCACATCATCATCATCATCATTAATGAAA
TGCCCTCTAAAAGCTGTACGTTAATCTCATGTACTACTTGCTGTGACATCCAATGTAGTGACTTCTACTGTAATTCCCGTACTTACCGCCAAGTGTAGTAGTAGTAGTAGTAATTACTTT
      1090      1100      1110      1120      1130      1140      1150      1160      1170      1180      1190      1200

GGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCC
CCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGG
      1210      1220      1230      1240      1250      1260      1270      1280      1290      1300      1310      1320

TCTAAACGGGTCTTGAGGGGTTTTTTGCTGAAAGGAGGAACTATATCCGGAGCGACTCCCACGGCACGTTGGCAAGCTCG
AGATTTGCCCAGAACTCCCCAAAAAACGACTTTCCTCCTTGATATAGGCCTCGCTGAGGGTGCCGTGCAACCGTTCGAGC
      1330      1340      1350      1360      1370      1380      1390      1400
```

FIG. 42 (Continued)

FIG. 43 - Exemplary Expression Construct for msLacBP6_187C_F68M

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                   10                            20
                                                   M  A  T  T  W  K  I  Q  S  V  W  D  A  G  T  V  G  Y  D  L  F  K  E  W
GGTTTCCCTCTAGAAATAATTTTGTTTAACTTTAAGAAGGAGATATACCATGGCAACAACTTGGAAAATTCAAAGTGTATGGGATGCAGGGACGGTGGGCTATGACCTCTTCAAGGAGTG
CCAAAGGGAGATCTTTATTAAAACAAATTGAAATTCTTCCTCTATATGGTACCGTTGTTGAACCTTTTAAGTTTCACATACCCTACGTCCCTGCCACCCGATACTGGAGAAGTTCCTCAC
       130       140       150       160       170       180       190       200       210       220       230       240

           30                            40                            50                            60
 C  D  G  M  E  E  K  T  G  G  E  L  K  F  T  C  F  P  A  K  A  V  A  A  D  N  N  G  L  F  D  A  V  R  N  G  V  L  Q  G
GTGCGACGGTATGGAAGAAAAGACGGGCGGTGAACTCAAATTCACGTGCTTCCCAGCCAAAGCCGTCGCCGCAGATAATAATGGTCTTTTTGATGCAGTACGGAATGGCGTCTTGCAAGG
CACGCTGCCATACCTTCTTTTCTGCCCGCCACTTGAGTTTAAGTGCACGAAGGGTCGGTTTCGGCAGCGGCGTCTATTATTACCAGAAAAACTACGTCATGCCTTACCGCAGAACGTTCC
       250       260       270       280       290       300       310       320       330       340       350       360

           70                            80                            90                           100
 M  N  P  M  T  L  Y  W  S  G  K  I  P  A  S  V  F  L  S  S  Y  P  A  G  P  D  Q  P  H  Q  W  D  T  M  F  Y  S  L  G  M
TATGAATCCTATGACCCTCTACTGGTCAGGTAAGATTCCGGCCTCCGTATTTCTCTCGTCGTACCCAGCCGGTCCAGATCAACCACATCAATGGGATACAATGTTCTACAGCCTTGGTAT
ATACTTAGGATACTGGGAGATGACCAGTCCATTCTAAGGCCGGAGGCATAAAGAGAGCAGCATGGGTCGGCCAGGTCTAGTTGGTGTAGTTACCCTATGTTACAAGATGTCGGAACCATA
       370       380       390       400       410       420       430       440       450       460       470       480

          110                           120                           130                           140
 L  E  K  T  R  E  I  Y  K  K  F  G  L  F  Y  V  G  P  I  Q  H  D  A  N  I  I  H  S  K  Q  P  I  N  S  L  D  D  L  K  G
GTTAGAAAAAAACACGTGAAATTTACAAAAAGTTCGGCCTCTTCTACGTCGGCCCAATTCAGCACGACGCAAACATTATCCACAGTAAACAGCCGATTAATTCCCTGGACGACCTTAAGGG
CAATCTTTTTTTGTGCACTTTAAATGTTTTTCAAGCCGGAGAAGATGCAGCCGGGTTAAGTCGTGCTGCGTTTGTAATAGGTGTCATTTGTCGGCTAATTAAGGGACCTGCTGGAATTCCC
       490       500       510       520       530       540       550       560       570       580       590       600

          150                           160                           170                           180
 L  K  M  R  L  P  G  G  M  V  A  E  V  F  A  K  F  G  V  A  A  V  S  L  P  G  S  D  I  F  P  A  L  E  K  G  T  I  D  A
TCTCAAAATGCGCTTACCTGGCGGGATGGTAGCGGAAGTCTTTGCAAAGTTTGGCGTCGCAGCGGTCAGTCTCCCAGGCAGCGACATCTTTCCAGCCTTAGAAAAAGGCACAATCGACGC
AGAGTTTTACGCGAATGGACCGCCCTACCATCGCCTTCAGAAACGTTTCAAACCGCAGCGTCGCCAGTCAGAGGGTCCGTCGCTGTAGAAAGGTCGGAATCTTTTTCCGTGTTAGCTGCG
       610       620       630       640       650       660       670       680       690       700       710       720

          190                           200                           210                           220
 A  D  C  V  G  P  A  V  N  W  E  L  G  F  S  Q  V  T  K  Y  I  L  M  G  P  P  G  I  M  S  V  Y  Q  P  V  D  L  M  D  L
TGCTGATTGTGTGGGTCCGGCTGTAAACTGGGAGCTCGGCTTCAGCCAAGTAACAAAGTACATCTTAATGGGTCCACCAGGCATCATGTCAGTCTACCAACCGGTCGACCTTATGGACCT
ACGACTAACACACCCAGGCCGACATTTGACCCTCGAGCCGAAGTCGGTTCATTGTTTCATGTAGAATTACCCAGGTGGTCCGTAGTACAGTCAGATGGTTGGCCAGCTGGAATACCTGGA
       730       740       750       760       770       780       790       800       810       820       830       840

          230                           240                           250                           260
 T  V  N  L  R  A  W  N  A  L  D  P  K  L  Q  Q  I  V  E  D  E  V  R  I  Y  S  Q  K  H  Y  L  A  I  Q  K  R  N  I  E  A
CACTGTCAATCTGCGGGCCTGGAACGCATTAGATCCAAAGTTACAGCAAATCGTTGAAGATGAAGTACGCATCTACTCTCAGAAGCATTACCTCGCAATTCAGAAACGGAATATTGAAGC
GTGACAGTTAGACGCCCGGACCTTGCGTAATCTAGGTTTCAATGTCGTTTAGCAACTTCTACTTCATGCGTAGATGAGAGTCTTCGTAATGGAGCGTTAAGTCTTTGCCTTATAACTTCG
       850       860       870       880       890       900       910       920       930       940       950       960
```

```
                 270                                     280                                     290                                     300
 M   K   K   F   E   A   A   G   T   T   V   T   R   L   S   Q   E   D   L   Q   E   F   R   R   A   A   I   P   I   W   Y   S   W   A   N   K   D   E   D   A
TATGAAGAAGTTCGAGGCCGCTGGTACAACCGTAACCCGTCTGTCACAAGAGGACCTCCAGGAGTTTCGTCGTGCAGCTATCCCAATTTGGTATTCATGGGCAAACAAAGATGAAGACGC
ATACTTCTTCAAGCTCCGGCGACCATGTTGGCATTGGGCAGACAGTGTTCTCCTGGAGGTCCTCAAAGCAGCACGTCGATAGGGTTAAACCATAAGTACCCGTTTGTTTCTACTTCTGCG
         970          980          990         1000         1010         1020         1030         1040         1050         1060         1070         1080

                 310                                     320                                     330                                     340
 R   E   I   F   D   M   Q   L   E   Y   M   M   N   D   T   V   G   Y   I   T   E   D   D   I   K   G   M   N   G   G   S   H   H   H   H   H   H   *   *
ACGGGAGATTTTCGACATGCAATTAGAGTACATGATGAACGACACTGTAGGTTACATCACTGAAGATGACATTAAGGGCATGAATGGCGGTTCACATCATCATCATCATCATTAATGAAA
TGCCCTCTAAAAGCTGTACGTTAATCTCATGTACTACTTGCTGTGACATCCAATGTAGTGACTTCTACTGTAATTCCCGTACTTACCGCCAAGTGTAGTAGTAGTAGTAGTAATTACTTT
        1090         1100         1110         1120         1130         1140         1150         1160         1170         1180         1190         1200


GGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCC
CCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGG
        1210         1220         1230         1240         1250         1260         1270         1280         1290         1300         1310         1320


TCTAAACGGGTCTTGAGGGGTTTTTTGCTGAAAGGAGGAACTATATCCGGAGCGACTCCCACGGCACGTTGGCAAGCTCG
AGATTTGCCCAGAACTCCCCAAAAAACGACTTTCCTCCTTGATATAGGCCTCGCTGAGGGTGCCGTGCAACCGTTCGAGC
        1330         1340         1350         1360         1370         1380         1390         1400
```

FIG. 43 (Continued)

FIG. 44 - Exemplary Expression Construct for msLacBP6_187C_L70F

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                            10                            20
                                                 M  A  T  T  W  K  I  Q  S  V  W  D  A  G  T  V  G  Y  D  L  F  K  E  W
GGTTTCCCTCTAGAAATAATTTTGTTTAACTTTAAGAAGGAGATATACCATGGCAACAACTTGGAAAATTCAAAGTGTATGGGATGCAGGGACGGTGGGCTATGACCTCTTCAAGGAGTG
CCAAAGGGAGATCTTTATTAAAACAAATTGAAATTCTTCCTCTATATGGTACCGTTGTTGAACCTTTTAAGTTTCACATACCCTACGTCCCTGCCACCCGATACTGGAGAAGTTCCTCAC
       130       140       150       160       170       180       190       200       210       220       230       240

              30                            40                            50                            60
  C  D  G  M  E  E  K  T  G  G  E  L  K  F  T  C  F  P  A  K  A  V  A  A  D  N  N  G  L  F  D  A  V  R  N  G  V  L  Q  G
GTGCGACGGTATGGAAGAAAAGACGGGCGGTGAACTCAAATTCACGTGCTTCCCAGCCAAAGCCGTCGCCGCAGATAATAATGGTCTTTTTGATGCAGTACGGAATGGCGTCTTGCAAGG
CACGCTGCCATACCTTCTTTTCTGCCCGCCACTTGAGTTTAAGTGCACGAAGGGTCGGTTTCGGCAGCGGCGTCTATTATTACCAGAAAAACTACGTCATGCCTTACCGCAGAACGTTCC
       250       260       270       280       290       300       310       320       330       340       350       360

              70                            80                            90                           100
  M  N  P  F  T  F  Y  W  S  G  K  I  P  A  S  V  F  L  S  S  Y  P  A  G  P  D  Q  P  H  Q  W  D  T  M  F  Y  S  L  G  M
TATGAATCCTTTCACCTTTTACTGGTCAGGTAAGATTCCGGCCTCCGTATTTCTCTCGTCGTACCCAGCCGGTCCAGATCAACCACATCAATGGGATACAATGTTCTACAGCCTTGGTAT
ATACTTAGGAAAGTGGAAAATGACCAGTCCATTCTAAGGCCGGAGGCATAAAGAGAGCAGCATGGGTCGGCCAGGTCTAGTTGGTGTAGTTACCCTATGTTACAAGATGTCGGAACCATA
       370       380       390       400       410       420       430       440       450       460       470       480

             110                           120                           130                           140
  L  E  K  T  R  E  I  Y  K  K  F  G  L  F  Y  V  G  P  I  Q  H  D  A  N  I  I  H  S  K  Q  P  I  N  S  L  D  D  L  K  G
GTTAGAAAAAACACGTGAAATTTACAAAAAGTTCGGCCTCTTCTACGTCGGCCCAATTCAGCACGACGCAAACATTATCCACAGTAAACAGCCGATTAATTCCCTGGACGACCTTAAGGG
CAATCTTTTTTGTGCACTTTAAATGTTTTTCAAGCCGGAGAAGATGCAGCCGGGTTAAGTCGTGCTGCGTTTGTAATAGGTGTCATTTGTCGGCTAATTAAGGGACCTGCTGGAATTCCC
       490       500       510       520       530       540       550       560       570       580       590       600

             150                           160                           170                           180
  L  K  M  R  L  P  G  G  M  V  A  E  V  F  A  K  F  G  V  A  A  V  S  L  P  G  S  D  I  F  P  A  L  E  K  G  T  I  D  A
TCTCAAAATGCGCTTACCTGGCGGGATGGTAGCGGAAGTCTTTGCAAAGTTTGGCGTCGCAGCGGTCAGTCTCCCAGGCAGCGACATCTTTCCAGCCTTAGAAAAAGGCACAATCGACGC
AGAGTTTTACGCGAATGGACCGCCCTACCATCGCCTTCAGAAACGTTTCAAACCGCAGCGTCGCCAGTCAGAGGGTCCGTCGCTGTAGAAAGGTCGGAATCTTTTTCCGTGTTAGCTGCG
       610       620       630       640       650       660       670       680       690       700       710       720

             190                           200                           210                           220
  A  D  C  V  G  P  A  V  N  W  E  L  G  F  S  Q  V  T  K  Y  I  L  M  G  P  P  G  I  M  S  V  Y  Q  P  V  D  L  M  D  L
TGCTGATTGTGTGGGTCCGGCTGTAAACTGGGAGCTCGGCTTCAGCCAAGTAACAAAGTACATCTTAATGGGTCCACCAGGCATCATGTCAGTCTACCAACCGGTCGACCTTATGGACCT
ACGACTAACACACCCAGGCCGACATTTGACCCTCGAGCCGAAGTCGGTTCATTGTTTCATGTAGAATTACCCAGGTGGTCCGTAGTACAGTCAGATGGTTGGCCAGCTGGAATACCTGGA
       730       740       750       760       770       780       790       800       810       820       830       840

             230                           240                           250                           260
  T  V  N  L  R  A  W  N  A  L  D  P  K  L  Q  Q  I  V  E  D  E  V  R  I  Y  S  Q  K  H  Y  L  A  I  Q  K  R  N  I  E  A
CACTGTCAATCTGCGGGCCTGGAACGCATTAGATCCAAAGTTACAGCAAATCGTTGAAGATGAAGTACGCATCTACTCTCAGAAGCATTACCTCGCAATTCAGAAACGGAATATTGAAGC
GTGACAGTTAGACGCCCGGACCTTGCGTAATCTAGGTTTCAATGTCGTTTAGCAACTTCTACTTCATGCGTAGATGAGAGTCTTCGTAATGGAGCGTTAAGTCTTTGCCTTATAACTTCG
       850       860       870       880       890       900       910       920       930       940       950       960
```

```
               270                           280                           290                           300
 M  K  K  F  E  A  A  G  T  T  V  T  R  L  S  Q  E  D  L  Q  E  F  R  R  A  A  I  P  I  W  Y  S  W  A  N  K  D  E  D  A
TATGAAGAAGTTCGAGGCCGCTGGTACAACCGTAACCCGTCTGTCACAAGAGGACCTCCAGGAGTTTCGTCGTGCAGCTATCCCAATTTGGTATTCATGGGCAAACAAAGATGAAGACGC
ATACTTCTTCAAGCTCCGGCGACCATGTTGGCATTGGGCAGACAGTGTTCTCCTGGAGGTCCTCAAAGCAGCACGTCGATAGGGTTAAACCATAAGTACCCGTTTGTTTCTACTTCTGCG
       970       980       990      1000      1010      1020      1030      1040      1050      1060      1070      1080

               310                           320                           330                           340
 R  E  I  F  D  M  Q  L  E  Y  M  M  N  D  T  V  G  Y  I  T  E  D  D  I  K  G  M  N  G  G  S  H  H  H  H  H  H  *  *
ACGGGAGATTTTCGACATGCAATTAGAGTACATGATGAACGACACTGTAGGTTACATCACTGAAGATGACATTAAGGGCATGAATGGCGGTTCACATCATCATCATCATCATTAATGAAA
TGCCCTCTAAAAGCTGTACGTTAATCTCATGTACTACTTGCTGTGACATCCAATGTAGTGACTTCTACTGTAATTCCCGTACTTACCGCCAAGTGTAGTAGTAGTAGTAGTAATTACTTT
      1090      1100      1110      1120      1130      1140      1150      1160      1170      1180      1190      1200

GGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCC
CCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGG
      1210      1220      1230      1240      1250      1260      1270      1280      1290      1300      1310      1320

TCTAAACGGGTCTTGAGGGGTTTTTTGCTGAAAGGAGGAACTATATCCGGAGCGACTCCCACGGCACGTTGGCAAGCTCG
AGATTTGCCCAGAACTCCCCAAAAAACGACTTTCCTCCTTGATATAGGCCTCGCTGAGGGTGCCGTGCAACCGTTCGAGC
      1330      1340      1350      1360      1370      1380      1390      1400
```

FIG. 44 (Continued)

FIG. 45 - Exemplary Expression Construct for msLacBP6_187C_L70I

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                 10                            20
                                                                M  A  T  T  W  K  I  Q  S  V  W  D  A  G  T  V  G  Y  D  L  F  K  E  W
GGTTTCCCTCTAGAAATAATTTTGTTTAACTTTAAGAAGGAGATATACCATGGCAACAACTTGGAAAATTCAAAGTGTATGGGATGCAGGGACGGTGGGCTATGACCTCTTCAAGGAGTG
CCAAAGGGAGATCTTTATTAAAACAAATTGAAATTCTTCCTCTATATGGTACCGTTGTTGAACCTTTTAAGTTTCACATACCCTACGTCCCTGCCACCCGATACTGGAGAAGTTCCTCAC
       130       140       150       160       170       180       190       200       210       220       230       240

             30                            40                            50                            60
 C  D  G  M  E  E  K  T  G  G  E  L  K  F  T  C  F  P  A  K  A  V  A  A  D  N  N  G  L  F  D  A  V  R  N  G  V  L  Q  G
GTGCGACGGTATGGAAGAAAAGACGGGCGGTGAACTCAAATTCACGTGCTTCCCAGCCAAAGCCGTCGCCGCAGATAATAATGGTCTTTTTGATGCAGTACGGAATGGCGTCTTGCAAGG
CACGCTGCCATACCTTCTTTTCTGCCCGCCACTTGAGTTTAAGTGCACGAAGGGTCGGTTTCGGCAGCGGCGTCTATTATTACCAGAAAAACTACGTCATGCCTTACCGCAGAACGTTCC
       250       260       270       280       290       300       310       320       330       340       350       360

             70                            80                            90                            100
 M  N  P  F  T  I  Y  W  S  G  K  I  P  A  S  V  F  L  S  S  Y  P  A  G  P  D  Q  P  H  Q  W  D  T  M  F  Y  S  L  G  M
TATGAATCCTTTCACCATTTACTGGTCAGGTAAGATTCCGGCCTCCGTATTTCTCTCGTCGTACCCAGCCGGTCCAGATCAACCACATCAATGGGATACAATGTTCTACAGCCTTGGTAT
ATACTTAGGAAAGTGGTAAATGACCAGTCCATTCTAAGGCCGGAGGCATAAAGAGAGCAGCATGGGTCGGCCAGGTCTAGTTGGTGTAGTTACCCTATGTTACAAGATGTCGGAACCATA
       370       380       390       400       410       420       430       440       450       460       470       480

            110                           120                           130                           140
 L  E  K  T  R  E  I  Y  K  K  F  G  L  F  Y  V  G  P  I  Q  H  D  A  N  I  I  H  S  K  Q  P  I  N  S  L  D  D  L  K  G
GTTAGAAAAAACACGTGAAATTTACAAAAAGTTCGGCCTCTTCTACGTCGGCCCAATTCAGCACGACGCAAACATTATCCACAGTAAACAGCCGATTAATTCCCTGGACGACCTTAAGGG
CAATCTTTTTTGTGCACTTTAAATGTTTTTCAAGCCGGAGAAGATGCAGCCGGGTTAAGTCGTGCTGCGTTTGTAATAGGTGTCATTTGTCGGCTAATTAAGGGACCTGCTGGAATTCCC
       490       500       510       520       530       540       550       560       570       580       590       600

            150                           160                           170                           180
 L  K  M  R  L  P  G  G  M  V  A  E  V  F  A  K  F  G  V  A  A  V  S  L  P  G  S  D  I  F  P  A  L  E  K  G  T  I  D  A
TCTCAAAATGCGCTTACCTGGCGGGATGGTAGCGGAAGTCTTTGCAAAGTTTGGCGTCGCAGCGGTCAGTCTCCCAGGCAGCGACATCTTTCCAGCCTTAGAAAAAGGCACAATCGACGC
AGAGTTTTACGCGAATGGACCGCCCTACCATCGCCTTCAGAAACGTTTCAAACCGCAGCGTCGCCAGTCAGAGGGTCCGTCGCTGTAGAAAGGTCGGAATCTTTTTCCGTGTTAGCTGCG
       610       620       630       640       650       660       670       680       690       700       710       720

            190                           200                           210                           220
 A  D  C  V  G  P  A  V  N  W  E  L  G  F  S  Q  V  T  K  Y  I  L  M  G  P  P  G  I  M  S  V  Y  Q  P  V  D  L  M  D  L
TGCTGATTGTGTGGGTCCGGCTGTAAACTGGGAGCTCGGCTTCAGCCAAGTAACAAAGTACATCTTAATGGGTCCACCAGGCATCATGTCAGTCTACCAACCGGTCGACCTTATGGACCT
ACGACTAACACACCCAGGCCGACATTTGACCCTCGAGCCGAAGTCGGTTCATTGTTTCATGTAGAATTACCCAGGTGGTCCGTAGTACAGTCAGATGGTTGGCCAGCTGGAATACCTGGA
       730       740       750       760       770       780       790       800       810       820       830       840

            230                           240                           250                           260
 T  V  N  L  R  A  W  N  A  L  D  P  K  L  Q  Q  I  V  E  D  E  V  R  I  Y  S  Q  K  H  Y  L  A  I  Q  K  R  N  I  E  A
CACTGTCAATCTGCGGGCCTGGAACGCATTAGATCCAAAGTTACAGCAAATCGTTGAAGATGAAGTACGCATCTACTCTCAGAAGCATTACCTCGCAATTCAGAAACGGAATATTGAAGC
GTGACAGTTAGACGCCCGGACCTTGCGTAATCTAGGTTTCAATGTCGTTTAGCAACTTCTACTTCATGCGTAGATGAGAGTCTTCGTAATGGAGCGTTAAGTCTTTGCCTTATAACTTCG
       850       860       870       880       890       900       910       920       930       940       950       960
```

```
               270                                     280                                     290                                     300
 M   K   K   F   E   A   A   G   T   T   V   T   R   L   S   Q   E   D   L   Q   E   F   R   R   A   A   I   P   I   W   Y   S   W   A   N   K   D   E   D   A
TATGAAGAAGTTCGAGGCCGCTGGTACAACCGTAACCCGTCTGTCACAAGAGGACCTCCAGGAGTTTCGTCGTGCAGCTATCCCAATTTGGTATTCATGGCAAACAAAGATGAAGACGC
ATACTTCTTCAAGCTCCGGCGACCATGTTGGCATTGGGCAGACAGTGTTCTCCTGGAGGTCCTCAAAGCAGCACGTCGATAGGGTTAAACCATAAGTACCCGTTTGTTTCTACTTCTGCG
        970       980       990      1000      1010      1020      1030      1040      1050      1060      1070      1080

               310                                     320                                     330                                     340
 R   E   I   F   D   M   Q   L   E   Y   M   M   N   D   T   V   G   Y   I   T   E   D   D   I   K   G   M   N   G   G   S   H   H   H   H   H   H   *   *
ACGGGAGATTTTCGACATGCAATTAGAGTACATGATGAACGACACTGTAGGTTACATCACTGAAGATGACATTAAGGGCATGAATGGCGGTTCACATCATCATCATCATCATTAATGAAA
TGCCCTCTAAAAGCTGTACGTTAATCTCATGTACTACTTGCTGTGACATCCAATGTAGTGACTTCTACTGTAATTCCCGTACTTACCGCCAAGTGTAGTAGTAGTAGTAGTAATTACTTT
      1090      1100      1110      1120      1130      1140      1150      1160      1170      1180      1190      1200


GGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCC
CCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGG
      1210      1220      1230      1240      1250      1260      1270      1280      1290      1300      1310      1320


TCTAAACGGGTCTTGAGGGGTTTTTTGCTGAAAGGAGGAACTATATCCGGAGCGACTCCCACGGCACGTTGGCAAGCTCG
AGATTTGCCCAGAACTCCCCAAAAAACGACTTTCCTCCTTGATATAGGCCTCGCTGAGGGTGCCGTGCAACCGTTCGAGC
      1330      1340      1350      1360      1370      1380      1390      1400
```

FIG. 45 (Continued)

FIG. 46 - Exemplary Expression Construct for msLacBP6_187C_L70M

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                     10                            20
                                                            M  A  T  T  W  K  I  Q  S  V  W  D  A  G  T  V  G  Y  D  L  F  K  E  W
GGTTTCCCTCTAGAAATAATTTTGTTTAACTTTAAGAAGGAGATATACCATGGCAACAACTTGGAAAATTCAAAGTGTATGGGATGCAGGGACGGTGGGCTATGACCTCTTCAAGGAGTG
CCAAAGGGAGATCTTTATTAAAACAAATTGAAATTCTTCCTCTATATGGTACCGTTGTTGAACCTTTTAAGTTTCACATACCCTACGTCCCTGCCACCCGATACTGGAGAAGTTCCTCAC
       130       140       150       160       170       180       190       200       210       220       230       240

           30                            40                            50                            60
 C  D  G  M  E  E  K  T  G  G  E  L  K  F  T  C  F  P  A  K  A  V  A  A  D  N  N  G  L  F  D  A  V  R  N  G  V  L  Q  G
GTGCGACGGTATGGAAGAAAAGACGGGCGGTGAACTCAAATTCACGTGCTTCCCAGCCAAAGCCGTCGCCGCAGATAATAATGGTCTTTTTGATGCAGTACGGAATGGCGTCTTGCAAGG
CACGCTGCCATACCTTCTTTTCTGCCCGCCACTTGAGTTTAAGTGCACGAAGGGTCGGTTTCGGCAGCGGCGTCTATTATTACCAGAAAAACTACGTCATGCCTTACCGCAGAACGTTCC
       250       260       270       280       290       300       310       320       330       340       350       360

           70                            80                            90                           100
 M  N  P  F  T  M  Y  W  S  G  K  I  P  A  S  V  F  L  S  S  Y  P  A  G  P  D  Q  P  H  Q  W  D  T  M  F  Y  S  L  G  M
TATGAATCCTTTCACCATGTACTGGTCAGGTAAGATTCCGGCCTCCGTATTTCTCTCGTCGTACCCAGCCGGTCCAGATCAACCACATCAATGGGATACAATGTTCTACAGCCTTGGTAT
ATACTTAGGAAAGTGGTACATGACCAGTCCATTCTAAGGCCGGAGGCATAAAGAGAGCAGCATGGGTCGGCCAGGTCTAGTTGGTGTAGTTACCCTATGTTACAAGATGTCGGAACCATA
       370       380       390       400       410       420       430       440       450       460       470       480

          110                           120                           130                           140
 L  E  K  T  R  E  I  Y  K  K  F  G  L  F  Y  V  G  P  I  Q  H  D  A  N  I  I  H  S  K  Q  P  I  N  S  L  D  D  L  K  G
GTTAGAAAAAACACGTGAAATTTACAAAAAGTTCGGCCTCTTCTACGTCGGCCCAATTCAGCACGACGCAAACATTATCCACAGTAAACAGCCGATTAATTCCCTGGACGACCTTAAGGG
CAATCTTTTTTGTGCACTTTAAATGTTTTTCAAGCCGGAGAAGATGCAGCCGGGTTAAGTCGTGCTGCGTTTGTAATAGGTGTCATTTGTCGGCTAATTAAGGGACCTGCTGGAATTCCC
       490       500       510       520       530       540       550       560       570       580       590       600

          150                           160                           170                           180
 L  K  M  R  L  P  G  G  M  V  A  E  V  F  A  K  F  G  V  A  A  V  S  L  P  G  S  D  I  F  P  A  L  E  K  G  T  I  D  A
TCTCAAAATGCGCTTACCTGGCGGGATGGTAGCGGAAGTCTTTGCAAAGTTTGGCGTCGCAGCGGTCAGTCTCCCAGGCAGCGACATCTTTCCAGCCTTAGAAAAAGGCACAATCGACGC
AGAGTTTTACGCGAATGGACCGCCCTACCATCGCCTTCAGAAACGTTTCAAACCGCAGCGTCGCCAGTCAGAGGGTCCGTCGCTGTAGAAAGGTCGGAATCTTTTTCCGTGTTAGCTGCG
       610       620       630       640       650       660       670       680       690       700       710       720

          190                           200                           210                           220
 A  D  C  V  G  P  A  V  N  W  E  L  G  F  S  Q  V  T  K  Y  I  L  M  G  P  P  G  I  M  S  V  Y  Q  P  V  D  L  M  D  L
TGCTGATTGTGTGGGTCCGGCTGTAAACTGGGAGCTCGGCTTCAGCCAAGTAACAAAGTACATCTTAATGGGTCCACCAGGCATCATGTCAGTCTACCAACCGGTCGACCTTATGGACCT
ACGACTAACACACCCAGGCCGACATTTGACCCTCGAGCCGAAGTCGGTTCATTGTTTCATGTAGAATTACCCAGGTGGTCCGTAGTACAGTCAGATGGTTGGCCAGCTGGAATACCTGGA
       730       740       750       760       770       780       790       800       810       820       830       840

          230                           240                           250                           260
 T  V  N  L  R  A  W  N  A  L  D  P  K  L  Q  Q  I  V  E  D  E  V  R  I  Y  S  Q  K  H  Y  L  A  I  Q  K  R  N  I  E  A
CACTGTCAATCTGCGGGCCTGGAACGCATTAGATCCAAAGTTACAGCAAATCGTTGAAGATGAAGTACGCATCTACTCTCAGAAGCATTACCTCGCAATTCAGAAACGGAATATTGAAGC
GTGACAGTTAGACGCCCGGACCTTGCGTAATCTAGGTTTCAATGTCGTTTAGCAACTTCTACTTCATGCGTAGATGAGAGTCTTCGTAATGGAGCGTTAAGTCTTTGCCTTATAACTTCG
       850       860       870       880       890       900       910       920       930       940       950       960
```

```
              270                                     280                                     290                                     300
  M   K   K   F   E   A   A   G   T   T   V   T   R   L   S   Q   E   D   L   Q   E   F   R   R   A   A   I   P   I   W   Y   S   W   A   N   K   D   E   D   A
TATGAAGAAGTTCGAGGCCGCTGGTACAACCGTAACCCGTCTGTCACAAGAGGACCTCCAGGAGTTTCGTCGTGCAGCTATCCCAATTTGGTATTCATGGGCAAACAAAGATGAAGACGC
ATACTTCTTCAAGCTCCGGCGACCATGTTGGCATTGGGCAGACAGTGTTCTCCTGGAGGTCCTCAAAGCAGCACGTCGATAGGGTTAAACCATAAGTACCCGTTTGTTTCTACTTCTGCG
        970         980         990        1000        1010        1020        1030        1040        1050        1060        1070        1080

              310                                     320                                     330                                     340
  R   E   I   F   D   M   Q   L   E   Y   M   M   N   D   T   V   G   Y   I   T   E   D   D   I   K   G   M   N   G   G   S   H   H   H   H   H   H   *   *
ACGGGAGATTTTCGACATGCAATTAGAGTACATGATGAACGACACTGTAGGTTACATCACTGAAGATGACATTAAGGGCATGAATGGCGGTTCACATCATCATCATCATCATTAATGAAA
TGCCCTCTAAAAGCTGTACGTTAATCTCATGTACTACTTGCTGTGACATCCAATGTAGTGACTTCTACTGTAATTCCCGTACTTACCGCCAAGTGTAGTAGTAGTAGTAGTAATTACTTT
       1090        1100        1110        1120        1130        1140        1150        1160        1170        1180        1190        1200

GGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCC
CCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGG
       1210        1220        1230        1240        1250        1260        1270        1280        1290        1300        1310        1320

TCTAAACGGGTCTTGAGGGGTTTTTTGCTGAAAGGAGGAACTATATCCGGAGCGACTCCCACGGCACGTTGGCAAGCTCG
AGATTTGCCCAGAACTCCCCAAAAAACGACTTTCCTCCTTGATATAGGCCTCGCTGAGGGTGCCGTGCAACCGTTCGAGC
       1330        1340        1350        1360        1370        1380        1390        1400
```

FIG. 46 (Continued)

FIG. 47 - Exemplary Expression Construct for msLacBP6_187C_P150A

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                  10                            20
                                                   M  A  T  T  W  K  I  Q  S  V  W  D  A  G  T  V  G  Y  D  L  F  K  E  W
GGTTTCCCTCTAGAAATAATTTTGTTTAACTTTAAGAAGGAGATATACCATGGCAACAACTTGGAAAATTCAAAGTGTATGGGATGCAGGGACGGTGGGCTATGACCTCTTCAAGGAGTG
CCAAAGGGAGATCTTTATTAAAACAAATTGAAATTCTTCCTCTATATGGTACCGTTGTTGAACCTTTTAAGTTTCACATACCCTACGTCCCTGCCACCCGATACTGGAGAAGTTCCTCAC
       130       140       150       160       170       180       190       200       210       220       230       240

              30                            40                            50                            60
 C  D  G  M  E  E  K  T  G  G  E  L  K  F  T  C  F  P  A  K  A  V  A  A  D  N  N  G  L  F  D  A  V  R  N  G  V  L  Q  G
GTGCGACGGTATGGAAGAAAAGACGGGCGGTGAACTCAAATTCACGTGCTTCCCAGCCAAAGCCGTCGCCGCAGATAATAATGGTCTTTTTGATGCAGTACGGAATGGCGTCTTGCAAGG
CACGCTGCCATACCTTCTTTTCTGCCCGCCACTTGAGTTTAAGTGCACGAAGGGTCGGTTTCGGCAGCGGCGTCTATTATTACCAGAAAAACTACGTCATGCCTTACCGCAGAACGTTCC
       250       260       270       280       290       300       310       320       330       340       350       360

              70                            80                            90                           100
 M  N  P  F  T  L  Y  W  S  G  K  I  P  A  S  V  F  L  S  S  Y  P  A  G  P  D  Q  P  H  Q  W  D  T  M  F  Y  S  L  G  M
TATGAATCCTTTCACCCTCTACTGGTCAGGTAAGATTCCGGCCTCCGTATTTCTCTCGTCGTACCCAGCCGGTCCAGATCAACCACATCAATGGGATACAATGTTCTACAGCCTTGGTAT
ATACTTAGGAAAGTGGGAGATGACCAGTCCATTCTAAGGCCGGAGGCATAAAGAGAGCAGCATGGGTCGGCCAGGTCTAGTTGGTGTAGTTACCCTATGTTACAAGATGTCGGAACCATA
       370       380       390       400       410       420       430       440       450       460       470       480

             110                           120                           130                           140
 L  E  K  T  R  E  I  Y  K  K  F  G  L  F  Y  V  G  P  I  Q  H  D  A  N  I  I  H  S  K  Q  P  I  N  S  L  D  D  L  K  G
GTTAGAAAAAACACGTGAAATTTACAAAAAGTTCGGCCTCTTCTACGTCGGCCCAATTCAGCACGACGCAAACATTATCCACAGTAAACAGCCGATTAATTCCCTGGACGACCTTAAGGG
CAATCTTTTTTGTGCACTTTAAATGTTTTTCAAGCCGGAGAAGATGCAGCCGGGTTAAGTCGTGCTGCGTTTGTAATAGGTGTCATTTGTCGGCTAATTAAGGGACCTGCTGGAATTCCC
       490       500       510       520       530       540       550       560       570       580       590       600

             150                           160                           170                           180
 L  K  M  R  L  A  G  G  M  V  A  E  V  F  A  K  F  G  V  A  A  V  S  L  P  G  S  D  I  F  P  A  L  E  K  G  T  I  D  A
TCTCAAAATGCGCTTAGCGGGCGGGATGGTAGCGGAAGTCTTTGCAAAGTTTGGCGTCGCAGCGGTCAGTCTCCCAGGCAGCGACATCTTTCCAGCCTTAGAAAAAGGCACAATCGACGC
AGAGTTTTACGCGAATCGCCCGCCCTACCATCGCCTTCAGAAACGTTTCAAACCGCAGCGTCGCCAGTCAGAGGGTCCGTCGCTGTAGAAAGGTCGGAATCTTTTTCCGTGTTAGCTGCG
       610       620       630       640       650       660       670       680       690       700       710       720

             190                           200                           210                           220
 A  D  C  V  G  P  A  V  N  W  E  L  G  F  S  Q  V  T  K  Y  I  L  M  G  P  P  G  I  M  S  V  Y  Q  P  V  D  L  M  D  L
TGCTGATTGTGTGGGTCCGGCTGTAAACTGGGAGCTCGGCTTCAGCCAAGTAACAAAGTACATCTTAATGGGTCCACCAGGCATCATGTCAGTCTACCAACCGGTCGACCTTATGGACCT
ACGACTAACACACCCAGGCCGACATTTGACCCTCGAGCCGAAGTCGGTTCATTGTTTCATGTAGAATTACCCAGGTGGTCCGTAGTACAGTCAGATGGTTGGCCAGCTGGAATACCTGGA
       730       740       750       760       770       780       790       800       810       820       830       840

             230                           240                           250                           260
 T  V  N  L  R  A  W  N  A  L  D  P  K  L  Q  Q  I  V  E  D  E  V  R  I  Y  S  Q  K  H  Y  L  A  I  Q  K  R  N  I  E  A
CACTGTCAATCTGCGGGCCTGGAACGCATTAGATCCAAAGTTACAGCAAATCGTTGAAGATGAAGTACGCATCTACTCTCAGAAGCATTACCTCGCAATTCAGAAACGGAATATTGAAGC
GTGACAGTTAGACGCCCGGACCTTGCGTAATCTAGGTTTCAATGTCGTTTAGCAACTTCTACTTCATGCGTAGATGAGAGTCTTCGTAATGGAGCGTTAAGTCTTTGCCTTATAACTTCG
       850       860       870       880       890       900       910       920       930       940       950       960
```

```
             270                           280                           290                           300
 M   K   K   F   E   A   A   G   T   T   V   T   R   L   S   Q   E   D   L   Q   E   F   R   R   A   A   I   P   I   W   Y   S   W   A   N   K   D   E   D   A
TATGAAGAAGTTCGAGGCCGCTGGTACAACCGTAACCCGTCTGTCACAAGAGGACCTCCAGGAGTTTCGTCGTGCAGCTATCCCAATTTGGTATTCATGGGCAAACAAAGATGAAGACGC
ATACTTCTTCAAGCTCCGGCGACCATGTTGGCATTGGGCAGACAGTGTTCTCCTGGAGGTCCTCAAAGCAGCACGTCGATAGGGTTAAACCATAAGTACCCGTTTGTTTCTACTTCTGCG
       970       980       990      1000      1010      1020      1030      1040      1050      1060      1070      1080

             310                           320                           330                           340
 R   E   I   F   D   M   Q   L   E   Y   M   M   N   D   T   V   G   Y   I   T   E   D   D   I   K   G   M   N   G   G   S   H   H   H   H   H   H   *   *
ACGGGAGATTTTCGACATGCAATTAGAGTACATGATGAACGACACTGTAGGTTACATCACTGAAGATGACATTAAGGGCATGAATGGCGGTTCACATCATCATCATCATCATTAATGAAA
TGCCCTCTAAAAGCTGTACGTTAATCTCATGTACTACTTGCTGTGACATCCAATGTAGTGACTTCTACTGTAATTCCCGTACTTACCGCCAAGTGTAGTAGTAGTAGTAGTAATTACTTT
      1090      1100      1110      1120      1130      1140      1150      1160      1170      1180      1190      1200

GGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCC
CCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGG
      1210      1220      1230      1240      1250      1260      1270      1280      1290      1300      1310      1320

TCTAAACGGGTCTTGAGGGGTTTTTTGCTGAAAGGAGGAACTATATCCGGAGCGACTCCCACGGCACGTTGGCAAGCTCG
AGATTTGCCCAGAACTCCCCAAAAAACGACTTTCCTCCTTGATATAGGCCTCGCTGAGGGTGCCGTGCAACCGTTCGAGC
      1330      1340      1350      1360      1370      1380      1390      1400
```

FIG. 47 (Continued)

FIG. 48 - Exemplary Expression Construct for msLacBP6_187C_P150S

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                 10                            20
                                                        M  A  T  T  W  K  I  Q  S  V  W  D  A  G  T  V  G  Y  D  L  F  K  E  W
GGTTTCCCTCTAGAAATAATTTTGTTTAACTTTAAGAAGGAGATATACCATGGCAACAACTTGGAAAATTCAAAGTGTATGGGATGCAGGGACGGTGGGCTATGACCTCTTCAAGGAGTG
CCAAAGGGAGATCTTTATTAAAACAAATTGAAATTCTTCCTCTATATGGTACCGTTGTTGAACCTTTTAAGTTTCACATACCCTACGTCCCTGCCACCCGATACTGGAGAAGTTCCTCAC
       130       140       150       160       170       180       190       200       210       220       230       240

         30                            40                            50                            60
 C  D  G  M  E  E  K  T  G  G  E  L  K  F  T  C  F  P  A  K  A  V  A  A  D  N  N  G  L  F  D  A  V  R  N  G  V  L  Q  G
GTGCGACGGTATGGAAGAAAAGACGGGCGGTGAACTCAAATTCACGTGCTTCCCAGCCAAAGCCGTCGCCGCAGATAATAATGGTCTTTTTGATGCAGTACGGAATGGCGTCTTGCAAGG
CACGCTGCCATACCTTCTTTTCTGCCCGCCACTTGAGTTTAAGTGCACGAAGGGTCGGTTTCGGCAGCGGCGTCTATTATTACCAGAAAAACTACGTCATGCCTTACCGCAGAACGTTCC
       250       260       270       280       290       300       310       320       330       340       350       360

         70                            80                            90                           100
 M  N  P  F  T  L  Y  W  S  G  K  I  P  A  S  V  F  L  S  S  Y  P  A  G  P  D  Q  P  H  Q  W  D  T  M  F  Y  S  L  G  M
TATGAATCCTTTCACCCTCTACTGGTCAGGTAAGATTCCGGCCTCCGTATTTCTCTCGTCGTACCCAGCCGGTCCAGATCAACCACATCAATGGGATACAATGTTCTACAGCCTTGGTAT
ATACTTAGGAAAGTGGGAGATGACCAGTCCATTCTAAGGCCGGAGGCATAAAGAGAGCAGCATGGGTCGGCCAGGTCTAGTTGGTGTAGTTACCCTATGTTACAAGATGTCGGAACCATA
       370       380       390       400       410       420       430       440       450       460       470       480

        110                           120                           130                           140
 L  E  K  T  R  E  I  Y  K  K  F  G  L  F  Y  V  G  P  I  Q  H  D  A  N  I  I  H  S  K  Q  P  I  N  S  L  D  D  L  K  G
GTTAGAAAAAAACACGTGAAATTTACAAAAAGTTCGGCCTCTTCTACGTCGGCCCAATTCAGCACGACGCAAACATTATCCACAGTAAACAGCCGATTAATTCCCTGGACGACCTTAAGGG
CAATCTTTTTTGTGCACTTTAAATGTTTTTCAAGCCGGAGAAGATGCAGCCGGGTTAAGTCGTGCTGCGTTTGTAATAGGTGTCATTTGTCGGCTAATTAAGGGACCTGCTGGAATTCCC
       490       500       510       520       530       540       550       560       570       580       590       600

        150                           160                           170                           180
 L  K  M  R  L  S  G  G  M  V  A  E  V  F  A  K  F  G  V  A  A  V  S  L  P  G  S  D  I  F  P  A  L  E  K  G  T  I  D  A
TCTCAAAATGCGCTTAAGCGGCGGGATGGTAGCGGAAGTCTTTGCAAAGTTTGGCGTCGCAGCGGTCAGTCTCCCAGGCAGCGACATCTTTCCAGCCTTAGAAAAAGGCACAATCGACGC
AGAGTTTTACGCGAATTCGCCGCCCTACCATCGCCTTCAGAAACGTTTCAAACCGCAGCGTCGCCAGTCAGAGGGTCCGTCGCTGTAGAAAGGTCGGAATCTTTTTCCGTGTTAGCTGCG
       610       620       630       640       650       660       670       680       690       700       710       720

        190                           200                           210                           220
 A  D  C  V  G  P  A  V  N  W  E  L  G  F  S  Q  V  T  K  Y  I  L  M  G  P  P  G  I  M  S  V  Y  Q  P  V  D  L  M  D  L
TGCTGATTGTGTGGGTCCGGCTGTAAACTGGGAGCTCGGCTTCAGCCAAGTAACAAAGTACATCTTAATGGGTCCACCAGGCATCATGTCAGTCTACCAACCGGTCGACCTTATGGACCT
ACGACTAACACACCCAGGCCGACATTTGACCCTCGAGCCGAAGTCGGTTCATTGTTTCATGTAGAATTACCCAGGTGGTCCGTAGTACAGTCAGATGGTTGGCCAGCTGGAATACCTGGA
       730       740       750       760       770       780       790       800       810       820       830       840

        230                           240                           250                           260
 T  V  N  L  R  A  W  N  A  L  D  P  K  L  Q  Q  I  V  E  D  E  V  R  I  Y  S  Q  K  H  Y  L  A  I  Q  K  R  N  I  E  A
CACTGTCAATCTGCGGGCCTGGAACGCATTAGATCCAAAGTTACAGCAAATCGTTGAAGATGAAGTACGCATCTACTCTCAGAAGCATTACCTCGCAATTCAGAAACGGAATATTGAAGC
GTGACAGTTAGACGCCCGGACCTTGCGTAATCTAGGTTTCAATGTCGTTTAGCAACTTCTACTTCATGCGTAGATGAGAGTCTTCGTAATGGAGCGTTAAGTCTTTGCCTTATAACTTCG
       850       860       870       880       890       900       910       920       930       940       950       960
```

```
             270                                     280                                     290                                     300
 M  K  K  F  E  A  A  G  T  T  V  T  R  L  S  Q  E  D  L  Q  E  F  R  R  A  A  I  P  I  W  Y  S  W  A  N  K  D  E  D  A
TATGAAGAAGTTCGAGGCCGCTGGTACAACCGTAACCCGTCTGTCACAAGAGGACCTCCAGGAGTTTCGTCGTGCAGCTATCCCAATTTGGTATTCATGGCAAACAAAGATGAAGACGC
ATACTTCTTCAAGCTCCGGCGACCATGTTGGCATTGGGCAGACAGTGTTCTCCTGGAGGTCCTCAAAGCAGCACGTCGATAGGGTTAAACCATAAGTACCCGTTTGTTTCTACTTCTGCG
        970       980       990      1000      1010      1020      1030      1040      1050      1060      1070      1080

             310                                     320                                     330                                     340
 R  E  I  F  D  M  Q  L  E  Y  M  M  N  D  T  V  G  Y  I  T  E  D  D  I  K  G  M  N  G  G  S  H  H  H  H  H  H  *  *
ACGGGAGATTTTCGACATGCAATTAGAGTACATGATGAACGACACTGTAGGTTACATCACTGAAGATGACATTAAGGGCATGAATGGCGGTTCACATCATCATCATCATCATTAATGAAA
TGCCCTCTAAAAGCTGTACGTTAATCTCATGTACTACTTGCTGTGACATCCAATGTAGTGACTTCTACTGTAATTCCCGTACTTACCGCCAAGTGTAGTAGTAGTAGTAGTAATTACTTT
       1090      1100      1110      1120      1130      1140      1150      1160      1170      1180      1190      1200

GGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCC
CCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGG
       1210      1220      1230      1240      1250      1260      1270      1280      1290      1300      1310      1320

TCTAAACGGGTCTTGAGGGGTTTTTTGCTGAAAGGAGGAACTATATCCGGAGCGACTCCCACGGCACGTTGGCAAGCTCG
AGATTTGCCCAGAACTCCCCAAAAAACGACTTTCCTCCTTGATATAGGCCTCGCTGAGGGTGCCGTGCAACCGTTCGAGC
       1330      1340      1350      1360      1370      1380      1390      1400
```

FIG. 48 (Continued)

FIG. 49 - Exemplary Expression Construct for msLacBP6_187C_D220E

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                    10                            20
                                                                 M  A  T  T  W  K  I  Q  S  V  W  D  A  G  T  V  G  Y  D  L  F  K  E  W
GGTTTCCCTCTAGAAATAATTTTGTTTAACTTTAAGAAGGAGATATACCATGGCAACAACTTGGAAAATTCAAAGTGTATGGGATGCAGGGACGGTGGGCTATGACCTCTTCAAGGAGTG
CCAAAGGGAGATCTTTATTAAAACAAATTGAAATTCTTCCTCTATATGGTACCGTTGTTGAACCTTTTAAGTTTCACATACCCTACGTCCCTGCCACCCGATACTGGAGAAGTTCCTCAC
       130       140       150       160       170       180       190       200       210       220       230       240

             30                            40                            50                            60
 C  D  G  M  E  E  K  T  G  G  E  L  K  F  T  C  F  P  A  K  A  V  A  A  D  N  N  G  L  F  D  A  V  R  N  G  V  L  Q  G
GTGCGACGGTATGGAAGAAAAGACGGGCGGTGAACTCAAATTCACGTGCTTCCCAGCCAAAGCCGTCGCCGCAGATAATAATGGTCTTTTTGATGCAGTACGGAATGGCGTCTTGCAAGG
CACGCTGCCATACCTTCTTTTCTGCCCGCCACTTGAGTTTAAGTGCACGAAGGGTCGGTTTCGGCAGCGGCGTCTATTATTACCAGAAAAACTACGTCATGCCTTACCGCAGAACGTTCC
       250       260       270       280       290       300       310       320       330       340       350       360

             70                            80                            90                           100
 M  N  P  F  T  L  Y  W  S  G  K  I  P  A  S  V  F  L  S  S  Y  P  A  G  P  D  Q  P  H  Q  W  D  T  M  F  Y  S  L  G  M
TATGAATCCTTTCACCCTCTACTGGTCAGGTAAGATTCCGGCCTCCGTATTTCTCTCGTCGTACCCAGCCGGTCCAGATCAACCACATCAATGGGATACAATGTTCTACAGCCTTGGTAT
ATACTTAGGAAAGTGGGAGATGACCAGTCCATTCTAAGGCCGGAGGCATAAAGAGAGCAGCATGGGTCGGCCAGGTCTAGTTGGTGTAGTTACCCTATGTTACAAGATGTCGGAACCATA
       370       380       390       400       410       420       430       440       450       460       470       480

            110                           120                           130                           140
 L  E  K  T  R  E  I  Y  K  K  F  G  L  F  Y  V  G  P  I  Q  H  D  A  N  I  I  H  S  K  Q  P  I  N  S  L  D  D  L  K  G
GTTAGAAAAAAACACGTGAAATTTACAAAAAGTTCGGCCTCTTCTACGTCGGCCCAATTCAGCACGACGCAAACATTATCCACAGTAAACAGCCGATTAATTCCCTGGACGACCTTAAGGG
CAATCTTTTTTTGTGCACTTTAAATGTTTTTCAAGCCGGAGAAGATGCAGCCGGGTTAAGTCGTGCTGCGTTTGTAATAGGTGTCATTTGTCGGCTAATTAAGGGACCTGCTGGAATTCCC
       490       500       510       520       530       540       550       560       570       580       590       600

            150                           160                           170                           180
 L  K  M  R  L  P  G  G  M  V  A  E  V  F  A  K  F  G  V  A  A  V  S  L  P  G  S  D  I  F  P  A  L  E  K  G  T  I  D  A
TCTCAAAATGCGCTTACCTGGCGGGATGGTAGCGGAAGTCTTTGCAAAGTTTGGCGTCGCAGCGGTCAGTCTCCCAGGCAGCGACATCTTTCCAGCCTTAGAAAAAGGCACAATCGACGC
AGAGTTTTACGCGAATGGACCGCCCTACCATCGCCTTCAGAAACGTTTCAAACCGCAGCGTCGCCAGTCAGAGGGTCCGTCGCTGTAGAAAGGTCGGAATCTTTTTCCGTGTTAGCTGCG
       610       620       630       640       650       660       670       680       690       700       710       720

            190                           200                           210                           220
 A  D  C  V  G  P  A  V  N  W  E  L  G  F  S  Q  V  T  K  Y  I  L  M  G  P  P  G  I  M  S  V  Y  Q  P  V  E  L  M  D  L
TGCTGATTGTGTGGGTCCGGCTGTAAACTGGGAGCTCGGCTTCAGCCAAGTAACAAAGTACATCTTAATGGGTCCACCAGGCATCATGTCAGTCTACCAACCGGTCGAACTTATGGACCT
ACGACTAACACACCCAGGCCGACATTTGACCCTCGAGCCGAAGTCGGTTCATTGTTTCATGTAGAATTACCCAGGTGGTCCGTAGTACAGTCAGATGGTTGGCCAGCTTGAATACCTGGA
       730       740       750       760       770       780       790       800       810       820       830       840

            230                           240                           250                           260
 T  V  N  L  R  A  W  N  A  L  D  P  K  L  Q  Q  I  V  E  D  E  V  R  I  Y  S  Q  K  H  Y  L  A  I  Q  K  R  N  I  E  A
CACTGTCAATCTGCGGGCCTGGAACGCATTAGATCCAAAGTTACAGCAAATCGTTGAAGATGAAGTACGCATCTACTCTCAGAAGCATTACCTCGCAATTCAGAAACGGAATATTGAAGC
GTGACAGTTAGACGCCCGGACCTTGCGTAATCTAGGTTTCAATGTCGTTTAGCAACTTCTACTTCATGCGTAGATGAGAGTCTTCGTAATGGAGCGTTAAGTCTTTGCCTTATAACTTCG
```

```
        850       860       870       880       890       900       910       920       930       940       950       960
                 270                           280                           290                           300
 M  K  K  F  E  A  A  G  T  T  V  T  R  L  S  Q  E  D  L  Q  E  F  R  R  A  A  I  P  I  W  Y  S  W  A  N  K  D  E  D  A
TATGAAGAAGTTCGAGGCCGCTGGTACAACCGTAACCCGTCTGTCACAAGAGGACCTCCAGGAGTTTCGTCGTGCAGCTATCCCAATTTGGTATTCATGGGCAAACAAAGATGAAGACGC
ATACTTCTTCAAGCTCCGGCGACCATGTTGGCATTGGGCAGACAGTGTTCTCCTGGAGGTCCTCAAAGCAGCACGTCGATAGGGTTAAACCATAAGTACCCGTTTGTTTCTACTTCTGCG
        970       980       990      1000      1010      1020      1030      1040      1050      1060      1070      1080

                 310                           320                           330                           340
 R  E  I  F  D  M  Q  L  E  Y  M  M  N  D  T  V  G  Y  I  T  E  D  D  I  K  G  M  N  G  G  S  H  H  H  H  H  H  *  *
ACGGGAGATTTTCGACATGCAATTAGAGTACATGATGAACGACACTGTAGGTTACATCACTGAAGATGACATTAAGGGCATGAATGGCGGTTCACATCATCATCATCATCATTAATGAAA
TGCCCTCTAAAAGCTGTACGTTAATCTCATGTACTACTTGCTGTGACATCCAATGTAGTGACTTCTACTGTAATTCCCGTACTTACCGCCAAGTGTAGTAGTAGTAGTAGTAATTACTTT
       1090      1100      1110      1120      1130      1140      1150      1160      1170      1180      1190      1200


GGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCC
CCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGG
       1210      1220      1230      1240      1250      1260      1270      1280      1290      1300      1310      1320


TCTAAACGGGTCTTGAGGGGTTTTTTGCTGAAAGGAGGAACTATATCCGGAGCGACTCCCACGGCACGTTGGCAAGCTCG
AGATTTGCCCAGAACTCCCCAAAAAACGACTTTCCTCCTTGATATAGGCCTCGCTGAGGGTGCCGTGCAACCGTTCGAGC
       1330      1340      1350      1360      1370      1380      1390      1400
```

FIG. 49 (Continued)

FIG. 50 - Exemplary Expression Construct for msLacBP6_187C_D220L

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                    10                            20
                                                   M  A  T  T  W  K  I  Q  S  V  W  D  A  G  T  V  G  Y  D  L  F  K  E  W
GGTTTCCCTCTAGAAATAATTTTGTTTAACTTTAAGAAGGAGATATACCATGGCAACAACTTGGAAAATTCAAAGTGTATGGGATGCAGGGACGGTGGGCTATGACCTCTTCAAGGAGTG
CCAAAGGGAGATCTTTATTAAAACAAATTGAAATTCTTCCTCTATATGGTACCGTTGTTGAACCTTTTAAGTTTCACATACCCTACGTCCCTGCCACCCGATACTGGAGAAGTTCCTCAC
       130       140       150       160       170       180       190       200       210       220       230       240

         30                            40                            50                            60
 C  D  G  M  E  E  K  T  G  G  E  L  K  F  T  C  F  P  A  K  A  V  A  A  D  N  N  G  L  F  D  A  V  R  N  G  V  L  Q  G
GTGCGACGGTATGGAAGAAAAGACGGGCGGTGAACTCAAATTCACGTGCTTCCCAGCCAAAGCCGTCGCCGCAGATAATAATGGTCTTTTTGATGCAGTACGGAATGGCGTCTTGCAAGG
CACGCTGCCATACCTTCTTTTCTGCCCGCCACTTGAGTTTAAGTGCACGAAGGGTCGGTTTCGGCAGCGGCGTCTATTATTACCAGAAAAACTACGTCATGCCTTACCGCAGAACGTTCC
       250       260       270       280       290       300       310       320       330       340       350       360

         70                            80                            90                           100
 M  N  P  F  T  L  Y  W  S  G  K  I  P  A  S  V  F  L  S  S  Y  P  A  G  P  D  Q  P  H  Q  W  D  T  M  F  Y  S  L  G  M
TATGAATCCTTTCACCCTCTACTGGTCAGGTAAGATTCCGGCCTCCGTATTTCTCTCGTCGTACCCAGCCGGTCCAGATCAACCACATCAATGGGATACAATGTTCTACAGCCTTGGTAT
ATACTTAGGAAAGTGGGAGATGACCAGTCCATTCTAAGGCCGGAGGCATAAAGAGAGCAGCATGGGTCGGCCAGGTCTAGTTGGTGTAGTTACCCTATGTTACAAGATGTCGGAACCATA
       370       380       390       400       410       420       430       440       450       460       470       480

        110                           120                           130                           140
 L  E  K  T  R  E  I  Y  K  K  F  G  L  F  Y  V  G  P  I  Q  H  D  A  N  I  I  H  S  K  Q  P  I  N  S  L  D  D  L  K  G
GTTAGAAAAAACACGTGAAATTTACAAAAAGTTCGGCCTCTTCTACGTCGGCCCAATTCAGCACGACGCAAACATTATCCACAGTAAACAGCCGATTAATTCCCTGGACGACCTTAAGGG
CAATCTTTTTTGTGCACTTTAAATGTTTTTCAAGCCGGAGAAGATGCAGCCGGGTTAAGTCGTGCTGCGTTTGTAATAGGTGTCATTTGTCGGCTAATTAAGGGACCTGCTGGAATTCCC
       490       500       510       520       530       540       550       560       570       580       590       600

        150                           160                           170                           180
 L  K  M  R  L  P  G  G  M  V  A  E  V  F  A  K  F  G  V  A  A  V  S  L  P  G  S  D  I  F  P  A  L  E  K  G  T  I  D  A
TCTCAAAATGCGCTTACCTGGCGGGATGGTAGCGGAAGTCTTTGCAAAGTTTGGCGTCGCAGCGGTCAGTCTCCCAGGCAGCGACATCTTTCCAGCCTTAGAAAAAGGCACAATCGACGC
AGAGTTTTACGCGAATGGACCGCCCTACCATCGCCTTCAGAAACGTTTCAAACCGCAGCGTCGCCAGTCAGAGGGTCCGTCGCTGTAGAAAGGTCGGAATCTTTTTCCGTGTTAGCTGCG
       610       620       630       640       650       660       670       680       690       700       710       720

        190                           200                           210                           220
 A  D  C  V  G  P  A  V  N  W  E  L  G  F  S  Q  V  T  K  Y  I  L  M  G  P  P  G  I  M  S  V  Y  Q  P  V  L  L  M  D  L
TGCTGATTGTGTGGGTCCGGCTGTAAACTGGGAGCTCGGCTTCAGCCAAGTAACAAAGTACATCTTAATGGGTCCACCAGGCATCATGTCAGTCTACCAACCGGTCCTGCTTATGGACCT
ACGACTAACACACCCAGGCCGACATTTGACCCTCGAGCCGAAGTCGGTTCATTGTTTCATGTAGAATTACCCAGGTGGTCCGTAGTACAGTCAGATGGTTGGCCAGGACGAATACCTGGA
       730       740       750       760       770       780       790       800       810       820       830       840

        230                           240                           250                           260
 T  V  N  L  R  A  W  N  A  L  D  P  K  L  Q  Q  I  V  E  D  E  V  R  I  Y  S  Q  K  H  Y  L  A  I  Q  K  R  N  I  E  A
CACTGTCAATCTGCGGGCCTGGAACGCATTAGATCCAAAGTTACAGCAAATCGTTGAAGATGAAGTACGCATCTACTCTCAGAAGCATTACCTCGCAATTCAGAAACGGAATATTGAAGC
GTGACAGTTAGACGCCCGGACCTTGCGTAATCTAGGTTTCAATGTCGTTTAGCAACTTCTACTTCATGCGTAGATGAGAGTCTTCGTAATGGAGCGTTAAGTCTTTGCCTTATAACTTCG
       850       860       870       880       890       900       910       920       930       940       950       960
```

```
               270                                     280                                     290                                     300
 M   K   K   F   E   A   A   G   T   T   V   T   R   L   S   Q   E   D   L   Q   E   F   R   R   A   A   I   P   I   W   Y   S   W   A   N   K   D   E   D   A
TATGAAGAAGTTCGAGGCCGCTGGTACAACCGTAACCCGTCTGTCACAAGAGGACCTCCAGGAGTTTCGTCGTGCAGCTATCCCAATTTGGTATTCATGGGCAAACAAAGATGAAGACGC
ATACTTCTTCAAGCTCCGGCGACCATGTTGGCATTGGGCAGACAGTGTTCTCCTGGAGGTCCTCAAAGCAGCACGTCGATAGGGTTAAACCATAAGTACCCGTTTGTTTCTACTTCTGCG
        970         980         990        1000        1010        1020        1030        1040        1050        1060        1070        1080

               310                                     320                                     330                                     340
 R   E   I   F   D   M   Q   L   E   Y   M   M   N   D   T   V   G   Y   I   T   E   D   D   I   K   G   M   N   G   G   S   H   H   H   H   H   H   *   *
ACGGGAGATTTTCGACATGCAATTAGAGTACATGATGAACGACACTGTAGGTTACATCACTGAAGATGACATTAAGGGCATGAATGGCGGTTCACATCATCATCATCATCATTAATGAAA
TGCCCTCTAAAAGCTGTACGTTAATCTCATGTACTACTTGCTGTGACATCCAATGTAGTGACTTCTACTGTAATTCCCGTACTTACCGCCAAGTGTAGTAGTAGTAGTAGTAATTACTTT
       1090        1100        1110        1120        1130        1140        1150        1160        1170        1180        1190        1200


GGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCC
CCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGG
       1210        1220        1230        1240        1250        1260        1270        1280        1290        1300        1310        1320


TCTAAACGGGTCTTGAGGGGTTTTTTGCTGAAAGGAGGAACTATATCCGGAGCGACTCCCACGGCACGTTGGCAAGCTCG
AGATTTGCCCAGAACTCCCCAAAAAACGACTTTCCTCCTTGATATAGGCCTCGCTGAGGGTGCCGTGCAACCGTTCGAGC
       1330        1340        1350        1360        1370        1380        1390        1400
```

FIG. 50 (Continued)

FIG. 51 - Exemplary Expression Construct for msLacBP6_187C_D220N

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                         10                            20
                                                 M  A  T  T  W  K  I  Q  S  V  W  D  A  G  T  V  G  Y  D  L  F  K  E  W
GGTTTCCCTCTAGAAATAATTTTGTTTAACTTTAAGAAGGAGATATACCATGGCAACAACTTGGAAAATTCAAAGTGTATGGGATGCAGGGACGGTGGGCTATGACCTCTTCAAGGAGTG
CCAAAGGGAGATCTTTATTAAAACAAATTGAAATTCTTCCTCTATATGGTACCGTTGTTGAACCTTTTAAGTTTCACATACCCTACGTCCCTGCCACCCGATACTGGAGAAGTTCCTCAC
       130       140       150       160       170       180       190       200       210       220       230       240

         30                            40                            50                            60
 C  D  G  M  E  E  K  T  G  G  E  L  K  F  T  C  F  P  A  K  A  V  A  A  D  N  N  G  L  F  D  A  V  R  N  G  V  L  Q  G
GTGCGACGGTATGGAAGAAAAGACGGGCGGTGAACTCAAATTCACGTGCTTCCCAGCCAAAGCCGTCGCCGCAGATAATAATGGTCTTTTTGATGCAGTACGGAATGGCGTCTTGCAAGG
CACGCTGCCATACCTTCTTTTCTGCCCGCCACTTGAGTTTAAGTGCACGAAGGGTCGGTTTCGGCAGCGGCGTCTATTATTACCAGAAAAACTACGTCATGCCTTACCGCAGAACGTTCC
       250       260       270       280       290       300       310       320       330       340       350       360

         70                            80                            90                           100
 M  N  P  F  T  L  Y  W  S  G  K  I  P  A  S  V  F  L  S  S  Y  P  A  G  P  D  Q  P  H  Q  W  D  T  M  F  Y  S  L  G  M
TATGAATCCTTTCACCCTCTACTGGTCAGGTAAGATTCCGGCCTCCGTATTTCTCTCGTCGTACCCAGCCGGTCCAGATCAACCACATCAATGGGATACAATGTTCTACAGCCTTGGTAT
ATACTTAGGAAAGTGGGAGATGACCAGTCCATTCTAAGGCCGGAGGCATAAAGAGAGCAGCATGGGTCGGCCAGGTCTAGTTGGTGTAGTTACCCTATGTTACAAGATGTCGGAACCATA
       370       380       390       400       410       420       430       440       450       460       470       480

        110                           120                           130                           140
 L  E  K  T  R  E  I  Y  K  K  F  G  L  F  Y  V  G  P  I  Q  H  D  A  N  I  I  H  S  K  Q  P  I  N  S  L  D  D  L  K  G
GTTAGAAAAAACACGTGAAATTTACAAAAAGTTCGGCCTCTTCTACGTCGGCCCAATTCAGCACGACGCAAACATTATCCACAGTAAACAGCCGATTAATTCCCTGGACGACCTTAAGGG
CAATCTTTTTTGTGCACTTTAAATGTTTTTCAAGCCGGAGAAGATGCAGCCGGGTTAAGTCGTGCTGCGTTTGTAATAGGTGTCATTTGTCGGCTAATTAAGGGACCTGCTGGAATTCCC
       490       500       510       520       530       540       550       560       570       580       590       600

        150                           160                           170                           180
 L  K  M  R  L  P  G  G  M  V  A  E  V  F  A  K  F  G  V  A  A  V  S  L  P  G  S  D  I  F  P  A  L  E  K  G  T  I  D  A
TCTCAAAATGCGCTTACCTGGCGGGATGGTAGCGGAAGTCTTTGCAAAGTTTGGCGTCGCAGCGGTCAGTCTCCCAGGCAGCGACATCTTTCCAGCCTTAGAAAAAGGCACAATCGACGC
AGAGTTTTACGCGAATGGACCGCCCTACCATCGCCTTCAGAAACGTTTCAAACCGCAGCGTCGCCAGTCAGAGGGTCCGTCGCTGTAGAAAGGTCGGAATCTTTTTCCGTGTTAGCTGCG
       610       620       630       640       650       660       670       680       690       700       710       720

        190                           200                           210                           220
 A  D  C  V  G  P  A  V  N  W  E  L  G  F  S  Q  V  T  K  Y  I  L  M  G  P  P  G  I  M  S  V  Y  Q  P  V  N  L  M  D  L
TGCTGATTGTGTGGGTCCGGCTGTAAACTGGGAGCTCGGCTTCAGCCAAGTAACAAAGTACATCTTAATGGGTCCACCAGGCATCATGTCAGTCTACCAACCGGTCAACCTTATGGACCT
ACGACTAACACACCCAGGCCGACATTTGACCCTCGAGCCGAAGTCGGTTCATTGTTTCATGTAGAATTACCCAGGTGGTCCGTAGTACAGTCAGATGGTTGGCCAGTTGGAATACCTGGA
       730       740       750       760       770       780       790       800       810       820       830       840

        230                           240                           250                           260
 T  V  N  L  R  A  W  N  A  L  D  P  K  L  Q  Q  I  V  E  D  E  V  R  I  Y  S  Q  K  H  Y  L  A  I  Q  K  R  N  I  E  A
CACTGTCAATCTGCGGGCCTGGAACGCATTAGATCCAAAGTTACAGCAAATCGTTGAAGATGAAGTACGCATCTACTCTCAGAAGCATTACCTCGCAATTCAGAAACGGAATATTGAAGC
GTGACAGTTAGACGCCCGGACCTTGCGTAATCTAGGTTTCAATGTCGTTTAGCAACTTCTACTTCATGCGTAGATGAGAGTCTTCGTAATGGAGCGTTAAGTCTTTGCCTTATAACTTCG
       850       860       870       880       890       900       910       920       930       940       950       960
```

```
            270                                     280                                     290                                     300
 M   K   K   F   E   A   A   G   T   T   V   T   R   L   S   Q   E   D   L   Q   E   F   R   R   A   A   I   P   I   W   Y   S   W   A   N   K   D   E   D   A
TATGAAGAAGTTCGAGGCCGCTGGTACAACCGTAACCCGTCTGTCACAAGAGGACCTCCAGGAGTTTCGTCGTGCAGCTATCCCAATTTGGTATTCATGGCAAACAAAGATGAAGACGC
ATACTTCTTCAAGCTCCGGCGACCATGTTGGCATTGGGCAGACAGTGTTCTCCTGGAGGTCCTCAAAGCAGCACGTCGATAGGGTTAAACCATAAGTACCCGTTTGTTTCTACTTCTGCG
        970       980       990      1000      1010      1020      1030      1040      1050      1060      1070      1080

            310                                     320                                     330                                     340
 R   E   I   F   D   M   Q   L   E   Y   M   M   N   D   T   V   G   Y   I   T   E   D   D   I   K   G   M   N   G   G   S   H   H   H   H   H   H   *   *
ACGGGAGATTTTCGACATGCAATTAGAGTACATGATGAACGACACTGTAGGTTACATCACTGAAGATGACATTAAGGGCATGAATGGCGGTTCACATCATCATCATCATCATTAATGAAA
TGCCCTCTAAAAGCTGTACGTTAATCTCATGTACTACTTGCTGTGACATCCAATGTAGTGACTTCTACTGTAATTCCCGTACTTACCGCCAAGTGTAGTAGTAGTAGTAGTAATTACTTT
      1090      1100      1110      1120      1130      1140      1150      1160      1170      1180      1190      1200


GGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCC
CCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGG
      1210      1220      1230      1240      1250      1260      1270      1280      1290      1300      1310      1320


TCTAAACGGGTCTTGAGGGGTTTTTTGCTGAAAGGAGGAACTATATCCGGAGCGACTCCCACGGCACGTTGGCAAGCTCG
AGATTTGCCCAGAACTCCCCAAAAAACGACTTTCCTCCTTGATATAGGCCTCGCTGAGGGTGCCGTGCAACCGTTCGAGC
      1330      1340      1350      1360      1370      1380      1390      1400
```

FIG. 51 (Continued)

FIG. 52 - Exemplary Expression Construct for msLacBP6_187C_D220Q

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10          20          30          40          50          60          70          80          90         100         110         120

                                                                                          10                                    20
                                                            M  A  T  T  W  K  I  Q  S  V  W  D  A  G  T  V  G  Y  D  L  F  K  E  W
GGTTTCCCTCTAGAAATAATTTTGTTTAACTTTAAGAAGGAGATATACCATGGCAACAACTTGGAAAATTCAAAGTGTATGGGATGCAGGGACGGTGGGCTATGACCTCTTCAAGGAGTG
CCAAAGGGAGATCTTTATTAAAACAAATTGAAATTCTTCCTCTATATGGTACCGTTGTTGAACCTTTTAAGTTTCACATACCCTACGTCCCTGCCACCCGATACTGGAGAAGTTCCTCAC
       130         140         150         160         170         180         190         200         210         220         230         240

           30                                    40                                    50                                    60
 C  D  G  M  E  E  K  T  G  G  E  L  K  F  T  C  F  P  A  K  A  V  A  A  D  N  N  G  L  F  D  A  V  R  N  G  V  L  Q  G
GTGCGACGGTATGGAAGAAAAGACGGGCGGTGAACTCAAATTCACGTGCTTCCCAGCCAAAGCCGTCGCCGCAGATAATAATGGTCTTTTTGATGCAGTACGGAATGGCGTCTTGCAAGG
CACGCTGCCATACCTTCTTTTCTGCCCGCCACTTGAGTTTAAGTGCACGAAGGGTCGGTTTCGGCAGCGGCGTCTATTATTACCAGAAAAACTACGTCATGCCTTACCGCAGAACGTTCC
       250         260         270         280         290         300         310         320         330         340         350         360

           70                                    80                                    90                                   100
 M  N  P  F  T  L  Y  W  S  G  K  I  P  A  S  V  F  L  S  S  Y  P  A  G  P  D  Q  P  H  Q  W  D  T  M  F  Y  S  L  G  M
TATGAATCCTTTCACCCTCTACTGGTCAGGTAAGATTCCGGCCTCCGTATTTCTCTCGTCGTACCCAGCCGGTCCAGATCAACCACATCAATGGGATACAATGTTCTACAGCCTTGGTAT
ATACTTAGGAAAGTGGGAGATGACCAGTCCATTCTAAGGCCGGAGGCATAAAGAGAGCAGCATGGGTCGGCCAGGTCTAGTTGGTGTAGTTACCCTATGTTACAAGATGTCGGAACCATA
       370         380         390         400         410         420         430         440         450         460         470         480

          110                                   120                                   130                                   140
 L  E  K  T  R  E  I  Y  K  K  F  G  L  F  Y  V  G  P  I  Q  H  D  A  N  I  I  H  S  K  Q  P  I  N  S  L  D  D  L  K  G
GTTAGAAAAAACACGTGAAATTTACAAAAAGTTCGGCCTCTTCTACGTCGGCCCAATTCAGCACGACGCAAACATTATCCACAGTAAACAGCCGATTAATTCCCTGGACGACCTTAAGGG
CAATCTTTTTTGTGCACTTTAAATGTTTTTCAAGCCGGAGAAGATGCAGCCGGGTTAAGTCGTGCTGCGTTTGTAATAGGTGTCATTTGTCGGCTAATTAAGGGACCTGCTGGAATTCCC
       490         500         510         520         530         540         550         560         570         580         590         600

          150                                   160                                   170                                   180
 L  K  M  R  L  P  G  G  M  V  A  E  V  F  A  K  F  G  V  A  A  V  S  L  P  G  S  D  I  F  P  A  L  E  K  G  T  I  D  A
TCTCAAAATGCGCTTACCTGGCGGGATGGTAGCGGAAGTCTTTGCAAAGTTTGGCGTCGCAGCGGTCAGTCTCCCAGGCAGCGACATCTTTCCAGCCTTAGAAAAAGGCACAATCGACGC
AGAGTTTTACGCGAATGGACCGCCCTACCATCGCCTTCAGAAACGTTTCAAACCGCAGCGTCGCCAGTCAGAGGGTCCGTCGCTGTAGAAAGGTCGGAATCTTTTTCCGTGTTAGCTGCG
       610         620         630         640         650         660         670         680         690         700         710         720

          190                                   200                                   210                                   220
 A  D  C  V  G  P  A  V  N  W  E  L  G  F  S  Q  V  T  K  Y  I  L  M  G  P  P  G  I  M  S  V  Y  Q  P  V  Q  L  M  D  L
TGCTGATTGTGTGGGTCCGGCTGTAAACTGGGAGCTCGGCTTCAGCCAAGTAACAAAGTACATCTTAATGGGTCCACCAGGCATCATGTCAGTCTACCAACCGGTCCAGCTTATGGACCT
ACGACTAACACACCCAGGCCGACATTTGACCCTCGAGCCGAAGTCGGTTCATTGTTTCATGTAGAATTACCCAGGTGGTCCGTAGTACAGTCAGATGGTTGGCCAGGTCGAATACCTGGA
       730         740         750         760         770         780         790         800         810         820         830         840

          230                                   240                                   250                                   260
 T  V  N  L  R  A  W  N  A  L  D  P  K  L  Q  Q  I  V  E  D  E  V  R  I  Y  S  Q  K  H  Y  L  A  I  Q  K  R  N  I  E  A
CACTGTCAATCTGCGGGCCTGGAACGCATTAGATCCAAAGTTACAGCAAATCGTTGAAGATGAAGTACGCATCTACTCTCAGAAGCATTACCTCGCAATTCAGAAACGGAATATTGAAGC
GTGACAGTTAGACGCCCGGACCTTGCGTAATCTAGGTTTCAATGTCGTTTAGCAACTTCTACTTCATGCGTAGATGAGAGTCTTCGTAATGGAGCGTTAAGTCTTTGCCTTATAACTTCG
       850         860         870         880         890         900         910         920         930         940         950         960
```

```
               270                                     280                                     290                                     300
 M   K   K   F   E   A   A   G   T   T   V   T   R   L   S   Q   E   D   L   Q   E   F   R   R   A   A   I   P   I   W   Y   S   W   A   N   K   D   E   D   A
TATGAAGAAGTTCGAGGCCGCTGGTACAACCGTAACCCGTCTGTCACAAGAGGACCTCCAGGAGTTTCGTCGTGCAGCTATCCCAATTTGGTATTCATGGGCAAACAAAGATGAAGACGC
ATACTTCTTCAAGCTCCGGCGACCATGTTGGCATTGGGCAGACAGTGTTCTCCTGGAGGTCCTCAAAGCAGCACGTCGATAGGGTTAAACCATAAGTACCCGTTTGTTTCTACTTCTGCG
        970       980       990      1000      1010      1020      1030      1040      1050      1060      1070      1080

               310                                     320                                     330                                     340
 R   E   I   F   D   M   Q   L   E   Y   M   M   N   D   T   V   G   Y   I   T   E   D   D   I   K   G   M   N   G   G   S   H   H   H   H   H   H   *   *
ACGGGAGATTTTCGACATGCAATTAGAGTACATGATGAACGACACTGTAGGTTACATCACTGAAGATGACATTAAGGGCATGAATGGCGGTTCACATCATCATCATCATCATTAATGAAA
TGCCCTCTAAAAGCTGTACGTTAATCTCATGTACTACTTGCTGTGACATCCAATGTAGTGACTTCTACTGTAATTCCCGTACTTACCGCCAAGTGTAGTAGTAGTAGTAGTAATTACTTT
       1090      1100      1110      1120      1130      1140      1150      1160      1170      1180      1190      1200

GGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCC
CCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGG
       1210      1220      1230      1240      1250      1260      1270      1280      1290      1300      1310      1320

TCTAAACGGGTCTTGAGGGGTTTTTTGCTGAAAGGAGGAACTATATCCGGAGCGACTCCCACGGCACGTTGGCAAGCTCG
AGATTTGCCCAGAACTCCCCAAAAAACGACTTTCCTCCTTGATATAGGCCTCGCTGAGGGTGCCGTGCAACCGTTCGAGC
       1330      1340      1350      1360      1370      1380      1390      1400
```

FIG. 52 (Continued)

FIG. 53 - Exemplary Expression Construct for msLacBP6_187C_D220S

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                      10                            20
                                                 M  A  T  T  W  K  I  Q  S  V  W  D  A  G  T  V  G  Y  D  L  F  K  E  W
GGTTTCCCTCTAGAAATAATTTTGTTTAACTTTAAGAAGGAGATATACCATGGCAACAACTTGGAAAATTCAAAGTGTATGGGATGCAGGGACGGTGGGCTATGACCTCTTCAAGGAGTG
CCAAAGGGAGATCTTTATTAAAACAAATTGAAATTCTTCCTCTATATGGTACCGTTGTTGAACCTTTTAAGTTTCACATACCCTACGTCCCTGCCACCCGATACTGGAGAAGTTCCTCAC
       130       140       150       160       170       180       190       200       210       220       230       240

        30                            40                            50                            60
 C  D  G  M  E  E  K  T  G  G  E  L  K  F  T  C  F  P  A  K  A  V  A  A  D  N  N  G  L  F  D  A  V  R  N  G  V  L  Q  G
GTGCGACGGTATGGAAGAAAAGACGGGCGGTGAACTCAAATTCACGTGCTTCCCAGCCAAAGCCGTCGCCGCAGATAATAATGGTCTTTTTGATGCAGTACGGAATGGCGTCTTGCAAGG
CACGCTGCCATACCTTCTTTTCTGCCCGCCACTTGAGTTTAAGTGCACGAAGGGTCGGTTTCGGCAGCGGCGTCTATTATTACCAGAAAAACTACGTCATGCCTTACCGCAGAACGTTCC
       250       260       270       280       290       300       310       320       330       340       350       360

        70                            80                            90                           100
 M  N  P  F  T  L  Y  W  S  G  K  I  P  A  S  V  F  L  S  S  Y  P  A  G  P  D  Q  P  H  Q  W  D  T  M  F  Y  S  L  G  M
TATGAATCCTTTCACCCTCTACTGGTCAGGTAAGATTCCGGCCTCCGTATTTCTCTCGTCGTACCCAGCCGGTCCAGATCAACCACATCAATGGGATACAATGTTCTACAGCCTTGGTAT
ATACTTAGGAAAGTGGGAGATGACCAGTCCATTCTAAGGCCGGAGGCATAAAGAGAGCAGCATGGGTCGGCCAGGTCTAGTTGGTGTAGTTACCCTATGTTACAAGATGTCGGAACCATA
       370       380       390       400       410       420       430       440       450       460       470       480

       110                           120                           130                           140
 L  E  K  T  R  E  I  Y  K  K  F  G  L  F  Y  V  G  P  I  Q  H  D  A  N  I  I  H  S  K  Q  P  I  N  S  L  D  D  L  K  G
GTTAGAAAAAACACGTGAAATTTACAAAAAGTTCGGCCTCTTCTACGTCGGCCCAATTCAGCACGACGCAAACATTATCCACAGTAAACAGCCGATTAATTCCCTGGACGACCTTAAGGG
CAATCTTTTTTGTGCACTTTAAATGTTTTTCAAGCCGGAGAAGATGCAGCCGGGTTAAGTCGTGCTGCGTTTGTAATAGGTGTCATTTGTCGGCTAATTAAGGGACCTGCTGGAATTCCC
       490       500       510       520       530       540       550       560       570       580       590       600

       150                           160                           170                           180
 L  K  M  R  L  P  G  G  M  V  A  E  V  F  A  K  F  G  V  A  A  V  S  L  P  G  S  D  I  F  P  A  L  E  K  G  T  I  D  A
TCTCAAAATGCGCTTACCTGGCGGGATGGTAGCGGAAGTCTTTGCAAAGTTTGGCGTCGCAGCGGTCAGTCTCCCAGGCAGCGACATCTTTCCAGCCTTAGAAAAAGGCACAATCGACGC
AGAGTTTTACGCGAATGGACCGCCCTACCATCGCCTTCAGAAACGTTTCAAACCGCAGCGTCGCCAGTCAGAGGGTCCGTCGCTGTAGAAAGGTCGGAATCTTTTTCCGTGTTAGCTGCG
       610       620       630       640       650       660       670       680       690       700       710       720

       190                           200                           210                           220
 A  D  C  V  G  P  A  V  N  W  E  L  G  F  S  Q  V  T  K  Y  I  L  M  G  P  P  G  I  M  S  V  Y  Q  P  V  S  L  M  D  L
TGCTGATTGTGTGGGTCCGGCTGTAAACTGGGAGCTCGGCTTCAGCCAAGTAACAAAGTACATCTTAATGGGTCCACCAGGCATCATGTCAGTCTACCAACCGGTCAGCCTTATGGACCT
ACGACTAACACACCCAGGCCGACATTTGACCCTCGAGCCGAAGTCGGTTCATTGTTTCATGTAGAATTACCCAGGTGGTCCGTAGTACAGTCAGATGGTTGGCCAGTCGGAATACCTGGA
       730       740       750       760       770       780       790       800       810       820       830       840

       230                           240                           250                           260
 T  V  N  L  R  A  W  N  A  L  D  P  K  L  Q  Q  I  V  E  D  E  V  R  I  Y  S  Q  K  H  Y  L  A  I  Q  K  R  N  I  E  A
CACTGTCAATCTGCGGGCCTGGAACGCATTAGATCCAAAGTTACAGCAAATCGTTGAAGATGAAGTACGCATCTACTCTCAGAAGCATTACCTCGCAATTCAGAAACGGAATATTGAAGC
GTGACAGTTAGACGCCCGGACCTTGCGTAATCTAGGTTTCAATGTCGTTTAGCAACTTCTACTTCATGCGTAGATGAGAGTCTTCGTAATGGAGCGTTAAGTCTTTGCCTTATAACTTCG
       850       860       870       880       890       900       910       920       930       940       950       960
```

```
                 270                           280                           290                           300
 M  K  K  F  E  A  A  G  T  T  V  T  R  L  S  Q  E  D  L  Q  E  F  R  R  A  A  I  P  I  W  Y  S  W  A  N  K  D  E  D  A
TATGAAGAAGTTCGAGGCCGCTGGTACAACCGTAACCCGTCTGTCACAAGAGGACCTCCAGGAGTTTCGTCGTGCAGCTATCCCAATTTGGTATTCATGGGCAAACAAAGATGAAGACGC
ATACTTCTTCAAGCTCCGGCGACCATGTTGGCATTGGGCAGACAGTGTTCTCCTGGAGGTCCTCAAAGCAGCACGTCGATAGGGTTAAACCATAAGTACCCGTTTGTTTCTACTTCTGCG
       970       980       990      1000      1010      1020      1030      1040      1050      1060      1070      1080

                 310                           320                           330                           340
 R  E  I  F  D  M  Q  L  E  Y  M  M  N  D  T  V  G  Y  I  T  E  D  D  I  K  G  M  N  G  G  S  H  H  H  H  H  H  *  *
ACGGGAGATTTTCGACATGCAATTAGAGTACATGATGAACGACACTGTAGGTTACATCACTGAAGATGACATTAAGGGCATGAATGGCGGTTCACATCATCATCATCATCATTAATGAAA
TGCCCTCTAAAAGCTGTACGTTAATCTCATGTACTACTTGCTGTGACATCCAATGTAGTGACTTCTACTGTAATTCCCGTACTTACCGCCAAGTGTAGTAGTAGTAGTAGTAATTACTTT
      1090      1100      1110      1120      1130      1140      1150      1160      1170      1180      1190      1200

GGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCC
CCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGG
      1210      1220      1230      1240      1250      1260      1270      1280      1290      1300      1310      1320

TCTAAACGGGTCTTGAGGGGTTTTTTGCTGAAAGGAGGAACTATATCCGGAGCGACTCCCACGGCACGTTGGCAAGCTCG
AGATTTGCCCAGAACTCCCCAAAAAACGACTTTCCTCCTTGATATAGGCCTCGCTGAGGGTGCCGTGCAACCGTTCGAGC
      1330      1340      1350      1360      1370      1380      1390      1400
```

FIG. 53 (Continued)

FIG. 54 - Exemplary Expression Construct for msLacBP6_187C_bZifC

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                          10                            20
                                                     M  A  T  T  W  K  I  Q  S  V  W  D  A  G  T  V  G  Y  D  L  F  K  E  W
GGTTTCCCTCTAGAAATAATTTTGTTTAACTTTAAGAAGGAGATATACCATGGCAACAACTTGGAAAATTCAAAGTGTATGGGATGCAGGGACGGTGGGCTATGACCTCTTCAAGGAGTG
CCAAAGGGAGATCTTTATTAAAACAAATTGAAATTCTTCCTCTATATGGTACCGTTGTTGAACCTTTTAAGTTTCACATACCCTACGTCCCTGCCACCCGATACTGGAGAAGTTCCTCAC
       130       140       150       160       170       180       190       200       210       220       230       240

             30                            40                            50                            60
 C  D  G  M  E  E  K  T  G  G  E  L  K  F  T  C  F  P  A  K  A  V  A  A  D  N  N  G  L  F  D  A  V  R  N  G  V  L  Q  G
GTGCGACGGTATGGAAGAAAAGACGGGCGGTGAACTCAAATTCACGTGCTTCCCAGCCAAAGCCGTCGCCGCAGATAATAATGGTCTTTTTGATGCAGTACGGAATGGCGTCTTGCAAGG
CACGCTGCCATACCTTCTTTTCTGCCCGCCACTTGAGTTTAAGTGCACGAAGGGTCGGTTTCGGCAGCGGCGTCTATTATTACCAGAAAAACTACGTCATGCCTTACCGCAGAACGTTCC
       250       260       270       280       290       300       310       320       330       340       350       360

             70                            80                            90                           100
 M  N  P  F  T  L  Y  W  S  G  K  I  P  A  S  V  F  L  S  S  Y  P  A  G  P  D  Q  P  H  Q  W  D  T  M  F  Y  S  L  G  M
TATGAATCCTTTCACCCTCTACTGGTCAGGTAAGATTCCGGCCTCCGTATTTCTCTCGTCGTACCCAGCCGGTCCAGATCAACCACATCAATGGGATACAATGTTCTACAGCCTTGGTAT
ATACTTAGGAAAGTGGGAGATGACCAGTCCATTCTAAGGCCGGAGGCATAAAGAGAGCAGCATGGGTCGGCCAGGTCTAGTTGGTGTAGTTACCCTATGTTACAAGATGTCGGAACCATA
       370       380       390       400       410       420       430       440       450       460       470       480

            110                           120                           130                           140
 L  E  K  T  R  E  I  Y  K  K  F  G  L  F  Y  V  G  P  I  Q  H  D  A  N  I  I  H  S  K  Q  P  I  N  S  L  D  D  L  K  G
GTTAGAAAAAACACGTGAAATTTACAAAAAGTTCGGCCTCTTCTACGTCGGCCCAATTCAGCACGACGCAAACATTATCCACAGTAAACAGCCGATTAATTCCCTGGACGACCTTAAGGG
CAATCTTTTTTGTGCACTTTAAATGTTTTTCAAGCCGGAGAAGATGCAGCCGGGTTAAGTCGTGCTGCGTTTGTAATAGGTGTCATTTGTCGGCTAATTAAGGGACCTGCTGGAATTCCC
       490       500       510       520       530       540       550       560       570       580       590       600

            150                           160                           170                           180
 L  K  M  R  L  P  G  G  M  V  A  E  V  F  A  K  F  G  V  A  A  V  S  L  P  G  S  D  I  F  P  A  L  E  K  G  T  I  D  A
TCTCAAAATGCGCTTACCTGGCGGGATGGTAGCGGAAGTCTTTGCAAAGTTTGGCGTCGCAGCGGTCAGTCTCCCAGGCAGCGACATCTTTCCAGCCTTAGAAAAAGGCACAATCGACGC
AGAGTTTTACGCGAATGGACCGCCCTACCATCGCCTTCAGAAACGTTTCAAACCGCAGCGTCGCCAGTCAGAGGGTCCGTCGCTGTAGAAAGGTCGGAATCTTTTTCCGTGTTAGCTGCG
       610       620       630       640       650       660       670       680       690       700       710       720

            190                           200                           210                           220
 A  D  C  V  G  P  A  V  N  W  E  L  G  F  S  Q  V  T  K  Y  I  L  M  G  P  P  G  I  M  S  V  Y  Q  P  V  D  L  M  D  L
TGCTGATTGTGTGGGTCCGGCTGTAAACTGGGAGCTCGGCTTCAGCCAAGTAACAAAGTACATCTTAATGGGTCCACCAGGCATCATGTCAGTCTACCAACCGGTCGACCTTATGGACCT
ACGACTAACACACCCAGGCCGACATTTGACCCTCGAGCCGAAGTCGGTTCATTGTTTCATGTAGAATTACCCAGGTGGTCCGTAGTACAGTCAGATGGTTGGCCAGCTGGAATACCTGGA
       730       740       750       760       770       780       790       800       810       820       830       840

            230                           240                           250                           260
 T  V  N  L  R  A  W  N  A  L  D  P  K  L  Q  Q  I  V  E  D  E  V  R  I  Y  S  Q  K  H  Y  L  A  I  Q  K  R  N  I  E  A
CACTGTCAATCTGCGGGCCTGGAACGCATTAGATCCAAAGTTACAGCAAATCGTTGAAGATGAAGTACGCATCTACTCTCAGAAGCATTACCTCGCAATTCAGAAACGGAATATTGAAGC
GTGACAGTTAGACGCCCGGACCTTGCGTAATCTAGGTTTCAATGTCGTTTAGCAACTTCTACTTCATGCGTAGATGAGAGTCTTCGTAATGGAGCGTTAAGTCTTTGCCTTATAACTTCG
       850       860       870       880       890       900       910       920       930       940       950       960
```

```
                270                                   280                                   290                                   300
  M   K   K   F   E   A   A   G   T   T   V   T   R   L   S   Q   E   D   L   Q   E   F   R   R   A   A   I   P   I   W   Y   S   W   A   N   K   D   E   D   A
TATGAAGAAGTTCGAGGCCGCTGGTACAACCGTAACCCGTCTGTCACAAGAGGACCTCCAGGAGTTTCGTCGTGCAGCTATCCCAATTTGGTATTCATGGGCAAACAAAGATGAAGACGC
ATACTTCTTCAAGCTCCGGCGACCATGTTGGCATTGGGCAGACAGTGTTCTCCTGGAGGTCCTCAAAGCAGCACGTCGATAGGGTTAAACCATAAGTACCCGTTTGTTTCTACTTCTGCG
        970       980       990      1000      1010      1020      1030      1040      1050      1060      1070      1080

                310                                   320                                   330                                   340
  R   E   I   F   D   M   Q   L   E   Y   M   M   N   D   T   V   G   Y   I   T   E   D   D   I   K   G   M   N   G   G   S   T   G   E   K   P   Y   K   C   P
ACGGGAGATTTTCGACATGCAATTAGAGTACATGATGAACGACACTGTAGGTTACATCACTGAAGATGACATTAAGGGCATGAATGGCGGCAGCACCGGCGAAAAACCGTATAAATGTCC
TGCCCTCTAAAAGCTGTACGTTAATCTCATGTACTACTTGCTGTGACATCCAATGTAGTGACTTCTACTGTAATTCCCGTACTTACCGCCGTCGTGGCCGCTTTTTGGCATATTTACAGG
       1090      1100      1110      1120      1130      1140      1150      1160      1170      1180      1190      1200

                350                                   360
  E   C   G   K   S   F   S   R   S   G   G   S   H   H   H   H   H   H   *   *
GGAATGTGGCAAAAGCTTTAGCCGCAGCGGCGGTTCACATCATCATCATCATCATTAATGAAAGGGCGATATCCAGCACACTGGCGGCCGTTACTAGTGGATCCGGCTGCTAACAAAGCC
CCTTACACCGTTTTCGAAATCGGCGTCGCCGCCAAGTGTAGTAGTAGTAGTAGTAATTACTTTCCCGCTATAGGTCGTGTGACCGCCGGCAATGATCACCTAGGCCGACGATTGTTTCGG
       1210      1220      1230      1240      1250      1260      1270      1280      1290      1300      1310      1320


CGAAAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACT
GCTTTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGA
       1330      1340      1350      1360      1370      1380      1390      1400      1410      1420      1430      1440


CCCACGGCACGTTGGCAAGCTCG
GGGTGCCGTGCAACCGTTCGAGC
       1450      1460
```

FIG. 54 (Continued)

FIG. 55 - Exemplary Expression Construct for msLacBP6_188C_bZifC

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                           10                            20
                                                  M  A  T  T  W  K  I  Q  S  V  W  D  A  G  T  V  G  Y  D  L  F  K  E  W
GGTTTCCCTCTAGAAATAATTTTGTTTAACTTTAAGAAGGAGATATACCATGGCAACAACTTGGAAAATTCAAAGTGTATGGGATGCAGGGACGGTGGGCTATGACCTCTTCAAGGAGTG
CCAAAGGGAGATCTTTATTAAAACAAATTGAAATTCTTCCTCTATATGGTACCGTTGTTGAACCTTTTAAGTTTCACATACCCTACGTCCCTGCCACCCGATACTGGAGAAGTTCCTCAC
       130       140       150       160       170       180       190       200       210       220       230       240

              30                            40                            50                            60
 C  D  G  M  E  E  K  T  G  G  E  L  K  F  T  C  F  P  A  K  A  V  A  A  D  N  N  G  L  F  D  A  V  R  N  G  V  L  Q  G
GTGCGACGGTATGGAAGAAAAGACGGGCGGTGAACTCAAATTCACGTGCTTCCCAGCCAAAGCCGTCGCCGCAGATAATAATGGTCTTTTTGATGCAGTACGGAATGGCGTCTTGCAAGG
CACGCTGCCATACCTTCTTTTCTGCCCGCCACTTGAGTTTAAGTGCACGAAGGGTCGGTTTCGGCAGCGGCGTCTATTATTACCAGAAAAACTACGTCATGCCTTACCGCAGAACGTTCC
       250       260       270       280       290       300       310       320       330       340       350       360

              70                            80                            90                            100
 M  N  P  F  T  L  Y  W  S  G  K  I  P  A  S  V  F  L  S  S  Y  P  A  G  P  D  Q  P  H  Q  W  D  T  M  F  Y  S  L  G  M
TATGAATCCTTTCACCCTCTACTGGTCAGGTAAGATTCCGGCCTCCGTATTTCTCTCGTCGTACCCAGCCGGTCCAGATCAACCACATCAATGGGATACAATGTTCTACAGCCTTGGTAT
ATACTTAGGAAAGTGGGAGATGACCAGTCCATTCTAAGGCCGGAGGCATAAAGAGAGCAGCATGGGTCGGCCAGGTCTAGTTGGTGTAGTTACCCTATGTTACAAGATGTCGGAACCATA
       370       380       390       400       410       420       430       440       450       460       470       480

             110                           120                           130                           140
 L  E  K  T  R  E  I  Y  K  K  F  G  L  F  Y  V  G  P  I  Q  H  D  A  N  I  I  H  S  K  Q  P  I  N  S  L  D  D  L  K  G
GTTAGAAAAAACACGTGAAATTTACAAAAAGTTCGGCCTCTTCTACGTCGGCCCAATTCAGCACGACGCAAACATTATCCACAGTAAACAGCCGATTAATTCCCTGGACGACCTTAAGGG
CAATCTTTTTTGTGCACTTTAAATGTTTTTCAAGCCGGAGAAGATGCAGCCGGGTTAAGTCGTGCTGCGTTTGTAATAGGTGTCATTTGTCGGCTAATTAAGGGACCTGCTGGAATTCCC
       490       500       510       520       530       540       550       560       570       580       590       600

             150                           160                           170                           180
 L  K  M  R  L  P  G  G  M  V  A  E  V  F  A  K  F  G  V  A  A  V  S  L  P  G  S  D  I  F  P  A  L  E  K  G  T  I  D  A
TCTCAAAATGCGCTTACCTGGCGGGATGGTAGCGGAAGTCTTTGCAAAGTTTGGCGTCGCAGCGGTCAGTCTCCCAGGCAGCGACATCTTTCCAGCCTTAGAAAAAGGCACAATCGACGC
AGAGTTTTACGCGAATGGACCGCCCTACCATCGCCTTCAGAAACGTTTCAAACCGCAGCGTCGCCAGTCAGAGGGTCCGTCGCTGTAGAAAGGTCGGAATCTTTTTCCGTGTTAGCTGCG
       610       620       630       640       650       660       670       680       690       700       710       720

             190                           200                           210                           220
 A  D  Y  C  G  P  A  V  N  W  E  L  G  F  S  Q  V  T  K  Y  I  L  M  G  P  P  G  I  M  S  V  Y  Q  P  V  D  L  M  D  L
TGCTGATTACTGTGGTCCGGCTGTAAACTGGGAGCTCGGCTTCAGCCAAGTAACAAAGTACATCTTAATGGGTCCACCAGGCATCATGTCAGTCTACCAACCGGTCGACCTTATGGACCT
ACGACTAATGACACCAGGCCGACATTTGACCCTCGAGCCGAAGTCGGTTCATTGTTTCATGTAGAATTACCCAGGTGGTCCGTAGTACAGTCAGATGGTTGGCCAGCTGGAATACCTGGA
       730       740       750       760       770       780       790       800       810       820       830       840

             230                           240                           250                           260
 T  V  N  L  R  A  W  N  A  L  D  P  K  L  Q  Q  I  V  E  D  E  V  R  I  Y  S  Q  K  H  Y  L  A  I  Q  K  R  N  I  E  A
CACTGTCAATCTGCGGGCCTGGAACGCATTAGATCCAAAGTTACAGCAAATCGTTGAAGATGAAGTACGCATCTACTCTCAGAAGCATTACCTCGCAATTCAGAAACGGAATATTGAAGC
GTGACAGTTAGACGCCCGGACCTTGCGTAATCTAGGTTTCAATGTCGTTTAGCAACTTCTACTTCATGCGTAGATGAGAGTCTTCGTAATGGAGCGTTAAGTCTTTGCCTTATAACTTCG
       850       860       870       880       890       900       910       920       930       940       950       960
```

```
                  270                                     280                                     290                                     300
 M   K   K   F   E   A   A   G   T   T   V   T   R   L   S   Q   E   D   L   Q   E   F   R   R   A   A   I   P   I   W   Y   S   W   A   N   K   D   E   D   A
TATGAAGAAGTTCGAGGCCGCTGGTACAACCGTAACCCGTCTGTCACAAGAGGACCTCCAGGAGTTTCGTCGTGCAGCTATCCCAATTTGGTATTCATGGGCAAACAAAGATGAAGACGC
ATACTTCTTCAAGCTCCGGCGACCATGTTGGCATTGGGCAGACAGTGTTCTCCTGGAGGTCCTCAAAGCAGCACGTCGATAGGGTTAAACCATAAGTACCCGTTTGTTTCTACTTCTGCG
         970       980       990      1000      1010      1020      1030      1040      1050      1060      1070      1080

                  310                                     320                                     330                                     340
 R   E   I   F   D   M   Q   L   E   Y   M   M   N   D   T   V   G   Y   I   T   E   D   D   I   K   G   M   N   G   G   S   T   G   E   K   P   Y   K   C   P
ACGGGAGATTTTCGACATGCAATTAGAGTACATGATGAACGACACTGTAGGTTACATCACTGAAGATGACATTAAGGGCATGAATGGCGGCAGCACCGGCGAAAAACCGTATAAATGTCC
TGCCCTCTAAAAGCTGTACGTTAATCTCATGTACTACTTGCTGTGACATCCAATGTAGTGACTTCTACTGTAATTCCCGTACTTACCGCCGTCGTGGCCGCTTTTTGGCATATTTACAGG
        1090      1100      1110      1120      1130      1140      1150      1160      1170      1180      1190      1200

                  350                                     360
 E   C   G   K   S   F   S   R   S   G   G   S   H   H   H   H   H   H   *   *
GGAATGTGGCAAAAGCTTTAGCCGCAGCGGCGGTTCACATCATCATCATCATCATTAATGAAAGGGCGATATCCAGCACACTGGCGGCCGTTACTAGTGGATCCGGCTGCTAACAAAGCC
CCTTACACCGTTTTCGAAATCGGCGTCGCCGCCAAGTGTAGTAGTAGTAGTAGTAATTACTTTCCCGCTATAGGTCGTGTGACCGCCGGCAATGATCACCTAGGCCGACGATTGTTTCGG
        1210      1220      1230      1240      1250      1260      1270      1280      1290      1300      1310      1320


CGAAAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACT
GCTTTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGA
        1330      1340      1350      1360      1370      1380      1390      1400      1410      1420      1430      1440


CCCACGGCACGTTGGCAAGCTCG
GGGTGCCGTGCAACCGTTCGAGC
        1450      1460
```

FIG. 55 (Continued)

FIG. 56 - taLacBP14.186C

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                          10                            20
                                                             M  E  E  Y  K  F  K  M  A  T  F  Y  L  K  G  D  S  A  F  D  V  I  D  H
GGTTTCCCTCTAGAAATAATTTTGTTTAACTTTAAGAAGGAGATATACCATGGAAGAATATAAATTTAAAATGGCAACTTTTTACCTGAAAGGTGATAGCGCCTTTGACGTGATCGACCA
CCAAAGGGAGATCTTTATTAAAACAAATTGAAATTCTTCCTCTATATGGTACCTTCTTATATTTAAATTTTACCGTTGAAAAATGGACTTTCCACTATCGCGGAAACTGCACTAGCTGGT
       130       140       150       160       170       180       190       200       210       220       230       240

             30                            40                            50                            60
 F  R  Q  L  V  W  K  K  T  G  G  K  V  R  I  D  A  F  Q  A  G  E  L  G  F  P  V  T  E  I  L  E  A  T  S  R  G  V  V  E
CTTTCGCCAACTGGTCTGGAAGAAAACCGGTGGTAAGGTACGCATCGATGCGTTCCAAGCTGGGGAACTGGGCTTTCCAGTGACCGAGATCCTGGAAGCGACCAGTCGTGGTGTGGTGGA
GAAAGCGGTTGACCAGACCTTCTTTTGGCCACCATTCCATGCGTAGCTACGCAAGGTTCGACCCCTTGACCCGAAAGGTCACTGGCTCTAGGACCTTCGCTGGTCAGCACCACACCACCT
       250       260       270       280       290       300       310       320       330       340       350       360

             70                            80                            90                           100
 M  S  I  F  Y  P  N  Y  K  A  A  Q  D  P  V  M  A  L  A  G  G  R  P  G  P  M  F  D  L  R  D  Q  K  A  Q  V  D  A  T  K
GATGAGCATCTTCTACCCGAACTACAAAGCGGCACAGGATCCGGTGATGGCCTTAGCGGGAGGACGTCCGGGTCCAATGTTCGACCTGCGTGATCAGAAAGCCCAAGTGGATGCGACCAA
CTACTCGTAGAAGATGGGCTTGATGTTTCGCCGTGTCCTAGGCCACTACCGGAATCGCCCTCCTGCAGGCCCAGGTTACAAGCTGGACGCACTAGTCTTTCGGGTTCACCTACGCTGGTT
       370       380       390       400       410       420       430       440       450       460       470       480

            110                           120                           130                           140
 D  L  L  E  R  S  F  G  R  F  G  V  R  Y  I  A  P  M  V  Y  G  E  P  E  I  L  V  S  R  R  P  M  S  S  L  K  D  L  K  G
AGATCTCCTGGAAAGGTCCTTCGGTCGTTTCGGAGTTCGCTACATTGCGCCTATGGTGTACGGTGAACCGGAGATCCTGGTCTCGAGACGTCCGATGAGTAGCCTCAAAGACCTGAAAGG
TCTAGAGGACCTTTCCAGGAAGCCAGCAAAGCCTCAAGCGATGTAACGCGGATACCACATGCCACTTGGCCTCTAGGACCAGAGCTCTGCAGGCTACTCATCGGAGTTTCTGGACTTTCC
       490       500       510       520       530       540       550       560       570       580       590       600

            150                           160                           170                           180
 R  I  F  R  A  S  G  M  A  A  E  F  Y  T  A  I  G  A  Q  A  M  M  L  P  A  G  E  L  Y  Q  A  L  Q  L  G  T  I  D  G  L
GCGTATCTTCCGTGCGAGTGGTATGGCAGCGGAGTTCTACACCGCAATTGGCGCACAAGCGATGATGCTTCCAGCAGGTGAGCTCTACCAGGCACTGCAGTTAGGCACCATCGATGGTCT
CGCATAGAAGGCACGCTCACCATACCGTCGCCTCAAGATGTGGCGTTAACCGCGTGTTCGCTACTACGAAGGTCGTCCACTCGAGATGGTCCGTGACGTCAATCCGTGGTAGCTACCAGA
       610       620       630       640       650       660       670       680       690       700       710       720

            190                           200                           210                           220
 E  C  T  D  Y  T  A  N  Y  K  L  G  F  H  E  V  A  K  N  V  L  E  P  T  K  G  V  N  L  H  S  E  A  T  V  H  A  F  L  V
GGAGTGCACCGACTATACCGCGAACTACAAGCTTGGCTTCCACGAAGTGGCGAAGAACGTGCTGGAACCGACGAAAGGTGTGAACCTCCATTCGGAAGCTACCGTTCATGCGTTCCTGGT
CCTCACGTGGCTGATATGGCGCTTGATGTTCGAACCGAAGGTGCTTCACCGCTTCTTGCACGACCTTGGCTGCTTTCCACACTTGGAGGTAAGCCTTCGATGGCAAGTACGCAAGGACCA
       730       740       750       760       770       780       790       800       810       820       830       840

            230                           240                           250                           260
 V  N  P  K  V  W  E  K  L  P  K  E  H  Q  K  A  I  Q  E  A  A  D  E  A  Y  K  W  G  A  D  H  L  A  K  L  N  K  T  Y  K
TGTGAACCCGAAAGTCTGGGAGAAACTGCCGAAGGAACACCAGAAAGCGATCCAGGAAGCGGCGGACGAAGCGTACAAATGGGGTGCGGATCACCTTGCGAAACTGAACAAAACCTACAA
ACACTTGGGCTTTCAGACCCTCTTTGACGGCTTCCTTGTGGTCTTTCGCTAGGTCCTTCGCCGCCTGCTTCGCATGTTTACCCCACGCCTAGTGGAACGCTTTGACTTGTTTTGGATGTT
       850       860       870       880       890       900       910       920       930       940       950       960
```

```
                270                                     280                                     290                                     300
 D   K   W   I   K   A   G   A   K   V   T   Q   L   P   K   E   D   Q   D   K   V   I   E   V   S   A   K   I   L   S   G   Y   S   A   K   S   P   D   A   K
GGACAAATGGATCAAAGCGGGTGCGAAGGTGACCCAACTGCCGAAAGAAGACCAGGACAAAGTGATCGAAGTGTCGGCAAAGATCCTGTCTGGCTATAGCGCGAAGAGTCCGGATGCGAA
CCTGTTTACCTAGTTTCGCCCACGCTTCCACTGGGTTGACGGCTTTCTTCTGGTCCTGTTTCACTAGCTTCACAGCCGTTTCTAGGACAGACCGATATCGCGCTTCTCAGGCCTACGCTT
        970       980       990      1000      1010      1020      1030      1040      1050      1060      1070      1080

                310                                     320                                     330                                     340
 E   Y   A   R   R   L   V   E   L   W   K   K   L   G   Y   T   K   W   S   D   A   L   A   K   Q   I   K   G   G   S   H   H   H   H   H   H   *   *   *
AGAGTACGCGCGTCGTCTAGTGGAGCTGTGGAAGAAACTGGGCTACACCAAATGGTCTGATGCATTAGCAAAACAGATTAAAGGCGGCAGCCATCATCATCATCATCATTAATAATGAAA
TCTCATGCGCGCAGCAGATCACCTCGACACCTTCTTTGACCCGATGTGGTTTACCAGACTACGTAATCGTTTTGTCTAATTTCCGCCGTCGGTAGTAGTAGTAGTAGTAATTATTACTTT
       1090      1100      1110      1120      1130      1140      1150      1160      1170      1180      1190      1200

GGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCC
CCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGG
       1210      1220      1230      1240      1250      1260      1270      1280      1290      1300      1310      1320

TCTAAACGGGTCTTGAGGGGTTTTTTGCTGAAAGGAGGAACTATATCCGGAGCGACTCCCACGGCACGTTGGCAAGCTCG
AGATTTGCCCAGAACTCCCCAAAAAACGACTTTCCTCCTTGATATAGGCCTCGCTGAGGGTGCCGTGCAACCGTTCGAGC
       1330      1340      1350      1360      1370      1380      1390      1400
```

FIG. 56 (Continued)

FIG. 57 - rsLacBP12

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                           10                            20
                                                   M  Q  A  P  L  V  M  K  M  Q  T  S  W  P  A  S  D  I  W  M  D  F  A  R
GGTTTCCCTCTAGAAATAATTTTGTTTAACTTTAAGAAGGAGATATACCATGCAAGCACCGTTAGTTATGAAAATGCAAACTAGTTGGCCAGCTAGCGATATCTGGATGGACTTCGCACG
CCAAAGGGAGATCTTTATTAAAACAAATTGAAATTCTTCCTCTATATGGTACGTTCGTGGCAATCAATACTTTTACGTTTGATCAACCGGTCGATCGCTATAGACCTACCTGAAGCGTGC
       130       140       150       160       170       180       190       200       210       220       230       240

            30                            40                            50                            60
 E  Y  V  T  R  V  E  E  M  S  G  G  R  I  K  V  D  L  L  P  A  G  A  V  V  G  A  F  Q  V  M  D  A  V  H  D  G  V  I  D
TGAGTACGTGACCAGAGTGGAAGAGATGTCAGGTGGACGCATCAAGGTGGATCTGCTGCCAGCAGGTGCGGTAGTTGGTGCGTTCCAGGTGATGGACGCAGTACACGATGGGGTCATCGA
ACTCATGCACTGGTCTCACCTTCTCTACAGTCCACCTGCGTAGTTCCACCTAGACGACGGTCGTCCACGCCATCAACCACGCAAGGTCCACTACCTGCGTCATGTGCTACCCCAGTAGCT
       250       260       270       280       290       300       310       320       330       340       350       360

            70                            80                            90                           100
 A  S  H  S  V  S  A  Y  W  Y  G  K  S  K  A  A  S  F  F  G  T  G  P  V  F  G  G  S  A  T  T  M  L  G  W  F  Y  Q  G  G
TGCTAGCCACTCGGTGAGCGCTTACTGGTATGGCAAGAGCAAAGCGGCTAGCTTCTTTGGCACTGGTCCAGTCTTTGGCGGTAGTGCAACCACGATGCTCGGCTGGTTCTACCAAGGTGG
ACGATCGGTGAGCCACTCGCGAATGACCATACCGTTCTCGTTTCGCCGATCGAAGAAACCGTGACCAGGTCAGAAACCGCCATCACGTTGGTGCTACGAGCCGACCAAGATGGTTCCACC
       370       380       390       400       410       420       430       440       450       460       470       480

           110                           120                           130                           140
 G  Q  D  L  Y  R  E  L  T  Q  D  I  L  G  M  N  I  V  G  F  Y  G  F  P  M  P  A  Q  P  F  G  W  F  K  T  E  V  N  G  V
AGGTCAGGACCTGTACCGTGAACTGACGCAAGACATCCTCGGAATGAACATCGTAGGCTTCTACGGTTTCCCGATGCCGGCACAGCCATTCGGCTGGTTCAAGACGGAAGTGAACGGCGT
TCCAGTCCTGGACATGGCACTTGACTGCGTTCTGTAGGAGCCTTACTTGTAGCATCCGAAGATGCCAAAGGGCTACGGCCGTGTCGGTAAGCCGACCAAGTTCTGCCTTCACTTGCCGCA
       490       500       510       520       530       540       550       560       570       580       590       600

           150                           160                           170                           180
 A  D  I  Q  G  F  K  Y  R  T  V  G  L  A  A  D  L  L  Q  A  M  G  M  S  V  A  Q  L  P  G  G  E  I  V  P  A  M  E  R  G
TGCGGACATCCAAGGCTTCAAGTACCGTACCGTTGGACTGGCAGCAGATCTGCTGCAGGCTATGGGCATGTCAGTGGCACAGCTGCCAGGTGGCGAAATCGTTCCGGCAATGGAGCGTGG
ACGCCTGTAGGTTCCGAAGTTCATGGCATGGCAACCTGACCGTCGTCTAGACGACGTCCGATACCCGTACAGTCACCGTGTCGACGGTCCACCGCTTTAGCAAGGCCGTTACCTCGCACC
       610       620       630       640       650       660       670       680       690       700       710       720

           190                           200                           210                           220
 V  I  D  A  F  E  F  N  N  P  S  S  D  M  R  F  G  A  Q  D  V  A  K  N  Y  Y  L  S  S  Y  H  Q  A  S  E  S  F  E  Y  T
TGTGATCGATGCGTTCGAGTTCAACAACCCTAGCTCGGATATGCGCTTTGGTGCACAAGATGTGGCGAAGAACTACTACCTGTCCTCCTACCATCAGGCATCTGAGAGCTTCGAGTACAC
ACACTAGCTACGCAAGCTCAAGTTGTTGGGATCGAGCCTATACGCGAAACCACGTGTTCTACACCGCTTCTTGATGATGGACAGGAGGATGGTAGTCCGTAGACTCTCGAAGCTCATGTG
       730       740       750       760       770       780       790       800       810       820       830       840

           230                           240                           250                           260
 F  N  R  D  F  Y  E  D  L  D  P  D  L  Q  A  I  L  K  Y  A  V  E  A  A  S  T  S  N  T  A  L  A  L  R  Q  Y  S  A  D  L
CTTCAATCGCGACTTCTACGAGGATCTGGATCCTGACCTGCAAGCCATCCTGAAGTACGCTGTGGAAGCAGCGAGTACCAGCAATACCGCGTTAGCGCTGAGGCAGTATAGCGCAGATCT
GAAGTTAGCGCTGAAGATGCTCCTAGACCTAGGACTGGACGTTCGGTAGGACTTCATGCGACACCTTCGTCGCTCATGGTCGTTATGGCGCAATCGCGACTCCGTCATATCGCGTCTAGA
       850       860       870       880       890       900       910       920       930       940       950       960
```

```
          270                                     280                                     290                                     300
 A    T    L    A    A    E    N    G    V    A    V    H    R    T    P    K    D    I    L    S    G    Q    L    E    A    W    D    K    L    I    V    D    L    E    A    D    E    F    F    K
TGCGACGTTAGCGGCTGAAAACGGTGTTGCAGTGCATCGGACTCCGAAAGACATCCTGTCTGGTCAGCTGGAAGCATGGGACAAGCTGATCGTGGATCTCGAAGCGGATGAGTTCTTCAA
ACGCTGCAATCGCCGACTTTTGCCACAACGTCACGTAGCCTGAGGCTTTCTGTAGGACAGACCAGTCGACCTTCGTACCCTGTTCGACTAGCACCTAGAGCTTCGCCTACTCAAGAAGTT
      970       980       990      1000      1010      1020      1030      1040      1050      1060      1070      1080

          310                                     320                                     330                                     340
 K    V    L    D    S    Q    R    A    W    V    E    Q    V    S    Y    Y    E    L    M    N    A    A    D    L    G    L    A    Y    E    H    H    F    P    G    K    L    K    L    G    G
GAAAGTGCTGGATTCCCAACGTGCATGGGTCGAACAGGTCTCCTACTACGAGCTGATGAACGCAGCGGATCTTGGACTGGCATACGAACATCATTTTCCAGGAAAATTAAAACTGGGCGG
CTTTCACGACCTAAGGGTTGCACGTACCCAGCTTGTCCAGAGGATGATGCTCGACTACTTGCGTCGCCTAGAACCTGACCGTATGCTTGTAGTAAAAGGTCCTTTTAATTTTGACCCGCC
     1090      1100      1110      1120      1130      1140      1150      1160      1170      1180      1190      1200

          350
 S    H    H    H    H    H    H    *    *    *
CAGCCATCATCATCATCATCATTAATAATGAAAGGGCGATATCCAGCACACTGGCGGCCGTTACTAGTGGATCCGGCTGCTAACAAAGCCCGAAAGGAAGCTGAGTTGGCTGCTGCCACC
GTCGGTAGTAGTAGTAGTAGTAATTATTACTTTCCCGCTATAGGTCGTGTGACCGCCGGCAATGATCACCTAGGCCGACGATTGTTTCGGGCTTTCCTTCGACTCAACCGACGACGGTGG
     1210      1220      1230      1240      1250      1260      1270      1280      1290      1300      1310      1320


GCTGAGCAATAACTAGCATAACCCCTTGGGGCCTCTAAACGGGTCTTGAGGGGTTTTTTGCTGAAAGGAGGAACTATATCCGGAGCGACTCCCACGGCACGTTGGCAAGCTCG
CGACTCGTTATTGATCGTATTGGGGAACCCCGGAGATTTGCCCAGAACTCCCCAAAAAACGACTTTCCTCCTTGATATAGGCCTCGCTGAGGGTGCCGTGCAACCGTTCGAGC
     1330      1340      1350      1360      1370      1380      1390      1400      1410      1420      1430
```

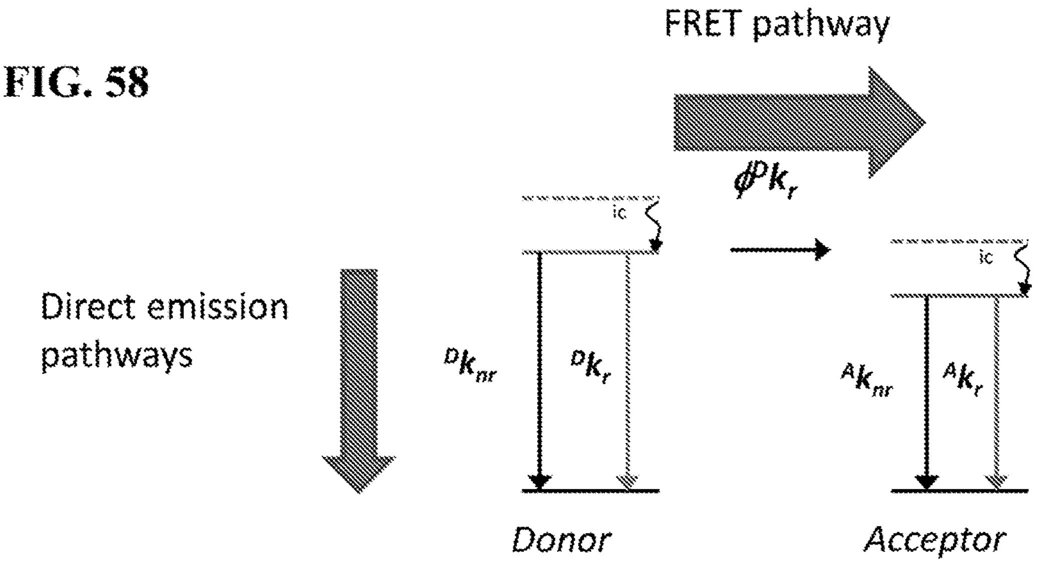

*Directly responsive partner*

- Responds directly to ligand-induced protein conformational changes
- Binds ligand (chemosensor)

Changes due to balance on photon flow in FRET and/or direct emission pathways

*Indirectly responsive partner*

No interactions with ligand of protein conformational changes
Changes only due photon flow in FRET pathway

Effects depend on role of directly responsive partner

*Donor:* Photon flow through competing output pathways
*Outputs*: Direct emission pathway (quenching) and FRET (spectral overlap) pathway

*Acceptor*

Balance of photon flow through input and output pathways
*Input:* FRET pathway (spectral overlap only)
*Output:* Direct emission pathway (quenching)

SEQUENCE LISTING

```
<160> NUMBER OF SEQ ID NOS: 157

<210> SEQ ID NO 1
<211> LENGTH: 361
<212> TYPE: PRT
<213> ORGANISM: Thermus thermophilus

<400> SEQUENCE: 1

Met Lys Arg Val Ser Arg Arg Ala Phe Leu Arg Arg Leu Gly Val Gly
1               5                   10                  15

Val Ala Ala Thr Ala Ala Phe Ser Pro Leu Ala Val Ala Gln Ala Arg
            20                  25                  30

Arg Tyr Arg Trp Arg Ile Gln Thr Ala Trp Asp Ala Gly Thr Val Gly
        35                  40                  45

Tyr Ser Leu Phe Gln Lys Phe Thr Glu Arg Val Lys Glu Leu Thr Asp
    50                  55                  60

Gly Gln Leu Glu Val Gln Pro Phe Pro Ala Gly Ala Val Val Gly Thr
65                  70                  75                  80
```

```
Phe Asp Met Phe Asp Ala Val Lys Thr Gly Val Leu Asp Gly Met Asn
                85                  90                  95

Pro Phe Thr Leu Tyr Trp Ala Gly Arg Met Pro Val Thr Ala Phe Leu
            100                 105                 110

Ser Ser Tyr Ala Leu Gly Leu Asp Arg Pro Asp Gln Trp Glu Thr Trp
        115                 120                 125

Phe Tyr Ser Leu Gly Gly Leu Asp Ile Ala Arg Arg Ala Phe Ala Glu
    130                 135                 140

Gln Gly Leu Phe Tyr Val Gly Pro Val Gln His Asp Leu Asn Ile Ile
145                 150                 155                 160

His Ser Lys Lys Pro Ile Arg Arg Phe Glu Asp Phe Lys Gly Val Lys
                165                 170                 175

Leu Arg Val Pro Gly Gly Met Ile Ala Glu Val Phe Ala Ala Ala Gly
            180                 185                 190

Ala Ser Thr Val Leu Leu Pro Gly Gly Glu Val Tyr Pro Ala Leu Glu
        195                 200                 205

Arg Gly Val Ile Asp Ala Ala Asp Phe Val Gly Pro Ala Val Asn Tyr
    210                 215                 220

Asn Leu Gly Phe His Gln Val Ala Lys Tyr Ile Ile Met Gly Pro Pro
225                 230                 235                 240

Glu Thr Pro Ala Ile His Gln Pro Val Asp Leu Met Asp Phe Thr Ile
                245                 250                 255

Asn Leu Asn Arg Trp Arg Ser Leu Pro Lys Pro Leu Gln Glu Arg Phe
            260                 265                 270

Ile Ala Ala Val His Glu Tyr Ser Trp Ile His Tyr Ala Gly Ile Gln
        275                 280                 285

Lys Ala Asn Leu Glu Ala Trp Pro Lys Tyr Arg Gln Ala Gly Val Glu
    290                 295                 300

Val Ile Arg Leu Ser Asn Glu Asp Val Arg Lys Phe Arg Arg Leu Ala
305                 310                 315                 320

Ile Pro Ile Trp Phe Lys Trp Ala Lys Met Asp Lys Tyr Ser Arg Glu
                325                 330                 335

Ala Phe Ala Ser Gln Leu Glu Tyr Met Lys Gly Ile Gly Tyr Val Thr
            340                 345                 350

Asp Glu Glu Leu Lys Gly Leu Ser Leu
        355                 360


<210> SEQ ID NO 2
<211> LENGTH: 360
<212> TYPE: PRT
<213> ORGANISM: Thermus scotoductus

<400> SEQUENCE: 2

Met Lys Glu Asn Arg Arg Asn Phe Ile Arg Lys Leu Ala Thr Gly Val
1               5                   10                  15

Ala Ala Ser Ser Val Phe Ser Pro Leu Ala Val Ala Gln Ala Pro Arg
            20                  25                  30

Phe Arg Trp Arg Ile Gln Ser Ala Trp Asp Ala Gly Thr Val Gly Tyr
        35                  40                  45

Ser Leu Phe Gln Lys Phe Ala Glu Arg Val Lys Glu Leu Thr Asp Gly
    50                  55                  60

Gln Ile Glu Ile Gln Thr Phe Pro Ala Gly Ala Val Val Gly Thr Phe
65                  70                  75                  80

Asp Met Phe Asp Ala Val Lys Thr Gly Val Leu Asp Gly Met His Pro
```

-continued

```
                85                  90                  95

Phe Thr Leu Tyr Trp Ala Gly Arg Met Pro Val Thr Ala Phe Leu Ser
            100                 105                 110

Ser Tyr Pro Leu Gly Leu Asp Arg Pro Asp Gln Trp Glu Thr Trp Tyr
        115                 120                 125

Tyr Gly Leu Gly Gly Leu Glu Leu Ala Arg Lys Ala Tyr Glu Glu Gln
    130                 135                 140

Gly Leu Phe Phe Val Gly Pro Val Gln His Asp Tyr Asn Leu Ile His
145                 150                 155                 160

Ser Lys Lys Pro Ile Lys Ser Phe Glu Asp Phe Lys Gly Val Lys Leu
                165                 170                 175

Arg Val Pro Gly Gly Met Ile Ala Glu Ile Phe Ala Ala Ala Gly Ala
            180                 185                 190

Ala Thr Val Leu Leu Pro Gly Gly Glu Val Tyr Pro Ala Leu Glu Arg
        195                 200                 205

Gly Val Ile Asp Ala Ala Asp Phe Val Gly Pro Ala Val Asn Tyr Asn
    210                 215                 220

Leu Gly Phe His Gln Val Thr Lys Tyr Ile Ile Met Gly Pro Pro Glu
225                 230                 235                 240

Thr Pro Cys Ile His Gln Pro Val Asp Leu Ala Asp Ile Thr Ile Asn
                245                 250                 255

Ile Asn Arg Trp Arg Ala Leu Pro Arg Asn Leu Gln Glu Arg Phe Glu
            260                 265                 270

Ala Ala Val His Glu Trp Ser Trp Ile His Tyr Ala Gly Ile Gln Lys
        275                 280                 285

Ala Asn Leu Glu Thr Trp Pro Lys Tyr Lys Ala Ala Gly Val Gln Val
    290                 295                 300

Ile Arg Leu Ser Thr Val Asp Val Arg Lys Phe Arg Arg Val Ala Ile
305                 310                 315                 320

Pro Ile Trp Phe Lys Trp Ala Lys Gln Asp Lys Tyr Thr Arg Glu Ala
                325                 330                 335

Phe Ala Ser Gln Leu Glu Tyr Met Lys Ala Leu Gly Tyr Val Thr Asp
            340                 345                 350

Ala Asp Ile Arg Gly Leu Ser Leu
        355                 360


<210> SEQ ID NO 3
<211> LENGTH: 360
<212> TYPE: PRT
<213> ORGANISM: Thermus oshimai

<400> SEQUENCE: 3

Met Lys Ser Thr Arg Arg Gln Phe Leu Lys Lys Ala Ala Ile Gly Val
1               5                   10                  15

Ala Ala Ser Ser Ala Phe Ser Pro Leu Ala Ile Ala Gln Ala Pro Arg
            20                  25                  30

Phe Arg Trp Arg Ile Gln Ser Ala Trp Asp Ala Gly Thr Val Gly Tyr
        35                  40                  45

Thr Leu Phe Gln Arg Phe Ala Glu Arg Val Lys Glu Leu Thr Asp Gly
    50                  55                  60

Gln Ile Glu Ile Gln Pro Phe Pro Ala Gly Ala Val Val Gly Thr Phe
65                  70                  75                  80

Asp Met Phe Asp Ala Val Lys Thr Gly Val Leu Asp Gly Met His Pro
                85                  90                  95
```

```
Phe Thr Leu Tyr Trp Ala Gly Arg Met Pro Val Thr Ala Phe Leu Ser
            100                 105                 110

Ser Tyr Pro Leu Gly Leu Asp Arg Pro Asp Gln Trp Glu Thr Trp Tyr
        115                 120                 125

Tyr Gly Leu Gly Gly Leu Glu Leu Ala Arg Lys Ala Tyr Glu Glu Gln
    130                 135                 140

Gly Leu Ala Tyr Ile Gly Pro Val Gln His Asp Tyr Asn Leu Ile His
145                 150                 155                 160

Ser Lys Lys Pro Ile Lys Ser Phe Glu Glu Phe Lys Gly Val Lys Leu
                165                 170                 175

Arg Val Pro Gly Gly Met Ile Ala Glu Ile Phe Ala Ala Ala Gly Ala
            180                 185                 190

Ala Thr Val Leu Leu Pro Gly Gly Glu Val Tyr Pro Ala Leu Glu Arg
        195                 200                 205

Gly Val Ile Asp Ala Ala Asp Phe Val Gly Pro Ala Val Asn Tyr Asn
    210                 215                 220

Leu Gly Phe His Gln Val Thr Lys Tyr Ile Ile Met Gly Pro Pro Glu
225                 230                 235                 240

Thr Pro Cys Ile His Gln Pro Val Asp Leu Ala Asp Ile Thr Leu Asn
                245                 250                 255

Leu Asn Arg Trp Arg Ala Val Pro Lys Asn Leu Gln Glu Arg Phe Glu
            260                 265                 270

Ala Ala Val His Glu Trp Ser Trp Val His Tyr Ala Gly Ile Gln Lys
        275                 280                 285

Ala Asn Leu Glu Ala Trp Pro Lys Tyr Arg Ala Ala Gly Val Gln Ile
    290                 295                 300

Ile Arg Leu Ser Thr Val Asp Val Arg Lys Phe Arg Arg Val Ala Ile
305                 310                 315                 320

Pro Ile Trp Phe Lys Trp Ala Lys Gln Asp Lys Tyr Ala Lys Glu Ala
                325                 330                 335

Phe Gln Ser Gln Leu Glu Tyr Met Lys Ala Leu Gly Tyr Val Thr Asp
            340                 345                 350

Val Asp Leu Arg Gly Leu Ser Leu
        355                 360


<210> SEQ ID NO 4
<211> LENGTH: 386
<212> TYPE: PRT
<213> ORGANISM: Unknown
<220> FEATURE:
<223> OTHER INFORMATION: Description of Unknown:
      Thioalkalivibrio sulfidophilus sequence

<400> SEQUENCE: 4

Met Ser Thr Lys Asp Asp Asn Gly Thr Gly Ile Val Thr Gly Ala Ala
1               5                   10                  15

Gln Glu Gly Ser Gln Thr Thr Ser Arg Arg Gly Phe Leu Lys Ala Ser
            20                  25                  30

Ala Ala Leu Gly Ala Gly Ala Ile Leu Gly Ala Pro Tyr Ile Gly Asn
        35                  40                  45

Ala Gln Thr Ala Arg Gly Val Arg Trp Arg Met Gln Ser Ala Trp Gln
    50                  55                  60

Pro Gly Thr Ile Gly Tyr Arg Thr Phe Glu Thr Trp Cys Arg Ser Ile
65                  70                  75                  80

Gln Glu Leu Thr Ser Gly Glu Leu Ser Ile Glu Pro Phe Pro Ala Gly
                85                  90                  95
```

Ala Val Ala Gly Thr Phe Glu Met Ala Asp Ala Val Arg Ser Gly Val
100 105 110

Leu Asp Gly Met Asn Trp Phe Thr Val Tyr Trp Pro Gly Lys Met Pro
115 120 125

Ala Gly Val Phe Met Ser Ala Tyr Pro Met Ala Leu Ser Leu Pro His
130 135 140

His Trp Asp Met Met Phe Asp Ser Phe Gly Gly Arg Gln Ile Val Asp
145 150 155 160

Glu Leu Tyr Asp Arg Gln Gly Leu Val Phe Leu Gly His Val Gln His
165 170 175

Asp Leu Asn Leu Ile His Ser Lys Val Pro Leu Arg Ser Phe Asp Asp
180 185 190

Phe Arg Gly Lys Arg Ile Arg Phe Pro Gly Gly Ile Ile Ala Glu Thr
195 200 205

Phe Ala Lys Val Gly Val Arg Thr Thr Leu Leu Pro Gly Gly Asp Val
210 215 220

Tyr Pro Ala Leu Glu Arg Gly Thr Ile Asp Ala Ala Asp Phe Val Gly
225 230 235 240

Pro Ala Val Asn Tyr Asp Leu Gly Phe His Gln Val Ala Asp Tyr Ile
245 250 255

Ile Met Gly Pro Pro Ser Thr Pro Cys Leu His Gln Pro Val Asp Leu
260 265 270

Met Asp Ile Ser Val Asn Lys Arg Ser Trp Ser Arg Ile Ser Glu His
275 280 285

Thr Gln Lys Leu Met Tyr Lys Phe Val Lys Ala Tyr Ser Ala Glu His
290 295 300

Phe Ala Ala Ile Gln Lys Ala Asn His Glu Ala Trp Pro Lys Tyr Lys
305 310 315 320

Glu Ala Gly Val Glu Val Ile His Leu Ser Glu Glu Asp Ala Ala Arg
325 330 335

Phe Arg Glu Ala Ala Ile Pro Leu Trp Phe Glu Trp Ala Asn Lys Asp
340 345 350

Arg Asp Ala Ala Arg Leu Phe Lys Val His Leu Glu Val Met Gln Asp
355 360 365

Pro Ser Val Ala Val Ile Thr Pro Asp Asp Ile Lys Asp Tyr Lys Leu
370 375 380

Asn Phe
385

<210> SEQ ID NO 5
<211> LENGTH: 366
<212> TYPE: PRT
<213> ORGANISM: Roseobacter denitrificans

<400> SEQUENCE: 5

Met Thr Ile Lys Thr Thr Ser Arg Arg Asn Ala Leu Arg Thr Leu Ala
1 5 10 15

Gly Ala Gly Ala Ala Thr Leu Ala Ala Pro His Ile Ala Thr Ala Ala
20 25 30

Gly Glu Gly Thr Thr Trp Lys Ile Gln Thr Ser His Thr Gly Gly Ile
35 40 45

Gly Leu Ala Thr Phe Lys Asp Trp Cys Ser Ser Ile Glu Glu Lys Thr
50 55 60

Gly Gly Glu Leu Ala Phe Thr Ala Phe Gly Ala Asn Asp Val Val Gly

```
65                  70                  75                  80

Asp Phe Gln Leu Tyr Asp Ala Val Lys Asn Gly Val Leu Asp Ala Val
                85                  90                  95

Asn Pro Phe Thr Ile Tyr Ala Gln Gly Ile Ile Pro Ala Ala Thr Phe
            100                 105                 110

Leu Thr Ser Tyr Pro Leu Gly Leu Arg Asn Pro His Glu Trp Asp Val
        115                 120                 125

Phe Phe Tyr Ser Leu Gly Gly Leu Glu Ile Ala Arg Glu Leu Tyr Ala
    130                 135                 140

Ala Gln Gly Met Lys Phe Val Gly Pro Val His His Gly Pro Asn Ile
145                 150                 155                 160

Ile His Ser Lys Val Pro Ile Arg Ser Ile Asp Asp Phe Ala Gly Leu
                165                 170                 175

Lys Met Arg Met Pro Gly Gly Met Val Ala Glu Val Phe Ser Glu Ile
            180                 185                 190

Gly Ala Glu Thr Thr Val Leu Pro Gly Ser Glu Ile Phe Pro Ala Leu
        195                 200                 205

Glu Lys Gly Thr Ile Asp Ala Ala Asp Phe Val Gly Pro Ala Val Asn
    210                 215                 220

Tyr Ala Leu Gly Phe Ser Gln Val Thr Asn Tyr Ile Ser Met Gly Pro
225                 230                 235                 240

Ala Gly Phe Met Ser Leu Tyr Gln Pro Val Asp Leu Met Asp Ile Thr
                245                 250                 255

Val Gly Gln Thr Ala Trp Asp Ala Leu Ser Pro Gln Met Gln Gln Phe
            260                 265                 270

Val Glu Met Glu Thr His Val Tyr Ser Asp Met His His Ala Ala Ile
        275                 280                 285

Gln Lys Ala Asp Gln Glu Ala Trp Ala Lys Phe Glu Ala Asp Gly Thr
    290                 295                 300

Glu Val Thr Arg Leu Ser Gln Asp Asp Val Glu Leu Met Thr Glu Val
305                 310                 315                 320

Ala Val Pro Ile Trp Phe Asp Tyr Ala Asn Arg Asp Lys Asp Ala Ala
                325                 330                 335

Arg Val Phe Lys Ile Gln Leu Asp Tyr Met Met Ser Gly Ser Leu Gly
            340                 345                 350

Tyr Val Thr Pro Glu Gln Ile Glu Gly Leu Thr Leu Asn Leu
        355                 360                 365


<210> SEQ ID NO 6
<211> LENGTH: 371
<212> TYPE: PRT
<213> ORGANISM: Unknown
<220> FEATURE:
<223> OTHER INFORMATION: Description of Unknown:
      Marinobacter sequence

<400> SEQUENCE: 6

Met Thr Asp Ile Thr Cys Lys Ile Glu Thr Lys Gly Ser Ala Arg Arg
1               5                   10                  15

Arg Gly Phe Leu Lys Thr Leu Ala Val Ser Ala Ala Ile Ser Ala Thr
            20                  25                  30

Leu Leu Ala Ser Ser Val Gln Ala Ala Thr Thr Trp Lys Ile Gln Ser
        35                  40                  45

Val Trp Asp Ala Gly Thr Val Gly Tyr Asp Leu Phe Lys Glu Trp Cys
    50                  55                  60
```

-continued

```
Asp Gly Met Glu Glu Lys Thr Gly Gly Glu Leu Lys Phe Thr Cys Phe
65                  70                  75                  80

Pro Ala Lys Ala Val Ala Ala Asp Asn Asn Gly Leu Phe Asp Ala Val
                85                  90                  95

Arg Asn Gly Val Leu Gln Gly Met Asn Pro Phe Thr Leu Tyr Trp Ser
            100                 105                 110

Gly Lys Ile Pro Ala Ser Val Phe Leu Ser Ser Tyr Pro Ala Gly Pro
        115                 120                 125

Asp Gln Pro His Gln Trp Asp Thr Met Phe Tyr Ser Leu Gly Met Leu
    130                 135                 140

Glu Lys Thr Arg Glu Ile Tyr Lys Lys Phe Gly Leu Phe Tyr Val Gly
145                 150                 155                 160

Pro Ile Gln His Asp Ala Asn Ile Ile His Ser Lys Gln Pro Ile Asn
                165                 170                 175

Ser Leu Asp Asp Leu Lys Gly Leu Lys Met Arg Leu Pro Gly Gly Met
            180                 185                 190

Val Ala Glu Val Phe Ala Lys Phe Gly Val Ala Ala Val Ser Leu Pro
        195                 200                 205

Gly Ser Asp Ile Phe Pro Ala Leu Glu Lys Gly Thr Ile Asp Ala Ala
    210                 215                 220

Asp Tyr Val Gly Pro Ala Val Asn Trp Glu Leu Gly Phe Ser Gln Val
225                 230                 235                 240

Thr Lys Tyr Ile Leu Met Gly Pro Pro Gly Ile Met Ser Val Tyr Gln
                245                 250                 255

Pro Val Asp Leu Met Asp Leu Thr Val Asn Leu Arg Ala Trp Asn Ala
            260                 265                 270

Leu Asp Pro Lys Leu Gln Gln Ile Val Glu Asp Glu Val Arg Ile Tyr
        275                 280                 285

Ser Gln Lys His Tyr Leu Ala Ile Gln Lys Arg Asn Ile Glu Ala Met
    290                 295                 300

Lys Lys Phe Glu Ala Ala Gly Thr Thr Val Thr Arg Leu Ser Gln Glu
305                 310                 315                 320

Asp Leu Gln Glu Phe Arg Arg Ala Ala Ile Pro Ile Trp Tyr Ser Trp
                325                 330                 335

Ala Asn Lys Asp Glu Asp Ala Arg Glu Ile Phe Asp Met Gln Leu Glu
            340                 345                 350

Tyr Met Met Asn Asp Thr Val Gly Tyr Ile Thr Glu Asp Asp Ile Lys
        355                 360                 365

Gly Met Asn
    370


<210> SEQ ID NO 7
<211> LENGTH: 360
<212> TYPE: PRT
<213> ORGANISM: Unknown
<220> FEATURE:
<223> OTHER INFORMATION: Description of Unknown:
      Thermus sp. sequence

<400> SEQUENCE: 7

Met Lys Glu Thr Arg Arg Ser Phe Ile Arg Lys Val Ala Thr Gly Val
1               5                   10                  15

Ala Ala Ser Ala Ala Phe Ser Pro Leu Ala Ile Ala Gln Ala Pro Arg
            20                  25                  30

Phe Arg Trp Arg Ile Gln Ser Ala Trp Asp Ala Gly Thr Val Gly Tyr
        35                  40                  45
```

```
Thr Leu Phe Gln Arg Phe Ala Glu Arg Val Lys Glu Leu Thr Asp Gly
    50                  55                  60

Gln Ile Glu Ile Gln Thr Phe Pro Ala Gly Ala Val Val Gly Thr Phe
65                  70                  75                  80

Asp Met Phe Asp Ala Val Lys Thr Gly Val Leu Asp Gly Met His Pro
                85                  90                  95

Phe Thr Leu Tyr Trp Ala Gly Arg Met Pro Val Thr Ala Phe Leu Ser
            100                 105                 110

Ser Tyr Pro Leu Gly Leu Asp Arg Pro Asp Gln Trp Glu Thr Trp Tyr
        115                 120                 125

Tyr Ala Leu Gly Gly Leu Asp Leu Ala Arg Arg Ala Phe Glu Glu Gln
    130                 135                 140

Gly Leu Phe Tyr Val Gly Pro Val Gln His Asp Tyr Asn Leu Ile His
145                 150                 155                 160

Ser Lys Lys Pro Ile Lys Ser Phe Glu Asp Phe Lys Gly Val Lys Leu
                165                 170                 175

Arg Val Pro Gly Gly Met Ile Ala Asp Val Phe Ser Ala Ala Gly Ala
            180                 185                 190

Ala Thr Val Leu Leu Pro Gly Gly Glu Val Tyr Pro Ala Leu Glu Arg
        195                 200                 205

Gly Val Ile Asp Ala Ala Asp Phe Val Gly Pro Ala Val Asn Tyr Asn
    210                 215                 220

Leu Gly Phe His Gln Val Thr Lys Tyr Ile Ile Met Gly Pro Pro Glu
225                 230                 235                 240

Thr Pro Cys Ile His Gln Pro Val Asp Leu Ala Asp Ile Thr Leu Asn
                245                 250                 255

Leu Ser Arg Trp Arg Ala Val Pro Lys Asn Leu Gln Glu Arg Phe Glu
            260                 265                 270

Ala Ala Val His Glu Trp Ser Trp Ile His Tyr Ala Gly Ile Gln Lys
        275                 280                 285

Ala Asn Leu Glu Thr Trp Pro Lys Tyr Lys Ala Ala Gly Val Gln Ile
    290                 295                 300

Ile Arg Leu Thr Thr Val Asp Val Arg Lys Phe Arg Arg Val Ala Ile
305                 310                 315                 320

Pro Ile Trp Phe Lys Trp Ala Lys Gln Asp Lys Tyr Ala Arg Glu Ala
                325                 330                 335

Phe Ala Ser Gln Leu Glu Tyr Met Lys Ala Leu Gly Tyr Val Thr Asp
            340                 345                 350

Ala Asp Val Arg Gly Leu Ser Leu
        355                 360
```

<210> SEQ ID NO 8
<211> LENGTH: 396
<212> TYPE: PRT
<213> ORGANISM: Unknown
<220> FEATURE:
<223> OTHER INFORMATION: Description of Unknown:
      Marinobacter adhaerens sequence

<400> SEQUENCE: 8

```
Met Ser Ala Cys Ala Gly Val Ala Ile Asp Ala Asp Lys Asn Lys Ala
1               5                   10                  15

Asn Gly Asp Val Ser Met Asn Ser Lys Asn Asn Ile Arg Asn Ser Cys
            20                  25                  30

Asp Thr Gly Glu Thr Pro Pro Arg Arg Ser Phe Leu Lys Thr Ile Ala
```

```
        35                  40                  45

Met Gly Ala Thr Leu Ala Gly Ala Met Leu Met Gly Ala Gly Gln Ala
    50                  55                  60

Gln Ala Ala Thr Thr Trp Lys Ile Gln Ser Thr Trp Asp Ala Gly Thr
65                  70                  75                  80

Val Gly Tyr Thr Leu Phe Glu Glu Trp Cys Lys Ser Ile Glu Ala Lys
                85                  90                  95

Ser Gly Gly Glu Leu Lys Phe Gln Cys Phe Pro Ala Lys Ala Val Ala
            100                 105                 110

Ala Asp Asn Asn Ala Leu Phe Asp Ala Val Arg Asn Gly Val Leu Gln
        115                 120                 125

Gly Met Asn Pro Phe Thr Leu Tyr Trp Ala Gly Lys Ile Pro Ala Ser
    130                 135                 140

Val Phe Leu Ser Ser Tyr Pro Ala Gly Pro Asp Gln Pro His Gln Trp
145                 150                 155                 160

Asp Thr Met Phe Tyr Ser Met Gly Met Leu Glu Lys Thr Arg Glu Ile
                165                 170                 175

Tyr Lys Lys Phe Gly Leu Phe Tyr Val Gly Pro Ile Gln His Asp Ala
            180                 185                 190

Asn Ile Ile His Ser Lys Gln Pro Val Asn Ser Leu Asp Asp Leu Lys
        195                 200                 205

Gly Met Lys Ile Arg Val Pro Gly Gly Met Val Ala Glu Val Phe Gln
    210                 215                 220

Gln Phe Gly Val Ser Thr Val Ser Leu Pro Gly Ser Asp Ile Phe Pro
225                 230                 235                 240

Ala Leu Glu Lys Gly Thr Ile Asp Ala Ala Asp Phe Val Gly Pro Ala
                245                 250                 255

Val Asn Tyr Glu Leu Gly Phe Ser Gln Val Thr Asp Tyr Ile Ile Phe
            260                 265                 270

Gly Pro Pro Gly Val Met Ser Ile Tyr Gln Pro Val Asp Leu Met Asp
        275                 280                 285

Leu Thr Val Ser Leu Arg Ala Trp Asn Ser Ile Ser Pro Glu Leu Gln
    290                 295                 300

Gln Leu Val Glu Asp Glu Val Arg Ile Tyr Ser Gln Lys His Tyr Leu
305                 310                 315                 320

Ala Ile Gln Ala Arg Asn Ile Glu Ala Met Glu Lys Phe Lys Ala Asp
                325                 330                 335

Gly Asp Thr Val Thr Arg Leu Ser Gln Glu Asp Leu Glu Thr Trp Arg
            340                 345                 350

Lys Ala Ala Ile Pro Ile Trp Phe Asn Trp Ala Asn Lys Asn Asp Asp
        355                 360                 365

Ala Arg Ala Ile Leu Asp Ile Gln Leu Lys Tyr Met Met Asn Asp Thr
    370                 375                 380

Val Gly Tyr Ile Thr Glu Glu Asp Ile Lys Gly Phe
385                 390                 395
```

<210> SEQ ID NO 9
<211> LENGTH: 387
<212> TYPE: PRT
<213> ORGANISM: Unknown
<220> FEATURE:
<223> OTHER INFORMATION: Description of Unknown:
      Anaeromyxobacter dehalogenans sequence

<400> SEQUENCE: 9

-continued

```
Met Lys Lys Thr Thr Ser Arg Ser Gln Pro Asp Thr Ala Pro Lys Ala
1               5                   10                  15

Ser Arg Arg Ser Phe Leu Lys Lys Ala Ala Leu Gly Ala Ala Gly Val
            20                  25                  30

Ala Ala Gly Ala Ala Ala Pro Thr Ile His Val Ala Gln Ala Pro Ile
        35                  40                  45

Thr Leu Arg Phe Gln Ser Thr Trp Pro Gln Lys Asp Ile Phe His Glu
    50                  55                  60

Phe Ala Leu Asp Tyr Ala Lys Lys Val Asn Glu Met Ser Gly Gly Arg
65                  70                  75                  80

Leu Lys Ile Glu Val Leu Ala Ala Gly Ser Val Val Lys Ala Phe Asp
                85                  90                  95

Leu Leu Asp Ala Val Ser Lys Gly Thr Leu Asp Gly Gly His Gly Val
            100                 105                 110

Val Ala Tyr Trp Tyr Gly Lys Asn Thr Ala Leu Ala Leu Trp Gly Ser
        115                 120                 125

Gly Pro Ala Phe Gly Met Asp Pro Asn Met Val Leu Ala Trp His His
    130                 135                 140

Tyr Gly Gly Gly Arg Gln Leu Leu Glu Glu Ile Tyr Arg Ser Leu Asn
145                 150                 155                 160

Leu Asp Val Val Ser Leu Met Tyr Gly Pro Met Pro Thr Gln Pro Leu
                165                 170                 175

Gly Trp Phe Lys Gln Lys Pro Ile Ala Lys Pro Asp Asp Met Lys Gly
            180                 185                 190

Leu Lys Phe Arg Thr Val Gly Leu Ser Ile Asp Ile Phe Asn Gly Leu
        195                 200                 205

Gly Ala Ala Val Asn Ala Leu Pro Gly Ala Glu Ile Val Pro Ala Met
    210                 215                 220

Asp Arg Gly Leu Leu Asp Ala Ala Glu Phe Asn Asn Ala Ser Ser Asp
225                 230                 235                 240

Arg Val Leu Gly Phe Pro Asp Val Ser Lys Ile Cys Met Leu Gln Ser
                245                 250                 255

Phe His Gln Cys Ser Glu Gln Phe Glu Ile Leu Phe Asn Gly Lys Arg
            260                 265                 270

Phe Gln Ala Leu Pro Ala Asp Leu Lys Ser Ile Ile Ser Ile Ala Ala
        275                 280                 285

Gln Ala Ala Ser Ala Asp Met Ser Trp Lys Ala Ile Asp Arg Tyr Ser
    290                 295                 300

Ser Asp Tyr Phe Glu Met Arg Asp Lys Gln Gly Val Lys Phe Tyr Ser
305                 310                 315                 320

Thr Arg Pro Glu Ile Leu Lys Arg Gln Leu Glu Ile Trp Asp Gln Val
                325                 330                 335

Met Glu Lys Arg Ala Ala Glu Asn Pro Thr Phe Lys Lys Val Leu Glu
            340                 345                 350

Ser Gln Arg Arg Phe Ala Gln Arg Ala Ala Arg Trp Gln Asn Asp Thr
        355                 360                 365

Asn Val Asp Phe Lys Met Ala Tyr Asn His Phe Phe Gly Gly Lys Lys
    370                 375                 380

Lys Ala Thr
385
```

<210> SEQ ID NO 10
<211> LENGTH: 343
<212> TYPE: PRT

<213> ORGANISM: Unknown
<220> FEATURE:
<223> OTHER INFORMATION: Description of Unknown:
Polymorphum gilvum sequence

<400> SEQUENCE: 10

```
Met Thr Glu Ile Ser Arg Arg Gly Leu Leu Ala Gly Ser Val Phe Gly
1               5                   10                  15

Gly Val Ala Leu Ala Ala Pro Thr Val Ala Arg Ala Gln Glu Ala Val
            20                  25                  30

Glu Trp Arg Met Gln Ala Leu Trp Asp Ala Gly Thr Thr Pro Phe Glu
        35                  40                  45

Phe Glu Lys Lys Phe Val Glu Arg Val Gly Glu Leu Thr Glu Gly Arg
    50                  55                  60

Phe Lys Ile Thr Leu Tyr Ser Ala Gly Gln Ile Val Pro Ala Asn Gln
65                  70                  75                  80

Ala Phe Asp Ala Val Arg Ser Gly Ala Phe Glu Met Met Lys Thr Phe
                85                  90                  95

Asp Gly Tyr Glu Ala Gly Lys Ile Pro Ala Phe Ala Phe Thr Ser Thr
            100                 105                 110

Ile Pro Phe Gly Phe Pro Gln Ser Asp Gln Tyr Glu Ala Trp Phe Tyr
        115                 120                 125

Glu Leu Gly Gly Leu Asp Leu Ala Arg Glu Ala Tyr Ala Lys Gly Gly
    130                 135                 140

Leu Phe Tyr Ile Ala Pro Thr Val Tyr Gly Glu Glu Pro Met His Ser
145                 150                 155                 160

Thr Val Lys Ile Glu Ser Ile Ala Asp Met Ala Gly Lys Lys Gly Arg
                165                 170                 175

Phe Val Gly Leu Ala Ser Ala Val Met Ala Asp Leu Gly Val Ala Val
            180                 185                 190

Ser Pro Leu Ala Thr Ala Glu Val Tyr Thr Ala Leu Glu Lys Gly Leu
        195                 200                 205

Ile Asp Phe Ala Asp Arg Gly Asp Leu Thr Ala Asn Tyr Glu Ala Gly
    210                 215                 220

Leu Gly Glu Val Ala Lys Phe Ile Ile Leu Pro Gly Val His Gln Pro
225                 230                 235                 240

Thr Thr Ala Thr Ser Tyr Val Ala Asn Gln Ala Ala Tyr Gln Lys Leu
                245                 250                 255

Pro Asp Gly Phe Lys Ala Ala Leu Ala Val Ala Ala Arg Glu Ile Ser
            260                 265                 270

Gly Ser Leu Arg Gln His Ile Leu Val Gln Asp Met Glu Val Leu Thr
        275                 280                 285

Lys Tyr Lys Asp Gln Gly Val Glu Val Val Arg Leu Asp Ala Ala Asp
    290                 295                 300

Ile Ala Ala Ala Arg Ala Lys Ala Val Glu Ser Trp Glu Lys Ala Thr
305                 310                 315                 320

Lys Gly Asp Glu Leu Ala Thr Arg Val Leu Lys Gly Gln Val Asp Phe
                325                 330                 335

Met Thr Ser Leu Gly Leu Leu
            340
```

<210> SEQ ID NO 11
<211> LENGTH: 365
<212> TYPE: PRT
<213> ORGANISM: Unknown
<220> FEATURE:

<223> OTHER INFORMATION: Description of Unknown:
Pseudomonas stuztzeri sequence

<400> SEQUENCE: 11

```
Met Lys Arg Arg His Leu Phe Gly Ala Ala Ala Leu Leu Ala Thr Leu
1               5                   10                  15

Ala Leu Ala Gly Cys Lys Asp Glu Gln Ser Gln Ala Pro Asn Gln Gln
            20                  25                  30

Ala Ala Gly Glu Pro Ala Lys Thr Tyr His Trp Lys Met Val Thr Ala
        35                  40                  45

Trp Pro Lys Asn Tyr Pro Gly Leu Gly Thr Ser Ala Glu Arg Leu Ala
    50                  55                  60

Glu Arg Val Asn Ala Met Ser Gly Gly Arg Leu Thr Ile Lys Val Tyr
65                  70                  75                  80

Ala Ala Gly Glu Leu Val Pro Ala Leu Glu Val Phe Asp Ala Val Ser
                85                  90                  95

Arg Gly Thr Ala Glu Leu Gly His Gly Ala Ser Tyr Tyr Trp Lys Gly
            100                 105                 110

Lys Val Pro Thr Ala Gln Phe Phe Thr Ser Val Pro Phe Gly Leu Ser
        115                 120                 125

Thr Ser Glu Met Asn Ala Trp Leu Ser Lys Gly Gly Gly Gln Ala Phe
    130                 135                 140

Trp Asp Glu Ala Tyr Ala Pro Phe Gly Val Lys Pro Leu Val Ile Gly
145                 150                 155                 160

Asn Thr Gly Met Gln Met Gly Gly Trp Tyr Asn Lys Glu Ile Asn Ser
                165                 170                 175

Leu Thr Asp Leu Lys Gly Leu Lys Ile Arg Met Pro Gly Leu Gly Gly
            180                 185                 190

Glu Val Leu Ser Arg Leu Gly Ala Thr Thr Val Asn Leu Pro Gly Gly
        195                 200                 205

Glu Val Phe Thr Ala Leu Gln Thr Gly Ala Ile Asp Ala Thr Asp Trp
    210                 215                 220

Val Ser Pro Tyr Asn Asp Leu Ala Phe Gly Leu His Lys Ala Ala Arg
225                 230                 235                 240

Tyr Tyr Tyr Tyr Pro Gly Trp Gln Glu Pro Gln Ala Val Leu Glu Leu
                245                 250                 255

Leu Ile Asn Gln Lys Ala Phe Asp Ser Leu Pro Ala Asp Leu Gln Ala
            260                 265                 270

Ile Val Thr Glu Ala Ser Leu Ala Ala Ser Arg Asp Met His Asp Asp
        275                 280                 285

Tyr Val Tyr Asn Asn Ala Leu Ala Leu Glu Gln Leu Lys Gln Gln Gly
    290                 295                 300

Thr Glu Leu Lys Arg Phe Pro Asp Glu Val Leu Ala Ala Met Arg Glu
305                 310                 315                 320

Gln Ser Asp Leu Ile Leu Gly Glu Leu Ala Ala Gln Ser Glu Leu Asn
                325                 330                 335

Gly Arg Ile Trp Ala Ser Met Lys Ala Phe Gln Ala Gln Val Glu Pro
            340                 345                 350

Met His Glu Ile Ser Glu Lys Glu Leu Tyr Asn Trp Arg
        355                 360                 365
```

<210> SEQ ID NO 12
<211> LENGTH: 379
<212> TYPE: PRT
<213> ORGANISM: Rhodobacter sphaeroides

<400> SEQUENCE: 12

```
Met Thr Ala Phe Glu Lys Lys Ala Ala Tyr Ser Arg Arg Ser Phe Leu
1               5                   10                  15

Arg Thr Gly Ala Leu Ala Gly Gly Ala Ala Ala Gly Ser Val Leu Ala
            20                  25                  30

Ala Pro Ala Val Leu Ala Gln Ala Pro Leu Val Met Lys Met Gln Thr
        35                  40                  45

Ser Trp Pro Ala Ser Asp Ile Trp Met Asp Phe Ala Arg Glu Tyr Val
    50                  55                  60

Thr Arg Val Glu Glu Met Ser Gly Gly Arg Ile Lys Val Asp Leu Leu
65                  70                  75                  80

Pro Ala Gly Ala Val Val Gly Ala Phe Gln Val Met Asp Ala Val His
                85                  90                  95

Asp Gly Val Ile Asp Ala Ser His Ser Val Ser Ala Tyr Trp Tyr Gly
            100                 105                 110

Lys Ser Lys Ala Ala Ser Phe Phe Gly Thr Gly Pro Val Phe Gly Gly
        115                 120                 125

Ser Ala Thr Thr Met Leu Gly Trp Phe Tyr Gln Gly Gly Gly Gln Asp
    130                 135                 140

Leu Tyr Arg Glu Leu Thr Gln Asp Ile Leu Gly Met Asn Ile Val Gly
145                 150                 155                 160

Phe Tyr Gly Phe Pro Met Pro Ala Gln Pro Phe Gly Trp Phe Lys Thr
                165                 170                 175

Glu Val Asn Gly Val Ala Asp Ile Gln Gly Phe Lys Tyr Arg Thr Val
            180                 185                 190

Gly Leu Ala Ala Asp Leu Leu Gln Ala Met Gly Met Ser Val Ala Gln
        195                 200                 205

Leu Pro Gly Gly Glu Ile Val Pro Ala Met Glu Arg Gly Val Ile Asp
    210                 215                 220

Ala Phe Glu Phe Asn Asn Pro Ser Ser Asp Met Arg Phe Gly Ala Gln
225                 230                 235                 240

Asp Val Ala Lys Asn Tyr Tyr Leu Ser Ser Tyr His Gln Ala Ser Glu
                245                 250                 255

Ser Phe Glu Tyr Thr Phe Asn Arg Asp Phe Tyr Glu Asp Leu Asp Pro
            260                 265                 270

Asp Leu Gln Ala Ile Leu Lys Tyr Ala Val Glu Ala Ala Ser Thr Ser
        275                 280                 285

Asn Thr Ala Leu Ala Leu Arg Gln Tyr Ser Ala Asp Leu Ala Thr Leu
    290                 295                 300

Ala Ala Glu Asn Gly Val Ala Val His Arg Thr Pro Lys Asp Ile Leu
305                 310                 315                 320

Ser Gly Gln Leu Glu Ala Trp Asp Lys Leu Ile Val Asp Leu Glu Ala
                325                 330                 335

Asp Glu Phe Phe Lys Lys Val Leu Asp Ser Gln Arg Ala Trp Val Glu
            340                 345                 350

Gln Val Ser Tyr Tyr Glu Leu Met Asn Ala Ala Asp Leu Gly Leu Ala
        355                 360                 365

Tyr Glu His His Phe Pro Gly Lys Leu Lys Leu
    370                 375
```

<210> SEQ ID NO 13
<211> LENGTH: 359
<212> TYPE: PRT

<213> ORGANISM: Flexistipes sinusarabici

<400> SEQUENCE: 13

```
Met Gly Met Met Lys Lys Leu Leu Tyr Ser Leu Leu Ile Ile Leu Leu
1               5                   10                  15

Val Ala Ser Ala Gly Phe Thr Ala Glu Lys Lys Ile Arg Trp Lys Leu
            20                  25                  30

Ala Met Thr Trp Gly Pro Thr Leu His Pro Leu Ser Asp Thr Ala Glu
        35                  40                  45

His Met Ala Glu Ile Val Lys Glu Leu Ser Asp Gly Asn Phe Val Ile
    50                  55                  60

Asn Ile Asp Ala Ser Asn Val His Lys Ala Pro Phe Gly Ile Phe Asp
65                  70                  75                  80

Met Val Lys Leu Gly Gln Tyr Glu Met Gly His Thr Ala Ser Tyr Tyr
                85                  90                  95

Tyr Lys Gly Lys Asn Ile Ala Phe Leu Pro Leu Thr Thr Met Pro Phe
            100                 105                 110

Gly Met Thr Ala Pro Glu Gln Tyr Ala Trp Phe Tyr Tyr Gly Gly Gly
        115                 120                 125

Leu Glu Leu Met Gln Glu Ala Tyr Thr Lys His Gly Met Leu Ala Phe
    130                 135                 140

Pro Gly Gly Asn Thr Gly Asn Gln Met Gly Gly Trp Phe Thr Lys Glu
145                 150                 155                 160

Ile Asn Ser Leu Asp Asp Leu Lys Gly Leu Lys Met Arg Ile Pro Gly
                165                 170                 175

Phe Ala Gly Gln Ile Met Ser Lys Leu Gly Val Thr Val Thr Asn Ile
            180                 185                 190

Pro Pro Gly Glu Leu Tyr Thr Ala Leu Glu Arg Gly Thr Val Asp Ala
        195                 200                 205

Val Glu Trp Thr Gly Pro Gly Met Asp Ile Asn Met Gly Phe His Lys
    210                 215                 220

Ile Ala Lys Tyr Tyr Tyr Thr Gly Trp His Glu Pro Gly Ser Glu Val
225                 230                 235                 240

Glu Phe Leu Ile Asn Glu Lys Glu Tyr Asn Lys Leu Pro Glu Lys Tyr
                245                 250                 255

Lys Lys Ile Leu Lys Ile Ala Met Lys Thr Ala Ala Tyr Asp Met Tyr
            260                 265                 270

Ile Gln Ser Tyr Glu Met Asn Ala Glu Ala Trp Gln Gln Met Lys Glu
        275                 280                 285

Lys Tyr Pro Asp Ile Lys Val Lys Val Phe Pro Glu Glu Val Leu Lys
    290                 295                 300

Glu Met Lys Thr Ala Tyr Asp Asn Leu Val Ala Ser Tyr Glu Lys Glu
305                 310                 315                 320

Ser Pro Met Phe Lys Lys Ile Met Glu Ser Lys Arg Ala Tyr Leu Asp
                325                 330                 335

Lys Val Arg Asp Trp Thr His Ile Ser Asp Tyr Leu Tyr Leu Lys Ser
            340                 345                 350

Thr Ser Glu Ser Asn Leu Asn
        355
```

<210> SEQ ID NO 14
<211> LENGTH: 357
<212> TYPE: PRT
<213> ORGANISM: Unknown
<220> FEATURE:

<223> OTHER INFORMATION: Description of Unknown:
Thermanaerovibrio acidaminovorans sequence

<400> SEQUENCE: 14

```
Met Lys Arg Ile Lys Leu Leu Leu Thr Leu Cys Val Ala Leu Val Ala
1               5                   10                  15

Leu Gly Ala Leu Cys Gly Gly Ala Leu Ala Ala Glu Glu Tyr Lys Phe
            20                  25                  30

Lys Met Ala Thr Phe Tyr Leu Lys Gly Asp Ser Ala Phe Asp Val Ile
        35                  40                  45

Asp His Phe Arg Gln Leu Val Trp Lys Lys Thr Gly Gly Lys Val Arg
    50                  55                  60

Ile Asp Ala Phe Gln Ala Gly Glu Leu Gly Phe Pro Val Thr Glu Ile
65                  70                  75                  80

Leu Glu Ala Thr Ser Arg Gly Val Val Glu Met Ser Ile Phe Tyr Pro
                85                  90                  95

Asn Tyr Lys Ala Ala Gln Asp Pro Val Met Ala Leu Ala Gly Gly Arg
            100                 105                 110

Pro Gly Pro Met Phe Asp Leu Arg Asp Gln Lys Ala Gln Val Asp Ala
        115                 120                 125

Thr Lys Asp Leu Leu Glu Arg Ser Phe Gly Arg Phe Gly Val Arg Tyr
    130                 135                 140

Ile Ala Pro Met Val Tyr Gly Glu Pro Glu Ile Leu Val Ser Arg Arg
145                 150                 155                 160

Pro Met Ser Ser Leu Lys Asp Leu Lys Gly Arg Ile Phe Arg Ala Ser
                165                 170                 175

Gly Met Ala Ala Glu Phe Tyr Thr Ala Ile Gly Ala Gln Ala Met Met
            180                 185                 190

Leu Pro Ala Gly Glu Leu Tyr Gln Ala Leu Gln Leu Gly Thr Ile Asp
        195                 200                 205

Gly Leu Glu Trp Thr Asp Tyr Thr Ala Asn Tyr Lys Leu Gly Phe His
    210                 215                 220

Glu Val Ala Lys Asn Val Leu Glu Pro Thr Lys Gly Val Asn Leu His
225                 230                 235                 240

Ser Glu Ala Thr Val His Ala Phe Leu Val Val Asn Pro Lys Val Trp
                245                 250                 255

Glu Lys Leu Pro Lys Glu His Gln Lys Ala Ile Gln Glu Ala Cys Asp
            260                 265                 270

Glu Ala Tyr Lys Trp Gly Ala Asp His Leu Ala Lys Leu Asn Lys Thr
        275                 280                 285

Tyr Lys Asp Lys Trp Ile Lys Ala Gly Ala Lys Val Thr Gln Leu Pro
    290                 295                 300

Lys Glu Asp Gln Asp Lys Val Ile Glu Val Ser Ala Lys Ile Leu Ser
305                 310                 315                 320

Gly Tyr Ser Ala Lys Ser Pro Asp Ala Lys Glu Tyr Cys Arg Arg Leu
                325                 330                 335

Val Glu Leu Trp Lys Lys Leu Gly Tyr Thr Lys Trp Ser Asp Ala Leu
            340                 345                 350

Ala Lys Gln Ile Lys
        355
```

<210> SEQ ID NO 15
<211> LENGTH: 349
<212> TYPE: PRT
<213> ORGANISM: Artificial Sequence
<220> FEATURE:
<223> OTHER INFORMATION: ttLacPB1 (with signal peptide replaced with M and a GGSHHHHHH at C-terminus)

<400> SEQUENCE: 15

Met Phe Ser Pro Leu Ala Val Ala Gln Ala Arg Arg Tyr Arg Trp Arg
1 5 10 15

Ile Gln Thr Ala Trp Asp Ala Gly Thr Val Gly Tyr Ser Leu Phe Gln
20 25 30

Lys Phe Thr Glu Arg Val Lys Glu Leu Thr Asp Gly Gln Leu Glu Val
35 40 45

Gln Pro Phe Pro Ala Gly Ala Val Val Gly Thr Phe Asp Met Phe Asp
50 55 60

Ala Val Lys Thr Gly Val Leu Asp Gly Met Asn Pro Phe Thr Leu Tyr
65 70 75 80

Trp Ala Gly Arg Met Pro Val Thr Ala Phe Leu Ser Ser Tyr Ala Leu
85 90 95

Gly Leu Asp Arg Pro Asp Gln Trp Glu Thr Trp Phe Tyr Ser Leu Gly
100 105 110

Gly Leu Asp Ile Ala Arg Arg Ala Phe Ala Glu Gln Gly Leu Phe Tyr
115 120 125

Val Gly Pro Val Gln His Asp Leu Asn Ile Ile His Ser Lys Lys Pro
130 135 140

Ile Arg Arg Phe Glu Asp Phe Lys Gly Val Lys Leu Arg Val Pro Gly
145 150 155 160

Gly Met Ile Ala Glu Val Phe Ala Ala Ala Gly Ala Ser Thr Val Leu
165 170 175

Leu Pro Gly Gly Glu Val Tyr Pro Ala Leu Glu Arg Gly Val Ile Asp
180 185 190

Ala Ala Asp Phe Val Gly Pro Ala Val Asn Tyr Asn Leu Gly Phe His
195 200 205

Gln Val Ala Lys Tyr Ile Ile Met Gly Pro Pro Glu Thr Pro Ala Ile
210 215 220

His Gln Pro Val Asp Leu Met Asp Phe Thr Ile Asn Leu Asn Arg Trp
225 230 235 240

Arg Ser Leu Pro Lys Pro Leu Gln Glu Arg Phe Ile Ala Ala Val His
245 250 255

Glu Tyr Ser Trp Ile His Tyr Ala Gly Ile Gln Lys Ala Asn Leu Glu
260 265 270

Ala Trp Pro Lys Tyr Arg Gln Ala Gly Val Glu Val Ile Arg Leu Ser
275 280 285

Asn Glu Asp Val Arg Lys Phe Arg Arg Leu Ala Ile Pro Ile Trp Phe
290 295 300

Lys Trp Ala Lys Met Asp Lys Tyr Ser Arg Glu Ala Phe Ala Ser Gln
305 310 315 320

Leu Glu Tyr Met Lys Gly Ile Gly Tyr Val Thr Asp Glu Glu Leu Lys
325 330 335

Gly Leu Ser Leu Gly Gly Ser His His His His His His
340 345

<210> SEQ ID NO 16
<211> LENGTH: 349
<212> TYPE: PRT
<213> ORGANISM: Artificial Sequence
<220> FEATURE:
<223> OTHER INFORMATION: tsLacBP2 (with signal peptide replaced with M and a GGSHHHHHH at C-terminus)

<400> SEQUENCE: 16

Met Phe Ser Pro Leu Ala Val Ala Gln Ala Pro Arg Phe Arg Trp Arg
1               5                   10                  15

Ile Gln Ser Ala Trp Asp Ala Gly Thr Val Gly Tyr Ser Leu Phe Gln
            20                  25                  30

Lys Phe Ala Glu Arg Val Lys Glu Leu Thr Asp Gly Gln Ile Glu Ile
        35                  40                  45

Gln Thr Phe Pro Ala Gly Ala Val Val Gly Thr Phe Asp Met Phe Asp
    50                  55                  60

Ala Val Lys Thr Gly Val Leu Asp Gly Met His Pro Phe Thr Leu Tyr
65                  70                  75                  80

Trp Ala Gly Arg Met Pro Val Thr Ala Phe Leu Ser Ser Tyr Pro Leu
                85                  90                  95

Gly Leu Asp Arg Pro Asp Gln Trp Glu Thr Trp Tyr Tyr Gly Leu Gly
            100                 105                 110

Gly Leu Glu Leu Ala Arg Lys Ala Tyr Glu Glu Gln Gly Leu Phe Phe
        115                 120                 125

Val Gly Pro Val Gln His Asp Tyr Asn Leu Ile His Ser Lys Lys Pro
    130                 135                 140

Ile Lys Ser Phe Glu Asp Phe Lys Gly Val Lys Leu Arg Val Pro Gly
145                 150                 155                 160

Gly Met Ile Ala Glu Ile Phe Ala Ala Ala Gly Ala Ala Thr Val Leu
                165                 170                 175

Leu Pro Gly Gly Glu Val Tyr Pro Ala Leu Glu Arg Gly Val Ile Asp
            180                 185                 190

Ala Ala Asp Phe Val Gly Pro Ala Val Asn Tyr Asn Leu Gly Phe His
        195                 200                 205

Gln Val Thr Lys Tyr Ile Ile Met Gly Pro Pro Glu Thr Pro Ala Ile
    210                 215                 220

His Gln Pro Val Asp Leu Ala Asp Ile Thr Ile Asn Ile Asn Arg Trp
225                 230                 235                 240

Arg Ala Leu Pro Arg Asn Leu Gln Glu Arg Phe Glu Ala Ala Val His
                245                 250                 255

Glu Trp Ser Trp Ile His Tyr Ala Gly Ile Gln Lys Ala Asn Leu Glu
            260                 265                 270

Thr Trp Pro Lys Tyr Lys Ala Ala Gly Val Gln Val Ile Arg Leu Ser
        275                 280                 285

Thr Val Asp Val Arg Lys Phe Arg Arg Val Ala Ile Pro Ile Trp Phe
    290                 295                 300

Lys Trp Ala Lys Gln Asp Lys Tyr Thr Arg Glu Ala Phe Ala Ser Gln
305                 310                 315                 320

Leu Glu Tyr Met Lys Ala Leu Gly Tyr Val Thr Asp Ala Asp Ile Arg
                325                 330                 335

Gly Leu Ser Leu Gly Gly Ser His His His His His His
            340                 345

<210> SEQ ID NO 17
<211> LENGTH: 369
<212> TYPE: PRT
<213> ORGANISM: Artificial Sequence
<220> FEATURE:
<223> OTHER INFORMATION: toLacBP3 (with signal peptide replaced with M
and a GGSHHHHHH at C-terminus)

<400> SEQUENCE: 17

```
Met Lys Ser Thr Arg Arg Gln Phe Leu Lys Lys Ala Ala Ile Gly Val
1               5                   10                  15

Ala Ala Ser Ser Ala Phe Ser Pro Leu Ala Ile Ala Gln Ala Pro Arg
            20                  25                  30

Phe Arg Trp Arg Ile Gln Ser Ala Trp Asp Ala Gly Thr Val Gly Tyr
        35                  40                  45

Thr Leu Phe Gln Arg Phe Ala Glu Arg Val Lys Glu Leu Thr Asp Gly
    50                  55                  60

Gln Ile Glu Ile Gln Pro Phe Pro Ala Gly Ala Val Val Gly Thr Phe
65                  70                  75                  80

Asp Met Phe Asp Ala Val Lys Thr Gly Val Leu Asp Gly Met His Pro
                85                  90                  95

Phe Thr Leu Tyr Trp Ala Gly Arg Met Pro Val Thr Ala Phe Leu Ser
            100                 105                 110

Ser Tyr Pro Leu Gly Leu Asp Arg Pro Asp Gln Trp Glu Thr Trp Tyr
        115                 120                 125

Tyr Gly Leu Gly Gly Leu Glu Leu Ala Arg Lys Ala Tyr Glu Glu Gln
    130                 135                 140

Gly Leu Ala Tyr Ile Gly Pro Val Gln His Asp Tyr Asn Leu Ile His
145                 150                 155                 160

Ser Lys Lys Pro Ile Lys Ser Phe Glu Glu Phe Lys Gly Val Lys Leu
                165                 170                 175

Arg Val Pro Gly Gly Met Ile Ala Glu Ile Phe Ala Ala Ala Gly Ala
            180                 185                 190

Ala Thr Val Leu Leu Pro Gly Gly Glu Val Tyr Pro Ala Leu Glu Arg
        195                 200                 205

Gly Val Ile Asp Ala Ala Asp Phe Val Gly Pro Ala Val Asn Tyr Asn
    210                 215                 220

Leu Gly Phe His Gln Val Thr Lys Tyr Ile Ile Met Gly Pro Pro Glu
225                 230                 235                 240

Thr Pro Ala Ile His Gln Pro Val Asp Leu Ala Asp Ile Thr Leu Asn
                245                 250                 255

Leu Asn Arg Trp Arg Ala Val Pro Lys Asn Leu Gln Glu Arg Phe Glu
            260                 265                 270

Ala Ala Val His Glu Trp Ser Trp Val His Tyr Ala Gly Ile Gln Lys
        275                 280                 285

Ala Asn Leu Glu Ala Trp Pro Lys Tyr Arg Ala Ala Gly Val Gln Ile
    290                 295                 300

Ile Arg Leu Ser Thr Val Asp Val Arg Lys Phe Arg Arg Val Ala Ile
305                 310                 315                 320

Pro Ile Trp Phe Lys Trp Ala Lys Gln Asp Lys Tyr Ala Lys Glu Ala
                325                 330                 335

Phe Gln Ser Gln Leu Glu Tyr Met Lys Ala Leu Gly Tyr Val Thr Asp
            340                 345                 350

Val Asp Leu Arg Gly Leu Ser Leu Gly Gly Ser His His His His His
        355                 360                 365

His
```

<210> SEQ ID NO 18
<211> LENGTH: 346
<212> TYPE: PRT
<213> ORGANISM: Artificial Sequence
<220> FEATURE:

<223> OTHER INFORMATION: tsLacBP4 (with signal peptide replaced with M and a GGSHHHHHH at C-terminus)

<400> SEQUENCE: 18

```
Met Thr Ala Arg Gly Val Arg Trp Arg Met Gln Ser Ala Trp Gln Pro
1               5                   10                  15

Gly Thr Ile Gly Tyr Arg Thr Phe Glu Thr Trp Ala Arg Ser Ile Gln
            20                  25                  30

Glu Leu Thr Ser Gly Glu Leu Ser Ile Glu Pro Phe Pro Ala Gly Ala
        35                  40                  45

Val Ala Gly Thr Phe Glu Met Ala Asp Ala Val Arg Ser Gly Val Leu
    50                  55                  60

Asp Gly Met Asn Trp Phe Thr Val Tyr Trp Pro Gly Lys Met Pro Ala
65                  70                  75                  80

Gly Val Phe Met Ser Ala Tyr Pro Met Ala Leu Ser Leu Pro His His
                85                  90                  95

Trp Asp Met Met Phe Asp Ser Phe Gly Gly Arg Gln Ile Val Asp Glu
            100                 105                 110

Leu Tyr Asp Arg Gln Gly Leu Val Phe Leu Gly His Val Gln His Asp
        115                 120                 125

Leu Asn Leu Ile His Ser Lys Val Pro Leu Arg Ser Phe Asp Asp Phe
    130                 135                 140

Arg Gly Lys Arg Ile Arg Phe Pro Gly Gly Ile Ile Ala Glu Thr Phe
145                 150                 155                 160

Ala Lys Val Gly Val Arg Thr Thr Leu Leu Pro Gly Gly Asp Val Tyr
                165                 170                 175

Pro Ala Leu Glu Arg Gly Thr Ile Asp Ala Ala Asp Phe Val Gly Pro
            180                 185                 190

Ala Val Asn Tyr Asp Leu Gly Phe His Gln Val Ala Asp Tyr Ile Ile
        195                 200                 205

Met Gly Pro Pro Ser Thr Pro Ala Leu His Gln Pro Val Asp Leu Met
    210                 215                 220

Asp Ile Ser Val Asn Lys Arg Ser Trp Ser Arg Ile Ser Glu His Thr
225                 230                 235                 240

Gln Lys Leu Met Tyr Lys Phe Val Lys Ala Tyr Ser Ala Glu His Phe
                245                 250                 255

Ala Ala Ile Gln Lys Ala Asn His Glu Ala Trp Pro Lys Tyr Lys Glu
            260                 265                 270

Ala Gly Val Glu Val Ile His Leu Ser Glu Glu Asp Ala Ala Arg Phe
        275                 280                 285

Arg Glu Ala Ala Ile Pro Leu Trp Phe Glu Trp Ala Asn Lys Asp Arg
    290                 295                 300

Asp Ala Ala Arg Leu Phe Lys Val His Leu Glu Val Met Gln Asp Pro
305                 310                 315                 320

Ser Val Ala Val Ile Thr Pro Asp Asp Ile Lys Asp Tyr Lys Leu Asn
                325                 330                 335

Phe Gly Gly Ser His His His His His His
            340                 345
```

<210> SEQ ID NO 19
<211> LENGTH: 346
<212> TYPE: PRT
<213> ORGANISM: Artificial Sequence
<220> FEATURE:
<223> OTHER INFORMATION: rdLacBP5 (with signal peptide replaced with M and a GGSHHHHHH at C-terminus)

<400> SEQUENCE: 19

Met Ala Ala Gly Glu Gly Thr Thr Trp Lys Ile Gln Thr Ser His Thr
1 5 10 15

Gly Gly Ile Gly Leu Ala Thr Phe Lys Asp Trp Ala Ser Ser Ile Glu
20 25 30

Glu Lys Thr Gly Gly Glu Leu Ala Phe Thr Ala Phe Gly Ala Asn Asp
35 40 45

Val Val Gly Asp Phe Gln Leu Tyr Asp Ala Val Lys Asn Gly Val Leu
50 55 60

Asp Ala Val Asn Pro Phe Thr Ile Tyr Ala Gln Gly Ile Ile Pro Ala
65 70 75 80

Ala Thr Phe Leu Thr Ser Tyr Pro Leu Gly Leu Arg Asn Pro His Glu
85 90 95

Trp Asp Val Phe Phe Tyr Ser Leu Gly Gly Leu Glu Ile Ala Arg Glu
100 105 110

Leu Tyr Ala Ala Gln Gly Met Lys Phe Val Gly Pro Val His His Gly
115 120 125

Pro Asn Ile Ile His Ser Lys Val Pro Ile Arg Ser Ile Asp Asp Phe
130 135 140

Ala Gly Leu Lys Met Arg Met Pro Gly Gly Met Val Ala Glu Val Phe
145 150 155 160

Ser Glu Ile Gly Ala Glu Thr Thr Val Leu Pro Gly Ser Glu Ile Phe
165 170 175

Pro Ala Leu Glu Lys Gly Thr Ile Asp Ala Ala Asp Phe Val Gly Pro
180 185 190

Ala Val Asn Tyr Ala Leu Gly Phe Ser Gln Val Thr Asn Tyr Ile Ser
195 200 205

Met Gly Pro Ala Gly Phe Met Ser Leu Tyr Gln Pro Val Asp Leu Met
210 215 220

Asp Ile Thr Val Gly Gln Thr Ala Trp Asp Ala Leu Ser Pro Gln Met
225 230 235 240

Gln Gln Phe Val Glu Met Glu Thr His Val Tyr Ser Asp Met His His
245 250 255

Ala Ala Ile Gln Lys Ala Asp Gln Glu Ala Trp Ala Lys Phe Glu Ala
260 265 270

Asp Gly Thr Glu Val Thr Arg Leu Ser Gln Asp Asp Val Glu Leu Met
275 280 285

Thr Glu Val Ala Val Pro Ile Trp Phe Asp Tyr Ala Asn Arg Asp Lys
290 295 300

Asp Ala Ala Arg Val Phe Lys Ile Gln Leu Asp Tyr Met Met Ser Gly
305 310 315 320

Ser Leu Gly Tyr Val Thr Pro Glu Gln Ile Glu Gly Leu Thr Leu Asn
325 330 335

Leu Gly Gly Ser His His His His His His
340 345

<210> SEQ ID NO 20
<211> LENGTH: 341
<212> TYPE: PRT
<213> ORGANISM: Artificial Sequence
<220> FEATURE:
<223> OTHER INFORMATION: msLacBP6 (with signal peptide replaced with M and a GGSHHHHHH at C-terminus)

<400> SEQUENCE: 20

```
Met Ala Thr Thr Trp Lys Ile Gln Ser Val Trp Asp Ala Gly Thr Val
1               5                   10                  15

Gly Tyr Asp Leu Phe Lys Glu Trp Cys Asp Gly Met Glu Glu Lys Thr
            20                  25                  30

Gly Gly Glu Leu Lys Phe Thr Cys Phe Pro Ala Lys Ala Val Ala Ala
        35                  40                  45

Asp Asn Asn Gly Leu Phe Asp Ala Val Arg Asn Gly Val Leu Gln Gly
    50                  55                  60

Met Asn Pro Phe Thr Leu Tyr Trp Ser Gly Lys Ile Pro Ala Ser Val
65                  70                  75                  80

Phe Leu Ser Ser Tyr Pro Ala Gly Pro Asp Gln Pro His Gln Trp Asp
                85                  90                  95

Thr Met Phe Tyr Ser Leu Gly Met Leu Glu Lys Thr Arg Glu Ile Tyr
            100                 105                 110

Lys Lys Phe Gly Leu Phe Tyr Val Gly Pro Ile Gln His Asp Ala Asn
        115                 120                 125

Ile Ile His Ser Lys Gln Pro Ile Asn Ser Leu Asp Asp Leu Lys Gly
    130                 135                 140

Leu Lys Met Arg Leu Pro Gly Gly Met Val Ala Glu Val Phe Ala Lys
145                 150                 155                 160

Phe Gly Val Ala Ala Val Ser Leu Pro Gly Ser Asp Ile Phe Pro Ala
                165                 170                 175

Leu Glu Lys Gly Thr Ile Asp Ala Ala Asp Tyr Val Gly Pro Ala Val
            180                 185                 190

Asn Trp Glu Leu Gly Phe Ser Gln Val Thr Lys Tyr Ile Leu Met Gly
        195                 200                 205

Pro Pro Gly Ile Met Ser Val Tyr Gln Pro Val Asp Leu Met Asp Leu
    210                 215                 220

Thr Val Asn Leu Arg Ala Trp Asn Ala Leu Asp Pro Lys Leu Gln Gln
225                 230                 235                 240

Ile Val Glu Asp Glu Val Arg Ile Tyr Ser Gln Lys His Tyr Leu Ala
                245                 250                 255

Ile Gln Lys Arg Asn Ile Glu Ala Met Lys Lys Phe Glu Ala Ala Gly
            260                 265                 270

Thr Thr Val Thr Arg Leu Ser Gln Glu Asp Leu Gln Glu Phe Arg Arg
        275                 280                 285

Ala Ala Ile Pro Ile Trp Tyr Ser Trp Ala Asn Lys Asp Glu Asp Ala
    290                 295                 300

Arg Glu Ile Phe Asp Met Gln Leu Glu Tyr Met Met Asn Asp Thr Val
305                 310                 315                 320

Gly Tyr Ile Thr Glu Asp Asp Ile Lys Gly Met Asn Gly Gly Ser His
                325                 330                 335

His His His His His
            340
```

<210> SEQ ID NO 21
<211> LENGTH: 342
<212> TYPE: PRT
<213> ORGANISM: Artificial Sequence
<220> FEATURE:
<223> OTHER INFORMATION: tsLacBP7 (with signal peptide replaced with M and a GGSHHHHHH at C-terminus)

<400> SEQUENCE: 21

```
Met Gln Ala Pro Arg Phe Arg Trp Arg Ile Gln Ser Ala Trp Asp Ala
```

```
1               5                   10                  15

Gly Thr Val Gly Tyr Thr Leu Phe Gln Arg Phe Ala Glu Arg Val Lys
            20                  25                  30

Glu Leu Thr Asp Gly Gln Ile Glu Ile Gln Thr Phe Pro Ala Gly Ala
        35                  40                  45

Val Val Gly Thr Phe Asp Met Phe Asp Ala Val Lys Thr Gly Val Leu
    50                  55                  60

Asp Gly Met His Pro Phe Thr Leu Tyr Trp Ala Gly Arg Met Pro Val
65                  70                  75                  80

Thr Ala Phe Leu Ser Ser Tyr Pro Leu Gly Leu Asp Arg Pro Asp Gln
                85                  90                  95

Trp Glu Thr Trp Tyr Tyr Ala Leu Gly Gly Leu Asp Leu Ala Arg Arg
            100                 105                 110

Ala Phe Glu Glu Gln Gly Leu Phe Tyr Val Gly Pro Val Gln His Asp
        115                 120                 125

Tyr Asn Leu Ile His Ser Lys Lys Pro Ile Lys Ser Phe Glu Asp Phe
    130                 135                 140

Lys Gly Val Lys Leu Arg Val Pro Gly Gly Met Ile Ala Asp Val Phe
145                 150                 155                 160

Ser Ala Ala Gly Ala Ala Thr Val Leu Leu Pro Gly Gly Glu Val Tyr
                165                 170                 175

Pro Ala Leu Glu Arg Gly Val Ile Asp Ala Ala Asp Phe Val Gly Pro
            180                 185                 190

Ala Val Asn Tyr Asn Leu Gly Phe His Gln Val Thr Lys Tyr Ile Ile
        195                 200                 205

Met Gly Pro Pro Glu Thr Pro Ala Ile His Gln Pro Val Asp Leu Ala
    210                 215                 220

Asp Ile Thr Leu Asn Leu Ser Arg Trp Arg Ala Val Pro Lys Asn Leu
225                 230                 235                 240

Gln Glu Arg Phe Glu Ala Ala Val His Glu Trp Ser Trp Ile His Tyr
                245                 250                 255

Ala Gly Ile Gln Lys Ala Asn Leu Glu Thr Trp Pro Lys Tyr Lys Ala
            260                 265                 270

Ala Gly Val Gln Ile Ile Arg Leu Thr Thr Val Asp Val Arg Lys Phe
        275                 280                 285

Arg Arg Val Ala Ile Pro Ile Trp Phe Lys Trp Ala Lys Gln Asp Lys
    290                 295                 300

Tyr Ala Arg Glu Ala Phe Ala Ser Gln Leu Glu Tyr Met Lys Ala Leu
305                 310                 315                 320

Gly Tyr Val Thr Asp Ala Asp Val Arg Gly Leu Ser Leu Gly Gly Ser
                325                 330                 335

His His His His His His
            340


<210> SEQ ID NO 22
<211> LENGTH: 342
<212> TYPE: PRT
<213> ORGANISM: Artificial Sequence
<220> FEATURE:
<223> OTHER INFORMATION: maLacBP8  (with signal peptide replaced with M
      and a GGSHHHHHH at C-terminus)

<400> SEQUENCE: 22

Met Gln Ala Ala Thr Thr Trp Lys Ile Gln Ser Thr Trp Asp Ala Gly
1               5                   10                  15
```

Thr Val Gly Tyr Thr Leu Phe Glu Glu Trp Ala Lys Ser Ile Glu Ala
20 25 30

Lys Ser Gly Gly Glu Leu Lys Phe Gln Ala Phe Pro Ala Lys Ala Val
35 40 45

Ala Ala Asp Asn Asn Ala Leu Phe Asp Ala Val Arg Asn Gly Val Leu
50 55 60

Gln Gly Met Asn Pro Phe Thr Leu Tyr Trp Ala Gly Lys Ile Pro Ala
65 70 75 80

Ser Val Phe Leu Ser Ser Tyr Pro Ala Gly Pro Asp Gln Pro His Gln
85 90 95

Trp Asp Thr Met Phe Tyr Ser Met Gly Met Leu Glu Lys Thr Arg Glu
100 105 110

Ile Tyr Lys Lys Phe Gly Leu Phe Tyr Val Gly Pro Ile Gln His Asp
115 120 125

Ala Asn Ile Ile His Ser Lys Gln Pro Val Asn Ser Leu Asp Asp Leu
130 135 140

Lys Gly Met Lys Ile Arg Val Pro Gly Gly Met Val Ala Glu Val Phe
145 150 155 160

Gln Gln Phe Gly Val Ser Thr Val Ser Leu Pro Gly Ser Asp Ile Phe
165 170 175

Pro Ala Leu Glu Lys Gly Thr Ile Asp Ala Ala Asp Phe Val Gly Pro
180 185 190

Ala Val Asn Tyr Glu Leu Gly Phe Ser Gln Val Thr Asp Tyr Ile Ile
195 200 205

Phe Gly Pro Pro Gly Val Met Ser Ile Tyr Gln Pro Val Asp Leu Met
210 215 220

Asp Leu Thr Val Ser Leu Arg Ala Trp Asn Ser Ile Ser Pro Glu Leu
225 230 235 240

Gln Gln Leu Val Glu Asp Glu Val Arg Ile Tyr Ser Gln Lys His Tyr
245 250 255

Leu Ala Ile Gln Ala Arg Asn Ile Glu Ala Met Glu Lys Phe Lys Ala
260 265 270

Asp Gly Asp Thr Val Thr Arg Leu Ser Gln Glu Asp Leu Glu Thr Trp
275 280 285

Arg Lys Ala Ala Ile Pro Ile Trp Phe Asn Trp Ala Asn Lys Asn Asp
290 295 300

Asp Ala Arg Ala Ile Leu Asp Ile Gln Leu Lys Tyr Met Met Asn Asp
305 310 315 320

Thr Val Gly Tyr Ile Thr Glu Glu Asp Ile Lys Gly Phe Gly Gly Ser
325 330 335

His His His His His His
340

<210> SEQ ID NO 23
<211> LENGTH: 353
<212> TYPE: PRT
<213> ORGANISM: Artificial Sequence
<220> FEATURE:
<223> OTHER INFORMATION: adLacBP9 (with signal peptide replaced with M and a GGSHHHHHH at C-terminus)

<400> SEQUENCE: 23

Met Gln Ala Pro Ile Thr Leu Arg Phe Gln Ser Thr Trp Pro Gln Lys
1 5 10 15

Asp Ile Phe His Glu Phe Ala Leu Asp Tyr Ala Lys Lys Val Asn Glu
20 25 30

Met Ser Gly Gly Arg Leu Lys Ile Glu Val Leu Ala Ala Gly Ser Val
35 40 45

Val Lys Ala Phe Asp Leu Leu Asp Ala Val Ser Lys Gly Thr Leu Asp
50 55 60

Gly Gly His Gly Val Val Ala Tyr Trp Tyr Gly Lys Asn Thr Ala Leu
65 70 75 80

Ala Leu Trp Gly Ser Gly Pro Ala Phe Gly Met Asp Pro Asn Met Val
85 90 95

Leu Ala Trp His His Tyr Gly Gly Gly Arg Gln Leu Leu Glu Glu Ile
100 105 110

Tyr Arg Ser Leu Asn Leu Asp Val Val Ser Leu Met Tyr Gly Pro Met
115 120 125

Pro Thr Gln Pro Leu Gly Trp Phe Lys Gln Lys Pro Ile Ala Lys Pro
130 135 140

Asp Asp Met Lys Gly Leu Lys Phe Arg Thr Val Gly Leu Ser Ile Asp
145 150 155 160

Ile Phe Asn Gly Leu Gly Ala Ala Val Asn Ala Leu Pro Gly Ala Glu
165 170 175

Ile Val Pro Ala Met Asp Arg Gly Leu Leu Asp Ala Ala Glu Phe Asn
180 185 190

Asn Ala Ser Ser Asp Arg Val Leu Gly Phe Pro Asp Val Ser Lys Ile
195 200 205

Ala Met Leu Gln Ser Phe His Gln Ala Ser Glu Gln Phe Glu Ile Leu
210 215 220

Phe Asn Gly Lys Arg Phe Gln Ala Leu Pro Ala Asp Leu Lys Ser Ile
225 230 235 240

Ile Ser Ile Ala Ala Gln Ala Ala Ser Ala Asp Met Ser Trp Lys Ala
245 250 255

Ile Asp Arg Tyr Ser Ser Asp Tyr Phe Glu Met Arg Asp Lys Gln Gly
260 265 270

Val Lys Phe Tyr Ser Thr Arg Pro Glu Ile Leu Lys Arg Gln Leu Glu
275 280 285

Ile Trp Asp Gln Val Met Glu Lys Arg Ala Ala Glu Asn Pro Thr Phe
290 295 300

Lys Lys Val Leu Glu Ser Gln Arg Arg Phe Ala Gln Arg Ala Ala Arg
305 310 315 320

Trp Gln Asn Asp Thr Asn Val Asp Phe Lys Met Ala Tyr Asn His Phe
325 330 335

Phe Gly Gly Lys Lys Lys Ala Thr Gly Gly Ser His His His His His
340 345 350

His

<210> SEQ ID NO 24
<211> LENGTH: 325
<212> TYPE: PRT
<213> ORGANISM: Artificial Sequence
<220> FEATURE:
<223> OTHER INFORMATION: pgLacBP10 (with signal peptide replaced with M and a GGSHHHHHH at C-terminus)

<400> SEQUENCE: 24

Met Gln Glu Ala Val Glu Trp Arg Met Gln Ala Leu Trp Asp Ala Gly
1 5 10 15

Thr Thr Pro Phe Glu Phe Glu Lys Lys Phe Val Glu Arg Val Gly Glu
20 25 30

```
Leu Thr Glu Gly Arg Phe Lys Ile Thr Leu Tyr Ser Ala Gly Gln Ile
        35                  40                  45

Val Pro Ala Asn Gln Ala Phe Asp Ala Val Arg Ser Gly Ala Phe Glu
    50                  55                  60

Met Met Lys Thr Phe Asp Gly Tyr Glu Ala Gly Lys Ile Pro Ala Phe
65                  70                  75                  80

Ala Phe Thr Ser Thr Ile Pro Phe Gly Phe Pro Gln Ser Asp Gln Tyr
                85                  90                  95

Glu Ala Trp Phe Tyr Glu Leu Gly Gly Leu Asp Leu Ala Arg Glu Ala
            100                 105                 110

Tyr Ala Lys Gly Gly Leu Phe Tyr Ile Ala Pro Thr Val Tyr Gly Glu
        115                 120                 125

Glu Pro Met His Ser Thr Val Lys Ile Glu Ser Ile Ala Asp Met Ala
    130                 135                 140

Gly Lys Lys Gly Arg Phe Val Gly Leu Ala Ser Ala Val Met Ala Asp
145                 150                 155                 160

Leu Gly Val Ala Val Ser Pro Leu Ala Thr Ala Glu Val Tyr Thr Ala
                165                 170                 175

Leu Glu Lys Gly Leu Ile Asp Phe Ala Asp Arg Gly Asp Leu Thr Ala
            180                 185                 190

Asn Tyr Glu Ala Gly Leu Gly Glu Val Ala Lys Phe Ile Ile Leu Pro
        195                 200                 205

Gly Val His Gln Pro Thr Thr Ala Thr Ser Tyr Val Ala Asn Gln Ala
    210                 215                 220

Ala Tyr Gln Lys Leu Pro Asp Gly Phe Lys Ala Ala Leu Ala Val Ala
225                 230                 235                 240

Ala Arg Glu Ile Ser Gly Ser Leu Arg Gln His Ile Leu Val Gln Asp
                245                 250                 255

Met Glu Val Leu Thr Lys Tyr Lys Asp Gln Gly Val Glu Val Val Arg
            260                 265                 270

Leu Asp Ala Ala Asp Ile Ala Ala Ala Arg Ala Lys Ala Val Glu Ser
        275                 280                 285

Trp Glu Lys Ala Thr Lys Gly Asp Glu Leu Ala Thr Arg Val Leu Lys
    290                 295                 300

Gly Gln Val Asp Phe Met Thr Ser Leu Gly Leu Leu Gly Gly Ser His
305                 310                 315                 320

His His His His His
                325
```

<210> SEQ ID NO 25
<211> LENGTH: 345
<212> TYPE: PRT
<213> ORGANISM: Artificial Sequence
<220> FEATURE:
<223> OTHER INFORMATION: psLacBP11 (with signal peptide replaced with M and a GGSHHHHHH at C-terminus)

<400> SEQUENCE: 25

```
Met Gln Gln Ala Ala Gly Glu Pro Ala Lys Thr Tyr His Trp Lys Met
1               5                   10                  15

Val Thr Ala Trp Pro Lys Asn Tyr Pro Gly Leu Gly Thr Ser Ala Glu
            20                  25                  30

Arg Leu Ala Glu Arg Val Asn Ala Met Ser Gly Gly Arg Leu Thr Ile
        35                  40                  45

Lys Val Tyr Ala Ala Gly Glu Leu Val Pro Ala Leu Glu Val Phe Asp
```

```
    50                  55                  60

Ala Val Ser Arg Gly Thr Ala Glu Leu Gly His Gly Ala Ser Tyr Tyr
65                  70                  75                  80

Trp Lys Gly Lys Val Pro Thr Ala Gln Phe Phe Thr Ser Val Pro Phe
                85                  90                  95

Gly Leu Ser Thr Ser Glu Met Asn Ala Trp Leu Ser Lys Gly Gly Gly
            100                 105                 110

Gln Ala Phe Trp Asp Glu Ala Tyr Ala Pro Phe Gly Val Lys Pro Leu
        115                 120                 125

Val Ile Gly Asn Thr Gly Met Gln Met Gly Gly Trp Tyr Asn Lys Glu
    130                 135                 140

Ile Asn Ser Leu Thr Asp Leu Lys Gly Leu Lys Ile Arg Met Pro Gly
145                 150                 155                 160

Leu Gly Gly Glu Val Leu Ser Arg Leu Gly Ala Thr Thr Val Asn Leu
                165                 170                 175

Pro Gly Gly Glu Val Phe Thr Ala Leu Gln Thr Gly Ala Ile Asp Ala
            180                 185                 190

Thr Asp Trp Val Ser Pro Tyr Asn Asp Leu Ala Phe Gly Leu His Lys
        195                 200                 205

Ala Ala Arg Tyr Tyr Tyr Tyr Pro Gly Trp Gln Glu Pro Gln Ala Val
    210                 215                 220

Leu Glu Leu Leu Ile Asn Gln Lys Ala Phe Asp Ser Leu Pro Ala Asp
225                 230                 235                 240

Leu Gln Ala Ile Val Thr Glu Ala Ser Leu Ala Ala Ser Arg Asp Met
                245                 250                 255

His Asp Asp Tyr Val Tyr Asn Asn Ala Leu Ala Leu Glu Gln Leu Lys
            260                 265                 270

Gln Gln Gly Thr Glu Leu Lys Arg Phe Pro Asp Glu Val Leu Ala Ala
        275                 280                 285

Met Arg Glu Gln Ser Asp Leu Ile Leu Gly Glu Leu Ala Ala Gln Ser
    290                 295                 300

Glu Leu Asn Gly Arg Ile Trp Ala Ser Met Lys Ala Phe Gln Ala Gln
305                 310                 315                 320

Val Glu Pro Met His Glu Ile Ser Glu Lys Glu Leu Tyr Asn Trp Arg
                325                 330                 335

Gly Gly Ser His His His His His His
            340                 345
```

<210> SEQ ID NO 26
<211> LENGTH: 350
<212> TYPE: PRT
<213> ORGANISM: Artificial Sequence
<220> FEATURE:
<223> OTHER INFORMATION: rsLacBP12 (with signal peptide replaced with M and a GGSHHHHHH at C-terminus)

<400> SEQUENCE: 26

```
Met Gln Ala Pro Leu Val Met Lys Met Gln Thr Ser Trp Pro Ala Ser
1               5                   10                  15

Asp Ile Trp Met Asp Phe Ala Arg Glu Tyr Val Thr Arg Val Glu Glu
            20                  25                  30

Met Ser Gly Gly Arg Ile Lys Val Asp Leu Leu Pro Ala Gly Ala Val
        35                  40                  45

Val Gly Ala Phe Gln Val Met Asp Ala Val His Asp Gly Val Ile Asp
    50                  55                  60
```

```
Ala Ser His Ser Val Ser Ala Tyr Trp Tyr Gly Lys Ser Lys Ala Ala
65                  70                  75                  80

Ser Phe Phe Gly Thr Gly Pro Val Phe Gly Gly Ser Ala Thr Thr Met
                85                  90                  95

Leu Gly Trp Phe Tyr Gln Gly Gly Gly Gln Asp Leu Tyr Arg Glu Leu
            100                 105                 110

Thr Gln Asp Ile Leu Gly Met Asn Ile Val Gly Phe Tyr Gly Phe Pro
        115                 120                 125

Met Pro Ala Gln Pro Phe Gly Trp Phe Lys Thr Glu Val Asn Gly Val
    130                 135                 140

Ala Asp Ile Gln Gly Phe Lys Tyr Arg Thr Val Gly Leu Ala Ala Asp
145                 150                 155                 160

Leu Leu Gln Ala Met Gly Met Ser Val Ala Gln Leu Pro Gly Gly Glu
                165                 170                 175

Ile Val Pro Ala Met Glu Arg Gly Val Ile Asp Ala Phe Glu Phe Asn
            180                 185                 190

Asn Pro Ser Ser Asp Met Arg Phe Gly Ala Gln Asp Val Ala Lys Asn
        195                 200                 205

Tyr Tyr Leu Ser Ser Tyr His Gln Ala Ser Glu Ser Phe Glu Tyr Thr
    210                 215                 220

Phe Asn Arg Asp Phe Tyr Glu Asp Leu Asp Pro Asp Leu Gln Ala Ile
225                 230                 235                 240

Leu Lys Tyr Ala Val Glu Ala Ala Ser Thr Ser Asn Thr Ala Leu Ala
                245                 250                 255

Leu Arg Gln Tyr Ser Ala Asp Leu Ala Thr Leu Ala Ala Glu Asn Gly
            260                 265                 270

Val Ala Val His Arg Thr Pro Lys Asp Ile Leu Ser Gly Gln Leu Glu
        275                 280                 285

Ala Trp Asp Lys Leu Ile Val Asp Leu Glu Ala Asp Glu Phe Phe Lys
    290                 295                 300

Lys Val Leu Asp Ser Gln Arg Ala Trp Val Glu Gln Val Ser Tyr Tyr
305                 310                 315                 320

Glu Leu Met Asn Ala Ala Asp Leu Gly Leu Ala Tyr Glu His His Phe
                325                 330                 335

Pro Gly Lys Leu Lys Leu Gly Gly Ser His His His His His
            340                 345                 350


<210> SEQ ID NO 27
<211> LENGTH: 345
<212> TYPE: PRT
<213> ORGANISM: Artificial Sequence
<220> FEATURE:
<223> OTHER INFORMATION: fsLacBP13  (with signal peptide replaced with M
      and a GGSHHHHHH at C-terminus)

<400> SEQUENCE: 27

Met Glu Lys Lys Ile Arg Trp Lys Leu Ala Met Thr Trp Gly Pro Thr
1               5                   10                  15

Leu His Pro Leu Ser Asp Thr Ala Glu His Met Ala Glu Ile Val Lys
            20                  25                  30

Glu Leu Ser Asp Gly Asn Phe Val Ile Asn Ile Asp Ala Ser Asn Val
        35                  40                  45

His Lys Ala Pro Phe Gly Ile Phe Asp Met Val Lys Leu Gly Gln Tyr
    50                  55                  60

Glu Met Gly His Thr Ala Ser Tyr Tyr Tyr Lys Gly Lys Asn Ile Ala
65                  70                  75                  80
```

```
Phe Leu Pro Leu Thr Thr Met Pro Phe Gly Met Thr Ala Pro Glu Gln
                85                  90                  95

Tyr Ala Trp Phe Tyr Tyr Gly Gly Gly Leu Glu Leu Met Gln Glu Ala
            100                 105                 110

Tyr Thr Lys His Gly Met Leu Ala Phe Pro Gly Gly Asn Thr Gly Asn
        115                 120                 125

Gln Met Gly Gly Trp Phe Thr Lys Glu Ile Asn Ser Leu Asp Asp Leu
    130                 135                 140

Lys Gly Leu Lys Met Arg Ile Pro Gly Phe Ala Gly Gln Ile Met Ser
145                 150                 155                 160

Lys Leu Gly Val Thr Val Thr Asn Ile Pro Pro Gly Glu Leu Tyr Thr
                165                 170                 175

Ala Leu Glu Arg Gly Thr Val Asp Ala Val Glu Trp Thr Gly Pro Gly
            180                 185                 190

Met Asp Ile Asn Met Gly Phe His Lys Ile Ala Lys Tyr Tyr Tyr Thr
        195                 200                 205

Gly Trp His Glu Pro Gly Ser Glu Val Glu Phe Leu Ile Asn Glu Lys
    210                 215                 220

Glu Tyr Asn Lys Leu Pro Glu Lys Tyr Lys Lys Ile Leu Lys Ile Ala
225                 230                 235                 240

Met Lys Thr Ala Ala Tyr Asp Met Tyr Ile Gln Ser Tyr Glu Met Asn
                245                 250                 255

Ala Glu Ala Trp Gln Gln Met Lys Glu Lys Tyr Pro Asp Ile Lys Val
            260                 265                 270

Lys Val Phe Pro Glu Glu Val Leu Lys Glu Met Lys Thr Ala Tyr Asp
        275                 280                 285

Asn Leu Val Ala Ser Tyr Glu Lys Glu Ser Pro Met Phe Lys Lys Ile
    290                 295                 300

Met Glu Ser Lys Arg Ala Tyr Leu Asp Lys Val Arg Asp Trp Thr His
305                 310                 315                 320

Ile Ser Asp Tyr Leu Tyr Leu Lys Ser Thr Ser Glu Ser Asn Leu Asn
                325                 330                 335

Gly Gly Ser His His His His His His
            340                 345


<210> SEQ ID NO 28
<211> LENGTH: 340
<212> TYPE: PRT
<213> ORGANISM: Artificial Sequence
<220> FEATURE:
<223> OTHER INFORMATION: taLacBP14  (with signal peptide replaced with M
      and a GGSHHHHHH at C-terminus)

<400> SEQUENCE: 28

Met Glu Glu Tyr Lys Phe Lys Met Ala Thr Phe Tyr Leu Lys Gly Asp
1               5                   10                  15

Ser Ala Phe Asp Val Ile Asp His Phe Arg Gln Leu Val Trp Lys Lys
            20                  25                  30

Thr Gly Gly Lys Val Arg Ile Asp Ala Phe Gln Ala Gly Glu Leu Gly
        35                  40                  45

Phe Pro Val Thr Glu Ile Leu Glu Ala Thr Ser Arg Gly Val Val Glu
    50                  55                  60

Met Ser Ile Phe Tyr Pro Asn Tyr Lys Ala Ala Gln Asp Pro Val Met
65                  70                  75                  80

Ala Leu Ala Gly Gly Arg Pro Gly Pro Met Phe Asp Leu Arg Asp Gln
```

```
                85                  90                  95

Lys Ala Gln Val Asp Ala Thr Lys Asp Leu Leu Glu Arg Ser Phe Gly
            100                 105                 110

Arg Phe Gly Val Arg Tyr Ile Ala Pro Met Val Tyr Gly Glu Pro Glu
        115                 120                 125

Ile Leu Val Ser Arg Arg Pro Met Ser Ser Leu Lys Asp Leu Lys Gly
    130                 135                 140

Arg Ile Phe Arg Ala Ser Gly Met Ala Ala Glu Phe Tyr Thr Ala Ile
145                 150                 155                 160

Gly Ala Gln Ala Met Met Leu Pro Ala Gly Glu Leu Tyr Gln Ala Leu
                165                 170                 175

Gln Leu Gly Thr Ile Asp Gly Leu Glu Trp Thr Asp Tyr Thr Ala Asn
            180                 185                 190

Tyr Lys Leu Gly Phe His Glu Val Ala Lys Asn Val Leu Glu Pro Thr
        195                 200                 205

Lys Gly Val Asn Leu His Ser Glu Ala Thr Val His Ala Phe Leu Val
    210                 215                 220

Val Asn Pro Lys Val Trp Glu Lys Leu Pro Lys Glu His Gln Lys Ala
225                 230                 235                 240

Ile Gln Glu Ala Ala Asp Glu Ala Tyr Lys Trp Gly Ala Asp His Leu
                245                 250                 255

Ala Lys Leu Asn Lys Thr Tyr Lys Asp Lys Trp Ile Lys Ala Gly Ala
            260                 265                 270

Lys Val Thr Gln Leu Pro Lys Glu Asp Gln Asp Lys Val Ile Glu Val
        275                 280                 285

Ser Ala Lys Ile Leu Ser Gly Tyr Ser Ala Lys Ser Pro Asp Ala Lys
    290                 295                 300

Glu Tyr Ala Arg Arg Leu Val Glu Leu Trp Lys Lys Leu Gly Tyr Thr
305                 310                 315                 320

Lys Trp Ser Asp Ala Leu Ala Lys Gln Ile Lys Gly Gly Ser His His
                325                 330                 335

His His His His
            340


<210> SEQ ID NO 29
<211> LENGTH: 341
<212> TYPE: PRT
<213> ORGANISM: Artificial Sequence
<220> FEATURE:
<223> OTHER INFORMATION: msLacBP6.10C (10C substitution mutant with
      signal peptide replaced with M and a GGSHHHHHH at C-terminus)

<400> SEQUENCE: 29

Met Ala Thr Thr Trp Lys Ile Gln Ser Cys Trp Asp Ala Gly Thr Val
1               5                   10                  15

Gly Tyr Asp Leu Phe Lys Glu Trp Ser Asp Gly Met Glu Glu Lys Thr
            20                  25                  30

Gly Gly Glu Leu Lys Phe Thr Ala Phe Pro Ala Lys Ala Val Ala Ala
        35                  40                  45

Asp Asn Asn Gly Leu Phe Asp Ala Val Arg Asn Gly Val Leu Gln Gly
    50                  55                  60

Met Asn Pro Phe Thr Leu Tyr Trp Ser Gly Lys Ile Pro Ala Ser Val
65                  70                  75                  80

Phe Leu Ser Ser Tyr Pro Ala Gly Pro Asp Gln Pro His Gln Trp Asp
                85                  90                  95
```

```
Thr Met Phe Tyr Ser Leu Gly Met Leu Glu Lys Thr Arg Glu Ile Tyr
            100                 105                 110

Lys Lys Phe Gly Leu Phe Tyr Val Gly Pro Ile Gln His Asp Ala Asn
        115                 120                 125

Ile Ile His Ser Lys Gln Pro Ile Asn Ser Leu Asp Asp Leu Lys Gly
    130                 135                 140

Leu Lys Met Arg Leu Pro Gly Gly Met Val Ala Glu Val Phe Ala Lys
145                 150                 155                 160

Phe Gly Val Ala Ala Val Ser Leu Pro Gly Ser Asp Ile Phe Pro Ala
                165                 170                 175

Leu Glu Lys Gly Thr Ile Asp Ala Ala Asp Tyr Val Gly Pro Ala Val
            180                 185                 190

Asn Trp Glu Leu Gly Phe Ser Gln Val Thr Lys Tyr Ile Leu Met Gly
        195                 200                 205

Pro Pro Gly Ile Met Ser Val Tyr Gln Pro Val Asp Leu Met Asp Leu
    210                 215                 220

Thr Val Asn Leu Arg Ala Trp Asn Ala Leu Asp Pro Lys Leu Gln Gln
225                 230                 235                 240

Ile Val Glu Asp Glu Val Arg Ile Tyr Ser Gln Lys His Tyr Leu Ala
                245                 250                 255

Ile Gln Lys Arg Asn Ile Glu Ala Met Lys Lys Phe Glu Ala Ala Gly
            260                 265                 270

Thr Thr Val Thr Arg Leu Ser Gln Glu Asp Leu Gln Glu Phe Arg Arg
        275                 280                 285

Ala Ala Ile Pro Ile Trp Tyr Ser Trp Ala Asn Lys Asp Glu Asp Ala
    290                 295                 300

Arg Glu Ile Phe Asp Met Gln Leu Glu Tyr Met Met Asn Asp Thr Val
305                 310                 315                 320

Gly Tyr Ile Thr Glu Asp Asp Ile Lys Gly Met Asn Gly Gly Ser His
                325                 330                 335

His His His His His
            340


<210> SEQ ID NO 30
<211> LENGTH: 341
<212> TYPE: PRT
<213> ORGANISM: Artificial Sequence
<220> FEATURE:
<223> OTHER INFORMATION: msLacBP6.12C (12C substitution mutant with
      signal peptide replaced with M and a GGSHHHHHH at C-terminus)

<400> SEQUENCE: 30

Met Ala Thr Thr Trp Lys Ile Gln Ser Val Trp Cys Ala Gly Thr Val
1               5                   10                  15

Gly Tyr Asp Leu Phe Lys Glu Trp Ser Asp Gly Met Glu Glu Lys Thr
            20                  25                  30

Gly Gly Glu Leu Lys Phe Thr Ala Phe Pro Ala Lys Ala Val Ala Ala
        35                  40                  45

Asp Asn Asn Gly Leu Phe Asp Ala Val Arg Asn Gly Val Leu Gln Gly
    50                  55                  60

Met Asn Pro Phe Thr Leu Tyr Trp Ser Gly Lys Ile Pro Ala Ser Val
65                  70                  75                  80

Phe Leu Ser Ser Tyr Pro Ala Gly Pro Asp Gln Pro His Gln Trp Asp
                85                  90                  95

Thr Met Phe Tyr Ser Leu Gly Met Leu Glu Lys Thr Arg Glu Ile Tyr
            100                 105                 110
```

```
Lys Lys Phe Gly Leu Phe Tyr Val Gly Pro Ile Gln His Asp Ala Asn
        115                 120                 125

Ile Ile His Ser Lys Gln Pro Ile Asn Ser Leu Asp Asp Leu Lys Gly
    130                 135                 140

Leu Lys Met Arg Leu Pro Gly Gly Met Val Ala Glu Val Phe Ala Lys
145                 150                 155                 160

Phe Gly Val Ala Ala Val Ser Leu Pro Gly Ser Asp Ile Phe Pro Ala
                165                 170                 175

Leu Glu Lys Gly Thr Ile Asp Ala Ala Asp Tyr Val Gly Pro Ala Val
            180                 185                 190

Asn Trp Glu Leu Gly Phe Ser Gln Val Thr Lys Tyr Ile Leu Met Gly
        195                 200                 205

Pro Pro Gly Ile Met Ser Val Tyr Gln Pro Val Asp Leu Met Asp Leu
    210                 215                 220

Thr Val Asn Leu Arg Ala Trp Asn Ala Leu Asp Pro Lys Leu Gln Gln
225                 230                 235                 240

Ile Val Glu Asp Glu Val Arg Ile Tyr Ser Gln Lys His Tyr Leu Ala
                245                 250                 255

Ile Gln Lys Arg Asn Ile Glu Ala Met Lys Lys Phe Glu Ala Ala Gly
            260                 265                 270

Thr Thr Val Thr Arg Leu Ser Gln Glu Asp Leu Gln Glu Phe Arg Arg
        275                 280                 285

Ala Ala Ile Pro Ile Trp Tyr Ser Trp Ala Asn Lys Asp Glu Asp Ala
    290                 295                 300

Arg Glu Ile Phe Asp Met Gln Leu Glu Tyr Met Met Asn Asp Thr Val
305                 310                 315                 320

Gly Tyr Ile Thr Glu Asp Asp Ile Lys Gly Met Asn Gly Gly Ser His
                325                 330                 335

His His His His His
            340


<210> SEQ ID NO 31
<211> LENGTH: 341
<212> TYPE: PRT
<213> ORGANISM: Artificial Sequence
<220> FEATURE:
<223> OTHER INFORMATION: msLacBP6.43C (43C substitution mutant with
      signal peptide replaced with M and a GGSHHHHHH at C-terminus)

<400> SEQUENCE: 31

Met Ala Thr Thr Trp Lys Ile Gln Ser Val Trp Asp Ala Gly Thr Val
1               5                   10                  15

Gly Tyr Asp Leu Phe Lys Glu Trp Ser Asp Gly Met Glu Glu Lys Thr
            20                  25                  30

Gly Gly Glu Leu Lys Phe Thr Ala Phe Pro Cys Lys Ala Val Ala Ala
        35                  40                  45

Asp Asn Asn Gly Leu Phe Asp Ala Val Arg Asn Gly Val Leu Gln Gly
    50                  55                  60

Met Asn Pro Phe Thr Leu Tyr Trp Ser Gly Lys Ile Pro Ala Ser Val
65                  70                  75                  80

Phe Leu Ser Ser Tyr Pro Ala Gly Pro Asp Gln Pro His Gln Trp Asp
                85                  90                  95

Thr Met Phe Tyr Ser Leu Gly Met Leu Glu Lys Thr Arg Glu Ile Tyr
            100                 105                 110

Lys Lys Phe Gly Leu Phe Tyr Val Gly Pro Ile Gln His Asp Ala Asn
```

```
        115                 120                 125

Ile Ile His Ser Lys Gln Pro Ile Asn Ser Leu Asp Asp Leu Lys Gly
    130                 135                 140

Leu Lys Met Arg Leu Pro Gly Gly Met Val Ala Glu Val Phe Ala Lys
145                 150                 155                 160

Phe Gly Val Ala Ala Val Ser Leu Pro Gly Ser Asp Ile Phe Pro Ala
                165                 170                 175

Leu Glu Lys Gly Thr Ile Asp Ala Ala Asp Tyr Val Gly Pro Ala Val
            180                 185                 190

Asn Trp Glu Leu Gly Phe Ser Gln Val Thr Lys Tyr Ile Leu Met Gly
        195                 200                 205

Pro Pro Gly Ile Met Ser Val Tyr Gln Pro Val Asp Leu Met Asp Leu
    210                 215                 220

Thr Val Asn Leu Arg Ala Trp Asn Ala Leu Asp Pro Lys Leu Gln Gln
225                 230                 235                 240

Ile Val Glu Asp Glu Val Arg Ile Tyr Ser Gln Lys His Tyr Leu Ala
                245                 250                 255

Ile Gln Lys Arg Asn Ile Glu Ala Met Lys Lys Phe Glu Ala Ala Gly
            260                 265                 270

Thr Thr Val Thr Arg Leu Ser Gln Glu Asp Leu Gln Glu Phe Arg Arg
        275                 280                 285

Ala Ala Ile Pro Ile Trp Tyr Ser Trp Ala Asn Lys Asp Glu Asp Ala
    290                 295                 300

Arg Glu Ile Phe Asp Met Gln Leu Glu Tyr Met Met Asn Asp Thr Val
305                 310                 315                 320

Gly Tyr Ile Thr Glu Asp Asp Ile Lys Gly Met Asn Gly Gly Ser His
                325                 330                 335

His His His His His
            340
```

<210> SEQ ID NO 32
<211> LENGTH: 341
<212> TYPE: PRT
<213> ORGANISM: Artificial Sequence
<220> FEATURE:
<223> OTHER INFORMATION: msLacBP6.49C (49C substitution mutant with signal peptide replaced with M and a GGSHHHHHH at C-terminus)

<400> SEQUENCE: 32

```
Met Ala Thr Thr Trp Lys Ile Gln Ser Val Trp Asp Ala Gly Thr Val
1               5                   10                  15

Gly Tyr Asp Leu Phe Lys Glu Trp Ser Asp Gly Met Glu Glu Lys Thr
            20                  25                  30

Gly Gly Glu Leu Lys Phe Thr Ala Phe Pro Ala Lys Ala Val Ala Ala
        35                  40                  45

Cys Asn Asn Gly Leu Phe Asp Ala Val Arg Asn Gly Val Leu Gln Gly
    50                  55                  60

Met Asn Pro Phe Thr Leu Tyr Trp Ser Gly Lys Ile Pro Ala Ser Val
65                  70                  75                  80

Phe Leu Ser Ser Tyr Pro Ala Gly Pro Asp Gln Pro His Gln Trp Asp
                85                  90                  95

Thr Met Phe Tyr Ser Leu Gly Met Leu Glu Lys Thr Arg Glu Ile Tyr
            100                 105                 110

Lys Lys Phe Gly Leu Phe Tyr Val Gly Pro Ile Gln His Asp Ala Asn
        115                 120                 125
```

```
Ile Ile His Ser Lys Gln Pro Ile Asn Ser Leu Asp Asp Leu Lys Gly
    130                 135                 140

Leu Lys Met Arg Leu Pro Gly Gly Met Val Ala Glu Val Phe Ala Lys
145                 150                 155                 160

Phe Gly Val Ala Ala Val Ser Leu Pro Gly Ser Asp Ile Phe Pro Ala
                165                 170                 175

Leu Glu Lys Gly Thr Ile Asp Ala Ala Asp Tyr Val Gly Pro Ala Val
            180                 185                 190

Asn Trp Glu Leu Gly Phe Ser Gln Val Thr Lys Tyr Ile Leu Met Gly
        195                 200                 205

Pro Pro Gly Ile Met Ser Val Tyr Gln Pro Val Asp Leu Met Asp Leu
    210                 215                 220

Thr Val Asn Leu Arg Ala Trp Asn Ala Leu Asp Pro Lys Leu Gln Gln
225                 230                 235                 240

Ile Val Glu Asp Glu Val Arg Ile Tyr Ser Gln Lys His Tyr Leu Ala
                245                 250                 255

Ile Gln Lys Arg Asn Ile Glu Ala Met Lys Lys Phe Glu Ala Ala Gly
            260                 265                 270

Thr Thr Val Thr Arg Leu Ser Gln Glu Asp Leu Gln Glu Phe Arg Arg
        275                 280                 285

Ala Ala Ile Pro Ile Trp Tyr Ser Trp Ala Asn Lys Asp Glu Asp Ala
    290                 295                 300

Arg Glu Ile Phe Asp Met Gln Leu Glu Tyr Met Met Asn Asp Thr Val
305                 310                 315                 320

Gly Tyr Ile Thr Glu Asp Asp Ile Lys Gly Met Asn Gly Gly Ser His
                325                 330                 335

His His His His His
            340


<210> SEQ ID NO 33
<211> LENGTH: 341
<212> TYPE: PRT
<213> ORGANISM: Artificial Sequence
<220> FEATURE:
<223> OTHER INFORMATION: msLacBP6.50C  (50C substitution mutant with
      signal peptide replaced with M and a GGSHHHHHH at C-terminus)

<400> SEQUENCE: 33

Met Ala Thr Thr Trp Lys Ile Gln Ser Val Trp Asp Ala Gly Thr Val
1               5                   10                  15

Gly Tyr Asp Leu Phe Lys Glu Trp Ser Asp Gly Met Glu Glu Lys Thr
            20                  25                  30

Gly Gly Glu Leu Lys Phe Thr Ala Phe Pro Ala Lys Ala Val Ala Ala
        35                  40                  45

Asp Cys Asn Gly Leu Phe Asp Ala Val Arg Asn Gly Val Leu Gln Gly
    50                  55                  60

Met Asn Pro Phe Thr Leu Tyr Trp Ser Gly Lys Ile Pro Ala Ser Val
65                  70                  75                  80

Phe Leu Ser Ser Tyr Pro Ala Gly Pro Asp Gln Pro His Gln Trp Asp
                85                  90                  95

Thr Met Phe Tyr Ser Leu Gly Met Leu Glu Lys Thr Arg Glu Ile Tyr
            100                 105                 110

Lys Lys Phe Gly Leu Phe Tyr Val Gly Pro Ile Gln His Asp Ala Asn
        115                 120                 125

Ile Ile His Ser Lys Gln Pro Ile Asn Ser Leu Asp Asp Leu Lys Gly
    130                 135                 140
```

```
Leu Lys Met Arg Leu Pro Gly Gly Met Val Ala Glu Val Phe Ala Lys
145                 150                 155                 160

Phe Gly Val Ala Ala Val Ser Leu Pro Gly Ser Asp Ile Phe Pro Ala
                165                 170                 175

Leu Glu Lys Gly Thr Ile Asp Ala Ala Asp Tyr Val Gly Pro Ala Val
            180                 185                 190

Asn Trp Glu Leu Gly Phe Ser Gln Val Thr Lys Tyr Ile Leu Met Gly
        195                 200                 205

Pro Pro Gly Ile Met Ser Val Tyr Gln Pro Val Asp Leu Met Asp Leu
    210                 215                 220

Thr Val Asn Leu Arg Ala Trp Asn Ala Leu Asp Pro Lys Leu Gln Gln
225                 230                 235                 240

Ile Val Glu Asp Glu Val Arg Ile Tyr Ser Gln Lys His Tyr Leu Ala
                245                 250                 255

Ile Gln Lys Arg Asn Ile Glu Ala Met Lys Lys Phe Glu Ala Ala Gly
            260                 265                 270

Thr Thr Val Thr Arg Leu Ser Gln Glu Asp Leu Gln Glu Phe Arg Arg
        275                 280                 285

Ala Ala Ile Pro Ile Trp Tyr Ser Trp Ala Asn Lys Asp Glu Asp Ala
    290                 295                 300

Arg Glu Ile Phe Asp Met Gln Leu Glu Tyr Met Met Asn Asp Thr Val
305                 310                 315                 320

Gly Tyr Ile Thr Glu Asp Asp Ile Lys Gly Met Asn Gly Gly Ser His
                325                 330                 335

His His His His His
            340
```

<210> SEQ ID NO 34
<211> LENGTH: 341
<212> TYPE: PRT
<213> ORGANISM: Artificial Sequence
<220> FEATURE:
<223> OTHER INFORMATION: msLacBP6.68C (68C substitution mutant with signal peptide replaced with M and a GGSHHHHHH at C-terminus)

<400> SEQUENCE: 34

```
Met Ala Thr Thr Trp Lys Ile Gln Ser Val Trp Asp Ala Gly Thr Val
1               5                   10                  15

Gly Tyr Asp Leu Phe Lys Glu Trp Ser Asp Gly Met Glu Glu Lys Thr
            20                  25                  30

Gly Gly Glu Leu Lys Phe Thr Ala Phe Pro Ala Lys Ala Val Ala Ala
        35                  40                  45

Asp Asn Asn Gly Leu Phe Asp Ala Val Arg Asn Gly Val Leu Gln Gly
    50                  55                  60

Met Asn Pro Cys Thr Leu Tyr Trp Ser Gly Lys Ile Pro Ala Ser Val
65                  70                  75                  80

Phe Leu Ser Ser Tyr Pro Ala Gly Pro Asp Gln Pro His Gln Trp Asp
                85                  90                  95

Thr Met Phe Tyr Ser Leu Gly Met Leu Glu Lys Thr Arg Glu Ile Tyr
            100                 105                 110

Lys Lys Phe Gly Leu Phe Tyr Val Gly Pro Ile Gln His Asp Ala Asn
        115                 120                 125

Ile Ile His Ser Lys Gln Pro Ile Asn Ser Leu Asp Asp Leu Lys Gly
    130                 135                 140

Leu Lys Met Arg Leu Pro Gly Gly Met Val Ala Glu Val Phe Ala Lys
```

```
145                 150                 155                 160

Phe Gly Val Ala Ala Val Ser Leu Pro Gly Ser Asp Ile Phe Pro Ala
                165                 170                 175

Leu Glu Lys Gly Thr Ile Asp Ala Ala Asp Tyr Val Gly Pro Ala Val
            180                 185                 190

Asn Trp Glu Leu Gly Phe Ser Gln Val Thr Lys Tyr Ile Leu Met Gly
        195                 200                 205

Pro Pro Gly Ile Met Ser Val Tyr Gln Pro Val Asp Leu Met Asp Leu
    210                 215                 220

Thr Val Asn Leu Arg Ala Trp Asn Ala Leu Asp Pro Lys Leu Gln Gln
225                 230                 235                 240

Ile Val Glu Asp Glu Val Arg Ile Tyr Ser Gln Lys His Tyr Leu Ala
                245                 250                 255

Ile Gln Lys Arg Asn Ile Glu Ala Met Lys Lys Phe Glu Ala Ala Gly
            260                 265                 270

Thr Thr Val Thr Arg Leu Ser Gln Glu Asp Leu Gln Glu Phe Arg Arg
        275                 280                 285

Ala Ala Ile Pro Ile Trp Tyr Ser Trp Ala Asn Lys Asp Glu Asp Ala
    290                 295                 300

Arg Glu Ile Phe Asp Met Gln Leu Glu Tyr Met Met Asn Asp Thr Val
305                 310                 315                 320

Gly Tyr Ile Thr Glu Asp Asp Ile Lys Gly Met Asn Gly Gly Ser His
                325                 330                 335

His His His His His
            340


<210> SEQ ID NO 35
<211> LENGTH: 341
<212> TYPE: PRT
<213> ORGANISM: Artificial Sequence
<220> FEATURE:
<223> OTHER INFORMATION: msLacBP6.169C  (169C substitution mutant with
      signal peptide replaced with M and a GGSHHHHHH at C-terminus)

<400> SEQUENCE: 35

Met Ala Thr Thr Trp Lys Ile Gln Ser Val Trp Asp Ala Gly Thr Val
1               5                   10                  15

Gly Tyr Asp Leu Phe Lys Glu Trp Ser Asp Gly Met Glu Glu Lys Thr
            20                  25                  30

Gly Gly Glu Leu Lys Phe Thr Ala Phe Pro Ala Lys Ala Val Ala Ala
        35                  40                  45

Asp Asn Asn Gly Leu Phe Asp Ala Val Arg Asn Gly Val Leu Gln Gly
    50                  55                  60

Met Asn Pro Phe Thr Leu Tyr Trp Ser Gly Lys Ile Pro Ala Ser Val
65                  70                  75                  80

Phe Leu Ser Ser Tyr Pro Ala Gly Pro Asp Gln Pro His Gln Trp Asp
                85                  90                  95

Thr Met Phe Tyr Ser Leu Gly Met Leu Glu Lys Thr Arg Glu Ile Tyr
            100                 105                 110

Lys Lys Phe Gly Leu Phe Tyr Val Gly Pro Ile Gln His Asp Ala Asn
        115                 120                 125

Ile Ile His Ser Lys Gln Pro Ile Asn Ser Leu Asp Asp Leu Lys Gly
    130                 135                 140

Leu Lys Met Arg Leu Pro Gly Gly Met Val Ala Glu Val Phe Ala Lys
145                 150                 155                 160
```

-continued

Phe Gly Val Ala Ala Val Ser Leu Cys Gly Ser Asp Ile Phe Pro Ala
165 170 175

Leu Glu Lys Gly Thr Ile Asp Ala Ala Asp Tyr Val Gly Pro Ala Val
180 185 190

Asn Trp Glu Leu Gly Phe Ser Gln Val Thr Lys Tyr Ile Leu Met Gly
195 200 205

Pro Pro Gly Ile Met Ser Val Tyr Gln Pro Val Asp Leu Met Asp Leu
210 215 220

Thr Val Asn Leu Arg Ala Trp Asn Ala Leu Asp Pro Lys Leu Gln Gln
225 230 235 240

Ile Val Glu Asp Glu Val Arg Ile Tyr Ser Gln Lys His Tyr Leu Ala
245 250 255

Ile Gln Lys Arg Asn Ile Glu Ala Met Lys Lys Phe Glu Ala Ala Gly
260 265 270

Thr Thr Val Thr Arg Leu Ser Gln Glu Asp Leu Gln Glu Phe Arg Arg
275 280 285

Ala Ala Ile Pro Ile Trp Tyr Ser Trp Ala Asn Lys Asp Glu Asp Ala
290 295 300

Arg Glu Ile Phe Asp Met Gln Leu Glu Tyr Met Met Asn Asp Thr Val
305 310 315 320

Gly Tyr Ile Thr Glu Asp Asp Ile Lys Gly Met Asn Gly Gly Ser His
325 330 335

His His His His His
340

<210> SEQ ID NO 36
<211> LENGTH: 341
<212> TYPE: PRT
<213> ORGANISM: Artificial Sequence
<220> FEATURE:
<223> OTHER INFORMATION: msLacBP6.170C (170C substitution mutant with signal peptide replaced with M and a GGSHHHHHH at C-terminus)

<400> SEQUENCE: 36

Met Ala Thr Thr Trp Lys Ile Gln Ser Val Trp Asp Ala Gly Thr Val
1 5 10 15

Gly Tyr Asp Leu Phe Lys Glu Trp Ser Asp Gly Met Glu Glu Lys Thr
20 25 30

Gly Gly Glu Leu Lys Phe Thr Ala Phe Pro Ala Lys Ala Val Ala Ala
35 40 45

Asp Asn Asn Gly Leu Phe Asp Ala Val Arg Asn Gly Val Leu Gln Gly
50 55 60

Met Asn Pro Phe Thr Leu Tyr Trp Ser Gly Lys Ile Pro Ala Ser Val
65 70 75 80

Phe Leu Ser Ser Tyr Pro Ala Gly Pro Asp Gln Pro His Gln Trp Asp
85 90 95

Thr Met Phe Tyr Ser Leu Gly Met Leu Glu Lys Thr Arg Glu Ile Tyr
100 105 110

Lys Lys Phe Gly Leu Phe Tyr Val Gly Pro Ile Gln His Asp Ala Asn
115 120 125

Ile Ile His Ser Lys Gln Pro Ile Asn Ser Leu Asp Asp Leu Lys Gly
130 135 140

Leu Lys Met Arg Leu Pro Gly Gly Met Val Ala Glu Val Phe Ala Lys
145 150 155 160

Phe Gly Val Ala Ala Val Ser Leu Pro Cys Ser Asp Ile Phe Pro Ala
165 170 175

```
Leu Glu Lys Gly Thr Ile Asp Ala Ala Asp Tyr Val Gly Pro Ala Val
            180                 185                 190

Asn Trp Glu Leu Gly Phe Ser Gln Val Thr Lys Tyr Ile Leu Met Gly
        195                 200                 205

Pro Pro Gly Ile Met Ser Val Tyr Gln Pro Val Asp Leu Met Asp Leu
    210                 215                 220

Thr Val Asn Leu Arg Ala Trp Asn Ala Leu Asp Pro Lys Leu Gln Gln
225                 230                 235                 240

Ile Val Glu Asp Glu Val Arg Ile Tyr Ser Gln Lys His Tyr Leu Ala
                245                 250                 255

Ile Gln Lys Arg Asn Ile Glu Ala Met Lys Lys Phe Glu Ala Ala Gly
            260                 265                 270

Thr Thr Val Thr Arg Leu Ser Gln Glu Asp Leu Gln Glu Phe Arg Arg
        275                 280                 285

Ala Ala Ile Pro Ile Trp Tyr Ser Trp Ala Asn Lys Asp Glu Asp Ala
    290                 295                 300

Arg Glu Ile Phe Asp Met Gln Leu Glu Tyr Met Met Asn Asp Thr Val
305                 310                 315                 320

Gly Tyr Ile Thr Glu Asp Asp Ile Lys Gly Met Asn Gly Gly Ser His
                325                 330                 335

His His His His His
            340


<210> SEQ ID NO 37
<211> LENGTH: 341
<212> TYPE: PRT
<213> ORGANISM: Artificial Sequence
<220> FEATURE:
<223> OTHER INFORMATION: msLacBP6.171C  (171C substitution mutant with
      signal peptide replaced with M and a GGSHHHHHH at C-terminus)

<400> SEQUENCE: 37

Met Ala Thr Thr Trp Lys Ile Gln Ser Val Trp Asp Ala Gly Thr Val
1               5                   10                  15

Gly Tyr Asp Leu Phe Lys Glu Trp Ser Asp Gly Met Glu Glu Lys Thr
            20                  25                  30

Gly Gly Glu Leu Lys Phe Thr Ala Phe Pro Ala Lys Ala Val Ala Ala
        35                  40                  45

Asp Asn Asn Gly Leu Phe Asp Ala Val Arg Asn Gly Val Leu Gln Gly
    50                  55                  60

Met Asn Pro Phe Thr Leu Tyr Trp Ser Gly Lys Ile Pro Ala Ser Val
65                  70                  75                  80

Phe Leu Ser Ser Tyr Pro Ala Gly Pro Asp Gln Pro His Gln Trp Asp
                85                  90                  95

Thr Met Phe Tyr Ser Leu Gly Met Leu Glu Lys Thr Arg Glu Ile Tyr
            100                 105                 110

Lys Lys Phe Gly Leu Phe Tyr Val Gly Pro Ile Gln His Asp Ala Asn
        115                 120                 125

Ile Ile His Ser Lys Gln Pro Ile Asn Ser Leu Asp Asp Leu Lys Gly
    130                 135                 140

Leu Lys Met Arg Leu Pro Gly Gly Met Val Ala Glu Val Phe Ala Lys
145                 150                 155                 160

Phe Gly Val Ala Ala Val Ser Leu Pro Gly Cys Asp Ile Phe Pro Ala
                165                 170                 175

Leu Glu Lys Gly Thr Ile Asp Ala Ala Asp Tyr Val Gly Pro Ala Val
```

```
            180                 185                 190

Asn Trp Glu Leu Gly Phe Ser Gln Val Thr Lys Tyr Ile Leu Met Gly
        195                 200                 205

Pro Pro Gly Ile Met Ser Val Tyr Gln Pro Val Asp Leu Met Asp Leu
    210                 215                 220

Thr Val Asn Leu Arg Ala Trp Asn Ala Leu Asp Pro Lys Leu Gln Gln
225                 230                 235                 240

Ile Val Glu Asp Glu Val Arg Ile Tyr Ser Gln Lys His Tyr Leu Ala
                245                 250                 255

Ile Gln Lys Arg Asn Ile Glu Ala Met Lys Lys Phe Glu Ala Ala Gly
            260                 265                 270

Thr Thr Val Thr Arg Leu Ser Gln Glu Asp Leu Gln Glu Phe Arg Arg
        275                 280                 285

Ala Ala Ile Pro Ile Trp Tyr Ser Trp Ala Asn Lys Asp Glu Asp Ala
    290                 295                 300

Arg Glu Ile Phe Asp Met Gln Leu Glu Tyr Met Met Asn Asp Thr Val
305                 310                 315                 320

Gly Tyr Ile Thr Glu Asp Asp Ile Lys Gly Met Asn Gly Gly Ser His
                325                 330                 335

His His His His His
            340


<210> SEQ ID NO 38
<211> LENGTH: 341
<212> TYPE: PRT
<213> ORGANISM: Artificial Sequence
<220> FEATURE:
<223> OTHER INFORMATION: msLacBP6.187C  (187C substitution mutant with
      signal peptide replaced with M and a GGSHHHHHH at C-terminus)

<400> SEQUENCE: 38

Met Ala Thr Thr Trp Lys Ile Gln Ser Val Trp Asp Ala Gly Thr Val
1               5                   10                  15

Gly Tyr Asp Leu Phe Lys Glu Trp Ser Asp Gly Met Glu Glu Lys Thr
            20                  25                  30

Gly Gly Glu Leu Lys Phe Thr Ala Phe Pro Ala Lys Ala Val Ala Ala
        35                  40                  45

Asp Asn Asn Gly Leu Phe Asp Ala Val Arg Asn Gly Val Leu Gln Gly
    50                  55                  60

Met Asn Pro Phe Thr Leu Tyr Trp Ser Gly Lys Ile Pro Ala Ser Val
65                  70                  75                  80

Phe Leu Ser Ser Tyr Pro Ala Gly Pro Asp Gln Pro His Gln Trp Asp
                85                  90                  95

Thr Met Phe Tyr Ser Leu Gly Met Leu Glu Lys Thr Arg Glu Ile Tyr
            100                 105                 110

Lys Lys Phe Gly Leu Phe Tyr Val Gly Pro Ile Gln His Asp Ala Asn
        115                 120                 125

Ile Ile His Ser Lys Gln Pro Ile Asn Ser Leu Asp Asp Leu Lys Gly
    130                 135                 140

Leu Lys Met Arg Leu Pro Gly Gly Met Val Ala Glu Val Phe Ala Lys
145                 150                 155                 160

Phe Gly Val Ala Ala Val Ser Leu Pro Gly Ser Asp Ile Phe Pro Ala
                165                 170                 175

Leu Glu Lys Gly Thr Ile Asp Ala Ala Asp Cys Val Gly Pro Ala Val
            180                 185                 190
```

-continued

```
Asn Trp Glu Leu Gly Phe Ser Gln Val Thr Lys Tyr Ile Leu Met Gly
        195                 200                 205

Pro Pro Gly Ile Met Ser Val Tyr Gln Pro Val Asp Leu Met Asp Leu
    210                 215                 220

Thr Val Asn Leu Arg Ala Trp Asn Ala Leu Asp Pro Lys Leu Gln Gln
225                 230                 235                 240

Ile Val Glu Asp Glu Val Arg Ile Tyr Ser Gln Lys His Tyr Leu Ala
                245                 250                 255

Ile Gln Lys Arg Asn Ile Glu Ala Met Lys Lys Phe Glu Ala Ala Gly
            260                 265                 270

Thr Thr Val Thr Arg Leu Ser Gln Glu Asp Leu Gln Glu Phe Arg Arg
        275                 280                 285

Ala Ala Ile Pro Ile Trp Tyr Ser Trp Ala Asn Lys Asp Glu Asp Ala
    290                 295                 300

Arg Glu Ile Phe Asp Met Gln Leu Glu Tyr Met Met Asn Asp Thr Val
305                 310                 315                 320

Gly Tyr Ile Thr Glu Asp Asp Ile Lys Gly Met Asn Gly Gly Ser His
                325                 330                 335

His His His His His
            340


<210> SEQ ID NO 39
<211> LENGTH: 341
<212> TYPE: PRT
<213> ORGANISM: Artificial Sequence
<220> FEATURE:
<223> OTHER INFORMATION: msLacBP6.188C  (188C substitution mutant with
      signal peptide replaced with M and a GGSHHHHHH at C-terminus)

<400> SEQUENCE: 39

Met Ala Thr Thr Trp Lys Ile Gln Ser Val Trp Asp Ala Gly Thr Val
1               5                   10                  15

Gly Tyr Asp Leu Phe Lys Glu Trp Ser Asp Gly Met Glu Glu Lys Thr
            20                  25                  30

Gly Gly Glu Leu Lys Phe Thr Ala Phe Pro Ala Lys Ala Val Ala Ala
        35                  40                  45

Asp Asn Asn Gly Leu Phe Asp Ala Val Arg Asn Gly Val Leu Gln Gly
    50                  55                  60

Met Asn Pro Phe Thr Leu Tyr Trp Ser Gly Lys Ile Pro Ala Ser Val
65                  70                  75                  80

Phe Leu Ser Ser Tyr Pro Ala Gly Pro Asp Gln Pro His Gln Trp Asp
                85                  90                  95

Thr Met Phe Tyr Ser Leu Gly Met Leu Glu Lys Thr Arg Glu Ile Tyr
            100                 105                 110

Lys Lys Phe Gly Leu Phe Tyr Val Gly Pro Ile Gln His Asp Ala Asn
        115                 120                 125

Ile Ile His Ser Lys Gln Pro Ile Asn Ser Leu Asp Asp Leu Lys Gly
    130                 135                 140

Leu Lys Met Arg Leu Pro Gly Gly Met Val Ala Glu Val Phe Ala Lys
145                 150                 155                 160

Phe Gly Val Ala Ala Val Ser Leu Pro Gly Ser Asp Ile Phe Pro Ala
                165                 170                 175

Leu Glu Lys Gly Thr Ile Asp Ala Ala Asp Tyr Cys Gly Pro Ala Val
            180                 185                 190

Asn Trp Glu Leu Gly Phe Ser Gln Val Thr Lys Tyr Ile Leu Met Gly
        195                 200                 205
```

-continued

```
Pro Pro Gly Ile Met Ser Val Tyr Gln Pro Val Asp Leu Met Asp Leu
    210                 215                 220

Thr Val Asn Leu Arg Ala Trp Asn Ala Leu Asp Pro Lys Leu Gln Gln
225                 230                 235                 240

Ile Val Glu Asp Glu Val Arg Ile Tyr Ser Gln Lys His Tyr Leu Ala
                245                 250                 255

Ile Gln Lys Arg Asn Ile Glu Ala Met Lys Lys Phe Glu Ala Ala Gly
            260                 265                 270

Thr Thr Val Thr Arg Leu Ser Gln Glu Asp Leu Gln Glu Phe Arg Arg
        275                 280                 285

Ala Ala Ile Pro Ile Trp Tyr Ser Trp Ala Asn Lys Asp Glu Asp Ala
    290                 295                 300

Arg Glu Ile Phe Asp Met Gln Leu Glu Tyr Met Met Asn Asp Thr Val
305                 310                 315                 320

Gly Tyr Ile Thr Glu Asp Asp Ile Lys Gly Met Asn Gly Gly Ser His
                325                 330                 335

His His His His His
            340


<210> SEQ ID NO 40
<211> LENGTH: 341
<212> TYPE: PRT
<213> ORGANISM: Artificial Sequence
<220> FEATURE:
<223> OTHER INFORMATION: msLacBP6.192C  (192C substitution mutant with
      signal peptide replaced with M and a GGSHHHHHH at C-terminus)

<400> SEQUENCE: 40

Met Ala Thr Thr Trp Lys Ile Gln Ser Val Trp Asp Ala Gly Thr Val
1               5                   10                  15

Gly Tyr Asp Leu Phe Lys Glu Trp Ser Asp Gly Met Glu Glu Lys Thr
            20                  25                  30

Gly Gly Glu Leu Lys Phe Thr Ala Phe Pro Ala Lys Ala Val Ala Ala
        35                  40                  45

Asp Asn Asn Gly Leu Phe Asp Ala Val Arg Asn Gly Val Leu Gln Gly
    50                  55                  60

Met Asn Pro Phe Thr Leu Tyr Trp Ser Gly Lys Ile Pro Ala Ser Val
65                  70                  75                  80

Phe Leu Ser Ser Tyr Pro Ala Gly Pro Asp Gln Pro His Gln Trp Asp
                85                  90                  95

Thr Met Phe Tyr Ser Leu Gly Met Leu Glu Lys Thr Arg Glu Ile Tyr
            100                 105                 110

Lys Lys Phe Gly Leu Phe Tyr Val Gly Pro Ile Gln His Asp Ala Asn
        115                 120                 125

Ile Ile His Ser Lys Gln Pro Ile Asn Ser Leu Asp Asp Leu Lys Gly
    130                 135                 140

Leu Lys Met Arg Leu Pro Gly Gly Met Val Ala Glu Val Phe Ala Lys
145                 150                 155                 160

Phe Gly Val Ala Ala Val Ser Leu Pro Gly Ser Asp Ile Phe Pro Ala
                165                 170                 175

Leu Glu Lys Gly Thr Ile Asp Ala Ala Asp Tyr Val Gly Pro Ala Cys
            180                 185                 190

Asn Trp Glu Leu Gly Phe Ser Gln Val Thr Lys Tyr Ile Leu Met Gly
        195                 200                 205

Pro Pro Gly Ile Met Ser Val Tyr Gln Pro Val Asp Leu Met Asp Leu
```

```
    210                 215                 220

Thr Val Asn Leu Arg Ala Trp Asn Ala Leu Asp Pro Lys Leu Gln Gln
225                 230                 235                 240

Ile Val Glu Asp Glu Val Arg Ile Tyr Ser Gln Lys His Tyr Leu Ala
                245                 250                 255

Ile Gln Lys Arg Asn Ile Glu Ala Met Lys Lys Phe Glu Ala Ala Gly
            260                 265                 270

Thr Thr Val Thr Arg Leu Ser Gln Glu Asp Leu Gln Glu Phe Arg Arg
        275                 280                 285

Ala Ala Ile Pro Ile Trp Tyr Ser Trp Ala Asn Lys Asp Glu Asp Ala
    290                 295                 300

Arg Glu Ile Phe Asp Met Gln Leu Glu Tyr Met Met Asn Asp Thr Val
305                 310                 315                 320

Gly Tyr Ile Thr Glu Asp Asp Ile Lys Gly Met Asn Gly Gly Ser His
                325                 330                 335

His His His His His
            340


<210> SEQ ID NO 41
<211> LENGTH: 341
<212> TYPE: PRT
<213> ORGANISM: Artificial Sequence
<220> FEATURE:
<223> OTHER INFORMATION: msLacBP6.196C  (196C substitution mutant with
      signal peptide replaced with M and a GGSHHHHHH at C-terminus)

<400> SEQUENCE: 41

Met Ala Thr Thr Trp Lys Ile Gln Ser Val Trp Asp Ala Gly Thr Val
1               5                   10                  15

Gly Tyr Asp Leu Phe Lys Glu Trp Ser Asp Gly Met Glu Glu Lys Thr
            20                  25                  30

Gly Gly Glu Leu Lys Phe Thr Ala Phe Pro Ala Lys Ala Val Ala Ala
        35                  40                  45

Asp Asn Asn Gly Leu Phe Asp Ala Val Arg Asn Gly Val Leu Gln Gly
    50                  55                  60

Met Asn Pro Phe Thr Leu Tyr Trp Ser Gly Lys Ile Pro Ala Ser Val
65                  70                  75                  80

Phe Leu Ser Ser Tyr Pro Ala Gly Pro Asp Gln Pro His Gln Trp Asp
                85                  90                  95

Thr Met Phe Tyr Ser Leu Gly Met Leu Glu Lys Thr Arg Glu Ile Tyr
            100                 105                 110

Lys Lys Phe Gly Leu Phe Tyr Val Gly Pro Ile Gln His Asp Ala Asn
        115                 120                 125

Ile Ile His Ser Lys Gln Pro Ile Asn Ser Leu Asp Asp Leu Lys Gly
    130                 135                 140

Leu Lys Met Arg Leu Pro Gly Gly Met Val Ala Glu Val Phe Ala Lys
145                 150                 155                 160

Phe Gly Val Ala Ala Val Ser Leu Pro Gly Ser Asp Ile Phe Pro Ala
                165                 170                 175

Leu Glu Lys Gly Thr Ile Asp Ala Ala Asp Tyr Val Gly Pro Ala Val
            180                 185                 190

Asn Trp Glu Cys Gly Phe Ser Gln Val Thr Lys Tyr Ile Leu Met Gly
        195                 200                 205

Pro Pro Gly Ile Met Ser Val Tyr Gln Pro Val Asp Leu Met Asp Leu
    210                 215                 220
```

Thr Val Asn Leu Arg Ala Trp Asn Ala Leu Asp Pro Lys Leu Gln Gln
225 230 235 240

Ile Val Glu Asp Glu Val Arg Ile Tyr Ser Gln Lys His Tyr Leu Ala
245 250 255

Ile Gln Lys Arg Asn Ile Glu Ala Met Lys Lys Phe Glu Ala Ala Gly
260 265 270

Thr Thr Val Thr Arg Leu Ser Gln Glu Asp Leu Gln Glu Phe Arg Arg
275 280 285

Ala Ala Ile Pro Ile Trp Tyr Ser Trp Ala Asn Lys Asp Glu Asp Ala
290 295 300

Arg Glu Ile Phe Asp Met Gln Leu Glu Tyr Met Met Asn Asp Thr Val
305 310 315 320

Gly Tyr Ile Thr Glu Asp Asp Ile Lys Gly Met Asn Gly Gly Ser His
325 330 335

His His His His His
340

<210> SEQ ID NO 42
<211> LENGTH: 342
<212> TYPE: PRT
<213> ORGANISM: Artificial Sequence
<220> FEATURE:
<223> OTHER INFORMATION: tsLacBP7.189C (189C substitution mutant with signal peptide replaced with M and a GGSHHHHHH at C-terminus)

<400> SEQUENCE: 42

Met Gln Ala Pro Arg Phe Arg Trp Arg Ile Gln Ser Ala Trp Asp Ala
1 5 10 15

Gly Thr Val Gly Tyr Thr Leu Phe Gln Arg Phe Ala Glu Arg Val Lys
20 25 30

Glu Leu Thr Asp Gly Gln Ile Glu Ile Gln Thr Phe Pro Ala Gly Ala
35 40 45

Val Val Gly Thr Phe Asp Met Phe Asp Ala Val Lys Thr Gly Val Leu
50 55 60

Asp Gly Met His Pro Phe Thr Leu Tyr Trp Ala Gly Arg Met Pro Val
65 70 75 80

Thr Ala Phe Leu Ser Ser Tyr Pro Leu Gly Leu Asp Arg Pro Asp Gln
85 90 95

Trp Glu Thr Trp Tyr Tyr Ala Leu Gly Gly Leu Asp Leu Ala Arg Arg
100 105 110

Ala Phe Glu Glu Gln Gly Leu Phe Tyr Val Gly Pro Val Gln His Asp
115 120 125

Tyr Asn Leu Ile His Ser Lys Lys Pro Ile Lys Ser Phe Glu Asp Phe
130 135 140

Lys Gly Val Lys Leu Arg Val Pro Gly Gly Met Ile Ala Asp Val Phe
145 150 155 160

Ser Ala Ala Gly Ala Ala Thr Val Leu Leu Pro Gly Gly Glu Val Tyr
165 170 175

Pro Ala Leu Glu Arg Gly Val Ile Asp Ala Ala Asp Cys Val Gly Pro
180 185 190

Ala Val Asn Tyr Asn Leu Gly Phe His Gln Val Thr Lys Tyr Ile Ile
195 200 205

Met Gly Pro Pro Glu Thr Pro Ala Ile His Gln Pro Val Asp Leu Ala
210 215 220

Asp Ile Thr Leu Asn Leu Ser Arg Trp Arg Ala Val Pro Lys Asn Leu
225 230 235 240

Gln Glu Arg Phe Glu Ala Ala Val His Glu Trp Ser Trp Ile His Tyr
245 250 255

Ala Gly Ile Gln Lys Ala Asn Leu Glu Thr Trp Pro Lys Tyr Lys Ala
260 265 270

Ala Gly Val Gln Ile Ile Arg Leu Thr Thr Val Asp Val Arg Lys Phe
275 280 285

Arg Arg Val Ala Ile Pro Ile Trp Phe Lys Trp Ala Lys Gln Asp Lys
290 295 300

Tyr Ala Arg Glu Ala Phe Ala Ser Gln Leu Glu Tyr Met Lys Ala Leu
305 310 315 320

Gly Tyr Val Thr Asp Ala Asp Val Arg Gly Leu Ser Leu Gly Gly Ser
325 330 335

His His His His His His
340

<210> SEQ ID NO 43
<211> LENGTH: 342
<212> TYPE: PRT
<213> ORGANISM: Artificial Sequence
<220> FEATURE:
<223> OTHER INFORMATION: maLacBP8.189C (189C substitution mutant with signal peptide replaced with M and a GGSHHHHHH at C-terminus)

<400> SEQUENCE: 43

Met Gln Ala Ala Thr Thr Trp Lys Ile Gln Ser Thr Trp Asp Ala Gly
1 5 10 15

Thr Val Gly Tyr Thr Leu Phe Glu Glu Trp Ala Lys Ser Ile Glu Ala
20 25 30

Lys Ser Gly Gly Glu Leu Lys Phe Gln Ala Phe Pro Ala Lys Ala Val
35 40 45

Ala Ala Asp Asn Asn Ala Leu Phe Asp Ala Val Arg Asn Gly Val Leu
50 55 60

Gln Gly Met Asn Pro Phe Thr Leu Tyr Trp Ala Gly Lys Ile Pro Ala
65 70 75 80

Ser Val Phe Leu Ser Ser Tyr Pro Ala Gly Pro Asp Gln Pro His Gln
85 90 95

Trp Asp Thr Met Phe Tyr Ser Met Gly Met Leu Glu Lys Thr Arg Glu
100 105 110

Ile Tyr Lys Lys Phe Gly Leu Phe Tyr Val Gly Pro Ile Gln His Asp
115 120 125

Ala Asn Ile Ile His Ser Lys Gln Pro Val Asn Ser Leu Asp Asp Leu
130 135 140

Lys Gly Met Lys Ile Arg Val Pro Gly Gly Met Val Ala Glu Val Phe
145 150 155 160

Gln Gln Phe Gly Val Ser Thr Val Ser Leu Pro Gly Ser Asp Ile Phe
165 170 175

Pro Ala Leu Glu Lys Gly Thr Ile Asp Ala Ala Asp Cys Val Gly Pro
180 185 190

Ala Val Asn Tyr Glu Leu Gly Phe Ser Gln Val Thr Asp Tyr Ile Ile
195 200 205

Phe Gly Pro Pro Gly Val Met Ser Ile Tyr Gln Pro Val Asp Leu Met
210 215 220

Asp Leu Thr Val Ser Leu Arg Ala Trp Asn Ser Ile Ser Pro Glu Leu
225 230 235 240

Gln Gln Leu Val Glu Asp Glu Val Arg Ile Tyr Ser Gln Lys His Tyr

```
                245                 250                 255

Leu Ala Ile Gln Ala Arg Asn Ile Glu Ala Met Glu Lys Phe Lys Ala
            260                 265                 270

Asp Gly Asp Thr Val Thr Arg Leu Ser Gln Glu Asp Leu Glu Thr Trp
        275                 280                 285

Arg Lys Ala Ala Ile Pro Ile Trp Phe Asn Trp Ala Asn Lys Asn Asp
    290                 295                 300

Asp Ala Arg Ala Ile Leu Asp Ile Gln Leu Lys Tyr Met Met Asn Asp
305                 310                 315                 320

Thr Val Gly Tyr Ile Thr Glu Glu Asp Ile Lys Gly Phe Gly Gly Ser
                325                 330                 335

His His His His His His
            340


<210> SEQ ID NO 44
<211> LENGTH: 353
<212> TYPE: PRT
<213> ORGANISM: Artificial Sequence
<220> FEATURE:
<223> OTHER INFORMATION: adLacBP9.C191  (191C substitution mutant with
      signal peptide replaced with M and a GGSHHHHHH at C-terminus)

<400> SEQUENCE: 44

Met Gln Ala Pro Ile Thr Leu Arg Phe Gln Ser Thr Trp Pro Gln Lys
1               5                   10                  15

Asp Ile Phe His Glu Phe Ala Leu Asp Tyr Ala Lys Lys Val Asn Glu
            20                  25                  30

Met Ser Gly Gly Arg Leu Lys Ile Glu Val Leu Ala Ala Gly Ser Val
        35                  40                  45

Val Lys Ala Phe Asp Leu Leu Asp Ala Val Ser Lys Gly Thr Leu Asp
    50                  55                  60

Gly Gly His Gly Val Val Ala Tyr Trp Tyr Gly Lys Asn Thr Ala Leu
65                  70                  75                  80

Ala Leu Trp Gly Ser Gly Pro Ala Phe Gly Met Asp Pro Asn Met Val
                85                  90                  95

Leu Ala Trp His His Tyr Gly Gly Gly Arg Gln Leu Leu Glu Glu Ile
            100                 105                 110

Tyr Arg Ser Leu Asn Leu Asp Val Val Ser Leu Met Tyr Gly Pro Met
        115                 120                 125

Pro Thr Gln Pro Leu Gly Trp Phe Lys Gln Lys Pro Ile Ala Lys Pro
    130                 135                 140

Asp Asp Met Lys Gly Leu Lys Phe Arg Thr Val Gly Leu Ser Ile Asp
145                 150                 155                 160

Ile Phe Asn Gly Leu Gly Ala Ala Val Asn Ala Leu Pro Gly Ala Glu
                165                 170                 175

Ile Val Pro Ala Met Asp Arg Gly Leu Leu Asp Ala Ala Glu Cys Asn
            180                 185                 190

Asn Ala Ser Ser Asp Arg Val Leu Gly Phe Pro Asp Val Ser Lys Ile
        195                 200                 205

Ala Met Leu Gln Ser Phe His Gln Ala Ser Glu Gln Phe Glu Ile Leu
    210                 215                 220

Phe Asn Gly Lys Arg Phe Gln Ala Leu Pro Ala Asp Leu Lys Ser Ile
225                 230                 235                 240

Ile Ser Ile Ala Ala Gln Ala Ala Ser Ala Asp Met Ser Trp Lys Ala
                245                 250                 255
```

```
Ile Asp Arg Tyr Ser Ser Asp Tyr Phe Glu Met Arg Asp Lys Gln Gly
            260                 265                 270

Val Lys Phe Tyr Ser Thr Arg Pro Glu Ile Leu Lys Arg Gln Leu Glu
        275                 280                 285

Ile Trp Asp Gln Val Met Glu Lys Arg Ala Ala Glu Asn Pro Thr Phe
    290                 295                 300

Lys Lys Val Leu Glu Ser Gln Arg Arg Phe Ala Gln Arg Ala Ala Arg
305                 310                 315                 320

Trp Gln Asn Asp Thr Asn Val Asp Phe Lys Met Ala Tyr Asn His Phe
                325                 330                 335

Phe Gly Gly Lys Lys Lys Ala Thr Gly Gly Ser His His His His His
            340                 345                 350

His


<210> SEQ ID NO 45
<211> LENGTH: 345
<212> TYPE: PRT
<213> ORGANISM: Artificial Sequence
<220> FEATURE:
<223> OTHER INFORMATION: psLacBP11.195C  (195C substitution mutant with
      signal peptide replaced with M and a GGSHHHHHH at C-terminus)

<400> SEQUENCE: 45

Met Gln Gln Ala Ala Gly Glu Pro Ala Lys Thr Tyr His Trp Lys Met
1               5                   10                  15

Val Thr Ala Trp Pro Lys Asn Tyr Pro Gly Leu Gly Thr Ser Ala Glu
            20                  25                  30

Arg Leu Ala Glu Arg Val Asn Ala Met Ser Gly Gly Arg Leu Thr Ile
        35                  40                  45

Lys Val Tyr Ala Ala Gly Glu Leu Val Pro Ala Leu Glu Val Phe Asp
    50                  55                  60

Ala Val Ser Arg Gly Thr Ala Glu Leu Gly His Gly Ala Ser Tyr Tyr
65                  70                  75                  80

Trp Lys Gly Lys Val Pro Thr Ala Gln Phe Phe Thr Ser Val Pro Phe
                85                  90                  95

Gly Leu Ser Thr Ser Glu Met Asn Ala Trp Leu Ser Lys Gly Gly Gly
            100                 105                 110

Gln Ala Phe Trp Asp Glu Ala Tyr Ala Pro Phe Gly Val Lys Pro Leu
        115                 120                 125

Val Ile Gly Asn Thr Gly Met Gln Met Gly Gly Trp Tyr Asn Lys Glu
    130                 135                 140

Ile Asn Ser Leu Thr Asp Leu Lys Gly Leu Lys Ile Arg Met Pro Gly
145                 150                 155                 160

Leu Gly Gly Glu Val Leu Ser Arg Leu Gly Ala Thr Thr Val Asn Leu
                165                 170                 175

Pro Gly Gly Glu Val Phe Thr Ala Leu Gln Thr Gly Ala Ile Asp Ala
            180                 185                 190

Thr Asp Cys Val Ser Pro Tyr Asn Asp Leu Ala Phe Gly Leu His Lys
        195                 200                 205

Ala Ala Arg Tyr Tyr Tyr Tyr Pro Gly Trp Gln Glu Pro Gln Ala Val
    210                 215                 220

Leu Glu Leu Leu Ile Asn Gln Lys Ala Phe Asp Ser Leu Pro Ala Asp
225                 230                 235                 240

Leu Gln Ala Ile Val Thr Glu Ala Ser Leu Ala Ala Ser Arg Asp Met
                245                 250                 255
```

```
His Asp Asp Tyr Val Tyr Asn Asn Ala Leu Ala Leu Glu Gln Leu Lys
            260                 265                 270

Gln Gln Gly Thr Glu Leu Lys Arg Phe Pro Asp Glu Val Leu Ala Ala
        275                 280                 285

Met Arg Glu Gln Ser Asp Leu Ile Leu Gly Glu Leu Ala Ala Gln Ser
    290                 295                 300

Glu Leu Asn Gly Arg Ile Trp Ala Ser Met Lys Ala Phe Gln Ala Gln
305                 310                 315                 320

Val Glu Pro Met His Glu Ile Ser Glu Lys Glu Leu Tyr Asn Trp Arg
                325                 330                 335

Gly Gly Ser His His His His His His
            340                 345


<210> SEQ ID NO 46
<211> LENGTH: 351
<212> TYPE: PRT
<213> ORGANISM: Artificial Sequence
<220> FEATURE:
<223> OTHER INFORMATION: rsLacBP12.191C  (191C substitution mutant with
      signal peptide replaced with M and a GGSHHHHHH at C-terminus)

<400> SEQUENCE: 46

Met Gln Ala Pro Leu Val Met Lys Met Gln Thr Ser Trp Pro Ala Ser
1               5                   10                  15

Asp Ile Trp Met Asp Phe Ala Arg Glu Tyr Val Thr Arg Val Glu Glu
            20                  25                  30

Met Ser Gly Gly Arg Ile Lys Val Asp Leu Leu Pro Ala Gly Ala Val
        35                  40                  45

Val Gly Ala Phe Gln Val Met Asp Ala Val His Asp Gly Val Ile Asp
    50                  55                  60

Ala Ser His Ser Val Ser Ala Tyr Trp Tyr Gly Lys Ser Lys Ala Ala
65                  70                  75                  80

Ser Phe Phe Gly Thr Gly Pro Val Phe Gly Gly Ser Ala Thr Thr Met
                85                  90                  95

Leu Gly Trp Phe Tyr Gln Gly Gly Gly Gln Asp Leu Tyr Arg Glu Leu
            100                 105                 110

Thr Gln Asp Ile Leu Gly Met Asn Ile Val Gly Phe Tyr Gly Phe Pro
        115                 120                 125

Met Pro Ala Gln Pro Phe Gly Trp Phe Lys Thr Glu Val Asn Gly Val
    130                 135                 140

Ala Asp Ile Gln Gly Phe Lys Tyr Arg Thr Val Gly Leu Ala Ala Asp
145                 150                 155                 160

Leu Leu Gln Ala Met Gly Met Ser Val Ala Gln Leu Pro Gly Gly Glu
                165                 170                 175

Ile Val Pro Ala Met Glu Arg Gly Val Ile Asp Ala Phe Glu Cys Asn
            180                 185                 190

Asn Pro Ser Ser Asp Met Arg Phe Gly Ala Gln Asp Val Ala Lys Asn
        195                 200                 205

Tyr Tyr Leu Ser Ser Tyr His Gln Ala Ser Glu Ser Phe Glu Tyr Thr
    210                 215                 220

Phe Asn Arg Asp Phe Tyr Glu Asp Leu Asp Pro Asp Leu Gln Ala Ile
225                 230                 235                 240

Leu Lys Tyr Ala Val Glu Ala Ala Ser Thr Ser Asn Thr Ala Leu Ala
                245                 250                 255

Leu Arg Gln Tyr Ser Ala Asp Leu Ala Thr Leu Ala Ala Glu Asn Gly
            260                 265                 270
```

```
Val Ala Val His Arg Thr Pro Lys Asp Ile Leu Ser Gly Gln Leu Glu
        275                 280                 285

Ala Trp Asp Lys Leu Ile Val Asp Leu Glu Ala Asp Glu Phe Phe Lys
    290                 295                 300

Lys Val Leu Asp Ser Gln Arg Ala Trp Val Glu Gln Val Ser Tyr Tyr
305                 310                 315                 320

Glu Leu Met Asn Ala Ala Asp Leu Gly Leu Ala Tyr Glu His His Phe
                325                 330                 335

Pro Gly Lys Leu Lys Leu Gly Gly Ser His His His His His His
            340                 345                 350


<210> SEQ ID NO 47
<211> LENGTH: 345
<212> TYPE: PRT
<213> ORGANISM: Artificial Sequence
<220> FEATURE:
<223> OTHER INFORMATION: fsLacBP13.188C  (188C substitution mutant with
      signal peptide replaced with M and a GGSHHHHHH at C-terminus)

<400> SEQUENCE: 47

Met Glu Lys Lys Ile Arg Trp Lys Leu Ala Met Thr Trp Gly Pro Thr
1               5                   10                  15

Leu His Pro Leu Ser Asp Thr Ala Glu His Met Ala Glu Ile Val Lys
            20                  25                  30

Glu Leu Ser Asp Gly Asn Phe Val Ile Asn Ile Asp Ala Ser Asn Val
        35                  40                  45

His Lys Ala Pro Phe Gly Ile Phe Asp Met Val Lys Leu Gly Gln Tyr
    50                  55                  60

Glu Met Gly His Thr Ala Ser Tyr Tyr Tyr Lys Gly Lys Asn Ile Ala
65                  70                  75                  80

Phe Leu Pro Leu Thr Thr Met Pro Phe Gly Met Thr Ala Pro Glu Gln
                85                  90                  95

Tyr Ala Trp Phe Tyr Tyr Gly Gly Gly Leu Glu Leu Met Gln Glu Ala
            100                 105                 110

Tyr Thr Lys His Gly Met Leu Ala Phe Pro Gly Gly Asn Thr Gly Asn
        115                 120                 125

Gln Met Gly Gly Trp Phe Thr Lys Glu Ile Asn Ser Leu Asp Asp Leu
    130                 135                 140

Lys Gly Leu Lys Met Arg Ile Pro Gly Phe Ala Gly Gln Ile Met Ser
145                 150                 155                 160

Lys Leu Gly Val Thr Val Thr Asn Ile Pro Pro Gly Glu Leu Tyr Thr
                165                 170                 175

Ala Leu Glu Arg Gly Thr Val Asp Ala Val Glu Cys Thr Gly Pro Gly
            180                 185                 190

Met Asp Ile Asn Met Gly Phe His Lys Ile Ala Lys Tyr Tyr Tyr Thr
        195                 200                 205

Gly Trp His Glu Pro Gly Ser Glu Val Glu Phe Leu Ile Asn Glu Lys
    210                 215                 220

Glu Tyr Asn Lys Leu Pro Glu Lys Tyr Lys Lys Ile Leu Lys Ile Ala
225                 230                 235                 240

Met Lys Thr Ala Ala Tyr Asp Met Tyr Ile Gln Ser Tyr Glu Met Asn
                245                 250                 255

Ala Glu Ala Trp Gln Gln Met Lys Glu Lys Tyr Pro Asp Ile Lys Val
            260                 265                 270

Lys Val Phe Pro Glu Glu Val Leu Lys Glu Met Lys Thr Ala Tyr Asp
```

275 280 285

Asn Leu Val Ala Ser Tyr Glu Lys Glu Ser Pro Met Phe Lys Lys Ile
290 295 300

Met Glu Ser Lys Arg Ala Tyr Leu Asp Lys Val Arg Asp Trp Thr His
305 310 315 320

Ile Ser Asp Tyr Leu Tyr Leu Lys Ser Thr Ser Glu Ser Asn Leu Asn
325 330 335

Gly Gly Ser His His His His His His
340 345

<210> SEQ ID NO 48
<211> LENGTH: 340
<212> TYPE: PRT
<213> ORGANISM: Artificial Sequence
<220> FEATURE:
<223> OTHER INFORMATION: taLacBP14.186C (186C substitution mutant with signal peptide replaced with M and a GGSHHHHHH at C-terminus)

<400> SEQUENCE: 48

Met Glu Glu Tyr Lys Phe Lys Met Ala Thr Phe Tyr Leu Lys Gly Asp
1 5 10 15

Ser Ala Phe Asp Val Ile Asp His Phe Arg Gln Leu Val Trp Lys Lys
20 25 30

Thr Gly Gly Lys Val Arg Ile Asp Ala Phe Gln Ala Gly Glu Leu Gly
35 40 45

Phe Pro Val Thr Glu Ile Leu Glu Ala Thr Ser Arg Gly Val Val Glu
50 55 60

Met Ser Ile Phe Tyr Pro Asn Tyr Lys Ala Ala Gln Asp Pro Val Met
65 70 75 80

Ala Leu Ala Gly Gly Arg Pro Gly Pro Met Phe Asp Leu Arg Asp Gln
85 90 95

Lys Ala Gln Val Asp Ala Thr Lys Asp Leu Leu Glu Arg Ser Phe Gly
100 105 110

Arg Phe Gly Val Arg Tyr Ile Ala Pro Met Val Tyr Gly Glu Pro Glu
115 120 125

Ile Leu Val Ser Arg Arg Pro Met Ser Ser Leu Lys Asp Leu Lys Gly
130 135 140

Arg Ile Phe Arg Ala Ser Gly Met Ala Ala Glu Phe Tyr Thr Ala Ile
145 150 155 160

Gly Ala Gln Ala Met Met Leu Pro Ala Gly Glu Leu Tyr Gln Ala Leu
165 170 175

Gln Leu Gly Thr Ile Asp Gly Leu Glu Cys Thr Asp Tyr Thr Ala Asn
180 185 190

Tyr Lys Leu Gly Phe His Glu Val Ala Lys Asn Val Leu Glu Pro Thr
195 200 205

Lys Gly Val Asn Leu His Ser Glu Ala Thr Val His Ala Phe Leu Val
210 215 220

Val Asn Pro Lys Val Trp Glu Lys Leu Pro Lys Glu His Gln Lys Ala
225 230 235 240

Ile Gln Glu Ala Ala Asp Glu Ala Tyr Lys Trp Gly Ala Asp His Leu
245 250 255

Ala Lys Leu Asn Lys Thr Tyr Lys Asp Lys Trp Ile Lys Ala Gly Ala
260 265 270

Lys Val Thr Gln Leu Pro Lys Glu Asp Gln Asp Lys Val Ile Glu Val
275 280 285

```
Ser Ala Lys Ile Leu Ser Gly Tyr Ser Ala Lys Ser Pro Asp Ala Lys
    290                 295                 300

Glu Tyr Ala Arg Arg Leu Val Glu Leu Trp Lys Lys Leu Gly Tyr Thr
305                 310                 315                 320

Lys Trp Ser Asp Ala Leu Ala Lys Gln Ile Lys Gly Gly Ser His His
                325                 330                 335

His His His His
            340


<210> SEQ ID NO 49
<211> LENGTH: 341
<212> TYPE: PRT
<213> ORGANISM: Artificial Sequence
<220> FEATURE:
<223> OTHER INFORMATION: msLacBP6_187C_F68L (187C, 68L double
      substitution mutant with signal peptide replaced with M and a
      GGSHHHHHH at C-terminus)

<400> SEQUENCE: 49

Met Ala Thr Thr Trp Lys Ile Gln Ser Val Trp Asp Ala Gly Thr Val
1               5                   10                  15

Gly Tyr Asp Leu Phe Lys Glu Trp Cys Asp Gly Met Glu Glu Lys Thr
            20                  25                  30

Gly Gly Glu Leu Lys Phe Thr Cys Phe Pro Ala Lys Ala Val Ala Ala
        35                  40                  45

Asp Asn Asn Gly Leu Phe Asp Ala Val Arg Asn Gly Val Leu Gln Gly
    50                  55                  60

Met Asn Pro Leu Thr Leu Tyr Trp Ser Gly Lys Ile Pro Ala Ser Val
65                  70                  75                  80

Phe Leu Ser Ser Tyr Pro Ala Gly Pro Asp Gln Pro His Gln Trp Asp
                85                  90                  95

Thr Met Phe Tyr Ser Leu Gly Met Leu Glu Lys Thr Arg Glu Ile Tyr
            100                 105                 110

Lys Lys Phe Gly Leu Phe Tyr Val Gly Pro Ile Gln His Asp Ala Asn
        115                 120                 125

Ile Ile His Ser Lys Gln Pro Ile Asn Ser Leu Asp Asp Leu Lys Gly
    130                 135                 140

Leu Lys Met Arg Leu Pro Gly Gly Met Val Ala Glu Val Phe Ala Lys
145                 150                 155                 160

Phe Gly Val Ala Ala Val Ser Leu Pro Gly Ser Asp Ile Phe Pro Ala
                165                 170                 175

Leu Glu Lys Gly Thr Ile Asp Ala Ala Asp Cys Val Gly Pro Ala Val
            180                 185                 190

Asn Trp Glu Leu Gly Phe Ser Gln Val Thr Lys Tyr Ile Leu Met Gly
        195                 200                 205

Pro Pro Gly Ile Met Ser Val Tyr Gln Pro Val Asp Leu Met Asp Leu
    210                 215                 220

Thr Val Asn Leu Arg Ala Trp Asn Ala Leu Asp Pro Lys Leu Gln Gln
225                 230                 235                 240

Ile Val Glu Asp Glu Val Arg Ile Tyr Ser Gln Lys His Tyr Leu Ala
                245                 250                 255

Ile Gln Lys Arg Asn Ile Glu Ala Met Lys Lys Phe Glu Ala Ala Gly
            260                 265                 270

Thr Thr Val Thr Arg Leu Ser Gln Glu Asp Leu Gln Glu Phe Arg Arg
        275                 280                 285

Ala Ala Ile Pro Ile Trp Tyr Ser Trp Ala Asn Lys Asp Glu Asp Ala
```

```
    290                 295                 300

Arg Glu Ile Phe Asp Met Gln Leu Glu Tyr Met Met Asn Asp Thr Val
305                 310                 315                 320

Gly Tyr Ile Thr Glu Asp Asp Ile Lys Gly Met Asn Gly Gly Ser His
                325                 330                 335

His His His His His
            340
```

<210> SEQ ID NO 50
<211> LENGTH: 341
<212> TYPE: PRT
<213> ORGANISM: Artificial Sequence
<220> FEATURE:
<223> OTHER INFORMATION: msLacBP6_187C_F68M (187C, 68M double substitution mutant with signal peptide replaced with M and a GGSHHHHHH at C-terminus)

<400> SEQUENCE: 50

```
Met Ala Thr Thr Trp Lys Ile Gln Ser Val Trp Asp Ala Gly Thr Val
1               5                   10                  15

Gly Tyr Asp Leu Phe Lys Glu Trp Cys Asp Gly Met Glu Glu Lys Thr
            20                  25                  30

Gly Gly Glu Leu Lys Phe Thr Cys Phe Pro Ala Lys Ala Val Ala Ala
        35                  40                  45

Asp Asn Asn Gly Leu Phe Asp Ala Val Arg Asn Gly Val Leu Gln Gly
    50                  55                  60

Met Asn Pro Met Thr Leu Tyr Trp Ser Gly Lys Ile Pro Ala Ser Val
65                  70                  75                  80

Phe Leu Ser Ser Tyr Pro Ala Gly Pro Asp Gln Pro His Gln Trp Asp
                85                  90                  95

Thr Met Phe Tyr Ser Leu Gly Met Leu Glu Lys Thr Arg Glu Ile Tyr
            100                 105                 110

Lys Lys Phe Gly Leu Phe Tyr Val Gly Pro Ile Gln His Asp Ala Asn
        115                 120                 125

Ile Ile His Ser Lys Gln Pro Ile Asn Ser Leu Asp Asp Leu Lys Gly
    130                 135                 140

Leu Lys Met Arg Leu Pro Gly Gly Met Val Ala Glu Val Phe Ala Lys
145                 150                 155                 160

Phe Gly Val Ala Ala Val Ser Leu Pro Gly Ser Asp Ile Phe Pro Ala
                165                 170                 175

Leu Glu Lys Gly Thr Ile Asp Ala Ala Asp Cys Val Gly Pro Ala Val
            180                 185                 190

Asn Trp Glu Leu Gly Phe Ser Gln Val Thr Lys Tyr Ile Leu Met Gly
        195                 200                 205

Pro Pro Gly Ile Met Ser Val Tyr Gln Pro Val Asp Leu Met Asp Leu
    210                 215                 220

Thr Val Asn Leu Arg Ala Trp Asn Ala Leu Asp Pro Lys Leu Gln Gln
225                 230                 235                 240

Ile Val Glu Asp Glu Val Arg Ile Tyr Ser Gln Lys His Tyr Leu Ala
                245                 250                 255

Ile Gln Lys Arg Asn Ile Glu Ala Met Lys Lys Phe Glu Ala Ala Gly
            260                 265                 270

Thr Thr Val Thr Arg Leu Ser Gln Glu Asp Leu Gln Glu Phe Arg Arg
        275                 280                 285

Ala Ala Ile Pro Ile Trp Tyr Ser Trp Ala Asn Lys Asp Glu Asp Ala
    290                 295                 300
```

```
Arg Glu Ile Phe Asp Met Gln Leu Glu Tyr Met Met Asn Asp Thr Val
305                 310                 315                 320

Gly Tyr Ile Thr Glu Asp Asp Ile Lys Gly Met Asn Gly Gly Ser His
                325                 330                 335

His His His His His
            340


<210> SEQ ID NO 51
<211> LENGTH: 341
<212> TYPE: PRT
<213> ORGANISM: Artificial Sequence
<220> FEATURE:
<223> OTHER INFORMATION: msLacBP6_187C_L70F  (187C, 70F double
      substitution mutant with signal peptide replaced with M and a
      GGSHHHHHH at C-terminus)

<400> SEQUENCE: 51

Met Ala Thr Thr Trp Lys Ile Gln Ser Val Trp Asp Ala Gly Thr Val
1               5                   10                  15

Gly Tyr Asp Leu Phe Lys Glu Trp Cys Asp Gly Met Glu Glu Lys Thr
            20                  25                  30

Gly Gly Glu Leu Lys Phe Thr Cys Phe Pro Ala Lys Ala Val Ala Ala
        35                  40                  45

Asp Asn Asn Gly Leu Phe Asp Ala Val Arg Asn Gly Val Leu Gln Gly
    50                  55                  60

Met Asn Pro Phe Thr Phe Tyr Trp Ser Gly Lys Ile Pro Ala Ser Val
65                  70                  75                  80

Phe Leu Ser Ser Tyr Pro Ala Gly Pro Asp Gln Pro His Gln Trp Asp
                85                  90                  95

Thr Met Phe Tyr Ser Leu Gly Met Leu Glu Lys Thr Arg Glu Ile Tyr
            100                 105                 110

Lys Lys Phe Gly Leu Phe Tyr Val Gly Pro Ile Gln His Asp Ala Asn
        115                 120                 125

Ile Ile His Ser Lys Gln Pro Ile Asn Ser Leu Asp Asp Leu Lys Gly
    130                 135                 140

Leu Lys Met Arg Leu Pro Gly Gly Met Val Ala Glu Val Phe Ala Lys
145                 150                 155                 160

Phe Gly Val Ala Ala Val Ser Leu Pro Gly Ser Asp Ile Phe Pro Ala
                165                 170                 175

Leu Glu Lys Gly Thr Ile Asp Ala Ala Asp Cys Val Gly Pro Ala Val
            180                 185                 190

Asn Trp Glu Leu Gly Phe Ser Gln Val Thr Lys Tyr Ile Leu Met Gly
        195                 200                 205

Pro Pro Gly Ile Met Ser Val Tyr Gln Pro Val Asp Leu Met Asp Leu
    210                 215                 220

Thr Val Asn Leu Arg Ala Trp Asn Ala Leu Asp Pro Lys Leu Gln Gln
225                 230                 235                 240

Ile Val Glu Asp Glu Val Arg Ile Tyr Ser Gln Lys His Tyr Leu Ala
                245                 250                 255

Ile Gln Lys Arg Asn Ile Glu Ala Met Lys Lys Phe Glu Ala Ala Gly
            260                 265                 270

Thr Thr Val Thr Arg Leu Ser Gln Glu Asp Leu Gln Glu Phe Arg Arg
        275                 280                 285

Ala Ala Ile Pro Ile Trp Tyr Ser Trp Ala Asn Lys Asp Glu Asp Ala
    290                 295                 300
```

```
Arg Glu Ile Phe Asp Met Gln Leu Glu Tyr Met Met Asn Asp Thr Val
305                 310                 315                 320

Gly Tyr Ile Thr Glu Asp Asp Ile Lys Gly Met Asn Gly Gly Ser His
                325                 330                 335

His His His His His
            340


<210> SEQ ID NO 52
<211> LENGTH: 341
<212> TYPE: PRT
<213> ORGANISM: Artificial Sequence
<220> FEATURE:
<223> OTHER INFORMATION: msLacBP6_187C_L70I  (187C, 70I double
      substitution mutant with signal peptide replaced with M and a
      GGSHHHHHH at C-terminus)

<400> SEQUENCE: 52

Met Ala Thr Thr Trp Lys Ile Gln Ser Val Trp Asp Ala Gly Thr Val
1               5                   10                  15

Gly Tyr Asp Leu Phe Lys Glu Trp Cys Asp Gly Met Glu Glu Lys Thr
            20                  25                  30

Gly Gly Glu Leu Lys Phe Thr Cys Phe Pro Ala Lys Ala Val Ala Ala
        35                  40                  45

Asp Asn Asn Gly Leu Phe Asp Ala Val Arg Asn Gly Val Leu Gln Gly
    50                  55                  60

Met Asn Pro Phe Thr Ile Tyr Trp Ser Gly Lys Ile Pro Ala Ser Val
65                  70                  75                  80

Phe Leu Ser Ser Tyr Pro Ala Gly Pro Asp Gln Pro His Gln Trp Asp
                85                  90                  95

Thr Met Phe Tyr Ser Leu Gly Met Leu Glu Lys Thr Arg Glu Ile Tyr
            100                 105                 110

Lys Lys Phe Gly Leu Phe Tyr Val Gly Pro Ile Gln His Asp Ala Asn
        115                 120                 125

Ile Ile His Ser Lys Gln Pro Ile Asn Ser Leu Asp Asp Leu Lys Gly
    130                 135                 140

Leu Lys Met Arg Leu Pro Gly Gly Met Val Ala Glu Val Phe Ala Lys
145                 150                 155                 160

Phe Gly Val Ala Ala Val Ser Leu Pro Gly Ser Asp Ile Phe Pro Ala
                165                 170                 175

Leu Glu Lys Gly Thr Ile Asp Ala Ala Asp Cys Val Gly Pro Ala Val
            180                 185                 190

Asn Trp Glu Leu Gly Phe Ser Gln Val Thr Lys Tyr Ile Leu Met Gly
        195                 200                 205

Pro Pro Gly Ile Met Ser Val Tyr Gln Pro Val Asp Leu Met Asp Leu
    210                 215                 220

Thr Val Asn Leu Arg Ala Trp Asn Ala Leu Asp Pro Lys Leu Gln Gln
225                 230                 235                 240

Ile Val Glu Asp Glu Val Arg Ile Tyr Ser Gln Lys His Tyr Leu Ala
                245                 250                 255

Ile Gln Lys Arg Asn Ile Glu Ala Met Lys Lys Phe Glu Ala Ala Gly
            260                 265                 270

Thr Thr Val Thr Arg Leu Ser Gln Glu Asp Leu Gln Glu Phe Arg Arg
        275                 280                 285

Ala Ala Ile Pro Ile Trp Tyr Ser Trp Ala Asn Lys Asp Glu Asp Ala
    290                 295                 300

Arg Glu Ile Phe Asp Met Gln Leu Glu Tyr Met Met Asn Asp Thr Val
```

305 310 315 320

Gly Tyr Ile Thr Glu Asp Asp Ile Lys Gly Met Asn Gly Gly Ser His
325 330 335

His His His His His
340

<210> SEQ ID NO 53
<211> LENGTH: 341
<212> TYPE: PRT
<213> ORGANISM: Artificial Sequence
<220> FEATURE:
<223> OTHER INFORMATION: msLacBP6_187C_L70M (187C, 70M double substitution mutant with signal peptide replaced with M and a GGSHHHHHH at C-terminus)

<400> SEQUENCE: 53

Met Ala Thr Thr Trp Lys Ile Gln Ser Val Trp Asp Ala Gly Thr Val
1 5 10 15

Gly Tyr Asp Leu Phe Lys Glu Trp Cys Asp Gly Met Glu Glu Lys Thr
20 25 30

Gly Gly Glu Leu Lys Phe Thr Cys Phe Pro Ala Lys Ala Val Ala Ala
35 40 45

Asp Asn Asn Gly Leu Phe Asp Ala Val Arg Asn Gly Val Leu Gln Gly
50 55 60

Met Asn Pro Phe Thr Met Tyr Trp Ser Gly Lys Ile Pro Ala Ser Val
65 70 75 80

Phe Leu Ser Ser Tyr Pro Ala Gly Pro Asp Gln Pro His Gln Trp Asp
85 90 95

Thr Met Phe Tyr Ser Leu Gly Met Leu Glu Lys Thr Arg Glu Ile Tyr
100 105 110

Lys Lys Phe Gly Leu Phe Tyr Val Gly Pro Ile Gln His Asp Ala Asn
115 120 125

Ile Ile His Ser Lys Gln Pro Ile Asn Ser Leu Asp Asp Leu Lys Gly
130 135 140

Leu Lys Met Arg Leu Pro Gly Gly Met Val Ala Glu Val Phe Ala Lys
145 150 155 160

Phe Gly Val Ala Ala Val Ser Leu Pro Gly Ser Asp Ile Phe Pro Ala
165 170 175

Leu Glu Lys Gly Thr Ile Asp Ala Ala Asp Cys Val Gly Pro Ala Val
180 185 190

Asn Trp Glu Leu Gly Phe Ser Gln Val Thr Lys Tyr Ile Leu Met Gly
195 200 205

Pro Pro Gly Ile Met Ser Val Tyr Gln Pro Val Asp Leu Met Asp Leu
210 215 220

Thr Val Asn Leu Arg Ala Trp Asn Ala Leu Asp Pro Lys Leu Gln Gln
225 230 235 240

Ile Val Glu Asp Glu Val Arg Ile Tyr Ser Gln Lys His Tyr Leu Ala
245 250 255

Ile Gln Lys Arg Asn Ile Glu Ala Met Lys Lys Phe Glu Ala Ala Gly
260 265 270

Thr Thr Val Thr Arg Leu Ser Gln Glu Asp Leu Gln Glu Phe Arg Arg
275 280 285

Ala Ala Ile Pro Ile Trp Tyr Ser Trp Ala Asn Lys Asp Glu Asp Ala
290 295 300

Arg Glu Ile Phe Asp Met Gln Leu Glu Tyr Met Met Asn Asp Thr Val
305 310 315 320

```
Gly Tyr Ile Thr Glu Asp Asp Ile Lys Gly Met Asn Gly Gly Ser His
                325                 330                 335

His His His His His
            340


<210> SEQ ID NO 54
<211> LENGTH: 341
<212> TYPE: PRT
<213> ORGANISM: Artificial Sequence
<220> FEATURE:
<223> OTHER INFORMATION: msLacBP6_187C_P150A  (187C, 150A double
      substitution mutant with signal peptide replaced with M and a
      GGSHHHHHH at C-terminus)

<400> SEQUENCE: 54

Met Ala Thr Thr Trp Lys Ile Gln Ser Val Trp Asp Ala Gly Thr Val
1               5                   10                  15

Gly Tyr Asp Leu Phe Lys Glu Trp Cys Asp Gly Met Glu Glu Lys Thr
            20                  25                  30

Gly Gly Glu Leu Lys Phe Thr Cys Phe Pro Ala Lys Ala Val Ala Ala
        35                  40                  45

Asp Asn Asn Gly Leu Phe Asp Ala Val Arg Asn Gly Val Leu Gln Gly
    50                  55                  60

Met Asn Pro Phe Thr Leu Tyr Trp Ser Gly Lys Ile Pro Ala Ser Val
65                  70                  75                  80

Phe Leu Ser Ser Tyr Pro Ala Gly Pro Asp Gln Pro His Gln Trp Asp
                85                  90                  95

Thr Met Phe Tyr Ser Leu Gly Met Leu Glu Lys Thr Arg Glu Ile Tyr
            100                 105                 110

Lys Lys Phe Gly Leu Phe Tyr Val Gly Pro Ile Gln His Asp Ala Asn
        115                 120                 125

Ile Ile His Ser Lys Gln Pro Ile Asn Ser Leu Asp Asp Leu Lys Gly
    130                 135                 140

Leu Lys Met Arg Leu Ala Gly Gly Met Val Ala Glu Val Phe Ala Lys
145                 150                 155                 160

Phe Gly Val Ala Ala Val Ser Leu Pro Gly Ser Asp Ile Phe Pro Ala
                165                 170                 175

Leu Glu Lys Gly Thr Ile Asp Ala Ala Asp Cys Val Gly Pro Ala Val
            180                 185                 190

Asn Trp Glu Leu Gly Phe Ser Gln Val Thr Lys Tyr Ile Leu Met Gly
        195                 200                 205

Pro Pro Gly Ile Met Ser Val Tyr Gln Pro Val Asp Leu Met Asp Leu
    210                 215                 220

Thr Val Asn Leu Arg Ala Trp Asn Ala Leu Asp Pro Lys Leu Gln Gln
225                 230                 235                 240

Ile Val Glu Asp Glu Val Arg Ile Tyr Ser Gln Lys His Tyr Leu Ala
                245                 250                 255

Ile Gln Lys Arg Asn Ile Glu Ala Met Lys Lys Phe Glu Ala Ala Gly
            260                 265                 270

Thr Thr Val Thr Arg Leu Ser Gln Glu Asp Leu Gln Glu Phe Arg Arg
        275                 280                 285

Ala Ala Ile Pro Ile Trp Tyr Ser Trp Ala Asn Lys Asp Glu Asp Ala
    290                 295                 300

Arg Glu Ile Phe Asp Met Gln Leu Glu Tyr Met Met Asn Asp Thr Val
305                 310                 315                 320
```

```
Gly Tyr Ile Thr Glu Asp Asp Ile Lys Gly Met Asn Gly Gly Ser His
                325                 330                 335

His His His His His
            340


<210> SEQ ID NO 55
<211> LENGTH: 341
<212> TYPE: PRT
<213> ORGANISM: Artificial Sequence
<220> FEATURE:
<223> OTHER INFORMATION: msLacBP6_187C_P150S  (187C, 150S double
      substitution mutant with signal peptide replaced with M and a
      GGSHHHHHH at C-terminus)

<400> SEQUENCE: 55

Met Ala Thr Thr Trp Lys Ile Gln Ser Val Trp Asp Ala Gly Thr Val
1               5                   10                  15

Gly Tyr Asp Leu Phe Lys Glu Trp Cys Asp Gly Met Glu Glu Lys Thr
            20                  25                  30

Gly Gly Glu Leu Lys Phe Thr Cys Phe Pro Ala Lys Ala Val Ala Ala
        35                  40                  45

Asp Asn Asn Gly Leu Phe Asp Ala Val Arg Asn Gly Val Leu Gln Gly
    50                  55                  60

Met Asn Pro Phe Thr Leu Tyr Trp Ser Gly Lys Ile Pro Ala Ser Val
65                  70                  75                  80

Phe Leu Ser Ser Tyr Pro Ala Gly Pro Asp Gln Pro His Gln Trp Asp
                85                  90                  95

Thr Met Phe Tyr Ser Leu Gly Met Leu Glu Lys Thr Arg Glu Ile Tyr
            100                 105                 110

Lys Lys Phe Gly Leu Phe Tyr Val Gly Pro Ile Gln His Asp Ala Asn
        115                 120                 125

Ile Ile His Ser Lys Gln Pro Ile Asn Ser Leu Asp Asp Leu Lys Gly
    130                 135                 140

Leu Lys Met Arg Leu Ser Gly Gly Met Val Ala Glu Val Phe Ala Lys
145                 150                 155                 160

Phe Gly Val Ala Ala Val Ser Leu Pro Gly Ser Asp Ile Phe Pro Ala
                165                 170                 175

Leu Glu Lys Gly Thr Ile Asp Ala Ala Asp Cys Val Gly Pro Ala Val
            180                 185                 190

Asn Trp Glu Leu Gly Phe Ser Gln Val Thr Lys Tyr Ile Leu Met Gly
        195                 200                 205

Pro Pro Gly Ile Met Ser Val Tyr Gln Pro Val Asp Leu Met Asp Leu
    210                 215                 220

Thr Val Asn Leu Arg Ala Trp Asn Ala Leu Asp Pro Lys Leu Gln Gln
225                 230                 235                 240

Ile Val Glu Asp Glu Val Arg Ile Tyr Ser Gln Lys His Tyr Leu Ala
                245                 250                 255

Ile Gln Lys Arg Asn Ile Glu Ala Met Lys Lys Phe Glu Ala Ala Gly
            260                 265                 270

Thr Thr Val Thr Arg Leu Ser Gln Glu Asp Leu Gln Glu Phe Arg Arg
        275                 280                 285

Ala Ala Ile Pro Ile Trp Tyr Ser Trp Ala Asn Lys Asp Glu Asp Ala
    290                 295                 300

Arg Glu Ile Phe Asp Met Gln Leu Glu Tyr Met Met Asn Asp Thr Val
305                 310                 315                 320

Gly Tyr Ile Thr Glu Asp Asp Ile Lys Gly Met Asn Gly Gly Ser His
```

325 330 335

His His His His His
340

<210> SEQ ID NO 56
<211> LENGTH: 341
<212> TYPE: PRT
<213> ORGANISM: Artificial Sequence
<220> FEATURE:
<223> OTHER INFORMATION: msLacBP6_187C_D220E (187C, 220E double substitution mutant with signal peptide replaced with M and a GGSHHHHHH at C-terminus)

<400> SEQUENCE: 56

Met Ala Thr Thr Trp Lys Ile Gln Ser Val Trp Asp Ala Gly Thr Val
1 5 10 15

Gly Tyr Asp Leu Phe Lys Glu Trp Cys Asp Gly Met Glu Glu Lys Thr
20 25 30

Gly Gly Glu Leu Lys Phe Thr Cys Phe Pro Ala Lys Ala Val Ala Ala
35 40 45

Asp Asn Asn Gly Leu Phe Asp Ala Val Arg Asn Gly Val Leu Gln Gly
50 55 60

Met Asn Pro Phe Thr Leu Tyr Trp Ser Gly Lys Ile Pro Ala Ser Val
65 70 75 80

Phe Leu Ser Ser Tyr Pro Ala Gly Pro Asp Gln Pro His Gln Trp Asp
85 90 95

Thr Met Phe Tyr Ser Leu Gly Met Leu Glu Lys Thr Arg Glu Ile Tyr
100 105 110

Lys Lys Phe Gly Leu Phe Tyr Val Gly Pro Ile Gln His Asp Ala Asn
115 120 125

Ile Ile His Ser Lys Gln Pro Ile Asn Ser Leu Asp Asp Leu Lys Gly
130 135 140

Leu Lys Met Arg Leu Pro Gly Gly Met Val Ala Glu Val Phe Ala Lys
145 150 155 160

Phe Gly Val Ala Ala Val Ser Leu Pro Gly Ser Asp Ile Phe Pro Ala
165 170 175

Leu Glu Lys Gly Thr Ile Asp Ala Ala Asp Cys Val Gly Pro Ala Val
180 185 190

Asn Trp Glu Leu Gly Phe Ser Gln Val Thr Lys Tyr Ile Leu Met Gly
195 200 205

Pro Pro Gly Ile Met Ser Val Tyr Gln Pro Val Glu Leu Met Asp Leu
210 215 220

Thr Val Asn Leu Arg Ala Trp Asn Ala Leu Asp Pro Lys Leu Gln Gln
225 230 235 240

Ile Val Glu Asp Glu Val Arg Ile Tyr Ser Gln Lys His Tyr Leu Ala
245 250 255

Ile Gln Lys Arg Asn Ile Glu Ala Met Lys Lys Phe Glu Ala Ala Gly
260 265 270

Thr Thr Val Thr Arg Leu Ser Gln Glu Asp Leu Gln Glu Phe Arg Arg
275 280 285

Ala Ala Ile Pro Ile Trp Tyr Ser Trp Ala Asn Lys Asp Glu Asp Ala
290 295 300

Arg Glu Ile Phe Asp Met Gln Leu Glu Tyr Met Met Asn Asp Thr Val
305 310 315 320

Gly Tyr Ile Thr Glu Asp Asp Ile Lys Gly Met Asn Gly Gly Ser His
325 330 335

```
His His His His His
            340


<210> SEQ ID NO 57
<211> LENGTH: 341
<212> TYPE: PRT
<213> ORGANISM: Artificial Sequence
<220> FEATURE:
<223> OTHER INFORMATION: msLacBP6_187C_D220L  (187C, 220L double
      substitution mutant with signal peptide replaced with M and a
      GGSHHHHHH at C-terminus)

<400> SEQUENCE: 57

Met Ala Thr Thr Trp Lys Ile Gln Ser Val Trp Asp Ala Gly Thr Val
1               5                   10                  15

Gly Tyr Asp Leu Phe Lys Glu Trp Cys Asp Gly Met Glu Glu Lys Thr
            20                  25                  30

Gly Gly Glu Leu Lys Phe Thr Cys Phe Pro Ala Lys Ala Val Ala Ala
        35                  40                  45

Asp Asn Asn Gly Leu Phe Asp Ala Val Arg Asn Gly Val Leu Gln Gly
    50                  55                  60

Met Asn Pro Phe Thr Leu Tyr Trp Ser Gly Lys Ile Pro Ala Ser Val
65                  70                  75                  80

Phe Leu Ser Ser Tyr Pro Ala Gly Pro Asp Gln Pro His Gln Trp Asp
                85                  90                  95

Thr Met Phe Tyr Ser Leu Gly Met Leu Glu Lys Thr Arg Glu Ile Tyr
            100                 105                 110

Lys Lys Phe Gly Leu Phe Tyr Val Gly Pro Ile Gln His Asp Ala Asn
        115                 120                 125

Ile Ile His Ser Lys Gln Pro Ile Asn Ser Leu Asp Asp Leu Lys Gly
    130                 135                 140

Leu Lys Met Arg Leu Pro Gly Gly Met Val Ala Glu Val Phe Ala Lys
145                 150                 155                 160

Phe Gly Val Ala Ala Val Ser Leu Pro Gly Ser Asp Ile Phe Pro Ala
                165                 170                 175

Leu Glu Lys Gly Thr Ile Asp Ala Ala Asp Cys Val Gly Pro Ala Val
            180                 185                 190

Asn Trp Glu Leu Gly Phe Ser Gln Val Thr Lys Tyr Ile Leu Met Gly
        195                 200                 205

Pro Pro Gly Ile Met Ser Val Tyr Gln Pro Val Leu Leu Met Asp Leu
    210                 215                 220

Thr Val Asn Leu Arg Ala Trp Asn Ala Leu Asp Pro Lys Leu Gln Gln
225                 230                 235                 240

Ile Val Glu Asp Glu Val Arg Ile Tyr Ser Gln Lys His Tyr Leu Ala
                245                 250                 255

Ile Gln Lys Arg Asn Ile Glu Ala Met Lys Lys Phe Glu Ala Ala Gly
            260                 265                 270

Thr Thr Val Thr Arg Leu Ser Gln Glu Asp Leu Gln Glu Phe Arg Arg
        275                 280                 285

Ala Ala Ile Pro Ile Trp Tyr Ser Trp Ala Asn Lys Asp Glu Asp Ala
    290                 295                 300

Arg Glu Ile Phe Asp Met Gln Leu Glu Tyr Met Met Asn Asp Thr Val
305                 310                 315                 320

Gly Tyr Ile Thr Glu Asp Asp Ile Lys Gly Met Asn Gly Gly Ser His
                325                 330                 335
```

His His His His His
340

<210> SEQ ID NO 58
<211> LENGTH: 341
<212> TYPE: PRT
<213> ORGANISM: Artificial Sequence
<220> FEATURE:
<223> OTHER INFORMATION: msLacBP6_187C_D220N (187C, 220N double substitution mutant with signal peptide replaced with M and a GGSHHHHHH at C-terminus)

<400> SEQUENCE: 58

Met Ala Thr Thr Trp Lys Ile Gln Ser Val Trp Asp Ala Gly Thr Val
1 5 10 15

Gly Tyr Asp Leu Phe Lys Glu Trp Cys Asp Gly Met Glu Glu Lys Thr
20 25 30

Gly Gly Glu Leu Lys Phe Thr Cys Phe Pro Ala Lys Ala Val Ala Ala
35 40 45

Asp Asn Asn Gly Leu Phe Asp Ala Val Arg Asn Gly Val Leu Gln Gly
50 55 60

Met Asn Pro Phe Thr Leu Tyr Trp Ser Gly Lys Ile Pro Ala Ser Val
65 70 75 80

Phe Leu Ser Ser Tyr Pro Ala Gly Pro Asp Gln Pro His Gln Trp Asp
85 90 95

Thr Met Phe Tyr Ser Leu Gly Met Leu Glu Lys Thr Arg Glu Ile Tyr
100 105 110

Lys Lys Phe Gly Leu Phe Tyr Val Gly Pro Ile Gln His Asp Ala Asn
115 120 125

Ile Ile His Ser Lys Gln Pro Ile Asn Ser Leu Asp Asp Leu Lys Gly
130 135 140

Leu Lys Met Arg Leu Pro Gly Gly Met Val Ala Glu Val Phe Ala Lys
145 150 155 160

Phe Gly Val Ala Ala Val Ser Leu Pro Gly Ser Asp Ile Phe Pro Ala
165 170 175

Leu Glu Lys Gly Thr Ile Asp Ala Ala Asp Cys Val Gly Pro Ala Val
180 185 190

Asn Trp Glu Leu Gly Phe Ser Gln Val Thr Lys Tyr Ile Leu Met Gly
195 200 205

Pro Pro Gly Ile Met Ser Val Tyr Gln Pro Val Asn Leu Met Asp Leu
210 215 220

Thr Val Asn Leu Arg Ala Trp Asn Ala Leu Asp Pro Lys Leu Gln Gln
225 230 235 240

Ile Val Glu Asp Glu Val Arg Ile Tyr Ser Gln Lys His Tyr Leu Ala
245 250 255

Ile Gln Lys Arg Asn Ile Glu Ala Met Lys Lys Phe Glu Ala Ala Gly
260 265 270

Thr Thr Val Thr Arg Leu Ser Gln Glu Asp Leu Gln Glu Phe Arg Arg
275 280 285

Ala Ala Ile Pro Ile Trp Tyr Ser Trp Ala Asn Lys Asp Glu Asp Ala
290 295 300

Arg Glu Ile Phe Asp Met Gln Leu Glu Tyr Met Met Asn Asp Thr Val
305 310 315 320

Gly Tyr Ile Thr Glu Asp Asp Ile Lys Gly Met Asn Gly Gly Ser His
325 330 335

His His His His His

340

<210> SEQ ID NO 59
<211> LENGTH: 341
<212> TYPE: PRT
<213> ORGANISM: Artificial Sequence
<220> FEATURE:
<223> OTHER INFORMATION: msLacBP6_187C_D220Q (187C, 220Q double substitution mutant with signal peptide replaced with M and a GGSHHHHHH at C-terminus)

<400> SEQUENCE: 59

```
Met Ala Thr Thr Trp Lys Ile Gln Ser Val Trp Asp Ala Gly Thr Val
1               5                   10                  15

Gly Tyr Asp Leu Phe Lys Glu Trp Cys Asp Gly Met Glu Glu Lys Thr
            20                  25                  30

Gly Gly Glu Leu Lys Phe Thr Cys Phe Pro Ala Lys Ala Val Ala Ala
        35                  40                  45

Asp Asn Asn Gly Leu Phe Asp Ala Val Arg Asn Gly Val Leu Gln Gly
    50                  55                  60

Met Asn Pro Phe Thr Leu Tyr Trp Ser Gly Lys Ile Pro Ala Ser Val
65                  70                  75                  80

Phe Leu Ser Ser Tyr Pro Ala Gly Pro Asp Gln Pro His Gln Trp Asp
                85                  90                  95

Thr Met Phe Tyr Ser Leu Gly Met Leu Glu Lys Thr Arg Glu Ile Tyr
            100                 105                 110

Lys Lys Phe Gly Leu Phe Tyr Val Gly Pro Ile Gln His Asp Ala Asn
        115                 120                 125

Ile Ile His Ser Lys Gln Pro Ile Asn Ser Leu Asp Asp Leu Lys Gly
    130                 135                 140

Leu Lys Met Arg Leu Pro Gly Gly Met Val Ala Glu Val Phe Ala Lys
145                 150                 155                 160

Phe Gly Val Ala Ala Val Ser Leu Pro Gly Ser Asp Ile Phe Pro Ala
                165                 170                 175

Leu Glu Lys Gly Thr Ile Asp Ala Ala Asp Cys Val Gly Pro Ala Val
            180                 185                 190

Asn Trp Glu Leu Gly Phe Ser Gln Val Thr Lys Tyr Ile Leu Met Gly
        195                 200                 205

Pro Pro Gly Ile Met Ser Val Tyr Gln Pro Val Gln Leu Met Asp Leu
    210                 215                 220

Thr Val Asn Leu Arg Ala Trp Asn Ala Leu Asp Pro Lys Leu Gln Gln
225                 230                 235                 240

Ile Val Glu Asp Glu Val Arg Ile Tyr Ser Gln Lys His Tyr Leu Ala
                245                 250                 255

Ile Gln Lys Arg Asn Ile Glu Ala Met Lys Lys Phe Glu Ala Ala Gly
            260                 265                 270

Thr Thr Val Thr Arg Leu Ser Gln Glu Asp Leu Gln Glu Phe Arg Arg
        275                 280                 285

Ala Ala Ile Pro Ile Trp Tyr Ser Trp Ala Asn Lys Asp Glu Asp Ala
    290                 295                 300

Arg Glu Ile Phe Asp Met Gln Leu Glu Tyr Met Met Asn Asp Thr Val
305                 310                 315                 320

Gly Tyr Ile Thr Glu Asp Asp Ile Lys Gly Met Asn Gly Gly Ser His
                325                 330                 335

His His His His His
            340
```

<210> SEQ ID NO 60
<211> LENGTH: 341
<212> TYPE: PRT
<213> ORGANISM: Artificial Sequence
<220> FEATURE:
<223> OTHER INFORMATION: msLacBP6_187C_D220S (187C, 220S double substitution mutant with signal peptide replaced with M and a GGSHHHHHH at C-terminus)

<400> SEQUENCE: 60

```
Met Ala Thr Thr Trp Lys Ile Gln Ser Val Trp Asp Ala Gly Thr Val
1               5                   10                  15

Gly Tyr Asp Leu Phe Lys Glu Trp Cys Asp Gly Met Glu Glu Lys Thr
            20                  25                  30

Gly Gly Glu Leu Lys Phe Thr Cys Phe Pro Ala Lys Ala Val Ala Ala
        35                  40                  45

Asp Asn Asn Gly Leu Phe Asp Ala Val Arg Asn Gly Val Leu Gln Gly
    50                  55                  60

Met Asn Pro Phe Thr Leu Tyr Trp Ser Gly Lys Ile Pro Ala Ser Val
65                  70                  75                  80

Phe Leu Ser Ser Tyr Pro Ala Gly Pro Asp Gln Pro His Gln Trp Asp
                85                  90                  95

Thr Met Phe Tyr Ser Leu Gly Met Leu Glu Lys Thr Arg Glu Ile Tyr
            100                 105                 110

Lys Lys Phe Gly Leu Phe Tyr Val Gly Pro Ile Gln His Asp Ala Asn
        115                 120                 125

Ile Ile His Ser Lys Gln Pro Ile Asn Ser Leu Asp Asp Leu Lys Gly
    130                 135                 140

Leu Lys Met Arg Leu Pro Gly Gly Met Val Ala Glu Val Phe Ala Lys
145                 150                 155                 160

Phe Gly Val Ala Ala Val Ser Leu Pro Gly Ser Asp Ile Phe Pro Ala
                165                 170                 175

Leu Glu Lys Gly Thr Ile Asp Ala Ala Asp Cys Val Gly Pro Ala Val
            180                 185                 190

Asn Trp Glu Leu Gly Phe Ser Gln Val Thr Lys Tyr Ile Leu Met Gly
        195                 200                 205

Pro Pro Gly Ile Met Ser Val Tyr Gln Pro Val Ser Leu Met Asp Leu
    210                 215                 220

Thr Val Asn Leu Arg Ala Trp Asn Ala Leu Asp Pro Lys Leu Gln Gln
225                 230                 235                 240

Ile Val Glu Asp Glu Val Arg Ile Tyr Ser Gln Lys His Tyr Leu Ala
                245                 250                 255

Ile Gln Lys Arg Asn Ile Glu Ala Met Lys Lys Phe Glu Ala Ala Gly
            260                 265                 270

Thr Thr Val Thr Arg Leu Ser Gln Glu Asp Leu Gln Glu Phe Arg Arg
        275                 280                 285

Ala Ala Ile Pro Ile Trp Tyr Ser Trp Ala Asn Lys Asp Glu Asp Ala
    290                 295                 300

Arg Glu Ile Phe Asp Met Gln Leu Glu Tyr Met Met Asn Asp Thr Val
305                 310                 315                 320

Gly Tyr Ile Thr Glu Asp Asp Ile Lys Gly Met Asn Gly Gly Ser His
                325                 330                 335

His His His His His
            340
```

<210> SEQ ID NO 61
<211> LENGTH: 362
<212> TYPE: PRT
<213> ORGANISM: Artificial Sequence
<220> FEATURE:
<223> OTHER INFORMATION: msLacBP6_187C_bZifC (187C substitution mutant, with bZif fusion, signal peptide replaced with M and a GGSHHHHHH at C-terminus)

<400> SEQUENCE: 61

```
Met Ala Thr Thr Trp Lys Ile Gln Ser Val Trp Asp Ala Gly Thr Val
1               5                   10                  15

Gly Tyr Asp Leu Phe Lys Glu Trp Cys Asp Gly Met Glu Glu Lys Thr
            20                  25                  30

Gly Gly Glu Leu Lys Phe Thr Cys Phe Pro Ala Lys Ala Val Ala Ala
        35                  40                  45

Asp Asn Asn Gly Leu Phe Asp Ala Val Arg Asn Gly Val Leu Gln Gly
    50                  55                  60

Met Asn Pro Phe Thr Leu Tyr Trp Ser Gly Lys Ile Pro Ala Ser Val
65                  70                  75                  80

Phe Leu Ser Ser Tyr Pro Ala Gly Pro Asp Gln Pro His Gln Trp Asp
                85                  90                  95

Thr Met Phe Tyr Ser Leu Gly Met Leu Glu Lys Thr Arg Glu Ile Tyr
            100                 105                 110

Lys Lys Phe Gly Leu Phe Tyr Val Gly Pro Ile Gln His Asp Ala Asn
        115                 120                 125

Ile Ile His Ser Lys Gln Pro Ile Asn Ser Leu Asp Asp Leu Lys Gly
    130                 135                 140

Leu Lys Met Arg Leu Pro Gly Gly Met Val Ala Glu Val Phe Ala Lys
145                 150                 155                 160

Phe Gly Val Ala Ala Val Ser Leu Pro Gly Ser Asp Ile Phe Pro Ala
                165                 170                 175

Leu Glu Lys Gly Thr Ile Asp Ala Ala Asp Cys Val Gly Pro Ala Val
            180                 185                 190

Asn Trp Glu Leu Gly Phe Ser Gln Val Thr Lys Tyr Ile Leu Met Gly
        195                 200                 205

Pro Pro Gly Ile Met Ser Val Tyr Gln Pro Val Asp Leu Met Asp Leu
    210                 215                 220

Thr Val Asn Leu Arg Ala Trp Asn Ala Leu Asp Pro Lys Leu Gln Gln
225                 230                 235                 240

Ile Val Glu Asp Glu Val Arg Ile Tyr Ser Gln Lys His Tyr Leu Ala
                245                 250                 255

Ile Gln Lys Arg Asn Ile Glu Ala Met Lys Lys Phe Glu Ala Ala Gly
            260                 265                 270

Thr Thr Val Thr Arg Leu Ser Gln Glu Asp Leu Gln Glu Phe Arg Arg
        275                 280                 285

Ala Ala Ile Pro Ile Trp Tyr Ser Trp Ala Asn Lys Asp Glu Asp Ala
    290                 295                 300

Arg Glu Ile Phe Asp Met Gln Leu Glu Tyr Met Met Asn Asp Thr Val
305                 310                 315                 320

Gly Tyr Ile Thr Glu Asp Asp Ile Lys Gly Met Asn Gly Gly Ser Thr
                325                 330                 335

Gly Glu Lys Pro Tyr Lys Cys Pro Glu Cys Gly Lys Ser Phe Ser Arg
            340                 345                 350

Ser Gly Gly Ser His His His His His His
```

355 360

<210> SEQ ID NO 62
<211> LENGTH: 362
<212> TYPE: PRT
<213> ORGANISM: Artificial Sequence
<220> FEATURE:
<223> OTHER INFORMATION: msLacBP6_188C_bZifC (188C substitution mutant, with bZif fusion, signal peptide replaced with M and a GGSHHHHHH at C-terminus)

<400> SEQUENCE: 62

Met Ala Thr Thr Trp Lys Ile Gln Ser Val Trp Asp Ala Gly Thr Val
1 5 10 15

Gly Tyr Asp Leu Phe Lys Glu Trp Cys Asp Gly Met Glu Glu Lys Thr
20 25 30

Gly Gly Glu Leu Lys Phe Thr Cys Phe Pro Ala Lys Ala Val Ala Ala
35 40 45

Asp Asn Asn Gly Leu Phe Asp Ala Val Arg Asn Gly Val Leu Gln Gly
50 55 60

Met Asn Pro Phe Thr Leu Tyr Trp Ser Gly Lys Ile Pro Ala Ser Val
65 70 75 80

Phe Leu Ser Ser Tyr Pro Ala Gly Pro Asp Gln Pro His Gln Trp Asp
85 90 95

Thr Met Phe Tyr Ser Leu Gly Met Leu Glu Lys Thr Arg Glu Ile Tyr
100 105 110

Lys Lys Phe Gly Leu Phe Tyr Val Gly Pro Ile Gln His Asp Ala Asn
115 120 125

Ile Ile His Ser Lys Gln Pro Ile Asn Ser Leu Asp Asp Leu Lys Gly
130 135 140

Leu Lys Met Arg Leu Pro Gly Gly Met Val Ala Glu Val Phe Ala Lys
145 150 155 160

Phe Gly Val Ala Ala Val Ser Leu Pro Gly Ser Asp Ile Phe Pro Ala
165 170 175

Leu Glu Lys Gly Thr Ile Asp Ala Ala Asp Tyr Cys Gly Pro Ala Val
180 185 190

Asn Trp Glu Leu Gly Phe Ser Gln Val Thr Lys Tyr Ile Leu Met Gly
195 200 205

Pro Pro Gly Ile Met Ser Val Tyr Gln Pro Val Asp Leu Met Asp Leu
210 215 220

Thr Val Asn Leu Arg Ala Trp Asn Ala Leu Asp Pro Lys Leu Gln Gln
225 230 235 240

Ile Val Glu Asp Glu Val Arg Ile Tyr Ser Gln Lys His Tyr Leu Ala
245 250 255

Ile Gln Lys Arg Asn Ile Glu Ala Met Lys Lys Phe Glu Ala Ala Gly
260 265 270

Thr Thr Val Thr Arg Leu Ser Gln Glu Asp Leu Gln Glu Phe Arg Arg
275 280 285

Ala Ala Ile Pro Ile Trp Tyr Ser Trp Ala Asn Lys Asp Glu Asp Ala
290 295 300

Arg Glu Ile Phe Asp Met Gln Leu Glu Tyr Met Met Asn Asp Thr Val
305 310 315 320

Gly Tyr Ile Thr Glu Asp Asp Ile Lys Gly Met Asn Gly Gly Ser Thr
325 330 335

Gly Glu Lys Pro Tyr Lys Cys Pro Glu Cys Gly Lys Ser Phe Ser Arg
340 345 350

Ser Gly Gly Ser His His His His His His
355 360

<210> SEQ ID NO 63
<211> LENGTH: 1451
<212> TYPE: DNA
<213> ORGANISM: Artificial Sequence
<220> FEATURE:
<223> OTHER INFORMATION: Exemplary ttLacBP1 expression sequence.

<400> SEQUENCE: 63
gccagtaagc ttcggtcacg cttgggactg ccataggctg gcccggtgat gccggccacg 60
atgcgtccgg cgtagaggat cgagatctcg atcccgcgaa attaatacga ctcactatag 120
ggagaccaca acggtttccc tctagaaata attttgttta actttaagaa ggagatatac 180
catgtttagt cctttagcag tagcacaagc tcgtcgctat cgttggcgta ttcagacagc 240
atgggacgca gggaccgtgg ggtactctct ttttcaaaag tttaccgagc gcgtaaaaga 300
actcacagac gggcagttag aggtacaacc gttcccggct ggtgcggtag tagggacctt 360
tgacatgttc gacgccgtca agacaggtgt attagacggg atgaatcctt tcacactcta 420
ttgggccggt cgtatgccag tcaccgcatt tttgagcagt tacgcgctgg gtctcgatcg 480
gccagaccaa tgggaaacgt ggttctacag tctcggcggt ttagatatcg cacgccgtgc 540
gttcgcggag cagggtctct tttacgtagg gccagtacaa cacgatctca atattattca 600
ttcaaagaag ccaatccgcc gtttcgaaga cttcaagggt gtaaagttac gggtaccggg 660
tggcatgatt gctgaagtct tcgcagctgc aggtgcctca acagtgctcc tccctggcgg 720
ggaagtatat ccggccttag agcgtggtgt catcgacgca gccgatttcg taggtccagc 780
cgttaattac aacttaggtt tccaccaggt agccaaatac atcatcatgg gtccaccaga 840
aacaccggca attcatcaac cagtagacct catggacttt acgatcaatc tgaatcgttg 900
gcgtagtttg ccaaaaccat tacaagaacg cttcattgca gctgtccatg agtattcctg 960
gatccattac gctggcattc aaaaggcgaa tctggaagcc tggccaaaat accggcaagc 1020
aggtgtcgaa gtcatccggt tatccaatga agacgtgcgt aaattccgtc gtctcgccat 1080
tcctatctgg tttaagtggg caaaaatgga caaatatagc cgtgaggcat tcgccagtca 1140
attggaatac atgaagggca ttgggtacgt aaccgacgag gaattaaagg gtttgtcctt 1200
aggtggttca catcatcatc atcatcatta atgaaagggc gatatccagc acactggcgg 1260
ccgttactag tggatccggc tgctaacaaa gcccgaaagg aagctgagtt ggctgctgcc 1320
accgctgagc aataactagc ataacccctt ggggcctcta aacgggtctt gaggggtttt 1380
ttgctgaaag gaggaactat atccggagcg actcccacgg cacgttggca agctcggaat 1440
tcggcgtaat c 1451

<210> SEQ ID NO 64
<211> LENGTH: 1451
<212> TYPE: DNA
<213> ORGANISM: Artificial Sequence
<220> FEATURE:
<223> OTHER INFORMATION: Exemplary tsLacBP2 expression sequence.

<400> SEQUENCE: 64
gccagtaagc ttcggtcacg cttgggactg ccataggctg gcccggtgat gccggccacg 60
atgcgtccgg cgtagaggat cgagatctcg atcccgcgaa attaatacga ctcactatag 120
ggagaccaca acggtttccc tctagaaata attttgttta actttaagaa ggagatatac 180

```
catgtttagt ccattagcag tagcacaagc accacgtttt cgttggcgta tccaatctgc    240

ctgggacgca gggacagtgg gctattccct ttttcaaaaa tttgccgaac gggtcaagga    300

actcacggac ggtcaaattg aaatccagac attcccagca ggcgcggtcg ttggtacttt    360

cgatatgttt gacgcagtaa aaaccggggt cctcgatggg atgcacccgt ttaccctcta    420

ctgggccggc cggatgccag tcactgcttt tttgtcatca tatccacttg gcctcgaccg    480

gcctgatcaa tgggagacgt ggtattacgg cctcggtggt ctggaattag cacgtaaagc    540

atatgaagaa caaggcctct tttttgtcgg cccggttcaa cacgattaca acttaattca    600

ttccaaaaag ccaatcaaat cattcgagga ttttaagggt gtcaaactcc gcgtcccagg    660

cggcatgatt gccgagattt tcgccgcagc aggggccgca acagtactcc tcccaggcgg    720

ggaagtctat ccggcccttg agcgtggtgt catcgacgcg gccgacttcg taggtccagc    780

cgtaaactac aatttaggtt ttcatcaagt caccaaatac atcatcatgg gcccgcctga    840

aacaccggcc attcaccagc cagtcgactt agccgacatt accattaata tcaatcgctg    900

gcgggcgctt ccacgtaacc tgcaagaacg ctttgaggct gccgtgcacg agtggtcctg    960

gattcactat gccggtattc aaaaggcgaa ccttgagacc tggccgaagt acaaagccgc   1020

cggcgtgcaa gtgattcgct tatccaccgt agacgtccgt aaatttcgcc gtgtcgcgat   1080

cccaatttgg ttcaagtggg cgaaacagga caaatataca cgcgaggcat tcgcaagtca   1140

attggagtat atgaaagcat taggttatgt aacagacgca gacatccggg ggctgagctt   1200

aggtggttct catcatcatc atcatcatta atgaaagggc gatatccagc acactggcgg   1260

ccgttactag tggatccggc tgctaacaaa gcccgaaagg aagctgagtt ggctgctgcc   1320

accgctgagc aataactagc ataacccctt ggggcctcta aacgggtctt gaggggtttt   1380

ttgctgaaag gaggaactat atccggagcg actcccacgg cacgttggca agctcggaat   1440

tcggcgtaat c                                                        1451
```

<210> SEQ ID NO 65
<211> LENGTH: 1511
<212> TYPE: DNA
<213> ORGANISM: Artificial Sequence
<220> FEATURE:
<223> OTHER INFORMATION: Exemplary toLacBP3 expression sequence.

<400> SEQUENCE: 65

```
gccagtaagc ttcggtcacg cttgggactg ccataggctg gcccggtgat gccggccacg     60

atgcgtccgg cgtagaggat cgagatctcg atcccgcgaa attaatacga ctcactatag    120

ggagaccaca acggtttccc tctagaaata attttgttta actttaagaa ggagatatac    180

catgaaatca acacggcgtc aatttttaaa aaaagcagca atcggtgtgg ccgcctcctc    240

agcattttca cctctcgcaa tcgcgcaggc tccacggttc cgttggcgta tccaatcggc    300

atgggacgca ggcacagtag gttacacgtt atttcaacgc ttcgccgaac gcgtcaaaga    360

gcttacagac ggccagattg aaattcagcc ttttccggca ggcgcagtcg taggcacctt    420

cgatatgttc gacgcggtga aaacaggggt cctcgatggg atgcacccat ttaccctgta    480

ctgggctggc cgtatgcctg tcaccgcatt cttatcatcc tacccgcttg gcttagatcg    540

cccagatcaa tgggaaacct ggtactacgg cttagggggc ttggagttag cccgtaaagc    600

atatgaggag cagggtttgg catatattgg cccagtacaa cacgattata acctcatcca    660

ttcaaagaaa cctattaagt cgttcgaaga gttcaaaggc gtcaagttac gcgtgccagg    720
```

-continued tgggatgatc gctgaaatct tcgcagcagc aggtgcggct actgtcttat taccaggggg 780
ggaagtctac ccggctctcg agcgtggcgt cattgatgca gctgatttcg taggcccagc 840
tgtcaattac aatttaggct ttcatcaagt aacaaagtat atcattatgg gcccgccaga 900
aacaccggcc attcaccaac cagtagacct cgcggatatc accttgaact taaatcgttg 960
gcgggcagta cctaagaatt tgcaagagcg cttcgaagcc gctgtacacg aatggtcatg 1020
ggtccattac gcaggcatcc aaaaagccaa cctcgaagcc tggccaaaat atcgggctgc 1080
aggtgtgcag atcatccgct taagtacagt tgacgtccgc aagtttcgtc gtgtggcaat 1140
tccgatttgg ttcaaatggg caaagcaaga caagtatgca aaagaagcct ttcaatcaca 1200
gctggaatac atgaaggcgt tagggtatgt taccgacgtc gacctgcggg gtttgtcctt 1260
aggtggttca catcatcatc atcatcatta atgaaagggc gatatccagc acactggcgg 1320
ccgttactag tggatccggc tgctaacaaa gcccgaaagg aagctgagtt ggctgctgcc 1380
accgctgagc aataactagc ataacccctt ggggcctcta aacgggtctt gaggggtttt 1440
ttgctgaaag gaggaactat atccggagcg actcccacgg cacgttggca agctcggaat 1500
tcggcgtaat c 1511

<210> SEQ ID NO 66
<211> LENGTH: 1442
<212> TYPE: DNA
<213> ORGANISM: Artificial Sequence
<220> FEATURE:
<223> OTHER INFORMATION: Exemplary tsLacBP4 expression sequence.

<400> SEQUENCE: 66
gccagtaagc ttcggtcacg cttgggactg ccataggctg gcccggtgat gccggccacg 60
atgcgtccgg cgtagaggat cgagatctcg atcccgcgaa attaatacga ctcactatag 120
ggagaccaca acggtttccc tctagaaata attttgttta actttaagaa ggagatatac 180
catgacagca cgtggtgttc gttggcgtat gcaatcagca tggcaaccag gcacaatcgg 240
ttatcgtaca ttcgaaactt gggcacgttc cattcaagag ctcaccagtg gtgaattgtc 300
gatcgaacct tttccggccg gggcagtagc cggtaccttc gaaatggcag acgcggtccg 360
gtctggggtc ctcgacggca tgaattggtt cactgtctat tggccgggga aaatgccagc 420
aggtgtcttt atgtcggcgt accctatggc gctctccctg ccacaccact gggatatgat 480
gttcgattct tttgggggcc gtcagatcgt cgacgagctc tacgaccgtc aggggcttgt 540
atttctcggc catgtacaac acgatctcaa tttaattcac tcaaaagttc ctttgcgttc 600
cttcgacgac tttcggggta agcgtattcg ttttccaggt ggtattatcg cagaaacatt 660
tgccaaggtc ggcgtacgta caacattatt accgggggt gacgtatatc cggccttaga 720
gcgtggtacc attgacgcag cagactttgt aggcccagcg gtaaactacg atttaggttt 780
tcatcaggtg gccgattata tcatcatggg ccctccaagt accccagcgt tacaccaacc 840
agttgatctc atggacatct ctgtaaacaa gcgtagctgg tcgcgtatct cggagcacac 900
ccagaaatta atgtataaat tcgtcaaagc atattccgca gagcactttg cagccatcca 960
aaaagccaac catgaggcat ggccgaaata caaggaggcc ggtgtcgaag tcatccactt 1020
aagtgaagag gatgcagcac gtttccggga ggcagcaatc ccgctctggt tcgaatgggc 1080
aaacaaagac cgtgatgcgg cccggctctt taaggttcat ttagaagtca tgcaagaccc 1140
atcggtagcg gtcatcaccc cagatgacat taaagattac aaattgaact ttggcggttc 1200
tcatcatcat catcatcatt aatgaaaggg cgatatccag cacactggcg gccgttacta 1260
gtggatccgg ctgctaacaa agcccgaaag gaagctgagt tggctgctgc caccgctgag 1320
caataactag cataacccct tggggcctct aaacgggtct tgaggggttt tttgctgaaa 1380
ggaggaacta tatccggagc gactcccacg gcacgttggc aagctcggaa ttcggcgtaa 1440
tc 1442

<210> SEQ ID NO 67
<211> LENGTH: 1442
<212> TYPE: DNA
<213> ORGANISM: Artificial Sequence
<220> FEATURE:
<223> OTHER INFORMATION: Exemplary rdLacBP5 expression sequence.

<400> SEQUENCE: 67
gccagtaagc ttcggtcacg cttgggactg ccataggctg gcccggtgat gccggccacg 60
atgcgtccgg cgtagaggat cgagatctcg atcccgcgaa attaatacga ctcactatag 120
ggagaccaca acggtttccc tctagaaata attttgttta actttaagaa ggagatatac 180
catggcagct ggtgaaggta caacttggaa aattcagaca agtcataccg gtggtattgg 240
cctcgcgact tttaaagact gggcgtcctc tatcgaggag aagacgggtg gtgagttagc 300
ctttacagct tttggtgcca atgatgtggt aggtgacttt caactttacg acgcagtcaa 360
aaacggtgtt ttagatgcgg tcaacccatt cacaatttat gcacaaggta tcatcccggc 420
tgcaacattt ctgacttcat acccactcgg tctccgcaat ccgcacgaat gggacgtctt 480
cttttacagc cttggcggcc tcgaaattgc ccgtgaactc tacgccgcac aaggtatgaa 540
attcgtcggg cctgtccatc atggtccaaa tatcattcat tcgaaggtgc ctattcgttc 600
catcgatgac ttcgcgggtc tcaaaatgcg tatgccaggc ggcatggtcg cagaagtctt 660
cagtgaaatc ggtgccgaga caaccgtctt acctggtagc gagattttcc cggcgcttga 720
aaaaggtaca atcgacgccg ctgacttcgt tggcccagca gtaaattatg cgttaggctt 780
cagccaggtc accaactata tttccatggg tccagccggt ttcatgtcct tgtaccaacc 840
agtagattta atggatatta cggtaggcca aaccgcatgg gacgcactct caccgcagat 900
gcaacagttt gtagagatgg aaacccacgt atacagcgac atgcatcacg ccgccattca 960
aaaagcagac caagaggcat gggctaaatt cgaggccgac ggtactgagg ttacccgttt 1020
gtcccaagat gatgtagaat taatgaccga agtcgccgtt ccaatctggt tcgactatgc 1080
aaaccgtgat aaggacgcag cacgggtctt caaaatccaa ttagactaca tgatgtcagg 1140
cagtctcggg tatgtgacac cagaacaaat tgaaggcttg accttgaatt taggtggttc 1200
acatcatcat catcatcatt aatgaaaggg cgatatccag cacactggcg gccgttacta 1260
gtggatccgg ctgctaacaa agcccgaaag gaagctgagt tggctgctgc caccgctgag 1320
caataactag cataacccct tggggcctct aaacgggtct tgaggggttt tttgctgaaa 1380
ggaggaacta tatccggagc gactcccacg gcacgttggc aagctcggaa ttcggcgtaa 1440
tc 1442

<210> SEQ ID NO 68
<211> LENGTH: 1400
<212> TYPE: DNA
<213> ORGANISM: Artificial Sequence
<220> FEATURE:
<223> OTHER INFORMATION: Exemplary msLacBP6 expression sequence.

<400> SEQUENCE: 68

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tggcaacaac    180

ttggaaaatt caaagtgtat gggatgcagg gacggtgggc tatgacctct tcaaggagtg    240

gtgcgacggt atggaagaaa agacgggcgg tgaactcaaa ttcacgtgct tcccagccaa    300

agccgtcgcc gcagataata atggtctttt tgatgcagta cggaatggcg tcttgcaagg    360

tatgaatcct ttcaccctct actggtcagg taagattccg gcctccgtat ttctctcgtc    420

gtacccagcc ggtccagatc aaccacatca atgggataca atgttctaca gccttggtat    480

gttagaaaaa acacgtgaaa tttacaaaaa gttcggcctc ttctacgtcg gcccaattca    540

gcacgacgca aacattatcc acagtaaaca gccgattaat tccctggacg accttaaggg    600

tctcaaaatg cgcttacctg gcgggatggt agcggaagtc tttgcaaagt ttggcgtcgc    660

agcggtcagt ctcccaggca gcgacatctt tccagcctta gaaaaaggca caatcgacgc    720

tgctgattac gtgggtccgg ctgtaaactg ggagctcggc ttcagccaag taacaaagta    780

catcttaatg ggtccaccag gcatcatgtc agtctaccaa ccggtcgacc ttatggacct    840

cactgtcaat ctgcgggcct ggaacgcatt agatccaaag ttacagcaaa tcgttgaaga    900

tgaagtacgc atctactctc agaagcatta cctcgcaatt cagaaacgga atattgaagc    960

tatgaagaag ttcgaggccg ctggtacaac cgtaacccgt ctgtcacaag aggacctcca   1020

ggagtttcgt cgtgcagcta tcccaatttg gtattcatgg gcaaacaaag atgaagacgc   1080

acgggagatt ttcgacatgc aattagagta catgatgaac gacactgtag gttacatcac   1140

tgaagatgac attaagggca tgaatggcgg ttcacatcat catcatcatc attaatgaaa   1200

gggcgatatc cagcacactg gcggccgtta ctagtggatc cggctgctaa caaagcccga   1260

aaggaagctg agttggctgc tgccaccgct gagcaataac tagcataacc ccttggggcc   1320

tctaaacggg tcttgagggg ttttttgctg aaaggaggaa ctatatccgg agcgactccc   1380

acggcacgtt ggcaagctcg                                               1400
```

<210> SEQ ID NO 69
<211> LENGTH: 1406
<212> TYPE: DNA
<213> ORGANISM: Artificial Sequence
<220> FEATURE:
<223> OTHER INFORMATION: Exemplary tsLacBP7 expression sequence.

<400> SEQUENCE: 69

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgcaagcacc    180

acgttttcgt tggcgtattc aaagtgcatg ggatgcagga acagtgggtt acaccctctt    240

tcagcgcttt gcagaacgcg tcaaagagct gaccgatgga cagatcgaga tccagacctt    300

tccagcgggt gcagtcgtgg gtaccttcga catgttcgac gcagtcaaaa ccggagtgct    360

ggatggcatg catcccttta ccctctattg ggcaggtcga atgccggtta ccgcctttct    420

cagcagctac ccgttaggcc tggatcgacc agatcagtgg gaaacgtggt actacgcact    480

tggcggtctg gatctggcga gacgtgcatt cgaggaacag ggtctgttct acgttggtcc    540

agtgcagcat gactacaacc tgatccacag caaaaagccg atcaagtcct tcgaggactt    600

caaaggcgtg aagctgagag tgcctggtgg catgatagca gacgtcttct cagcagctgg    660
```

agcagcaaca gtcctcttgc ctggtggtga ggtctatccg gctctggaac gtggtgtgat 720
cgatgcagca gacttcgtgg gtcctgcagt gaactacaac cttggcttcc atcaggtgac 780
caagtacatc atcatgggtc ctccagaaac ccctgcgatc catcagccag tggatctggc 840
agacatcacc ctgaacctca gccgttggcg tgcagtgccc aaaaacctgc aggaacgatt 900
cgaagcagcg gttcacgaat ggagctggat ccactatgcc ggtatccaga aagccaacct 960
ggagacctgg ccgaagtaca aagcggcagg tgtgcagatc atcaggctga ctaccgtgga 1020
tgtgcgcaag tttcgtcgtg ttgcgattcc gatctggttc aaatgggcga aacaggacaa 1080
gtatgcccgt gaagcctttg caagccagct ggagtacatg aaagcactgg gctatgtgac 1140
agatgcagat gttcgtggtt taagcttagg cggcagccat catcatcatc atcattaata 1200
atgaaagggc gatatccagc acactggcgg ccgttactag tggatccggc tgctaacaaa 1260
gcccgaaagg aagctgagtt ggctgctgcc accgctgagc aataactagc ataacccctt 1320
ggggcctcta aacgggtctt gaggggtttt ttgctgaaag gaggaactat atccggagcg 1380
actcccacgg cacgttggca agctcg 1406

<210> SEQ ID NO 70
<211> LENGTH: 1406
<212> TYPE: DNA
<213> ORGANISM: Artificial Sequence
<220> FEATURE:
<223> OTHER INFORMATION: Exemplary maLacBP8 expression sequence.

<400> SEQUENCE: 70
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgcaagcagc 180
aactacttgg aaaattcaaa gtacctggga tgctggtacg gttggctaca ccctcttcga 240
agagtgggcg aagagcatcg aagccaaatc cggtggtgaa ctgaagttcc aggcgtttcc 300
ggcaaaagcc gttgctgctg acaacaacgc gctctttgac gctgttcgca acggtgtgct 360
tcagggcatg aacccgttca ccctgtactg ggcgggcaaa atccctgcct ctgtgttcct 420
gtcgagctac ccagcaggtc cggatcaacc ccatcagtgg gataccatgt tctactcgat 480
gggtatgctg gagaaaaccc gcgaaatcta caagaaattt ggcctgttct acgttggtcc 540
gatccagcat gatgcgaaca tcatccacag caaacagcca gtcaactctc tggacgacct 600
gaaagggatg aagatccgtg tacctggtgg catggttgcc gaagtcttcc agcagtttgg 660
cgtttccacc gtcagtctgc cgggtagcga catcttcccg gcattggaga aaggcacgat 720
tgacgctgca gacttcgtag gtccagcagt caactacgaa ctgggcttta gccaggttac 780
ggactacatc atcttcggac cacctggcgt catgagcatc tatcaaccgg tggacctgat 840
ggatctgacc gtcagtctgc gtgcttggaa ctcgatctca ccagagctgc agcagctggt 900
tgaggatgaa gtgcgcatct actcgcagaa acactatctg gcgattcagg ctcgcaacat 960
cgaagcgatg gagaaattca aagccgatgg tgacacggta acccgtctga gccaggaaga 1020
cctggaaacc tggcgtaagg ctgcaatccc gatctggttc aactgggcga acaagaacga 1080
tgatgctcgt gcgatcctgg atatccagct gaaatacatg atgaacgaca ctgtgggcta 1140
cattactgaa gaagatatta aaggatttgg cggcagccat catcatcatc atcattaatg 1200
ataaaagggc gatatccagc acactggcgg ccgttactag tggatccggc tgctaacaaa 1260
gcccgaaagg aagctgagtt ggctgctgcc accgctgagc aataactagc ataacccctt 1320
ggggcctcta aacgggtctt gaggggtttt ttgctgaaag gaggaactat atccggagcg 1380
actcccacgg cacgttggca agctcg 1406

<210> SEQ ID NO 71
<211> LENGTH: 1439
<212> TYPE: DNA
<213> ORGANISM: Artificial Sequence
<220> FEATURE:
<223> OTHER INFORMATION: Exemplary adLacBP9 expression sequence.

<400> SEQUENCE: 71
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgcaagcacc 180
aattactctg agatttcaga gtacttggcc gcagaaagac atcttccacg agtttgccct 240
ggattacgcc aaaaaggtca acgagatgag cggtggacgt ctgaagatcg aggttctggc 300
agcaggcagt gtggtgaagg cgttcgatct cctggatgca gtgagcaagg gtacgctgga 360
tggaggtcat ggcgtagtcg cctactggta cggcaagaac accgcattag cgctgtgggg 420
ctctggacct gcattcggca tggacccaaa catggtgctt gcatggcacc attacggcgg 480
aggtcgtcag ctcctggaag agatctaccg aagcctcaac ctggatgtcg tcagcctcat 540
gtacggacca atgccgactc agccgttagg ctggttcaag cagaaaccca ttgcgaaacc 600
tgacgacatg aaagggctga agttccgtac ggtaggtctg agcatcgaca tcttcaacgg 660
actgggtgct gcagtgaacg cgttaccagg tgccgaaatc gttccggcta tggatcgagg 720
tctgctcgat gcggcagagt tcaacaacgc ttcttccgat cgtgtgctag ggtttccgga 780
tgtctcgaag atcgcgatgc tgcaatcgtt ccatcaggcg tcagagcagt tcgagatcct 840
gttcaacggc aagcgtttcc aggcgttacc ggctgatctg aagagcatca tctccattgc 900
tgcgcaagct gcaagcgccg acatgtcctg gaaggccatc gatcgctact ctagcgacta 960
cttcgagatg cgtgacaagc agggcgtgaa gttctacagc accagaccgg aaatcctgaa 1020
acggcaactg gagatctggg accaggtgat ggagaagcgt gcagccgaaa acccgacgtt 1080
caaaaaggtc ctggagagcc aacgcaggtt tgcacagcgt gctgcgagat ggcagaacga 1140
caccaacgtg gacttcaaga tggcctacaa ccacttcttt ggtggtaaga aaaaagctac 1200
tggcggcagc catcatcatc atcatcatta ataatgaaag ggcgatatcc agcacactgg 1260
cggccgttac tagtggatcc ggctgctaac aaagcccgaa aggaagctga gttggctgct 1320
gccaccgctg agcaataact agcataaccc cttggggcct ctaaacgggt cttgaggggt 1380
tttttgctga aaggaggaac tatatccgga gcgactccca cggcacgttg gcaagctcg 1439

<210> SEQ ID NO 72
<211> LENGTH: 1355
<212> TYPE: DNA
<213> ORGANISM: Artificial Sequence
<220> FEATURE:
<223> OTHER INFORMATION: Exemplary pgLacBP10 expression sequence.

<400> SEQUENCE: 72
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgcaagaagc 180

```
agttgaatgg agaatgcaag cattgtggga tgcaggtacg accccattcg aattcgaaaa    240

gaagttcgtg gaacgtgtag gcgagttgac ggaaggtcgc ttcaagatca cgctgtacag    300

cgcaggtcag atagtgccgg caaaccaggc cttcgatgct gtgcgttctg gtgccttcga    360

gatgatgaaa accttcgatg gctatgaggc aggcaaaatc ccggcattcg ccttcacctc    420

gaccattccg ttcggtttcc cgcagtctga ccagtacgag gcatggttct acgaactggg    480

tggtctggat cttgctcgcg aagcttacgc caaaggtggc ctgttctaca tcgcaccgac    540

cgtctatggc gaagaaccca tgcacagcac cgtgaagatc gaatccatcg cggatatggc    600

ggggaagaaa ggccgttttg tcggtttggc atctgcggtg atggcagatc tcggtgtagc    660

ggtgtcgccg ttagcgactg ccgaagtgta cactgcgctc gaaaaaggcc tgatcgactt    720

tgcggatcgt ggtgatctga cagccaacta cgaagcagga cttggcgaag tggcgaaatt    780

catcatcctt ccgggtgtgc atcaaccgac cactgcaacc agctatgtcg cgaatcaggc    840

agcgtaccag aagcttccgg atggcttcaa agcggcgtta gcggttgctg cacgtgagat    900

ctccggttca ctgcgtcagc acatcctggt tcaggacatg gaagtgctca ccaagtacaa    960

ggatcagggt gtggaagtgg tacgtctcga tgcagcggat attgctgcgg caagagcgaa   1020

agcggtcgaa tcctgggaaa aggcgaccaa aggggatgaa ctggcgacca gagtgctgaa   1080

gggacaggtg gattttatga cttctttagg tttactgggc ggcagccatc atcatcatca   1140

tcattaataa tgaaagggcg atatccagca cactggcggc cgttactagt ggatccggct   1200

gctaacaaag cccgaaagga agctgagttg gctgctgcca ccgctgagca ataactagca   1260

taaccccttg gggcctctaa acgggtcttg aggggttttt tgctgaaagg aggaactata   1320

tccggagcga ctcccacggc acgttggcaa gctcg                              1355
```

<210> SEQ ID NO 73
<211> LENGTH: 1415
<212> TYPE: DNA
<213> ORGANISM: Artificial Sequence
<220> FEATURE:
<223> OTHER INFORMATION: Exemplary psLacBP11 expression sequence.

<400> SEQUENCE: 73

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgcaacaagc    180

agcaggtgaa ccagcaaaaa cctatcactg gaagatggtg accgcttggc cgaagaacta    240

tccgggttta ggcaccagtg cggaacgact ggcagaacgt gtgaacgcga tgagtggtgg    300

acgtctgacc atcaaggtgt atgcagcagg agaactggtt ccagctctgg aagtgttcga    360

tgcagtctct cgtggtaccg cagaactggg tcatggagca agctactact ggaaaggcaa    420

ggttccgact gcgcagttct tcaccagtgt accgtttggt ctgtcaacca gcgagatgaa    480

cgcatggctg agcaaaggtg gtggacaggc gttctgggac gaagcctacg ctcctttcgg    540

cgtgaaaccg cttgtgatcg gcaataccgg catgcagatg ggtggatggt acaacaaaga    600

gatcaacagc ctgactgacc tcaaaggcct gaaaatccgc atgccaggtc tgggtggtga    660

agtgctaagc agactgggtg caaccaccgt gaaccttcca ggtggtgaag tctttaccgc    720

actgcagaca ggagcgatcg atgcaaccga ttgggtgagt ccctacaacg atctggcctt    780

tggtctgcac aaagcagcac gctactacta ctacccgggt tggcaggaac cacaggctgt    840
```

-continued

```
actggaactg ctgatcaacc agaaggcgtt cgatagctta ccggcagatc tgcaggcgat    900

cgtgaccgaa gcaagcctgg cagcaagccg cgatatgcat gacgattacg tctacaacaa    960

cgctctggct ctggaacagc tcaaacagca gggaaccgaa ctgaagcgct ttccggacga   1020

agtgctggca gcaatgcgcg aacagtctga cctgatcctc ggtgaactgg ctgcacagag   1080

cgaactgaac ggtcgtatct gggcaagcat gaaggccttt caggctcagg tcgaaccgat   1140

gcacgagatt agcgaaaaag aattgtataa ttggagaggc ggcagccatc atcatcatca   1200

tcattaataa tgaaagggcg atatccagca cactggcggc cgttactagt ggatccggct   1260

gctaacaaag cccgaaagga agctgagttg gctgctgcca ccgctgagca ataactagca   1320

taaccccttg gggcctctaa acgggtcttg aggggttttt tgctgaaagg aggaactata   1380

tccggagcga ctcccacggc acgttggcaa gctcg                              1415
```

```
<210> SEQ ID NO 74
<211> LENGTH: 1415
<212> TYPE: DNA
<213> ORGANISM: Artificial Sequence
<220> FEATURE:
<223> OTHER INFORMATION: Exemplary fsLacBP13 expression sequence.

<400> SEQUENCE: 74
```

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tggaaaaaaa    180

aattcgttgg aaattagcaa tgacttgggg tccgaccttg catccgttgt ccgacacagc    240

agagcatatg gcggaaatcg tgaaggagtt gagcgatggc aacttcgtga tcaacatcga    300

tgcgtcgaac gtgcacaaag cgccgtttgg catcttcgat atggtgaaac tcggtcagta    360

cgagatgggc catactgcga gctactacta caaaggcaaa aacatcgcgt tttaccgct     420

gacgaccatg cctttcggta tgaccgcacc ggaacagtat gcgtggttct actatggtgg    480

cggtctggag ctgatgcagg aagcgtacac caagcatggc atgctggcgt ttcctggtgg    540

taacaccggt aaccagatgg gaggttggtt caccaaggag atcaacagcc tggatgacct    600

caagggtctc aagatgagga tcccaggctt tgcgggccag atcatgtcca aactgggtgt    660

gaccgtgacc aacatccctc caggtgagct gtacaccgca ctggaacgtg gtaccgtgga    720

tgcggtggaa tggaccggtc ctggtatgga catcaacatg ggattccaca agatcgcgaa    780

atactactat accggttggc atgaaccggg atccgaagtg gagttcctga tcaacgaaaa    840

ggaatacaac aaactgccgg aaaaatacaa aaagatcctg aaaatcgcca tgaaaaccgc    900

agcgtacgac atgtacatcc agtcgtacga gatgaacgct gaagcttggc agcagatgaa    960

agagaaatac ccggatatca aggtcaaggt ttttccggaa gaagtgctga aagagatgaa   1020

gaccgcgtac gacaaccttg tggcgagcta cgagaaagaa agcccgatgt tcaagaaaat   1080

catggagagc aaacgtgcgt atctggacaa ggttcgagac tggacccaca tatcggacta   1140

cctctacctg aaaagtactt ctgaaagtaa tctgaatggc ggcagccatc atcatcatca   1200

tcattaatga taaaagggcg atatccagca cactggcggc cgttactagt ggatccggct   1260

gctaacaaag cccgaaagga agctgagttg gctgctgcca ccgctgagca ataactagca   1320

taaccccttg gggcctctaa acgggtcttg aggggttttt tgctgaaagg aggaactata   1380

tccggagcga ctcccacggc acgttggcaa gctcg                              1415
```

<210> SEQ ID NO 75
<211> LENGTH: 1400
<212> TYPE: DNA
<213> ORGANISM: Artificial Sequence
<220> FEATURE:
<223> OTHER INFORMATION: Exemplary taLacBP14 expression sequence.

<400> SEQUENCE: 75
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tggaagaata 180
taaatttaaa atggcaactt tttacctgaa aggtgatagc gcctttgacg tgatcgacca 240
ctttcgccaa ctggtctgga agaaaaccgg tggtaaggta cgcatcgatg cgttccaagc 300
tggggaactg ggctttccag tgaccgagat cctggaagcg accagtcgtg gtgtggtgga 360
gatgagcatc ttctacccga actacaaagc ggcacaggat ccggtgatgg ccttagcggg 420
aggacgtccg ggtccaatgt tcgacctgcg tgatcagaaa gcccaagtgg atgcgaccaa 480
agatctcctg gaaaggtcct tcggtcgttt cggagttcgc tacattgcgc ctatggtgta 540
cggtgaaccg gagatcctgg tctcgagacg tccgatgagt agcctcaaag acctgaaagg 600
gcgtatcttc cgtgcgagtg gtatggcagc ggagttctac accgcaattg gcgcacaagc 660
gatgatgctt ccagcaggtg agctctacca ggcactgcag ttaggcacca tcgatggtct 720
ggagtggacc gactataccg cgaactacaa gcttggcttc cacgaagtgg cgaagaacgt 780
gctggaaccg acgaaaggtg tgaacctcca ttcggaagct accgttcatg cgttcctggt 840
tgtgaacccg aaagtctggg agaaactgcc gaaggaacac cagaaagcga tccaggaagc 900
ggcggacgaa gcgtacaaat ggggtgcgga tcaccttgcg aaactgaaca aaacctacaa 960
ggacaaatgg atcaaagcgg gtgcgaaggt gacccaactg ccgaaagaag accaggacaa 1020
agtgatcgaa gtgtcggcaa agatcctgtc tggctatagc gcgaagagtc cggatgcgaa 1080
agagtacgcg cgtcgtctag tggagctgtg gaagaaactg ggctacacca aatggtctga 1140
tgcattagca aaacagatta aaggcggcag ccatcatcat catcatcatt aataatgaaa 1200
gggcgatatc cagcacactg gcggccgtta ctagtggatc cggctgctaa caaagcccga 1260
aaggaagctg agttggctgc tgccaccgct gagcaataac tagcataacc ccttggggcc 1320
tctaaacggg tcttgagggg ttttttgctg aaaggaggaa ctatatccgg agcgactccc 1380
acggcacgtt ggcaagctcg 1400

<210> SEQ ID NO 76
<211> LENGTH: 1400
<212> TYPE: DNA
<213> ORGANISM: Artificial Sequence
<220> FEATURE:
<223> OTHER INFORMATION: Exemplary msLacBP6.10C expression sequence.

<400> SEQUENCE: 76
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tggcaacaac 180
ttggaaaatt caaagttgtt gggatgcagg gacggtgggc tatgacctct tcaaggagtg 240
gagcgacggt atggaagaaa agacgggcgg tgaactcaaa ttcacggcgt tcccagccaa 300
agccgtcgcc gcagataata atggtctttt tgatgcagta cggaatggcg tcttgcaagg 360

-continued

```
tatgaatcct ttcaccctct actggtcagg taagattccg gcctccgtat ttctctcgtc    420

gtacccagcc ggtccagatc aaccacatca atgggataca atgttctaca gccttggtat    480

gttagaaaaa acacgtgaaa tttacaaaaa gttcggcctc ttctacgtcg gcccaattca    540

gcacgacgca aacattatcc acagtaaaca gccgattaat tccctggacg accttaaggg    600

tctcaaaatg cgcttacctg gcgggatggt agcggaagtc tttgcaaagt ttggcgtcgc    660

agcggtcagt ctcccaggca gcgacatctt tccagcctta gaaaaaggca caatcgacgc    720

tgctgattac gtgggtccgg ctgtaaactg ggagctcggc ttcagccaag taacaaagta    780

catcttaatg ggtccaccag gcatcatgtc agtctaccaa ccggtcgacc ttatggacct    840

cactgtcaat ctgcgggcct ggaacgcatt agatccaaag ttacagcaaa tcgttgaaga    900

tgaagtacgc atctactctc agaagcatta cctcgcaatt cagaaacgga atattgaagc    960

tatgaagaag ttcgaggccg ctggtacaac cgtaacccgt ctgtcacaag aggacctcca   1020

ggagtttcgt cgtgcagcta tcccaatttg gtattcatgg gcaaacaaag atgaagacgc   1080

acgggagatt ttcgacatgc aattagagta catgatgaac gacactgtag gttacatcac   1140

tgaagatgac attaagggca tgaatggcgg ttcacatcat catcatcatc attaatgaaa   1200

gggcgatatc cagcacactg gcggccgtta ctagtggatc cggctgctaa caaagcccga   1260

aaggaagctg agttggctgc tgccaccgct gagcaataac tagcataacc ccttggggcc   1320

tctaaacggg tcttgagggg ttttttgctg aaaggaggaa ctatatccgg agcgactccc   1380

acggcacgtt ggcaagctcg                                               1400


<210> SEQ ID NO 77
<211> LENGTH: 1400
<212> TYPE: DNA
<213> ORGANISM: Artificial Sequence
<220> FEATURE:
<223> OTHER INFORMATION: Exemplary msLacBP6.12C expression sequence.

<400> SEQUENCE: 77

cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tggcaacaac    180

ttggaaaatt caaagtgtat ggtgtgcagg gacggtgggc tatgacctct tcaaggagtg    240

gagcgacggt atggaagaaa agacgggcgg tgaactcaaa ttcacggcgt tcccagccaa    300

agccgtcgcc gcagataata atggtctttt tgatgcagta cggaatggcg tcttgcaagg    360

tatgaatcct ttcaccctct actggtcagg taagattccg gcctccgtat ttctctcgtc    420

gtacccagcc ggtccagatc aaccacatca atgggataca atgttctaca gccttggtat    480

gttagaaaaa acacgtgaaa tttacaaaaa gttcggcctc ttctacgtcg gcccaattca    540

gcacgacgca aacattatcc acagtaaaca gccgattaat tccctggacg accttaaggg    600

tctcaaaatg cgcttacctg gcgggatggt agcggaagtc tttgcaaagt ttggcgtcgc    660

agcggtcagt ctcccaggca gcgacatctt tccagcctta gaaaaaggca caatcgacgc    720

tgctgattac gtgggtccgg ctgtaaactg ggagctcggc ttcagccaag taacaaagta    780

catcttaatg ggtccaccag gcatcatgtc agtctaccaa ccggtcgacc ttatggacct    840

cactgtcaat ctgcgggcct ggaacgcatt agatccaaag ttacagcaaa tcgttgaaga    900

tgaagtacgc atctactctc agaagcatta cctcgcaatt cagaaacgga atattgaagc    960

tatgaagaag ttcgaggccg ctggtacaac cgtaacccgt ctgtcacaag aggacctcca   1020
```

ggagtttcgt cgtgcagcta tcccaatttg gtattcatgg gcaaacaaag atgaagacgc 1080
acgggagatt ttcgacatgc aattagagta catgatgaac gacactgtag gttacatcac 1140
tgaagatgac attaagggca tgaatggcgg ttcacatcat catcatcatc attaatgaaa 1200
gggcgatatc cagcacactg gcggccgtta ctagtggatc cggctgctaa caaagcccga 1260
aaggaagctg agttggctgc tgccaccgct gagcaataac tagcataacc ccttggggcc 1320
tctaaacggg tcttgagggg ttttttgctg aaaggaggaa ctatatccgg agcgactccc 1380
acggcacgtt ggcaagctcg 1400

<210> SEQ ID NO 78
<211> LENGTH: 1400
<212> TYPE: DNA
<213> ORGANISM: Artificial Sequence
<220> FEATURE:
<223> OTHER INFORMATION: Exemplary msLacBP6.43C expression sequence.

<400> SEQUENCE: 78
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tggcaacaac 180
ttggaaaatt caaagtgtat gggatgcagg gacggtgggc tatgacctct tcaaggagtg 240
gagcgacggt atggaagaaa agacgggcgg tgaactcaaa ttcacggcgt tcccatgtaa 300
agccgtcgcc gcagataata atggtctttt tgatgcagta cggaatggcg tcttgcaagg 360
tatgaatcct ttcaccctct actggtcagg taagattccg gcctccgtat ttctctcgtc 420
gtacccagcc ggtccagatc aaccacatca atgggataca atgttctaca gccttggtat 480
gttagaaaaa acacgtgaaa tttacaaaaa gttcggcctc ttctacgtcg gcccaattca 540
gcacgacgca aacattatcc acagtaaaca gccgattaat tccctggacg accttaaggg 600
tctcaaaatg cgcttacctg gcgggatggt agcggaagtc tttgcaaagt ttggcgtcgc 660
agcggtcagt ctcccaggca gcgacatctt tccagcctta gaaaaaggca caatcgacgc 720
tgctgattac gtgggtccgg ctgtaaactg ggagctcggc ttcagccaag taacaaagta 780
catcttaatg ggtccaccag gcatcatgtc agtctaccaa ccggtcgacc ttatggacct 840
cactgtcaat ctgcgggcct ggaacgcatt agatccaaag ttacagcaaa tcgttgaaga 900
tgaagtacgc atctactctc agaagcatta cctcgcaatt cagaaacgga atattgaagc 960
tatgaagaag ttcgaggccg ctggtacaac cgtaacccgt ctgtcacaag aggacctcca 1020
ggagtttcgt cgtgcagcta tcccaatttg gtattcatgg gcaaacaaag atgaagacgc 1080
acgggagatt ttcgacatgc aattagagta catgatgaac gacactgtag gttacatcac 1140
tgaagatgac attaagggca tgaatggcgg ttcacatcat catcatcatc attaatgaaa 1200
gggcgatatc cagcacactg gcggccgtta ctagtggatc cggctgctaa caaagcccga 1260
aaggaagctg agttggctgc tgccaccgct gagcaataac tagcataacc ccttggggcc 1320
tctaaacggg tcttgagggg ttttttgctg aaaggaggaa ctatatccgg agcgactccc 1380
acggcacgtt ggcaagctcg 1400

<210> SEQ ID NO 79
<211> LENGTH: 1400
<212> TYPE: DNA
<213> ORGANISM: Artificial Sequence
<220> FEATURE:

<223> OTHER INFORMATION: Exemplary msLacBP6.49C expression sequence.

<400> SEQUENCE: 79

```
cggtcacgct tgggactgcc ataggctggc ccggtgatgc cggccacgat gcgtccggcg     60
tagaggatcg agatctcgat cccgcgaaat taatacgact cactataggg agaccacaac    120
ggtttccctc tagaaataat tttgtttaac tttaagaagg agatatacca tggcaacaac    180
ttggaaaatt caaagtgtat gggatgcagg gacggtgggc tatgacctct tcaaggagtg    240
gagcgacggt atggaagaaa agacgggcgg tgaactcaaa ttcacggcgt tcccagccaa    300
agccgtcgcc gcatgtaata atggtctttt tgatgcagta cggaatggcg tcttgcaagg    360
tatgaatcct ttcaccctct actggtcagg taagattccg gcctccgtat ttctctcgtc    420
gtacccagcc ggtccagatc aaccacatca atgggataca atgttctaca gccttggtat    480
gttagaaaaa acacgtgaaa tttacaaaaa gttcggcctc ttctacgtcg gcccaattca    540
gcacgacgca aacattatcc acagtaaaca gccgattaat tccctggacg accttaaggg    600
tctcaaaatg cgcttacctg gcgggatggt agcggaagtc tttgcaaagt ttggcgtcgc    660
agcggtcagt ctcccaggca gcgacatctt tccagcctta gaaaaaggca caatcgacgc    720
tgctgattac gtgggtccgg ctgtaaactg ggagctcggc ttcagccaag taacaaagta    780
catcttaatg ggtccaccag gcatcatgtc agtctaccaa ccggtcgacc ttatggacct    840
cactgtcaat ctgcgggcct ggaacgcatt agatccaaag ttacagcaaa tcgttgaaga    900
tgaagtacgc atctactctc agaagcatta cctcgcaatt cagaaacgga atattgaagc    960
tatgaagaag ttcgaggccg ctggtacaac cgtaacccgt ctgtcacaag aggacctcca   1020
ggagtttcgt cgtgcagcta tcccaatttg gtattcatgg gcaaacaaag atgaagacgc   1080
acgggagatt ttcgacatgc aattagagta catgatgaac gacactgtag gttacatcac   1140
tgaagatgac attaagggca tgaatggcgg ttcacatcat catcatcatc attaatgaaa   1200
gggcgatatc cagcacactg gcggccgtta ctagtggatc cggctgctaa caaagcccga   1260
aaggaagctg agttggctgc tgccaccgct gagcaataac tagcataacc ccttggggcc   1320
tctaaacggg tcttgagggg ttttttgctg aaaggaggaa ctatatccgg agcgactccc   1380
acggcacgtt ggcaagctcg                                               1400
```

<210> SEQ ID NO 80
<211> LENGTH: 1400
<212> TYPE: DNA
<213> ORGANISM: Artificial Sequence
<220> FEATURE:
<223> OTHER INFORMATION: Exemplary msLacBP6.50C expression sequence.

<400> SEQUENCE: 80

```
cggtcacgct tgggactgcc ataggctggc ccggtgatgc cggccacgat gcgtccggcg     60
tagaggatcg agatctcgat cccgcgaaat taatacgact cactataggg agaccacaac    120
ggtttccctc tagaaataat tttgtttaac tttaagaagg agatatacca tggcaacaac    180
ttggaaaatt caaagtgtat gggatgcagg gacggtgggc tatgacctct tcaaggagtg    240
gagcgacggt atggaagaaa agacgggcgg tgaactcaaa ttcacggcgt tcccagccaa    300
agccgtcgcc gcagattgta atggtctttt tgatgcagta cggaatggcg tcttgcaagg    360
tatgaatcct ttcaccctct actggtcagg taagattccg gcctccgtat ttctctcgtc    420
gtacccagcc ggtccagatc aaccacatca atgggataca atgttctaca gccttggtat    480
gttagaaaaa acacgtgaaa tttacaaaaa gttcggcctc ttctacgtcg gcccaattca    540
```

gcacgacgca aacattatcc acagtaaaca gccgattaat tccctggacg accttaaggg 600
tctcaaaatg cgcttacctg gcgggatggt agcggaagtc tttgcaaagt ttggcgtcgc 660
agcggtcagt ctcccaggca gcgacatctt tccagcctta gaaaaaggca caatcgacgc 720
tgctgattac gtgggtccgg ctgtaaactg ggagctcggc ttcagccaag taacaaagta 780
catcttaatg ggtccaccag gcatcatgtc agtctaccaa ccggtcgacc ttatggacct 840
cactgtcaat ctgcgggcct ggaacgcatt agatccaaag ttacagcaaa tcgttgaaga 900
tgaagtacgc atctactctc agaagcatta cctcgcaatt cagaaacgga atattgaagc 960
tatgaagaag ttcgaggccg ctggtacaac cgtaacccgt ctgtcacaag aggacctcca 1020
ggagtttcgt cgtgcagcta tcccaatttg gtattcatgg gcaaacaaag atgaagacgc 1080
acgggagatt ttcgacatgc aattagagta catgatgaac gacactgtag gttacatcac 1140
tgaagatgac attaagggca tgaatggcgg ttcacatcat catcatcatc attaatgaaa 1200
gggcgatatc cagcacactg gcggccgtta ctagtggatc cggctgctaa caaagcccga 1260
aaggaagctg agttggctgc tgccaccgct gagcaataac tagcataacc ccttggggcc 1320
tctaaacggg tcttgagggg ttttttgctg aaaggaggaa ctatatccgg agcgactccc 1380
acggcacgtt ggcaagctcg 1400

<210> SEQ ID NO 81
<211> LENGTH: 1400
<212> TYPE: DNA
<213> ORGANISM: Artificial Sequence
<220> FEATURE:
<223> OTHER INFORMATION: Exemplary msLacBP6.68C expression sequence.

<400> SEQUENCE: 81
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tggcaacaac 180
ttggaaaatt caaagtgtat gggatgcagg gacggtgggc tatgacctct tcaaggagtg 240
gagcgacggt atggaagaaa agacgggcgg tgaactcaaa ttcacggcgt tcccagccaa 300
agccgtcgcc gcagataata atggtctttt tgatgcagta cggaatggcg tcttgcaagg 360
tatgaatcct tgtaccctct actggtcagg taagattccg gcctccgtat ttctctcgtc 420
gtacccagcc ggtccagatc aaccacatca atgggataca atgttctaca gccttggtat 480
gttagaaaaa acacgtgaaa tttacaaaaa gttcggcctc ttctacgtcg gcccaattca 540
gcacgacgca aacattatcc acagtaaaca gccgattaat tccctggacg accttaaggg 600
tctcaaaatg cgcttacctg gcgggatggt agcggaagtc tttgcaaagt ttggcgtcgc 660
agcggtcagt ctcccaggca gcgacatctt tccagcctta gaaaaaggca caatcgacgc 720
tgctgattac gtgggtccgg ctgtaaactg ggagctcggc ttcagccaag taacaaagta 780
catcttaatg ggtccaccag gcatcatgtc agtctaccaa ccggtcgacc ttatggacct 840
cactgtcaat ctgcgggcct ggaacgcatt agatccaaag ttacagcaaa tcgttgaaga 900
tgaagtacgc atctactctc agaagcatta cctcgcaatt cagaaacgga atattgaagc 960
tatgaagaag ttcgaggccg ctggtacaac cgtaacccgt ctgtcacaag aggacctcca 1020
ggagtttcgt cgtgcagcta tcccaatttg gtattcatgg gcaaacaaag atgaagacgc 1080
acgggagatt ttcgacatgc aattagagta catgatgaac gacactgtag gttacatcac 1140
tgaagatgac attaagggca tgaatggcgg ttcacatcat catcatcatc attaatgaaa 1200
gggcgatatc cagcacactg gcggccgtta ctagtggatc cggctgctaa caaagcccga 1260
aaggaagctg agttggctgc tgccaccgct gagcaataac tagcataacc ccttggggcc 1320
tctaaacggg tcttgagggg ttttttgctg aaaggaggaa ctatatccgg agcgactccc 1380
acggcacgtt ggcaagctcg 1400

<210> SEQ ID NO 82
<211> LENGTH: 1400
<212> TYPE: DNA
<213> ORGANISM: Artificial Sequence
<220> FEATURE:
<223> OTHER INFORMATION: Exemplary msLacBP6.169C expression sequence.

<400> SEQUENCE: 82
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tggcaacaac 180
ttggaaaatt caaagtgtat gggatgcagg gacggtgggc tatgacctct tcaaggagtg 240
gagcgacggt atggaagaaa agacgggcgg tgaactcaaa ttcacggcgt tcccagccaa 300
agccgtcgcc gcagataata atggtctttt tgatgcagta cggaatggcg tcttgcaagg 360
tatgaatcct ttcaccctct actggtcagg taagattccg gcctccgtat ttctctcgtc 420
gtacccagcc ggtccagatc aaccacatca atgggataca atgttctaca gccttggtat 480
gttagaaaaa acacgtgaaa tttacaaaaa gttcggcctc ttctacgtcg gcccaattca 540
gcacgacgca aacattatcc acagtaaaca gccgattaat tccctggacg accttaaggg 600
tctcaaaatg cgcttacctg gcgggatggt agcggaagtc tttgcaaagt ttggcgtcgc 660
agcggtcagt ctctgtggca gcgacatctt tccagcctta gaaaaaggca caatcgacgc 720
tgctgattac gtgggtccgg ctgtaaactg ggagctcggc ttcagccaag taacaaagta 780
catcttaatg ggtccaccag gcatcatgtc agtctaccaa ccggtcgacc ttatggacct 840
cactgtcaat ctgcgggcct ggaacgcatt agatccaaag ttacagcaaa tcgttgaaga 900
tgaagtacgc atctactctc agaagcatta cctcgcaatt cagaaacgga atattgaagc 960
tatgaagaag ttcgaggccg ctggtacaac cgtaacccgt ctgtcacaag aggacctcca 1020
ggagtttcgt cgtgcagcta tcccaatttg gtattcatgg gcaaacaaag atgaagacgc 1080
acgggagatt ttcgacatgc aattagagta catgatgaac gacactgtag gttacatcac 1140
tgaagatgac attaagggca tgaatggcgg ttcacatcat catcatcatc attaatgaaa 1200
gggcgatatc cagcacactg gcggccgtta ctagtggatc cggctgctaa caaagcccga 1260
aaggaagctg agttggctgc tgccaccgct gagcaataac tagcataacc ccttggggcc 1320
tctaaacggg tcttgagggg ttttttgctg aaaggaggaa ctatatccgg agcgactccc 1380
acggcacgtt ggcaagctcg 1400

<210> SEQ ID NO 83
<211> LENGTH: 1400
<212> TYPE: DNA
<213> ORGANISM: Artificial Sequence
<220> FEATURE:
<223> OTHER INFORMATION: Exemplary msLacBP6.170C expression sequence.

<400> SEQUENCE: 83
cggtcacgct tgggactgcc ataggctggc ccggtgatgc cggccacgat gcgtccggcg 60

```
tagaggatcg agatctcgat cccgcgaaat taatacgact cactataggg agaccacaac    120
ggtttccctc tagaaataat tttgtttaac tttaagaagg agatatacca tggcaacaac    180
ttggaaaatt caaagtgtat gggatgcagg gacggtgggc tatgacctct tcaaggagtg    240
gagcgacggt atggaagaaa agacgggcgg tgaactcaaa ttcacggcgt tcccagccaa    300
agccgtcgcc gcagataata atggtctttt tgatgcagta cggaatggcg tcttgcaagg    360
tatgaatcct ttcaccctct actggtcagg taagattccg gcctccgtat ttctctcgtc    420
gtacccagcc ggtccagatc aaccacatca atgggataca atgttctaca gccttggtat    480
gttagaaaaa acacgtgaaa tttacaaaaa gttcggcctc ttctacgtcg gcccaattca    540
gcacgacgca aacattatcc acagtaaaca gccgattaat tccctggacg accttaaggg    600
tctcaaaatg cgcttacctg gcgggatggt agcggaagtc tttgcaaagt ttggcgtcgc    660
agcggtcagt ctcccatgta gcgacatctt tccagcctta gaaaaaggca caatcgacgc    720
tgctgattac gtgggtccgg ctgtaaactg ggagctcggc ttcagccaag taacaaagta    780
catcttaatg ggtccaccag gcatcatgtc agtctaccaa ccggtcgacc ttatggacct    840
cactgtcaat ctgcgggcct ggaacgcatt agatccaaag ttacagcaaa tcgttgaaga    900
tgaagtacgc atctactctc agaagcatta cctcgcaatt cagaaacgga atattgaagc    960
tatgaagaag ttcgaggccg ctggtacaac cgtaacccgt ctgtcacaag aggacctcca   1020
ggagtttcgt cgtgcagcta tcccaatttg gtattcatgg gcaaacaaag atgaagacgc   1080
acgggagatt ttcgacatgc aattagagta catgatgaac gacactgtag gttacatcac   1140
tgaagatgac attaagggca tgaatggcgg ttcacatcat catcatcatc attaatgaaa   1200
gggcgatatc cagcacactg gcggccgtta ctagtggatc cggctgctaa caaagcccga   1260
aaggaagctg agttggctgc tgccaccgct gagcaataac tagcataacc ccttggggcc   1320
tctaaacggg tcttgagggg ttttttgctg aaaggaggaa ctatatccgg agcgactccc   1380
acggcacgtt ggcaagctcg                                               1400
```

<210> SEQ ID NO 84
<211> LENGTH: 1400
<212> TYPE: DNA
<213> ORGANISM: Artificial Sequence
<220> FEATURE:
<223> OTHER INFORMATION: Exemplary msLacBP6.171C expression sequence.

<400> SEQUENCE: 84

```
cggtcacgct tgggactgcc ataggctggc ccggtgatgc cggccacgat gcgtccggcg     60
tagaggatcg agatctcgat cccgcgaaat taatacgact cactataggg agaccacaac    120
ggtttccctc tagaaataat tttgtttaac tttaagaagg agatatacca tggcaacaac    180
ttggaaaatt caaagtgtat gggatgcagg gacggtgggc tatgacctct tcaaggagtg    240
gagcgacggt atggaagaaa agacgggcgg tgaactcaaa ttcacggcgt tcccagccaa    300
agccgtcgcc gcagataata atggtctttt tgatgcagta cggaatggcg tcttgcaagg    360
tatgaatcct ttcaccctct actggtcagg taagattccg gcctccgtat ttctctcgtc    420
gtacccagcc ggtccagatc aaccacatca atgggataca atgttctaca gccttggtat    480
gttagaaaaa acacgtgaaa tttacaaaaa gttcggcctc ttctacgtcg gcccaattca    540
gcacgacgca aacattatcc acagtaaaca gccgattaat tccctggacg accttaaggg    600
tctcaaaatg cgcttacctg gcgggatggt agcggaagtc tttgcaaagt ttggcgtcgc    660
```

agcggtcagt ctcccaggct gtgacatctt tccagcctta gaaaaaggca caatcgacgc 720
tgctgattac gtgggtccgg ctgtaaactg ggagctcggc ttcagccaag taacaaagta 780
catcttaatg ggtccaccag gcatcatgtc agtctaccaa ccggtcgacc ttatggacct 840
cactgtcaat ctgcgggcct ggaacgcatt agatccaaag ttacagcaaa tcgttgaaga 900
tgaagtacgc atctactctc agaagcatta cctcgcaatt cagaaacgga atattgaagc 960
tatgaagaag ttcgaggccg ctggtacaac cgtaacccgt ctgtcacaag aggacctcca 1020
ggagtttcgt cgtgcagcta tcccaatttg gtattcatgg gcaaacaaag atgaagacgc 1080
acgggagatt ttcgacatgc aattagagta catgatgaac gacactgtag gttacatcac 1140
tgaagatgac attaagggca tgaatggcgg ttcacatcat catcatcatc attaatgaaa 1200
gggcgatatc cagcacactg gcggccgtta ctagtggatc cggctgctaa caaagcccga 1260
aaggaagctg agttggctgc tgccaccgct gagcaataac tagcataacc ccttggggcc 1320
tctaaacggg tcttgagggg ttttttgctg aaaggaggaa ctatatccgg agcgactccc 1380
acggcacgtt ggcaagctcg 1400

<210> SEQ ID NO 85
<211> LENGTH: 1400
<212> TYPE: DNA
<213> ORGANISM: Artificial Sequence
<220> FEATURE:
<223> OTHER INFORMATION: Exemplary msLacBP6.187C expression sequence.

<400> SEQUENCE: 85
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tggcaacaac 180
ttggaaaatt caaagtgtat gggatgcagg gacggtgggc tatgacctct tcaaggagtg 240
gagcgacggt atggaagaaa agacgggcgg tgaactcaaa ttcacggcgt tcccagccaa 300
agccgtcgcc gcagataata atggtctttt tgatgcagta cggaatggcg tcttgcaagg 360
tatgaatcct ttcaccctct actggtcagg taagattccg gcctccgtat ttctctcgtc 420
gtacccagcc ggtccagatc aaccacatca atgggataca atgttctaca gccttggtat 480
gttagaaaaa acacgtgaaa tttacaaaaa gttcggcctc ttctacgtcg gcccaattca 540
gcacgacgca aacattatcc acagtaaaca gccgattaat tccctggacg accttaaggg 600
tctcaaaatg cgcttacctg gcgggatggt agcggaagtc tttgcaaagt ttggcgtcgc 660
agcggtcagt ctcccaggca gcgacatctt tccagcctta gaaaaaggca caatcgacgc 720
tgctgattgt gtgggtccgg ctgtaaactg ggagctcggc ttcagccaag taacaaagta 780
catcttaatg ggtccaccag gcatcatgtc agtctaccaa ccggtcgacc ttatggacct 840
cactgtcaat ctgcgggcct ggaacgcatt agatccaaag ttacagcaaa tcgttgaaga 900
tgaagtacgc atctactctc agaagcatta cctcgcaatt cagaaacgga atattgaagc 960
tatgaagaag ttcgaggccg ctggtacaac cgtaacccgt ctgtcacaag aggacctcca 1020
ggagtttcgt cgtgcagcta tcccaatttg gtattcatgg gcaaacaaag atgaagacgc 1080
acgggagatt ttcgacatgc aattagagta catgatgaac gacactgtag gttacatcac 1140
tgaagatgac attaagggca tgaatggcgg ttcacatcat catcatcatc attaatgaaa 1200
gggcgatatc cagcacactg gcggccgtta ctagtggatc cggctgctaa caaagcccga 1260
aaggaagctg agttggctgc tgccaccgct gagcaataac tagcataacc ccttggggcc 1320
tctaaacggg tcttgagggg ttttttgctg aaaggaggaa ctatatccgg agcgactccc 1380
acggcacgtt ggcaagctcg 1400

<210> SEQ ID NO 86
<211> LENGTH: 1400
<212> TYPE: DNA
<213> ORGANISM: Artificial Sequence
<220> FEATURE:
<223> OTHER INFORMATION: Exemplary msLacBP6.188C expression sequence.

<400> SEQUENCE: 86
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tggcaacaac 180
ttggaaaatt caaagtgtat gggatgcagg gacggtgggc tatgacctct tcaaggagtg 240
gagcgacggt atggaagaaa agacgggcgg tgaactcaaa ttcacggcgt tcccagccaa 300
agccgtcgcc gcagataata atggtctttt tgatgcagta cggaatggcg tcttgcaagg 360
tatgaatcct ttcaccctct actggtcagg taagattccg gcctccgtat ttctctcgtc 420
gtacccagcc ggtccagatc aaccacatca atgggataca atgttctaca gccttggtat 480
gttagaaaaa acacgtgaaa tttacaaaaa gttcggcctc ttctacgtcg gcccaattca 540
gcacgacgca aacattatcc acagtaaaca gccgattaat tccctggacg accttaaggg 600
tctcaaaatg cgcttacctg gcgggatggt agcggaagtc tttgcaaagt ttggcgtcgc 660
agcggtcagt ctcccaggca gcgacatctt tccagcctta gaaaaaggca caatcgacgc 720
tgctgattac tgtggtccgg ctgtaaactg ggagctcggc ttcagccaag taacaaagta 780
catcttaatg ggtccaccag gcatcatgtc agtctaccaa ccggtcgacc ttatggacct 840
cactgtcaat ctgcgggcct ggaacgcatt agatccaaag ttacagcaaa tcgttgaaga 900
tgaagtacgc atctactctc agaagcatta cctcgcaatt cagaaacgga atattgaagc 960
tatgaagaag ttcgaggccg ctggtacaac cgtaacccgt ctgtcacaag aggacctcca 1020
ggagtttcgt cgtgcagcta tcccaatttg gtattcatgg gcaaacaaag atgaagacgc 1080
acgggagatt ttcgacatgc aattagagta catgatgaac gacactgtag gttacatcac 1140
tgaagatgac attaagggca tgaatggcgg ttcacatcat catcatcatc attaatgaaa 1200
gggcgatatc cagcacactg gcggccgtta ctagtggatc cggctgctaa caaagcccga 1260
aaggaagctg agttggctgc tgccaccgct gagcaataac tagcataacc ccttggggcc 1320
tctaaacggg tcttgagggg ttttttgctg aaaggaggaa ctatatccgg agcgactccc 1380
acggcacgtt ggcaagctcg 1400

<210> SEQ ID NO 87
<211> LENGTH: 1400
<212> TYPE: DNA
<213> ORGANISM: Artificial Sequence
<220> FEATURE:
<223> OTHER INFORMATION: Exemplary msLacBP6.192C expression sequence.

<400> SEQUENCE: 87
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tggcaacaac 180

-continued

```
ttggaaaatt caaagtgtat gggatgcagg gacggtgggc tatgacctct tcaaggagtg    240

gagcgacggt atggaagaaa agacgggcgg tgaactcaaa ttcacggcgt tcccagccaa    300

agccgtcgcc gcagataata atggtctttt tgatgcagta cggaatggcg tcttgcaagg    360

tatgaatcct ttcaccctct actggtcagg taagattccg gcctccgtat ttctctcgtc    420

gtacccagcc ggtccagatc aaccacatca atgggataca atgttctaca gccttggtat    480

gttagaaaaa acacgtgaaa tttacaaaaa gttcggcctc ttctacgtcg gcccaattca    540

gcacgacgca aacattatcc acagtaaaca gccgattaat tccctggacg accttaaggg    600

tctcaaaatg cgcttacctg gcgggatggt agcggaagtc tttgcaaagt ttggcgtcgc    660

agcggtcagt ctcccaggca gcgacatctt tccagcctta gaaaaaggca caatcgacgc    720

tgctgattac gtgggtccgg cttgtaactg ggagctcggc ttcagccaag taacaaagta    780

catcttaatg ggtccaccag gcatcatgtc agtctaccaa ccggtcgacc ttatggacct    840

cactgtcaat ctgcgggcct ggaacgcatt agatccaaag ttacagcaaa tcgttgaaga    900

tgaagtacgc atctactctc agaagcatta cctcgcaatt cagaaacgga atattgaagc    960

tatgaagaag ttcgaggccg ctggtacaac cgtaacccgt ctgtcacaag aggacctcca   1020

ggagtttcgt cgtgcagcta tcccaatttg gtattcatgg gcaaacaaag atgaagacgc   1080

acgggagatt ttcgacatgc aattagagta catgatgaac gacactgtag gttacatcac   1140

tgaagatgac attaagggca tgaatggcgg ttcacatcat catcatcatc attaatgaaa   1200

gggcgatatc cagcacactg gcggccgtta ctagtggatc cggctgctaa caaagcccga   1260

aaggaagctg agttggctgc tgccaccgct gagcaataac tagcataacc ccttggggcc   1320

tctaaacggg tcttgagggg ttttttgctg aaaggaggaa ctatatccgg agcgactccc   1380

acggcacgtt ggcaagctcg                                               1400
```

```
<210> SEQ ID NO 88
<211> LENGTH: 1400
<212> TYPE: DNA
<213> ORGANISM: Artificial Sequence
<220> FEATURE:
<223> OTHER INFORMATION: Exemplary msLacBP6.196C expression sequence.

<400> SEQUENCE: 88
```

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tggcaacaac    180

ttggaaaatt caaagtgtat gggatgcagg gacggtgggc tatgacctct tcaaggagtg    240

gagcgacggt atggaagaaa agacgggcgg tgaactcaaa ttcacggcgt tcccagccaa    300

agccgtcgcc gcagataata atggtctttt tgatgcagta cggaatggcg tcttgcaagg    360

tatgaatcct ttcaccctct actggtcagg taagattccg gcctccgtat ttctctcgtc    420

gtacccagcc ggtccagatc aaccacatca atgggataca atgttctaca gccttggtat    480

gttagaaaaa acacgtgaaa tttacaaaaa gttcggcctc ttctacgtcg gcccaattca    540

gcacgacgca aacattatcc acagtaaaca gccgattaat tccctggacg accttaaggg    600

tctcaaaatg cgcttacctg gcgggatggt agcggaagtc tttgcaaagt ttggcgtcgc    660

agcggtcagt ctcccaggca gcgacatctt tccagcctta gaaaaaggca caatcgacgc    720

tgctgattac gtgggtccgg ctgtaaactg ggagtgtggc ttcagccaag taacaaagta    780

catcttaatg ggtccaccag gcatcatgtc agtctaccaa ccggtcgacc ttatggacct    840
```

```
cactgtcaat ctgcgggcct ggaacgcatt agatccaaag ttacagcaaa tcgttgaaga    900

tgaagtacgc atctactctc agaagcatta cctcgcaatt cagaaacgga atattgaagc    960

tatgaagaag ttcgaggccg ctggtacaac cgtaacccgt ctgtcacaag aggacctcca   1020

ggagtttcgt cgtgcagcta tcccaatttg gtattcatgg gcaaacaaag atgaagacgc   1080

acgggagatt ttcgacatgc aattagagta catgatgaac gacactgtag gttacatcac   1140

tgaagatgac attaagggca tgaatggcgg ttcacatcat catcatcatc attaatgaaa   1200

gggcgatatc cagcacactg gcggccgtta ctagtggatc cggctgctaa caaagcccga   1260

aaggaagctg agttggctgc tgccaccgct gagcaataac tagcataacc ccttggggcc   1320

tctaaacggg tcttgagggg ttttttgctg aaaggaggaa ctatatccgg agcgactccc   1380

acggcacgtt ggcaagctcg                                               1400
```

<210> SEQ ID NO 89
<211> LENGTH: 1406
<212> TYPE: DNA
<213> ORGANISM: Artificial Sequence
<220> FEATURE:
<223> OTHER INFORMATION: Exemplary tsLacBP7.189C expression sequence.

<400> SEQUENCE: 89

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgcaagcacc    180

acgttttcgt tggcgtattc aaagtgcatg ggatgcagga acagtgggtt acaccctctt    240

tcagcgcttt gcagaacgcg tcaaagagct gaccgatgga cagatcgaga tccagacctt    300

tccagcgggt gcagtcgtgg gtaccttcga catgttcgac gcagtcaaaa ccggagtgct    360

ggatggcatg catcccttta ccctctattg ggcaggtcga atgccggtta ccgcctttct    420

cagcagctac ccgttaggcc tggatcgacc agatcagtgg gaaacgtggt actacgcact    480

tggcggtctg gatctggcga gacgtgcatt cgaggaacag ggtctgttct acgttggtcc    540

agtgcagcat gactacaacc tgatccacag caaaaagccg atcaagtcct tcgaggactt    600

caaaggcgtg aagctgagag tgcctggtgg catgatagca gacgtcttct cagcagctgg    660

agcagcaaca gtcctcttgc ctggtggtga ggtctatccg gctctggaac gtggtgtgat    720

cgatgcagca gactgcgtgg gtcctgcagt gaactacaac cttggcttcc atcaggtgac    780

caagtacatc atcatgggtc ctccagaaac ccctgcgatc catcagccag tggatctggc    840

agacatcacc ctgaacctca gccgttggcg tgcagtgccc aaaaacctgc aggaacgatt    900

cgaagcagcg gttcacgaat ggagctggat ccactatgcc ggtatccaga aagccaacct    960

ggagacctgg ccgaagtaca aagcggcagg tgtgcagatc atcaggctga ctaccgtgga   1020

tgtgcgcaag tttcgtcgtg ttgcgattcc gatctggttc aaatgggcga aacaggacaa   1080

gtatgcccgt gaagcctttg caagccagct ggagtacatg aaagcactgg gctatgtgac   1140

agatgcagat gttcgtggtt taagcttagg cggcagccat catcatcatc atcattaata   1200

atgaaagggc gatatccagc acactggcgg ccgttactag tggatccggc tgctaacaaa   1260

gcccgaaagg aagctgagtt ggctgctgcc accgctgagc aataactagc ataacccctt   1320

ggggcctcta aacgggtctt gaggggtttt ttgctgaaag gaggaactat atccggagcg   1380

actcccacgg cacgttggca agctcg                                        1406
```

<210> SEQ ID NO 90
<211> LENGTH: 1406
<212> TYPE: DNA
<213> ORGANISM: Artificial Sequence
<220> FEATURE:
<223> OTHER INFORMATION: Exemplary maLacBP8.189C expression sequence.

<400> SEQUENCE: 90
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgcaagcagc 180
aactacttgg aaaattcaaa gtacctggga tgctggtacg gttggctaca ccctcttcga 240
agagtgggcg aagagcatcg aagccaaatc cggtggtgaa ctgaagttcc aggcgtttcc 300
ggcaaaagcc gttgctgctg acaacaacgc gctctttgac gctgttcgca acggtgtgct 360
tcagggcatg aacccgttca ccctgtactg ggcgggcaaa atccctgcct ctgtgttcct 420
gtcgagctac ccagcaggtc cggatcaacc ccatcagtgg gataccatgt tctactcgat 480
gggtatgctg gagaaaaccc gcgaaatcta caagaaattt ggcctgttct acgttggtcc 540
gatccagcat gatgcgaaca tcatccacag caaacagcca gtcaactctc tggacgacct 600
gaaagggatg aagatccgtg tacctggtgg catggttgcc gaagtcttcc agcagtttgg 660
cgtttccacc gtcagtctgc cgggtagcga catcttcccg gcattggaga aaggcacgat 720
tgacgctgca gactgcgtag gtccagcagt caactacgaa ctgggcttta gccaggttac 780
ggactacatc atcttcggac cacctggcgt catgagcatc tatcaaccgg tggacctgat 840
ggatctgacc gtcagtctgc gtgcttggaa ctcgatctca ccagagctgc agcagctggt 900
tgaggatgaa gtgcgcatct actcgcagaa acactatctg gcgattcagg ctcgcaacat 960
cgaagcgatg gagaaattca aagccgatgg tgacacggta acccgtctga gccaggaaga 1020
cctggaaacc tggcgtaagg ctgcaatccc gatctggttc aactgggcga acaagaacga 1080
tgatgctcgt gcgatcctgg atatccagct gaaatacatg atgaacgaca ctgtgggcta 1140
cattactgaa gaagatatta aaggatttgg cggcagccat catcatcatc atcattaatg 1200
ataaaagggc gatatccagc acactggcgg ccgttactag tggatccggc tgctaacaaa 1260
gcccgaaagg aagctgagtt ggctgctgcc accgctgagc aataactagc ataacccctt 1320
ggggcctcta aacgggtctt gaggggtttt ttgctgaaag gaggaactat atccggagcg 1380
actcccacgg cacgttggca agctcg 1406

<210> SEQ ID NO 91
<211> LENGTH: 1439
<212> TYPE: DNA
<213> ORGANISM: Artificial Sequence
<220> FEATURE:
<223> OTHER INFORMATION: Exemplary adLacBP9.C191 expression sequence.

<400> SEQUENCE: 91
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgcaagcacc 180
aattactctg agatttcaga gtacttggcc gcagaaagac atcttccacg agtttgccct 240
ggattacgcc aaaaaggtca acgagatgag cggtggacgt ctgaagatcg aggttctggc 300
agcaggcagt gtggtgaagg cgttcgatct cctggatgca gtgagcaagg gtacgctgga 360
tggaggtcat ggcgtagtcg cctactggta cggcaagaac accgcattag cgctgtgggg 420
ctctggacct gcattcggca tggacccaaa catggtgctt gcatggcacc attacggcgg 480
aggtcgtcag ctcctggaag agatctaccg aagcctcaac ctggatgtcg tcagcctcat 540
gtacggacca atgccgactc agccgttagg ctggttcaag cagaaaccca ttgcgaaacc 600
tgacgacatg aaagggctga agttccgtac ggtaggtctg agcatcgaca tcttcaacgg 660
actgggtgct gcagtgaacg cgttaccagg tgccgaaatc gttccggcta tggatcgagg 720
tctgctcgat gcggcagagt gcaacaacgc ttcttccgat cgtgtgctag ggtttccgga 780
tgtctcgaag atcgcgatgc tgcaatcgtt ccatcaggcg tcagagcagt tcgagatcct 840
gttcaacggc aagcgtttcc aggcgttacc ggctgatctg aagagcatca tctccattgc 900
tgcgcaagct gcaagcgccg acatgtcctg gaaggccatc gatcgctact ctagcgacta 960
cttcgagatg cgtgacaagc agggcgtgaa gttctacagc accagaccgg aaatcctgaa 1020
acggcaactg gagatctggg accaggtgat ggagaagcgt gcagccgaaa acccgacgtt 1080
caaaaaggtc ctggagagcc aacgcaggtt tgcacagcgt gctgcgagat ggcagaacga 1140
caccaacgtg gacttcaaga tggcctacaa ccacttcttt ggtggtaaga aaaaagctac 1200
tggcggcagc catcatcatc atcatcatta ataatgaaag ggcgatatcc agcacactgg 1260
cggccgttac tagtggatcc ggctgctaac aaagcccgaa aggaagctga gttggctgct 1320
gccaccgctg agcaataact agcataaccc cttggggcct ctaaacgggt cttgaggggt 1380
tttttgctga aaggaggaac tatatccgga gcgactccca cggcacgttg gcaagctcg 1439

<210> SEQ ID NO 92
<211> LENGTH: 1415
<212> TYPE: DNA
<213> ORGANISM: Artificial Sequence
<220> FEATURE:
<223> OTHER INFORMATION: Exemplary psLacBP11.195C expression sequence.

<400> SEQUENCE: 92
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgcaacaagc 180
agcaggtgaa ccagcaaaaa cctatcactg gaagatggtg accgcttggc cgaagaacta 240
tccgggttta ggcaccagtg cggaacgact ggcagaacgt gtgaacgcga tgagtggtgg 300
acgtctgacc atcaaggtgt atgcagcagg agaactggtt ccagctctgg aagtgttcga 360
tgcagtctct cgtggtaccg cagaactggg tcatggagca agctactact ggaaaggcaa 420
ggttccgact gcgcagttct tcaccagtgt accgtttggt ctgtcaacca gcgagatgaa 480
cgcatggctg agcaaaggtg gtggacaggc gttctgggac gaagcctacg ctcctttcgg 540
cgtgaaaccg cttgtgatcg gcaataccgg catgcagatg ggtggatggt acaacaaaga 600
gatcaacagc ctgactgacc tcaaaggcct gaaaatccgc atgccaggtc tgggtggtga 660
agtgctaagc agactgggtg caaccaccgt gaaccttcca ggtggtgaag tctttaccgc 720
actgcagaca ggagcgatcg atgcaaccga ttgcgtgagt ccctacaacg atctggcctt 780
tggtctgcac aaagcagcac gctactacta ctacccgggt tggcaggaac cacaggctgt 840
actggaactg ctgatcaacc agaaggcgtt cgatagctta ccggcagatc tgcaggcgat 900
cgtgaccgaa gcaagcctgg cagcaagccg cgatatgcat gacgattacg tctacaacaa 960

-continued

```
cgctctggct ctggaacagc tcaaacagca gggaaccgaa ctgaagcgct ttccggacga   1020

agtgctggca gcaatgcgcg aacagtctga cctgatcctc ggtgaactgg ctgcacagag   1080

cgaactgaac ggtcgtatct gggcaagcat gaaggccttt caggctcagg tcgaaccgat   1140

gcacgagatt agcgaaaaag aattgtataa ttggagaggc ggcagccatc atcatcatca   1200

tcattaataa tgaaagggcg atatccagca cactggcggc cgttactagt ggatccggct   1260

gctaacaaag cccgaaagga agctgagttg gctgctgcca ccgctgagca ataactagca   1320

taaccccttg gggcctctaa acgggtcttg aggggttttt tgctgaaagg aggaactata   1380

tccggagcga ctcccacggc acgttggcaa gctcg                              1415
```

<210> SEQ ID NO 93
<211> LENGTH: 1433
<212> TYPE: DNA
<213> ORGANISM: Artificial Sequence
<220> FEATURE:
<223> OTHER INFORMATION: Exemplary rsLacBP12.191C expression sequence.

<400> SEQUENCE: 93

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgcaagcacc    180

gttagttatg aaaatgcaaa ctagttggcc agctagcgat atctggatgg acttcgcacg    240

tgagtacgtg accagagtgg aagagatgtc aggtggacgc atcaaggtgg atctgctgcc    300

agcaggtgcg gtagttggtg cgttccaggt gatggacgca gtacacgatg ggtcatcga    360

tgctagccac tcggtgagcg cttactggta tggcaagagc aaagcggcta gcttctttgg    420

cactggtcca gtctttggcg gtagtgcaac cacgatgctc ggctggttct accaaggtgg    480

aggtcaggac ctgtaccgtg aactgacgca agacatcctc ggaatgaaca tcgtaggctt    540

ctacggtttc ccgatgccgg cacagccatt cggctggttc aagacggaag tgaacggcgt    600

tgcggacatc caaggcttca agtaccgtac cgttggactg gcagcagatc tgctgcaggc    660

tatgggcatg tcagtggcac agctgccagg tggcgaaatc gttccggcaa tggagcgtgg    720

tgtgatcgat gcgttcgagt gcaacaaccc tagctcggat atgcgctttg gtgcacaaga    780

tgtggcgaag aactactacc tgtcctccta ccatcaggca tctgagagct tcgagtacac    840

cttcaatcgc gacttctacg aggatctgga tcctgacctg caagccatcc tgaagtacgc    900

tgtggaagca gcgagtacca gcaataccgc gttagcgctg aggcagtata gcgcagatct    960

tgcgacgtta gcggctgaaa acggtgttgc agtgcatcgg actccgaaag acatcctgtc   1020

tggtcagctg gaagcatggg acaagctgat cgtggatctc gaagcggatg agttcttcaa   1080

gaaagtgctg gattcccaac gtgcatgggt cgaacaggtc tcctactacg agctgatgaa   1140

cgcagcggat cttggactgg catacgaaca tcattttcca ggaaaattaa aactgggcgg   1200

cagccatcat catcatcatc attaataatg aaagggcgat atccagcaca ctggcggccg   1260

ttactagtgg atccggctgc taacaaagcc cgaaaggaag ctgagttggc tgctgccacc   1320

gctgagcaat aactagcata accccttggg gcctctaaac gggtcttgag gggttttttg   1380

ctgaaaggag gaactatatc cggagcgact cccacggcac gttggcaagc tcg          1433
```

<210> SEQ ID NO 94
<211> LENGTH: 1415
<212> TYPE: DNA
<213> ORGANISM: Artificial Sequence
<220> FEATURE:
<223> OTHER INFORMATION: Exemplary fsLacBP13.188C expression sequence.

<400> SEQUENCE: 94

```
cggtcacgct tgggactgcc ataggctggc ccggtgatgc cggccacgat gcgtccggcg     60
tagaggatcg agatctcgat cccgcgaaat taatacgact cactataggg agaccacaac    120
ggtttccctc tagaaataat tttgtttaac tttaagaagg agatatacca tggaaaaaaa    180
aattcgttgg aaattagcaa tgacttgggg tccgaccttg catccgttgt ccgacacagc    240
agagcatatg gcggaaatcg tgaaggagtt gagcgatggc aacttcgtga tcaacatcga    300
tgcgtcgaac gtgcacaaag cgccgtttgg catcttcgat atggtgaaac tcggtcagta    360
cgagatgggc catactgcga gctactacta caaaggcaaa aacatcgcgt tttaccgct     420
gacgaccatg cctttcggta tgaccgcacc ggaacagtat gcgtggttct actatggtgg    480
cggtctggag ctgatgcagg aagcgtacac caagcatggc atgctggcgt ttcctggtgg    540
taacaccggt aaccagatgg gaggttggtt caccaaggag atcaacagcc tggatgacct    600
caagggtctc aagatgagga tcccaggctt tgcgggccag atcatgtcca aactgggtgt    660
gaccgtgacc aacatccctc caggtgagct gtacaccgca ctggaacgtg gtaccgtgga    720
tgcggtggaa tgcaccggtc ctggtatgga catcaacatg ggattccaca agatcgcgaa    780
atactactat accggttggc atgaaccggg atccgaagtg gagttcctga tcaacgaaaa    840
ggaatacaac aaactgccgg aaaaatacaa aaagatcctg aaaatcgcca tgaaaaccgc    900
agcgtacgac atgtacatcc agtcgtacga gatgaacgct gaagcttggc agcagatgaa    960
agagaaatac ccggatatca aggtcaaggt ttttccggaa gaagtgctga aagagatgaa   1020
gaccgcgtac gacaaccttg tggcgagcta cgagaaagaa agcccgatgt tcaagaaaat   1080
catggagagc aaacgtgcgt atctggacaa ggttcgagac tggacccaca tatcggacta   1140
cctctacctg aaaagtactt ctgaaagtaa tctgaatggc ggcagccatc atcatcatca   1200
tcattaatga taaaagggcg atatccagca cactggcggc cgttactagt ggatccggct   1260
gctaacaaag cccgaaagga agctgagttg gctgctgcca ccgctgagca ataactagca   1320
taaccccttg gggcctctaa acgggtcttg aggggttttt tgctgaaagg aggaactata   1380
tccggagcga ctcccacggc acgttggcaa gctcg                              1415
```

<210> SEQ ID NO 95
<211> LENGTH: 1400
<212> TYPE: DNA
<213> ORGANISM: Artificial Sequence
<220> FEATURE:
<223> OTHER INFORMATION: Exemplary msLacBP6_187C_F68L expression sequence.

<400> SEQUENCE: 95

```
cggtcacgct tgggactgcc ataggctggc ccggtgatgc cggccacgat gcgtccggcg     60
tagaggatcg agatctcgat cccgcgaaat taatacgact cactataggg agaccacaac    120
ggtttccctc tagaaataat tttgtttaac tttaagaagg agatatacca tggcaacaac    180
ttggaaaatt caaagtgtat gggatgcagg gacggtgggc tatgacctct tcaaggagtg    240
gtgcgacggt atggaagaaa agacgggcgg tgaactcaaa ttcacgtgct tcccagccaa    300
agccgtcgcc gcagataata atggtctttt tgatgcagta cggaatggcg tcttgcaagg    360
tatgaatcct ctgaccctct actggtcagg taagattccg gcctccgtat ttctctcgtc    420
gtacccagcc ggtccagatc aaccacatca atgggataca atgttctaca gccttggtat    480
```

```
gttagaaaaa acacgtgaaa tttacaaaaa gttcggcctc ttctacgtcg gcccaattca    540

gcacgacgca aacattatcc acagtaaaca gccgattaat tccctggacg accttaaggg    600

tctcaaaatg cgcttacctg gcgggatggt agcggaagtc tttgcaaagt ttggcgtcgc    660

agcggtcagt ctcccaggca gcgacatctt tccagcctta gaaaaaggca caatcgacgc    720

tgctgattgt gtgggtccgg ctgtaaactg ggagctcggc ttcagccaag taacaaagta    780

catcttaatg ggtccaccag gcatcatgtc agtctaccaa ccggtcgacc ttatggacct    840

cactgtcaat ctgcgggcct ggaacgcatt agatccaaag ttacagcaaa tcgttgaaga    900

tgaagtacgc atctactctc agaagcatta cctcgcaatt cagaaacgga atattgaagc    960

tatgaagaag ttcgaggccg ctggtacaac cgtaacccgt ctgtcacaag aggacctcca   1020

ggagtttcgt cgtgcagcta tcccaatttg gtattcatgg gcaaacaaag atgaagacgc   1080

acgggagatt ttcgacatgc aattagagta catgatgaac gacactgtag gttacatcac   1140

tgaagatgac attaagggca tgaatggcgg ttcacatcat catcatcatc attaatgaaa   1200

gggcgatatc cagcacactg gcggccgtta ctagtggatc cggctgctaa caaagcccga   1260

aaggaagctg agttggctgc tgccaccgct gagcaataac tagcataacc ccttggggcc   1320

tctaaacggg tcttgagggg ttttttgctg aaaggaggaa ctatatccgg agcgactccc   1380

acggcacgtt ggcaagctcg                                                1400
```

```
<210> SEQ ID NO 96
<211> LENGTH: 1400
<212> TYPE: DNA
<213> ORGANISM: Artificial Sequence
<220> FEATURE:
<223> OTHER INFORMATION: Exemplary msLacBP6_187C_F68M expression
      sequence.

<400> SEQUENCE: 96

cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tggcaacaac    180

ttggaaaatt caaagtgtat gggatgcagg gacggtgggc tatgacctct tcaaggagtg    240

gtgcgacggt atggaagaaa agacgggcgg tgaactcaaa ttcacgtgct tcccagccaa    300

agccgtcgcc gcagataata atggtctttt tgatgcagta cggaatggcg tcttgcaagg    360

tatgaatcct atgaccctct actggtcagg taagattccg gcctccgtat ttctctcgtc    420

gtacccagcc ggtccagatc aaccacatca atgggataca atgttctaca gccttggtat    480

gttagaaaaa acacgtgaaa tttacaaaaa gttcggcctc ttctacgtcg gcccaattca    540

gcacgacgca aacattatcc acagtaaaca gccgattaat tccctggacg accttaaggg    600

tctcaaaatg cgcttacctg gcgggatggt agcggaagtc tttgcaaagt ttggcgtcgc    660

agcggtcagt ctcccaggca gcgacatctt tccagcctta gaaaaaggca caatcgacgc    720

tgctgattgt gtgggtccgg ctgtaaactg ggagctcggc ttcagccaag taacaaagta    780

catcttaatg ggtccaccag gcatcatgtc agtctaccaa ccggtcgacc ttatggacct    840

cactgtcaat ctgcgggcct ggaacgcatt agatccaaag ttacagcaaa tcgttgaaga    900

tgaagtacgc atctactctc agaagcatta cctcgcaatt cagaaacgga atattgaagc    960

tatgaagaag ttcgaggccg ctggtacaac cgtaacccgt ctgtcacaag aggacctcca   1020

ggagtttcgt cgtgcagcta tcccaatttg gtattcatgg gcaaacaaag atgaagacgc   1080
```

acgggagatt ttcgacatgc aattagagta catgatgaac gacactgtag gttacatcac 1140
tgaagatgac attaagggca tgaatggcgg ttcacatcat catcatcatc attaatgaaa 1200
gggcgatatc cagcacactg gcggccgtta ctagtggatc cggctgctaa caaagcccga 1260
aaggaagctg agttggctgc tgccaccgct gagcaataac tagcataacc ccttggggcc 1320
tctaaacggg tcttgagggg ttttttgctg aaaggaggaa ctatatccgg agcgactccc 1380
acggcacgtt ggcaagctcg 1400

<210> SEQ ID NO 97
<211> LENGTH: 1400
<212> TYPE: DNA
<213> ORGANISM: Artificial Sequence
<220> FEATURE:
<223> OTHER INFORMATION: Exemplary msLacBP6_187C_L70F expression sequence

<400> SEQUENCE: 97
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tggcaacaac 180
ttggaaaatt caaagtgtat gggatgcagg gacggtgggc tatgacctct tcaaggagtg 240
gtgcgacggt atggaagaaa agacgggcgg tgaactcaaa ttcacgtgct tcccagccaa 300
agccgtcgcc gcagataata atggtctttt tgatgcagta cggaatggcg tcttgcaagg 360
tatgaatcct ttcacctttt actggtcagg taagattccg gcctccgtat ttctctcgtc 420
gtacccagcc ggtccagatc aaccacatca atgggataca atgttctaca gccttggtat 480
gttagaaaaa acacgtgaaa tttacaaaaa gttcggcctc ttctacgtcg gcccaattca 540
gcacgacgca aacattatcc acagtaaaca gccgattaat tccctggacg accttaaggg 600
tctcaaaatg cgcttacctg gcgggatggt agcggaagtc tttgcaaagt ttggcgtcgc 660
agcggtcagt ctcccaggca gcgacatctt tccagcctta gaaaaaggca caatcgacgc 720
tgctgattgt gtgggtccgg ctgtaaactg ggagctcggc ttcagccaag taacaaagta 780
catcttaatg ggtccaccag gcatcatgtc agtctaccaa ccggtcgacc ttatggacct 840
cactgtcaat ctgcgggcct ggaacgcatt agatccaaag ttacagcaaa tcgttgaaga 900
tgaagtacgc atctactctc agaagcatta cctcgcaatt cagaaacgga atattgaagc 960
tatgaagaag ttcgaggccg ctggtacaac cgtaacccgt ctgtcacaag aggacctcca 1020
ggagtttcgt cgtgcagcta tcccaatttg gtattcatgg gcaaacaaag atgaagacgc 1080
acgggagatt ttcgacatgc aattagagta catgatgaac gacactgtag gttacatcac 1140
tgaagatgac attaagggca tgaatggcgg ttcacatcat catcatcatc attaatgaaa 1200
gggcgatatc cagcacactg gcggccgtta ctagtggatc cggctgctaa caaagcccga 1260
aaggaagctg agttggctgc tgccaccgct gagcaataac tagcataacc ccttggggcc 1320
tctaaacggg tcttgagggg ttttttgctg aaaggaggaa ctatatccgg agcgactccc 1380
acggcacgtt ggcaagctcg 1400

<210> SEQ ID NO 98
<211> LENGTH: 1400
<212> TYPE: DNA
<213> ORGANISM: Artificial Sequence
<220> FEATURE:
<223> OTHER INFORMATION: Exemplary msLacBP6_187C_L70I expression sequence.

<400> SEQUENCE: 98
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tggcaacaac 180
ttggaaaatt caaagtgtat gggatgcagg gacggtgggc tatgacctct tcaaggagtg 240
gtgcgacggt atggaagaaa agacgggcgg tgaactcaaa ttcacgtgct tcccagccaa 300
agccgtcgcc gcagataata atggtctttt tgatgcagta cggaatggcg tcttgcaagg 360
tatgaatcct ttcaccattt actggtcagg taagattccg gcctccgtat ttctctcgtc 420
gtacccagcc ggtccagatc aaccacatca atgggataca atgttctaca gccttggtat 480
gttagaaaaa acacgtgaaa tttacaaaaa gttcggcctc ttctacgtcg gcccaattca 540
gcacgacgca aacattatcc acagtaaaca gccgattaat tccctggacg accttaaggg 600
tctcaaaatg cgcttacctg gcgggatggt agcggaagtc tttgcaaagt ttggcgtcgc 660
agcggtcagt ctcccaggca gcgacatctt tccagcctta gaaaaaggca caatcgacgc 720
tgctgattgt gtgggtccgg ctgtaaactg ggagctcggc ttcagccaag taacaaagta 780
catcttaatg ggtccaccag gcatcatgtc agtctaccaa ccggtcgacc ttatggacct 840
cactgtcaat ctgcgggcct ggaacgcatt agatccaaag ttacagcaaa tcgttgaaga 900
tgaagtacgc atctactctc agaagcatta cctcgcaatt cagaaacgga atattgaagc 960
tatgaagaag ttcgaggccg ctggtacaac cgtaacccgt ctgtcacaag aggacctcca 1020
ggagtttcgt cgtgcagcta tcccaatttg gtattcatgg gcaaacaaag atgaagacgc 1080
acgggagatt ttcgacatgc aattagagta catgatgaac gacactgtag gttacatcac 1140
tgaagatgac attaagggca tgaatggcgg ttcacatcat catcatcatc attaatgaaa 1200
gggcgatatc cagcacactg gcggccgtta ctagtggatc cggctgctaa caaagcccga 1260
aaggaagctg agttggctgc tgccaccgct gagcaataac tagcataacc ccttggggcc 1320
tctaaacggg tcttgagggg ttttttgctg aaaggaggaa ctatatccgg agcgactccc 1380
acggcacgtt ggcaagctcg 1400

<210> SEQ ID NO 99
<211> LENGTH: 1400
<212> TYPE: DNA
<213> ORGANISM: Artificial Sequence
<220> FEATURE:
<223> OTHER INFORMATION: Exemplary msLacBP6_187C_L70M expression
sequence.

<400> SEQUENCE: 99
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tggcaacaac 180
ttggaaaatt caaagtgtat gggatgcagg gacggtgggc tatgacctct tcaaggagtg 240
gtgcgacggt atggaagaaa agacgggcgg tgaactcaaa ttcacgtgct tcccagccaa 300
agccgtcgcc gcagataata atggtctttt tgatgcagta cggaatggcg tcttgcaagg 360
tatgaatcct ttcaccatgt actggtcagg taagattccg gcctccgtat ttctctcgtc 420
gtacccagcc ggtccagatc aaccacatca atgggataca atgttctaca gccttggtat 480
gttagaaaaa acacgtgaaa tttacaaaaa gttcggcctc ttctacgtcg gcccaattca 540
gcacgacgca aacattatcc acagtaaaca gccgattaat tccctggacg accttaaggg 600
tctcaaaatg cgcttacctg gcgggatggt agcggaagtc tttgcaaagt ttggcgtcgc 660
agcggtcagt ctcccaggca gcgacatctt tccagcctta gaaaaaggca caatcgacgc 720
tgctgattgt gtgggtccgg ctgtaaactg ggagctcggc ttcagccaag taacaaagta 780
catcttaatg ggtccaccag gcatcatgtc agtctaccaa ccggtcgacc ttatggacct 840
cactgtcaat ctgcgggcct ggaacgcatt agatccaaag ttacagcaaa tcgttgaaga 900
tgaagtacgc atctactctc agaagcatta cctcgcaatt cagaaacgga atattgaagc 960
tatgaagaag ttcgaggccg ctggtacaac cgtaacccgt ctgtcacaag aggacctcca 1020
ggagtttcgt cgtgcagcta tcccaatttg gtattcatgg gcaaacaaag atgaagacgc 1080
acgggagatt ttcgacatgc aattagagta catgatgaac gacactgtag gttacatcac 1140
tgaagatgac attaagggca tgaatggcgg ttcacatcat catcatcatc attaatgaaa 1200
gggcgatatc cagcacactg gcggccgtta ctagtggatc cggctgctaa caaagcccga 1260
aaggaagctg agttggctgc tgccaccgct gagcaataac tagcataacc ccttggggcc 1320
tctaaacggg tcttgagggg ttttttgctg aaaggaggaa ctatatccgg agcgactccc 1380
acggcacgtt ggcaagctcg 1400

<210> SEQ ID NO 100
<211> LENGTH: 1400
<212> TYPE: DNA
<213> ORGANISM: Artificial Sequence
<220> FEATURE:
<223> OTHER INFORMATION: Exemplary msLacBP6_187C_P150A expression sequence.

<400> SEQUENCE: 100
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tggcaacaac 180
ttggaaaatt caaagtgtat gggatgcagg gacggtgggc tatgacctct tcaaggagtg 240
gtgcgacggt atggaagaaa agacgggcgg tgaactcaaa ttcacgtgct tcccagccaa 300
agccgtcgcc gcagataata atggtctttt tgatgcagta cggaatggcg tcttgcaagg 360
tatgaatcct ttcaccctct actggtcagg taagattccg gcctccgtat ttctctcgtc 420
gtacccagcc ggtccagatc aaccacatca atgggataca atgttctaca gccttggtat 480
gttagaaaaa acacgtgaaa tttacaaaaa gttcggcctc ttctacgtcg gcccaattca 540
gcacgacgca aacattatcc acagtaaaca gccgattaat tccctggacg accttaaggg 600
tctcaaaatg cgcttagcgg gcgggatggt agcggaagtc tttgcaaagt ttggcgtcgc 660
agcggtcagt ctcccaggca gcgacatctt tccagcctta gaaaaaggca caatcgacgc 720
tgctgattgt gtgggtccgg ctgtaaactg ggagctcggc ttcagccaag taacaaagta 780
catcttaatg ggtccaccag gcatcatgtc agtctaccaa ccggtcgacc ttatggacct 840
cactgtcaat ctgcgggcct ggaacgcatt agatccaaag ttacagcaaa tcgttgaaga 900
tgaagtacgc atctactctc agaagcatta cctcgcaatt cagaaacgga atattgaagc 960
tatgaagaag ttcgaggccg ctggtacaac cgtaacccgt ctgtcacaag aggacctcca 1020
ggagtttcgt cgtgcagcta tcccaatttg gtattcatgg gcaaacaaag atgaagacgc 1080

```
acgggagatt ttcgacatgc aattagagta catgatgaac gacactgtag gttacatcac   1140

tgaagatgac attaagggca tgaatggcgg ttcacatcat catcatcatc attaatgaaa   1200

gggcgatatc cagcacactg gcggccgtta ctagtggatc cggctgctaa caaagcccga   1260

aaggaagctg agttggctgc tgccaccgct gagcaataac tagcataacc ccttggggcc   1320

tctaaacggg tcttgagggg ttttttgctg aaaggaggaa ctatatccgg agcgactccc   1380

acggcacgtt ggcaagctcg                                               1400
```

<210> SEQ ID NO 101
<211> LENGTH: 1400
<212> TYPE: DNA
<213> ORGANISM: Artificial Sequence
<220> FEATURE:
<223> OTHER INFORMATION: Exemplary msLacBP6_187C_P150S expression sequence.

<400> SEQUENCE: 101

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tggcaacaac    180

ttggaaaatt caaagtgtat gggatgcagg gacggtgggc tatgacctct tcaaggagtg    240

gtgcgacggt atggaagaaa agacgggcgg tgaactcaaa ttcacgtgct tcccagccaa    300

agccgtcgcc gcagataata atggtctttt tgatgcagta cggaatggcg tcttgcaagg    360

tatgaatcct ttcaccctct actggtcagg taagattccg gcctccgtat ttctctcgtc    420

gtacccagcc ggtccagatc aaccacatca atgggataca atgttctaca gccttggtat    480

gttagaaaaa acacgtgaaa tttacaaaaa gttcggcctc ttctacgtcg gcccaattca    540

gcacgacgca aacattatcc acagtaaaca gccgattaat tccctggacg accttaaggg    600

tctcaaaatg cgcttaagcg gcgggatggt agcggaagtc tttgcaaagt ttggcgtcgc    660

agcggtcagt ctcccaggca gcgacatctt tccagcctta gaaaaaggca caatcgacgc    720

tgctgattgt gtgggtccgg ctgtaaactg ggagctcggc ttcagccaag taacaaagta    780

catcttaatg ggtccaccag gcatcatgtc agtctaccaa ccggtcgacc ttatggacct    840

cactgtcaat ctgcgggcct ggaacgcatt agatccaaag ttacagcaaa tcgttgaaga    900

tgaagtacgc atctactctc agaagcatta cctcgcaatt cagaaacgga atattgaagc    960

tatgaagaag ttcgaggccg ctggtacaac cgtaacccgt ctgtcacaag aggacctcca   1020

ggagtttcgt cgtgcagcta tcccaatttg gtattcatgg gcaaacaaag atgaagacgc   1080

acgggagatt ttcgacatgc aattagagta catgatgaac gacactgtag gttacatcac   1140

tgaagatgac attaagggca tgaatggcgg ttcacatcat catcatcatc attaatgaaa   1200

gggcgatatc cagcacactg gcggccgtta ctagtggatc cggctgctaa caaagcccga   1260

aaggaagctg agttggctgc tgccaccgct gagcaataac tagcataacc ccttggggcc   1320

tctaaacggg tcttgagggg ttttttgctg aaaggaggaa ctatatccgg agcgactccc   1380

acggcacgtt ggcaagctcg                                               1400
```

<210> SEQ ID NO 102
<211> LENGTH: 1400
<212> TYPE: DNA
<213> ORGANISM: Artificial Sequence
<220> FEATURE:
<223> OTHER INFORMATION: Exemplary msLacBP6_187C_D220E expression sequence.

<400> SEQUENCE: 102
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tggcaacaac 180
ttggaaaatt caaagtgtat gggatgcagg gacggtgggc tatgacctct tcaaggagtg 240
gtgcgacggt atggaagaaa agacgggcgg tgaactcaaa ttcacgtgct tcccagccaa 300
agccgtcgcc gcagataata atggtctttt tgatgcagta cggaatggcg tcttgcaagg 360
tatgaatcct ttcaccctct actggtcagg taagattccg gcctccgtat ttctctcgtc 420
gtacccagcc ggtccagatc aaccacatca atgggataca atgttctaca gccttggtat 480
gttagaaaaa acacgtgaaa tttacaaaaa gttcggcctc ttctacgtcg gcccaattca 540
gcacgacgca aacattatcc acagtaaaca gccgattaat tccctggacg accttaaggg 600
tctcaaaatg cgcttacctg gcgggatggt agcggaagtc tttgcaaagt ttggcgtcgc 660
agcggtcagt ctcccaggca gcgacatctt tccagcctta gaaaaaggca caatcgacgc 720
tgctgattgt gtgggtccgg ctgtaaactg ggagctcggc ttcagccaag taacaaagta 780
catcttaatg ggtccaccag gcatcatgtc agtctaccaa ccggtcgaac ttatggacct 840
cactgtcaat ctgcgggcct ggaacgcatt agatccaaag ttacagcaaa tcgttgaaga 900
tgaagtacgc atctactctc agaagcatta cctcgcaatt cagaaacgga atattgaagc 960
tatgaagaag ttcgaggccg ctggtacaac cgtaacccgt ctgtcacaag aggacctcca 1020
ggagtttcgt cgtgcagcta tcccaatttg gtattcatgg gcaaacaaag atgaagacgc 1080
acgggagatt ttcgacatgc aattagagta catgatgaac gacactgtag gttacatcac 1140
tgaagatgac attaagggca tgaatggcgg ttcacatcat catcatcatc attaatgaaa 1200
gggcgatatc cagcacactg gcggccgtta ctagtggatc cggctgctaa caaagcccga 1260
aaggaagctg agttggctgc tgccaccgct gagcaataac tagcataacc ccttggggcc 1320
tctaaacggg tcttgagggg ttttttgctg aaaggaggaa ctatatccgg agcgactccc 1380
acggcacgtt ggcaagctcg 1400

<210> SEQ ID NO 103
<211> LENGTH: 1400
<212> TYPE: DNA
<213> ORGANISM: Artificial Sequence
<220> FEATURE:
<223> OTHER INFORMATION: Exemplary msLacBP6_187C_D220L expression sequence.

<400> SEQUENCE: 103
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tggcaacaac 180
ttggaaaatt caaagtgtat gggatgcagg gacggtgggc tatgacctct tcaaggagtg 240
gtgcgacggt atggaagaaa agacgggcgg tgaactcaaa ttcacgtgct tcccagccaa 300
agccgtcgcc gcagataata atggtctttt tgatgcagta cggaatggcg tcttgcaagg 360
tatgaatcct ttcaccctct actggtcagg taagattccg gcctccgtat ttctctcgtc 420
gtacccagcc ggtccagatc aaccacatca atgggataca atgttctaca gccttggtat 480
gttagaaaaa acacgtgaaa tttacaaaaa gttcggcctc ttctacgtcg gcccaattca 540

```
gcacgacgca aacattatcc acagtaaaca gccgattaat tccctggacg accttaaggg    600

tctcaaaatg cgcttacctg gcgggatggt agcggaagtc tttgcaaagt ttggcgtcgc    660

agcggtcagt ctcccaggca gcgacatctt tccagcctta gaaaaaggca caatcgacgc    720

tgctgattgt gtgggtccgg ctgtaaactg ggagctcggc ttcagccaag taacaaagta    780

catcttaatg ggtccaccag gcatcatgtc agtctaccaa ccggtcctgc ttatggacct    840

cactgtcaat ctgcgggcct ggaacgcatt agatccaaag ttacagcaaa tcgttgaaga    900

tgaagtacgc atctactctc agaagcatta cctcgcaatt cagaaacgga atattgaagc    960

tatgaagaag ttcgaggccg ctggtacaac cgtaacccgt ctgtcacaag aggacctcca   1020

ggagtttcgt cgtgcagcta tcccaatttg gtattcatgg gcaaacaaag atgaagacgc   1080

acgggagatt ttcgacatgc aattagagta catgatgaac gacactgtag gttacatcac   1140

tgaagatgac attaagggca tgaatggcgg ttcacatcat catcatcatc attaatgaaa   1200

gggcgatatc cagcacactg gcggccgtta ctagtggatc cggctgctaa caaagcccga   1260

aaggaagctg agttggctgc tgccaccgct gagcaataac tagcataacc ccttggggcc   1320

tctaaacggg tcttgagggg ttttttgctg aaaggaggaa ctatatccgg agcgactccc   1380

acggcacgtt ggcaagctcg                                               1400
```

<210> SEQ ID NO 104
<211> LENGTH: 1400
<212> TYPE: DNA
<213> ORGANISM: Artificial Sequence
<220> FEATURE:
<223> OTHER INFORMATION: Exemplary msLacBP6_187C_D220N expression sequence.

<400> SEQUENCE: 104

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tggcaacaac    180

ttggaaaatt caaagtgtat gggatgcagg gacggtgggc tatgacctct tcaaggagtg    240

gtgcgacggt atggaagaaa agacgggcgg tgaactcaaa ttcacgtgct tcccagccaa    300

agccgtcgcc gcagataata atggtctttt tgatgcagta cggaatggcg tcttgcaagg    360

tatgaatcct ttcaccctct actggtcagg taagattccg gcctccgtat ttctctcgtc    420

gtacccagcc ggtccagatc aaccacatca atgggataca atgttctaca gccttggtat    480

gttagaaaaa acacgtgaaa tttacaaaaa gttcggcctc ttctacgtcg gcccaattca    540

gcacgacgca aacattatcc acagtaaaca gccgattaat tccctggacg accttaaggg    600

tctcaaaatg cgcttacctg gcgggatggt agcggaagtc tttgcaaagt ttggcgtcgc    660

agcggtcagt ctcccaggca gcgacatctt tccagcctta gaaaaaggca caatcgacgc    720

tgctgattgt gtgggtccgg ctgtaaactg ggagctcggc ttcagccaag taacaaagta    780

catcttaatg ggtccaccag gcatcatgtc agtctaccaa ccggtcaacc ttatggacct    840

cactgtcaat ctgcgggcct ggaacgcatt agatccaaag ttacagcaaa tcgttgaaga    900

tgaagtacgc atctactctc agaagcatta cctcgcaatt cagaaacgga atattgaagc    960

tatgaagaag ttcgaggccg ctggtacaac cgtaacccgt ctgtcacaag aggacctcca   1020

ggagtttcgt cgtgcagcta tcccaatttg gtattcatgg gcaaacaaag atgaagacgc   1080

acgggagatt ttcgacatgc aattagagta catgatgaac gacactgtag gttacatcac   1140
```

```
tgaagatgac attaagggca tgaatggcgg ttcacatcat catcatcatc attaatgaaa   1200

gggcgatatc cagcacactg gcggccgtta ctagtggatc cggctgctaa caaagcccga   1260

aaggaagctg agttggctgc tgccaccgct gagcaataac tagcataacc ccttggggcc   1320

tctaaacggg tcttgagggg ttttttgctg aaaggaggaa ctatatccgg agcgactccc   1380

acggcacgtt ggcaagctcg                                               1400
```

<210> SEQ ID NO 105
<211> LENGTH: 1400
<212> TYPE: DNA
<213> ORGANISM: Artificial Sequence
<220> FEATURE:
<223> OTHER INFORMATION: Exemplary msLacBP6_187C_D220Q expression sequence.

<400> SEQUENCE: 105

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tggcaacaac    180

ttggaaaatt caaagtgtat gggatgcagg gacggtgggc tatgacctct tcaaggagtg    240

gtgcgacggt atggaagaaa agacgggcgg tgaactcaaa ttcacgtgct tcccagccaa    300

agccgtcgcc gcagataata atggtctttt tgatgcagta cggaatggcg tcttgcaagg    360

tatgaatcct ttcaccctct actggtcagg taagattccg gcctccgtat ttctctcgtc    420

gtacccagcc ggtccagatc aaccacatca atgggataca atgttctaca gccttggtat    480

gttagaaaaa acacgtgaaa tttacaaaaa gttcggcctc ttctacgtcg gcccaattca    540

gcacgacgca aacattatcc acagtaaaca gccgattaat tccctggacg accttaaggg    600

tctcaaaatg cgcttacctg gcgggatggt agcggaagtc tttgcaaagt ttggcgtcgc    660

agcggtcagt ctcccaggca gcgacatctt tccagcctta gaaaaaggca caatcgacgc    720

tgctgattgt gtgggtccgg ctgtaaactg ggagctcggc ttcagccaag taacaaagta    780

catcttaatg ggtccaccag gcatcatgtc agtctaccaa ccggtccagc ttatggacct    840

cactgtcaat ctgcgggcct ggaacgcatt agatccaaag ttacagcaaa tcgttgaaga    900

tgaagtacgc atctactctc agaagcatta cctcgcaatt cagaaacgga atattgaagc    960

tatgaagaag ttcgaggccg ctggtacaac cgtaacccgt ctgtcacaag aggacctcca   1020

ggagtttcgt cgtgcagcta tcccaatttg gtattcatgg gcaaacaaag atgaagacgc   1080

acgggagatt ttcgacatgc aattagagta catgatgaac gacactgtag gttacatcac   1140

tgaagatgac attaagggca tgaatggcgg ttcacatcat catcatcatc attaatgaaa   1200

gggcgatatc cagcacactg gcggccgtta ctagtggatc cggctgctaa caaagcccga   1260

aaggaagctg agttggctgc tgccaccgct gagcaataac tagcataacc ccttggggcc   1320

tctaaacggg tcttgagggg ttttttgctg aaaggaggaa ctatatccgg agcgactccc   1380

acggcacgtt ggcaagctcg                                               1400
```

<210> SEQ ID NO 106
<211> LENGTH: 1400
<212> TYPE: DNA
<213> ORGANISM: Artificial Sequence
<220> FEATURE:
<223> OTHER INFORMATION: Exemplary msLacBP6_187C_D220S expression sequence.

<400> SEQUENCE: 106
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tggcaacaac 180
ttggaaaatt caaagtgtat gggatgcagg gacggtgggc tatgacctct tcaaggagtg 240
gtgcgacggt atggaagaaa agacgggcgg tgaactcaaa ttcacgtgct tcccagccaa 300
agccgtcgcc gcagataata atggtctttt tgatgcagta cggaatggcg tcttgcaagg 360
tatgaatcct ttcaccctct actggtcagg taagattccg gcctccgtat ttctctcgtc 420
gtacccagcc ggtccagatc aaccacatca atgggataca atgttctaca gccttggtat 480
gttagaaaaa acacgtgaaa tttacaaaaa gttcggcctc ttctacgtcg gcccaattca 540
gcacgacgca aacattatcc acagtaaaca gccgattaat tccctggacg accttaaggg 600
tctcaaaatg cgcttacctg gcgggatggt agcggaagtc tttgcaaagt ttggcgtcgc 660
agcggtcagt ctcccaggca gcgacatctt tccagcctta gaaaaaggca caatcgacgc 720
tgctgattgt gtgggtccgg ctgtaaactg ggagctcggc ttcagccaag taacaaagta 780
catcttaatg ggtccaccag gcatcatgtc agtctaccaa ccggtcagcc ttatggacct 840
cactgtcaat ctgcgggcct ggaacgcatt agatccaaag ttacagcaaa tcgttgaaga 900
tgaagtacgc atctactctc agaagcatta cctcgcaatt cagaaacgga atattgaagc 960
tatgaagaag ttcgaggccg ctggtacaac cgtaacccgt ctgtcacaag aggacctcca 1020
ggagtttcgt cgtgcagcta tcccaatttg gtattcatgg gcaaacaaag atgaagacgc 1080
acgggagatt ttcgacatgc aattagagta catgatgaac gacactgtag gttacatcac 1140
tgaagatgac attaagggca tgaatggcgg ttcacatcat catcatcatc attaatgaaa 1200
gggcgatatc cagcacactg gcggccgtta ctagtggatc cggctgctaa caaagcccga 1260
aaggaagctg agttggctgc tgccaccgct gagcaataac tagcataacc ccttggggcc 1320
tctaaacggg tcttgagggg ttttttgctg aaaggaggaa ctatatccgg agcgactccc 1380
acggcacgtt ggcaagctcg 1400

<210> SEQ ID NO 107
<211> LENGTH: 1463
<212> TYPE: DNA
<213> ORGANISM: Artificial Sequence
<220> FEATURE:
<223> OTHER INFORMATION: Exemplary msLacBP6_187C_bZifC expression sequence.

<400> SEQUENCE: 107
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tggcaacaac 180
ttggaaaatt caaagtgtat gggatgcagg gacggtgggc tatgacctct tcaaggagtg 240
gtgcgacggt atggaagaaa agacgggcgg tgaactcaaa ttcacgtgct tcccagccaa 300
agccgtcgcc gcagataata atggtctttt tgatgcagta cggaatggcg tcttgcaagg 360
tatgaatcct ttcaccctct actggtcagg taagattccg gcctccgtat ttctctcgtc 420
gtacccagcc ggtccagatc aaccacatca atgggataca atgttctaca gccttggtat 480
gttagaaaaa acacgtgaaa tttacaaaaa gttcggcctc ttctacgtcg gcccaattca 540

```
gcacgacgca aacattatcc acagtaaaca gccgattaat tccctggacg accttaaggg    600

tctcaaaatg cgcttacctg gcgggatggt agcggaagtc tttgcaaagt ttggcgtcgc    660

agcggtcagt ctcccaggca gcgacatctt tccagcctta gaaaaaggca caatcgacgc    720

tgctgattgt gtgggtccgg ctgtaaactg ggagctcggc ttcagccaag taacaaagta    780

catcttaatg ggtccaccag gcatcatgtc agtctaccaa ccggtcgacc ttatggacct    840

cactgtcaat ctgcgggcct ggaacgcatt agatccaaag ttacagcaaa tcgttgaaga    900

tgaagtacgc atctactctc agaagcatta cctcgcaatt cagaaacgga atattgaagc    960

tatgaagaag ttcgaggccg ctggtacaac cgtaacccgt ctgtcacaag aggacctcca   1020

ggagtttcgt cgtgcagcta tcccaatttg gtattcatgg gcaaacaaag atgaagacgc   1080

acgggagatt ttcgacatgc aattagagta catgatgaac gacactgtag gttacatcac   1140

tgaagatgac attaagggca tgaatggcgg cagcaccggc gaaaaaccgt ataaatgtcc   1200

ggaatgtggc aaaagcttta gccgcagcgg cggttcacat catcatcatc atcattaatg   1260

aaagggcgat atccagcaca ctggcggccg ttactagtgg atccggctgc taacaaagcc   1320

cgaaaggaag ctgagttggc tgctgccacc gctgagcaat aactagcata accccttggg   1380

gcctctaaac gggtcttgag gggttttttg ctgaaaggag gaactatatc cggagcgact   1440

cccacggcac gttggcaagc tcg                                           1463
```

<210> SEQ ID NO 108
<211> LENGTH: 1463
<212> TYPE: DNA
<213> ORGANISM: Artificial Sequence
<220> FEATURE:
<223> OTHER INFORMATION: Exemplary msLacBP6_188C_bZifC expression sequence.

<400> SEQUENCE: 108

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tggcaacaac    180

ttggaaaatt caaagtgtat gggatgcagg gacggtgggc tatgacctct tcaaggagtg    240

gtgcgacggt atggaagaaa agacgggcgg tgaactcaaa ttcacgtgct tcccagccaa    300

agccgtcgcc gcagataata atggtctttt tgatgcagta cggaatggcg tcttgcaagg    360

tatgaatcct ttcaccctct actggtcagg taagattccg gcctccgtat ttctctcgtc    420

gtacccagcc ggtccagatc aaccacatca atgggataca atgttctaca gccttggtat    480

gttagaaaaa acacgtgaaa tttacaaaaa gttcggcctc ttctacgtcg gcccaattca    540

gcacgacgca aacattatcc acagtaaaca gccgattaat tccctggacg accttaaggg    600

tctcaaaatg cgcttacctg gcgggatggt agcggaagtc tttgcaaagt ttggcgtcgc    660

agcggtcagt ctcccaggca gcgacatctt tccagcctta gaaaaaggca caatcgacgc    720

tgctgattac tgtggtccgg ctgtaaactg ggagctcggc ttcagccaag taacaaagta    780

catcttaatg ggtccaccag gcatcatgtc agtctaccaa ccggtcgacc ttatggacct    840

cactgtcaat ctgcgggcct ggaacgcatt agatccaaag ttacagcaaa tcgttgaaga    900

tgaagtacgc atctactctc agaagcatta cctcgcaatt cagaaacgga atattgaagc    960

tatgaagaag ttcgaggccg ctggtacaac cgtaacccgt ctgtcacaag aggacctcca   1020

ggagtttcgt cgtgcagcta tcccaatttg gtattcatgg gcaaacaaag atgaagacgc   1080
```

-continued

```
acgggagatt ttcgacatgc aattagagta catgatgaac gacactgtag gttacatcac   1140

tgaagatgac attaagggca tgaatggcgg cagcaccggc gaaaaaccgt ataaatgtcc   1200

ggaatgtggc aaaagcttta gccgcagcgg cggttcacat catcatcatc atcattaatg   1260

aaagggcgat atccagcaca ctggcggccg ttactagtgg atccggctgc taacaaagcc   1320

cgaaaggaag ctgagttggc tgctgccacc gctgagcaat aactagcata accccttggg   1380

gcctctaaac gggtcttgag gggttttttg ctgaaaggag gaactatatc cggagcgact   1440

cccacggcac gttggcaagc tcg                                           1463
```

```
<210> SEQ ID NO 109
<211> LENGTH: 18
<212> TYPE: PRT
<213> ORGANISM: Artificial Sequence
<220> FEATURE:
<223> OTHER INFORMATION: bZif

<400> SEQUENCE: 109

Thr Gly Glu Lys Pro Tyr Lys Cys Pro Glu Cys Gly Lys Ser Phe Ser
1               5                   10                  15

Arg Ser


<210> SEQ ID NO 110
<211> LENGTH: 32
<212> TYPE: PRT
<213> ORGANISM: Artificial Sequence
<220> FEATURE:
<223> OTHER INFORMATION: ZF-QNK

<400> SEQUENCE: 110

Thr Gly Glu Lys Pro Tyr Lys Cys Pro Glu Cys Gly Lys Ser Phe Ser
1               5                   10                  15

Arg Ser Asp His Leu Ser Arg His Gln Arg Thr His Gln Asn Lys Lys
            20                  25                  30


<210> SEQ ID NO 111
<211> LENGTH: 6
<212> TYPE: PRT
<213> ORGANISM: Artificial Sequence
<220> FEATURE:
<223> OTHER INFORMATION: Hexahistidine Tag

<400> SEQUENCE: 111

His His His His His His
1               5


<210> SEQ ID NO 112
<211> LENGTH: 6
<212> TYPE: PRT
<213> ORGANISM: Artificial Sequence
<220> FEATURE:
<223> OTHER INFORMATION: Hexalysine Tag

<400> SEQUENCE: 112

Lys Lys Lys Lys Lys Lys
1               5


<210> SEQ ID NO 113
<211> LENGTH: 9
<212> TYPE: PRT
<213> ORGANISM: Artificial Sequence
<220> FEATURE:
<223> OTHER INFORMATION: GGSHHHHHH
```

<400> SEQUENCE: 113

Gly Gly Ser His His His His His His
1               5

<210> SEQ ID NO 114
<211> LENGTH: 309
<212> TYPE: PRT
<213> ORGANISM: Artificial Sequence
<220> FEATURE:
<223> OTHER INFORMATION: E. coli GGBP (with signal peptide removed)

<400> SEQUENCE: 114

Ala Asp Thr Arg Ile Gly Val Thr Ile Tyr Lys Tyr Asp Asp Asn Phe
1               5                   10                  15

Met Ser Val Val Arg Lys Ala Ile Glu Gln Asp Ala Lys Ala Ala Pro
            20                  25                  30

Asp Val Gln Leu Leu Met Asn Asp Ser Gln Asn Asp Gln Ser Lys Gln
        35                  40                  45

Asn Asp Gln Ile Asp Val Leu Leu Ala Lys Gly Val Lys Ala Leu Ala
    50                  55                  60

Ile Asn Leu Val Asp Pro Ala Ala Ala Gly Thr Val Ile Glu Lys Ala
65                  70                  75                  80

Arg Gly Gln Asn Val Pro Val Val Phe Phe Asn Lys Glu Pro Ser Arg
                85                  90                  95

Lys Ala Leu Asp Ser Tyr Asp Lys Ala Tyr Tyr Val Gly Thr Asp Ser
            100                 105                 110

Lys Glu Ser Gly Ile Ile Gln Gly Asp Leu Ile Ala Lys His Trp Ala
        115                 120                 125

Ala Asn Gln Gly Trp Asp Leu Asn Lys Asp Gly Gln Ile Gln Phe Val
    130                 135                 140

Leu Leu Lys Gly Glu Pro Gly His Pro Asp Ala Glu Ala Arg Thr Thr
145                 150                 155                 160

Tyr Val Ile Lys Glu Leu Asn Asp Lys Gly Ile Lys Thr Glu Gln Leu
                165                 170                 175

Gln Leu Asp Thr Ala Met Trp Asp Thr Ala Gln Ala Lys Asp Lys Met
            180                 185                 190

Asp Ala Trp Leu Ser Gly Pro Asn Ala Asn Lys Ile Glu Val Val Ile
        195                 200                 205

Ala Asn Asn Asp Ala Met Ala Met Gly Ala Val Glu Ala Leu Lys Ala
    210                 215                 220

His Asn Lys Ser Ser Ile Pro Val Phe Gly Val Asp Ala Leu Pro Glu
225                 230                 235                 240

Ala Leu Ala Leu Val Lys Ser Gly Ala Leu Ala Gly Thr Val Leu Asn
                245                 250                 255

Asp Ala Asn Asn Gln Ala Lys Ala Thr Phe Asp Leu Ala Lys Asn Gln
            260                 265                 270

Ala Asp Gly Lys Gly Ala Ala Asp Gly Thr Asn Trp Lys Ile Asp Asn
        275                 280                 285

Lys Val Val Arg Val Pro Tyr Val Gly Val Asp Lys Asp Asn Leu Ala
    290                 295                 300

Glu Phe Ser Lys Lys
305

<210> SEQ ID NO 115
<211> LENGTH: 340
<212> TYPE: PRT

<213> ORGANISM: Artificial Sequence
<220> FEATURE:
<223> OTHER INFORMATION: ttLacPB1 (with signal peptide replaced with M)

<400> SEQUENCE: 115

```
Met Phe Ser Pro Leu Ala Val Ala Gln Ala Arg Arg Tyr Arg Trp Arg
1               5                   10                  15

Ile Gln Thr Ala Trp Asp Ala Gly Thr Val Gly Tyr Ser Leu Phe Gln
            20                  25                  30

Lys Phe Thr Glu Arg Val Lys Glu Leu Thr Asp Gly Gln Leu Glu Val
        35                  40                  45

Gln Pro Phe Pro Ala Gly Ala Val Val Gly Thr Phe Asp Met Phe Asp
    50                  55                  60

Ala Val Lys Thr Gly Val Leu Asp Gly Met Asn Pro Phe Thr Leu Tyr
65                  70                  75                  80

Trp Ala Gly Arg Met Pro Val Thr Ala Phe Leu Ser Ser Tyr Ala Leu
                85                  90                  95

Gly Leu Asp Arg Pro Asp Gln Trp Glu Thr Trp Phe Tyr Ser Leu Gly
            100                 105                 110

Gly Leu Asp Ile Ala Arg Arg Ala Phe Ala Glu Gln Gly Leu Phe Tyr
        115                 120                 125

Val Gly Pro Val Gln His Asp Leu Asn Ile Ile His Ser Lys Lys Pro
    130                 135                 140

Ile Arg Arg Phe Glu Asp Phe Lys Gly Val Lys Leu Arg Val Pro Gly
145                 150                 155                 160

Gly Met Ile Ala Glu Val Phe Ala Ala Ala Gly Ala Ser Thr Val Leu
                165                 170                 175

Leu Pro Gly Gly Glu Val Tyr Pro Ala Leu Glu Arg Gly Val Ile Asp
            180                 185                 190

Ala Ala Asp Phe Val Gly Pro Ala Val Asn Tyr Asn Leu Gly Phe His
        195                 200                 205

Gln Val Ala Lys Tyr Ile Ile Met Gly Pro Pro Glu Thr Pro Ala Ile
    210                 215                 220

His Gln Pro Val Asp Leu Met Asp Phe Thr Ile Asn Leu Asn Arg Trp
225                 230                 235                 240

Arg Ser Leu Pro Lys Pro Leu Gln Glu Arg Phe Ile Ala Ala Val His
                245                 250                 255

Glu Tyr Ser Trp Ile His Tyr Ala Gly Ile Gln Lys Ala Asn Leu Glu
            260                 265                 270

Ala Trp Pro Lys Tyr Arg Gln Ala Gly Val Glu Val Ile Arg Leu Ser
        275                 280                 285

Asn Glu Asp Val Arg Lys Phe Arg Arg Leu Ala Ile Pro Ile Trp Phe
    290                 295                 300

Lys Trp Ala Lys Met Asp Lys Tyr Ser Arg Glu Ala Phe Ala Ser Gln
305                 310                 315                 320

Leu Glu Tyr Met Lys Gly Ile Gly Tyr Val Thr Asp Glu Glu Leu Lys
                325                 330                 335

Gly Leu Ser Leu
            340
```

<210> SEQ ID NO 116
<211> LENGTH: 340
<212> TYPE: PRT
<213> ORGANISM: Artificial Sequence
<220> FEATURE:
<223> OTHER INFORMATION: tsLacBP2 (with signal peptide replaced with M)

<400> SEQUENCE: 116

Met Phe Ser Pro Leu Ala Val Ala Gln Ala Pro Arg Phe Arg Trp Arg
1               5                   10                  15

Ile Gln Ser Ala Trp Asp Ala Gly Thr Val Gly Tyr Ser Leu Phe Gln
            20                  25                  30

Lys Phe Ala Glu Arg Val Lys Glu Leu Thr Asp Gly Gln Ile Glu Ile
        35                  40                  45

Gln Thr Phe Pro Ala Gly Ala Val Val Gly Thr Phe Asp Met Phe Asp
    50                  55                  60

Ala Val Lys Thr Gly Val Leu Asp Gly Met His Pro Phe Thr Leu Tyr
65                  70                  75                  80

Trp Ala Gly Arg Met Pro Val Thr Ala Phe Leu Ser Ser Tyr Pro Leu
                85                  90                  95

Gly Leu Asp Arg Pro Asp Gln Trp Glu Thr Trp Tyr Tyr Gly Leu Gly
            100                 105                 110

Gly Leu Glu Leu Ala Arg Lys Ala Tyr Glu Glu Gln Gly Leu Phe Phe
        115                 120                 125

Val Gly Pro Val Gln His Asp Tyr Asn Leu Ile His Ser Lys Lys Pro
    130                 135                 140

Ile Lys Ser Phe Glu Asp Phe Lys Gly Val Lys Leu Arg Val Pro Gly
145                 150                 155                 160

Gly Met Ile Ala Glu Ile Phe Ala Ala Ala Gly Ala Ala Thr Val Leu
                165                 170                 175

Leu Pro Gly Gly Glu Val Tyr Pro Ala Leu Glu Arg Gly Val Ile Asp
            180                 185                 190

Ala Ala Asp Phe Val Gly Pro Ala Val Asn Tyr Asn Leu Gly Phe His
        195                 200                 205

Gln Val Thr Lys Tyr Ile Ile Met Gly Pro Pro Glu Thr Pro Ala Ile
    210                 215                 220

His Gln Pro Val Asp Leu Ala Asp Ile Thr Ile Asn Ile Asn Arg Trp
225                 230                 235                 240

Arg Ala Leu Pro Arg Asn Leu Gln Glu Arg Phe Glu Ala Ala Val His
                245                 250                 255

Glu Trp Ser Trp Ile His Tyr Ala Gly Ile Gln Lys Ala Asn Leu Glu
            260                 265                 270

Thr Trp Pro Lys Tyr Lys Ala Ala Gly Val Gln Val Ile Arg Leu Ser
        275                 280                 285

Thr Val Asp Val Arg Lys Phe Arg Arg Val Ala Ile Pro Ile Trp Phe
    290                 295                 300

Lys Trp Ala Lys Gln Asp Lys Tyr Thr Arg Glu Ala Phe Ala Ser Gln
305                 310                 315                 320

Leu Glu Tyr Met Lys Ala Leu Gly Tyr Val Thr Asp Ala Asp Ile Arg
                325                 330                 335

Gly Leu Ser Leu
            340

<210> SEQ ID NO 117
<211> LENGTH: 360
<212> TYPE: PRT
<213> ORGANISM: Artificial Sequence
<220> FEATURE:
<223> OTHER INFORMATION: toLacBP3 (with signal peptide replaced with M)

<400> SEQUENCE: 117

```
Met Lys Ser Thr Arg Arg Gln Phe Leu Lys Lys Ala Ala Ile Gly Val
1               5                   10                  15

Ala Ala Ser Ser Ala Phe Ser Pro Leu Ala Ile Ala Gln Ala Pro Arg
            20                  25                  30

Phe Arg Trp Arg Ile Gln Ser Ala Trp Asp Ala Gly Thr Val Gly Tyr
        35                  40                  45

Thr Leu Phe Gln Arg Phe Ala Glu Arg Val Lys Glu Leu Thr Asp Gly
    50                  55                  60

Gln Ile Glu Ile Gln Pro Phe Pro Ala Gly Ala Val Val Gly Thr Phe
65                  70                  75                  80

Asp Met Phe Asp Ala Val Lys Thr Gly Val Leu Asp Gly Met His Pro
                85                  90                  95

Phe Thr Leu Tyr Trp Ala Gly Arg Met Pro Val Thr Ala Phe Leu Ser
            100                 105                 110

Ser Tyr Pro Leu Gly Leu Asp Arg Pro Asp Gln Trp Glu Thr Trp Tyr
        115                 120                 125

Tyr Gly Leu Gly Gly Leu Glu Leu Ala Arg Lys Ala Tyr Glu Glu Gln
    130                 135                 140

Gly Leu Ala Tyr Ile Gly Pro Val Gln His Asp Tyr Asn Leu Ile His
145                 150                 155                 160

Ser Lys Lys Pro Ile Lys Ser Phe Glu Glu Phe Lys Gly Val Lys Leu
                165                 170                 175

Arg Val Pro Gly Gly Met Ile Ala Glu Ile Phe Ala Ala Ala Gly Ala
            180                 185                 190

Ala Thr Val Leu Leu Pro Gly Gly Glu Val Tyr Pro Ala Leu Glu Arg
        195                 200                 205

Gly Val Ile Asp Ala Ala Asp Phe Val Gly Pro Ala Val Asn Tyr Asn
    210                 215                 220

Leu Gly Phe His Gln Val Thr Lys Tyr Ile Ile Met Gly Pro Pro Glu
225                 230                 235                 240

Thr Pro Ala Ile His Gln Pro Val Asp Leu Ala Asp Ile Thr Leu Asn
                245                 250                 255

Leu Asn Arg Trp Arg Ala Val Pro Lys Asn Leu Gln Glu Arg Phe Glu
            260                 265                 270

Ala Ala Val His Glu Trp Ser Trp Val His Tyr Ala Gly Ile Gln Lys
        275                 280                 285

Ala Asn Leu Glu Ala Trp Pro Lys Tyr Arg Ala Ala Gly Val Gln Ile
    290                 295                 300

Ile Arg Leu Ser Thr Val Asp Val Arg Lys Phe Arg Arg Val Ala Ile
305                 310                 315                 320

Pro Ile Trp Phe Lys Trp Ala Lys Gln Asp Lys Tyr Ala Lys Glu Ala
                325                 330                 335

Phe Gln Ser Gln Leu Glu Tyr Met Lys Ala Leu Gly Tyr Val Thr Asp
            340                 345                 350

Val Asp Leu Arg Gly Leu Ser Leu
        355                 360
```

<210> SEQ ID NO 118
<211> LENGTH: 337
<212> TYPE: PRT
<213> ORGANISM: Artificial Sequence
<220> FEATURE:
<223> OTHER INFORMATION: tsLacBP4 (with signal peptide replaced with M)

<400> SEQUENCE: 118

-continued

```
Met Thr Ala Arg Gly Val Arg Trp Arg Met Gln Ser Ala Trp Gln Pro
1               5                   10                  15

Gly Thr Ile Gly Tyr Arg Thr Phe Glu Thr Trp Ala Arg Ser Ile Gln
            20                  25                  30

Glu Leu Thr Ser Gly Glu Leu Ser Ile Glu Pro Phe Pro Ala Gly Ala
        35                  40                  45

Val Ala Gly Thr Phe Glu Met Ala Asp Ala Val Arg Ser Gly Val Leu
    50                  55                  60

Asp Gly Met Asn Trp Phe Thr Val Tyr Trp Pro Gly Lys Met Pro Ala
65                  70                  75                  80

Gly Val Phe Met Ser Ala Tyr Pro Met Ala Leu Ser Leu Pro His His
                85                  90                  95

Trp Asp Met Met Phe Asp Ser Phe Gly Gly Arg Gln Ile Val Asp Glu
            100                 105                 110

Leu Tyr Asp Arg Gln Gly Leu Val Phe Leu Gly His Val Gln His Asp
        115                 120                 125

Leu Asn Leu Ile His Ser Lys Val Pro Leu Arg Ser Phe Asp Asp Phe
    130                 135                 140

Arg Gly Lys Arg Ile Arg Phe Pro Gly Gly Ile Ile Ala Glu Thr Phe
145                 150                 155                 160

Ala Lys Val Gly Val Arg Thr Thr Leu Leu Pro Gly Gly Asp Val Tyr
                165                 170                 175

Pro Ala Leu Glu Arg Gly Thr Ile Asp Ala Ala Asp Phe Val Gly Pro
            180                 185                 190

Ala Val Asn Tyr Asp Leu Gly Phe His Gln Val Ala Asp Tyr Ile Ile
        195                 200                 205

Met Gly Pro Pro Ser Thr Pro Ala Leu His Gln Pro Val Asp Leu Met
    210                 215                 220

Asp Ile Ser Val Asn Lys Arg Ser Trp Ser Arg Ile Ser Glu His Thr
225                 230                 235                 240

Gln Lys Leu Met Tyr Lys Phe Val Lys Ala Tyr Ser Ala Glu His Phe
                245                 250                 255

Ala Ala Ile Gln Lys Ala Asn His Glu Ala Trp Pro Lys Tyr Lys Glu
            260                 265                 270

Ala Gly Val Glu Val Ile His Leu Ser Glu Glu Asp Ala Ala Arg Phe
        275                 280                 285

Arg Glu Ala Ala Ile Pro Leu Trp Phe Glu Trp Ala Asn Lys Asp Arg
    290                 295                 300

Asp Ala Ala Arg Leu Phe Lys Val His Leu Glu Val Met Gln Asp Pro
305                 310                 315                 320

Ser Val Ala Val Ile Thr Pro Asp Asp Ile Lys Asp Tyr Lys Leu Asn
                325                 330                 335

Phe
```

<210> SEQ ID NO 119
<211> LENGTH: 337
<212> TYPE: PRT
<213> ORGANISM: Artificial Sequence
<220> FEATURE:
<223> OTHER INFORMATION: rdLacBP5 (with signal peptide replaced with M)

<400> SEQUENCE: 119

```
Met Ala Ala Gly Glu Gly Thr Thr Trp Lys Ile Gln Thr Ser His Thr
1               5                   10                  15

Gly Gly Ile Gly Leu Ala Thr Phe Lys Asp Trp Ala Ser Ser Ile Glu
```

```
            20                  25                  30

Glu Lys Thr Gly Gly Glu Leu Ala Phe Thr Ala Phe Gly Ala Asn Asp
        35                  40                  45

Val Val Gly Asp Phe Gln Leu Tyr Asp Ala Val Lys Asn Gly Val Leu
    50                  55                  60

Asp Ala Val Asn Pro Phe Thr Ile Tyr Ala Gln Gly Ile Ile Pro Ala
65                  70                  75                  80

Ala Thr Phe Leu Thr Ser Tyr Pro Leu Gly Leu Arg Asn Pro His Glu
                85                  90                  95

Trp Asp Val Phe Phe Tyr Ser Leu Gly Gly Leu Glu Ile Ala Arg Glu
            100                 105                 110

Leu Tyr Ala Ala Gln Gly Met Lys Phe Val Gly Pro Val His His Gly
        115                 120                 125

Pro Asn Ile Ile His Ser Lys Val Pro Ile Arg Ser Ile Asp Asp Phe
    130                 135                 140

Ala Gly Leu Lys Met Arg Met Pro Gly Gly Met Val Ala Glu Val Phe
145                 150                 155                 160

Ser Glu Ile Gly Ala Glu Thr Thr Val Leu Pro Gly Ser Glu Ile Phe
                165                 170                 175

Pro Ala Leu Glu Lys Gly Thr Ile Asp Ala Ala Asp Phe Val Gly Pro
            180                 185                 190

Ala Val Asn Tyr Ala Leu Gly Phe Ser Gln Val Thr Asn Tyr Ile Ser
        195                 200                 205

Met Gly Pro Ala Gly Phe Met Ser Leu Tyr Gln Pro Val Asp Leu Met
    210                 215                 220

Asp Ile Thr Val Gly Gln Thr Ala Trp Asp Ala Leu Ser Pro Gln Met
225                 230                 235                 240

Gln Gln Phe Val Glu Met Glu Thr His Val Tyr Ser Asp Met His His
                245                 250                 255

Ala Ala Ile Gln Lys Ala Asp Gln Glu Ala Trp Ala Lys Phe Glu Ala
            260                 265                 270

Asp Gly Thr Glu Val Thr Arg Leu Ser Gln Asp Asp Val Glu Leu Met
        275                 280                 285

Thr Glu Val Ala Val Pro Ile Trp Phe Asp Tyr Ala Asn Arg Asp Lys
    290                 295                 300

Asp Ala Ala Arg Val Phe Lys Ile Gln Leu Asp Tyr Met Met Ser Gly
305                 310                 315                 320

Ser Leu Gly Tyr Val Thr Pro Glu Gln Ile Glu Gly Leu Thr Leu Asn
                325                 330                 335

Leu


<210> SEQ ID NO 120
<211> LENGTH: 332
<212> TYPE: PRT
<213> ORGANISM: Artificial Sequence
<220> FEATURE:
<223> OTHER INFORMATION: msLacBP6  (with signal peptide replaced with M)

<400> SEQUENCE: 120

Met Ala Thr Thr Trp Lys Ile Gln Ser Val Trp Asp Ala Gly Thr Val
1               5                   10                  15

Gly Tyr Asp Leu Phe Lys Glu Trp Cys Asp Gly Met Glu Glu Lys Thr
            20                  25                  30

Gly Gly Glu Leu Lys Phe Thr Cys Phe Pro Ala Lys Ala Val Ala Ala
        35                  40                  45
```

```
Asp Asn Asn Gly Leu Phe Asp Ala Val Arg Asn Gly Val Leu Gln Gly
    50                  55                  60

Met Asn Pro Phe Thr Leu Tyr Trp Ser Gly Lys Ile Pro Ala Ser Val
65                  70                  75                  80

Phe Leu Ser Ser Tyr Pro Ala Gly Pro Asp Gln Pro His Gln Trp Asp
                85                  90                  95

Thr Met Phe Tyr Ser Leu Gly Met Leu Glu Lys Thr Arg Glu Ile Tyr
            100                 105                 110

Lys Lys Phe Gly Leu Phe Tyr Val Gly Pro Ile Gln His Asp Ala Asn
        115                 120                 125

Ile Ile His Ser Lys Gln Pro Ile Asn Ser Leu Asp Asp Leu Lys Gly
    130                 135                 140

Leu Lys Met Arg Leu Pro Gly Gly Met Val Ala Glu Val Phe Ala Lys
145                 150                 155                 160

Phe Gly Val Ala Ala Val Ser Leu Pro Gly Ser Asp Ile Phe Pro Ala
                165                 170                 175

Leu Glu Lys Gly Thr Ile Asp Ala Ala Asp Tyr Val Gly Pro Ala Val
            180                 185                 190

Asn Trp Glu Leu Gly Phe Ser Gln Val Thr Lys Tyr Ile Leu Met Gly
        195                 200                 205

Pro Pro Gly Ile Met Ser Val Tyr Gln Pro Val Asp Leu Met Asp Leu
    210                 215                 220

Thr Val Asn Leu Arg Ala Trp Asn Ala Leu Asp Pro Lys Leu Gln Gln
225                 230                 235                 240

Ile Val Glu Asp Glu Val Arg Ile Tyr Ser Gln Lys His Tyr Leu Ala
                245                 250                 255

Ile Gln Lys Arg Asn Ile Glu Ala Met Lys Lys Phe Glu Ala Ala Gly
            260                 265                 270

Thr Thr Val Thr Arg Leu Ser Gln Glu Asp Leu Gln Glu Phe Arg Arg
        275                 280                 285

Ala Ala Ile Pro Ile Trp Tyr Ser Trp Ala Asn Lys Asp Glu Asp Ala
    290                 295                 300

Arg Glu Ile Phe Asp Met Gln Leu Glu Tyr Met Met Asn Asp Thr Val
305                 310                 315                 320

Gly Tyr Ile Thr Glu Asp Asp Ile Lys Gly Met Asn
                325                 330


<210> SEQ ID NO 121
<211> LENGTH: 333
<212> TYPE: PRT
<213> ORGANISM: Artificial Sequence
<220> FEATURE:
<223> OTHER INFORMATION: tsLacBP7  (with signal peptide replaced with M)

<400> SEQUENCE: 121

Met Gln Ala Pro Arg Phe Arg Trp Arg Ile Gln Ser Ala Trp Asp Ala
1               5                   10                  15

Gly Thr Val Gly Tyr Thr Leu Phe Gln Arg Phe Ala Glu Arg Val Lys
            20                  25                  30

Glu Leu Thr Asp Gly Gln Ile Glu Ile Gln Thr Phe Pro Ala Gly Ala
        35                  40                  45

Val Val Gly Thr Phe Asp Met Phe Asp Ala Val Lys Thr Gly Val Leu
    50                  55                  60

Asp Gly Met His Pro Phe Thr Leu Tyr Trp Ala Gly Arg Met Pro Val
65                  70                  75                  80
```

```
Thr Ala Phe Leu Ser Ser Tyr Pro Leu Gly Leu Asp Arg Pro Asp Gln
                85                  90                  95

Trp Glu Thr Trp Tyr Tyr Ala Leu Gly Gly Leu Asp Leu Ala Arg Arg
            100                 105                 110

Ala Phe Glu Glu Gln Gly Leu Phe Tyr Val Gly Pro Val Gln His Asp
        115                 120                 125

Tyr Asn Leu Ile His Ser Lys Lys Pro Ile Lys Ser Phe Glu Asp Phe
    130                 135                 140

Lys Gly Val Lys Leu Arg Val Pro Gly Gly Met Ile Ala Asp Val Phe
145                 150                 155                 160

Ser Ala Ala Gly Ala Ala Thr Val Leu Leu Pro Gly Gly Glu Val Tyr
                165                 170                 175

Pro Ala Leu Glu Arg Gly Val Ile Asp Ala Ala Asp Phe Val Gly Pro
            180                 185                 190

Ala Val Asn Tyr Asn Leu Gly Phe His Gln Val Thr Lys Tyr Ile Ile
        195                 200                 205

Met Gly Pro Pro Glu Thr Pro Ala Ile His Gln Pro Val Asp Leu Ala
    210                 215                 220

Asp Ile Thr Leu Asn Leu Ser Arg Trp Arg Ala Val Pro Lys Asn Leu
225                 230                 235                 240

Gln Glu Arg Phe Glu Ala Ala Val His Glu Trp Ser Trp Ile His Tyr
                245                 250                 255

Ala Gly Ile Gln Lys Ala Asn Leu Glu Thr Trp Pro Lys Tyr Lys Ala
            260                 265                 270

Ala Gly Val Gln Ile Ile Arg Leu Thr Thr Val Asp Val Arg Lys Phe
        275                 280                 285

Arg Arg Val Ala Ile Pro Ile Trp Phe Lys Trp Ala Lys Gln Asp Lys
    290                 295                 300

Tyr Ala Arg Glu Ala Phe Ala Ser Gln Leu Glu Tyr Met Lys Ala Leu
305                 310                 315                 320

Gly Tyr Val Thr Asp Ala Asp Val Arg Gly Leu Ser Leu
                325                 330
```

<210> SEQ ID NO 122
<211> LENGTH: 333
<212> TYPE: PRT
<213> ORGANISM: Artificial Sequence
<220> FEATURE:
<223> OTHER INFORMATION: maLacBP8 (with signal peptide replaced with M)

<400> SEQUENCE: 122

```
Met Gln Ala Ala Thr Thr Trp Lys Ile Gln Ser Thr Trp Asp Ala Gly
1               5                   10                  15

Thr Val Gly Tyr Thr Leu Phe Glu Glu Trp Ala Lys Ser Ile Glu Ala
            20                  25                  30

Lys Ser Gly Gly Glu Leu Lys Phe Gln Ala Phe Pro Ala Lys Ala Val
        35                  40                  45

Ala Ala Asp Asn Asn Ala Leu Phe Asp Ala Val Arg Asn Gly Val Leu
    50                  55                  60

Gln Gly Met Asn Pro Phe Thr Leu Tyr Trp Ala Gly Lys Ile Pro Ala
65                  70                  75                  80

Ser Val Phe Leu Ser Ser Tyr Pro Ala Gly Pro Asp Gln Pro His Gln
                85                  90                  95

Trp Asp Thr Met Phe Tyr Ser Met Gly Met Leu Glu Lys Thr Arg Glu
            100                 105                 110
```

```
Ile Tyr Lys Lys Phe Gly Leu Phe Tyr Val Gly Pro Ile Gln His Asp
        115                 120                 125

Ala Asn Ile Ile His Ser Lys Gln Pro Val Asn Ser Leu Asp Asp Leu
    130                 135                 140

Lys Gly Met Lys Ile Arg Val Pro Gly Gly Met Val Ala Glu Val Phe
145                 150                 155                 160

Gln Gln Phe Gly Val Ser Thr Val Ser Leu Pro Gly Ser Asp Ile Phe
                165                 170                 175

Pro Ala Leu Glu Lys Gly Thr Ile Asp Ala Ala Asp Phe Val Gly Pro
            180                 185                 190

Ala Val Asn Tyr Glu Leu Gly Phe Ser Gln Val Thr Asp Tyr Ile Ile
        195                 200                 205

Phe Gly Pro Pro Gly Val Met Ser Ile Tyr Gln Pro Val Asp Leu Met
    210                 215                 220

Asp Leu Thr Val Ser Leu Arg Ala Trp Asn Ser Ile Ser Pro Glu Leu
225                 230                 235                 240

Gln Gln Leu Val Glu Asp Glu Val Arg Ile Tyr Ser Gln Lys His Tyr
                245                 250                 255

Leu Ala Ile Gln Ala Arg Asn Ile Glu Ala Met Glu Lys Phe Lys Ala
            260                 265                 270

Asp Gly Asp Thr Val Thr Arg Leu Ser Gln Glu Asp Leu Glu Thr Trp
        275                 280                 285

Arg Lys Ala Ala Ile Pro Ile Trp Phe Asn Trp Ala Asn Lys Asn Asp
    290                 295                 300

Asp Ala Arg Ala Ile Leu Asp Ile Gln Leu Lys Tyr Met Met Asn Asp
305                 310                 315                 320

Thr Val Gly Tyr Ile Thr Glu Glu Asp Ile Lys Gly Phe
                325                 330


<210> SEQ ID NO 123
<211> LENGTH: 344
<212> TYPE: PRT
<213> ORGANISM: Artificial Sequence
<220> FEATURE:
<223> OTHER INFORMATION: adLacBP9  (with signal peptide replaced with M)

<400> SEQUENCE: 123

Met Gln Ala Pro Ile Thr Leu Arg Phe Gln Ser Thr Trp Pro Gln Lys
1               5                   10                  15

Asp Ile Phe His Glu Phe Ala Leu Asp Tyr Ala Lys Lys Val Asn Glu
            20                  25                  30

Met Ser Gly Gly Arg Leu Lys Ile Glu Val Leu Ala Ala Gly Ser Val
        35                  40                  45

Val Lys Ala Phe Asp Leu Leu Asp Ala Val Ser Lys Gly Thr Leu Asp
    50                  55                  60

Gly Gly His Gly Val Val Ala Tyr Trp Tyr Gly Lys Asn Thr Ala Leu
65                  70                  75                  80

Ala Leu Trp Gly Ser Gly Pro Ala Phe Gly Met Asp Pro Asn Met Val
                85                  90                  95

Leu Ala Trp His His Tyr Gly Gly Gly Arg Gln Leu Leu Glu Glu Ile
            100                 105                 110

Tyr Arg Ser Leu Asn Leu Asp Val Val Ser Leu Met Tyr Gly Pro Met
        115                 120                 125

Pro Thr Gln Pro Leu Gly Trp Phe Lys Gln Lys Pro Ile Ala Lys Pro
    130                 135                 140
```

```
Asp Asp Met Lys Gly Leu Lys Phe Arg Thr Val Gly Leu Ser Ile Asp
145                 150                 155                 160

Ile Phe Asn Gly Leu Gly Ala Ala Val Asn Ala Leu Pro Gly Ala Glu
                165                 170                 175

Ile Val Pro Ala Met Asp Arg Gly Leu Leu Asp Ala Ala Glu Phe Asn
            180                 185                 190

Asn Ala Ser Ser Asp Arg Val Leu Gly Phe Pro Asp Val Ser Lys Ile
        195                 200                 205

Ala Met Leu Gln Ser Phe His Gln Ala Ser Glu Gln Phe Glu Ile Leu
    210                 215                 220

Phe Asn Gly Lys Arg Phe Gln Ala Leu Pro Ala Asp Leu Lys Ser Ile
225                 230                 235                 240

Ile Ser Ile Ala Ala Gln Ala Ala Ser Ala Asp Met Ser Trp Lys Ala
                245                 250                 255

Ile Asp Arg Tyr Ser Ser Asp Tyr Phe Glu Met Arg Asp Lys Gln Gly
            260                 265                 270

Val Lys Phe Tyr Ser Thr Arg Pro Glu Ile Leu Lys Arg Gln Leu Glu
        275                 280                 285

Ile Trp Asp Gln Val Met Glu Lys Arg Ala Ala Glu Asn Pro Thr Phe
    290                 295                 300

Lys Lys Val Leu Glu Ser Gln Arg Arg Phe Ala Gln Arg Ala Ala Arg
305                 310                 315                 320

Trp Gln Asn Asp Thr Asn Val Asp Phe Lys Met Ala Tyr Asn His Phe
                325                 330                 335

Phe Gly Gly Lys Lys Lys Ala Thr
            340
```

<210> SEQ ID NO 124
<211> LENGTH: 316
<212> TYPE: PRT
<213> ORGANISM: Artificial Sequence
<220> FEATURE:
<223> OTHER INFORMATION: pgLacBP10  (with signal peptide replaced with M)

<400> SEQUENCE: 124

```
Met Gln Glu Ala Val Glu Trp Arg Met Gln Ala Leu Trp Asp Ala Gly
1               5                   10                  15

Thr Thr Pro Phe Glu Phe Glu Lys Lys Phe Val Glu Arg Val Gly Glu
            20                  25                  30

Leu Thr Glu Gly Arg Phe Lys Ile Thr Leu Tyr Ser Ala Gly Gln Ile
        35                  40                  45

Val Pro Ala Asn Gln Ala Phe Asp Ala Val Arg Ser Gly Ala Phe Glu
    50                  55                  60

Met Met Lys Thr Phe Asp Gly Tyr Glu Ala Gly Lys Ile Pro Ala Phe
65                  70                  75                  80

Ala Phe Thr Ser Thr Ile Pro Phe Gly Phe Pro Gln Ser Asp Gln Tyr
                85                  90                  95

Glu Ala Trp Phe Tyr Glu Leu Gly Gly Leu Asp Leu Ala Arg Glu Ala
            100                 105                 110

Tyr Ala Lys Gly Gly Leu Phe Tyr Ile Ala Pro Thr Val Tyr Gly Glu
        115                 120                 125

Glu Pro Met His Ser Thr Val Lys Ile Glu Ser Ile Ala Asp Met Ala
    130                 135                 140

Gly Lys Lys Gly Arg Phe Val Gly Leu Ala Ser Ala Val Met Ala Asp
```

```
145                 150                 155                 160

Leu Gly Val Ala Val Ser Pro Leu Ala Thr Ala Glu Val Tyr Thr Ala
                165                 170                 175

Leu Glu Lys Gly Leu Ile Asp Phe Ala Asp Arg Gly Asp Leu Thr Ala
            180                 185                 190

Asn Tyr Glu Ala Gly Leu Gly Glu Val Ala Lys Phe Ile Ile Leu Pro
        195                 200                 205

Gly Val His Gln Pro Thr Thr Ala Thr Ser Tyr Val Ala Asn Gln Ala
    210                 215                 220

Ala Tyr Gln Lys Leu Pro Asp Gly Phe Lys Ala Ala Leu Ala Val Ala
225                 230                 235                 240

Ala Arg Glu Ile Ser Gly Ser Leu Arg Gln His Ile Leu Val Gln Asp
                245                 250                 255

Met Glu Val Leu Thr Lys Tyr Lys Asp Gln Gly Val Glu Val Val Arg
            260                 265                 270

Leu Asp Ala Ala Asp Ile Ala Ala Ala Arg Ala Lys Ala Val Glu Ser
        275                 280                 285

Trp Glu Lys Ala Thr Lys Gly Asp Glu Leu Ala Thr Arg Val Leu Lys
    290                 295                 300

Gly Gln Val Asp Phe Met Thr Ser Leu Gly Leu Leu
305                 310                 315


<210> SEQ ID NO 125
<211> LENGTH: 336
<212> TYPE: PRT
<213> ORGANISM: Artificial Sequence
<220> FEATURE:
<223> OTHER INFORMATION: psLacBP11  (with signal peptide replaced with
      M)

<400> SEQUENCE: 125

Met Gln Gln Ala Ala Gly Glu Pro Ala Lys Thr Tyr His Trp Lys Met
1               5                   10                  15

Val Thr Ala Trp Pro Lys Asn Tyr Pro Gly Leu Gly Thr Ser Ala Glu
            20                  25                  30

Arg Leu Ala Glu Arg Val Asn Ala Met Ser Gly Gly Arg Leu Thr Ile
        35                  40                  45

Lys Val Tyr Ala Ala Gly Glu Leu Val Pro Ala Leu Glu Val Phe Asp
    50                  55                  60

Ala Val Ser Arg Gly Thr Ala Glu Leu Gly His Gly Ala Ser Tyr Tyr
65                  70                  75                  80

Trp Lys Gly Lys Val Pro Thr Ala Gln Phe Phe Thr Ser Val Pro Phe
                85                  90                  95

Gly Leu Ser Thr Ser Glu Met Asn Ala Trp Leu Ser Lys Gly Gly Gly
            100                 105                 110

Gln Ala Phe Trp Asp Glu Ala Tyr Ala Pro Phe Gly Val Lys Pro Leu
        115                 120                 125

Val Ile Gly Asn Thr Gly Met Gln Met Gly Gly Trp Tyr Asn Lys Glu
    130                 135                 140

Ile Asn Ser Leu Thr Asp Leu Lys Gly Leu Lys Ile Arg Met Pro Gly
145                 150                 155                 160

Leu Gly Gly Glu Val Leu Ser Arg Leu Gly Ala Thr Thr Val Asn Leu
                165                 170                 175

Pro Gly Gly Glu Val Phe Thr Ala Leu Gln Thr Gly Ala Ile Asp Ala
            180                 185                 190
```

```
Thr Asp Trp Val Ser Pro Tyr Asn Asp Leu Ala Phe Gly Leu His Lys
        195                 200                 205

Ala Ala Arg Tyr Tyr Tyr Tyr Pro Gly Trp Gln Glu Pro Gln Ala Val
    210                 215                 220

Leu Glu Leu Leu Ile Asn Gln Lys Ala Phe Asp Ser Leu Pro Ala Asp
225                 230                 235                 240

Leu Gln Ala Ile Val Thr Glu Ala Ser Leu Ala Ala Ser Arg Asp Met
                245                 250                 255

His Asp Asp Tyr Val Tyr Asn Asn Ala Leu Ala Leu Glu Gln Leu Lys
            260                 265                 270

Gln Gln Gly Thr Glu Leu Lys Arg Phe Pro Asp Glu Val Leu Ala Ala
        275                 280                 285

Met Arg Glu Gln Ser Asp Leu Ile Leu Gly Glu Leu Ala Ala Gln Ser
    290                 295                 300

Glu Leu Asn Gly Arg Ile Trp Ala Ser Met Lys Ala Phe Gln Ala Gln
305                 310                 315                 320

Val Glu Pro Met His Glu Ile Ser Glu Lys Glu Leu Tyr Asn Trp Arg
                325                 330                 335


<210> SEQ ID NO 126
<211> LENGTH: 342
<212> TYPE: PRT
<213> ORGANISM: Artificial Sequence
<220> FEATURE:
<223> OTHER INFORMATION: rsLacBP12  (with signal peptide replaced with
      M)

<400> SEQUENCE: 126

Met Gln Ala Pro Leu Val Met Lys Met Gln Thr Ser Trp Pro Ala Ser
1               5                   10                  15

Asp Ile Trp Met Asp Phe Ala Arg Glu Tyr Val Thr Arg Val Glu Glu
            20                  25                  30

Met Ser Gly Gly Arg Ile Lys Val Asp Leu Leu Pro Ala Gly Ala Val
        35                  40                  45

Val Gly Ala Phe Gln Val Met Asp Ala Val His Asp Gly Val Ile Asp
    50                  55                  60

Ala Ser His Ser Val Ser Ala Tyr Trp Tyr Gly Lys Ser Lys Ala Ala
65                  70                  75                  80

Ser Phe Phe Gly Thr Gly Pro Val Phe Gly Gly Ser Ala Thr Thr Met
                85                  90                  95

Leu Gly Trp Phe Tyr Gln Gly Gly Gly Gln Asp Leu Tyr Arg Glu Leu
            100                 105                 110

Thr Gln Asp Ile Leu Gly Met Asn Ile Val Gly Phe Tyr Gly Phe Pro
        115                 120                 125

Met Pro Ala Gln Pro Phe Gly Trp Phe Lys Thr Glu Val Asn Gly Val
    130                 135                 140

Ala Asp Ile Gln Gly Phe Lys Tyr Arg Thr Val Gly Leu Ala Ala Asp
145                 150                 155                 160

Leu Leu Gln Ala Met Gly Met Ser Val Ala Gln Leu Pro Gly Gly Glu
                165                 170                 175

Ile Val Pro Ala Met Glu Arg Gly Val Ile Asp Ala Phe Glu Phe Asn
            180                 185                 190

Asn Pro Ser Ser Asp Met Arg Phe Gly Ala Gln Asp Val Ala Lys Asn
        195                 200                 205

Tyr Tyr Leu Ser Ser Tyr His Gln Ala Ser Glu Ser Phe Glu Tyr Thr
    210                 215                 220
```

```
Phe Asn Arg Asp Phe Tyr Glu Asp Leu Asp Pro Asp Leu Gln Ala Ile
225                 230                 235                 240

Leu Lys Tyr Ala Val Glu Ala Ala Ser Thr Ser Asn Thr Ala Leu Ala
                245                 250                 255

Leu Arg Gln Tyr Ser Ala Asp Leu Ala Thr Leu Ala Ala Glu Asn Gly
            260                 265                 270

Val Ala Val His Arg Thr Pro Lys Asp Ile Leu Ser Gly Gln Leu Glu
        275                 280                 285

Ala Trp Asp Lys Leu Ile Val Asp Leu Glu Ala Asp Glu Phe Phe Lys
    290                 295                 300

Lys Val Leu Asp Ser Gln Arg Ala Trp Val Glu Gln Val Ser Tyr Tyr
305                 310                 315                 320

Glu Leu Met Asn Ala Ala Asp Leu Gly Leu Ala Tyr Glu His His Phe
                325                 330                 335

Pro Gly Lys Leu Lys Leu
            340


<210> SEQ ID NO 127
<211> LENGTH: 336
<212> TYPE: PRT
<213> ORGANISM: Artificial Sequence
<220> FEATURE:
<223> OTHER INFORMATION: fsLacBP13  (with signal peptide replaced with
      M)

<400> SEQUENCE: 127

Met Glu Lys Lys Ile Arg Trp Lys Leu Ala Met Thr Trp Gly Pro Thr
1               5                   10                  15

Leu His Pro Leu Ser Asp Thr Ala Glu His Met Ala Glu Ile Val Lys
            20                  25                  30

Glu Leu Ser Asp Gly Asn Phe Val Ile Asn Ile Asp Ala Ser Asn Val
        35                  40                  45

His Lys Ala Pro Phe Gly Ile Phe Asp Met Val Lys Leu Gly Gln Tyr
    50                  55                  60

Glu Met Gly His Thr Ala Ser Tyr Tyr Tyr Lys Gly Lys Asn Ile Ala
65                  70                  75                  80

Phe Leu Pro Leu Thr Thr Met Pro Phe Gly Met Thr Ala Pro Glu Gln
                85                  90                  95

Tyr Ala Trp Phe Tyr Tyr Gly Gly Gly Leu Glu Leu Met Gln Glu Ala
            100                 105                 110

Tyr Thr Lys His Gly Met Leu Ala Phe Pro Gly Gly Asn Thr Gly Asn
        115                 120                 125

Gln Met Gly Gly Trp Phe Thr Lys Glu Ile Asn Ser Leu Asp Asp Leu
    130                 135                 140

Lys Gly Leu Lys Met Arg Ile Pro Gly Phe Ala Gly Gln Ile Met Ser
145                 150                 155                 160

Lys Leu Gly Val Thr Val Thr Asn Ile Pro Pro Gly Glu Leu Tyr Thr
                165                 170                 175

Ala Leu Glu Arg Gly Thr Val Asp Ala Val Glu Trp Thr Gly Pro Gly
            180                 185                 190

Met Asp Ile Asn Met Gly Phe His Lys Ile Ala Lys Tyr Tyr Tyr Thr
        195                 200                 205

Gly Trp His Glu Pro Gly Ser Glu Val Glu Phe Leu Ile Asn Glu Lys
    210                 215                 220

Glu Tyr Asn Lys Leu Pro Glu Lys Tyr Lys Lys Ile Leu Lys Ile Ala
```

```
225                 230                 235                 240

Met Lys Thr Ala Ala Tyr Asp Met Tyr Ile Gln Ser Tyr Glu Met Asn
                245                 250                 255

Ala Glu Ala Trp Gln Gln Met Lys Glu Lys Tyr Pro Asp Ile Lys Val
            260                 265                 270

Lys Val Phe Pro Glu Glu Val Leu Lys Glu Met Lys Thr Ala Tyr Asp
        275                 280                 285

Asn Leu Val Ala Ser Tyr Glu Lys Glu Ser Pro Met Phe Lys Lys Ile
    290                 295                 300

Met Glu Ser Lys Arg Ala Tyr Leu Asp Lys Val Arg Asp Trp Thr His
305                 310                 315                 320

Ile Ser Asp Tyr Leu Tyr Leu Lys Ser Thr Ser Glu Ser Asn Leu Asn
                325                 330                 335


<210> SEQ ID NO 128
<211> LENGTH: 331
<212> TYPE: PRT
<213> ORGANISM: Artificial Sequence
<220> FEATURE:
<223> OTHER INFORMATION: taLacBP14  (with signal peptide replaced with
      M)

<400> SEQUENCE: 128

Met Glu Glu Tyr Lys Phe Lys Met Ala Thr Phe Tyr Leu Lys Gly Asp
1               5                   10                  15

Ser Ala Phe Asp Val Ile Asp His Phe Arg Gln Leu Val Trp Lys Lys
            20                  25                  30

Thr Gly Gly Lys Val Arg Ile Asp Ala Phe Gln Ala Gly Glu Leu Gly
        35                  40                  45

Phe Pro Val Thr Glu Ile Leu Glu Ala Thr Ser Arg Gly Val Val Glu
    50                  55                  60

Met Ser Ile Phe Tyr Pro Asn Tyr Lys Ala Ala Gln Asp Pro Val Met
65                  70                  75                  80

Ala Leu Ala Gly Gly Arg Pro Gly Pro Met Phe Asp Leu Arg Asp Gln
                85                  90                  95

Lys Ala Gln Val Asp Ala Thr Lys Asp Leu Leu Glu Arg Ser Phe Gly
            100                 105                 110

Arg Phe Gly Val Arg Tyr Ile Ala Pro Met Val Tyr Gly Glu Pro Glu
        115                 120                 125

Ile Leu Val Ser Arg Arg Pro Met Ser Ser Leu Lys Asp Leu Lys Gly
    130                 135                 140

Arg Ile Phe Arg Ala Ser Gly Met Ala Ala Glu Phe Tyr Thr Ala Ile
145                 150                 155                 160

Gly Ala Gln Ala Met Met Leu Pro Ala Gly Glu Leu Tyr Gln Ala Leu
                165                 170                 175

Gln Leu Gly Thr Ile Asp Gly Leu Glu Trp Thr Asp Tyr Thr Ala Asn
            180                 185                 190

Tyr Lys Leu Gly Phe His Glu Val Ala Lys Asn Val Leu Glu Pro Thr
        195                 200                 205

Lys Gly Val Asn Leu His Ser Glu Ala Thr Val His Ala Phe Leu Val
    210                 215                 220

Val Asn Pro Lys Val Trp Glu Lys Leu Pro Lys Glu His Gln Lys Ala
225                 230                 235                 240

Ile Gln Glu Ala Ala Asp Glu Ala Tyr Lys Trp Gly Ala Asp His Leu
                245                 250                 255
```

-continued

```
Ala Lys Leu Asn Lys Thr Tyr Lys Asp Lys Trp Ile Lys Ala Gly Ala
            260                 265                 270

Lys Val Thr Gln Leu Pro Lys Glu Asp Gln Asp Lys Val Ile Glu Val
        275                 280                 285

Ser Ala Lys Ile Leu Ser Gly Tyr Ser Ala Lys Ser Pro Asp Ala Lys
    290                 295                 300

Glu Tyr Ala Arg Arg Leu Val Glu Leu Trp Lys Lys Leu Gly Tyr Thr
305                 310                 315                 320

Lys Trp Ser Asp Ala Leu Ala Lys Gln Ile Lys
                325                 330


<210> SEQ ID NO 129
<211> LENGTH: 5
<212> TYPE: PRT
<213> ORGANISM: Artificial Sequence
<220> FEATURE:
<223> OTHER INFORMATION: Conserved sequence.
<220> FEATURE:
<221> NAME/KEY: MISC_FEATURE
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be any naturally occurring amino acid

<400> SEQUENCE: 129

Phe Thr Xaa Tyr Xaa
1               5


<210> SEQ ID NO 130
<211> LENGTH: 6
<212> TYPE: PRT
<213> ORGANISM: Artificial Sequence
<220> FEATURE:
<223> OTHER INFORMATION: Conserved sequence
<220> FEATURE:
<221> NAME/KEY: MISC_FEATURE
<222> LOCATION: (2)..(2)
<223> OTHER INFORMATION: Xaa can be any naturally occurring amino acid

<400> SEQUENCE: 130

Asn Xaa Ile His Ser Lys
1               5


<210> SEQ ID NO 131
<211> LENGTH: 5
<212> TYPE: PRT
<213> ORGANISM: Artificial Sequence
<220> FEATURE:
<223> OTHER INFORMATION: Conserved sequence
<220> FEATURE:
<221> NAME/KEY: MISC_FEATURE
<222> LOCATION: (2)..(2)
<223> OTHER INFORMATION: Xaa can be any naturally occurring amino acid

<400> SEQUENCE: 131

Arg Xaa Pro Gly Gly
1               5


<210> SEQ ID NO 132
<211> LENGTH: 4
<212> TYPE: PRT
<213> ORGANISM: Artificial Sequence
<220> FEATURE:
<223> OTHER INFORMATION: Conserved sequence
<220> FEATURE:
<221> NAME/KEY: MISC_FEATURE
```

<222> LOCATION: (4)..(4)
<223> OTHER INFORMATION: Xaa can be any naturally occurring amino acid

<400> SEQUENCE: 132

Leu Pro Gly Xaa
1

<210> SEQ ID NO 133
<211> LENGTH: 6
<212> TYPE: PRT
<213> ORGANISM: Artificial Sequence
<220> FEATURE:
<223> OTHER INFORMATION: Conserved sequence

<400> SEQUENCE: 133

Val Gly Pro Ala Val Asn
1 5

<210> SEQ ID NO 134
<211> LENGTH: 5
<212> TYPE: PRT
<213> ORGANISM: Artificial Sequence
<220> FEATURE:
<223> OTHER INFORMATION: Conserved sequence

<400> SEQUENCE: 134

Gln Pro Val Asp Leu
1 5

<210> SEQ ID NO 135
<211> LENGTH: 1400
<212> TYPE: DNA
<213> ORGANISM: Artificial Sequence
<220> FEATURE:
<223> OTHER INFORMATION: Exemplary taLacBP14.186C expression sequence.

<400> SEQUENCE: 135
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tggaagaata 180
taaatttaaa atggcaactt tttacctgaa aggtgatagc gcctttgacg tgatcgacca 240
ctttcgccaa ctggtctgga agaaaaccgg tggtaaggta cgcatcgatg cgttccaagc 300
tggggaactg ggctttccag tgaccgagat cctggaagcg accagtcgtg gtgtggtgga 360
gatgagcatc ttctacccga actacaaagc ggcacaggat ccggtgatgg ccttagcggg 420
aggacgtccg ggtccaatgt tcgacctgcg tgatcagaaa gcccaagtgg atgcgaccaa 480
agatctcctg gaaaggtcct tcggtcgttt cggagttcgc tacattgcgc ctatggtgta 540
cggtgaaccg gagatcctgg tctcgagacg tccgatgagt agcctcaaag acctgaaagg 600
gcgtatcttc cgtgcgagtg gtatggcagc ggagttctac accgcaattg gcgcacaagc 660
gatgatgctt ccagcaggtg agctctacca ggcactgcag ttaggcacca tcgatggtct 720
ggagtgcacc gactataccg cgaactacaa gcttggcttc cacgaagtgg cgaagaacgt 780
gctggaaccg acgaaaggtg tgaacctcca ttcggaagct accgttcatg cgttcctggt 840
tgtgaacccg aaagtctggg agaaactgcc gaaggaacac cagaaagcga tccaggaagc 900
ggcggacgaa gcgtacaaat ggggtgcgga tcaccttgcg aaactgaaca aaacctacaa 960
ggacaaatgg atcaaagcgg gtgcgaaggt gacccaactg ccgaaagaag accaggacaa 1020
agtgatcgaa gtgtcggcaa agatcctgtc tggctatagc gcgaagagtc cggatgcgaa 1080
agagtacgcg cgtcgtctag tggagctgtg gaagaaactg ggctacacca aatggtctga 1140
tgcattagca aaacagatta aaggcggcag ccatcatcat catcatcatt aataatgaaa 1200
gggcgatatc cagcacactg gcggccgtta ctagtggatc cggctgctaa caaagcccga 1260
aaggaagctg agttggctgc tgccaccgct gagcaataac tagcataacc ccttggggcc 1320
tctaaacggg tcttgagggg ttttttgctg aaaggaggaa ctatatccgg agcgactccc 1380
acggcacgtt ggcaagctcg 1400

<210> SEQ ID NO 136
<211> LENGTH: 1433
<212> TYPE: DNA
<213> ORGANISM: Artificial Sequence
<220> FEATURE:
<223> OTHER INFORMATION: Exemplary rsLacBP12 expression sequence.

<400> SEQUENCE: 136
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgcaagcacc 180
gttagttatg aaaatgcaaa ctagttggcc agctagcgat atctggatgg acttcgcacg 240
tgagtacgtg accagagtgg aagagatgtc aggtggacgc atcaaggtgg atctgctgcc 300
agcaggtgcg gtagttggtg cgttccaggt gatggacgca gtacacgatg ggggtcatcga 360 tgctagccac tcggtgagcg cttactggta tggcaagagc aaagcggcta gcttctttgg 420
cactggtcca gtctttggcg gtagtgcaac cacgatgctc ggctggttct accaaggtgg 480
aggtcaggac ctgtaccgtg aactgacgca agacatcctc ggaatgaaca tcgtaggctt 540
ctacggtttc ccgatgccgg cacagccatt cggctggttc aagacggaag tgaacggcgt 600
tgcggacatc caaggcttca agtaccgtac cgttggactg gcagcagatc tgctgcaggc 660
tatgggcatg tcagtggcac agctgccagg tggcgaaatc gttccggcaa tggagcgtgg 720
tgtgatcgat gcgttcgagt tcaacaaccc tagctcggat atgcgctttg gtgcacaaga 780
tgtggcgaag aactactacc tgtcctccta ccatcaggca tctgagagct tcgagtacac 840
cttcaatcgc gacttctacg aggatctgga tcctgacctg caagccatcc tgaagtacgc 900
tgtggaagca gcgagtacca gcaataccgc gttagcgctg aggcagtata gcgcagatct 960
tgcgacgtta gcggctgaaa acggtgttgc agtgcatcgg actccgaaag acatcctgtc 1020
tggtcagctg gaagcatggg acaagctgat cgtggatctc gaagcggatg agttcttcaa 1080
gaaagtgctg gattcccaac gtgcatgggt cgaacaggtc tcctactacg agctgatgaa 1140
cgcagcggat cttggactgg catacgaaca tcattttcca ggaaaattaa aactgggcgg 1200
cagccatcat catcatcatc attaataatg aaagggcgat atccagcaca ctggcggccg 1260
ttactagtgg atccggctgc taacaaagcc cgaaaggaag ctgagttggc tgctgccacc 1320
gctgagcaat aactagcata accccttggg gcctctaaac gggtcttgag gggttttttg 1380
ctgaaaggag gaactatatc cggagcgact cccacggcac gttggcaagc tcg 1433

<210> SEQ ID NO 137
<211> LENGTH: 330
<212> TYPE: PRT
<213> ORGANISM: Artificial Sequence
<220> FEATURE:
<223> OTHER INFORMATION: 2ZZV seed sequence (ttLacBP1)

<400> SEQUENCE: 137

Arg Arg Tyr Arg Trp Arg Ile Gln Thr Ala Trp Asp Ala Gly Thr Val
1 5 10 15

Gly Tyr Ser Leu Phe Gln Lys Phe Thr Glu Arg Val Lys Glu Leu Thr
20 25 30

Asp Gly Gln Leu Glu Val Gln Pro Phe Pro Ala Gly Ala Val Val Gly
35 40 45

Thr Phe Asp Met Phe Asp Ala Val Lys Thr Gly Val Leu Asp Gly Met
50 55 60

Asn Pro Phe Thr Leu Tyr Trp Ala Gly Arg Met Pro Val Thr Ala Phe
65 70 75 80

Leu Ser Ser Tyr Ala Leu Gly Leu Asp Arg Pro Asp Gln Trp Glu Thr
85 90 95

Trp Phe Tyr Ser Leu Gly Gly Leu Asp Ile Ala Arg Arg Ala Phe Ala
100 105 110

Glu Gln Gly Leu Phe Tyr Val Gly Pro Val Gln His Asp Leu Asn Ile
115 120 125

Ile His Ser Lys Lys Pro Ile Arg Arg Phe Glu Asp Phe Lys Gly Val
130 135 140

Lys Leu Arg Val Pro Gly Gly Met Ile Ala Glu Val Phe Ala Ala Ala
145 150 155 160

Gly Ala Ser Thr Val Leu Leu Pro Gly Gly Glu Val Tyr Pro Ala Leu
165 170 175

Glu Arg Gly Val Ile Asp Ala Ala Asp Phe Val Gly Pro Ala Val Asn
180 185 190

Tyr Asn Leu Gly Phe His Gln Val Ala Lys Tyr Ile Ile Met Gly Pro
195 200 205

Pro Glu Thr Pro Ala Ile His Gln Pro Val Asp Leu Met Asp Phe Thr
210 215 220

Ile Asn Leu Asn Arg Trp Arg Ser Leu Pro Lys Pro Leu Gln Glu Arg
225 230 235 240

Phe Ile Ala Ala Val His Glu Tyr Ser Trp Ile His Tyr Ala Gly Ile
245 250 255

Gln Lys Ala Asn Leu Glu Ala Trp Pro Lys Tyr Arg Gln Ala Gly Val
260 265 270

Glu Val Ile Arg Leu Ser Asn Glu Asp Val Arg Lys Phe Arg Arg Leu
275 280 285

Ala Ile Pro Ile Trp Phe Lys Trp Ala Lys Met Asp Lys Tyr Ser Arg
290 295 300

Glu Ala Phe Ala Ser Gln Leu Glu Tyr Met Lys Gly Ile Gly Tyr Val
305 310 315 320

Thr Asp Glu Glu Leu Lys Gly Leu Ser Leu
325 330

<210> SEQ ID NO 138
<211> LENGTH: 109
<212> TYPE: PRT
<213> ORGANISM: Escherichia coli

<400> SEQUENCE: 138

Met Ser Asp Lys Ile Ile His Leu Thr Asp Asp Ser Phe Asp Thr Asp
1 5 10 15

Val Leu Lys Ala Asp Gly Ala Ile Leu Val Asp Phe Trp Ala Glu Trp
20 25 30

```
Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala
            100                 105


<210> SEQ ID NO 139
<211> LENGTH: 118
<212> TYPE: PRT
<213> ORGANISM: Artificial Sequence
<220> FEATURE:
<223> OTHER INFORMATION: Adaptor0

<400> SEQUENCE: 139

Met Ser Ala Lys Ile Ile His Leu Thr Asp Asp Ser Phe Asp Thr Asp
1               5                   10                  15

Val Leu Lys Ala Asp Gly Ala Ile Leu Val Ala Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Met Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Gly Ser
            100                 105                 110

His His His His His His
        115


<210> SEQ ID NO 140
<211> LENGTH: 118
<212> TYPE: PRT
<213> ORGANISM: Artificial Sequence
<220> FEATURE:
<223> OTHER INFORMATION: Adaptor1.0

<400> SEQUENCE: 140

Met Ser Ala Lys Ile Ile His Leu Thr Asp Asp Ser Phe Asp Thr Asp
1               5                   10                  15

Val Leu Lys Ala Asp Gly Ala Ile Leu Val Ala Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Met Leu Asn Ile Asp Gln Asn
    50                  55                  60

Pro Gly Thr Ala Pro Lys Tyr Gly Ile Cys Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Gly Ser
            100                 105                 110
```

His His His His His His
115

<210> SEQ ID NO 141
<211> LENGTH: 118
<212> TYPE: PRT
<213> ORGANISM: Artificial Sequence
<220> FEATURE:
<223> OTHER INFORMATION: Adaptor2.0a

<400> SEQUENCE: 141

```
Met Ser Ala Lys Ile Ile His Leu Thr Asp Asp Ser Phe Asp Thr Asp
1               5                   10                  15

Val Leu Lys Ala Asp Gly Ala Ile Leu Val Ala Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Met Leu Asn Ile Asp Gln Asn
    50                  55                  60

Pro Gly Thr Ala Pro Lys Tyr Gly Ile Cys Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Gly Ser
            100                 105                 110

His His His His His His
        115
```

<210> SEQ ID NO 142
<211> LENGTH: 118
<212> TYPE: PRT
<213> ORGANISM: Artificial Sequence
<220> FEATURE:
<223> OTHER INFORMATION: Adaptor2.0b

<400> SEQUENCE: 142

```
Met Ser Ala Lys Ile Ile His Leu Thr Asp Asp Ser Phe Asp Thr Asp
1               5                   10                  15

Val Leu Lys Ala Asp Gly Ala Ile Leu Val Ala Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Met Leu Asn Ile Asp Gln Asn
    50                  55                  60

Pro Gly Thr Ala Pro Lys Tyr Gly Ile Cys Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Gly Ser
            100                 105                 110

His His His His His His
        115
```

<210> SEQ ID NO 143
<211> LENGTH: 118
<212> TYPE: PRT
<213> ORGANISM: Artificial Sequence
<220> FEATURE:
<223> OTHER INFORMATION: Adaptor3.0

<400> SEQUENCE: 143

Met Ser Ala Lys Ile Ile His Leu Thr Asp Cys Ser Phe Asp Thr Asp
1 5 10 15

Val Leu Lys Ala Asp Gly Ala Ile Leu Val Ala Phe Trp Ala Glu Trp
20 25 30

Cys Gly Pro Cys Lys Met Ile Ala Pro Ile Leu Asp Glu Ile Ala Asp
35 40 45

Glu Tyr Gln Gly Lys Leu Thr Val Ala Met Leu Asn Ile Asp Gln Asn
50 55 60

Pro Gly Thr Ala Pro Lys Tyr Gly Ile Arg Gly Ile Pro Thr Leu Leu
65 70 75 80

Leu Phe Lys Asn Gly Glu Val Ala Ala Thr Lys Val Gly Ala Leu Ser
85 90 95

Lys Gly Gln Leu Lys Glu Phe Leu Asp Ala Asn Leu Ala Gly Gly Ser
100 105 110

His His His His His His
115

<210> SEQ ID NO 144
<211> LENGTH: 118
<212> TYPE: PRT
<213> ORGANISM: Artificial Sequence
<220> FEATURE:
<223> OTHER INFORMATION: Adaptor4.0

<400> SEQUENCE: 144

Met Ser Ala Lys Ile Ile His Leu Thr Asp Asp Ser Phe Asp Cys Asp
1 5 10 15

Val Leu Lys Ala Asp Gly Ala Ile Leu Val Ala Phe Trp Ala Glu Trp
20 25 30

Cys Gly Pro Cys Lys Met Ile Ala Pro Ile Leu Asp Glu Ile Ala Asp
35 40 45

Glu Tyr Gln Gly Lys Leu Thr Val Ala Met Leu Asn Ile Asp Gln Asn
50 55 60

Pro Gly Thr Ala Pro Lys Tyr Gly Ile Arg Gly Ile Pro Thr Leu Leu
65 70 75 80

Leu Phe Lys Asn Gly Glu Val Ala Ala Thr Lys Val Gly Ala Leu Ser
85 90 95

Lys Gly Gln Leu Lys Glu Phe Leu Asp Ala Asn Leu Ala Gly Gly Ser
100 105 110

His His His His His His
115

<210> SEQ ID NO 145
<211> LENGTH: 118
<212> TYPE: PRT
<213> ORGANISM: Artificial Sequence
<220> FEATURE:
<223> OTHER INFORMATION: Adaptor5.0

<400> SEQUENCE: 145

Met Ser Ala Lys Ile Ile His Leu Thr Asp Asp Ser Phe Asp Thr Asp
1 5 10 15

Val Leu Lys Ala Cys Gly Ala Ile Leu Val Ala Phe Trp Ala Glu Trp
20 25 30

Cys Gly Pro Cys Lys Met Ile Ala Pro Ile Leu Asp Glu Ile Ala Asp
35 40 45

```
Glu Tyr Gln Gly Lys Leu Thr Val Ala Met Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Gly Ser
            100                 105                 110

His His His His His His
        115
```

<210> SEQ ID NO 146
<211> LENGTH: 118
<212> TYPE: PRT
<213> ORGANISM: Artificial Sequence
<220> FEATURE:
<223> OTHER INFORMATION: Adaptor6.0

<400> SEQUENCE: 146

```
Met Ser Ala Lys Ile Ile His Leu Thr Asp Asp Ser Phe Asp Thr Asp
1               5                   10                  15

Val Leu Lys Ala Asp Gly Ala Ile Leu Val Ala Phe Trp Ala Glu Cys
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Met Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Gly Ser
            100                 105                 110

His His His His His His
        115
```

<210> SEQ ID NO 147
<211> LENGTH: 118
<212> TYPE: PRT
<213> ORGANISM: Artificial Sequence
<220> FEATURE:
<223> OTHER INFORMATION: Adaptor7.0

<400> SEQUENCE: 147

```
Met Ser Ala Lys Ile Ile His Leu Thr Asp Asp Ser Phe Asp Thr Asp
1               5                   10                  15

Val Leu Lys Ala Asp Gly Ala Ile Leu Val Ala Phe Trp Ala Glu Trp
            20                  25                  30

Cys Gly Pro Cys Lys Cys Ile Ala Pro Ile Leu Asp Glu Ile Ala Asp
        35                  40                  45

Glu Tyr Gln Gly Lys Leu Thr Val Ala Met Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Gly Ser
```

```
            100                 105                 110

His His His His His His
        115


<210> SEQ ID NO 148
<211> LENGTH: 118
<212> TYPE: PRT
<213> ORGANISM: Artificial Sequence
<220> FEATURE:
<223> OTHER INFORMATION: Adaptor8.0

<400> SEQUENCE: 148

Met Ser Ala Lys Ile Ile His Leu Thr Asp Asp Ser Phe Asp Thr Asp
1               5                   10                  15

Val Leu Lys Ala Asp Gly Ala Ile Leu Val Ala Phe Trp Ala Glu Trp
            20                  25                  30

Cys Gly Pro Cys Lys Met Ile Ala Pro Ile Leu Asp Cys Ile Ala Asp
        35                  40                  45

Glu Tyr Gln Gly Lys Leu Thr Val Ala Met Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Gly Ser
            100                 105                 110

His His His His His His
        115


<210> SEQ ID NO 149
<211> LENGTH: 118
<212> TYPE: PRT
<213> ORGANISM: Artificial Sequence
<220> FEATURE:
<223> OTHER INFORMATION: Adaptor9.0

<400> SEQUENCE: 149

Met Ser Ala Lys Ile Ile His Leu Thr Asp Asp Ser Phe Asp Thr Asp
1               5                   10                  15

Val Leu Lys Ala Asp Gly Ala Ile Leu Val Ala Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Cys Leu Thr Val Ala Met Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Gly Ser
            100                 105                 110

His His His His His His
        115


<210> SEQ ID NO 150
<211> LENGTH: 118
<212> TYPE: PRT
<213> ORGANISM: Artificial Sequence
<220> FEATURE:
```

```
<223> OTHER INFORMATION: Adaptor10.0

<400> SEQUENCE: 150

Met Ser Ala Lys Ile Ile His Leu Thr Asp Asp Ser Phe Asp Thr Asp
1               5                   10                  15

Val Leu Lys Ala Asp Gly Ala Ile Leu Val Ala Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Met Leu Asn Ile Asp Cys Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Gly Ser
            100                 105                 110

His His His His His His
        115


<210> SEQ ID NO 151
<211> LENGTH: 118
<212> TYPE: PRT
<213> ORGANISM: Artificial Sequence
<220> FEATURE:
<223> OTHER INFORMATION: Adaptor11.0

<400> SEQUENCE: 151

Met Ser Ala Lys Ile Ile His Leu Thr Asp Asp Ser Phe Asp Thr Asp
1               5                   10                  15

Val Leu Lys Ala Asp Gly Ala Ile Leu Val Ala Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Met Leu Asn Ile Asp Gln Asn
    50                  55                  60

Pro Gly Thr Ala Pro Lys Cys Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Gly Ser
            100                 105                 110

His His His His His His
        115


<210> SEQ ID NO 152
<211> LENGTH: 118
<212> TYPE: PRT
<213> ORGANISM: Artificial Sequence
<220> FEATURE:
<223> OTHER INFORMATION: Adaptor12.0

<400> SEQUENCE: 152

Met Ser Ala Lys Ile Ile His Leu Thr Asp Asp Ser Phe Asp Thr Asp
1               5                   10                  15

Val Leu Lys Ala Asp Gly Ala Ile Leu Val Ala Phe Trp Ala Glu Trp
            20                  25                  30

Cys Gly Pro Cys Lys Met Ile Ala Pro Ile Leu Asp Glu Ile Ala Asp
```

```
        35                  40                  45

Glu Tyr Gln Gly Lys Leu Thr Val Ala Met Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Cys Ala Ala Thr Lys Val Gly Ala Leu Ser
                85                  90                  95

Lys Gly Gln Leu Lys Glu Phe Leu Asp Ala Asn Leu Ala Gly Gly Ser
            100                 105                 110

His His His His His His
        115


<210> SEQ ID NO 153
<211> LENGTH: 118
<212> TYPE: PRT
<213> ORGANISM: Artificial Sequence
<220> FEATURE:
<223> OTHER INFORMATION: Adaptor13.0

<400> SEQUENCE: 153

Met Ser Ala Lys Ile Ile His Leu Thr Asp Asp Ser Phe Asp Thr Asp
1               5                   10                  15

Val Leu Lys Ala Asp Gly Ala Ile Leu Val Ala Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Met Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Cys Gly Ala Leu Ser
                85                  90                  95

Lys Gly Gln Leu Lys Glu Phe Leu Asp Ala Asn Leu Ala Gly Gly Ser
            100                 105                 110

His His His His His His
        115


<210> SEQ ID NO 154
<211> LENGTH: 118
<212> TYPE: PRT
<213> ORGANISM: Artificial Sequence
<220> FEATURE:
<223> OTHER INFORMATION: Adaptor14.0

<400> SEQUENCE: 154

Met Ser Ala Lys Ile Ile His Leu Thr Asp Asp Ser Phe Asp Thr Asp
1               5                   10                  15

Val Leu Lys Ala Asp Gly Ala Ile Leu Val Ala Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Met Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95
```

```
Cys Gly Gln Leu Lys Glu Phe Leu Asp Ala Asn Leu Ala Gly Gly Ser
            100                 105                 110

His His His His His His
        115


<210> SEQ ID NO 155
<211> LENGTH: 118
<212> TYPE: PRT
<213> ORGANISM: Artificial Sequence
<220> FEATURE:
<223> OTHER INFORMATION: Adaptor15.0

<400> SEQUENCE: 155

Met Ser Ala Lys Ile Ile His Leu Thr Asp Asp Ser Phe Asp Thr Asp
1               5                   10                  15

Val Leu Lys Ala Asp Gly Ala Ile Leu Val Ala Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Met Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Cys Leu Lys Glu Phe Leu Asp Ala Asn Leu Ala Gly Gly Ser
            100                 105                 110

His His His His His His
        115


<210> SEQ ID NO 156
<211> LENGTH: 118
<212> TYPE: PRT
<213> ORGANISM: Artificial Sequence
<220> FEATURE:
<223> OTHER INFORMATION: Adaptor16.0

<400> SEQUENCE: 156

Met Ser Ala Lys Ile Ile His Leu Thr Asp Asp Ser Phe Asp Thr Asp
1               5                   10                  15

Val Leu Lys Ala Asp Gly Ala Ile Leu Val Ala Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Met Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Cys Asn Leu Ala Gly Gly Ser
            100                 105                 110

His His His His His His
        115


<210> SEQ ID NO 157
<211> LENGTH: 337
<212> TYPE: PRT
<213> ORGANISM: Artificial Sequence
```

<220> FEATURE:
<223> OTHER INFORMATION: Description of Artificial Sequence: Synthetic
polypeptide
<220> FEATURE:
<221> NAME/KEY: VARIANT
<222> LOCATION: (3)..(3)
<223> OTHER INFORMATION: Xaa can be any amino acid
<220> FEATURE:
<221> NAME/KEY: MISC_FEATURE
<222> LOCATION: (3)..(3)
<223> OTHER INFORMATION: residue 3 can be either present or absent
<220> FEATURE:
<221> NAME/KEY: VARIANT
<222> LOCATION: (5)..(6)
<223> OTHER INFORMATION: Xaa can be any amino acid
<220> FEATURE:
<221> NAME/KEY: MISC_FEATURE
<222> LOCATION: (5)..(6)
<223> OTHER INFORMATION: each of residues 5 and 6 can be either present
or absent
<220> FEATURE:
<221> NAME/KEY: VARIANT
<222> LOCATION: (8)..(9)
<223> OTHER INFORMATION: Xaa can be any amino acid
<220> FEATURE:
<221> NAME/KEY: MISC_FEATURE
<222> LOCATION: (8)..(9)
<223> OTHER INFORMATION: each of residues 8 and 9 can be either present
or absent
<220> FEATURE:
<221> NAME/KEY: VARIANT
<222> LOCATION: (11)..(12)
<223> OTHER INFORMATION: Xaa can be any amino acid
<220> FEATURE:
<221> NAME/KEY: MISC_FEATURE
<222> LOCATION: (11)..(12)
<223> OTHER INFORMATION: each of residues 11 and 12 can be either
present or absent
<220> FEATURE:
<221> NAME/KEY: VARIANT
<222> LOCATION: (14)..(21)
<223> OTHER INFORMATION: Xaa can be any amino acid
<220> FEATURE:
<221> NAME/KEY: MISC_FEATURE
<222> LOCATION: (14)..(21)
<223> OTHER INFORMATION: each of residues 14 to 21 can be either present
or absent
<220> FEATURE:
<221> NAME/KEY: VARIANT
<222> LOCATION: (23)..(24)
<223> OTHER INFORMATION: Xaa can be any amino acid
<220> FEATURE:
<221> NAME/KEY: MISC_FEATURE
<222> LOCATION: (23)..(24)
<223> OTHER INFORMATION: each of residues 23 and 24 can be either
present or absent
<220> FEATURE:
<221> NAME/KEY: VARIANT
<222> LOCATION: (25)..(25)
<223> OTHER INFORMATION: Xaa can be Ile or Val
<220> FEATURE:
<221> NAME/KEY: VARIANT
<222> LOCATION: (26)..(26)
<223> OTHER INFORMATION: Xaa can be any amino acid
<220> FEATURE:
<221> NAME/KEY: MISC_FEATURE
<222> LOCATION: (26)..(26)
<223> OTHER INFORMATION: residue 26 can be either present or absent
<220> FEATURE:
<221> NAME/KEY: VARIANT
<222> LOCATION: (28)..(28)
<223> OTHER INFORMATION: Xaa can be any amino acid
<220> FEATURE:
<221> NAME/KEY: MISC_FEATURE
<222> LOCATION: (28)..(28)
<223> OTHER INFORMATION: residue 28 can be either present or absent
<220> FEATURE:
<221> NAME/KEY: VARIANT
<222> LOCATION: (32)..(32)

<223> OTHER INFORMATION: Xaa can be any amino acid
<220> FEATURE:
<221> NAME/KEY: MISC_FEATURE
<222> LOCATION: (32)..(32)
<223> OTHER INFORMATION: residue 32 can be either present or absent
<220> FEATURE:
<221> NAME/KEY: VARIANT
<222> LOCATION: (34)..(34)
<223> OTHER INFORMATION: Xaa can be any amino acid
<220> FEATURE:
<221> NAME/KEY: MISC_FEATURE
<222> LOCATION: (34)..(34)
<223> OTHER INFORMATION: residue 34 can be either present or absent
<220> FEATURE:
<221> NAME/KEY: VARIANT
<222> LOCATION: (36)..(37)
<223> OTHER INFORMATION: Xaa can be any amino acid
<220> FEATURE:
<221> NAME/KEY: MISC_FEATURE
<222> LOCATION: (36)..(37)
<223> OTHER INFORMATION: each of residues 36 and 37 can be either present or absent
<220> FEATURE:
<221> NAME/KEY: VARIANT
<222> LOCATION: (39)..(39)
<223> OTHER INFORMATION: Xaa can be any amino acid
<220> FEATURE:
<221> NAME/KEY: MISC_FEATURE
<222> LOCATION: (39)..(39)
<223> OTHER INFORMATION: residue 39 can be either present or absent
<220> FEATURE:
<221> NAME/KEY: VARIANT
<222> LOCATION: (42)..(42)
<223> OTHER INFORMATION: Xaa can be any amino acid
<220> FEATURE:
<221> NAME/KEY: MISC_FEATURE
<222> LOCATION: (42)..(42)
<223> OTHER INFORMATION: residue 42 can be either present or absent
<220> FEATURE:
<221> NAME/KEY: VARIANT
<222> LOCATION: (45)..(46)
<223> OTHER INFORMATION: Xaa can be any amino acid
<220> FEATURE:
<221> NAME/KEY: MISC_FEATURE
<222> LOCATION: (45)..(46)
<223> OTHER INFORMATION: each of residues 45 and 46 can be either present or absent
<220> FEATURE:
<221> NAME/KEY: VARIANT
<222> LOCATION: (48)..(50)
<223> OTHER INFORMATION: Xaa can be any amino acid
<220> FEATURE:
<221> NAME/KEY: MISC_FEATURE
<222> LOCATION: (48)..(50)
<223> OTHER INFORMATION: each of residues 48 to 50 can be either present or absent
<220> FEATURE:
<221> NAME/KEY: VARIANT
<222> LOCATION: (52)..(52)
<223> OTHER INFORMATION: Xaa can be Asn, Asp, Gln, or Glu
<220> FEATURE:
<221> NAME/KEY: VARIANT
<222> LOCATION: (55)..(56)
<223> OTHER INFORMATION: Xaa can be any amino acid
<220> FEATURE:
<221> NAME/KEY: MISC_FEATURE
<222> LOCATION: (55)..(56)
<223> OTHER INFORMATION: each of residues 55 and 56 can be either present or absent
<220> FEATURE:
<221> NAME/KEY: VARIANT
<222> LOCATION: (60)..(60)
<223> OTHER INFORMATION: Xaa can be Asn, Asp, Gln, or Glu
<220> FEATURE:
<221> NAME/KEY: VARIANT
<222> LOCATION: (61)..(64)
<223> OTHER INFORMATION: Xaa can be any amino acid
<220> FEATURE:
<221> NAME/KEY: MISC_FEATURE
<222> LOCATION: (61)..(64)
<223> OTHER INFORMATION: each of residues 61 to 64 can be either present
or absent
<220> FEATURE:
<221> NAME/KEY: VARIANT
<222> LOCATION: (66)..(67)
<223> OTHER INFORMATION: Xaa can be any amino acid
<220> FEATURE:
<221> NAME/KEY: MISC_FEATURE
<222> LOCATION: (66)..(67)
<223> OTHER INFORMATION: each of residues 66 and 67 can be either
present or absent
<220> FEATURE:
<221> NAME/KEY: VARIANT
<222> LOCATION: (70)..(70)
<223> OTHER INFORMATION: Xaa can be any amino acid
<220> FEATURE:
<221> NAME/KEY: MISC_FEATURE
<222> LOCATION: (70)..(70)
<223> OTHER INFORMATION: residue 70 can be either present or absent
<220> FEATURE:
<221> NAME/KEY: VARIANT
<222> LOCATION: (73)..(73)
<223> OTHER INFORMATION: Xaa can be any amino acid
<220> FEATURE:
<221> NAME/KEY: MISC_FEATURE
<222> LOCATION: (73)..(73)
<223> OTHER INFORMATION: residue 73 can be either present or absent
<220> FEATURE:
<221> NAME/KEY: VARIANT
<222> LOCATION: (76)..(76)
<223> OTHER INFORMATION: Xaa can be any amino acid
<220> FEATURE:
<221> NAME/KEY: MISC_FEATURE
<222> LOCATION: (76)..(76)
<223> OTHER INFORMATION: residue 76 can be either present or absent
<220> FEATURE:
<221> NAME/KEY: VARIANT
<222> LOCATION: (79)..(80)
<223> OTHER INFORMATION: Xaa can be any amino acid
<220> FEATURE:
<221> NAME/KEY: MISC_FEATURE
<222> LOCATION: (79)..(80)
<223> OTHER INFORMATION: each of residues 79 and 80 can be either
present or absent
<220> FEATURE:
<221> NAME/KEY: VARIANT
<222> LOCATION: (82)..(82)
<223> OTHER INFORMATION: Xaa can be any amino acid
<220> FEATURE:
<221> NAME/KEY: MISC_FEATURE
<222> LOCATION: (82)..(82)
<223> OTHER INFORMATION: residue 82 can be either present or absent
<220> FEATURE:
<221> NAME/KEY: VARIANT
<222> LOCATION: (84)..(88)
<223> OTHER INFORMATION: Xaa can be any amino acid
<220> FEATURE:
<221> NAME/KEY: MISC_FEATURE
<222> LOCATION: (84)..(88)
<223> OTHER INFORMATION: each of residues 84 to 88 can be either present
or absent
<220> FEATURE:
<221> NAME/KEY: VARIANT
<222> LOCATION: (90)..(93)
<223> OTHER INFORMATION: Xaa can be any amino acid
<220> FEATURE:
<221> NAME/KEY: MISC_FEATURE
<222> LOCATION: (90)..(93)
<223> OTHER INFORMATION: each of residues 90 to 93 can be either present
or absent
<220> FEATURE:
<221> NAME/KEY: VARIANT
<222> LOCATION: (98)..(99)
<223> OTHER INFORMATION: Xaa can be any amino acid
<220> FEATURE:
<221> NAME/KEY: MISC_FEATURE
<222> LOCATION: (98)..(99)
<223> OTHER INFORMATION: each of residues 98 and 99 can be either

```
      present or absent
<220> FEATURE:
<221> NAME/KEY: VARIANT
<222> LOCATION: (103)..(103)
<223> OTHER INFORMATION: Xaa can be any amino acid
<220> FEATURE:
<221> NAME/KEY: MISC_FEATURE
<222> LOCATION: (103)..(103)
<223> OTHER INFORMATION: residue 103 can be either present or absent
<220> FEATURE:
<221> NAME/KEY: VARIANT
<222> LOCATION: (105)..(106)
<223> OTHER INFORMATION: Xaa can be any amino acid
<220> FEATURE:
<221> NAME/KEY: MISC_FEATURE
<222> LOCATION: (105)..(106)
<223> OTHER INFORMATION: each of residues 105 and 106 can be either
      present or absent
<220> FEATURE:
<221> NAME/KEY: VARIANT
<222> LOCATION: (108)..(108)
<223> OTHER INFORMATION: Xaa can be any amino acid
<220> FEATURE:
<221> NAME/KEY: MISC_FEATURE
<222> LOCATION: (108)..(108)
<223> OTHER INFORMATION: residue 108 can be either present or absent
<220> FEATURE:
<221> NAME/KEY: VARIANT
<222> LOCATION: (109)..(109)
<223> OTHER INFORMATION: Xaa can be Phe or Val
<220> FEATURE:
<221> NAME/KEY: VARIANT
<222> LOCATION: (110)..(112)
<223> OTHER INFORMATION: Xaa can be any amino acid
<220> FEATURE:
<221> NAME/KEY: MISC_FEATURE
<222> LOCATION: (110)..(112)
<223> OTHER INFORMATION: each of residues 110 to 112 can be either
      present or absent
<220> FEATURE:
<221> NAME/KEY: VARIANT
<222> LOCATION: (114)..(116)
<223> OTHER INFORMATION: Xaa can be any amino acid
<220> FEATURE:
<221> NAME/KEY: MISC_FEATURE
<222> LOCATION: (114)..(116)
<223> OTHER INFORMATION: each of residues 114 to 116 can be either
      present or absent
<220> FEATURE:
<221> NAME/KEY: VARIANT
<222> LOCATION: (118)..(120)
<223> OTHER INFORMATION: Xaa can be any amino acid
<220> FEATURE:
<221> NAME/KEY: MISC_FEATURE
<222> LOCATION: (118)..(120)
<223> OTHER INFORMATION: each of residues 118 to 120 can be either
      present or absent
<220> FEATURE:
<221> NAME/KEY: VARIANT
<222> LOCATION: (123)..(131)
<223> OTHER INFORMATION: Xaa can be any amino acid
<220> FEATURE:
<221> NAME/KEY: MISC_FEATURE
<222> LOCATION: (123)..(131)
<223> OTHER INFORMATION: each of residues 123 to 131 can be either
      present or absent
<220> FEATURE:
<221> NAME/KEY: VARIANT
<222> LOCATION: (134)..(135)
<223> OTHER INFORMATION: Xaa can be any amino acid
<220> FEATURE:
<221> NAME/KEY: MISC_FEATURE
<222> LOCATION: (134)..(135)
<223> OTHER INFORMATION: each of residues 134 and 135 can be either
      present or absent
<220> FEATURE:
<221> NAME/KEY: VARIANT
<222> LOCATION: (138)..(138)
<223> OTHER INFORMATION: Xaa can be any amino acid
```

<220> FEATURE:
<221> NAME/KEY: MISC_FEATURE
<222> LOCATION: (138)..(138)
<223> OTHER INFORMATION: residue 138 can be either present or absent
<220> FEATURE:
<221> NAME/KEY: VARIANT
<222> LOCATION: (140)..(140)
<223> OTHER INFORMATION: Xaa can be any amino acid
<220> FEATURE:
<221> NAME/KEY: MISC_FEATURE
<222> LOCATION: (140)..(140)
<223> OTHER INFORMATION: residue 140 can be either present or absent
<220> FEATURE:
<221> NAME/KEY: VARIANT
<222> LOCATION: (143)..(143)
<223> OTHER INFORMATION: Xaa can be any amino acid
<220> FEATURE:
<221> NAME/KEY: MISC_FEATURE
<222> LOCATION: (143)..(143)
<223> OTHER INFORMATION: residue 143 can be either present or absent
<220> FEATURE:
<221> NAME/KEY: VARIANT
<222> LOCATION: (146)..(146)
<223> OTHER INFORMATION: Xaa can be any amino acid
<220> FEATURE:
<221> NAME/KEY: MISC_FEATURE
<222> LOCATION: (146)..(146)
<223> OTHER INFORMATION: residue 146 can be either present or absent
<220> FEATURE:
<221> NAME/KEY: VARIANT
<222> LOCATION: (148)..(148)
<223> OTHER INFORMATION: Xaa can be any amino acid
<220> FEATURE:
<221> NAME/KEY: MISC_FEATURE
<222> LOCATION: (148)..(148)
<223> OTHER INFORMATION: residue 148 can be either present or absent
<220> FEATURE:
<221> NAME/KEY: VARIANT
<222> LOCATION: (150)..(150)
<223> OTHER INFORMATION: Xaa can be any amino acid
<220> FEATURE:
<221> NAME/KEY: MISC_FEATURE
<222> LOCATION: (150)..(150)
<223> OTHER INFORMATION: residue 150 can be either present or absent
<220> FEATURE:
<221> NAME/KEY: VARIANT
<222> LOCATION: (153)..(155)
<223> OTHER INFORMATION: Xaa can be any amino acid
<220> FEATURE:
<221> NAME/KEY: MISC_FEATURE
<222> LOCATION: (153)..(155)
<223> OTHER INFORMATION: each of residues 153 to 155 can be either
present or absent
<220> FEATURE:
<221> NAME/KEY: VARIANT
<222> LOCATION: (160)..(162)
<223> OTHER INFORMATION: Xaa can be any amino acid
<220> FEATURE:
<221> NAME/KEY: MISC_FEATURE
<222> LOCATION: (160)..(162)
<223> OTHER INFORMATION: each of residues 160 to 162 can be either
present or absent
<220> FEATURE:
<221> NAME/KEY: VARIANT
<222> LOCATION: (165)..(168)
<223> OTHER INFORMATION: Xaa can be any amino acid
<220> FEATURE:
<221> NAME/KEY: MISC_FEATURE
<222> LOCATION: (165)..(168)
<223> OTHER INFORMATION: each of residues 165 to 168 can be either
present or absent
<220> FEATURE:
<221> NAME/KEY: VARIANT
<222> LOCATION: (173)..(173)
<223> OTHER INFORMATION: Xaa can be Asn, Asp, Gln, or Glu
<220> FEATURE:
<221> NAME/KEY: VARIANT
<222> LOCATION: (174)..(174)
<223> OTHER INFORMATION: Xaa can be any amino acid
<220> FEATURE:
<221> NAME/KEY: MISC_FEATURE
<222> LOCATION: (174)..(174)
<223> OTHER INFORMATION: residue 174 can be either present or absent
<220> FEATURE:
<221> NAME/KEY: VARIANT
<222> LOCATION: (178)..(178)
<223> OTHER INFORMATION: Xaa can be Leu or Met
<220> FEATURE:
<221> NAME/KEY: VARIANT
<222> LOCATION: (179)..(179)
<223> OTHER INFORMATION: Xaa can be Asn, Asp, Gln, or Glu
<220> FEATURE:
<221> NAME/KEY: VARIANT
<222> LOCATION: (180)..(180)
<223> OTHER INFORMATION: Xaa can be any amino acid
<220> FEATURE:
<221> NAME/KEY: MISC_FEATURE
<222> LOCATION: (180)..(180)
<223> OTHER INFORMATION: residue 180 can be either present or absent
<220> FEATURE:
<221> NAME/KEY: VARIANT
<222> LOCATION: (187)..(187)
<223> OTHER INFORMATION: Xaa can be Asn, Asp, Gln, or Glu
<220> FEATURE:
<221> NAME/KEY: VARIANT
<222> LOCATION: (188)..(188)
<223> OTHER INFORMATION: Xaa can be any amino acid
<220> FEATURE:
<221> NAME/KEY: MISC_FEATURE
<222> LOCATION: (188)..(188)
<223> OTHER INFORMATION: residue 188 can be either present or absent
<220> FEATURE:
<221> NAME/KEY: VARIANT
<222> LOCATION: (192)..(193)
<223> OTHER INFORMATION: Xaa can be any amino acid
<220> FEATURE:
<221> NAME/KEY: MISC_FEATURE
<222> LOCATION: (192)..(193)
<223> OTHER INFORMATION: each of residues 192 and 193 can be either present or absent
<220> FEATURE:
<221> NAME/KEY: VARIANT
<222> LOCATION: (194)..(194)
<223> OTHER INFORMATION: Xaa can be Asn, Asp, Gln, or Glu
<220> FEATURE:
<221> NAME/KEY: VARIANT
<222> LOCATION: (196)..(196)
<223> OTHER INFORMATION: Xaa can be any amino acid
<220> FEATURE:
<221> NAME/KEY: MISC_FEATURE
<222> LOCATION: (196)..(196)
<223> OTHER INFORMATION: residue 196 can be either present or absent
<220> FEATURE:
<221> NAME/KEY: VARIANT
<222> LOCATION: (201)..(201)
<223> OTHER INFORMATION: Xaa can be any amino acid
<220> FEATURE:
<221> NAME/KEY: MISC_FEATURE
<222> LOCATION: (201)..(201)
<223> OTHER INFORMATION: residue 201 can be either present or absent
<220> FEATURE:
<221> NAME/KEY: VARIANT
<222> LOCATION: (207)..(216)
<223> OTHER INFORMATION: Xaa can be any amino acid
<220> FEATURE:
<221> NAME/KEY: MISC_FEATURE
<222> LOCATION: (207)..(216)
<223> OTHER INFORMATION: each of residues 207 to 216 can be either present or absent
<220> FEATURE:
<221> NAME/KEY: VARIANT
<222> LOCATION: (218)..(218)
<223> OTHER INFORMATION: Xaa can be Asn, Asp, Gln, or Glu
<220> FEATURE:
<221> NAME/KEY: VARIANT
<222> LOCATION: (220)..(227)
<223> OTHER INFORMATION: Xaa can be any amino acid
<220> FEATURE:

<221> NAME/KEY: MISC_FEATURE
<222> LOCATION: (220)..(227)
<223> OTHER INFORMATION: each of residues 220 to 227 can be either
present or absent
<220> FEATURE:
<221> NAME/KEY: VARIANT
<222> LOCATION: (229)..(231)
<223> OTHER INFORMATION: Xaa can be any amino acid
<220> FEATURE:
<221> NAME/KEY: MISC_FEATURE
<222> LOCATION: (229)..(231)
<223> OTHER INFORMATION: each of residues 229 to 231 can be either
present or absent
<220> FEATURE:
<221> NAME/KEY: VARIANT
<222> LOCATION: (233)..(234)
<223> OTHER INFORMATION: Xaa can be any amino acid
<220> FEATURE:
<221> NAME/KEY: MISC_FEATURE
<222> LOCATION: (233)..(234)
<223> OTHER INFORMATION: each of residues 233 and 234 can be either
present or absent
<220> FEATURE:
<221> NAME/KEY: VARIANT
<222> LOCATION: (237)..(239)
<223> OTHER INFORMATION: Xaa can be any amino acid
<220> FEATURE:
<221> NAME/KEY: MISC_FEATURE
<222> LOCATION: (237)..(239)
<223> OTHER INFORMATION: each of residues 237 to 239 can be either
present or absent
<220> FEATURE:
<221> NAME/KEY: VARIANT
<222> LOCATION: (241)..(245)
<223> OTHER INFORMATION: Xaa can be any amino acid
<220> FEATURE:
<221> NAME/KEY: MISC_FEATURE
<222> LOCATION: (241)..(245)
<223> OTHER INFORMATION: each of residues 241 to 245 can be either
present or absent
<220> FEATURE:
<221> NAME/KEY: VARIANT
<222> LOCATION: (247)..(250)
<223> OTHER INFORMATION: Xaa can be any amino acid
<220> FEATURE:
<221> NAME/KEY: MISC_FEATURE
<222> LOCATION: (247)..(250)
<223> OTHER INFORMATION: each of residues 247 to 250 can be either
present or absent
<220> FEATURE:
<221> NAME/KEY: VARIANT
<222> LOCATION: (252)..(257)
<223> OTHER INFORMATION: Xaa can be any amino acid
<220> FEATURE:
<221> NAME/KEY: MISC_FEATURE
<222> LOCATION: (252)..(257)
<223> OTHER INFORMATION: each of residues 252 to 257 can be either
present or absent
<220> FEATURE:
<221> NAME/KEY: VARIANT
<222> LOCATION: (259)..(261)
<223> OTHER INFORMATION: Xaa can be any amino acid
<220> FEATURE:
<221> NAME/KEY: MISC_FEATURE
<222> LOCATION: (259)..(261)
<223> OTHER INFORMATION: each of residues 259 to 261 can be either
present or absent
<220> FEATURE:
<221> NAME/KEY: VARIANT
<222> LOCATION: (263)..(263)
<223> OTHER INFORMATION: Xaa can be any amino acid
<220> FEATURE:
<221> NAME/KEY: MISC_FEATURE
<222> LOCATION: (263)..(263)
<223> OTHER INFORMATION: residue 263 can be either present or absent
<220> FEATURE:
<221> NAME/KEY: VARIANT
<222> LOCATION: (266)..(266)
<223> OTHER INFORMATION: Xaa can be any amino acid
<220> FEATURE:
<221> NAME/KEY: MISC_FEATURE
<222> LOCATION: (266)..(266)
<223> OTHER INFORMATION: residue 266 can be either present or absent
<220> FEATURE:
<221> NAME/KEY: VARIANT
<222> LOCATION: (268)..(268)
<223> OTHER INFORMATION: Xaa can be any amino acid
<220> FEATURE:
<221> NAME/KEY: MISC_FEATURE
<222> LOCATION: (268)..(268)
<223> OTHER INFORMATION: residue 268 can be either present or absent
<220> FEATURE:
<221> NAME/KEY: VARIANT
<222> LOCATION: (270)..(271)
<223> OTHER INFORMATION: Xaa can be any amino acid
<220> FEATURE:
<221> NAME/KEY: MISC_FEATURE
<222> LOCATION: (270)..(271)
<223> OTHER INFORMATION: each of residues 270 and 271 can be either present or absent
<220> FEATURE:
<221> NAME/KEY: VARIANT
<222> LOCATION: (273)..(274)
<223> OTHER INFORMATION: Xaa can be any amino acid
<220> FEATURE:
<221> NAME/KEY: MISC_FEATURE
<222> LOCATION: (273)..(274)
<223> OTHER INFORMATION: each of residue 273 and 274 can be either present or absent
<220> FEATURE:
<221> NAME/KEY: VARIANT
<222> LOCATION: (276)..(276)
<223> OTHER INFORMATION: Xaa can be any amino acid
<220> FEATURE:
<221> NAME/KEY: MISC_FEATURE
<222> LOCATION: (276)..(276)
<223> OTHER INFORMATION: residue 276 can be either present or absent
<220> FEATURE:
<221> NAME/KEY: VARIANT
<222> LOCATION: (278)..(279)
<223> OTHER INFORMATION: Xaa can be any amino acid
<220> FEATURE:
<221> NAME/KEY: MISC_FEATURE
<222> LOCATION: (278)..(279)
<223> OTHER INFORMATION: each of residues 278 and 279 can be either present or absent
<220> FEATURE:
<221> NAME/KEY: VARIANT
<222> LOCATION: (281)..(282)
<223> OTHER INFORMATION: Xaa can be any amino acid
<220> FEATURE:
<221> NAME/KEY: MISC_FEATURE
<222> LOCATION: (281)..(282)
<223> OTHER INFORMATION: each of residues 281 and 282 can be either present or absent
<220> FEATURE:
<221> NAME/KEY: VARIANT
<222> LOCATION: (285)..(288)
<223> OTHER INFORMATION: Xaa can be any amino acid
<220> FEATURE:
<221> NAME/KEY: MISC_FEATURE
<222> LOCATION: (285)..(288)
<223> OTHER INFORMATION: each of residues 285 to 288 can be either present or absent
<220> FEATURE:
<221> NAME/KEY: VARIANT
<222> LOCATION: (291)..(291)
<223> OTHER INFORMATION: Xaa can be any amino acid
<220> FEATURE:
<221> NAME/KEY: MISC_FEATURE
<222> LOCATION: (291)..(291)
<223> OTHER INFORMATION: residue 291 can be either present or absent
<220> FEATURE:
<221> NAME/KEY: VARIANT
<222> LOCATION: (293)..(294)
<223> OTHER INFORMATION: Xaa can be any amino acid
<220> FEATURE:
<221> NAME/KEY: MISC_FEATURE
<222> LOCATION: (293)..(294)
<223> OTHER INFORMATION: each of residues 293 and 294 can be either present or absent
<220> FEATURE:
<221> NAME/KEY: VARIANT
<222> LOCATION: (297)..(299)
<223> OTHER INFORMATION: Xaa can be any amino acid
<220> FEATURE:
<221> NAME/KEY: MISC_FEATURE
<222> LOCATION: (297)..(299)
<223> OTHER INFORMATION: each of residues 297 and 299 can be either present or absent
<220> FEATURE:
<221> NAME/KEY: VARIANT
<222> LOCATION: (301)..(305)
<223> OTHER INFORMATION: Xaa can be any amino acid
<220> FEATURE:
<221> NAME/KEY: MISC_FEATURE
<222> LOCATION: (301)..(305)
<223> OTHER INFORMATION: each of residues 301 to 305 can be either present or absent
<220> FEATURE:
<221> NAME/KEY: VARIANT
<222> LOCATION: (307)..(312)
<223> OTHER INFORMATION: Xaa can be any amino acid
<220> FEATURE:
<221> NAME/KEY: MISC_FEATURE
<222> LOCATION: (307)..(312)
<223> OTHER INFORMATION: each of residues 307 to 312 can be either present or absent
<220> FEATURE:
<221> NAME/KEY: VARIANT
<222> LOCATION: (314)..(316)
<223> OTHER INFORMATION: Xaa can be any amino acid
<220> FEATURE:
<221> NAME/KEY: MISC_FEATURE
<222> LOCATION: (314)..(316)
<223> OTHER INFORMATION: each of residues 314 to 316 can be either present or absent
<220> FEATURE:
<221> NAME/KEY: VARIANT
<222> LOCATION: (318)..(322)
<223> OTHER INFORMATION: Xaa can be any amino acid
<220> FEATURE:
<221> NAME/KEY: MISC_FEATURE
<222> LOCATION: (318)..(322)
<223> OTHER INFORMATION: each of residues 318 to 322 can be either present or absent
<220> FEATURE:
<221> NAME/KEY: VARIANT
<222> LOCATION: (324)..(337)
<223> OTHER INFORMATION: Xaa can be any amino acid
<220> FEATURE:
<221> NAME/KEY: MISC_FEATURE
<222> LOCATION: (324)..(337)
<223> OTHER INFORMATION: each of residues 324 to 337 can be either present or absent

<400> SEQUENCE: 157

```
Trp Lys Xaa Gln Xaa Xaa Trp Xaa Xaa Gly Xaa Xaa Gly Xaa Xaa Xaa
1               5                   10                  15

Xaa Xaa Xaa Xaa Xaa Ala Xaa Xaa Xaa Xaa Glu Xaa Thr Gly Gly Xaa
            20                  25                  30

Leu Xaa Ile Xaa Xaa Phe Xaa Ala Gly Xaa Val Val Xaa Xaa Phe Xaa
        35                  40                  45

Xaa Xaa Phe Xaa Ala Val Xaa Xaa Gly Val Leu Xaa Xaa Xaa Xaa Xaa
    50                  55                  60

Phe Xaa Xaa Tyr Trp Xaa Gly Lys Xaa Pro Ala Xaa Ala Phe Xaa Xaa
65                  70                  75                  80

Ser Xaa Pro Xaa Xaa Xaa Xaa Xaa Pro Xaa Xaa Xaa Xaa Ala Trp Phe
                85                  90                  95

Tyr Xaa Xaa Gly Gly Leu Xaa Leu Xaa Xaa Glu Xaa Xaa Xaa Xaa Xaa
```

-continued

```
            100                 105                 110

Gly Xaa Xaa Xaa Leu Xaa Xaa Xaa Gly Pro Xaa Xaa Xaa Xaa Xaa Xaa
        115                 120                 125

Xaa Xaa Xaa His Ser Xaa Xaa Pro Ile Xaa Ser Xaa Asp Asp Xaa Lys
    130                 135                 140

Gly Xaa Lys Xaa Arg Xaa Pro Gly Xaa Xaa Xaa Ala Glu Val Phe Xaa
145                 150                 155                 160

Xaa Xaa Gly Ala Xaa Xaa Xaa Xaa Leu Pro Gly Gly Xaa Xaa Tyr Pro
                165                 170                 175

Ala Xaa Xaa Xaa Gly Thr Ile Asp Ala Ala Xaa Xaa Val Gly Pro Xaa
            180                 185                 190

Xaa Xaa Tyr Xaa Leu Gly Phe His Xaa Val Ala Lys Tyr Ile Xaa Xaa
        195                 200                 205

Xaa Xaa Xaa Xaa Xaa Xaa Xaa Xaa His Xaa Pro Xaa Xaa Xaa Xaa Xaa
    210                 215                 220

Xaa Xaa Xaa Asn Xaa Xaa Xaa Trp Xaa Xaa Leu Pro Xaa Xaa Xaa Gln
225                 230                 235                 240

Xaa Xaa Xaa Xaa Xaa Ala Xaa Xaa Xaa Xaa Ser Xaa Xaa Xaa Xaa Xaa
                245                 250                 255

Xaa Ile Xaa Xaa Xaa Asn Xaa Glu Ala Xaa Lys Xaa Lys Xaa Xaa Gly
            260                 265                 270

Xaa Xaa Val Xaa Arg Xaa Xaa Leu Xaa Xaa Glu Asp Xaa Xaa Xaa Xaa
        275                 280                 285

Arg Glu Xaa Ala Xaa Xaa Ile Trp Xaa Xaa Xaa Ala Xaa Xaa Xaa Xaa
    290                 295                 300

Xaa Ala Xaa Xaa Xaa Xaa Xaa Xaa Gln Xaa Xaa Xaa Met Xaa Xaa Xaa
305                 310                 315                 320

Xaa Xaa Gly Xaa Xaa Xaa Xaa Xaa Xaa Xaa Xaa Xaa Xaa Xaa Xaa Xaa
                325                 330                 335

Xaa
```

LACTATE BIOSENSORS AND USES THEREOF

RELATED APPLICATIONS

This application is a national stage application, filed under 35 U.S.C. § 371, of International Application No. PCT/US2016/062961 filed Nov. 19, 2016, which claims benefit of priority to U.S. Provisional Application No. 62/257,856, filed Nov. 20, 2015 and U.S. Provisional Application No. 62/257,796, filed Nov. 20, 2015, the entire contents of each of which are incorporated herein by reference.

INCORPORATION-BY-REFERENCE OF SEQUENCE LISTING

The contents of the text file named "035327-523N01US_SL.txt", which was created on Dec. 21, 2020 and is 381,759 bytes in size, is hereby incorporated by reference in its entirety.

FIELD OF THE INVENTION

The present invention relates to compositions and methods for detecting and determining the concentration of lactate.

BACKGROUND

Current lactate sensors tend to be either electrochemical or optical biosensors using the enzyme lactate dehydrogenase, lactate oxidase, alpha-hydroxy acid oxidase, lactate monooxygenase, lactate peroxidase. Despite the number of developed lactate biosensors, there is still a need to improve stability, sensibility and applicability of such devices. Most of these sensors suffer from long response time, short stability, and poor reproducibility.

SUMMARY OF THE INVENTION

Aspects of the present subject matter provide improved biosensors that rapidly, reliably, and accurately detect and quantify lactate with significant advantages over previous systems. The present disclosure provides a biosensor for lactate, comprising a reporter group that is attached to a lactate-binding protein. The lactate-binding protein includes a domain or region(s) that binds the lactate. The domain or region involved in ligand binding is comprised of a plurality of residues, e.g., non-contiguous amino acids of the ligand-binding protein, which are contact points or sites of contact between the ligand and its cognate ligand-binding protein. The binding of a lactate to the lactate-binding domain of the lactate-binding protein causes a change in signaling by the reporter group. In various implementations, the biosensor may produce a signal when a lactate is bound to the lactate binding domain that is not produced (and/or that is different from a signal that is produced) when the lactate is absent from the lactate binding domain. These biosensors have widespread utility including in clinical, food and beverage, industrial, and environmental settings.

A reporter group that transduces a detectable signal may be attached to the lactate-binding proteins (biosensors) described herein. As used herein, "transduce" means the conversion of ligand occupancy in the binding site of a ligand-binding protein to a detectable signal. Occupancy refers to the state of ligand being bound or not bound to a cognate ligand-binding protein. In embodiments, detectable signal comprises a fluorescent, electrochemical, nuclear magnetic resonance (NMR), or electron paramagnetic resonance (EPR) signal. The reporter group is attached to the lactate-binding protein so that a signal transduced by the reporter group when the lactate-binding protein is bound to lactate differs from a signal transduced by the reporter group when the lactate-binding protein is not bound to lactate. The proteins may be engineered to include a single cysteine to which the detectable label, e.g., a fluorophore is covalently attached. The biosensors are reagentless in that their monitoring mechanism requires neither additional substrates for a signal to develop, nor measurement of substrate consumption or product generation rates to determine lactate concentrations.

The lactate-binding proteins (as well as biosensors comprising the ligand-binding proteins) provided herein lack enzymatic activity and are not enzymes. As used herein, an "enzyme" is a protein that catalyzes a specific biochemical reaction. The lactate is not chemically altered (i.e., no chemical bond or atom of the lactate is added or removed) by the lactate-binding protein. Thus, when lactate dissociates from a lactate-binding protein described herein, the lactate contains the same chemical structure it had before it became bound to the lactate-binding protein.

In some embodiments, the biosensor proteins include a second fluorophore, thereby permitting ratiometric sensing/detection of an analyte using establishing non-geometrically modulated Förster resonance energy transfer (ngmFRET).

Among the advantages of these fluorophore-containing protein constructs is their high durability. The constructs retain their ability to bind lactate, change shape and thus detect the analyte, lactate, (a) even when immobilized (directly or indirectly) onto a solid surface such as a bead, plate, or sheet; (b) even after desiccation (and subsequent reconstitution in a physiological buffer solution); (c) even when subjected to ambient conditions, e.g., conditions that can be encountered in storage and/or transportation; and (d) even when aged/stored for extended periods of time. e.g., weeks, months, or even years. Thus, the biosensors do not require refrigeration or a cold chain for distribution, permitting a wider range of applicability such as in-the-field use and reducing the cost of the sensor product.

For clinical applications, microliter volumes (e.g., less than 0.1, 0.5, 1, 2, 3, 4, 5, 6, 7, 8, 9, or 10, or less than 10 μl) of a bodily fluid such as blood may be used. Moreover compared to conventional enzyme-based or antibody based assay systems, the results are achieved virtually instantaneously, e.g., 0.1-5 minutes, e.g., 0.1-1 minutes, or within 30-60 seconds. A further advantage is that the sensors consistently and reliably bind to and detect the analyte (lactate) in complex fluids such as whole blood, plasma, serum, saliva, urine, and environmental fluids. Thus in a clinical setting, whole blood need not be processed, thereby reducing time and cost of the diagnostic procedure. Alternatively or in addition, the biosensors provided herein may be used to monitor lactate levels continuously. In a non-limiting example, one or more biosensors is immobilized at the tip of a thin optical fiber to construct a lactate-responsive optode. Such an optode can be introduced into the body (e.g., subcutaneously). The sensor may be in continuous contact with the sample, and excitation and emission light are passed to and from the immobilized sensor, respectively. Fluctuations in the lactate sample alter the dynamic equilibrium between the open and closed states of the lactate-binding protein, which is transduced into fluctuations of the fluorescent emission signal, by virtue of the sensing mechanism of the conjugated fluorophore. The emitted light intensities may be read by a reader connected to the optode.

In non-clinical situations, e.g., food and beverage composition (e.g. meat, canned food, dairy, nondairy, a fermented food, a fruit, a vegetable, a tuber, a starch, a grain, pasta, yogurt, soup, ice cream, a broth, a puree, a shake, a smoothie, a batter, a condiment, a sauce, a soft drink, a fountain beverage, water, coffee, tea, milk, a dairy-based beverages, soy-based beverage, an almond-based beverage, vegetable juice, fruit juice, a fruit juice-flavored drink, an energy drink, or an alcoholic beverage) production and/or storage, industrial, environmental (e.g., wetlands, rivers, streams, ponds, marine environments, wells, aquariums, pools, lakes, rivers, brooks, reservoirs, ground water, residential land, commercial/industrial land, agricultural land, or land abutting agricultural land), or commercial settings such as analysis of waste water, food or beverage production, or bioreactor/fermentation monitoring, the samples to be analyzed can be used directly upon sampling without further purification or processing, similarly reducing time and expense of the test. Moreover, the immobilized sensors need not be washed to remove unbound material following contacting the test sample with the sensors, because the unbound material ("contaminants") do not materially affect the production of a precise, reliable detectable assay signal.

Included herein are lactate biosensors that produce a dichromatic, ratiometric signal, i.e., the signal is defined as the quotient of the intensities at two independent wavelengths. The advantage of such a signal is that it provides an internally consistent reference. The self-calibrating nature of a ratiometric measurement removes the necessity for carrying out on-board calibration tests prior to each measurement.

Thus, reagentless, fluorescently responsive lactate sensors present a number of advantages over enzyme-based biosensors, including elimination of chemical transformations, elimination of substrate requirements, and self-calibration, which together lead to rapid response times, continuous monitoring capabilities, simple sample-handling, and lower cost due to simplified manufacturing and distribution processes.

Ligand-Binding Proteins

Aspects of the present subject matter provide biosensors comprising a ligand-binding protein that binds lactate (i.e., a lactate-binding protein). Typically, a natural lactate-binding protein has a lactate dissociation constant ($K_d$) of about 10 μM or less at room temperature. However, lactate-binding proteins may be selected, designed, or engineered (e.g., via mutation) to have a different affinity for lactate (e.g., to detect higher or lower levels of lactate). In various embodiments, a lactate-binding protein has a $K_d$ for lactate in the millimolar, micromolar, nanomolar, picomolar, or femtomolar range. For example, a lactate-binding protein may have a $K_d$ for lactate of at least about 0.00001 mM, 0.0001 mM, 0.001 mM, 0.005 mM, 0.1 mM, 0.2 mM, 0.3 mM, 0.4 mM, 0.5 mM, 0.6 mM, 0.7 mM, 0.8 mM, 0.9 mM, 1 mM, 1.1 mM, 1.2 mM, 1.3 mM, 1.4 mM, 1.5 mM, 1.6 mM, 1.7 mM, 1.8 mM, 1.9 mM, 2 mM, 2.1 mM, 2.2 mM, 2.3 mM, 2.4 mM, 2.5 mM, 2.6 mM, 2.7 mM, 2.8 mM, 2.9 mM, 3 mM, 3.1 mM, 3.2 mM, 3.3 mM, 3.4 mM, 3.5 mM, 4 mM, 4.5 mM, 5 mM, 5.5 mM, 6 mM, 7 mM, 8 mM, 9 mM, 10 mM, 15 mM, 20 mM, 25 mM, 30 mM, 35 mM, 40 mM, 45 mM, 50 mM, 75 mM, or 100 mM, and/or less than about 0.00001 mM, 0.0001 mM, 0.001 mM, 0.005 mM, 0.1 mM, 0.2 mM, 0.3 mM, 0.4 mM, 0.5 mM, 0.6 mM, 0.7 mM, 0.8 mM, 0.9 mM, 1 mM, 1.1 mM, 1.2 mM, 1.3 mM, 1.4 mM, 1.5 mM, 1.6 mM, 1.7 mM, 1.8 mM, 1.9 mM, 2 mM, 2.1 mM, 2.2 mM, 2.3 mM, 2.4 mM, 2.5 mM, 2.6 mM, 2.7 mM, 2.8 mM, 2.9 mM, 3 mM, 3.1 mM, 3.2 mM, 3.3 mM, 3.4 mM, 3.5 mM, 4 mM, 4.5 mM, 5 mM, 5.5 mM, 6 mM, 7 mM, 8 mM, 9 mM, 10 mM, 15 mM, 20 mM, 25 mM, 30 mM, 35 mM, 40 mM, 45 mM, 50 mM, 75 mM, or 100 mM. In some embodiments, a lactate-binding protein has a $K_d$ for lactate below, within, or above the normal range of lactate in human blood. Physiological lactate levels for a healthy human under resting conditions are typically between 0.5 to 2.5 mM but during vigorous physical activity the concentration can rise up to 20-30 mM. See. e.g., Warrel 2010 Oxford Textbook of Medicine. Oxford University Press; Burtis 2012 Tietz Textbook of Clinical Chemistry and Molecular Diagnostics. Elsevier; Romero 2010 Anal. Chem., 82, 5568-5572; Suman 2005 Sens Actuators B Chem, 107, 768-772, the entire contents of each of which is incorporated herein by reference. Hyperlactatemia is a persistent, mild to moderate (2.5-4 mM) increase in blood lactate concentration without metabolic acidosis, whereas lactic acidosis is characterized by persistently increased blood lactate levels (usually >5 mM) in association with metabolic acidosis.

Preferably, the lactate-binding protein has a higher affinity (lower $K_d$) for lactate than for pyruvate and L-alanine. In various embodiments, the affinity of the lactate-binding protein for lactate is at least about 2-fold, 3-fold, 4-fold, 5-fold, 6-fold, 7-fold, 8-fold, 9-fold, 10-fold, 20-fold, 30-fold, 40-fold, 50-fold, or 100-fold higher than the affinity of the lactate-binding protein for pyruvate. In various embodiments, the affinity of the lactate-binding protein for lactate is at least about 2-fold, 3-fold, 4-fold, 5-fold, 6-fold, 7-fold, 8-fold, 9-fold, 10-fold, 20-fold, 30-fold, 40-fold, 50-fold, or 100-fold higher than the affinity of the lactate-binding protein for L-alanine.

With respect to the present subject matter, $K_d$ is the equilibrium dissociation constant between a ligand-binding protein and its ligand. $K_d$ decreases with increasing affinity, and $K_d$ may be used as an expression of affinity (the lower the value, the higher the affinity). The $K_d$ value relates to the concentration of ligand required for detectable ligand-binding to occur and so the lower the $K_d$ value (lower concentration required), the higher the affinity of the ligand-binding protein for the ligand. The $K_d$ value corresponds to the ligand concentration at which the binding protein is 50% saturated.

| $K_d$ value | Molar concentration |
|---|---|
| $10^{-1}$ to $10^{-3}$ | Millimolar (mM) |
| $10^{-4}$ to $10^{-6}$ | Micromolar (μM) |
| $10^{-7}$ to $10^{-9}$ | Nanomolar (nM) |
| $10^{-10}$ to $10^{-12}$ | Picomolar (pM) |
| $10^{-13}$ to $10^{-15}$ | Femtomolar (fM) |

The ligand-binding protein may comprise a naturally occurring protein or a protein that is modified compared to a naturally occurring protein. For example, the ligand-binding protein may comprise one or more mutations compared to a naturally occurring protein. In some embodiments, the naturally occurring protein is a naturally occurring counterpart of the ligand-binding protein (e.g., the ligand-binding protein is a mutant of the naturally occurring counterpart).

A "naturally occurring counterpart" of a mutant polypeptide is a polypeptide produced in nature from which the mutant polypeptide has been or may be derived (e.g., by one or more mutations). For example, the naturally occurring counterpart is an endogenous polypeptide produced by an organism in nature, wherein the endogenous polypeptide typically does not have one or more of the mutations present in the mutant polypeptide. For convenience and depending on context, a naturally occurring counterpart may be referred to herein for the purpose of comparison and to illustrate the location and/or presence of one or more mutations, binding activities, and/or structural features.

As used herein, a "mutation" is a difference between the amino acid sequence of a modified polypeptide/protein and a naturally occurring counterpart. A polypeptide having a mutation may be referred to as a "mutant." Non-limiting examples of mutations include insertions, deletions, and substitutions. However, the term "mutation" excludes (i) the addition of amino acids to the N-terminus or C-terminus of a polypeptide, and (ii) the omission/deletion/replacement of a polypeptide's signal peptide (e.g., replacement with another signal peptide or with a methionine).

The addition of amino acids to the N-terminus or C-terminus of a protein via a peptide bond may be referred to herein as a "fusion" of the amino acids to the protein. Similarly, an exogenous protein fused to amino acids (e.g., another protein, a fragment, a tag, or a polypeptide moiety) at its N-terminus or C-terminus may be referred to as a "fusion protein." The added amino acids may comprise a non-native polypeptide, e.g., a polypeptide reporter group such as a fluorescent protein, a moiety that facilitates the isolation or modification of a polypeptide, or a moiety that facilitates the attachment of a polypeptide to a substrate or surface. As used herein, "non-native" when referring to the added amino acids (e.g., a "polypeptide") of a fusion protein indicates that the polypeptide is not naturally part of the protein to which it is fused in the fusion protein. For example, the sequence of a non-native polypeptide ("added amino acids") that is fused to a protein is encoded by an organism other than the organism from which the protein is derived, is not known to be naturally encoded by any organism, or is encoded by a gene other than the wild-type gene that encodes an endogenous version of the protein.

As used herein the term "signal peptide" refers to a short (e.g., 5-30 or 10-100 amino acids long) stretch of amino acids at the N-terminus of a protein that directs the transport of the protein. In various embodiments, the signal peptide is cleaved off during the post-translational modification of a protein by a cell. Signal peptides may also be referred to as "targeting signals," "leader sequences," "signal sequences," "transit peptides," or "localization signals." In instances where a signal peptide is not defined for a lactate-binding protein discussed herein, the signal peptide may optionally be considered to be, e.g., the first 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 5-15, 5-20, 5-25, 5-100, 10-15, 10-20, 10-25, 10-50, 10-100, 25-50, 25-75, or 25-100 amino acids from the N-terminus of the translated protein (compared to a protein that has not had the signal peptide removed, e.g., compared to a naturally occurring protein).

In some embodiments, the ligand-binding protein comprises 1, 2, 3, 4, 5, 6, 7, 8, 9, 10, 15, 20, 25, 30, 40, 50, 60, 70, 80, 90, 100, 1-10, 1-15, 1-20, 5-15, 5-20, 10-25, 10-50, 20-50, 25-75, 25-100 or more mutations compared to a naturally occurring protein while retaining at least about 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 99.5%, or about 100% of the activity of the naturally occurring protein. Mutations include but are not limited to substitutions, insertions, and deletions. Non-limiting examples of ligand-binding proteins may have 1, 2, 3, 4, 5, 6, 7, 8, 9, 10, 15, 20, 25, 30, 40, 50, 60, 70, 80, 90, 100, 1-10, 1-15, 1-20, 5-15, 5-20, 10-25, 10-50, 20-50, 25-75, 25-100, or more substitution mutations compared to a naturally occurring protein while retaining at least about 10%, 15%, 201%, 25%, 30%, 35%, 40%, 45%, 50%, 55%, 60%, 65%, 70%, 75%, 80%, 85%, 90%, 95%, 96%, 97%, 98%, 99%, or 99.5%, or about 100% of the activity of the naturally occurring protein. In embodiments, at least one amino acid of the ligand-binding protein has been substituted with a cysteine. Alternatively or in addition, a ligand-binding protein may include one or more mutations that remove a cysteine, e.g., 1, 2, 3, 4, 5, 6, 7, 8, 9, 10 or more substitutions or deletions of a cysteine compared to a naturally occurring protein.

Alternatively, the ligand-binding protein is not a mutant. For example, a reporter group is fused to the N-terminus or the C-terminus of the ligand-binding protein.

In some embodiments, the reporter group is conjugated to an amino acid that is no more than about 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 5-15, 5-20, 5-25, 5-100, 10-15, 10-20, 10-25, 10-50, 10-100, 25-50, 25-75, or 25-100 amino acids from the N-terminus or the C-terminus of the ligand-binding protein. In some embodiments, the reporter group is conjugated to an amino acid that is at least about 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 5-15, 5-20, 5-25, 5-100, 10-15, 10-20, 10-25, 10-50, 10-100, 25-50, 25-75, or 25-100 amino acids from the N-terminus or the C-terminus of the ligand-binding protein. In some embodiments, about 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 5-15, 5-20, 5-25, 5-100, 10-15, 10-20, 10-25, 10-50, 10-100, 25-50, 25-75, or 25-100 amino acids (including or not including the signal peptide) have been deleted (e.g. are absent) from the N-terminus of the protein compared to its naturally occurring counterpart. In some embodiments, less than 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 5-15, 5-20, 5-25, 5-100, 10-15, 10-20, 10-25, 10-50, 10-100, 25-50, 25-75, or 25-100 amino acids (including or not including the signal peptide) have been deleted (e.g. are absent) from the N-terminus of the protein compared to its naturally occurring counterpart. In some embodiments, about 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 5-15, 5-20, 5-25, 5-100, 10-15, 10-20, 10-25, 10-50, 10-100, 25-50, 25-75, or 25-100 amino acids have been deleted (e.g. are absent) from the C-terminus of the protein compared to its naturally occurring counterpart. In some embodiments, less than 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 5-15, 5-20, 5-25, 5-100, 10-15, 10-20, 10-25, 10-50, 10-100, 25-50, 25-75, or 25-100 amino acids have been deleted (e.g. are absent) from the C-terminus of the protein compared to its naturally occurring counterpart.

In various embodiments, a ligand-binding protein may comprise a stretch of amino acids (e.g., the entire length of the ligand-binding protein or a portion comprising at least about 50, 100, 200, 250, 300, or 350 amino acids) in a sequence that is at least about 90%, 91%, 92%, 93%, 94%, 95%, 96%, 97%, 98%, 99%, 99.1%, 99.2%, 99.3%, 99.4%, or 99.5% identical to an amino acid sequence of a naturally occurring protein.

In some embodiments, the mutations are conservative, and the present subject matter includes many ligand-binding proteins in which the only mutations are substitution mutations. In non-limiting examples, a ligand-binding protein has no deletions or insertions compared to a naturally occurring protein (e.g., a naturally occurring counterpart). In non-limiting examples, the lactate-binding protein does not comprise a deletion or insertion compared to ttLacBP1, tsLacBP2, toLacBP3, tsLacBP4, rdLacBP5, msLacBP6, tsLacBP7, maLacBP8, adLacBP9, pgLacBP10, psLacBP11, rsLacBP12, fsLacBP13, or taLacBP14. Alternatively, a ligand-binding protein may have (i) less than about 5, 4, 3, 2, or 1 inserted amino acids, and/or (ii) less than about 5, 4, 3, 2, or 1 deleted amino acids compared to a naturally occurring protein.

In various embodiments, a naturally occurring protein to which a ligand-binding protein is compared or has been derived (e.g., by mutation, fusion, or other modification) from a prokaryotic ligand-binding protein such as a bacterial ligand-binding protein. For example, the prokaryotic ligand-binding protein is a mutant, fragment, or variant of a natural (i.e., wild-type) bacterial protein. In various embodiments, the bacterial ligand-binding protein is from a thermophilic, mesophilic, or cryophilic prokaryotic microorganism (e.g., a thermophilic, mesophilic, or cryophilic bacterium).

A microorganism is "thermophilic" if it is capable of surviving, growing, and reproducing at temperatures between 41 and 140° C. (106 and 284 OF), inclusive. In various embodiments, a thermophilic organism has an optimal growth temperature between 41 and 140° C., or that is at least about 45, 50, 55, 60, 65, 70, 75, 80, 85, 90, 95, 100, 105, 110, 115, 120, 125, 130, 135, or 140° C. Many thermophiles are archaea. Thermophilic eubacteria are suggested to have been among the earliest bacteria. Thermophiles are found in various geothermally heated regions of the Earth, such as hot springs and deep sea hydrothermal vents, as well as decaying plant matter, such as peat bogs and compost. Unlike other types of microorganisms, thermophiles can survive at much hotter temperatures, whereas other bacteria would be damaged and sometimes killed if exposed to the same temperatures. Thermophiles may be classified into three groups: (1) obligate thermophiles; (2) facultative thermophiles; and (3) hyperthermophiles. Obligate thermophiles (also called extreme thermophiles) require such high temperatures for growth, whereas facultative thermophiles (also called moderate thermophiles) can thrive at high temperatures, but also at lower temperatures (e.g. below 50° C.). Hyperthermophiles are particularly extreme thermophiles for which the optimal temperatures are above 80° C. Some microorganisms can live at temperatures higher than 100° C. at large depths in the ocean where water does not boil because of high pressure. Many hyperthermophiles are also able to withstand other environmental extremes such as high acidity or radiation levels. A compound (e.g., a protein or biosensor) is "thermotolerant" if it is capable of surviving exposure to temperatures above 41° C. For example, in some embodiments a thermotolerant biosensor retains its function and does not become denatured when exposed to a temperature of about 45, 50, 55, 60, 65, 70, 75, 80, 85, 90, 95, 100, 105, 110, 115, 120, 125, 130, 135, or 140° C. for at least about 1, 2, 3, 4, 5, 6, 7, 8, 9, 10, 15, 20, 25, 30 or more minutes. In some embodiments, the thermotolerant compound survives exposure to 45, 50, 55, 60, 65, 70, 75, 80, 85, 90, 95, 100, 105, 110, 115, 120, 125, 130, 135, or 140° C. under pressure.

A microorganism is "mesophilic" if it is capable of surviving, growing, and reproducing at temperatures between 20 and 40° C. (68 and 104° F.), inclusive. "Psychrophiles" or "cryophiles" are microorganisms that are capable of growth and reproduction in cold temperatures. In various embodiments, a psychrophile is capable of growth and reproduction at a temperature of 10° C. or less, e.g., between −20° C. and +10° C.

In some embodiments, the microbial protein is produced by a bacterial microorganism, an archaean microorganism, an algal microorganism, a protozoan microorganism, or a fungal microorganism. In non-limiting examples, the microbial protein is produced by a Gram-positive bacterium or a Gram-negative bacterium. In various embodiments, a biosensor comprises a modified (e.g., mutated, fused, and/or conjugated) periplasmic binding protein or a cytoplasmic binding protein.

Aspects of the present subject matter provide a ligand-binding protein with a mutation that alters the interaction of the ligand-binding protein with a ligand (i.e. lactate). For example, the ligand-binding protein comprises a mutation that alters the interaction of the ligand-binding protein with the ligand compared to a naturally occurring counterpart. In some embodiments, the ligand-binding protein comprises a mutation that alters the interaction of an amino acid of the ligand-binding protein with a water molecule compared to a naturally occurring counterpart.

In some embodiments, the ligand-binding protein does not comprise a signal peptide. For example, the signal peptide (e.g., that is present in a naturally occurring counterpart) may be replaced with a methionine.

Exemplary implementations relate to a ligand such as lactate, wherein the ligand-binding protein comprises a lactate-binding protein. For example, the lactate-binding protein may comprise a mutant of, a fragment of, or a fusion protein comprising a microbial lactate-binding protein. In embodiments, the lactate-binding protein is not a mutant or fragment to which a non-native polypeptide has been attached or added. In some embodiments, the ligand-binding protein has an affinity ($K_d$) for lactate within the concentration range of lactate in a subject. In certain embodiments, the ligand-binding protein has an affinity ($K_d$) for lactate in the range of about 0.01 mM to about 50 mM, about 0.01 mM to about 25 mM, about 0.01 mM to about 0.1 mM, about 0.01 mM to about 0.5 mM, about 0.1 mM to about 2 mM, about 0.2 mM to about 2 mM, about 0.3 mM to about 2 mM, about 0.4 mM to about 2 mM, about 0.5 mM to about 2 mM, about 0.6 mM to about 2 mM, about 0.7 mM to about 2 mM, about 0.8 mM to about 2 mM, about 0.9 mM to about 2 mM, about 1 mM to about 2 mM, about 1.25 mM to about 2 mM, about 1.5 mM to about 2 mM, about 0.1 mM to about 2.5 mM, about 0.2 mM to about 2.5 mM, about 0.3 mM to about 2.5 mM, about 0.4 mM to about 2.5 mM, about 0.5 mM to about 2.5 mM, about 0.6 mM to about 2.5 mM, about 0.7 mM to about 2.5 mM, about 0.8 mM to about 2.5 mM, about 0.9 mM to about 2.5 mM, about 1 mM to about 2.5 mM, about 1.25 mM to about 2.5 mM, about 1.5 mM to about 2.5 mM, about 1.1 mM to about 5 mM, about 1.2 mM to about 5 mM, about 1.3 mM to about 5 mM, about 1.4 mM to about 5 mM, about 1.5 mM to about 5 mM, about 1.6 mM to about 5 mM, about 1.7 mM to about 5 mM, about 1.8 mM to about 5 mM, about 1.9 mM to about 5 mM, about 2 mM to about 5 mM, about 2.25 mM to about 5 mM, about 2.5 mM to about 5 mM, about 0.01 mM to about 10 mM, about 0.01 mM to about 5 mM, about 0.1 mM to about 50 mM, about 0.1 mM to about 25 mM, about 0.1 mM to about 10 mM, about 0.1 mM to about 5 mM, about 1 mM to about 50 mM, about 1 mM to about 25 mM, about 1 mM to about 10 mM, about 1 mM to about 5 mM, about 0.5 mM to about 1 mM, or about 2 to about 4 mM. In various embodiments, the biosensor is capable of detecting lactate when lactate is present at a concentration of at least about 0.001 mM, 0.1 mM, 0.5 mM, 1 mM, 1.5 mM, 2 mM, 2.5 mM, 3 mM, 4 mM, 5 mM, 6 mM, 7 mM, 8 mM, 9 mM, 10 mM, 15 mM, 20 mM, 25 mM, 50 mM, 75 mM, or 100 mM. The ratiometric reagentless lactate biosensors produce precise measurements over an extended concentration ranges, as noted above, as well as in sample volumes of less than about. e.g., 10 µl, 9 µl, 8 µl, 7 µl, 6 µl, 5 µl, 4 µl, 3 µl, 2 µl, or 1 µl. In some embodiments, the volume of sample that is applied to a biosensor or a device comprising a biosensor is less than 0.1, 0.5, 1, 2, 3, 4, 5, 6, 7, 8, 9, 10, 25, 50, 75, 100, 150, 300, 500, or 1000 µl. In some embodiments, the volume is about 0.1 µl to about 1000 µl, about 0.1 µl to about 100 µl, about 1 µl to about 1000 µl, about 1 µl to about 10 µl, about 1 µl to about 100 µl, about 1 µl to about 50 µl, about 10 µl to about 50 µl, or about 5 µl to about 50 µl. In some embodiments, the ligand-binding protein comprises a mutation that alters (e.g., increases or decreases) the interaction of the mutant with bound lactate compared to a naturally occurring protein (e.g., a microbial lactate-binding protein), wherein the interaction is with a portion of the lactate selected from the group consisting of a —CH3 group, an —OH group, a —C(═O)O$^-$ group, or any combination thereof. In non-limiting examples, the ligand-binding protein comprises a mutation that alters (e.g., increases or decreases) the mutant's affinity and/or specificity for lactate compared to an unmutated ligand-binding protein (e.g., a microbial lactate-binding protein). In non-limiting examples, the mutant's $K_d$ for the ligand is at least 0.001, 0.01, 0.1, 1, 2, 3, 4, 5, 6, 7, 8, 9, 10, 20, 30, 40, 50, 60, 70, 80, 90, or 100 mM higher or lower than the unmutated ligand-binding protein. In certain embodiments, the ligand-binding protein comprises a mutation that alters the interaction between the protein and bound lactate, a mutation that alters the equilibrium between the open and closed states of the ligand-binding protein, a mutation that alters the interaction between the ligand-binding protein and a reporter group (such as a fluorescent conjugate, e.g., the interaction with a carbonyl group or a naphthalene ring of a prodan-derived fluorophore such as Acrylodan or Badan), and/or a mutation that impacts indirect interactions that alter the geometry of the ligand binding site. In various embodiments, the mutation does not reduce, or negligibly impacts, the thermostability of the ligand-binding protein. In some embodiments, the mutation alters the thermostability of the ligand-binding protein by less than about 1, 2, 3, 4, 5, or 10° C. In some embodiments, the naturally occurring counterpart of the ligand-binding protein is from a Gram-positive bacterium or a Gram-negative bacterium. Non-limiting examples of Gram-negative bacteria include *Thermus* sp., *Thioalkalivibrio* sp., *Roseobacter* sp., *Marinobacter* sp., *Anaeromyxobacter* sp., *Polymorphum* sp., *Pseudomonas* sp., *Rhodobacter* sp., *Flexistipes* sp., and *Thermanaerovibrio* sp.

In various embodiments, the lactate-binding protein is purified.

The present subject matter provides a lactate-binding protein that is or is a mutant of: a *Thermus* sp. (e.g., *T. caldophilus, T. eggertssonii, T. kawarayensis, T. murrieta, T. nonproteolyticus, T. parvatiensis, T. rehai, T. yunnanensis, T. amyloliquefaciens, T. antranikianii, T. aquaticus, T. arciformis, T. brockianus, T. caliditerrae, T. chliarophilus, T. composti, T. filiformis, T. igniterrae, T. islandicus, T. oshimai, T. profundus, T. scotoductus, T. shimai, T. tengchongensis, or T. thermophilus*) lactate-binding protein, a *Thioalkalivibrio* sp. (e.g., *T. denitrificans, T. halophilus, T. jannaschii, T. nitratireducens, T. nitratis, T. paradoxus, T. sulfidiphilus, T. thiocanodenitrificans, T. thiocyanoxidans*, and *T. versutus*) lactate-binding protein, a *Roseobacter* sp. (e.g., *R. dentrificans, R. litoralis, R. pelophilus, R. prionitis*, R. sp. 1411/A01/004, R. sp. 1922, R. sp. 27-4, R. sp. 3008, R. sp. 38.98, R. sp. 3X/A02/234, R. sp. 4318-8/1, R. sp. 812, R. sp. 8-1, R. sp. ANT8230, R. sp. ANT9082, R. sp. ANT909, R. sp. ANT9234, R. sp. ANT9240, R. sp. ANT9270, R. sp. ANT9274, R. sp. ANT9276a, R. sp. ANT9283, R. sp. ARCTIC-P4, R. sp. ARK9990, R. sp. AzwK-3b, R sp. AzwLept-1c, R. sp. B09, R. sp. B-1039, R. sp. B11, R. sp. Ber2105, R. sp. Ber2107, R. sp. BS36, R sp. BS90, R. sp. C115, R. sp. C23, R sp. CCS2, R. sp. COL2P, R. sp. COLSP, R. sp. DG1132, R. sp. DG869, R. sp. DG889, R. sp. DG942, R. sp. Do-34, R. sp. DSS-1, R sp. DSS-8, R. sp. H264, R. sp. H265, R. sp. H454, R. HJ105, R sp. HJ247, R sp. HYL-SA-18, R sp. HZBC52, R. sp. HZDC27, R. sp. HZDC41, R sp. HZDC42, R. sp. HZDC43, R. sp. HZDC7, R sp. J2W, R. sp. J356, R. sp. J392, R. sp. J483, R. sp. J486, R. sp. J504, R. sp. J8W, R. sp. JL-126, R. sp. JL-129, R sp. JL-131, R. JL-132, R. sp. JL-135, R. sp. JL-137, R. sp. JL-351, R sp. JL985, R sp. JLN-A020, R. sp. JLN-A036, R. sp. JLN-A530, R. sp. KAT10, R. sp. KAT3, R. sp. KT0202a, R. sp. KT0917, R. sp. KT1117, R. sp. LA7, R. sp. LA9, R. sp. LOB-8, R. sp. LZXC12, R. sp. LZXC14, R sp. LZXC15, R sp. LZXC16, R. sp. LZXC20, R sp. LZXC23, R. sp. LZXC26, R. sp. LZXC29, R. sp. LZXC4, R. sp. LZXC7, R. sp. MBT21, R sp. MBT22, R. sp. MED001, R. sp. MED006, R. sp. MED007, R. sp. MED008, R. sp. MED193, R. sp. MED24, R. sp. MED26, R. sp. MED61, R. sp. MED6, R sp. MSI042, R. sp. N05I, R. sp. NJSS27, R. sp. NT N37, R. sp. OC-B2-7, R. sp. OC-C4-20, R. sp. OO-A3-7, R. sp. OO-C4-10, R. sp. Pht-4. R sp. PIC-68, R. sp. PRLIST02, R. sp. PRLIST06, R. sp. PRLISY01, R. sp. PRLISY03, R. sp. QSSC9-8, R. sp. RED15, R. sp. RED1, R. sp. RED59, R sp. RED68, R sp. RED85, R. sp. S03, R. sp. SC-B2-2, R. sp. SCB28, R. sp. SCB31, R sp. SCB34, R. sp. SCB48, R. sp. SDBC1, R sp. SDBC6, R. sp. SFLA13, R. sp. SIO, R. sp. SK209-2-6, R. sp. SKA26, R sp. SKA44, R. sp. SL25, R. sp. SO3, R. sp. SPO804, R. sp. SYOP1, R. sp. SYOP2, R sp. TM1035, R. sp. TM1038, R. sp. TM1040, R. sp. TM1042, R. sp. TP9, R. sp. UAzPsJAC-1b, R sp. UAzPsK-5, R. sp. WED10.10, R sp. WED1.1, R sp. WHOI JT-01, R. sp. WHOI JT-08, R. sp. WHOI JT-22, R. sp. WM2, R. sp. Y2, R sp. Y3F, R. sp. YS-57, R. sp. YSCB-1, or R sp. YSCB-3) lactate-binding protein, a *Marinobacter* sp. (e.g., *M. adhaerens, M algicola, M alkaliphilus, M. antarcticus, M. arcticus, M. aromaticivorans, M. bryozoorum, M. daepoensis, M. daqiaonensis, M. excellens, M. flavimaris, M. gudaonensis, M. guineae, M. halophilus, M. gudaonensis, M. hydrocarbonoclasticus, M. koreensis, M. lacisalsi, M. lipolyticus, M. litoralis, M. lutaoensis, M. maritimus, M. mobilis. M. nitratireducens, M. oulmenensis, M pelagius, M. persicus, M. psychrophilus, M. nanhaiticus, M. salarius, M. salicampi, M. salsuginis, M. santorintensis, M. sediminum, M. segnicrescens, M. shengliensis, M. squalenivorans, M. similis, M. szutsaonensis, M. vinifirmus, M. xestospongiae, M. zhanjiangensis*, or *M. zhejiangensis*) lactate-binding protein, a *Anaeromyxobacter* sp. (e.g., *A. dehalogenans*) lactate-binding protein, a *Polymorphum* sp. (e.g., *P. gilvum*) lactate-binding protein, a *Pseudomonas* sp. (e.g., *P. aeruginosa, P. alcaligenes, P. anguilliseptica, P. argentinensis, P. borbori, P. citronellolis, P. flavescens, P. mendocina, P. nitroreducens, P. oleovorans, P. pseudoalcaligenes, P. resinovorans, P. straminea, P. chlororaphis, P. asplenti, P. aurantiaca, P. aureolaciens, P. chlororaphis, P. corrugata, P. fragi, P. lundensis, P. taetrolens, P. antarctica, P. azotoformans, P. blatchfordae, P. brassicacearum, P. brenneri, P. cedrina, P. corrugata, P. fluorescens, P. gessardii, P. libanensis, P. mandelii, P. marginalis, P. mediterranea, P. meridiana, P. migulae, P. mucidolens, P. orientalis, P. panacis, P. protegens, P. proteolytica, P. rhodesiae, P. synxantha, P. thiver-*

*valensis, P. tolaasii, P. veronii, P. denitrificans, P. pertucinogena, P. cremoricolorata, P. entomophila, P. iulva, P. monteilii, P. mosselii, P. oryzihabitans, P. parafulva, P. plecoglossicida, P. putida, P. balearica, P. luteola, P. stutzeri, P. amygdali, P. avellanae, P. caricapapayae, P. cichorii, P. coronafaciens, P. ficuserectae, P. helianthi, P. meliae, P. savastanoi, P. syringae, P. tomato*, or *P. viridiflava*) lactate-binding protein, a *Rhodobacter* sp. (e.g., *R. aestuarii, R. azotoformans, R. blasticus, R. capsulatus, R. johrii, R. maris, R. megalophilus, R. ovatus, R sphaeroides, R. veldkampi, R. vinaykumani*, or *R. viridis*) lactate-binding protein, a *Flexistipes* sp. (e.g., *F. sinusarabici*) lactate-binding protein, or a *Thermanaerovibrio* sp. (e.g., *T. acidaminovorans* or *T. velox*) lactate-binding protein.

In various embodiments, a biosensor comprises a lactate-binding protein that is or is a mutant of: a lactate-binding protein from *Thermus thermophilus* (ttLacBP1; SEQ ID NO: 1, 15, or 115); a lactate-binding protein from *Thermus scotoductus* (tsLacBP2; SEQ ID NO: 2, 16, or 116); a lactate-binding protein from *Thermus oshimai* (toLacBP3; SEQ ID NO: 3, 17, or 117); a lactate-binding protein from *Thioalkalivibrio sulfidophilus* (tsLacBP4; SEQ ID NO: 4, 18, or 118); a lactate-binding protein from *Roseobacter denitrificans* (rdLacBP5; SEQ ID NO: 5, 19, or 119); or a lactate-binding protein from *Marinobacter* sp. (msLacBP6; SEQ ID NO: 6, 20, or 120); a lactate-binding protein from *Thermus* sp. (tsLacBP7; SEQ ID NO: 7, 21, or 121); a lactate-binding protein from *Marinobacter adhaerens* (maLacBP8; SEQ ID NO: 8, 22, or 122); a lactate-binding protein from *Anaeromyxobacter dehalogenans* (adLacBP9; SEQ ID NO: 9, 23, or 123); a lactate-binding protein from *Polymorphum gilvum* (pgLacBP10; SEQ ID NO: 10, 24, or 124); a lactate-binding protein from *Pseudomonas stuztzeri* (psLacBP11; SEQ ID NO: 11, 25, or 125); a lactate-binding protein from *Rhodobacter sphaeroides* (rsLacBP12; SEQ ID NO: 12, 26, or 126); a lactate-binding protein from *Flexistipes sinusarabici* (fsLacBP13; SEQ ID NO: 13, 27, or 127); or a lactate-binding protein from *Thermanaerovibrio acidaminovorans* (taLacBP14; SEQ ID NO: 14, 28, or 128).

Aspects of the present subject matter include a lactate-binding protein that is or is a mutant of a protein listed in Table 2, e.g., the protein numbered 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, or 140 in Table 2.

With regard to a defined polypeptide, % identity figures higher or lower than those provided herein will encompass various embodiments. Thus, where applicable, in light of a minimum % identity figure, a polypeptide may comprise an amino acid sequence which is at least 60%, 65%, 70%, 75%, 76%, 80%, 85%, 90%, 91%, 92%, 93%, 94%, 95%, 96%, 97%, 98%, 99%, 99.1%, 99.2%, 99.3%, 99.4% 99.5%, 99.6%, 99.7%, 99.8%, or 99.9% identical to the reference SEQ ID NO or to each of the reference SEQ ID NOs. In embodiments, the polypeptide comprises an amino acid sequence that is 100% identical to the reference SEQ ID NO. Where applicable, in light of a maximum % identity to a reference sequence, a polypeptide may comprise an amino acid sequence which is less than 75%, 70%, 65%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36, 35%, 34%, 33%, 32%, 31%, 30%, 29%, 28%, 27%, 26%, 25%, 24%, 23%, 22%, 21%, 20%, 19%, 18%, 17%, 16%, or 15% identical to the reference SEQ ID NO or to each of the reference SEQ ID NOs. In certain embodiments, a polypeptide comprises amino acids in a sequence that is preferably at least about 10%, 11%, 12%, 13%, 14%, 15%, 16%, 17%, 18%, 19%, 20%, 21%, 22%, 23%, 24%, 25%, 26%, 27%, 28%, 29%, or 30% and less than about 75%, 70%, 65%, 60%, 55%, 50%, 45%, 44%, 43%, 42%, 41%, 40%, 39%, 38%, 37%, 36%, 35%, 34%, 33%, 32%, 31%, or 30% identical to the reference SEQ ID NO or to each of the reference SEQ ID NOs. In certain embodiments, a polypeptide comprises amino acids in a sequence that is between about 10% and about 60%, 11% and about 60%, 12% and about 60%, 13% and about 60%, 14% and about 60%, 15% and about 60%, 16% and about 60%, 17% and about 60%, 18% and about 60%, 19% and about 60%, 20% and about 60%, 21% and about 60%, 22% and about 60%, 23% and about 60%, 24% and about 60%, 25% and about 60%, 26% and about 60%, 27% and about 60%, 28% and about 60%, 29% and about 60%, 30% and about 60%, about 25% and about 100%, about 25% and about 95%, about 25% and about 85%, about 25% and about 75%, about 25% and about 70%, about 25% and about 65%, 60%, about 25% and about 55%, about 25% and about 50%, about 25% and about 45%, about 25% and about 44%, about 25% and about 43%, about 25% and about 42%, about 25% and about 41%, about 25% and about 40%, about 25% and about 39%, about 25% and about 38%, about 25% and about 37%, about 25% and about 36%, about 25% and about 35%, about 25% and about 34%, about 25% and about 33%, about 25% and about 32%, about 25% and about 31%, or about 25% and about 30% identical to the reference SEQ ID NO or to each of the reference SEQ ID NOs. Non-limiting examples of reference proteins and amino acid sequences disclosed herein include:

(i) a lactate-binding protein from *Thermus thermophilus* (ttLacBP1; genome, NC_006461, protein, YP_144032.1; SEQ ID NO: 1);

(ii) a lactate-binding protein from *Thermus scotoductus* (tsLacBP2; genome, NC_014974, protein YP_004202714.1; SEQ ID NO: 2);

(iii) a lactate-binding protein from *Thermus oshimai* (toLacBP3; genome, NC_019386, protein YP_006972155.1; SEQ ID NO: 3);

(iv) a lactate-binding protein from *Thioalkalivibrio sulfidophilus* (tsLacBP4; genome, NC_011901, protein YP_002514099.1; SEQ ID NO: 4);

(v) a lactate-binding protein from *Roseobacter denitrificans* (rdLacBP5; genome, NC_008209, protein YP_683924.1; SEQ ID NO: 5):

(vi) a lactate-binding protein from *Marinobacter* sp. (msLacBP6; genome. NC_018268, protein YP_006556686.1; SEQ ID NO: 6);

(vii) a lactate-binding protein from *Thermus* sp. (tsLacBP7; genome, NC_017278, protein YP_005654632.1; SEQ ID NO: 7);

(viii) a lactate-binding protein from *Marinobacter adhaerens* (maLacBP8; genome, NC_017506, protein YP_005886720.1; SEQ ID NO: 8);

(ix) a lactate-binding protein from *Anaeromyxobacter dehalogenans* (adLacBP9; genome. NC_007760, protein YP_466099.1; SEQ ID NO: 9);

(x) a lactate-binding protein from *Polymorphum gilvum* (pgLacBP10; genome, NC_015259, protein YP_004304976.1; SEQ ID NO: 10);

(xi) a lactate-binding protein from *Pseudomonas* stuztzeri (psLacBP11; genome, NC_018177, protein YP_006522676.1; SEQ ID NO: 11);

(xii) a lactate-binding protein from *Rhodobacter sphaeroides* (rsLacBP12; genome, NC_007494, protein RSP_3372; SEQ ID NO: 12);

(xiii) a lactate-binding protein from *Flexistipes sinusarabici* (fsLacBP13; genome, NC_015672, protein YP_004603455.1; SEQ ID NO: 13); and (xiv) a lactate-binding protein from *Thermanaerovibrio acidaminovorans* (taLacBP14; genome, NC_013522, protein YP_003317968.1; SEQ ID NO: 14).

In some embodiments, the lactate-binding protein comprises an amino acid sequence with at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100% identity to 1, 2, 3, 4, 5, 6, 7, 8, 9, 10 or more lactate-binding proteins disclosed herein.

The lactate-binding proteins disclosed herein may optionally be fused (e.g., at their N-terminal and/or C-terminal ends) to a motif comprising a stretch of amino acids that facilitates the isolation or other manipulation such as conjugation to a moiety or immobilization on a substrate such as a plastic, a cellulose product such as paper, polymer, metal, noble metal, semi-conductor, or quantum dot (e.g., a fluorescent quantum dot). A non-limiting example of such a stretch of amino acids has the sequence: GGSHHHHHH (SEQ ID NO: 113). This motif is not required for, is not believed to influence or affect ligand-binding activity or signal transduction, and may be omitted from any ligand-binding protein or biosensor disclosed herein. Additionally, for every sequence disclosed herein that includes GGSHHHHHH (SEQ ID NO: 113), a corresponding sequence that is identical except that it lacks GGSHHHHHH (SEQ ID NO: 113) is also provided and intended to be disclosed. For example, each of SEQ ID NOs: 15-62 (and the non-limiting examples of other proteins used in the experiments disclosed herein) comprises this motif (SEQ ID NO: 113). Alternatively or in addition, a ligand-binding protein may be fused to a non-native polypeptide or "added amino acids" that facilitates the attachment thereof to a surface, such as the surface of a device.

In some embodiments, a polypeptide comprises 1, 2, 3, 4, 5, or more substitutions or deletions of a cysteine compared to the naturally occurring counterpart of the polypeptide (i.e., 1, 2, 3, 4, 5, or more native cysteines have been removed), e.g., 1, 2, 3, 4, 5, or more cysteine to alanine substitutions compared to the naturally occurring counterpart of the polypeptide. In some embodiments, all of the cysteines of a polypeptide have been deleted and/or substituted compared to its natural counterpart. In some embodiments, one or more cysteines of a polypeptide have been substituted with an alanine, a serine, or a threonine.

In embodiments, the amino acid sequence of a protein comprises no more than 1, 2, 3, 4, 5, 6, 7, 8, 9, 10, 15, 20, 25, 30, 35, 40, 45, or 50 mutations compared to its naturally occurring counterpart. In some embodiments, less than 50, 45, 40, 35, 30, 25, 20, 15, 10, 9, 8, 7, 6, 5, 4, 3, or 2 of the mutations is a deletion or insertion of 1, 2, 3, 4, or 5 or no more than 1, 2, 3, 4, or 5 amino acids. In some embodiments, 1, 2, 3, 4, 5, 6, 7, 8, 9, 10, 15, 20, 25, 30, 35, 40, 45, 50 or more of the mutations is a substitution mutation. In certain embodiments, every mutation to a protein compared to its naturally occurring counterpart is a substitution mutation. In various embodiments, 1, 2, 3, 4, 5, 6, 7, 8, 9, 10, 15, 20, 25, 30, 35, 40, 45, 50 or more or all of the mutations to a protein compared to its naturally occurring counterpart is a conservative substitution mutation.

In various embodiments, a polypeptide does not have any insertion or deletion compared to its natural counterpart, other than (optionally) the removal of the signal peptide and/or the fusion of compounds such as another polypeptide at the N-terminus or C-terminus thereof.

Ligand-Binding Proteins Comprising a Primary Complementary Surface (PCS)

The following BLAST parameters are used to identify sequence homologues of a lactate-binding protein (such as ttLacBP1): (1) Expect threshold is 10.0; (2) Gap cost is Existence: 11 and Extension: 1; (3) The Matrix employed is BLOSUM62; (4) The filter for low complexity regions is "on." Such an alignment may be generated using the ProteinHunter program. The ProteinHunter package always executes BLAST searches, with the following command "blastall -p blastp -m 8 -b 50000 -d % s -i<INPUT FILE>-o<OUTPUT FILE>"

where <INPUT FILE> and <OUTPUT FILE> specify the input and output files, respectively for a given calculation. This command executes the BLAST alignment program for protein sequences with default parameters, intrinsically set by the program. The BLAST program version is 2.2.24.

Sequence homologues of ttLacBP1 identified using BLAST may be aligned with ttLacBP1 using ClustalW to identify homologues that share a PCS with ttLacBP1 as discussed below.

Aspects of the present subject matter provide ligand-binding proteins that share a PCS with a lactate-binding protein disclosed herein. In embodiments, the PCS comprises at least about 5, 6, 7, or 8 amino acid positions used to identify a lactate-binding protein. For example, the PCS of ttLacBP1 may comprise positions 98, 101, 158, 178, 180, 216, 247, and 250, wherein each position is counted as in ttLacBP1 (SEQ ID NO: 15 or 115; in which the signal peptide has been replaced with a methionine). In various embodiments, a protein shares a PCS with ttLacBP1 if the amino acid sequence of the protein has (i) F, W, or Y at the position that aligns with position 98 of ttLacBP1;

(ii) Y, N, Q, H, E, or D at the position that aligns with position 101 of ttLacBP1;

(iii) N, D, E, Q, or H at the position that aligns with position 158 of ttLacBP1;

(iv) R at the position that aligns with position 178 of ttLacBP1;

(v) P, A, V, L, 1, or G at the position that aligns with position 180 of ttLacBP1;

(vi) D, N, Q, or E at the position that aligns with position 216 of ttLacBP1;

(vii) Q, E, N, or D at the position that aligns with position 247 of ttLacBP1; and (viii) D, N, E, Q, S, T, or H at the position that aligns with position 250 of ttLacBP1, wherein the alignment between ttLacBP1 (SEQ ID NO: 15 or 115) and the protein is constructed using the ClustalW alignment program.

The ProteinHunter package always executes multiple sequence alignments with the following command "clustalw -infile=<INPUT FILE>-outfile=<OUTPUTFILE>-align -quiet"

This command executes the CLUSTALW multi-sequence alignment program for protein sequences. There are no user-specified parameter settings that alter the alignment behavior of the program. The CLUSTALW program version is 2.1.

For convenience and depending on context, a position that aligns with a stated position of ttLacBP1 may be referred to herein as "equivalent" to the stated position.

Exemplary Ligand-Binding Proteins

Various biosensors provided herein comprise lactate-binding proteins, such as lactate-binding proteins that have altered amino acid sequences compared to their naturally occurring counterparts. In embodiments, such proteins are conjugated to reporter groups, ttLacBP1 is a non-limiting reference protein respect to lactate-binding proteins. An alignment of ttLacBP1 with other polypeptides is provided in FIG. 4.

In various embodiments, a lactate-binding protein (or its naturally occurring counterpart) comprises (a) an amino acid sequence that is preferably (i) at least about 10%, 11%, 12%, 13%, 14%, 15%, 16%0, 17%, 18%, 19%, 20%, 21%, 22%, 23%, 24%, 25%, 26%, 27%, 28%, 29%, or 30%, and (ii) less than about 75%, 70%, 65%, 60%, 55%, 50%, 45%, 44%, 43, 42%, 41%, 40%, 39%, 38%, 37%, 36%, or 35% identical to ttLacBP1;

(b) a cysteine substitution (compared to its naturally occurring counterpart) within a stretch of at least 5, 10, or 20 amino acids having at least about 50%, 55%, 60%, 65%, 75%, 80%, 85%, 90%, or 95% identity to a stretch of consecutive amino acids including position 78 of ttLacBP1;

(c) a stretch of at least 4, 5, 6, 7, 8, 9, 10, 11, 12, 13, 14, 15, 20, 25, or 30 amino acids having at least about 50%, 55%, 60%, 65%, 75%, 80%, 85%, 90%, or 95% identity to a stretch of consecutive amino acids including position 78 of ttLacBP1;

(d) a stretch of amino acids in the sequence $FTX_1YX_2$ (where $X_1$ is any amino acid, or where $X_1$ is L, V, or I; and where $X_2$ is any amino acid, or where $X_2$ is W or A) (SEQ ID NO: 129);

(e) a cysteine substitution (compared to its naturally occurring counterpart) within a stretch of at least 5, 10, or 20 amino acids having at least about 50%, 55%, 60%, 65%, 75%, 80%, 85%, 90%, or 95% identity to a stretch of consecutive amino acids including position 138 of ttLacBP1;

(f) a stretch of at least 4, 5, 6, 7, 8, 9, 10, 11, 12, 13, 14, 15, 20, 25, or 30 amino acids having at least about 50%, 55%, 60%, 65%, 75%, 80%, 85%, 90%, or 95% identity to a stretch of consecutive amino acids including position 138 of ttLacBP1;

(g) a stretch of amino acids in the sequence NXIHSK (where X is any amino acid, or where X is L or I) (SEQ ID NO: 130);

(h) a cysteine substitution (compared to its naturally occurring counterpart) within a stretch of at least 5, 10, or 20 amino acids having at least about 50%, 55%, 60%, 65%, 75%, 80%, 85%, 90%, or 95% identity to a stretch of consecutive amino acids including position 160 of ttLacBP1;

(i) a stretch of at least 4, 5, 6, 7, 8, 9, 10, 11, 12, 13, 14, 15, 20, 25, or 30 amino acids having at least about 50%, 55%, 60%, 65%, 75%, 80%, 85%, 90%, or 95% identity to a stretch of consecutive amino acids including position 160 of ttLacBP1;

(j) a stretch of amino acids in the sequence RXPGG (where X is any amino acid, or where X is L, V, F, or M) (SEQ ID NO: 131);

(k) a cysteine substitution (compared to its naturally occurring counterpart) within a stretch of at least 5, 10, or 20 amino acids having at least about 50%, 55%, 60%, 65%, 75%, 80%, 85%, 90%, or 95% identity to a stretch of consecutive amino acids including position 178 of ttLacBP1;

(l) a stretch of at least 4, 5, 6, 7, 8, 9, 10, 11, 12, 13, 14, 15, 20, 25, or 30 amino acids having at least about 50%, 55%, 60%, 65%6, 75%, 80%, 85%, 90%, or 95% identity to a stretch of consecutive amino acids including position 178 of ttLacBP1;

(m) a stretch of amino acids in the sequence LPGX (where X is any amino acid or where X is S or G) (SEQ ID NO: 132);

(n) a cysteine substitution (compared to its naturally occurring counterpart) within a stretch of at least 5, 10, or 20 amino acids having at least about 50%, 55%, 60%, 65%, 75%, 80%, 85%, 90%, or 95% identity to a stretch of consecutive amino acids including position 197 of ttLacBP1;

(o) a stretch of at least 4, 5, 6, 7, 8, 9, 10, 11, 12, 13, 14, 15, 20, 25, or 30 amino acids having at least about 50%, 55%, 60%, 65%, 75%, 80%, 85%, 90%, or 95% identity to a stretch of consecutive amino acids including position 197 of ttLacBP1;

(p) a stretch of amino acids in the sequence VGPAVN (SEQ ID NO: 133);

(q) a cysteine substitution (compared to its naturally occurring counterpart) within a stretch of at least 5, 10, or 20 amino acids having at least about 50%, 55%, 60%, 65%, 75%, 80%, 85%, 90%, or 95% identity to a stretch of consecutive amino acids including position 228 of ttLacBP1;

(r) a stretch of at least 4, 5, 6, 7, 8, 9, 10, 11, 12, 13, 14, 15, 20, 25, or 30 amino acids having at least about 50%, 55%, 60%, 65%, 75%, 80%, 85%, 90%, or 95% identity to a stretch of consecutive amino acids including position 228 of ttLacBP1;

(s) a stretch of amino acids in the sequence QPVDL (SEQ ID NO: 134);

(t) no more than 1, 2, 3, 4, 5, 6, 7, 8, 9, 10, or 15 deleted or inserted amino acids compared to ttLacBP1, not including amino acids added to the N-terminus or C-terminus of the polypeptide compared to its natural counterpart, and including or not including the signal peptide of the natural counterpart of the polypeptide;

(u) at least 5, 6, 7, or 8, or exactly 5, 6, 7, or 8 α-helices; and/or (v) at least 5, 6, 7, 8, 9, or 10 β-strands or exactly 5, 6, 7, 8, 9, or 10 β-strands.

In embodiments, two or more or each of features (b)-(s) above occurs in the polypeptide in the order listed above as the amino acid sequence of the polypeptide is viewed or read from the N-terminus to the C-terminus (with additional features and/or amino acid sequences therebetween). For example, the polypeptide may have an N-terminus, followed by feature (b), (c), or (d), followed by feature (e), (f), or (g), followed by feature (h), (i), or (j), followed by feature (k), (l), or (m), followed by feature (n), (o), or (p), followed by feature (q), (r), or (s), followed by the C-terminus.

As used herein when referring to the order of features in an amino acid read from the N terminus to the C-terminus, a first feature is "followed by" a second feature when the second feature occurs after the first feature in the amino acid sequence. The words "followed by" do not require that the second feature immediately follow or be close to the first feature. For example, the N-terminus is followed by the C-terminus.

The features listed above are not limiting and may be combined with any other relevant features disclosed herein, including those listed below.

```
                                    (SEQ ID NO: 157)
WKXQXXWXXGXXGXXXXXXXXXAXX!XEXTGGXLXIXXFXAGXVVXXFXXX

F#AVXXGVL#XXXXFXXYWXGKXPAXAFXXSXPXXXXXPXXXXAWFYXXG

GLXLXXEX%XXXGXXXLXXXGPXXXXXXXXXHSXXPIXSXDDXKGXKXRX

PGXXXAEVFXXXGAXXXXLPGG#XYPA$#XGTIDAA#XVGPXX#YXLGFH

XVAKYIXXXXXXXXXXH#PXXXXXXXXNXXXWXXLPXXXQXXXXXAXXXX

SXXXXXXIXXXNXEAXKXKXXGXXVXRXXLXXEDXXXKREXAXXIWXXXA

XXXXXAXXXXXXQXXYMXXXXXGXXXXXXXXXXXXXX
```

In a non-limiting example, the lactate-binding protein comprises an N-terminal domain and a C-terminal domain connected by a flexible hinge, with the ligand-binding site (the ligand binding domain) located in the cleft between the N-terminal and the C-terminal domain.

In some embodiments, the lactate-binding protein comprises, from the N-terminus to the C-terminus, a first β-strand (β1), followed by a first α-helix (α1), followed by a second β-strand (β2), followed by a second α-helix (α2), followed by a third β-strand (β3), followed by a third α-helix (α3), followed by a fourth β-strand (β4), followed by a fifth β-strand (β5), followed by a sixth β-strand (β6), followed by a fourth α-helix (α4), followed by a fifth α-helix (α5), followed by a seventh β-strand (β7), followed by a sixth α-helix (α6), followed by an eighth β-strand (β8), followed by a ninth β-strand (β9), followed by a seventh α-helix (α7), followed by a tenth β-strand (β10), followed by an eighth α-helix (α8). In some embodiments, the polypeptide comprises (i) 1, 2, or 3 amino acid substitutions between β1 and α1; (ii) 1, 2, or 3 amino acid substitutions between β2 and α2; (iii) 1, 2, or 3 amino acid substitutions between β3 and α3; (iv) 1, 2, or 3 amino acid substitutions between β4 and β5, (v) 1, 2, or 3 amino acid substitutions between β5 and β6, (vi) 1, 2, or 3 amino acid substitutions between β6 and α4. (vii) 1, 2, or 3 amino acid substitutions between α4 and α5, (viii) 1, 2, or 3 amino acid substitutions between α5 and β7, (ix) 1, 2, or 3 amino acid substitutions between β7 and α6, (x) 1, 2, or 3 amino acid substitutions between α6 and β8, (xi) 1, 2, or 3 amino acid substitutions between β8 and β9, (xi) 1, 2, or 3 amino acid substitutions between β9 and α7, (xiii) 1, 2, or 3 amino acid substitutions between α7 and β10, (xiv) 1, 2, or 3 amino acid substitutions between β10 and α68, (xv) 1, 2, or 3 amino acid substitutions in any one of or any combination of α1, α2, α3, α4, α5, α6. α7, and/or α8, and/or (xv) 1, 2, or 3 amino acid substitutions in any one of or any combination of β1, β2, β3, β4, β5, β6, β7, β8, β9, and/or β10. In some embodiments, the substitutions comprise conservative substitutions. In various embodiments, the polypeptide comprises a cysteine substitution between β1 and α1, between β2 and α2, within α2, within β3, between β3 and α3, within β5, within β6, between α4 and α5, within β7, between β7 and α6, within α6, or within β9.

In various embodiments, the lactate-binding protein binds both lactate as well as a calcium ion. The a $Ca^{2+}$ ion is required for, improves, or facilitates lactate-binding protein binding to lactate. Wherein the lactate-binding protein comprises a lactate-$Ca^{2+}$ complex when bound to lactate and a $Ca^{2+}$ ion.

Beta sheets consist of beta strands (also β-strand) connected laterally by at least two or three backbone hydrogen bonds, forming a generally twisted, pleated sheet. A β-strand is a stretch of polypeptide chain, e.g. 3 to 20 amino acids long, with backbone in an extended conformation.

Alpha-helical and β-strand segments assignments are calculated from a three-dimensional protein structure as follows, and as described in C. A. F. Andersen, B. Rost, 2003, *Structural Bioinformatics,* 341-363, P. E. Boume, ed., Wiley, the entire content of which is incorporated herein by reference. First for a given residue, i, the backbone trace angle, $\tau$, is calculated, defined as the dihedral angle between the four successive $C_\alpha$, atom positions of residues in the linear protein sequence i, i+1, i+2, i+3. These values are calculated for all residues. Second, the residues that form backbone hydrogen bonds with each other are recorded. A hydrogen bond is scored if the distance between the backbone amide nitrogen and carbonyl oxygen of two different residues in the protein is calculated to be 2.5 Å or less, and if the calculated angle between the nitrogen, its amide proton, and the carbonyl is greater than 120°. A residue is deemed to be in an α-helix, if $35 \le \tau \le 65$, and it makes a backbone hydrogen bond with its $i+4^{th}$ neighbor in the linear amino acid sequence. It is deemed to be in a β-strand, if the absolute t value falls in the interval $120 \le |\tau| \le 180$ and if it makes at least one hydrogen bond with another residue with the same $\tau$ value range. Alpha-helical segments comprise at least four residues; β-strand residues comprise at least three residues.

In various embodiments, the $C_\alpha$ root-mean-square deviation (RMSD) between the backbone of the lactate-binding polypeptide and ttLacBP1, tsLacBP2, toLacBP3, tsLacBP4, rdLacBP5, msLacBP6, tsLacBP7, maLacBP8, adLacBP9, pgLacBP10, psLacBP11, rsLacBP12, fsLacBP13, and/or taLacBP14 is, e.g., between about 0-3 Å, 0-1 Å, 0-1.5 Å, 0-2 Å, 0.1-3 Å, 0.5-1 Å, 0.5-1.5 Å, or 0.5-2 Å, or less than about 0.1 Å, 0.2 Å, 0.3 Å, 0.4 Å, 0.5 Å, 0.6 Å, 0.7 Å, 0.8 Å, 0.9 Å, 0.0 Å, 1.5 Å, 1.6 Å, 1.7 Å, 1.8 Å, 1.9 Å, 2.0 Å, 2.5 Å, or 3 Å. In some embodiments, the $C_\alpha$ RMSD between the N-terminal domain (i.e., the portion of the protein at the N-terminal side of the binding domain hinge) backbone of the lactate-binding polypeptide and the corresponding domain of ttLacBP1, tsLacBP2, toLacBP3, tsLacBP4, rdLacBP5, msLacBP6, tsLacBP7, maLacBP8, adLacBP9, pgLacBP10, psLacBP11, rsLacBP12, fsLacBP13, and/or taLacBP14 is, e.g., between about 0-3 Å, 0-1 Å, 0-1.5 Å, 0-2 Å, 0.1-3 Å, 0.5-1 Å, 0.5-1.5 Å, or 0.5-2 Å, or less than about 0.1 Å, 0.2 Å, 0.3 Å, 0.4 Å, 0.5 Å, 0.6 Å, 0.7 Å, 0.8 Å, 0.9 Å, 1.0 Å, 1.5 Å, 1.6 Å, 1.7 Å, 1.8 Å, 1.9 Å, 2.0 Å, 2.5 Å, or 3 Å. In certain embodiments, the $C_\alpha$ RMSD between the C-terminal domain (i.e., the portion of the protein at the C-terminal side of the binding domain hinge) backbone of the lactate-binding polypeptide and the corresponding domain of ttLacBP1, tsLacBP2, toLacBP3, tsLacBP4, rdLacBP5, msLacBP6, tsLacBP7, maLacBP8, adLacBP9, pgLacBP10, psLacBP11, rsLacBP12, fsLacBP13, and/or taLacBP14 is, e.g., between about 0-3 Å, 0-1 Å, 0-1.5 Å, 0-2 Å, 0.1-3 Å, 0.5-1 Å, 0.5-1.5 Å, or 0.5-2 Å, or less than about 0.1 Å, 0.2 Å, 0.3 Å, 0.4 Å, 0.5 Å, 0.6 Å, 0.7 Å, 0.8 Å, 0.9 Å, 1.0 Å, 1.5 Å, 1.6 Å, 1.7 Å, 1.8 Å, 1.9 Å, 2.0 Å, 2.5 Å, or 3 Å. Non-limiting considerations relating to the sequence and structural differences between homologous proteins are discussed in Chothia and Lesk (1986) *The EMBO Journal,* 5(4):823-826, the entire content of which is incorporated herein by reference.

Non-limiting examples of lactate-binding polypeptides that are useful in biosensors include ttLacBP1, tsLacBP2, toLacBP3, tsLacBP4, rdLacBP5, msLacBP6, tsLacBP7, maLacBP8, adLacBP9, pgLacBP10, psLacBP11, rsLacBP12, fsLacBP13, and taLacBP14taLacBP14. In embodiments, a biosensor comprises a modified ttLacBP1, tsLacBP2, toLacBP3, tsLacBP4, rdLacBP5, msLacBP6, tsLacBP7, maLacBP8, adLacBP9, pgLacBP10, psLacBP11, rsLacBP12, fsLacBP13, or taLacBP14 polypeptide having an amino acid substitution compared to its naturally occurring counterpart, such that the polypeptide has a cysteine at position 1, 2, 3, 4, 5, 6, 7, 8, 9, 10, 1, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 270, 271, 272, 273, 274, 275, 276, 277, 278, 279, 280, 281, 282, 283, 284, 285, 286, 287, 288, 289, 290, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, or 400, or any combination of 1, 2, 3, 4, or 5 thereof, wherein the position corresponds a SEQ ID NO disclosed herein for ttLacBP1, tsLacBP2, toLacBP3, tsLacBP4, rdLacBP5, msLacBP6, tsLacBP7, maLacBP8, adLacBP9, pgLacBP10, psLacBP11, rsLacBP12, fsLacBP13, or taLacBP14. In embodiments, the cysteine is conjugated to a reporter group.

In embodiments, a biosensor comprises a modified ttLacBP1. In non-limiting examples, the modified ttLacBP1 may comprise one or more, or any combination of the following substitutions compared to its naturally occurring counterpart: A20X, W21X, D22X, A53X, T59X, F77X, L79X, Y80X, P159X, P178X, G179X, G180X, F196X, V197X, V201X, L205X, and D229X, where X is any amino acid, an amino acid that results in a conservative substitution, or a cysteine, and where each position is counted in ttLacBP1 with the signal peptide replaced with a methionine (SEQ ID NO: 15 or 115). In some embodiments, the modified ttLacBP1 comprises 1, 2, 3, 4, 5, 6, 7, 8, 9, 10, 11, 12, 13, 14, 15, 16, or 17 of the following substitutions: A20C, W21C, D22C, A53C, T59C, F77C, F77M. F77L, L79C, L791, L79M, L79F, Y80C, P159C, P159 A, P159S, P178C, G179C, G180C, F196C, V197C, V201C, L205C, D229N, D229S, D229Q, D229E, and D229L.

In embodiments, a biosensor comprises a modified tsLacBP2. In non-limiting examples, the modified tsLacBP2 may comprise one or more, or any combination of the following substitutions compared to its naturally occurring counterpart: A20X, W21X, D22X, A53X, T59X, F77X, L79X, Y80X, P159X, P178X, G179X, G180X, F196X, V197X, V201X, L205X, and D229X, where X is any amino acid, an amino acid that results in a conservative substitution, or a cysteine, and where each position is counted in tsLacBP2 with the signal peptide replaced with a methionine (SEQ ID NO: 16 or 116). In some embodiments, the modified tsLacBP2 comprises 1, 2, 3, 4, 5, 6, 7, 8, 9, 10, 11, 12, 13, 14, 15, 16, or 17 of the following substitutions: A20C, W21C, D22C, A53C, T59C, F77C, F77M, F77L. L79C, L791, L79M, L79F, Y80C, P159C, P159A, P159S, P178C, G179C, G180C, F196C, V197C, V201C, L205C, D229N, D229S, D229Q, D229E, and D229L.

In embodiments, a biosensor comprises a modified toLacBP3. In non-limiting examples, the modified toLacBP3 may comprise one or more, or any combination of the following substitutions compared to its naturally occurring counterpart: A40X, W41X, D42X, A73X, T79X, F97X, L99X, Y100X, P179X, P198X, G199X, G200X, F216X, V217X, V221X, L225X, and D249X, where X is any amino acid, an amino acid that results in a conservative substitution, or a cysteine, and where each position is counted in toLacBP3 with the signal peptide replaced with a methionine (SEQ ID NO: 17 or 117). In some embodiments, the modified toLacBP3 comprises 1, 2, 3, 4, 5, 6, 7, 8, 9, 10, 11, 12, 13, 14, 15, 16, or 17 of the following substitutions: A40C, W21C, D42C, A73C, T79C, F97C, F97M, F97L, L99C, L99I, L99I, L99M L99F, Y100C, P179C, P179A, P179S, P198C, G199C, G200C, F216C, V217C, V221C, L225C, D249N, D249S, D249Q, D249E, and D249L.

In embodiments, a biosensor comprises a modified tsLacBP4. In non-limiting examples, the modified tsLacBP4 may comprise one or more, or any combination of the following substitutions compared to its naturally occurring counterpart: A13X, W14X, Q15X, A46X, T52X, F70X, V72X, Y73X, P152X, P171X, G172X, G173X, F189X, V190X, V194X, L198X, and D222X, where X is any amino acid, an amino acid that results in a conservative substitution, or a cysteine, and where each position is counted in tsLacBP4 with the signal peptide replaced with a methionine (SEQ ID NO: 18 or 118). In some embodiments, the modified tsLacBP4 comprises 1, 2, 3, 4, 5, 6, 7, 8, 9, 10, 11, 12, 13, 14, 15, 16, or 17 of the following substitutions: A13C, W14C, Q15C, A46C, T52C, F70C, F70M. F70L, V72C, V721, V72M, V72F, Y73C, P152C, P152A, P152S, P171C, G172C, G173C, F189C, V190C, V194C, L198C, D222N, D222S, D222Q, D222E, and D222L.

In embodiments, a biosensor comprises a modified rdLacBP5. In non-limiting examples, the modified rdLacBP5 may comprise one or more, or any combination of the following substitutions compared to its naturally occurring counterpart: S14X, H15X, T16X, A46X, D52X, F70X, 172X, Y73X, P152X, P171X, G172X, S173X, F189X, V190X, V194X, L198X, and D222X, where X is any amino acid, an amino acid that results in a conservative substitution, or a cysteine, and where each position is counted in rdLacBP5 with the signal peptide replaced with a methionine (SEQ ID NO: 19 or 119). In some embodiments, the modified rdLacBP5 comprises 1, 2, 3, 4, 5, 6, 7, 8, 9, 10, 11, 12, 13, 14, 15, 16, or 17 of the following substitutions: S14C, H15C, T16C, A46C, D52C, F70C, F70M, F70L, 172C, 172V, 172M, 172F, Y73C, P152C, P152A, P152S, P171C, G172C, S173C, F189C, V190C, V194C, L198C, D222N, D222S, D222Q, D222E, and D222L.

In embodiments, a biosensor comprises a modified msLacBP6. In non-limiting examples, the modified msLacBP6 may comprise one or more, or any combination of the following substitutions compared to its naturally occurring counterpart: V10X, W11X D12X, A43X, D49X, N50X, F68X, L70X, Y71X, P150X, P169X, G170X, S171X, Y187X, V1188X, V192X, L196X, and D220X, where X is any amino acid, an amino acid that results in a conservative substitution, or a cysteine, and where each position is counted in msLacBP6 with the signal peptide replaced with a methionine (SEQ ID NO: 20 or 120). In some embodiments, the modified msLacBP6 comprises 1, 2, 3, 4, 5, 6, 7, 8, 9, 10, 11, 12, 13, 14, 15, 16, 17, or 18 of the following substitutions: V10C, W11C, D12C, A43C, D49C, N50C, F68C, F68M. F68L, L70C, L70I, L70M, L70F, Y71C, P150C, P150A, P150S, P169C, G170C, S171C, Y187C, V188C, V192C, L196C, D220N, D220S, D220Q, D220E, and D220L.

In embodiments, a biosensor comprises a modified tsLacBP7. In non-limiting examples, the modified tsLacBP7 may comprise one or more, or any combination of the following substitutions compared to its naturally occurring counterpart: A13X, W14X, D15X, A46X, T52X, F70X, L72X, Y73X, P152X, P171X, G172X, G173X, F189X, V190X, V194X, L198X, and D222X, where X is any amino acid, an amino acid that results in a conservative substitution, or a cysteine, and where each position is counted in tsLacBP7 with the signal peptide replaced with a methionine (SEQ ID NO: 21 or 121). In some embodiments, the modified tsLacBP7 comprises 1, 2, 3, 4, 5, 6, 7, 8, 9, 10, 11, 12, 13, 14, 15, 16, 17, or 18 of the following substitutions: A13C, W14C, DISC, A46C, T52C, F70C, F70M, F70L, L72C, L721, L72M. L72F, Y73C, P152C, P152A, P152S, P171C, G172C, G173C, F189C, V190C, V194C, L198C, D222N, D222S, D222Q, D222E, and D222L.

In embodiments, a biosensor comprises a modified maLacBP8. In non-limiting examples, the modified maLacBP8 may comprise one or more, or any combination of the following substitutions compared to its naturally occurring counterpart: T12X, W13X, D14X, A45X, D51X, F70X, L72X, Y73X, P152X, P171X, G172X, S173X, F189X, V190X V194X, L198X, and D222X, where X is any amino acid, an amino acid that results in a conservative substitution, or a cysteine, and where each position is counted in maLacBP8 with the signal peptide replaced with a methionine (SEQ ID NO: 22 or 122). In some embodiments, the modified maLacBP8 comprises 1, 2, 3, 4, 5, 6, 7, 8, 9, 10, 1, 12, 13, 14, 15, 16, 17, or 18 of the following substitutions: T12C, W13C, D14C, A45C, D51C, F70C, F70M, F70L, L72C, L721, L72M, L72F, Y73C, P152C, P152A, P152S, P171C, G172C, S173C, F189C, V190C, V194C, L198C, D222N, D222S, D222Q, D222E, and D222L.

In embodiments, a biosensor comprises a modified adLacBP9. In non-limiting examples, the modified adLacBP9 may comprise one or more, or any combination of the following substitutions compared to its naturally occurring counterpart: T12X, W13X, P14X, A45X, A51X, V69X, A71X, Y72X, V155X, P173X, G174X, A175X, F191X, N192X, S196X, L200X, and E219X, where X is any amino acid, an amino acid that results in a conservative substitution, or a cysteine, and where each position is counted in adLacBP9 with the signal peptide replaced with a methionine (SEQ ID NO: 23 or 123). In some embodiments, the modified adLacBP9 comprises 1, 2, 3, 4, 5, 6, 7, 8, 9, 10, 11, 12, 13, 14, 15, 16, 17, or 18 of the following substitutions: T12C, W13C, D14C, A45C, A51C, V69C, V69M, V69L, A71C, A711, A71M, A71F, Y72C, V155C, V155A, V155S, P173C, G174C, A175C, F191C, N192C, S196C, L200C, E219N, E219S, E219Q, E219D, and E219L.

In embodiments, a biosensor comprises a modified pgLacBP10. In non-limiting examples, the modified pgLacBP10 may comprise one or more, or any combination of the following substitutions compared to its naturally occurring counterpart: L12X, W13X, D14X, A45X, A51X, F69X, G71X, Y72X, V151X, A169X, T170X, A171X, R187X, G188X, A192X, A196X, and T215X, where X is any amino acid, an amino acid that results in a conservative substitution, or a cysteine, and where each position is counted in pgLacBP with the signal peptide replaced with a methionine (SEQ ID NO: 24 or 124). In some embodiments, the modified pgLacBP10 comprises 1, 2, 3, 4, 5, 6, 7, 8, 9, 10, 11, 12, 13, 14, 15, 16, 17, or 18 of the following substitutions: L12C, W13C, D14C, A45C, A51C, F69C, F69M. F69L, G71C, G711, G71M. G71F, Y72C, V151C, V151A, V151S, A169C, T170C, A171C, R187C, G188C, A192C, A196C, T215N, T215S, T215Q, T215E, and T215L.

In embodiments, a biosensor comprises a modified psLacBP11. In non-limiting examples, the modified psLacBP11 may comprise one or more, or any combination of the following substitutions compared to its naturally occurring counterpart: A19X, W20X, P21X, A53X, A59X, A77X, Y79X, Y80X, P159X, P177X, G178X, G179X, W195X, V196X, N200X, F204X, and A223X, where X is any amino acid, an amino acid that results in a conservative substitution, or a cysteine, and where each position is counted in psLacBP11 with the signal peptide replaced with a methionine (SEQ ID NO: 25 or 125). In some embodiments, the modified psLacBP11 comprises 1, 2, 3, 4, 5, 6, 7, 8, 9, 10, 11, 12, 13, 14, 15, 16, 17, or 18 of the following substitutions: A19C, W20C, P21C, A53C, A59C, A77C, A77M, A77L, Y79C, Y79L Y79M, Y79F, Y80C, P159C, P159A, P159S, P177C, G178C, G179C, W195C, V196C, N200C, F204C, A223N, A223S, A223Q, A223E, and A223L.

In embodiments, a biosensor comprises a modified rsLacBP12. In non-limiting examples, the modified rsLacBP12 may comprise one or more, or any combination of the following substitutions compared to its naturally occurring counterpart: S12X, W13X, P14X, A45X, A51X, V69X, A71X, Y72X, V155X, P173X, G174X, G175X, F191X, N192X, S196X, F200X, and E219X, where X is any amino acid, an amino acid that results in a conservative substitution, or a cysteine, and where each position is counted in rsLacBP12 with the signal peptide replaced with a methionine (SEQ ID NO: 26 or 126). In some embodiments, the modified rsLacBP12 comprises 1, 2, 3, 4, 5, 6, 7, 8, 9, 10, 11, 12, 13, 14, 15, 16, 17, or 18 of the following substitutions: S12C, W13C, P14C, A45C, A51C, V69C, V69M, V69L, Y72C, Y721, Y72M, Y72F, Y72C, V155C, V155A, V155S, P173C, G174C, G175C, F191C, N192C, S196C, F200C, E219N, E219S, E219Q, E219D, and E219L.

In embodiments, a biosensor comprises a modified fsLacBP13. In non-limiting examples, the modified fsLacBP13 may comprise one or more, or any combination of the following substitutions compared to its naturally occurring counterpart: T12X, W13X, G14X, S46X, P52X, A70X, Y72X, Y73X, P152X, P170X, P171X G172X, W188X, T189X, M193X, M197X, and S215X, where X is any amino acid, an amino acid that results in a conservative substitution, or a cysteine, and where each position is counted in fsLacBP13 with the signal peptide replaced with a methionine (SEQ ID NO: 27 or 127). In some embodiments, the modified fsLacBP13 comprises 1, 2, 3, 4, 5, 6, 7, 8, 9, 10, 11, 12, 13, 14, 15, 16, 17, or 18 of the following substitutions: T12C, W13C, G14C, S46C, P52C, A70C, A70X M, A70X L, Y72C, Y721, Y72M, Y72F, Y73C, P152C, P152A, P152S, P170C, P171C, G172C, W188C, T189C, M193C, M197C, S215N, S215S, S215Q, S215E, and S215L.

In embodiments, a biosensor comprises a modified taLacBP14. In non-limiting examples, the modified taLacBP14 may comprise one or more, or any combination of the following substitutions compared to its naturally occurring counterpart: F11X, Y12X, L13X, A44X, V51X, Y69X, N71X, Y72X, S150X, P168X, A169X, G170X, W186X, T187X, A191X, L195X, and V219X, where X is any amino acid, an amino acid that results in a conservative substitution, or a cysteine, and where each position is counted in taLacBP14 with the signal peptide replaced with a methionine (SEQ ID NO: 28 or 128). In some embodiments, the modified taLacBP14 comprises 1, 2, 3, 4, 5, 6, 7, 8, 9, 10, 11, 12, 13, 14, 15, 16, 17, or 18 of the following substitutions: F11C, Y12C, L13C, A44C, V51C, Y69C, Y69X M, Y69X L, N71C, N711, N71M, N71F, Y72C, S150C, S150A, S150S, P168C, A169C, G170C, W186C, T187C, A191C, L195C, V219N, V219S, V219Q, V219E, and V219L.

In various embodiments, the disassociation constant of the mutant lactate-binding polypeptide differs by at least about 1 μM, 5 μM, 10 μM, 20 μM, 25 μM, 30 μM, 35 μM, 40 μM, 45 μM, 50 μM, 75 μM, 100 μM, 200 μM, 300 μM, 400 μM, 500 μM, 600 μM, 700 μM, 800 μM, 900 μM, 1 mM, 2 mM, 3 mM, 4 mM, 5 mM, 6 mM, 7 mM, 8 mM, 9 mM, 10 mM, 20 mM, 30 mM, 40 mM, 50 mM, 60 mM, 70 mM, 80 mM, 90 mM, or 100 mM (increase or decrease) compared to its naturally occurring counterpart.

The biosensors and ligand-binding proteins provided herein are robust and useful at a wide range of physical conditions, e.g., pressure, temperature, salinity, osmolality, and pH conditions. For example, biosensors and ligand-binding proteins provided herein may survive substantial periods of time after being dried or exposed to high temperatures. In some embodiments, the biosensor maintains at least about 75%, 80%, 85%, 90%, 95%, 96%, 97%, 98%, 99%, 99.5%, 99.9%, or more of its signal transduction activity after exposure to a temperature of about 40, 45, 50, 55, 60, 65, 70, 75, 80, 85, 90, 95, 100, 105, 110, 115, 120, or 125, or 40-125° C. for about 1, 2, 3, 4, 5, 6, 15, 30, 60, 120, 180, 240, or 360 minutes. In certain embodiments, the biosensor maintains at least about 75%, 80%, 85%, 90%, 95%, 96, 97%, 98%, 99%, 99.5%, 99.9%, or more of its signal transduction activity after 1, 2, 3, 4, or 5 freeze-thaw cycles in an aqueous solution. In various embodiments, the biosensor maintains at least about 750/%, 80%, 85%, 90%, 95%, 96%, 97%, 98%, 99%, 99.5%, 99.9%, or more of its signal transduction activity after storage at a temperature of between 20-37° C. for about 1, 2, 3, 4, 5, 6, 7, 8, 9, 10, 11, 12, 18, 24, or 1-24 months in dry form. In some embodiments, the optimal functional temperature of the biosensor is between 41 and 122° C., between 20 and 40° C., or less than about 10° C. (e.g., between −20 and +10° C.). Devices, compositions, and biosensors provided herein may be stored, e.g., with or without protection from exposure to light. In some embodiments, the devices, compositions, and biosensors are stored in the dark, e.g., with protection from light.

Reporter Group Attachment

Aspects of the present subject matter provide a biosensor that comprises a one or more reporter groups attached to a ligand-binding protein, wherein binding of a ligand to a ligand-binding domain of the ligand-binding protein causes a change in signaling by the reporter group. In various embodiments, the reporter group is attached to an endosteric site, an allosteric site, or a peristeric site of the ligand-binding protein. In embodiments, the reporter group is covalently or noncovalently attached to the ligand-binding protein.

As used herein, "signaling" refers to the emission of energy (which may be referred to as a "signal") by one or more reporter groups. In various implementations, the signal comprises electromagnetic radiation such as a light. In some embodiments, the signal is detected as a complete emission spectrum (or spectrums) or a portion (or portions) thereof. For example, a signal may comprise emitted light at a particular wavelength or wavelengths, or range(s) of wavelengths. In some embodiments, a change in signaling comprises a spectral change (e.g., a spectral shift and/or change in intensity). In some embodiments, a change in signaling comprises a dichromatic shift or a monochromatic fluorescence intensity change.

For convenience and depending on context, a reporter group may be referred to by a name of an unattached form of the reporter group regardless of whether the reporter group is attached to a ligand-binding protein. For example, a compound known as "Compound A" when in an unconjugated form may be referred to herein as "Compound A" when in a form that is attached to a ligand-binding protein. In a specific example, the term "Acrylodan" is used to refer to unreacted/unconjugated Acrylodan, as well as Acrylodan that is conjugated to a ligand-binding protein.

In certain embodiments, a biosensor comprises a reporter group that is conjugated to a ligand-binding protein, and the reporter group is conjugated to an amino acid of the protein that is at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 angstroms (Å) from the ligand when the ligand is bound to the protein. In embodiments, the reporter group is conjugated to an amino acid of the protein that is about 0.1 Å to about 100 Å, about 0.1 Å to about 5 Å, about 5 Å to about 10 Å, about 10 Å to about 20 Å, about 20 Å to about 50 Å, about 50 Å to about 75 Å, or about 75 Å to about 100 Å from the ligand when the ligand is bound to the protein. In some embodiments, the reporter group is conjugated to an amino acid of the protein that is within an α-helix or a β-strand. In some embodiments, the reporter group is conjugated to an amino acid that (i) is not within an α-helix or a β-strand, but is within about 10, 9, 8, 7, 6, 5, 4, 3, 2, or 1 amino acids of an amino acid of the protein's amino acid sequence that is within an α-helix or a β-strand. In some embodiments, the reporter group is conjugated to an amino acid that is in an inter-domain hinge amino acid region between two domains of a protein. In some embodiments, the reporter group is conjugated to an amino acid that is between (i) an α-helix and a β-strand; (ii) two α-helixes; or (iii) two β-strands of a protein. In some embodiments, the reporter group is conjugated to an amino acid (e.g., a cysteine such as a cysteine added by substitution compared to a naturally corresponding polypeptide) between positions 1-25, 25-50, 50-75, 75-100, 100-125, 125-150, 150-175, 175-200, 200-225, 225-250, 250-275, 275-350, 275-300, 275-325, 300-325, 300-350, 300-400, or 350-400 (inclusive) of a polypeptide (e.g., not including N-terminal fusion proteins compared to the polypeptide's naturally occurring counterpart).

Periplasmic binding proteins are characterized by two lobes connected by a hinge region; ligand bind at a location at the interface between the two domains. Such proteins or engineered versions thereof (as described herein) can adopt two different conformations: a ligand-free open form and a ligand-bound closed form, which interconvert through a relatively large bending motion around the hinge (FIG. 1A; Dwyer et al., 2004, Current Opinion in Structural Biology 12:495-504).

The remarkable adaptability of this superfamily of ligand-binding proteins is likely to have arisen from positioning the location of binding of the ligand at the interface between the lobes and from the large ligand-mediated conformational change. In this arrangement, ligands are placed within an environment that resembles a protein interior, but the residues forming the contact points or contact sites with the ligand are positioned at the surface of the lobes.

Direct signaling relationships between proteins and reporter groups are readily designed by replacing a residue known to form a ligand contact with a cysteine to which the fluorophore is attached ("endosteric" attachment site). Other, indirect signaling relationships can be established in two ways. The first relies on visual inspection of the ligand complex structure, and identifying residues that are located in the vicinity of the binding site, but do not interact directly with the ligand, and that are likely to be involved in conformational changes. Typically, such "peristeric" sites are located adjacent to the residues that form direct contacts with the bound ligand. In the case of the bPBPs, such residues are located at the perimeter of the inter-domain cleft that forms the ligand binding site location. The environment of these peristeric sites changes significantly upon formation of the closed state. These are examples of positions which are proximal to the ligand-binding pocket/domain. The second, most general, approach identifies sites in the protein structure that are located anywhere in the protein, including locations at some distance away from the ligand-binding site (i.e., distal to the ligand-binding pocket/domain), and undergo a local conformational change in concert with ligand binding. If the structures of both the open and closed states are known, then such "allosteric" sites can be identified using a computational method that analyzes the conformational changes that accompany ligand binding (Marvin et al., Proc. Natl. Acad. Sci. USA 94:4366-4371, 1997). Alternatively, once allosteric sites have been identified in one bPBP, modeling and structural homology arguments can be invoked to identify such sites in other bPBPs in which only one state has been characterized (Marvin & Hellinga, J. Am. Chem. Soc. 120:7-11, 1998). This generalized conformational analysis also may identify peristeric and endosteric sites, which were identified and classified by visual inspection.

In non-limiting implementations, the reporter group is attached to the ligand-binding protein via a biotin-avidin interaction. The reporter group may be, e.g., conjugated to biotin and the ligand-binding protein is conjugated to avidin. In an example, the avidin is bound to four biotin molecules wherein each biotin molecule is individually conjugated to a reporter group. Alternatively, the reporter group is conjugated to avidin and the ligand-binding protein is conjugated to biotin. For example, the avidin is bound to four biotin molecules, wherein each biotin molecule is individually conjugated to a ligand-binding protein.

As used herein, "conjugated" means covalently attached. One compound may be directly conjugated to another compound, or indirectly conjugated, e.g., via a linker.

In some embodiments, the reporter group is directly attached to the ligand-binding protein. In various embodiments, the reporter group is attached to an amino acid of the ligand-binding protein that is at least about 2, 4, 6, 8, 10, 11, 12, 13, 14, 15, 16, 17, 18, 19, 20, 25, 30, 35, 40, 45, 50, 55, 60, 65, 70, 75, 80, 85, 90, 95, or 100 angstroms (Å) from the ligand when the ligand is bound to the ligand-binding protein. In certain embodiments, the reporter group is conjugated to an amino acid having a position within positions 1-25, 25-50, 50-75, 75-100, 100-125, 125-150, 150-175, 175-200, 200-225, 225-250, 250-275, or 275-300 of the ligand-binding protein, wherein position 1 is the N-terminal amino acid of the ligand-binding protein. In non-limiting examples, the reporter group is conjugated to an amino acid of the ligand-binding protein that is (a) within an α-helix or a β-strand of the ligand-binding protein; (b) not within an α-helix; (c) not within a β-strand; (d) within about 5 or 10 amino acids of an amino acid that is within an α-helix or β-strand; (e) within a stretch of consecutive amino acids that links two domains of the ligand-binding protein; (f) within a stretch of consecutive amino acids that links an α-helix and a β-strand; (g) within a stretch of consecutive amino acids that links two α-helices; or (h) within a stretch of consecutive amino acids that links two β-strands. In some embodiments, the reporter group is directly attached to the N-terminus or the C-terminus of the ligand-binding protein.

The reporter group may be conjugated to the ligand-binding protein a variety of linkers or bonds, including (but not limited to) a disulfide bond, an ester bond, a thioester bond, an amide bond, or a bond that has been formed by a click reaction. In some embodiments, the click reaction is a reaction between (a) an azide and an alkyne; (b) an azide and an alkyne in the presence of Cu(I); (c) an azide and a strained cyclooctyne; (d) an azide and a dibenzylcvclooctyne, a difluorooctyne, or a biarylazacyclooctynone; (e) a diaryl-strained-cyclooctyne and a 1,3-nitrone; (f) an azide, a tetrazine, or a tetrazole and a strained alkene; (g) an azide, a tetrazine, or a tretrazole and a oxanorbomadiene, a cyclooctene, or a trans-cycloalkene; (h) a tetrazole and an alkene; or (i) a tetrazole with an amino or styryl group that is activated by ultraviolet light and an alkene. These exemplary click chemistry reactions have high specificity, efficient kinetics, and occur in vivo under physiological conditions. See. e.g., Baskin et al. Proc. Natl. Acad. Sci. USA 104(2007): 16793; Oneto et al. Acta biomaterilia (2014); Neves et al. Bioconjugate chemistry 24(2013):934; Koo et al. Angewandte Chemie 51(2012): 11836; Rossin et al. Angewandte Chemie 49(2010):3375, and U.S. Patent Application Publication No. 20160220686, published Aug. 4, 2016, the entire content of each of which is incorporated herein by reference. For a review of a wide variety of click chemistry reactions and their methodologies, see e.g., Nwe K and Brechbiel M W, 2009 Cancer Biotherapy and Radiopharmaceuticals, 24(3): 289-302; Kolb H C et al., 2001 Angew. Chem. Int. Ed. 40: 2004-2021. The entire contents of each of the foregoing references are incorporated herein by reference.

As used herein, the term "linker" refers to a molecule or sequence (such as an amino acid sequence), that attaches, as in a bridge, one molecule or sequence to another molecule or sequence. "Linked" means attached or bound by covalent bonds, or non-covalent bonds, or other bonds, such as van der Waals forces. In some embodiments, a linker comprises a chemical structure that has resulted from a reaction used to attach one molecule to another.

In various implementations of the present subject matter, the reporter group is conjugated to a cysteine of the ligand-binding protein. The cysteine may be present in the amino acid sequence of a natural counterpart or version of the ligand-binding protein or added to the ligand-binding protein by a substitution mutation in a coding sequence or by altering the sequence synthetically using known chemical means. In some embodiments, the cysteine is at the N-terminus or the C-terminus of the ligand-binding protein. In some embodiments, the cysteine is no more than about 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 5-15, 5-20, 5-25, 5-100, 10-15, 10-20, 10-25, 10-50, 10-100, 25-50, 25-75, or 25-100 amino acids from the N-terminus or the C-terminus of the ligand-binding protein. In some embodiments, the cysteine is at least about 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 5-15, 5-20, 5-25, 5-100, 10-15, 10-20, 10-25, 10-50, 10-100, 25-50, 25-75, or 25-100 amino acids from the N-terminus or the C-terminus of the ligand-binding protein.

Non-limiting examples relate to the conjugation of a reporter group to a primary amine of the ligand-binding protein. In certain embodiments, the primary amine is present in a lysine of the ligand-binding protein. The lysine may be present in the amino acid sequence of a natural counterpart or version of the ligand-binding protein or added to the ligand-binding protein by a substitution mutation in a coding sequence or by altering the sequence synthetically using known chemical means. In some embodiments, the lysine is at the N-terminus or the C-terminus of the ligand-binding protein. In some embodiments, the lysine is no more than about 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 5-15, 5-20, 5-25, 5-100, 10-15, 10-20, 10-25, 10-50, 10-100, 25-50, 25-75, or 25-100 amino acids from the N-terminus or the C-terminus of the ligand-binding protein. In some embodiments, the lysine is at least about 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 5-15, 5-20, 5-25, 5-100, 10-15, 10-20, 10-25, 10-50, 10-100, 25-50, 25-75, or 25-100 amino acids from the N-terminus or the C-terminus of the ligand-binding protein.

Aspects of the present subject matter provide a biosensor in which the reporter group is attached to the ligand-binding protein via a linker. In some embodiments, the linker comprises an organic compound that is less than about 30, 20, 15, or 10 Å long. Non-limiting examples of linkers include O, S, NH, PH, and alkyl linkers.

"Alkyl," as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone (e.g., $C_1$-$C_{30}$ for straight chain, $C_3$-$C_{30}$ for branched chain), more preferably 20 or fewer carbon atoms, more preferably 12 or fewer carbon atoms, and most preferably 8 or fewer carbon atoms. Likewise, preferred cycloalkyls have from 3-10 carbon atoms in their ring structure, and more preferably have 5, 6 or 7 carbons in the ring structure. The ranges provided above are inclusive of all values between the minimum value and the maximum value. The term "alkyl" includes both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety. Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. The alkyl groups may also contain one or more heteroatoms within the carbon backbone. Preferably the heteroatoms incorporated into the carbon backbone are oxygen, nitrogen, sulfur, and combinations thereof. In certain embodiments, the alkyl group contains between one and four heteroatoms.

In some embodiments, the linker comprises a bond formed by a chemical reaction involving a reactive group such as a maleimide group. Alternatively or in addition, the linker comprises a stretch of amino acids. In a non-limiting example, the linker comprises a polyglycine linker. In embodiments, the polyglycine linker comprises 2, 3, 4, 5, or more glycines. Optionally, the polyglycine linker further comprises a serine.

In various implementations, the reporter group is attached to a linker via a covalent bond and the linker is attached to a ligand-binding protein via a covalent bond. In embodiments, the covalent bond between the linker and the reporter group and/or the covalent bond between the linker and the ligand-binding protein is a disulfide bond, an ester bond, a thioester bond, an amide bond, a carbamate bond, or a bond that has been formed by a click reaction. Non-limiting examples of click reactions include reactions between an azide and an alkyne; an azide and an alkyne in the presence of Cu(I); an azide and a strained cyclooctyne; an azide and a dibenzylcyclooctyne, a difluorooctyne, or a biarylazacyclooctynone; a diaryl-strained-cyclooctyne and a 1,3-nitrone; an azide, a tetrazine, or a tetrazole and a strained alkene; an azide, a tetrazine, or a tretrazole and a oxanorbomadiene, a cyclooctene, or a trans-cycloalkene; a tetrazole and an alkene; or a tetrazole with an amino or styryl group that is activated by ultraviolet light and an alkene.

Reporter Groups

Various types of reporter groups may be used in embodiments of the present subject matter. For example, the reporter group may comprise a fluorophore that produces a fluorescent signal. Biosensors comprising a fluorophore may be referred to herein as fluorescently responsive sensors (FRSs).

Preferably, the binding of ligand to an FRS results in a change in ratiometric ΔR in the signal from a reporter group. A ratiometric signal ($R_{1,2}$) is defined as the quotient of two intensities, $I_{\lambda 1}$ and $I_{\lambda 2}$ measured at two independent wavelengths, $\lambda_1$ and $\lambda_2$ and may be calculated according to the following equation:

$$R_{1,2}=I_{\lambda 1}/I_{\lambda 2}$$

In some embodiments, intensities are, e.g., integrated, filtered, assessed, detected, or evaluated over a range of wavelengths. In some embodiments, intensities are integrated over a range of wavelengths in a recorded emission spectrum. In some embodiments, a range of wavelengths is selected using a filter. In some embodiments, $\lambda_1$ is the intensity over a 1 nm to 60 nm interval centered between 400 and 1000 nm, and $\lambda_2$ is the intensity over a 1 nm to 60 nm interval centered between 400 nm and 1000 nm. In some embodiments, intensities are integrated, filtered, assessed, detected, or evaluated over a 1 nm, 2 nm, 10 nm, 15 nm, 20 nm, 25 nm, 30 nm, 35 nm, 40 nm, 45 nm, 50 nm, 55 nm, 60 nm, 75 nm, 100 nm, 10-40 nm, 10-50 nm, 20-50 nm, or 10-100 nm regions, centered between 400-1000 nm, e.g. between 420 nm and 520 nm for $\lambda_1$, and 400-1000 nm, e.g. between 500 nm to 600 nm for $\lambda_2$. In some embodiments, intensities are recorded through a bandpass filter. A non-limiting example of a bandpass filter is a 10 nm, 15 nm, 20 nm, 25 nm, 30 nm, 35 nm, 40 nm, 45 nm, 50 nm, 75 nm, 100 nm, 10-40 nm, 10-50 nm, 20-50 nm, or 10-100 nm bandpass filter, centered between 400-1000 nm, e.g. at 452 nm for $\lambda_1$ and at 400-1000 nm, e.g. at 528 nm ($\lambda_2$).

Aspects of the present subject matter provide FRSs whose emission spectra change (e.g., the shape of the emission spectra change) in response to ligand binding. In various embodiments, the ratio of intensities at two chosen wavelengths of an FRS's emission spectrum changes upon ligand binding. In some embodiments, the emission spectral shape and/or intensity of the fluorophore changes when the position of atoms within the fluorophore changes with respect to each other (e.g., due to the rotation of bound atoms with respect to each other or a change in the angle of a bond). In non-limiting examples, the spectral shape and/or intensity of the fluorophore changes when (i) one portion of the fluorophore rotates around a bond axis compared to another portion of the fluorophore and/or (ii) when the angle of a bond between two atoms of the fluorophore changes. In a non-limiting example, the fluorophore is a prodan-derived fluorophore (e.g., Acrylodan or Badan) and binding of ligand alters the orientation of a dimethylamino group, a naphthalene ring, and/or a carbonyl with respect to the ligand-binding protein and/or each other. In a non-limiting example, the degree of polarization of a dipole on the fluorophore changes in response to ligand binding. In various embodiments, the spectral shape and/or intensity of the fluorophore changes when an atom electrostatically interacts with the fluorophore. For example, the spectral shape and/or intensity of the fluorophore changes when the source of a positive or negative charge changes its distance with respect to the fluorophore within about 1, 2, 3, 4, 5, or 10 Å of the fluorophore. In some embodiments, the fluorophore exhibits hypsochromicity or bathochromicity upon ligand binding to the ligand-binding domain of the ligand-binding protein. In certain embodiments, the fluorophore has an emission spectrum comprising radiation with a wavelength (e.g., a peak emission wavelength) of about 400 nm, 410 nm, 420 nm, 430 nm, 440 nm, 450 nm, 460 nm, 470 nm, 480 nm, 490 nm, 500 nm, 510 nm, 520 nm, 530 nm, 540 nm, 550 nm, 560 nm, 570 nm, 580 nm, 590 nm, 600 nm, 610 nm, 620 nm, 630 nm, 640 nm, 650 nm, 660 nm, 670 nm, 680 nm, 690 nm, 700 nm, 710 nm, 720 nm, 730 nm, 740 nm, 750 nm, 760 nm, 770 nm, 780 nm, 790 nm, 800 nm, 850 nm, 900 nm, 950 nm, or 1000 nm, or about 400 nm to about 450 nm, about 450 nm to about 500 nm, about 500 nm to about 550 nm, about 550 nm to about 600 nm, about 600 nm to about 650 nm, about 650 to about 700 nm, about 700 nm to about 750 nm, about 750 nm to about 800 nm, or about 800 nm to about 1000 nm.

In some embodiments, the signal comprises the emission intensity of the fluorophore recorded at a single wavelength or range of wavelengths. The change in signal may be a shift in the single wavelength or range of wavelengths. In some embodiments, the shift in the wavelength is at least about 1 nm, at least about 2 nm, at least about 3 nm, at least about 4 nm, at least about 5 nm, at least about 6 nm, at least about 7 nm, at least about 8 nm, at least about 9 nm, at least about 10 nm, at least about 11 nm, at least about 12 nm, at least about 13 nm, at least about 14 nm, at least about 15 nm, at least about 16 nm, at least about 17 nm, at least about 18 nm, at least about 19 nm, at least about 20 nm, at least about 25 nm, at least about 30 nm, at least about 35 nm, at least about 40 nm, at least about 45 nm, at least about 50 nm, at least about 55 nm, at least about 60 nm, at least about 65 nm, at least about 70 nm, at least about 75 nm, at least about 80 nm, at least about 85 nm, at least about 90 nm, at least about 95 nm, at least about 100 nm, at least about 105 nm, at least about 110 nm, at least about 115 nm, at least about 120 nm, at least about 125 nm, or at least about 130 nm. In some embodiments, the shift in the wavelength is about 1 nm to about 20 nm, about 2 nm to about 20 nm, about 3 nm to about 20 nm, about 4 nm to about 20 nm, about 5 nm to about 20 nm, about 1 nm to about 19 nm, about 1 nm to about 18 nm, about 1 nm to about 17 nm, 1 nm to about 16 nm, about 1 nm to about 15 nm, about 1 nm to about 14 nm, about 1 nm to about 13 nm, about 1 nm to about 12 nm, about 1 nm to about 11 nm, or about 1 nm to about 10 nm. In some embodiments, the shift in the wavelength is about 1 nm to about 20 nm. In some embodiments, the shift in the wavelength is about 1 nm to about 130 nm.

In certain embodiments, the signal comprises the ratio or quotient of the emission intensities recorded at two distinct wavelengths or ranges of wavelengths, i.e., a ratiometric signal. For example, as shown in FIGS. 1A-D, ligand binding may be determined by measuring the ratio of blue to green emission intensities. The change in signal may be decreased emission intensity at one wavelength, and no change in emission intensity at the other wavelength. The change in signal may be increased emission intensity at one wavelength, and no change in emission intensity at the other wavelength. The change in signal may be increased emission intensity at one wavelength, and increased emission intensity at the other wavelength. The change in signal may be decreased emission intensity at one wavelength, and decreased emission intensity at the other wavelength. The change in signal may be increased emission intensity at one wavelength, and decreased emission intensity at the other wavelength. In some embodiments, the change in ratio of the emission intensities recorded at two distinct wavelengths or ranges of wavelengths may be at least about 1.1-fold, at least about 1.2-fold, at least about 1.4-fold, at least about 1.6-fold, at least about 1.8-fold, at least about 2.0-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, at least about 10-fold, at least about 12-fold, at least about 14-fold, at least about 16-fold, at least about 18-fold, at least about 20-fold, at least about 25-fold, at least about 30-fold, at least about 35-fold, at least about 40-fold, at least about 45-fold, at least about 50-fold, at least about 55-fold, at least about 60-fold, at least about 65-fold, at least about 70-fold, at least about 75-fold, at least about 80-fold, at least about 85-fold, at least about 90-fold, at least about 95-fold, or at least about 100-fold. In some embodiments, the change in ratio of the emission intensities recorded at two distinct wavelengths or ranges of wavelengths may be a decrease of at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%, or of 5-25%, 25-50%, 25-75%, 50-75%, 50-90%, or 75-99% or the reciprocal thereof.

The change in signal may be a change in the ratio of the two distinct wavelengths or ranges of wavelengths. The change in signal may be a shift in the two distinct wavelengths or ranges of wavelengths. In some embodiments, one wavelength shifts. In some embodiments, both wavelengths shift. In some embodiments, the shift in the wavelength is at least about 1 nm, at least about 2 nm, at least about 3 nm, at least about 4 nm, at least about 5 nm, at least about 6 nm, at least about 7 nm, at least about 8 nm, at least about 9 nm, at least about 10 nm, at least about 11 nm, at least about 12 nm, at least about 13 nm, at least about 14 nm, at least about 15 nm, at least about 16 nm, at least about 17 nm, at least about 18 nm, at least about 19 nm, at least about 20 nm, at least about 25 nm, at least about 30 nm, at least about 35 nm, at least about 40 nm, at least about 45 nm, at least about 50 nm, at least about 55 nm, at least about 60 nm, at least about 65 nm, at least about 70 nm, at least about 75 nm, at least about 80 nm, at least about 85 nm, at least about 90 nm, at least about 95 nm, at least about 100 nm, at least about 105 nm, at least about 110 nm, at least about 115 nm, at least about 120 nm, at least about 125 nm, or at least about 130 nm. In some embodiments, the shift in the wavelength is about 1 nm to about 20 nm, about 2 nm to about 20 nm, about 3 nm to about 20 nm, about 4 nm to about 20 nm, about 5 nm to about 20 nm, about 1 nm to about 19 nm, about 1 nm to about 18 nm, about 1 nm to about 17 nm, 1 nm to about 16 nm, about 1 nm to about 15 nm, about 1 nm to about 14 nm, about 1 nm to about 13 nm, about 1 nm to about 12 nm, about 1 nm to about 11 nm, or about 1 nm to about 10 nm. In some embodiments, the shift in the wavelength is about 1 nm to about 20 nm. In some embodiments, the shift in the wavelength is about 1 nm to about 130 nm.

A fluorophore may comprise. e.g., a fluorescent protein or an organic compound having a molecular weight less than about 2000 Daltons (Da). Non-limiting examples of commercially available fluorophores include such as 5-iodoacetamidofluorescein (5-IAF) or 6-iodoacetamidofluorescein (6-IAF), rhodamine, Oregon Green, eosin. Texas Red, indocarbocyanine, oxacarbocyanine, thiacarbocyanine, merocyanine. Badan, Acrylodan, IAEDANS, comprising 3-cyano-7-hydroxycoumarin, 7-hydroxycoumarin-3-carboxylic acid, 6,8-difluoro-7-hydroxy-4-methylcoumarin, or 7-amino-4-methylcoumarin, pyridyloxazole, nitrobenzoxadiazole, benzoxadiazole, DRAQ5, DRAQ7, or CyTRAK Orange, cascade blue, Nile red, Nile blue, cresyl violet, oxazine 170, proflavin, acridine orange, acridine yellow, auramine, crystal violet, malachite green, porphin, phthalocyanine, bilirubin, pyrene, N,N'-dimethyl-N-(iodoacetyl)-N'-(7-nitrobenz-2-ox-a-1,3-diazol-4-yl)ethylenediamide (NBD). N-((2-(iodoacetoxy)ethyl)-N-methy-1)amino-7-nitrobenz-2-oxa-1,3-diazole (NBDE), JPW4039, JPW4042, JPW4045, Pacific Blue, CPM, N,N'-Dimethyl-N-(Iodoacetyl)-N'-(7-Nitrobenz-2-Oxa-1,3-Diazol-4-yl)Ethylenediamine (IANBD), 7-diethylamino-3-(4'-maleimidylphenyl)-4-methylcoumarin (CPM), BODIPY 499, BODIPY 507/545, BODIPY 499/508. Alexa 432, Alexa488, Alexa532, Alexa546, Cy5, or 1-(2-maleimidylethyl)-4-(5-(4-methoxyphenyl)oxazol-2-yl)pyridinium methanesulfonate (PyMPO maleimide) (PyMPO). In various embodiments, the reporter group was thiol-reactive prior to being conjugated to a polypeptide disclosed herein. In embodiments, the reporter group is linked to a polypeptide disclosed herein via a disulfide bond. Additional non-limiting examples of commercially available fluorophores include fluorescent proteins such as Blue Fluorescent Protein (BFP), TagBFP, mTagBFP2, Azurite, Enhanced Blue Florescent Protein 2 (EBFP2), mKalama1, Sirius, Sapphire, T-Sapphire, Cyan Fluorescent Protein (CFP); Enhanced Cyan Fluorescent Protein (ECFP), Cerulean, SCFP3A, mTurquoise, mTurquoise2, monomeric Midoriishi-Cyan, TagCFP, mTFP1, AmCyan1, Green Fluorescent Protein (GFP), Enhanced Green Fluorescent Protein (EGFP), Emerald, Superfolder GFP, AcGFP1, ZsGreen1, Monomeric Azami Green, TagGFP2, mUKG, mWasabi, Clover, mNeonGreen, Yellow Fluorescent Protein (YFP), Enhanced Yellow Fluorescent Protein (EYFP), Citrine, Venus, Super Yellow Fluorescent Protein 2 (SYFP2), TagYFP, ZsYellow1, mBanana, Orange Fluorescent Protein (OFP), Monomeric Kusabira-Orange (mKO), mKO, mKO2, mOrange, mOrange2, Red Fluorescent Protein (RFP), DsRed-Express, DsRed-Express2, DsRed2, AsRed2, mRaspberry, mCherry, mStrawberry, mTangerine, tdTomato, TagRFP, TagRFP-T, mApple, mRuby, mRuby2, mPlum, HcRed-Tandem, mKate2, mNeptune, HcRed1, E2-Crimson. NirFP, TagRFP657, IFP1.4, or iRFP.

In some embodiments, the fluorophore comprises xanthene, a xanthene derivative, cyanine, a cyanine derivative, squaraine, a squaraine derivative, naphthalene, a naphthalene derivative, coumarin, a coumarin derivative, oxadiazole, an oxadiazole derivative, anthracene, an anthracene derivative, a boradiazaindacine (BODIPY) family fluorophore, pyrene, a pyrene derivative, acridine, an acridine derivative, arylmethine, an arylmethine derivative, tetrapyrrole, or a tetrapyrrole derivative. For example, the fluorophore may comprise a xanthene derivative comprising fluorescein or a fluorescein derivative, rhodamine, Oregon Green, eosin, or Texas Red. Non-limiting examples of fluorescein derivatives include 5-fluorescein, 6-carboxyfluorescein, 3'6-carboxyfluorescein, 5(6)-carboxyfluorescein, 6-hexachlorofluorescein, 6-tetrachlorofluorescein, or isothiocyanate. In some embodiments, the fluorophore comprises a cyanine derivative comprising indocarbocyanine, oxacarbocyanine, thiacarbocyanine, or merocyanine. In certain embodiments, the fluorophore comprises a squaraine derivative comprising a ring-substituted squaraine. In various embodiments, the fluorophore comprises a naphthalene derivative comprising a dansyl or prodan naphthalene derivative. In a non-limiting example, the fluorophore comprises prodan or a derivative thereof. In certain embodiments, the fluorophore comprises Badan, Acrylodan, or N-(Iodoacetaminoethyl)-1-naphthylamine-5-sulfonic acid (IAEDANS). In some embodiments, the fluorophore comprises a coumarin derivative such as 3-cyano-7-hydroxycoumarin, 7-hydroxycoumarin-3-carboxylic acid, 6,8-difluoro-7-hydroxy-4-methylcoumarin (DiFMU), or 7-amino-4-methylcoumarin. In various embodiments, the fluorophore comprises an oxadiazole derivative such as pyridyloxazole, nitrobenzoxadiazole, or benzoxadiazole. In certain embodiments, the fluorophore comprises an anthracene derivative comprising an anthraquinone such as DRAQ5, DRAQ7, or CyTRAK Orange. In various embodiments, the fluorophore comprises a pyrene derivative comprising cascade blue. In non-limiting examples the fluorophore comprises an oxazine derivative such as Nile red. Nile blue, cresyl violet, or oxazine 170. In some embodiments, the fluorophore comprises an acridine derivative such as proflavin, acridine orange, or acridine yellow. In certain embodiments, the fluorophore comprises an arylmethine derivative such as auramine, crystal violet, or malachite green. In various embodiments, the fluorophore comprises a tetrapyrrole derivative comprising porphin, phthalocyanine, or bilirubin.

Aspects of the present subject matter relate to the use of fluorophores that may readily be attached to a ligand-binding protein disclosed herein, e.g., at a cysteine residue. For example, a fluorophore may comprise a sulfhydryl group prior to attachment to a ligand-binding protein that is reacted with a moiety of the ligand-binding protein to attach the fluorophore to the ligand-binding protein. In some embodiments, the fluorophore comprised a thiol group prior to attachment to the ligand-binding protein. For example, the fluorophore was thiol reactive prior to attachment to the ligand-binding protein. Non-limiting examples of fluorophores that may readily be attached to ligand-binding proteins using thiol reactions include fluorescein, pyrene, NBD, NBDE, Acrylodan (6-acryloyl 1-2-dimethylaminonaphthalene), Badan (6-bromo-acetyl-2-dimethylamino-naphthalene), JPW4039, JPW4042, or JPW4045.

In certain embodiments, the fluorophore comprises a derivative of a Prodan-based fluorophore such as Acrylodan or Badan. The excitation and emission properties of the Prodan-based fluorophores Acrylodan and Badan can be altered by manipulating the fluorescent ring system, while preserving the dimethylamino donor group, and the twistable carbonyl acceptor (Klymchenko 2013 Progress in *Molecular Biology and Translational Science,* 35-58). Replacement of the two-ring naphthalene with a three-ring anthracene (Lu 2006 *J. Org. Chem.,* 71, 9651-9657), fluorene (Kucherak 2010 *J. Phys. Chem. Lett.,* 1, 616-620), pyrene (Niko 2013 *Chem. Eur. J.,* 19, 9760-9765), or styrene (Benedetti 2012 *J. Am. Chem. Soc.,* 134, 12418-12421) cores significantly red-shift the excitation and emission properties, and in the case of the latter two, improve brightness through improvements in their excitation peak extinction coefficients. The entire content of each of the references cited above (as well as all other references referred to herein including the contents of nucleic acid and amino acid sequence accession number references) are incorporated herein by reference. Non-limiting examples of prodan analogues include 2-cyano-6-dihexylaminoanthracene and 2-propionyl-6-dihexylaminoanthracene, as well as fluorophores comprising the following structures:

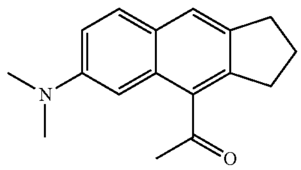

,

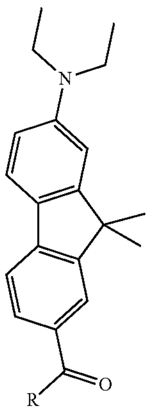

or

-continued

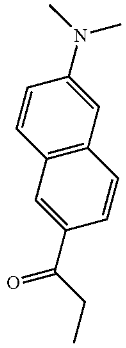

.

In some embodiments, the fluorophore comprises a fluorescent protein. Fluorescent proteins that emit blue, cyan, green, yellow, orange, red, far-red, or near infrared radiation when contacted with excitation radiation are known in the art and commercially available as proteins and via the expression of vectors that encode the fluorescent protein. Non-limiting examples of fluorescent proteins include Blue Fluorescent Protein (BFP), TagBFP, mTagBFP2, Azurite, Enhanced Blue Florescent Protein 2 (EBFP2), mKalama1, Sirius, Sapphire, T-Sapphire, Cyan Fluorescent Protein (CFP); Enhanced Cyan Fluorescent Protein (ECFP), Cerulean, SCFP3A, mTurquoise, mTurquoise2, monomeric Midoriishi-Cyan, TagCFP, mTFP1, AmCyan1, Green Fluorescent Protein (GFP), Enhanced Green Fluorescent Protein (EGFP), Emerald, Superfolder GFP, AcGFP1, ZsGreen1, Monomeric Azami Green, TagGFP2, mUKG, mWasabi, Clover, mNeonGreen, Yellow Fluorescent Protein (YFP), Enhanced Yellow Fluorescent Protein (EYFP), Citrine, Venus, Super Yellow Fluorescent Protein 2 (SYFP2). TagYFP, ZsYellow1, mBanana. Orange Fluorescent Protein (OFP), Monomeric Kusabira-Orange (mKO), mKOκ, mKO2, mOrange, mOrange2, Red Fluorescent Protein (RFP), DsRed-Express, DsRed-Express2, DsRed2, AsRed2, mRaspberry, mCherry, mStrawberry, mTangerine, tdTomato, TagRFP, TagRFP-T, mApple, mRuby, mRuby2, mPlum, HcRed-Tandem, mKate2, mNeptune, HcRed1, E2-Crimson, NirFP, TagRFP657, IFP1.4, or iRFP.

In some embodiments, the fluorophore comprises a quantum dot (Medintz et al. 2005) (Sapsford, Berti and Medintz 2006 Angew Chem Int Ed Engl, 45, 4562-89; Resch-Genger et al. 2008 Nat Methods, 5, 763-75). In some embodiments the emission properties of the conjugated protein are enhanced by immobilization on or near metallic nanoparticles (Zeng et al. 2014 *Chem Soc Rev,* 43, 3426-52; Shen et al. 2015 *Nanoscale,* 7, 20132-41).

In various embodiments, the peak emission wavelength and/or the emission intensity of the biosensor change when the ligand binds to the ligand-binding protein. In some embodiments, the biosensor exhibits a dichromatic signaling change when the ligand binds to the ligand-binding protein. In various embodiments, the peak emission wavelength of the biosensor shifts by at least about 5, 10, 15, 20, 30, 40, 50, or by about 5-50 nm when the biosensor binds to ligand. In certain embodiments, the emission intensity of the biosensor increases by at least about 5%, 10%, 20%, 30%, 40%, 50%, 60%, 70%, 80%, 90%, 100%, 150%, 200%, or 300% when the biosensor binds to ligand. In various embodiments, the signal produced by the reporter group persists for at least 1 nanoseconds (ns), 5 ns, 10 ns, 25 ns, 50 ns, 75 ns, 100 ns, 200 ns, 300 ns, 400 ns, 500 ns, 600 ns, 700 ns, 800 ns, 900 ns, 0.001 milliseconds (ms), 0.01 ms, 0.1 ms, 1 ms, 5 ms, 10 ms, 20 ms, 25 ms, 50 ms, 100 ms, or 500 ms when the ligand binds to the ligand-binding protein.

Ratiometric Sensing with Fluorescence Energy Transfer

The present subject matter provides methods for converting monochromatic responses into dichromatic responses that enable ratiometric sensing. If the fluorescence emission spectrum changes shape in response to analyte binding such that the ratio of emission intensities at two appropriately chosen wavelengths reports on analyte concentration (dichromatic response), then ratiometric measurements can be used to monitor analyte concentrations. In embodiments, these methods are based on establishing non-geometrically modulated Förster resonance energy transfer (ngmFRET) between a fluorophore (a directly responsive partner), and a second fluorophore that neither interacts directly with the ligand, nor is sensitive to ligand-mediated changes in its environment (an indirectly responsive partner). Biosensors that undergo ngmFRET (or altered ngmFRET) upon ligand binding are also provided herein, as well as compositions and devices comprising such biosensors.

Methods, compounds, and compositions provided herein overcome challenges regarding the design of biosensors that produce a ratiometric signal. For example, a biosensor that exhibits a monochromatic response (which does not produce a ratiometric signal) to ligand binding may be converted into a biosensor that produces a dichromatic/ratiometric signal. Moreover, the number of fluorophores that may be utilized in ratiometric biosensors is dramatically increased by the present subject matter. For example, fluorophores that typically do not show a dichromatic response to ligand binding (such as fluorescein and derivatives thereof) may be used together with an additional reporter group (such as another fluorophore) to produce a ratiometric signal. Also included are methods, compounds, and compositions relating to biosensors with multiple reporter groups that have improved ratiometric signals compared to other ratiometric biosensors (e.g., ratiometric biosensors having a single reporter group).

Traditional/conventional geometrically-modulated Fluorescence Resonance Energy Transfer (tgmFRET) is a physical phenomenon that was first described over 50 years ago. In tgmFRET, the transfer of excited state energy from a donor fluorophore to an acceptor fluorophore (i.e. energy transfer) is modulated by a ligand-binding event through changes in the distance and/or angle between the donor and acceptor fluorophores. tgmFRET is manifested by opposing changes in the fluorescence emission intensities of the donor and acceptor fluorophores, respectively, in response to ligand binding. For instance, a decrease in distance results in a decrease of the donor fluorescence emission intensity and an increase in the acceptor fluorescence intensity, as energy is transferred from the former to the latter. A ligand-mediated increase in the distance between the partners has the opposite effect (the fluorescence emission intensity of the donor increases, whereas that of the acceptor decreases). In tgmFRET, ligand-mediated modulation of fluorescence intensity arises from global changes in the entire system, and can occur only if both partners are present.

By contrast, in ngmFRET ligand-mediated modulation of fluorescence intensity arises from changes that are localized to the photophysics of the directly responsive fluorophore. Unlike tgmFRET, ligand-mediated changes in fluorescence therefore occur also if only the directly responsive partner is present in isolation by itself. Although the entire ngmFRET system comprising two partners is not required for evincing ligand-mediated changes in fluorescence emission intensity, the response of such a system is qualitatively changed or quantitatively enhanced over the responses of the isolated directly responsive partner (e.g. converting a monochromatic into a dichromatic response, thereby enabling ratiometry). Furthermore, unlike tgmFRET, the pattern of fluorescence intensity changes manifested by ligand binding in ngmFRET systems are not limited to opposing changes only. Instead, in ngmFRET almost all combinations of emission intensity changes are possible: opposing changes in the two partners, both partners increase, both decrease, one partner remains unchanged whereas the other increases or decreases. The majority of these responses evince changes that are unequal in magnitude and/or direction (i.e. increase, decrease), and accordingly are manifested as ligand-mediated changes in the ratio of the two fluorescence emission intensities. This versatility of ngmFRET system response patterns has great utility in the field of fluorescent biosensors.

The ligand-mediated alteration of the photophysics of the directly responsive partner includes changes to its spectral properties such as the shape of the excitation or emission spectra, and the ratio of radiative to non-radiative emission rates. The fluorescence emission intensity of the indirectly responsive partner in isolation does not change in response to ligand binding; its intensity changes only in the presence of a directly responsive partner in the complete ngmFRET system. In the field fluorescence spectroscopy, the term “quenching” has often been used loosely to refer to a decrease fluorescence emission intensity. However, as used herein, the term “quenching” strictly means a “change in the ratio of radiative to non-radiative emission rates” of a fluorophore.

Aspects of the present subject matter provide biosensors in which ngmFRET occurs between two or more reporter groups (e.g., a donor fluorophore and an acceptor fluorophore) of the biosensor. For example, ngmFRET may change (e.g., increase or decrease) when ligand is bound to the biosensor and a donor fluorophore is contacted with radiation within its excitation wavelength. Effects from tgmFRET and ngmFRET may occur together and be combined into an overall ligand-mediated change in fluorescence emission intensity. In preferred embodiments, less than half or none of the change in overall ligand-mediated change in fluorescence emission intensity is due to tgmFRET. In embodiments, most of the overall ligand-mediated change in fluorescence emission intensity change is not due to a change in the distance between the donor and acceptor fluorophore or as a result of a change in the orientation between the donor and acceptor fluorophore. In non-limiting examples, less than about 25%, 20%, 15%, 10%, 5%, 4%, 3%, 2%, 1%, or 0.5% of the change in overall ligand-mediated change in fluorescence emission intensity is due to tgmFRET. In various embodiments, at least about 70%, 75%, 80%, 85%, 90%, 95%, 96%, 97%, 98%, 99%, 99.5%, 99.9%, or 99.99% of the ligand-mediated change in fluorescence emission intensity is due to ngmFRET. For example, the change in overall ligand-mediated change in fluorescence emission intensity comprises a spectral change (e.g., in the excitation or emission spectrum) and/or a change in the ratio of the radiative to non-radiative decay rates of one of the fluorophores (by itself and regardless of the presence of any other fluorophore/partner) upon ligand binding.

In some embodiments, ligand binding mediates spectral shifts in the absorption or emission spectrum of the directly responsive partner. In certain embodiments such changes are due at least in part to a switch between different excited states in the ligand-free and ligand-bound biosensor. The two excited states are associated with different transition dipoles. This class of changes is termed "dipole switching" herein.

In embodiments, the reporter groups include a directly responsive partner (which may be a donor fluorophore or an acceptor fluorophore) and an indirectly responsive partner (which may be a donor fluorophore or an acceptor fluorophore). Depending on context, a "directly responsive" partner is a fluorophore that responds to (i) ligand-induced protein conformational changes upon ligand binding to a ligand-binding protein; or (ii) ligand binding to the directly responsive partner itself. In some embodiments, the directly responsive partner comprises a fluorophore(i.e., it is a directly responsive fluorophore). In various embodiments, the directly responsive fluorophore exhibits a monochromatic or dichromatic spectral change, and/or a change in the ratio of radiative to non-radiative emission rates, upon ligand binding. In certain embodiments relating to ligand binding to the directly responsive partner itself, the directly responsive partner may be a fluorophore such as a fluorescent protein or a small molecule fluorescent compound. An "indirectly responsive" partner is a fluorophore for which no change in emission spectra, excitation spectra, or change in the ratio of radiative to non-radiative emission rates is caused by ligand binding in the absence of a directly responsive partner. In some embodiments, the indirectly responsive partner comprises a fluorophore (i.e., it is an indirectly responsive fluorophore). When paired with a directly responsive partner with which the indirectly responsive partner is a ngmFRET donor or acceptor, the emission fluorescence intensity of the indirectly responsive partner changes due to a change in energy flow in the ngmFRET pathway upon ligand binding. See, e.g., FIG. 58.

ngmFRET Biosensors

Provided herein are methods, compositions, biosensors, and devices comprising multiple reporter groups, e.g. a directly responsive fluorophore and an indirectly responsive fluorophore, between which ngmFRET occurs.

Aspects include a method of detecting a lactate in a sample, comprising contacting a biosensor with a lactate. The biosensor comprises a lactate-binding protein, a directly responsive fluorophore and an indirectly responsive fluorophore. The directly responsive and the indirectly responsive fluorophores are located at two distinct sites of the lactate-binding protein. In some embodiments, the directly responsive fluorophore is a donor fluorophore and the indirectly responsive fluorophore is an acceptor fluorophore. Alternatively, the directly responsive fluorophore is an acceptor fluorophore and the indirectly responsive fluorophore is a donor fluorophore. The method includes contacting the biosensor with radiation comprising a wavelength within the excitation spectrum of the donor fluorophore. When the biosensor is contacted with such radiation, a fluorescence property of the directly responsive fluorophore changes in response to lactate binding. This change in fluorescent property is independent of the indirectly responsive fluorophore, and occurs regardless of whether the indirectly responsive fluorophore is absent or present. The fluorescence properties of the indirectly responsive fluorophore do not change in response to lactate binding in the absence of the directly responsive fluorophore. When the biosensor is contacted with radiation comprising a wavelength within the excitation spectrum of the donor fluorophore, then (i) ngmFRET occurs between the directly responsive fluorophore and the indirectly responsive fluorophore; (ii) fluorescent light is emitted from the biosensor, and the light emitted from the biosensor comprises a combination of light emitted from the directly responsive fluorophore and light emitted from the indirectly responsive fluorophore; and (iii) the ratio of the fluorescence emission intensity emitted from the biosensor at each of two distinct wavelengths changes in response to lactate binding. In various embodiments, the method further comprises measuring fluorescent light that is emitted from the directly responsive fluorophore and the indirectly responsive fluorophore, and calculating a ratiometric signal to detect the lactate in the sample.

The ratiometric signal ($R_{1,2}$) comprises a quotient of two intensities, $I_{\lambda 1}$ and $I_{\lambda 2}$, measured at two independent wavelengths, $\lambda_1$ and $\lambda_2$ and is calculated according to the following equation:

$$R_{1,2}=I_{\lambda 1}/I_{\lambda 2}.$$

The two independent wavelengths $\lambda_1$ and $\lambda_2$ may be from a single fluorophore or from a combination of two or more fluorophores (e.g., a pair of fluorophores between which ngmFRET occurs). In some embodiments, $\lambda_1$ falls within the emission spectrum of a directly responsive fluorophore and $\lambda_2$ falls within the emission spectrum of an indirectly responsive fluorophore. In certain embodiments, $\lambda_1$ falls within the emission spectrum of an indirectly responsive fluorophore and $\lambda_2$ falls within the emission spectrum of a directly responsive fluorophore. In various embodiments, $\lambda_1$ falls within the emission spectrum of both a directly responsive fluorophore and an indirectly responsive fluorophore. In various embodiments, $\lambda_2$ falls within the emission spectrum of both a directly responsive fluorophore and an indirectly responsive fluorophore.

Aspects of the present subject matter provide FRSs whose emission spectra change (e.g., the shape of the emission spectra change) in response to lactate binding. In various embodiments, the ratio of intensities at two chosen wavelengths of an FRS's emission spectrum changes upon lactate binding.

In various embodiments, the emission spectra of two or more fluorophores contributes to $I_{\lambda 1}$ and/or $I_{\lambda 2}$. In some embodiments, the emission spectrum of a directly responsive fluorophore contributes to $I_{\lambda 1}$ and/or $I_{\lambda 2}$ and the emission spectrum of an indirectly responsive fluorophore contributes to $I_{\lambda 1}$ and/or $I_{\lambda 2}$. In certain embodiments, a directly responsive fluorophore contributes to $I_{\lambda 1}$ and the emission spectrum of an indirectly responsive fluorophore contributes to $I_{\lambda 2}$. In some embodiments, a directly responsive fluorophore contributes to $I_{\lambda 2}$ and the emission spectrum of an indirectly responsive fluorophore contributes to $I_{\lambda 1}$. In various embodiments, both the emission spectrum of a directly responsive fluorophore and the emission spectrum of an indirectly responsive fluorophore contributes to $I_{\lambda 1}$. In some embodiments, both the emission spectrum of a directly responsive fluorophore and the emission spectrum of an indirectly responsive fluorophore contributes to $I_{\lambda 2}$.

In some embodiments, the directly responsive fluorophore is Acrylodan and emission intensity is measured at a wavelength or range of wavelengths between about 400 nm and 1000 nm (e.g., including a wavelength of about 440, 441, 442, 443, 444, 445, 446, 447, 448, 449, 450, 451, 452, 453, 454, 455, 456, 457, 458, 459, or 460 nm), and wherein the indirectly responsive fluorophore is 5-IAF and emission intensity is measured at a wavelength or range of wavelengths between about 400 nm and 1000 nm (e.g., including a wavelength of about 510, 511, 512, 513, 514, 515, 516, 517, 518, 519, 520, 521, 522, 523, 524, 525, 526, 527, 528, 529, or 530 nm). In certain embodiments, the directly responsive fluorophore is Acrylodan and emission intensity is measured at a wavelength or range of wavelengths between about 400 nm and 1000 nm (e.g., including a wavelength of about 440, 441, 442, 443, 444, 445, 446, 447, 448, 449, 450, 451, 452, 453, 454, 455, 456, 457, 458, 459, or 460 nm), and wherein the indirectly responsive fluorophore is Alexa532 and emission intensity is measured at a wavelength or range of wavelengths between about 400 nm and 1000 nm (e.g. including a wavelength of about 540, 541, 542, 543, 544, 545, 546, 547, 548, 549, 550, 551, 552, 553, 554, 555, 556, 557, 558, 559, or 560 nm). In a non-limiting example, the lactate-binding protein comprises a cysteine at the position of its amino acid sequence that aligns with position 187 or 188 of msLacBP6 (SEQ ID NO: 20 or 120) when the amino acid sequence of the lactate-binding protein is aligned with the amino acid sequence of msLacBP6 using the ClustalW alignment program, and wherein the Acrylodan is covalently attached to the cysteine. In some embodiments, the 5-IAF or the Alexa532 is attached to the N-terminus or the C-terminus of the lactate-binding protein via a fluorophore attachment motif. In a non-limiting example, the lactate-binding protein comprises amino acids in the sequence of SEQ ID NO: 61 or 62.

In various embodiments, the change in the fluorescent property of the directly responsive fluorophore comprises (i) a bathochromic or hypsochromic shift in the emission or excitation spectrum thereof; and/or (ii) a change in the ratio of radiative to non-radiative emission rates thereof.

In embodiments, the directly responsive fluorophore comprises a donor fluorophore and the indirectly responsive fluorophore comprises an acceptor fluorophore. In some embodiments, the emission intensity of the donor fluorophore decreases and the emission intensity of the acceptor fluorophore increases upon lactate binding to the lactate-binding protein when the donor fluorophore is contacted with radiation within the excitation spectrum of the donor fluorophore. In some embodiments, the emission intensity of the donor fluorophore increases and the emission intensity of the acceptor fluorophore decreases upon lactate binding to the lactate-binding protein when the donor fluorophore is contacted with radiation within the excitation spectrum of the donor fluorophore. In some embodiments, the emission intensities of the donor fluorophore and the acceptor fluorophore both decrease upon lactate binding to the lactate-binding protein when the donor fluorophore is contacted with radiation within the excitation spectrum of the donor fluorophore. In some embodiments, the emission intensity of the donor fluorophore decreases and the emission intensity of the acceptor fluorophore increases, decreases, or remains about the same upon lactate binding to the lactate-binding protein when the donor fluorophore is contacted with radiation within the excitation spectrum of the donor fluorophore. In some embodiments, the emission intensity of the donor fluorophore increases, decreases, or remains about the same and the emission intensity of the acceptor fluorophore decreases upon lactate binding to the lactate-binding protein when the donor fluorophore is contacted with radiation within the excitation spectrum of the donor fluorophore. In some embodiments, the emission intensities of the donor fluorophore and the acceptor fluorophore both increase upon lactate binding to the lactate-binding protein when the donor fluorophore is contacted with radiation within the excitation spectrum of the donor fluorophore. In some embodiments, the emission intensity of the donor fluorophore increases, decreases, or remains about the same and the emission intensity of the acceptor fluorophore increases upon lactate binding to the lactate-binding protein when the donor fluorophore is contacted with radiation within the excitation spectrum of the donor fluorophore. In some embodiments, the emission intensity of the donor fluorophore increases and the emission intensity of the acceptor fluorophore increases, decreases, or remains about the same upon lactate binding to the lactate-binding protein when the donor fluorophore is contacted with radiation within the excitation spectrum of the donor fluorophore.

In embodiments the directly responsive fluorophore comprises an acceptor fluorophore and the indirectly responsive fluorophore comprises a donor fluorophore. In some embodiments, the emission intensity of the donor fluorophore decreases and the emission intensity of the acceptor fluorophore increases, decreases, or remains about the same upon lactate binding to the lactate-binding protein when the donor fluorophore is contacted with radiation within the excitation spectrum of the donor fluorophore. In some embodiments, the emission intensity of the donor fluorophore increases and the emission intensity of the acceptor fluorophore increases, decreases, or remains about the same upon lactate binding to the lactate-binding protein when the donor fluorophore is contacted with radiation within the excitation spectrum of the donor fluorophore. In some embodiments, the emission intensity of the donor fluorophore remains about the same and the emission intensity of the acceptor fluorophore decreases upon lactate binding to the lactate-binding protein when the donor fluorophore is contacted with radiation within the excitation spectrum of the donor fluorophore. In some embodiments, the emission intensity of the donor fluorophore decreases and the emission intensity of the acceptor fluorophore increases, decreases, or remains about the same upon lactate binding to the lactate-binding protein when the donor fluorophore is contacted with radiation within the excitation spectrum of the donor fluorophore. In some embodiments, the emission intensity of the donor fluorophore increases and the emission intensity of the acceptor fluorophore increases, decreases, or remains about the same upon lactate binding to the lactate-binding protein when the donor fluorophore is contacted with radiation within the excitation spectrum of the donor fluorophore. In some embodiments, the emission intensity of the donor fluorophore remains about the same and the emission intensity of the acceptor fluorophore increases upon lactate binding to the lactate-binding protein when the donor fluorophore is contacted with radiation within the excitation spectrum of the donor fluorophore. In some embodiments, the emission intensity of the donor fluorophore decreases and the emission intensity of the acceptor fluorophore increases upon lactate binding to the lactate-binding protein when the donor fluorophore is contacted with radiation within the excitation spectrum of the donor fluorophore. In some embodiments, the emission intensity of the donor fluorophore increases and the emission intensity of the acceptor fluorophore remains about the same, increases, or decreases upon lactate binding to the lactate-binding protein when the donor fluorophore is contacted with radiation within the excitation spectrum of the donor fluorophore.

In instances in which an emission intensity increases, the increase may be, e.g., between about 0.1% to 10%, 10% to 50%, or 50% to 100%, or at least about 0.1%, 0.5%, 1%, 2%, 3%, 4%, 5%, 10%, 15%, 20%, 25%, 50%, 75%, 100%, 2-fold, 3-fold, 4-fold, 5-fold, 6-fold, 7-fold, 8-fold, 9-fold, or 10-fold. In instances in which an emission intensity decreases, the decrease may be, e.g., a decrease of between about at least about 0.1% to 10%, 10% to 50%, or 50% to 00%, or at least about 0.1%, 0.5%, 1%, 2%, 3%, 4%, 5%, 10%, 15%, 20%, 25%, 30%, 35%, 40%, 45%, 50%, 55%, 60%, 65%, 70%, 75%, 80%, 85%, or 90%. In various embodiments in which both the emission intensity of the donor fluorophore and the acceptor fluorophore increases, then the increases are not equal. In certain embodiments in which both the emission intensity of the donor fluorophore and the acceptor fluorophore decreases, then the decreases are not equal.

In certain embodiments, the indirectly responsive fluorophore is attached to the lactate-binding protein via a covalent bond. Various approaches for attaching reporter groups such as directly and indirectly responsive fluorophores to a polypeptide such as a lactate-binding protein are described herein. In some embodiments, the covalent bond comprises a disulfide bond, a thioester bond, a thioether bond, an ester bond, an amide bond, or a bond that has been formed by a click reaction.

In some embodiments, the indirectly responsive fluorophore is attached to the lactate-binding protein via a non-covalent bond. In certain embodiments, the indirectly responsive fluorophore is attached to a cysteine or a lysine of the lactate-binding protein.

In various embodiments, the indirectly responsive fluorophore is attached to the N-terminus or the C-terminus of the protein. In some embodiments, the indirectly responsive fluorophore is attached to the N-terminus or the C-terminus of the protein via a fluorophore attachment motif.

In some embodiments, fluorophore attachment motif comprises a polypeptide. Various embodiments may be used to link a fluorophore with a lactate-binding protein. In some embodiments, the polypeptide comprises a stretch of at least 50, 60, 70, 80, 90, or 100 amino acids. In a non-limiting example, the polypeptide comprises amino acids in the sequence of βZif (SEQ ID NO: 109). In another non-limiting example, the polypeptide comprises a stretch of at least 50, 60, 70, 80, 90, or 100 amino acids in a sequence that is at least about 85%, 90%, 95%, or 99% identical to the amino acid sequence of *E. coli* thioredoxin (ecTRX; SEQ ID NO: 138).

In some embodiments, the directly responsive fluorophore is attached to the lactate-binding protein via a covalent bond. In various embodiments, the covalent bond comprises a disulfide bond, a thioester bond, a thioether bond, an ester bond, an amide bond, or a bond that has been formed by a click reaction. In directly responsive fluorophore is attached to a cysteine or a lysine of the protein.

In some embodiments, an overlap of the emission spectrum of the donor fluorophore and the excitation spectrum of the acceptor fluorophore increases upon lactate binding. In certain embodiments, the directly responsive fluorophore comprises the donor fluorophore, and the increase results from a bathochromic shift in the emission spectrum of the donor fluorophore. Alternatively, the directly responsive fluorophore comprises the acceptor fluorophore, and the increase results from a hypsochromic shift in the excitation spectrum of the acceptor fluorophore.

In various embodiments, an overlap of the emission spectrum of the donor fluorophore and the excitation spectrum of the acceptor fluorophore decreases upon lactate binding. In some embodiments, the directly responsive fluorophore comprises the donor fluorophore, and the decrease results from a hypsochromic shift in the emission spectrum of the donor fluorophore. In certain embodiments, the directly responsive fluorophore comprises the acceptor fluorophore, and the decrease results from a bathochromic shift in the excitation spectrum of the acceptor fluorophore.

In some embodiments, the directly responsive fluorophore has a monochromatic spectral change upon lactate binding. Alternatively, the directly responsive fluorophore has a dichromatic spectral change upon lactate binding.

In certain embodiments, the emission intensity of the donor fluorophore and/or the acceptor fluorophore increases in two phases as lactate concentration increases.

In various embodiments, the ratio of radiative to non-radiative emission or intensity of the directly responsive fluorophore increases by at least about 0.1%, 0.5%, 1%, 2%, 3%, 4%, 5%, 10%, 15%, 20%, 25%, 50%, 75%, 100%, 2-fold, 3-fold, 4-fold, 5-fold, 6-fold, 7-fold, 8-fold, 9-fold, or 10-fold upon lactate binding to the lactate-binding protein. Alternatively, the ratio of radiative to non-radiative emission or intensity of the directly responsive fluorophore decreases by at least about 0.1%, 0.5%, 1%, 2%, 3%, 4%, 5° %, 10%, 15%, 20%, 25%, 50%, 75%, 90%, 95%, or 99% upon lactate binding to the lactate-binding protein.

In embodiments, the directly responsive fluorophore and the indirectly responsive fluorophore are not a naphthalene derivative. In some embodiments, the directly responsive fluorophore and the indirectly responsive fluorophore are not Prodan, Acrylodan, or Badan. In certain embodiments, the directly responsive fluorophore is not a naphthalene derivative. In some embodiments, the directly responsive fluorophore is not Prodan. Acrylodan, or Badan.

In various embodiments, the directly responsive fluorophore comprises xanthene, a xanthene derivative, fluorescein, a fluorescein derivative, coumarin, a coumarin derivative, cyanine, a cyanine derivative, rhodamine, a rhodamine derivative, phenoxazine, a phenoxazine derivative, squaraine, a squaraine derivative, coumarin, a coumarin derivative, oxadiazole, an oxadiazole derivative, anthracene, an anthracene derivative, a boradiazaindacine (BODIPY) family fluorophore, pyrene, a pyrene derivative, acridine, an acridine derivative, arylmethine, an arylmethine derivative, tetrapyrrole, or a tetrapyrrole derivative. In some embodiments, the directly responsive fluorophore comprises fluorescein or a derivative thereof.

In some embodiments, the directly responsive fluorophore and/or the indirectly responsive fluorophore comprises a fluorescent protein. In various embodiments, the directly responsive fluorophore and/or the indirectly responsive fluorophore comprises an organic compound having a molecular weight less than about 2000 Da (e.g., 5-iodoacetamidofluorescein (5-IAF) or 6-iodoacetamidofluorescein (6-IAF), rhodamine, Oregon Green, eosin, Texas Red, indocarbocyanine, oxacarbocyanine, thiacarbocyanine, merocyanine, Badan, Acrylodan, IAEDANS, comprising 3-cyano-7-hydroxycoumarin, 7-hydroxycoumarin-3-carboxylic acid, 6,8-difluoro-7-hydroxy-4-methylcoumarin, or 7-amino-4-methylcoumarin, pyridyloxazole, nitrobenzoxadiazole, benzoxadiazole. DRAQ5, DRAQ7, or CyTRAK Orange, cascade blue, Nile red, Nile blue, cresyl violet, oxazine 170, proflavin, acridine orange, acridine yellow, auramine, crystal violet, malachite green, porphin, phthalocyanine, bilirubin, pyrene, N,N'-dimethyl-N-(iodoacetyl)-N'-(7-nitrobenz-2-ox-a-1,3-diazol-4-yl)ethylenediamide (NBD). N-((2-(iodoacetoxy)ethyl)-N-methy-1)amino-7-nitrobenz-2-oxa-1,3-diazole (NBDE), JPW4039, JPW4042, JPW4045, Pacific Blue, CPM, N,N'-Dimethyl-N-(Iodoacetyl)-N'-(7-Nitrobenz-2-Oxa-1,3-Diazol-4-yl)Ethylenediamine (IANBD), 7-diethylamino-3-(4'-maleimidylphenyl)-4-methylcoumarin (CPM), BODIPY 499, BODIPY 507/545, BODIPY 499/508, Alexa 432, Alexa488, Alexa532, Alexa546, Cy5, or 1-(2-maleimidyl ethyl)-4-(5-(4-methoxyphenyl)oxazol-2-yl)pyridinium methanesulfonate (PyMPO maleimide) (PyMPO)). Numerous combinations of directly responsive fluorophores and indirectly responsive fluorophores are possible. For example, in various non-limiting examples, (a) the donor fluorophore comprises Pacific Blue and the acceptor fluorophore comprises 5-IAF or 6-iodoacetamidofluorescein (6-IAF); (b) the donor fluorophore comprises Pacific Blue and the acceptor fluorophore comprises Oregon Green; (c) the donor fluorophore comprises IAEDANS and the acceptor fluorophore comprises 5-IAF or 6IAF; (d) the donor fluorophore comprises acrylodan and the acceptor fluorophore comprises Alexa532; (e) the donor fluorophore comprises acrylodan and the acceptor fluorophore comprises 5-IAF or 6-IAF; (f) the donor fluorophore comprises acrylodan and the acceptor fluorophore comprises Pacific Blue or YFP; (g) the donor fluorophore comprises 5-IAF or 6-IAF and the acceptor fluorophore comprises Pacific Blue; (h) the donor fluorophore comprises badan and the acceptor fluorophore comprises 5-IAF or 6-IAF; or (i) the donor fluorophore comprises badan and the acceptor fluorophore comprises Alexa532.

Aspects also include a biosensor for a lactate comprising a lactate-binding protein, a directly responsive fluorophore and an indirectly responsive fluorophore, the directly responsive and the indirectly responsive fluorophores being located at two distinct sites of the lactate-binding-protein, wherein (i) the directly responsive fluorophore is a donor fluorophore and the indirectly responsive fluorophore is an acceptor fluorophore; or (ii) the directly responsive fluorophore is an acceptor fluorophore and the indirectly responsive fluorophore is an donor fluorophore, and wherein if the acceptor fluorophore comprises ruthenium or osmium, then the acceptor fluorophore is not attached to the amino group of the N-terminus of the lactate-binding protein.

Any of the lactate-binding proteins disclosed herein, as well as others, may be included in the biosensors and methods that are provided.

Aspects of the present subject matter also provide a method for constructing a biosensor, comprising: (a) providing a lactate-binding protein; (b) identifying at least one putative allosteric, endosteric, or peristeric site of the lactate-binding based a structure of the lactate-binding protein; (c) mutating the lactate-binding protein to substitute an amino acid at the at least one putative allosteric, endosteric, or peristeric site of the second protein with a cysteine; (d) conjugating a donor fluorophore or an acceptor fluorophore to the cysteine to produce single labeled biosensor; (e) detecting whether there is a spectral shift or change in emission intensity of the single labeled biosensor upon lactate binding when the donor fluorophore or the acceptor fluorophore is fully excited; and (f) if a spectral shift or change in emission intensity is detected in (e), attaching a donor fluorophore to the second protein if an acceptor fluorophore is attached to the cysteine, and attaching an acceptor fluorophore to the second protein if an acceptor fluorophore is attached to the cysteine.

In various embodiments, the lactate-binding protein has been identified by (i) selecting a first protein having a known amino acid sequence (seed sequence), wherein the first protein is known to bind a lactate; (ii) identifying a second protein having an amino acid sequence (hit sequence) with at least 15% sequence identity to the seed sequence; (iii) aligning the seed amino acid sequence and the hit sequence, and comparing the hit sequence with the seed sequence at positions of the seed sequence that correspond to at least 5 primary complementary surface (PCS) amino acids, wherein each of the at least 5 PCS amino acids has a hydrogen bond interaction or a van der Waals interaction with lactate when lactate is bound to the first protein; and (iv) identifying the second protein to be a lactate-binding protein if the hit sequence comprises at least 5 amino acids that are consistent with the PCS.

In some embodiments, the spectral shift comprises a monochromatic fluorescence intensity change or a dichromatic spectral shift.

Also provided is a method of converting a biosensor that shows a monochromatic response upon lactate binding into a biosensor with a dichromatic response upon lactate binding, the method comprising (a) selecting a biosensor that exhibits a monochromatic response upon lactate binding, wherein the biosensor comprises a lactate-binding protein and a first reporter group; and (b) attaching a second reporter group to the biosensor, wherein the second reporter group has (i) an excitation spectrum that overlaps with the emission spectrum of the first reporter group; or (ii) an emission spectrum that overlaps with the excitation spectrum of the first reporter group.

Also provided is a method of increasing a dichromatic response of a biosensor to lactate binding, the method comprising (a) selecting a biosensor that exhibits a dichromatic response upon lactate binding, wherein the biosensor comprises a lactate-binding protein and a first reporter group; and (b) attaching a second reporter group to the biosensor, wherein the second reporter group has (i) an excitation spectrum that overlaps with the emission spectrum of the first reporter group; or (ii) an emission spectrum that overlaps with the excitation spectrum of the first reporter group.

In some embodiments, the second reporter group is within about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 4, 6, 8, 10, 11, 12, 13, 14, 15, 16, 17, 18, 19, 20, 25, 30, 35, 40, 45, 50, 55, 60, 65, 70, 75, 80, 85, 90, 95, 100, 125, 150, or 200 angstroms (Å) of the first reporter group regardless of whether ligand is bound to the biosensor. Suitable distances may be determined in part by the distance-dependence of the energy transfer between a given donor-acceptor pair (see. e.g. J. R. Lakowicz, 2006, Principles of Fluorescence Spectroscopy, Springer, incorporated herein by reference). In some embodiments, when the lactate is bound to the biosensor, the average distance between the first reporter group and the second reporter group changes by less than about 5, 4, 3, 2, 1, 0.9, 0.8, 0.7, 0.6, 0.5, 0.4, 0.3, 0.2, 0.1, 0.05, or 0.01 angstroms (Å) compared to when lactate is not bound to the lactate-binding protein.

In various embodiments, if the acceptor fluorophore comprises palladium, platinum, ruthenium, or osmium, then the acceptor fluorophore is not attached to the amino group of the N-terminus of the ligand-binding protein. In some embodiments, the acceptor fluorophore does not comprise $[Ru(bpy)_3]^{2+}$, $[Ru(Ph_2phen)_3]^{2+}$, $[Ru(bpy)_2(dcbpy)]^{2+}$, or $[Ru(bpy)_2(phen\text{-}ITC)]^{2+}$, where bpy is 2,2'-bipyridine, phen is 1,10-phenanthroline, dcbpy is 4,4'-dicarboxy-2,2'-bipyridine, and ITC is isothiocyanate. In certain embodiments, the biosensor does not comprise an *E. coli* glutamine-binding protein with Acrylodan attached to 179C, In some embodiments, the biosensor does not comprise *E. coli* lactate-binding protein with Acrylodan attached to 255C.

tgmFRET Biosensors

While ngmFRET is preferred to tgmFRET, tgmFRET may be used alternatively or in addition to ngmFRET in certain embodiments.

In various embodiments, the biosensor comprises multiple reporter groups, including a first reporter group and a second reporter group. For example, the first reporter group may comprise a donor fluorophore and the second reporter group may comprise an acceptor fluorophore. In certain embodiments, FRET is detectable by a change in the fluorescence of the acceptor fluorophore or by a decrease in of donor fluorophore fluorescence. In various embodiments, the donor fluorophore, and/or the acceptor fluorophore is fluorescent. In some embodiments, both the donor fluorophore and the acceptor fluorophore are fluorescent.

In various embodiments, the angle and/or distance between the donor fluorophore and the acceptor fluorophore changes upon lactate binding. In some embodiments, neither the donor fluorophore nor the acceptor fluorophore is directly responsive to lactate binding. In some embodiments the donor fluorophore and/or the acceptor fluorophore is attached to the N-terminus or the C-terminus of the lactate-binding protein (e.g., directly or via a fluorophore attachment motif). In certain embodiments, the donor fluorophore and/or the acceptor fluorophore is attached to a fluorophore attachment motif. For example, the fluorophore attachment motif may be conjugated to the N-terminus or the C-terminus of the lactate-binding protein.

In some embodiments, the donor fluorophore and/or the acceptor fluorophore comprises a fluorescent protein. In various embodiments, the donor fluorophore and/or the acceptor fluorophore comprises an organic compound having a molecular weight less than about 2000 Da (e.g., 5-iodoacetamidofluorescein (5-IAF) or 6-iodoacetamidofluorescein (6-IAF), rhodamine, Oregon Green, eosin, Texas Red, indocarbocyanine, oxacarbocyanine, thiacarbocyanine, merocyanine, Badan, Acrylodan. IAEDANS, comprising 3-cyano-7-hydroxycoumarin, 7-hydroxycoumarin-3-carboxylic acid, 6,8-difluoro-7-hydroxy-4-methylcoumarin, or 7-amino-4-methylcoumarin, pyridyloxazole, nitrobenzoxadiazole, benzoxadiazole, DRAQ5, DRAQ7, or CyTRAK Orange, cascade blue, Nile red, Nile blue, cresyl violet, oxazine 170, proflavin, acridine orange, acridine yellow, auramine, crystal violet, malachite green, porphin, phthalocyanine, bilirubin, pyrene, N,N'-dimethyl-N-(iodoacetyl)-N'-(7-nitrobenz-2-ox-a-1,3-diazol-4-yl)ethylenediamide (NBD), N-((2-(iodoacetoxy)ethyl)-N-methy-1)amino-7-nitrobenz-2-oxa-1,3-diazole (NBDE), Acrylodan, JPW4039, JPW4042, JPW4045, Oregon Green, Pacific Blue, CPM, N,N'-Dimethyl-N-(Iodoacetyl)-N'-(7-Nitrobenz-2-Oxa-1,3-Diazol-4-yl)Ethylenediamine (IANBD), 7-diethylamino-3-(4'-maleimidylphenyl)-4-methylcoumarin (CPM), BODIPY 499, BODIPY 507/545. BODIPY 499/508, Alexa 432, Alexa488, Alexa532, Alexa546, Cy5, or 1-(2-maleimidylethyl)-4-(5-(4-methoxyphenyl)oxazol-2-yl)pyridinium methanesulfonate (PyMPO maleimide) (PyMPO)). For example, the organic compound is a fluorophore. Numerous combinations of donor and acceptor fluorophores are possible.

Fluorophore Attachment Motifs

Aspects of the present subject matter include the use of one or more fluorophore attachment motifs to attach one or more reporter groups to a lactate-binding protein. For example, a reporter group may be attached to a fluorophore attachment motif that is attached to the N-terminus or the C-terminus of the lactate-binding protein.

In various implementations, the fluorophore attachment motif comprises a polypeptide. In some embodiments, the polypeptide comprises amino acids in the βZif amino acid sequence (SEQ ID NO: 109).

In some embodiments, the polypeptide comprises a stretch of at least 50, 60, 70, 80, 90, or 100 amino acids in a sequence that is at least about 85%, 90%, 95%, or 99% identical to the amino acid sequence of *E. coli* thioredoxin (ecTRX; SEQ ID NO: 138). In some embodiments, the polypeptide is a mutant of ecTRX comprising a D3X, K4X, K19X, D27X, K37X, K53X, K58X, K70X, R74X, K83X, K91X, K97X, or K101X mutation, or any combination thereof, wherein X is any amino acid, and wherein each ecTRX amino acid position is numbered as in SEQ ID NO: 138. In certain embodiments, the polypeptide is a mutant of ecTRX comprising a D3A, K4R, K4Q, K19R, K19Q, D27A, K37R, K53M, K53R, K58M. K70R, R74C, K83R, K91R, K97R, or K101R mutation, or any combination thereof, wherein each ecTRX amino acid position is numbered as in SEQ ID NO: 138.

In non-limiting examples, the polypeptide comprises amino acids in the sequence set forth as any one of SEQ ID NOS: 138-156.

In certain embodiments, the polypeptide comprises (a) at least 1, 2, or 3 thiol groups; (b) at least 1, 2, or 3 cysteines that each comprise a sulfhydryl group; (c) at least 1, 2, or 3 primary amine groups; and/or (d) at least 1, 2, or 3 lysines that each comprise a primary amine. In some embodiments there is no disulfide bond between cysteines within the amino acid sequence of the polypeptide.

In some embodiments, the polypeptide comprises a hexahistidine tag. In some embodiments, the hexahisidine tag is attached to another portion of the polypeptide via a GGS linker.

Exemplary Methods of Using Biosensors Provided Herein

Aspects of the present subject matter provide a method of assaying for a ligand (e.g., lactate) in a sample. The method may include contacting the sample with a biosensor disclosed herein under conditions such that the ligand-binding protein of the biosensor binds to the ligand if ligand is present in the sample. The method also comprises detecting (i) whether a signal is produced by a reporter group of the biosensor; and/or (ii) the a signal produced by a reporter group of the biosensor. In a non-limiting example, a reporter group of the biosensor is fluorescent, and the method further comprises contacting the reporter group with electromagnetic radiation having a wavelength that comprises a wavelength within the band of excitation wavelengths of the reporter group.

In various embodiments, the method further comprises (i) comparing a signal produced by a reporter group of the biosensor when the biosensor is contacted with the sample with a signal produced by a control sample containing a known quantity of ligand (e.g., ligand at a concentration of about 0.5, 1, 2, 3, 4, 5, 6, 7, 8, 9, 10, 15, 20, 25, 30, 35, 40, 45, 50, 75, or 100 mM, or a series of control samples having concentrations within the range of about 0.5 mM to about 100 mM); and (ii) detecting the presence or absence of ligand in the sample based on this comparison. In embodiments the control sample lacks lactate (e.g., the concentration of lactate is 0 mM). Alternatively or in addition, the method further comprises (i) comparing a signal produced by a reporter group of the biosensor when the biosensor is contacted with the sample with signals produced by a series of control samples containing known quantities of ligand; and (ii) determining the quantity of ligand in the sample based on this comparison. In some embodiments, the series of control samples comprises at least 2, 3, 4, 5, 6, 7, 8, 9, or 10 control samples, and wherein each control sample comprises a different quantity of ligand. Alternatively or in addition, the method further comprises determining the concentration of a ligand in a sample, wherein determining the concentration of the ligand in the sample comprises comparing the signal to a standard hyperbolic ligand binding curve to determine the concentration of the ligand in the test sample, wherein the standard hyperbolic ligand binding curve is prepared by measuring the signal produced by the reporter group of the biosensor when the biosensor is contacted with control samples containing known concentrations of ligand. In various embodiments, the method comprises (i) measuring a ratiometric change (ΔR) and/or an intensity change (ΔI) of a signal produced by the reporter group. In some embodiments, the method includes quantitating the level of ligand present in the sample.

In various embodiments, the ligand comprises lactate and the ligand-binding protein comprises a lactate-binding protein.

Aspects of the present subject matter also provide a method of assaying for multiple ligands in a sample, wherein the multiple ligands comprise a first ligand and a second ligand. Such a method may include contacting the sample with (i) a first biosensor a first ligand provided herein and (ii) a second biosensor for the second ligand, under conditions such that the ligand-binding protein of the first biosensor binds to the first ligand, if the first ligand is present in the sample, and detecting (i) a signal, e.g. magnitude of the signal, produced by a reporter group of the first biosensor, or (ii) whether a signal is produced by a reporter group of the first biosensor. In some embodiments, the second biosensor is also a biosensor provided herein, and the second biosensor is contacted with the second ligand under conditions such that the ligand-binding protein of the second biosensor binds to the second ligand it is present in the sample. The method may further comprise detecting (i) a signal, e.g. magnitude of the signal, produced by a reporter group of the second biosensor, or (ii) whether a signal is produced by a reporter group of the second biosensor.

In some embodiments, the signal produced by the reporter group of the first biosensor is different than the signal produced by the reporter group of the second biosensor. In a non-limiting example, the reporter group of the first biosensor and the reporter group of the second biosensor are each fluorescent, and the peak emission wavelength of the reporter group of the first biosensor is at least about 10, 25, 50, 75, or 100 nm greater or lower than the peak emission wavelength of the reporter group of the second biosensor.

Non-limiting examples of biosensors that may be used as the second biosensor include biosensors with ligand-binding proteins comprising a GGBP (e.g., an *E. coli* GGBP) or a derivative or mutant thereof; (ii) an *E. coli* arabinose binding protein (e.g., an *E coli* arabinose binding protein) or a derivative or mutant thereof, (iii) a dipeptide binding protein (e.g., an *E. coli* dipeptide binding protein) or a derivative or mutant thereof; (iv) a histidine binding protein (e.g., an *E. coli*, histidine binding protein) or a derivative or mutant thereof; (v) a ribose binding protein (e.g., an *E. coli* ribose binding protein) or a derivative or mutant thereof; (vi) a sulfate binding protein (e.g., an *E. coli* sulfate binding protein) or a derivative or mutant thereof; (vii) a maltose binding protein (e.g., an *E. coli* maltose binding protein) or a derivative or mutant thereof, (viii) a glutamine binding protein (e.g., an *E. coli* glutamine binding protein) or a derivative or mutant thereof; (ix) a glutamate/aspartate binding protein (e.g., an *E. coli* glutamate/aspartate binding protein) or a derivative or mutant thereof; (x) a phosphate binding protein (e.g., an *E. coli* phosphate binding protein) or a derivative or mutant thereof; or (xi) an iron binding protein [e.g., a *Haemophilus* influenza (*H. influenzae*) iron binding protein] or a derivative or mutant thereof. For example, the second biosensor comprises an *E. coli* GGBP having a Y10C, Y10A, D14A, D14Q, D14N, D14S, D14T, D14E, D14H, D14L, D14Y, D14F, D14C, N15C, F16L, F16A, F16Y, F16C, N91A, K92C, E93C, S112A, S115A, E149C, E149K, E149Q, E149S, H152A, H152F, H152Q, H152N, H152C, D154A, D154C, D154N, A155S, A155H, A155L, A155F, A155Y, A155N, A155K, A155M, A155W, A155Q, A155C, R158A, R158K, R158C, M182C, M182W, W183C, W183A, N211F, N211W, N211K, N211Q, N211S, N211H, N211M, N211C, D212C, D236A, D236N, L238C, L255C, N256A, N256D, D257C, V293C, P294C, or V296C mutation (e.g., comprising 1, 2, 3, 4, 5 or more of these mutations), wherein each amino acid position is numbered as in (SEQ ID NO: 114); (ii) an *E. coli* arabinose binding protein having a D257C, F23C, K301C, L253C, or L298C mutation (e.g., comprising 1, 2, 3, 4, or 5 of these mutations) (see. e.g., U.S. Patent Application Publication No. 2004/0118681, the entire contents of which are incorporated herein by reference) (see, e.g., U.S. Patent Application Publication No. 2004/0118681, the entire contents of which are incorporated herein by reference); (iii) an *E. coli* dipeptide binding protein having a D450C, K394C, R141C, S111C, T44C, or W315C mutation (e.g., comprising 1, 2, 3, 4, 5 or 6 of these mutations) (see, e.g., U.S. Patent Application Publication No. 2004/0118681, the entire contents of which are incorporated herein by reference); (iv) an *E. coli*, histidine binding protein having a E167C, K229C, V163C, Y230C, F231C, Y88C mutation (e.g., comprising 1, 2, 3, 4, 5 or 6 of these mutations) (see, e.g., U.S. Patent Application Publication No. 2004/0118681, the entire contents of which are incorporated herein by reference); (v) an *E. coli* ribose binding protein having a T135C, D165C, E192C, A234C, L236C, or L265C mutation (e.g., comprising 1, 2, 3, 4, 5 or 6 of these mutations) (see. e.g., U.S. Patent Application Publication No. 2004/0118681, the entire contents of which are incorporated herein by reference); (vi) an *E. coli* sulfate binding protein having a L65C, N70C, Q294C, R134C, W290C, or Y67C mutation (e.g., comprising 1, 2, 3, 4, 5 or 6 of these mutations) (see. e.g., U.S. Patent Application Publication No. 2004/0118681 the entire content of which is incorporated herein by reference); (vii) an *E. coli* maltose binding protein having a D95C, F92C, E163C, G174C, I329C, or S233C mutation (e.g., comprising 1, 2, 3, 4, 5 or 6 of these mutations) (see, e.g., U.S. Patent Application Publication No. 2004/0118681 the entire content of which is incorporated herein by reference); (viii) an *E. coli* glutamine binding protein having a N160C, F221C, K219C, L162C, W220C, Y163C, or Y86C mutation (e.g., comprising 1, 2, 3, 4, 5 or more of these mutations) (see, e.g., U.S. Patent Application Publication No. 2004/0118681 the entire content of which is incorporated herein by reference); (ix) an *E. coli* glutamate/aspartate binding protein having a A207C, A210C, E119C, F126C, F131C, F270C, G211C, K268C, Q123C, or T129C mutation (e.g., comprising 1, 2, 3, 4, 5 or more of these mutations) (see. e.g., U.S. Patent Application Publication No. 2004/0118681 the entire content of which is incorporated herein by reference); (x) an *E. coli* phosphate binding protein having a A225C, N223C, N226C, S164C, or S39C mutation (e.g., comprising 1, 2, 3, 4, or 5 of these mutations) (see. e.g., U.S. Patent Application Publication No. 2004/0118681 the entire content of which is incorporated herein by reference); or (xi) a *Haemophilus* influenza (*H. influenzae*) iron binding protein having a E203C, K202C, K85C, or V287C mutation (e.g., comprising 1, 2, 3, or 4 of these mutations) (see. e.g., U.S. Patent Application Publication No. 2004/0118681 the entire content of which is incorporated herein by reference). In various embodiments, the sample is suspected of comprising lactate.

References and PDB[a] files for bPBP structures, genes, and ligand binding

| | crystal structure | | | |
|---|---|---|---|---|
| bPBP | open form | closed form | DNA sequence | ligand affinity |
| arabinose BP | | Quiocho and Vyas, 1984 1ABE | Scripture et al., 1987 | Clark et al., 1982; Miller et al., 1983 |
| dipeptide BP | Nickitenko et al., 1995 1DPE | Dunten & Mowbray, 1995 1DPP | Abouhamad et al., 1991 | Guyer et al., 1986; Smith et al., 1999 |
| Glu/Asp BP | | | | Barash Halpern, 1975; Willis Furlong, 1975 |
| Fe(III) BP | Bruns et al., 2001 1D9V | Bruns et al., 1997 1MRP | Sanders et al., 1994 | Adhikari et al., 1995 |
| glucose BP | | Vyas et al., 1988; Vyas et al., 1994 1GLG | Scholle et al., 1987 | Anraku, 1968 |
| histidine BP | | Yao et al., 1994 1HSL | Joshi & Ames 1996 | Miller et al., 1983 |
| maltose BP | Sharff et al., 1992 1OMP | Spurlino et al., 1991; Quiocho et al., 1997 1ANF | Duplay et al., 1984 | Schwartz et al., 1976 |
| phosphate BP | Ledvina et al., 1996 1OIB | Luecke & Quiocho, 1990 1IXH | Magota et al., 1984 | Medveczky & Rosenberg, 1969 |
| glutamine BP | Hsiao et al., 1996 1GGG | Sun et al., 1998 1WDN | Nohno et al., 1986 | Weiner et al., 1971 |
| ribose BP | Bjorkman & Mowbray, 1998 1URP | Mowbray & Cole, 1992 2DRI | Groarke et al., 1983 | Willis & Furlong, 1974 |
| sulfate BP | | Pflugrath & Quiocho, 1985; He & Quiocho, 1993 1SBP | Hellinga & Evans, 1985 | Jacobson & Quiocho, 1988 |

[a]Protein Data Bank (Berman et al., 2000)

Abouhamad et al., Molec. Microbiol. 5: 1035-1047 (1991)
Adhikari et al., J. Biol. Chem. 270: 25142-25149 (1995)
Anraku, J. Biol. Chem. 243: 3116-3122 (1968)
Barash & Halpern, Biochim. Biophys, Acta 386: 168-180 (1975)
Bjorkman & Mowbray, J. Mol. Biol. 279: 651-664 (1998)
Bruns el al., Biochemistry 40: 15631-15637 (2001)
Bruns et al., Nat. Struct. Biol. 4: 919-924 (1997)
Clark et al., Biochemistry 21: 2227-2233 (1982)
Dunten & Mowbray, Protein Sci. 4: 2327-2334 (1995)
Duplay et al., J. Biol. Chem. 259: 10606-10613 (1984)
Groarke et al., J. Biol. Chem. 258: 12952-12956 (1983)
Guyer et al., J. Bacteriol. 168: 775-779 (1986)
He & Quiocho, Protein Sci. 2: 1643-1647 (1993)
Hellinga & Evans, Eur. J. Biochem. 149: 363-373 (1985)
Hsiao et al., J. Mol. Biol. 262: 225-242 (1996)
Jacobson & Quiocho, J. Mol. Biol. 204: 783-787 (1988)
Joshi & Ames, GenBank Accession Number U47027 (1996)
Ledvina et al., Proc. Natl. Acad. Sci. USA 93: 6786-6791 (1996)
Luecke & Quiocho, Nature 347: 402-406 (1990)
Magota et al., J. Bacteriol. 157: 909-917 (1984)
Medveczky & Rosenberg, Biochim. Biophys. Acta 192: 369-371 (1969)
Miller et al., J. Biol. Chem. 258: 13665-13672 (1983)
Mowbray & Cole, J. Mol. Biol. 225: 155-175 (1992)
Nickitenko et al., Biochemistry 34: 16585-16595 (1995)
Nohno et al., Molec. Gen. Genet. 205: 260-269 (1986)
Pflugrath & Quiocho, Nature 314: 257-260 (1985)
Quiocho et al., Structure 5: 997-1015 (1997)
Quiocho & Vyas, Nature 310: 381-386 (1984)
Sanders et al., Infect. Immun. 62: 4515-4525 (1994)
Scholle et al., Molec. Gen. Genet. 208: 247-253 (1987)
Scripture et al., J. Mol. Biol. 197: 37-46 (1987)
Schwartz et al., Eur, J. Biochem. 71: 167-170 (1976)
Sharff et al., Biochemistry 31: 10657-10663 (1992)
Smith et al., Microbiology 145: 2891-2901 (1999)
Spurlino et al., J. Biol. Chem. 266: 5202-5219 (1991)
Sun et al., J. Mol. Biol. 278: 219-229 (1998)
Vyas et al., Biochemistry 33: 4762-4768 (1994)
Vyas et al., Science 242: 1290-1295 (1988)
Weiner et al., Arch. Biochem. Biophys. 142: 715-717 (1971)
Willis & Furlong, J. Bid. Chem. 249: 6926-6929 (1974)
Willis & Furlong, J. Biol. Chem. 250: 2574-2580 (1975)
Yao et al., Biochemistry 33: 4769-4779 (1994)

Various types of samples may be used in methods provided herein. In non-limiting examples, a sample may comprise a reaction product, a buffer, and/or a solvent. In some embodiments, the solvent is an aqueous solvent. In some embodiments, the solvent comprises a non-polar solvent, a polar aprotic solvent, and/or a polar protic solvent. For example, a sample may comprise water, liquid ammonia, liquid sulfur dioxide, sulfuryl chloride, sulfuryl chloride fluoride, phosphoryl chloride, dinitrogen tetroxide, antimony trichloride, bromine pentafluoride, hydrogen fluoride, dimethyl sulfoxide, hexane, benzene, toluene, 1,4-dioxane, chloroform, diethyl ether, dichloromethane, N-methylpyrrolidone, tetrahydrofuran, ethyl acetate, acetone, dimethylformamide, acetonitrile, tormic acid, n-butanol, isopropanol, nitromethane, ethanol, methanol, and/or acetic acid.

In embodiments, a sample comprises a Newtonian liquid, a shear thickening liquid, a shear thinning liquid, a thixotropic liquid, a rheopectic liquid, or a Bingham plastic. In some implementations, a sample has a dynamic viscosity of at least about 0.5, 0.6, 0.7, 0.8, 0.9, 1, 1.1, 1.2, 1.3, 1.4, 1.5, or 2 pascal-seconds (Pa·s) or less than about 2, 1.5, 1.4, 1.3, 1.2, 1.1, 1, 0.9, 0.8, 0.7, 0.6, 0.5 Pa-s; and/or a kinematic viscosity of at least about 0.5, 0.6, 0.7, 0.8, 0.9, 1, 1.1, 1.2, 1.3, 1.4, 1.5, or 2 centistokes (cSt) or less than about 2, 1.5, 1.4, 1.3, 1.2, 1.1, 1, 0.9, 0.8, 0.7, 0.6, 0.5 cSt.

In various embodiments, the sample comprises a biological sample. The sample may comprise, e.g., a clinical sample (i.e., a sample collected in a clinical or veterinary setting, e.g., by or at the request or supervision or direction of a doctor, nurse, aid worker, or medic) and/or a physiological sample (a sample collected from an organism, e.g., a mammal such as a human). In certain embodiments, the biological sample comprises or has been provided or obtained from a skin surface or a mucosal surface. In some embodiments, the biological sample comprises a biological fluid. Non-limiting examples of biological fluids include sweat, tear fluid, blood, serum, plasma, interstitial fluid, amniotic fluid, sputum, gastric lavage, skin oil, milk, fecal matter, emesis, bile, saliva, urine, mucous, semen, lymph, spinal fluid, synovial fluid, a cell lysate, venom, hemolymph, and fluid obtained from plants such as the fluid transported in xylem cells or phloem sieve tube elements of a plant (e.g. sap).

The present subject matter also provides biosensors, methods, compositions, and devices useful for measuring the level of a ligand within a liquid solution or suspension or composition comprising cultured cells or tissue or a supernatant of such a solution or suspension, e.g., a sample of conditioned media or a sample of growth media in which a population of cells was cultured. In some embodiments, the sample is within a culture (e.g., inserted into a bioreactor) or provided from a media, culture, or reaction. e.g., in a bioreactor. For example, the sample may be within or provided from a fermenter such as a culture or culture supernatant from a fermentation reaction (e.g., an ongoing fermentation, the culture of cells in research settings, the production of a compound, etc.). Thus, the level of a ligand can be assayed at a timepoint of interest or at a series of timepoints over the duration of cell culture, e.g. continuously, in or from a reaction or culture. Bioreactors include devices or systems that support a biologically active environment. For example, a bioreactor may comprise a vessel in which a chemical process is carried out which involves organisms or biochemically active substances derived from such organisms. Such a process can either be aerobic or anaerobic. Organisms growing in bioreactors may be, e.g., submerged or suspended in liquid medium or may be attached to the surface of a solid medium. Submerged cultures may be suspended or immobilized. Suspension bioreactors can use a wider variety of organisms, since special attachment surfaces are not needed, and can operate at much larger scale than immobilized cultures. However, in a continuously operated process the organisms will be removed from the reactor with the effluent. Immobilization is a general term describing a wide variety of cell or particle attachment or entrapment. It can be applied to basically all types of biocatalysis including enzymes, cellular organelles, and cells (e.g., animal cells, plant cells, fungal cells, and bacterial cells). Immobilization is useful for continuously operated processes, since the organisms will not be removed with the reactor effluent, but is limited in scale because the cells are only present on the surfaces of the vessel. A bioreactor may also refer to a device or system meant to grow cells or tissues in the context of cell culture. The interrogation and/or monitoring of lactate levels in such samples permits the evaluation of the status of growth of the cells or production of secreted products by the cells to inform harvest or feeding or other modification of the culture.

Aspects of the present subject matter relate to the use of methods and biosensors provided herein to detect contamination.

In some embodiments, the sample comprises an environmental sample. Depending on context, there are instances in which a biological sample may also be, or may be within, an environmental sample. In certain embodiments, an environmental sample comprises a solute obtained from a biological composition, such as bone, nail, hair, shell, or cartilage. In various embodiments, an environmental sample comprises a solute obtained from an environmental substance and/or an environmental surface. For example, the solute may be dissolved/obtained from the environmental substance and/or an environmental surface using an aqueous or nonaqueous solution. In some embodiments, an aqueous may optionally comprise a nonaqueous solvent (e.g., mixed with an aqueous solvent). Non-limiting examples of environmental substances include rock soil, clay, sand, meteorites, asteroids, dust, plastic, metal, mineral, fossils, sediment, and wood. Non-limiting examples of environmental surfaces include the surface of a vehicle such as a civilian vehicle (e.g., a satellite, a bike, a rocket, an automobile, a truck, a motorcycle, a yacht, a bus, or a plane) or a military vehicle (e.g., a tank, an armored personnel carrier, a transport truck, a jeep, a mobile artillery unit, a mobile antiaircraft unit, a minesweeper, a Mine-Resistant Ambush Protected (MRAP) vehicle, a lightweight tactical all-terrain vehicle, a high mobility multipurpose wheeled vehicle, a mobile multiple rocket launch system, an amphibious landing vehicle, a ship, a hovercraft, a submarine, a transport plane, a fighter jet, a helicopter, a rocket, or an Unmanned Arial Vehicle), a drone, a robot, a building, furniture, or an organism other than a human. In some embodiments, the sample comprises an environmental fluid. Non-limiting examples of environmental fluids include marine water, well water, drinking well water, water at the bottom of well dug for petroleum extraction or exploration, melted ice water, pond water, aquarium water, pool water, lake water, mud, stream water, river water, brook water, waste water, treated waste water, reservoir water, rain water, and ground water. In some embodiments, waste water comprises sewage water, septic tank water, agricultural runoff, water from an area in which chemical or oil spill has or is suspected of having occurred (e.g., an oil spill into a marine environment), water from an area where a radiation leak has or is suspected of having occurred (e.g., coolant from a nuclear reactor), water within the plumbing of a building, water within or exiting a research facility, and/or water within or exiting a manufacturing facility such as a factory.

As used herein, "suspected" with respect to an event means that there has been at least one test (e.g., a test other than a method or assay provided herein), occurrence (e.g., that is likely to or that may cause the event such as an emergency, leak, accident, flood, earthquake, storm, fire, malfunction, sunk vessel, or crash), or report (e.g., by a witness, informant, or observer) that is consistent with the event having occurred.

In certain embodiments, the sample comprises a food or beverage additive and/or a food or beverage composition. In some embodiments, the food or beverage composition comprises a fermented composition. In various embodiments, the sample comprises a fluid obtained from a food composition. Alternatively or in addition, the sample may comprise a solute dissolved from a food composition. In some examples, a solute is or has been dissolved from a food composition with an aqueous or nonaqueous solution. In various implementations, an aqueous solution may optionally comprise a nonaqueous solvent. In certain embodiments, a sample comprises a food composition in semisolid or liquid form. Non-limiting examples of such compositions include yogurt, soup, ice cream, a broth, a puree, a shake, a smoothie, a batter, a condiment, a sauce, and any combination thereof. In some implementations, a sample is a food engineering process (e.g., obtained from a food design, storage, transport, or production process or from equipment intended to process, transport, or store food). A food composition may comprise, e.g., a plant or a composition isolated from a plant, and/or an animal or a composition isolated from an animal. In various embodiments, a sample comprises a beverage composition. Non-limiting examples of beverage compositions include soft drinks, fountain beverages, water, coffee, tea, milk, dairy-based beverages, soy-based beverages (e.g., soy milk), almond-based beverages (e.g., almond milk), vegetable juice, fruit juice, fruit juice-flavored drinks, energy drinks, sports and fitness drinks, alcoholic products, and beverages comprising any combination thereof. Non-limiting examples of beverage compositions comprising water include purified water (e.g., filtered water, distilled water, or water purified by reverse osmosis), flavored water, mineral water, spring water, sparkling water, tonic water, and any combination thereof. In various embodiments, the sample comprises alcohol. Non-limiting examples of such samples include samples comprising or obtained/provided from beer, malt beverages, liqueur, wine, spirits, and any combination thereof. In some embodiments, a food or beverage composition is a fermented food or beverage composition. Non-limiting examples of fermented food and beverage compositions (as well as those involving fermentation during the preparation thereof) include cheonggukjang, doenjang, miso, natto, soy sauce, stinky tofu, tempeh, oncom, soybean paste, Beijing mung bean milk, kinama, iru, amazake, beer, bread, choujiu, gamju, injera, kvass, makgeolli, murri, ogi, rejuvelac, sake, sikhye, sourdough, sowans, rice wine, malt whisky, grain whisky, idli, dosa, vodka, boza, kimchi, mixed pickle, sauerkraut, Indian pickle, gundruk, tursu, wine, vinegar, cider, perry, brandy, atchara, nata de coco, burong mangga, asinan, pickling, viinat, chocolate, raki, mead, metheglin, some types of cheese, kefir, kumis (mare milk), shubat (camel milk), cultured milk products (such as quark, filmjOlk, creme fraiche, smetana, skyr, and yogurt), bagoong, faseekh, fish sauce, Garum, Hakarl, jeotgal, rakfisk, shrimp paste, surstrimming, shidal, chorizo, salami, sucuk, pepperoni, nem chua, som moo, saucisson, pu-erh tea, and kombucha.

Aspects provide methods, compounds, and compositions for detecting lactate or the level thereof to assess or monitor a fermentative process (e.g., the level and/or progression of fermentation) during the preparation or manufacture of a food (e.g., a fermented food such as kefir, sauerkraut, pickles, miso, tempeh, natto, kimchi, or yogurt) or beverage product (e.g., a fermented beverage such as kombucha wine, beer, or a precursor for a spirit). Also provided are methods, compositions, and compounds for evaluating stability and freshness of food and beverage compositions such as dairy products, vegetables, fruits, juices, sausages, and wine. The amount of lactic acid in food products has a great impact on the stability, flavor and storage lifetime.

Lactic acid is naturally present in many food products. It is formed by natural fermentation in products such as cheese, yogurt, soy sauce, sourdough, meat products and pickled vegetables. Lactic acid is also used in a wide range of food applications such as bakery products, beverages, meat products, confectionery, dairy products, salads, dressings, ready meals, etc. Lactic acid in food products usually serves as either as a pH regulator or as a preservative. It is also used as a flavoring agent.

Some embodiments relate to determining the presence or concentration of lactic acid in a food composition comprising meat poultry of fish. Lactic acid can be used in meat, poultry and fish in the form of sodium or potassium lactate to extend shelf life, control pathogenic bacteria (improve food safety), enhance and protect meat flavor, improve water binding capacity and reduce sodium. Lactic acid is used as a food preservative, curing agent, and flavoring agent. It is an ingredient in processed foods and is used as a decontaminant during meat processing. Also provided are methods, compounds, and compositions for determining the presence or concentration of lactic acid in a beverage composition. Because of its mild taste, lactic acid is also used as an acidity regulator in beverages such as soft drinks and fruit juices. Various embodiments relate to assaying the level of lactic acid in a a food composition that comprises a pickled vegetable, a salad, and/or a salad dressing. Lactic acid is effective in preventing the spoilage of olives, gherkins, pearl onions and other vegetables preserved in brine. Lactic acid may be also used as a preservative in salads and dressings, resulting in products with a milder flavor while maintaining microbial stability and safety. Also provided are methods and compositions for detecting lactic acid and the level thereof in concectionary compositions. Formulating hard-boiled candy, fruit gums and other confectionery products with lactic acid results in a mild acid taste, improved quality, reduced stickiness and longer shelf life. In some embodiments, a food composition comprises a dairy product. The natural presence of lactic acid in dairy products, combined with the dairy flavor and good antimicrobial action of lactic acid, makes lactic acid an excellent acidification agent for many dairy products. In certain embodiments, the presence or level of lactic acid is detected in a baked composition. Lactic acid is also a natural sourdough acid, which gives the bread its characteristic flavor, and therefore it can be used for direct acidification in the production of sourdough. Lactic acid is used to enhance a broad range of savory flavors. Its natural occurrence in meat and dairy products makes lactic acid an attractive way to enhance savory flavors. Various embodiments relate to detecting lactic acid in animal feed. Lactic acid is a commonly used additive in animal nutrition. It has health promoting properties, thus enhancing the performance of farm animals. Lactic acid can be used as an additive in food and/or drinking water.

The presence and/or level of lactic acid may also be tested in various non-food compositions (e.g., in a final product, and/or during production or a stage of production), such as pharmaceuticals, biomaterials, detergents, industrial compositions, animal feed, biodegradable plastics, and cosmetics. Non-limiting examples of uses for lactic acid in pharmaceutical applications are: pH-regulation, metal sequestration, chiral intermediate and as a natural body constituent in pharmaceutical products. Lactic acid is also a valuable component in biomaterials such as resorbable screws, sutures and medical devices. With respect to detergents, lactic acid well known for its descaling properties, soap-scum remover and is widely applied in household cleaning products. Also, lactic acid is used as a natural anti-bacterial agent in disinfecting products. Lactic acid is also used in a wide variety of industrial processes where acidity is required and where its properties offer specific benefits. Examples are the manufacture of leather and textile products and computer disks, as well as car coating. With respect to biodegradable plastics, lactic Acid is the principal building block for Poly Lactic Acid (PLA). PLA is a biobased and bio-degradable polymer that can be used for producing renewable and compostable plastics. Lactic acid may be added to cosmetics, to adjust acidity and for its disinfectant and keratolytic properties. Methods, compositions, compounds and devices are provided for detecting, monitoring, and/or assaying the level of lactic acid in any composition and/or during the production thereof.

In some embodiments, a sample comprises a nutritional or supplement composition. In certain implementations, the nutritional or supplement composition comprises an omega-3 fatty acid, a vitamin, a mineral, a protein powder, or a meal supplement.

In certain embodiments, a biosensor is implanted in a subject's body. For example, a biosensor may be implanted in a subject's blood vessel, vein, eye, natural or artificial pancreas, alimentary canal, stomach, intestine, esophagus, or skin (e.g., within the skin or under the skin). In various embodiments, the biosensor is configured within or on the surface of a contact lens. In some embodiments, the biosensor is configured to be implanted in or under the skin. In non-limiting examples, the biosensor is implanted in a subject with an optode and/or a microbead. In certain embodiments, the biosensor generates a signal transdermally. Also provided are dermal skin patches, bands, straps, and other devices for monitoring the level of lactate in perspiration, e.g., during physical exertion (such as during sports training, military or occupational training, combat, or employment).

Aspects of the present subject matter provide a method for assaying the level of lactate in a subject. The method may comprise contacting a biological sample from the subject with a biosensor for lactate under conditions such that the biosensor binds to lactate present in the biological sample. The biosensor comprises a reporter group attached to a lactate-binding protein, and binding of lactate to a lactate-binding domain of the lactate-binding protein causes a change in signaling by the reporter group. In various embodiments, the subject has, is suspected of having, has previously had, or is undergoing routine (e.g., during a physical) testing for a disease or an injury associated with abnormal lactate levels (e.g., in a bodily fluid such as blood). Non-limiting examples of diseases and injuries associated with abnormal lactate levels include lactic acidosis, hyperlactatemia, sepsis, septic shock, carbon monoxide poisoning, severe asthma, a lung disease, respiratory insufficiency, Chronic Obstructive Pulmonary Disease (COPD), regional hypoperfusion, ischemia, severe anemia, cardiac arrest, heart failure, a tissue injury, thrombosis, a metabolic disorder, renal dysfunction, hepatic dysfunction, pyruvate dehydrogenase dysfunction, a thiamine deficiency, catecholamine excess, alcoholic ketoacidosis, diabetic ketoacidosis, uncoupling of oxidative phosphorylation, exposure to cyanide, exposure to a salicylate, exposure to methanol, exposure to ethylene glycol, administration of an anti-retroviral drug, exposure to valproic acid, exposure to a biguanide, a seizure, and a malignancy. In some embodiments, the subject has a liver disease, a kidney disease (such as chronic kidney disease or an acute kidney injury), or diabetes. In some embodiments, the biological sample comprises blood, plasma, serum, sweat, tear fluid, or urine. In certain embodiments, the biological sample is present in or on the surface of the subject. In various implementations, the biosensor is applied onto or inserted into the subject. For example, the biosensor may be tattooed into the subject or is in or on a device that is implanted into the subject. In some embodiments, the biosensor may be present in or on a contact lens that is worn by the subject. Methods for determining the level of lactate, e.g. in a subject who has, is suspected of having, has previously had, or is undergoing routine (e.g., during a physical) testing for a disease or an injury associated with abnormal lactate levels, may be performed without other testing related to lactate levels, or performed as part of a battery of clinical testing.

As used herein, "suspected" with respect to a subject's condition (e.g., disease or injury) means that the subject has at least one symptom or test (e.g., a test other than an assay or method provided herein) that is consistent with the condition.

Also provided are methods for detecting injury to tissues, thrombosis, and the physical condition of performance (e.g., working or racing) athletes and animals.

In some embodiments, the subject is a human athlete, a soldier, a marine, a sailor, a pilot, an astronaut, a work animal (e.g., a work dog such as a sled dog, a military dog, a police dog, a rescue dog, a work horse, a police or military horse, or ox), or a performance animal (e.g., a race dog, a race camel, a race horse, a performance seal or sea lion, or a performance dolphin or porpoise).

In some embodiments, the subject has, has previously had, is suspected of having hyperlactatemia or lactic acidosis. Physiological lactate levels (e.g., in the blood) for a healthy human under resting conditions are typically between 0.5 to 2.5 mM but during vigorous physical activity the concentration can rise up to 20-30 mM. Hyperlactatemia is a persistent, mild to moderate (2.5-4 mM) increase in blood lactate concentration without metabolic acidosis, whereas lactic acidosis is characterized by persistently increased blood lactate levels (usually >5 mM) in association with metabolic acidosis. Elevated resting blood lactate concentration is not only linked to survival risk (e.g. for subjects who have a disease or injury associated with abnormal lactate levels) but can also be used as an indicator of the patient oxygen supply.

Hyperlactatemia can occur in the setting of adequate tissue perfusion, intact buffering systems, and adequate tissue oxygenation. Lactic acidosis, on the other hand, is associated with major metabolic dysregulation, tissue hypoperfusion, the effects of certain drugs or toxins, and congenital abnormalities in carbohydrate metabolism. It also occurs as a result on markedly increased transient metabolic demand (e.g., post-seizure lactic acidosis). Congenital lactic acidosis is secondary to inborn errors of metabolism, such as defects in gluconeogenesis, pyruvate dehydrogenase, the tricarboxylic acid (TCA) cycle, or the respiratory chain. These disorders generally reflect situations in which the disposal of pyruvate by biosynthetic or oxidative routes is impaired.

Lactic acidosis may not necessarily produce acidemia in a subject. The development of lactic acidosis depends on the magnitude of hyperlactatemia, the buffering capacity of the body, and the coexistence of other conditions that produce tachypnea and alkalosis (e.g., liver disease, sepsis). Thus, hyperlactatemia or lactic acidosis may be associated with acidemia, a normal pH, or alkalemia. Numerous etiologies may be responsible for the presence of lactic acidosis, most commonly circulatory failure and hypoxia. Evidence suggests increased morbidity and mortality for subjects with persistently elevated or increasing lactate levels. Identification and discontinuation of any offending agents and treatment of known pathology should occur promptly.

Lactic acidosis may be divided into 2 categories: Type A and Type B. Type A is lactic acidosis occurring in association with clinical evidence of poor tissue perfusion or oxygenation of blood (e.g., hypotension, cyanosis, cool and mottled extremities). It can be caused by the overproduction of lactate or the underutilization of lactate. In cases of overproduction, circulatory, pulmonary, and hemoglobin transfer disorders are commonly responsible. In cases of underutilization of lactate, liver disease, gluconeogenesis inhibition, thiamine deficiency, and uncoupled oxidative phosphorylation can be responsible. Type B is lactic acidosis occurring when no clinical evidence of poor tissue perfusion or oxygenation exists. However, in many cases of type B lactic acidosis, occult tissue hypoperfusion is now recognized to accompany the primary etiology. Type B is divided into 3 subtypes based on underlying etiology. Type B1 occurs in association with systemic disease, such as renal and hepatic failure, diabetes and malignancy. Type B2 is caused by several classes of drugs and toxins, including biguanides, alcohols, iron, isoniazid, zidovudine, and salicylates. Type B3 is due to inborn errors of metabolism. Within these categories, septic shock may move from type A to type B, as the initial presentation is often associated with hypoperfusion, and with aggressive fluid resuscitation little evidence of tissue hypoperfusion exists, yet lactic acidosis often persists because of altered oxidative phosphorylation and leukocyte production of lactate caused by sustained increased inflammatory stimuli. Any type of abnormal lactate level may be assessed using the compounds, compositions, and methods provided herein. Additionally, any subject who has or is at risk of a disease or injury associated with an abnormal lactate level may be assessed and/or monitored using the compounds, compositions, and methods provided herein.

In some embodiments, the level of lactate is assessed as part of routine testing and/or a panel of biomarkers assessed for a subject. In certain embodiments, the level of lactate is assessed before (e.g., 1, 2, 3, 4, 5, 6, 7, 8, 9, 10, 12 or more hours before), during, and/or after (e.g., 1, 2, 3, 4, 5, 6, 7, 8, 9, 10, 12 or more hours after) physical exertion such as exercise, an athletic competition, or labor.

The present subject matter includes a method for monitoring the level of a ligand, comprising periodically or continuously detecting the level of the ligand, wherein detecting the level of the ligand comprises (a) providing or obtaining a sample; (b) contacting the sample with a biosensor for the ligand under conditions such that the ligand-binding protein of the biosensor binds to the ligand, and (c) detecting a signal produced by the biosensor.

Aspects of the present subject matter also provide a method for monitoring the level of a ligand (e.g., lactate) in a subject, comprising periodically detecting the level of the ligand in the subject. Detecting the level of the ligand in the subject may comprise (a) providing or obtaining a biological sample from the subject; (b) contacting the biological sample with a biosensor for the ligand provided herein under conditions such that the ligand-binding protein of the biosensor binds to the ligand, if the ligand is present in the biological sample, and (c) detecting (i) a signal produced by a reporter group of the biosensor, or (ii) whether a signal is produced by a reporter group of the biosensor. The level of the ligand may be detected, e.g., at least once every 1, 2, 3, 6, or 12 hours, at least once every 1, 2, 3, or 4 days, at least once every 1, 2, or three weeks, or at least once every 1, 2, 3, 4, 6, or 12 months.

The present subject matter also provides a method for monitoring the level of a ligand in a subject. The method comprises (a) administering a biosensor provided herein or a device comprising a biosensor provided herein to the subject, wherein after administration the biosensor is in contact with a bodily fluid or surface that typically comprises the ligand, and (b) detecting (i) a signal produced by a reporter group of the biosensor continuously or repeatedly at intervals less than about 30 minutes (m), 15 m, 10 m, 5 m, 1 m, 30 seconds (s), 15 s, 10 s, 5 s, 1 s, 0.1 s, 0.001 s, 0.0001 s, or 0.00001 apart, and/or (ii) whether a signal is produced by a reporter group of the biosensor continuously or repeatedly at intervals less than about 30 m, 15 m, 10 m, 5 m, 1 m, 30 s, 15 s, 10 s, 5 s, 1 s, 0.1 s, 0.001 s, 0.0001 s, or 0.00001 apart.

Non-limiting aspects of continuously monitoring ligand levels are described in Weidemaier et al. (2011) Biosensors and Bioelectronics 26, 4117-4123 and Judge et al. (2011) Diabetes Technology & Therapeutics, 13(3):309-317, the entire contents of each of which are hereby incorporated herein by reference.

Also within various implementations is a composition comprising a purified lactate-binding fluorescently-responsive sensor protein and a solid substrate, e.g., a particle, a bead such as a magnetic bead, or a planar surface such as a chip or slide, wherein the sensor protein is immobilized onto the solid substrate. In some embodiments, the biosensor is immobilized on a patch. In some embodiments, the patch comprises a polymer or copolymer comprising hydroxyethyl (meth)acrylate, a polyolefin, polyurethane, polystyrene, an ethylene/methacrylic acid copolymer, an ethylene/methyl methacrylate copolymer, a polyester, and/or a polyurethane. In some embodiments, the patch comprises a woven fabric, a knitted fabric, or a nonwoven fabric of a synthetic fiber and/or natural fiber. In certain embodiments, the patch has an adhesive layer. An exemplary solid substrate solid substrate comprises a cyclic olefin copolymer. In some embodiments, the lactate-binding protein is thermostable.

A thermostable lactate sensor protein is one in which the activity (lactate binding) is retained after exposure to relatively high temperatures. For example, the lactate sensor protein comprises a mid-point thermal melt transition greater than 30° C., greater than 40° C., greater than 50° C., greater than 60° C., greater than 70° C., greater than 80° C., greater than 90° C., or greater than 100° C., or about 30° C. to about 100° C., about 40° C. to about 100° C., about 50° C. to about 100° C., about 60° C. to about 100° C., about 70° C. to about 100° C., about 80° C. to about 100° C., or about 90° C. to about 100° C. In some embodiments, the sensor protein contains a single cysteine residue. In some embodiments, the single cysteine residue is located in a site of the ligand-binding protein, where it responds to ligand binding. In some examples, the protein comprises the amino acid sequence of SEQ ID NO: 42 (tsLacBP7_189C) or 53 (msLacBP6_187C_L70M), and in some examples, the single cysteine is conjugated to Badan, Acrylodan, or a derivative thereof. For example, the derivative comprises a replacement of the two-ring naphthalene of Acrylodan or Badan with a three-ring anthracene, a fluorene, or a styrene. A reporter group is covalently bound to the single cysteine. In some situations, the solid substrate comprises a plurality of sensor proteins, each of which comprises a different dissociation constant ($K_d$) for lactate, e.g., for detecting and quantifying lactate levels across many ranges of concentrations.

The present subject matter also includes a composition comprising purified lactate sensor protein with less than 65% identity and greater than 27% identity (e.g., 44-48% sequence identity) to any one of SEQ ID NOS: 1-28 or 115-128, wherein the sensor protein comprises a single cysteine residue, and a solid substrate, such that the sensor protein is immobilized onto the solid substrate. As described above, a reporter group is covalently bound to the single cysteine. In some example, the solid substrate comprises a plurality of sensor proteins, each of which comprises a different dissociation constant ($K_d$) for lactate for sensing over a wide range or ranges of lactate concentrations.

In some embodiments, a method of detecting the presence of or the quantity of lactate in a test sample is carried out using the following steps: contacting the test sample with the biosensor or sensor protein/solid support construct to yield a complex of lactate and the ligand-binding protein or biosensor protein; contacting the complex with an excitation light; measuring an emission intensity of the reporter group from at least two wavelengths; computing a ratiometric signal from the two (or more) wavelengths; and comparing the signal to a known lactate binding curve of signals to identify the presence of or calculate the quantity of lactate in the test sample. The test sample may be obtained from a variety of sources. For example, the test sample may be selected from a bodily fluid, a food, a beverage, or a bioreactor culture broth. The testing method may be carried out in vivo. e.g., using an implantable device or dermal patch, or ex vivo.

In various embodiments, the subject to be tested is a mammal, e.g., a primate (such as a human, a monkey, a chimpanzee, or a gorilla), a fish, a bird, a reptile, an amphibian, or an arthropod. In some embodiments, the subject is a fish, a cow, a pig, a camel, a llama, a horse, a race horse, a work horse, a goat, a rabbit, a sheep, a hamster, a guinea pig, a cat, a wolf, a dog (e.g., a pet dog, a work dog, a police dog, or a military dog), a rat, a mouse, a seal, a whale, a manatee, a lizard, a snake, a chicken, a goose, a swan, a duck, or a penguin.

Exemplary Devices and Compositions Comprising Biosensors

Aspects of the present subject matter provide a device comprising one or more biosensors provided herein. Such devices may be, e.g., wearable, implantable, portable, or fixed.

In some embodiments, the device is a nanoparticle or a microparticle comprising the biosensor. Non-limiting examples of devices include devices comprising a test strip, patch, plate, bead, or chip comprising a biosensor provided herein. In certain embodiments, a device may comprise a desiccated biosensor.

The present subject matter also provides a contact lens or a skin patch comprising a biosensor provided herein. In some embodiments, the biosensor is throughout the contact lens or skin patch or within a particular region or zone of a contact lens or skin patch (e.g., in one or more shapes (e.g., a square, circle, or star), dots, lines, or zones, located at the periphery or a portion of the periphery of a contact lens or patch). In some embodiments, the skin patch comprises an adhesive that facilitates attachment of the patch to the surface of skin.

Devices provided herein may include a variety of structural compositions. For example, many polymers (including copolymers), and plastics may be used. Non-limiting examples of compositions useful in certain devices include glass, polystyrene, polypropylene, cyclic olefin copolymers, ethylene-norbomene copolymers, polyethylene, dextran, nylon, amylase, paper, a natural cellulose, a modified cellulose, a polyacrylamide, gabbros, gold, and magnetite (as well as combinations thereof). In some embodiments, the device comprises a hydrogel, a cryogel, or a soluble gel. For example, the biosensor may be incorporated into or onto the hydrogel, cryogel, or soluble gel. In various embodiments, the device comprises a matrix comprising nanopores, micropores, and/or macropores. In certain embodiments, the surface of a device comprises a polymer. In an embodiment, the surface comprises the surface of a particle or a bead having a diameter of about 0.001-1, 0.001-0.1, 0.01-0.1, 0.001-0.01, 0.1-1, 0.1-0.5, or 0.01-0.5 centimeters (cm). For example, the particle comprises a nanoparticle or a microparticle.

Non-limiting examples of polymers include cyclic olefin copolymers, ethylene-norbomene copolymers, polylactic acid, polyglycolic acid, agarose, alginate, poly(lactide-co-glycolide), gelatin, collagen, agarose, natural and synthetic polysaccharides, polyamino acids, poly(lysine), polyesters, polyhydroxybutyrates, polyanhydrides, polyphosphazines, polyvinyl alcohol, polyalkylene oxide, polyethylene oxide, polyallylamines, polyacrylates, modified styrene polymers, poly(4-aminomethylstyrene), pluronic polyols, polyoxamers, polyuronic acid, polyvinylpyrrolidone, hydroxyethyl (meth)acrylate, polyolefins, polyurethane, polystyrene, ethylene/methacrylic acid copolymers, ethylene/methyl methacrylate copolymers, polyester, and polyurethane. In some embodiments, the patch comprises a woven fabric, a knitted fabric, or a nonwoven fabric of a synthetic fiber and/or natural fiber.

Non-limiting examples of temporary tattoo compositions for application to a subject's skin are discussed in U.S. Patent Application Publication No. 20090325221, published Dec. 31, 2009, and U.S. Pat. No. 6,428,797, the entire conents of each of which are incorporated herein by reference. Biosensor disclosed herein may be incorporated into any temporary tattoo or other composition for application to the skin. For example, a temporary tattoo decal for application to a subject's skin and configured to detect the presence of a ligand may comprise, e.g., a base paper or plastic; a water-soluble slip layer applied to the base paper or plastic; a temporary tattoo applied to the water-soluble release layer on the base paper, wherein the temporary tattoo comprises a biosensor disclosed herein; an adhesive layer overlying the temporary tattoo; and a protective sheet overlying the adhesive layer.

In some embodiments, the device comprises a plastic polymer comprising cyclic olefin copolymer (COC), such as e.g. TOPAS® COC. Several types of cyclic olefin copolymers are available based on different types of cyclic monomers and polymerization methods. Cyclic olefin copolymers are produced by chain copolymerization of cyclic monomers such as 8,9,10-trinorbom-2-ene (norbornene) or 1,2,3,4,4a, 5,8,8a-octahydro-1,4:5,8-dimethanonaphthalene (tetracyclododecene) with ethene (such as TOPAS Advanced Polymer's TOPAS. Mitsui Chemical's APEL), or by ring-opening metathesis polymerization of various cyclic monomers followed by hydrogenation (Japan Synthetic Rubber's ARTON, Zeon Chemical's Zeonex and Zeonor). See, e.g., International Union of Pure and Applied Chemistry (2005) *Purr. Appl. Chem.* 77(5):801-814. These later materials using a single type of monomer may be referred to as cyclic olefin polymers (COPs). A CAS Registry number for COC is 26007-43-2.

In some embodiments, the biosensor is covalently or noncovalently (e.g., electrostatically) attached to a surface of a device. In certain embodiments, the biosensor is attached to a surface of a device or is not attached to a surface of the device (e.g., the biosensor is physically present within the device as a component of a solution or powder but not chemically immobilized onto or into a device surface). For example, the biosensor may move within the confines of a device chamber.

A biosensor may be attached to a device via a variety or means, e.g., via attachment motif. In some embodiments, the attachment motif is attached to the N-terminus or the C-terminus of the biosensor. In certain embodiments, the biosensor is linked to an attachment motif via a covalent bond. In various embodiments, the biosensor is linked to the attachment motif via a linker. A non-limiting example of a linker is a polyglycine comprising 2, 3, 4, 5, or more glycines and optionally further comprising a serine. In some embodiments, the attachment motif comprises a polypeptide. Non-limiting examples of polypeptides useful in attachment moieties include hexahistidine peptides, hexalysine peptides, zinc-finger domains (ZF-QNKs), and disulfide-containing truncated zinc fingers (βZifs). An example of a hexalysine peptide comprises amino acids in the sequence of SEQ ID NO: 112, an example of a ZF-QNK comprises amino acids in the sequence of SEQ ID NO: 110, and an example of a βZif comprises amino acids in the sequence of SEQ ID NO: 109. In some embodiments, the attachment motif comprises a polypeptide that binds to plastic or cellulose.

The hexahistidine, hexalysine, βZif and QNK-ZF fusions enable FRSs to be immobilized onto chemically functionalized surfaces. Non-limiting aspects of chemically functionalized surfaces are discussed in Biju, V. (2014) *Chem Soc Rev,* 43, 744-64 and McDonagh (2008) *Chem Rev,* 108, 400-422, the entire contents of which are incorporated herein by reference. Directed evolution methods have been used to develop peptides that bind directly to non-functionalized surfaces (Care, Bergquist and Sunna 2015 *Trends Biotechnol,* 33, 259-68; Baneyx 2007 *Curr. Opin. Biotechnol.,* 18, 312-317; Gunay and Klok 2015 *Bioconjug Chem,* 26, 2002-15), including various plastics (Adey et al. 1995 *Gene,* 156, 27-31; Serizawa et al. 2005 *J Am Chem Soc,* 127, 13780-1; Serizawa, Sawada and Kitayama 2007a *Angew Chem Int Ed Engl.* 46, 723-6; Serizawa, Sawada and Matsuno 2007b *Langmuir,* 23, 11127-33; Serizawa, Techawanitchai and Matsuno 2007c *Chembiochem,* 8, 989-93; Matsuno et al. 2008 *Langmuir,* 24, 6399-403; Chen, Serizawa and Komiyama 2011 *J Pept Sci.* 17, 163-8; Kumada 2010 *J. Biosci. and BioEng.,* 109, 583-587; Date et al. 2011 *ACS Appl Mater Interfaces.* 3, 351-9; Kumada 2012, Vodnik, Strukelj and Lunder 2012 *J. Biotech.,* 160, 222-228; Kumada 2014 *Biochem. et Biophys. Acta.* 1844, 1960-1969; Ejima. Matsuno and Serizawa 2010 *Langmuir,* 26, 17278-85), inorganic materials (Hnilova 2012 *Soft Matter,* 8, 4327-4334; Care et al. 2015 *Trends Biotechnol.* 33, 259-68), nanoparticles (Avvakumova et al. 2014 *Trends Biotechnol.* 32, 11-20), and cellulosic paper (Guo et al. 2013 *Biomacromolecules,* 14, 1795-805). Such peptides, or natural material-binding domains (Oliveira et al. 2015 *Biotechnol Adv,* 33, 358-69), also can be fused to FRSs to direct site-specific, oriented immobilization on their target materials while preserving FRS function. For instance, plastic-binding peptides have been developed that direct immobilization on polystyrene (Adey et al. 1995 *Gene,* 156, 27-31; Serizawa et al. 2007c *Chembiochem,* 8, 989-93; Kumada 2010 *Biochem. et Biophys. Acta,* 1844, 1960-1969; Vodnik et al. 2012 *Anal Biochem,* 424, 83-6), polymethyl acrylate (Serizawa et al. 2005 *J Am Chem Soc.* 127, 13780-1; Serizawa et al. 2007a *Angew Chem Int Ed Engl.* 46, 723-6; Serizawa et al. 2007b *Langmuir,* 23, 11127-33; Kumada 2014 *Biochem. et Biophys. Acta.* 1844, 1960-1969), polycarbonate (Kumada 2012 *J. Biotech.,* 160, 222-228), polylactide (Matsuno et al. 2008 *Langmuir,* 24, 6399-403), and polyphenylene vinylene (Ejima et al. 2010 *Langmuir,* 26, 17278-85). Cellulose-binding peptides (Guo et al. 2013 *Biomacromolecules,* 14, 1795-805) and natural domains (Oliveira et al. 2015 *Biotechnol Adv.* 33, 358-69; Shoseyov, Shani and Levy 2006 *Microbiol Mol Biol Rev.* 70, 283-95) can be used to immobilize fusion proteins on paper. Inorganic material include noble metals (Hnilova 2012 *Soft Matter,* 8, 4327-4334), semi-conductors (Care et al. 2015 *Trends Biotechnol,* 33, 259-68), and fluorescent quantum dots (Medintz et al. 2005 *Nat Mater,* 4, 435-46; Lee et al. 2002 *Science,* 296, 892-5). The entire contents of each of the references above (and all other references herein) is incorporated herein by reference.

In some embodiments, the attachment motif is attached to a device surface and/or within a matrix of the device. In some embodiments, a biosensor is attached to an attachment motif via a covalent bond and the attachment motif is attached to a device via a covalent bond. Non-limiting examples of covalent bonds include disulfide bonds, ester bonds, thioester bonds, amide bonds, and bonds that have been formed by click reactions. Non-limiting examples of a click reaction include a reaction between an azide and an alkyne; an azide and an alkyne in the presence of Cu(I); an azide and a strained cyclooctyne; an azide and a dibenzylcyclooctyne, a difluorooctyne, or a biarylazacyclooctynone; a diaryl-strained-cyclooctyne and a 1,3-nitrone; an azide, a tetrazine, or a tetrazole and a strained alkene; an azide, a tetrazine, or a tretrazole and a oxanorbomadiene, a cyclooctene, or a trans-cycloalkene; a tetrazole and an alkene; or a tetrazole with an amino or styryl group that is activated by ultraviolet light and an alkene.

Alternatively or in addition, a surface of a device may be modified to contain a moiety (e.g. a reactive group) what facilitates the attachment of a biosensor and/or binds to the biosensor. In some embodiments, the biosensor is attached to a surface via a biotin-avidin interaction.

In various implementations, the device comprises a first region or chamber for receiving a sample and a second region or chamber that comprises the biosensor, wherein the first region or chamber is separated from the second region or chamber by a filter. In some examples, the filter is impermeable to compounds greater than about 1, 2, 3, 4, 5, 10, 50, 200, or 250 kiloDalton (kDa) in size. The sample may comprise, e.g., a tube, such as a tube that is configured for centrifugation. When sample is placed into the first region and the device is centrifuged, then a portion of the sample comprising a ligand flows through the filter into the second region where the biosensor is contacted.

Non-limiting examples of devices provided herein include endoscopy probes and colonoscopy probes.

In some embodiments, the device comprises an optode. In non-limiting examples, the optode comprises an optical fiber and a single biosensor or composite biosensor. In certain embodiments, the single biosensor or composite biosensor is immobilized on the surface or at an end of the optical fiber. In some embodiments, the optode is configured for implantation into a subject. Alternatively or in addition, the optode is configured for insertion into a sample.

The devices provided herein may optionally comprise a biosensor panel, a composite sensor, a sensor array, and/or a composition comprising a plurality of biosensors. In various embodiments, a device comprises multiple lactate biosensors that detect a range of different lactate concentrations in a single sample and/or assay run (i.e., each biosensor has a different affinity for lactate). Devices may provide spatial localization of multiple biosensors to provide the necessary addressability of different elements in a multi-sensor array comprising sensors that differ in their engineered affinities for coverage of a wide range of lactate concentrations, or sensors that each detects distinct analytes.

Aspects of the present subject matter provide a biosensor panel comprising a plurality of biosensors, wherein the plurality of biosensors comprises at least one biosensor disclosed herein. In some embodiments, the plurality comprises at least about 2, 3, 4, 5, 10, 20, 30, 40, 50, 60, 70, 80, 90, or 100 biosensors.

The present subject matter also provides a composite sensor. The composite sensor may comprise a sensor element, wherein the sensor element comprises 2 or more biosensors, wherein at least 1 of the 2 or more biosensors is a biosensor disclosed herein. In some embodiments, the biosensors are not spatially separated in the sensor element, e.g., the biosensors are mixed within a solution, or immobilized on a surface of the sensor element. Alternatively, a mixture of different biosensors is physically present, e.g., loose, within a region or chamber of a sensor device/structure. In various embodiments, the composite sensor comprises a plurality of sensor elements, wherein each sensor element of the plurality of sensor elements comprises 2 or more biosensors, wherein at least 1 of the 2 or more biosensors is a biosensor provided herein. In some embodiments, the plurality of sensor elements comprises at least about 2, 3, 4, 5, 10, 20, 30, 40, 50, 60, 70, 80, 90, or 100 sensor elements.

Also included herein is a sensor array comprising a plurality of biosensors of the present subject matter. The sensor array may include, e.g., multichannel array or a multiplexed array. In some embodiments, the biosensors of the plurality of biosensors are spatially separated from each other. In certain embodiments, the biosensors are arranged linearly or in a grid on a surface of the array.

The present subject matter provides a composition comprising a plurality of biosensors including at least one biosensor disclosed herein. Also provided is a non-human mammal comprising a biosensor or device disclosed herein.

Exemplary Polypeptides and Polynucleotides

The present subject matter provides polynucleotides encoding any one of the polypeptides disclosed herein. The polypeptides are also provided. In various embodiments, the polynucleotides are codon-optimized for expression in a desired host cell, such as bacterial cells (e.g., *E. coli*), yeast, insect cells, plant cells, algal cells, or mammalian cells. The polypeptides provided herein include polypeptides comprising the amino acid sequence of any one of SEQ ID NOS: 1-62 or 115-128. The polynucleotides provided herein include polynucleotides encoding a polypeptide comprising the amino acid sequence of any one of SEQ ID NOS: 1-62 or 115-128.

The polypeptides and biosensors provided herein may be in a variety of forms, e.g., purified in solution, dried (e.g. lyophilized) such as in the form of a powder, and in the form of a crystal (e.g., a crystal suitable for x-ray crystallography). Thus, aspects of the present subject matter provide crystal structures and crystalized forms of the ligand-binding proteins and biosensors disclosed herein. Such crystal structures and crystalized proteins are useful for designing and optimizing biosensors using principles and methods discussed herein.

Also provided are expression vectors comprising a polynucleotide of the present subject matter and/or encoding a polypeptide disclosed herein. Non-limiting examples of expression vectors include viral vectors and plasmid vectors. In some embodiments, an expression vector comprises nucleotides in the sequence set forth as any one of SEQ ID NOS: 81-108, 135, or 135. In various embodiments, a polynucleotide encoding a ligand-binding protein and/or biosensor is operably linked to a promoter. The promoter may be expressed, e.g., in a prokaryotic and/or a eukaryotic cell.

The subject matter further includes an isolated cell comprising an expression vector provided herein. The isolated cell may be, e.g., a bacterial cell, a yeast cell, an algal cell, a plant cell, an insect cell, or a mammalian cell. Also included is a non-human multicellular organism such as a plant or an animal (e.g., an insect, a mammal, a worm, a fish, a bird, or a reptile) comprising an expression vector disclosed herein.

Exemplary Methods for Designing Biosensors

Aspects of the present subject matter provide method of identifying a candidate ligand-binding protein for use in a biosensor, comprising: (a) selecting a first protein having a known amino acid sequence (seed sequence), wherein the first protein is known to bind lactate; (b) identifying a second protein having an amino acid sequence (hit sequence) with at least 15% sequence identity to the seed sequence; (c) aligning the seed amino acid sequence and the hit sequence, and comparing the hit sequence with the seed sequence at positions of the seed sequence that correspond to at least 5 primary complementary surface (PCS) amino acids, wherein each of the at least 5 PCS amino acids has a hydrogen bond interaction or a van der Waals interaction with lactate when lactate is bound to the first protein; and (d) identifying the second protein to be a candidate ligand-binding protein if the hit sequence comprises at least 5 amino acids that are consistent with the PCS.

The present subject matter also includes a method for constructing a candidate biosensor, comprising: (a) providing a candidate ligand-binding protein; (b) generating a structure of the second protein; (c) identifying at least one putative allosteric, endosteric, or peristeric site of the second protein based on the structure; (d) mutating the second protein to substitute an amino acid at the at least one putative allosteric, endosteric, or peristeric site of the second protein with a cysteine; and (e) conjugating a fluorescent compound to the cysteine. In some embodiments, the structure comprises a homology model of the second protein generated using a structure of the first protein. In some embodiments, the structure comprises a structure experimentally determined by nuclear magnetic resonance spectroscopy or X-ray crystallography.

Aspects of the present subject matter further provide a method for constructing a biosensor comprising a desired dissociation constant ($K_d$) for lactate, comprising: (a) providing an initial biosensor that does not comprise the desired $K_d$ for lactate, wherein the initial biosensor is a biosensor provided herein; (b) mutating the initial biosensor to (i) alter a direct interaction in the PCS between the initial biosensor and bound lactate; (ii) manipulate the equilibrium between open and closed states of the initial biosensor; (iii) alter an interaction between the ligand-binding protein and the reporter group of the initial biosensor; or (iv) alter an indirect interaction that alters the geometry of the binding site of the biosensor, to produce a modified biosensor; and (c) selecting the modified biosensor if the modified biosensor comprises the desired $K_d$ for lactate. In some embodiments, the reporter group comprises Acrylodan, Badan, or a derivative thereof, and mutating the initial biosensor in (b) comprises altering an interaction between the ligand-binding protein and a carbonyl group of the Acrylodan, Badan, or derivative thereof. In some embodiments, the reporter group comprises Acrylodan, Badan, or a derivative thereof, and mutating the initial biosensor in (b) comprises altering an interaction between the ligand-binding protein and a naphthalene ring of the Acrylodan, Badan, or derivative thereof. In some embodiments, mutating the initial biosensor comprises introducing a substitution mutation into the initial biosensor. In some embodiments, the method further comprises immobilizing the affinity-tuned biosensor on a substrate.

In some embodiments, the second protein comprises (i) amino acids in the sequence of any one of SEQ ID NOS: 1-62 or 115-128; (ii) a stretch of amino acids in a sequence that is least about 95, 96, 97, 98, or 99% identical to the sequence of any one of or any combination of any one of SEQ ID NOS: 1-62 and 115-128; (iii) a stretch of at least about 50, 100, 150, 200, 250, 300, 350, or 400 amino acids in a sequence that is at least about 95, 96, 97, 98, or 99% identical to a sequence within any one of SEQ ID NOS: 1-62 or 115-128; or (iv) a stretch of at least about 50, 100, 150, 200, 250, 300, 350, or 400 amino acids in a sequence that is identical to a sequence within any one of SEQ ID NOS: 1-62 or 115-128. In various embodiments, attaching the reporter group to the putative allosteric, endosteric, or peristeric site of the first protein comprises substituting a cysteine at the site with a cysteine. For example, the reporter group is conjugated to the cysteine. Preferably, attaching a reporter group to the corresponding amino acid of the second protein produces a functional biosensor.

The selected first protein (e.g., the amino acid sequence thereof) may be novel or known. However, in many instances, the function of the first protein will not be known. In a non-limiting example, identifying a protein not previously known to have lactate binding activity may comprise a structurally assisted functional evaluation (SAFE) homolog search method comprising the following steps:

(1) Collecting a sequence homology set using a BLAST sequence alignment tool starting with a lactate-binding protein sequence disclosed herein or a homologue thereof (e.g., ttLacBP1, tsLacBP2, toLacBP3, tsLacBP4, rdLacBP5, msLacBP6, tsLacBP7, maLacBP8, adLacBP9, pgLacBP10, psLacBP11, rsLacBP12, fsLacBP13, or taLacBP14) as a seed. Permissive settings are used, such that pairwise hits are required to have a minimum of only, e.g., 20%, 25%, 30%, 35% or 40% sequence identity with the seed sequence. The lengths of the hit and seed are mutually constrained such that the alignment covers at least, e.g., 60%, 65%, 70%, 85%, or 90% within each partner.

(2) Structure-based encoding of biological function: A primary complementary surface (PCS) comprising the protein residues that form hydrogen bonds and van der Waals contacts with a bound lactate is defined using computer-assisted, visual inspection of the three-dimensional structure of the protein-lactate complex. This definition specifies residue positions and their permitted amino acid identity. Multiple amino acid identities are permitted at each position to encode functionally equivalent residues. This definition establishes a search filter for the accurate prediction of lactate-binding proteins within the universe of sequence homologs collected in (1). For example, a candidate's residue corresponding to position 98 of ttLacBP1 may be F, W, or Y, a candidate's residue corresponding to position 101 of ttLacBP1 may be Y, N, Q, H, E, or D, a candidate's residue corresponding to position 158 of ttLacBP1 may be N, D, E, Q, or H, a candidate's residue corresponding to position 178 of ttLacBP1 may be R, a candidate's residue corresponding to position 180 of ttLacBP1 may be P, A, V, L, I, or G, a candidate's residue corresponding to position 216 of ttLacBP1 may be D, N, Q, or E, a candidate's residue corresponding to position 247 of ttLacBP1 may be Q, E, N, or D, and a candidate's residue corresponding to position 250 of ttLacBP1 may be D, N, E, Q, S, T, or H.

(3) Accurate sequence alignment: Tools such as ClustalW are used to construct an accurate alignment of all the sequence homologs. The seed sequence is included in the alignment. This multiple sequence alignment establishes the equivalent positions of the seed lactate-binding protein (primary complementary surface) PCS in each sequence homolog.

(4) Function evaluation: The lactate-binding properties of each of the aligned sequence homologs is determined by measuring their compliance with the PCS sequence filter. A "Hamming distance", H, is assigned for each homolog, which specifies the degree of sequence identity of all the residues at the aligned PCS positions. A value of $H=0$ indicates that the identities of all the residues at the aligned PCS positions match the amino acid(s) allowed in the PCS search filter; $H>0$, indicates that one or more aligned positions have disallowed residues. Sequences for which $H=0$ are predicted to encode lactate-binding proteins.

(5) Selection of representative SAFE homologs: The sequence homologs are ordered by (a) identity with the seed PCS, as measured by the Hamming distance. (b) fractional overall sequence identity with the seed sequence. A subset for sequences with $H=0$, sampling the fractional overall sequence identity is selected for experimental verification.

In a non-limiting example, identifying a protein not previously known to have lactate-binding activity may comprise the following steps:

(1) performing a computational search of sequence databases to define a broad group of simple sequence or structural homologs of any known, lactate-binding protein:

(2) using the list from step (1), deriving a search profile containing common sequence and/or structural motifs shared by the members of the list [e.g. by using computer programs such as MEME (Multiple Em for Motif Elicitation available at meme.sdsc.edu/meme/cgi-bin/meme.cgi) or BLAST];

(3) searching sequence/structural databases, using a derived search profile based on the common sequence or structural motif from step (2) as query (e.g., using computer programs such as BLAST, or MAST (Motif Alignment Search Tool available at meme.sdsc.edu/memecgi-bin/mast.cgi), and identifying a candidate sequence, wherein a sequence homology and/or structural similarity to a reference lactate-binding protein is a predetermined percentage threshold;

(4) compiling a list of candidate sequences to generate a list of candidate lactate-binding proteins;

(5) expressing the candidate lactate-binding proteins in a host organism; and (6) testing for lactate binding activity, wherein detection of lactate binding in the organism (or the media thereof) indicates that the candidate sequence comprises a novel lactate-binding protein.

In non-limiting examples, the MEME suite of sequence analysis tools (meme.sdsc.edu/meme/cgi-bin/meme.cgi) can also be used as an alternative to BLAST. Sequence motifs are discovered using the program "MEME". These motifs can then be used to search sequence databases using the program "MAST." The BLAST search algorithm is well-known.

In various embodiments relating to alignments using a ClustalW alignment program, the ClustalW alignment program may be, e.g., ClustalW alignment program version 2.1.

Each embodiment disclosed herein is contemplated as being applicable to each of the other disclosed embodiments. Thus, all combinations of the various elements described herein are within the scope of the invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

DESCRIPTION OF THE DRAWINGS

FIG. 1A: FRSs can be constructed by site-specifically attaching a fluorophore to a protein that undergoes a conformational change upon binding ligand (triangle) in a location between the two lobes of the protein (periplasmic binding protein or engineered derivative thereof), such that the shape and intensities of the fluorescent conjugate emission spectra changes. FIG. 1B: In the absence of ligand, the emitted fluorescence color is predominantly blue, whereas the ligand complex fluoresces green. Arrows indicate the direction of change upon ligand addition. FIG. 1C: The ligand dependence of the absolute blue and green intensities. FIG. 1D: The ratio of the blue and green emission intensities enables ligand binding to be determined.

FIG. 3A: Structure of ttLacBP1. Arrows indicate primary complementary surface (see Table 1), lactate (large gray spheres), and $Ca^{2+}$; small gray spheres, cysteine mutations (see Table 4). Structure from PDB accession code 2zzv (SEQ ID NO: 137). FIG. 3B: Variation in residue identity allowed at each position in the PCS search filter. The first amino acid listed at each position corresponds to the residue in ttLacBP1.

FIG. 5A: msLacBP6 187C-Acrylodan ($\lambda_1$=452 nm, $\lambda_2$=582 nm; $^{app}K_d$=0.4 mM; $^{true}K_d$=0.3 mM).

FIG. 6A shows Acrylodan; FIG. 6B shows Badan; FIG. 6C shows IAEDANS. Xanthene family: FIG. 6D shows Fluorescein (5-IAF and 6-IAF); FIG. 6E shows Oregon Green.

FIG. 7A: msLacBP6 187C•Acrylodan, βZif•Fluorescein ($\lambda_1$=452 nm, $\lambda_2$=520 nm; $^{app}K_d$=0.3 mM; $^{app}K_d$=0.3 mM).

FIG. 8A: Lactate titration curve determined for magnetic Ni-NTA beads coated with immobilized msLacBP6 187C, 70M•Acrylodan. Dichromatic signal ($\lambda_1$=452 nm, $\lambda_2$=525 nm); gray circles (showing four replicates), experimental data points; gray line, fit to binding isotherm, $^{app}K_d$=2.1 mM, $^{true}K_d$=1.2 mM. Panels FIGS. 8B-D: Thermostability was determined by measuring the ratio fluorescence emission intensities through 488 nm and 510 nm filters as a function of temperature in a Roche LightCycler. FIG. 8B:Solution ($T_m$=342 K). FIG. 8C: Immobilized on Ni-NTA beads ($T_m$=339 K). FIG. 8D: Reconstituted, desiccated Ni-NTA beads ($T_m$=344 K). The lines in each of FIG. 8B-D show data from repeat experiments.

FIG. 9A: Simplified Jablonski diagram illustrating radiative and non-radiative pathways in the donor and acceptor. The donor excited state (D*) is formed through illumination by the excitation source (wavy arrow) whereas the acceptor excited state (A*) is formed by resonance energy transfer (dashed arrow). The fluorescence intensity is determined by the ratio of radiative decay (gray arrows) of the excited states (gray lines) to the ground state (black line) relative to all non-radiative processes (black arrows), and the resonance energy transfer rate, $k_t$, from donor to acceptor. FIG. 9B: Inter-dipole geometry. Top, FRET efficiency ($f=Q_r/(Q_0-Q_\infty)$, where the $Q_r$, $Q_0$, $Q_\infty$ are the quantum efficiencies at distances r, closest approach, and infinity, respectively) varies as the $6^{th}$ power of the distance between two dipoles. Bottom, FRET efficiency varies as the square of the orientation factor κ, where $\kappa=\sin\theta_D \sin\theta_A \cos\theta_D \cos\theta_A$ with $\theta_D$ and $\theta_A$ the angles of the donor (blue) and acceptor (red) electronic transition dipoles with the line connecting them, and χ the angle between the planes within which they lie. FIG. 9C: Spectral overlap (gray area) between the donor fluorescence emission ($^D$I, gray) and acceptor fluorescence excitation ($^A$A, black) spectra. This overlap increases with bathochromic or hypsochromic shifts of the donor emission (red arrow) and acceptor excitation (dotted blue arrow) spectra, respectively. Shifts in the opposite directions decreases spectral overlap.

FIG. 10 shows the sequence of an exemplary ttLacBP1 expression construct (SEQ ID NO: 63).

FIG. 11 shows the sequence of an exemplary tsLacBP2 expression construct (SEQ ID NO: 64).

FIG. 12 shows the sequence of an exemplary toLacBP3 expression construct (SEQ ID NO: 65).

FIG. 13 shows the sequence of an exemplary tsLacBP4 expression construct (SEQ ID NO: 66).

FIG. 14 shows the sequence of an exemplary rdLacBP5 expression construct (SEQ ID NO: 67).

FIG. 15 shows the sequence of an exemplary msLacBP6 expression construct (SEQ ID NO: 68).

FIG. 16 shows the sequence of an exemplary tsLacBP7 expression construct (SEQ ID NO: 69).

FIG. 17 shows the sequence of an exemplary maLacBP8 expression construct (SEQ ID NO: 70).

FIG. 18 shows the sequence of an exemplary adLacBP9 expression construct (SEQ ID NO: 71).

FIG. 19 shows the sequence of an exemplary pgLacBP10 expression construct (SEQ ID NO: 72).

FIG. 20 shows the sequence of an exemplary psLacBP11 expression construct (SEQ ID NO: 73).

FIG. 21 shows the sequence of an exemplary fsLacBP13 expression construct (SEQ ID NO: 74).

FIG. 22 shows the sequence of an exemplary taLacBP14 expression construct (SEQ ID NO: 75).

FIG. 23 shows the sequence of an exemplary msLacBP6.10C expression construct (SEQ ID NO: 76).

FIG. 24 shows the sequence of an exemplary msLacBP6.12C expression construct (SEQ ID NO: 77).

FIG. 25 shows the sequence of an exemplary msLacBP6.43C expression construct (SEQ ID NO: 78).

FIG. 26 shows the sequence of an exemplary msLacBP6.49C expression construct (SEQ ID NO: 79).

FIG. 27 shows the sequence of an exemplary msLacBP6.50C expression construct (SEQ ID NO: 80).

FIG. 28 shows the sequence of an exemplary msLacBP6.68C expression construct (SEQ ID NO: 81).

FIG. 29 shows the sequence of an exemplary msLacBP6.169C expression construct (SEQ ID NO: 82).

FIG. 30 shows the sequence of an exemplary msLacBP6.170C expression construct (SEQ ID NO: 83).

FIG. 31 shows the sequence of an exemplary msLacBP6.171C expression construct (SEQ ID NO: 84).

FIG. 32 shows the sequence of an exemplary msLacBP6.187C expression construct (SEQ ID NO: 85).

FIG. 33 shows the sequence of an exemplary msLacBP6.188C expression construct (SEQ ID NO: 86).

FIG. 34 shows the sequence of an exemplary msLacBP6.192C expression construct (SEQ ID NO: 87).

FIG. 35 shows the sequence of an exemplary msLacBP6.196C expression construct (SEQ ID NO: 88).

FIG. 36 shows the sequence of an exemplary tsLacBP7.189C expression construct (SEQ ID NO: 89).

FIG. 37 shows the sequence of an exemplary maLacBP8.189C expression construct (SEQ ID NO: 90).

FIG. 38 shows the sequence of an exemplary adLacBP9.C191 expression construct (SEQ ID NO: 91).

FIG. 39 shows the sequence of an exemplary psLacBP11.195C expression construct (SEQ ID NO: 92).

FIG. 40 shows the sequence of an exemplary rsLacBP12.191C expression construct (SEQ ID NO: 93).

FIG. 41 shows the sequence of an exemplary fsLacBP13.188C expression construct (SEQ ID NO: 94).

FIG. 42 shows the sequence of an exemplary msLacBP6_187C_F68L expression construct (SEQ ID NO: 95).

FIG. 43 shows the sequence of an exemplary msLacBP6_187C_F68M expression construct (SEQ ID NO: 96).

FIG. 44 shows the sequence of an exemplary msLacBP6_187C_L70F expression construct (SEQ ID NO: 97).

FIG. 45 shows the sequence of an exemplary msLacBP6_187C_L70I expression construct (SEQ ID NO: 98).

FIG. 46 shows the sequence of an exemplary msLacBP6_187C_L70M expression construct (SEQ ID NO: 99).

FIG. 47 shows the sequence of an exemplary msLacBP6_187C_P150A expression construct (SEQ ID NO: 100).

FIG. 48 shows the sequence of an exemplary msLacBP6_187C_P150S expression construct (SEQ ID NO: 101).

FIG. 49 shows the sequence of an exemplary msLacBP6_187C_D220E expression construct (SEQ ID NO: 102).

FIG. 50 shows the sequence of an exemplary msLacBP6_187C_D220L expression construct (SEQ ID NO: 103).

FIG. 51 shows the sequence of an exemplar) msLacBP6_187C_D220N expression construct (SEQ ID NO: 104).

FIG. 52 shows the sequence of an exemplary msLacBP6_187C_D220Q expression construct (SEQ ID NO: 105).

FIG. 53 shows the sequence of an exemplary msLacBP6_187C_D220S expression construct (SEQ ID NO: 106).

FIG. 54 shows the sequence of an exemplary msLacBP6_187C_bZifC expression construct (SEQ ID NO: 107).

FIG. 55 shows the sequence of an exemplary msLacBP6_188C_bZifC expression construct (SEQ ID NO: 108).

FIG. 56 shows the sequence of an exemplary rsLacBP12 expression construct (SEQ ID NO: 136).

FIG. 57 shows the sequence of an exemplary taLacBP14.186C expression construct (SEQ ID NO: 135).

FIG. 58 is a diagram relating to directly responsive partners and indirectly responsive partners in ngmFRET pathways.

DETAILED DESCRIPTION

Fluorescently responsive sensors (FRSs) based on engineered proteins that couple ligand-binding events to changes in the emission properties of fluorophores (being fluorescent by themselves and regardless of the presence of any other fluorophore/partner) or semi-synthetically incorporated chromophores have wide-ranging applications in cell biology and analytical chemistry. If the fluorescence emission spectrum of an engineered FRS changes shape in response to ligand binding such that the ratio of intensities at two appropriately chosen wavelengths reports on ligand concentration (dichromatic response), then ratiometric measurements can be used to monitor analyte concentrations. Ratiometry is essential for devices that rely on changes in fluorescence emission intensities, because it provides an internally consistent reference. The self-calibrating nature of a ratiometric measurement removes the necessity for carrying out on-board calibration tests prior to each measurement, obviating the need for multiple components and fluidic circuitry. Accordingly, reagentless, ratiometric fluorescent sensors have many uses in process engineering, environmental or clinical chemistry, including single-use point-of-care applications, wearable devices, or implanted "tattoos" that are interrogated transdermally.

The periplasmic binding protein (PBP) superfamily provide a rich source of FRSs, because PBPs combine a large diversity of ligand specificities with a common structural mechanism that is well suited to the construction of fluorescence signal transduction schemes. The three-dimensional PBP monomer structure comprises two α/β domains linked by a β-strand hinge. Binding of ligand is accompanied by a large hinge-bending motion that transitions the protein from an open to a closed state in which the ligand is enveloped within a cleft between the two domains. Semi-synthetic FRSs can be engineered with PBPs by site-specifically attaching single, thiol-reactive, environmentally sensitive fluorophores that respond to the ligand-mediated conformational change (FIGS. 1A-D). Semisynthetic, fluorescently labeled glucose-binding proteins in the periplasmic binding protein superfamily have been engineered successfully as reagentless, ratiometric glucose biosensors that can be used for point-of-care diagnostics and in vive continuous glucose monitoring applications.

Figure 1A:
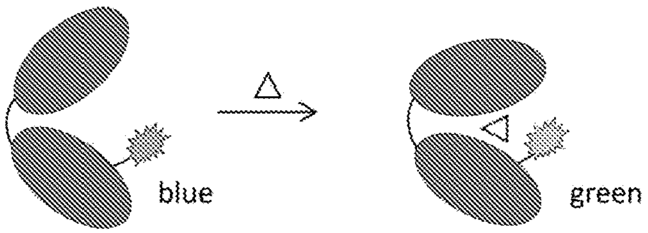
FIG. 1A is a cartoon and FIGS. 1B-D are graphs illustrating fluorescently responsive sensors.
Figure 1B:
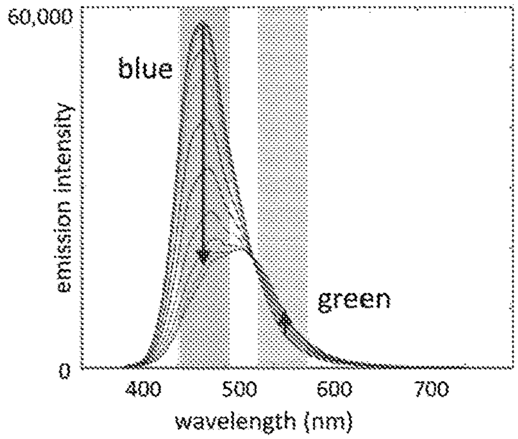
Figure 1C:
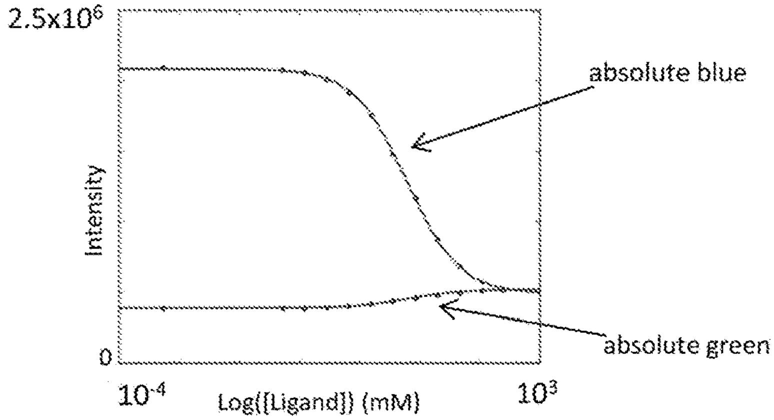
Figure 1D:
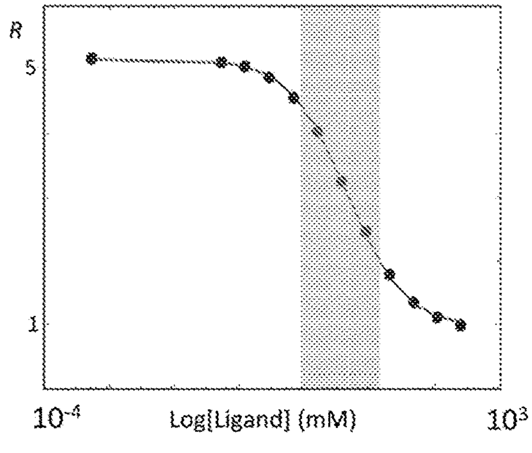
Figure 2A:
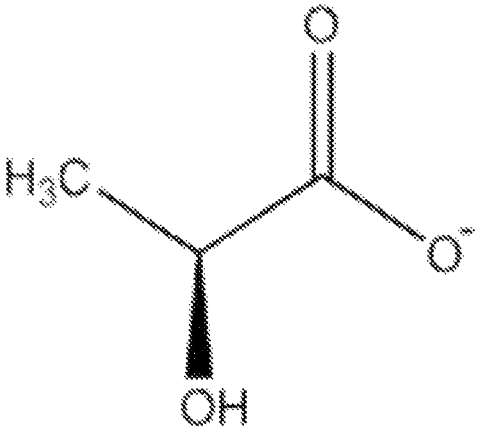
FIGS. 2A-D are the structures for lactic acid (FIG. 2A), L-lactic acid (FIG. 2B), and the closely related ligands pyruvic acid (FIG. 2C) and L-alanine (FIG. 2D).
Figure 2B:
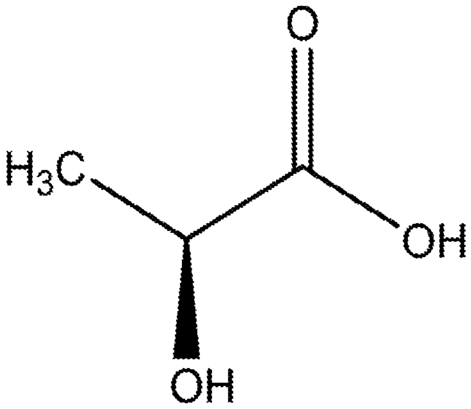
Figure 2C:
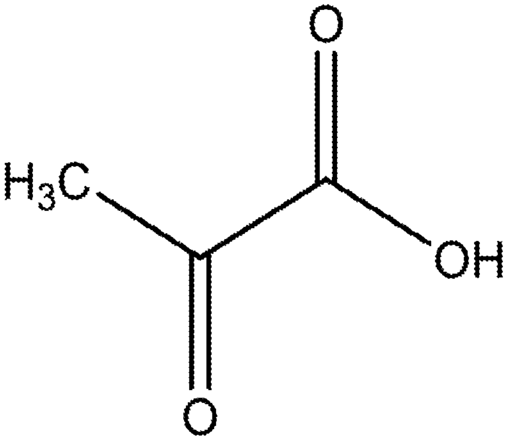
Figure 2D:
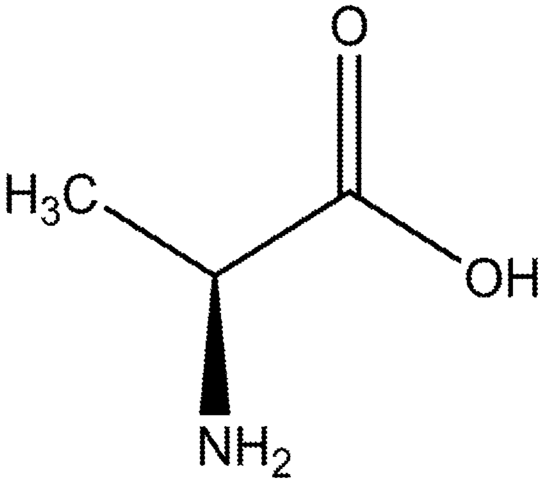

Lactate (FIG. 2A) is an indicator of anaerobic metabolism. The determination of lactate concentrations therefore is important for clinical diagnosis, sports medicine, and food and wine industry. Physiological lactate levels for a healthy person under resting conditions are typically between 0.5 to 2.5 mM but during vigorous physical activity the concentration can rise up to 20-30 mM (Warrel, 2010, Oxford Textbook of Medicine. Oxford University Press; Burtis, 2012. Tietz Textbook of Clinical Chemistry and Molecular Diagnostics. Elsevier; Romero, 2010*, Anal. Chem.,* 82, 5568-5572; Suman, 2005, *Sens Actuators B Chem,* 107, 768-772). Monitoring the lactate levels can predict multiple organ failure and death of patient with septic shock, respiratory insufficiency, heart failure and metabolic disorders (Parra, 2006, *Anal. Chim. Acta,* 555, 308-315). Elevated resting blood lactate concentration is not only linked to survival risk but can also be used as an indicator of the patient oxygen supply (Bakker, 1996, *Am. J. Surgery,* 171, 221-226; Romero, 2010, *Anal. Chem.,* 82, 5568-5572). For this reason, rapid determination of lactate is key in special care units (Jansen, 2010, *Am. J. Respir. Crit. Care Med.,* 182, 752-761; Romero, 2010*, Anal. Chem.,* 82, 5568-5572). In sports medicine monitoring the lactic acid level make it possible to detect injury to tissues, thrombosis and physical condition of racing athletes and animals (Sartain, 2006, *Anal. Chem.,* 78, 5664-5670).

Lactate levels also function as indicators of fermentative processes in food and wine industry and is useful for evaluating stability and freshness of such as dairy products, vegetables, fruits, juices, sausages and wine. The amount of lactic acid in food products has a great impact on the stability, flavor and storage life time.

Most current lactate sensors tend to be either electrochemical or optical biosensors using the enzyme lactate dehydrogenase, lactate oxidase, alpha-hydroxy acid oxidase, lactate monooxygenase, lactate peroxidase (Sartain, 2006, *Anal. Chem.,* 78, 5664-5670; Monosik, 2012*, Food Control,* 23, 238-244). Despite the number of developed lactate biosensors, there is still a need to improve stability, sensibility and applicability of such devices. Most of these sensors suffer from long response time, short stability, and poor reproducibility (Romero, 2010*, Anal. Chem.,* 82, 5568-5572).

In FRS-based sensors, signals arise from reversible binding equilibria of the analyte (ligand) to a receptor. These signals are most precise at ligand concentrations that match the receptor ligand-disassociation constant. Precision is maintained to within ~80% of this maximal level over a concentration range approximately 3-fold above or below this point. Construction of effective FRSs therefore requires matching of ligand-binding affinities to the relevant analyte concentrations. Arrays of multiple sensors may have to be used in concert to cover wide concentration ranges. Clinically relevant lactate levels vary approximately from ~0.5 mM to ~2.5 mM, requiring an array of multiple FRS sensors with distinct lactate affinities to report directly on the full range of clinically relevant lactate concentrations with high precision. The present subject matter provides appropriately tuned, lactate-responsive FRSs, constructed by mutating their lactate-binding site. A set of non-limiting examples is disclosed in the descriptive experiments described in the Figures, Tables, and Examples herein.

Immobilization of FRSs on solid surfaces with minimal perturbation of the molecular sensing mechanism is an important step for incorporating biosensors into devices. Immobilization enables retention of the sensor within the sampling element (e.g. optode surface or implanted bead for in vivo sensing applications; or in a sample-handling cartridge for ex vivo sensing). Immobilization also may provide spatial localization to provide the necessary addressability of different elements in a multi-sensor array comprising sensors that differ in their engineered affinities for coverage of a wide range of lactate concentrations, or sensors that each detects distinct analytes.

Ex vivo clinical chemistries such as point-of-care applications require that the FRS is incorporated into a cartridge into which a sample is introduced at the time of measurement. Such "disposables" need to have a long shelf life that preferably does not require temperature control (e.g. refrigeration) for storage or distribution. It is preferable to incorporate immobilized protein in a stable, dried form in such disposables. The resistance to denaturation of thermostable proteins minimizes the need for temperature control during manufacturing and storage, and may extend to the long-term stability of a desiccated state.

The spectral response, binding affinity, and thermostability of the robust thermostable lactate FRSs reported here are conserved following site-specific immobilization on beads. Furthermore, these properties are recovered rapidly upon reconstitution following drying and prolonged storage under accelerated ageing conditions. These engineered proteins therefore have significant potential for the development of next-generation robust, high-precision, wide-dynamic range lactate sensing applications, including continuous monitoring, point-of-care, wearable sensor systems.

Biosensors

Biosensors are molecular recognition elements that transduce ligand-binding events into physical signals. Biosensors as detailed herein bind at least one ligand and emit a signal. A ligand-bound biosensor results in a signal that is different from the unbound biosensor. This difference facilitates detection of the at least one ligand and/or determination of ligand concentration. The biosensors may be used without the assistance of other reagents.

Described herein are novel engineered biosensors. These biosensors may have altered ligand-binding affinities, tailored ligand-binding specificities, and/or temperature dependencies of ligand binding or stability. For example, the herein described engineered lactate biosensors provide high-accuracy information related to extended lactate concentration ranges.

Binding of ligand mediates conformational changes in the biosensor, such as hinge-bending motions of the polypeptide. The conformational changes affect the environment of the reporter such that a change in the reporter-generated signal occurs. That is, without ligand bound, the biosensor results in signal generated from the reporter, and when ligand is bound, the signal generated from the reporter changes. The ligand-bound biosensor results in a reporter-generated signal that is different from the unbound biosensor.

In some embodiments, the methods and compositions include a plurality of a single type of biosensor. The biosensors may be identical in structure and function. For example, the biosensors of a single type may have the same polypeptide, the same reporter, and the same ligand affinity.

In other embodiments, the methods and compositions include a plurality of different types of biosensors. A plurality of these different types of biosensors may be arranged or incorporated in a panel. As used herein, a "panel" refers to two or more biosensors. The two or more biosensors may be different from each other. The biosensors may differ in structure and/or function. Biosensors may differ in polypeptide sequence, reporter, ligand affinities, or a combination thereof. Accordingly, there may be different types of biosensors. In some embodiments, each biosensor in the panel comprises the same reporter group. In some embodiments, each biosensor in the panel comprises a different reporter group. The panel may include at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, or at least 100 biosensors.

The panel of biosensors includes at least one sensor element. "Sensor element" refers to a single spot, site, location, or well for the at least one biosensor, to which a sample or aliquot thereof may be applied. The panel may be a composite sensor or an array.

In some embodiments, the panel is a composite sensor. In a composite sensor, each sensor element includes a mixture of two or more different biosensors. In some embodiments, the composite sensor includes one sensor element. In some embodiments, the composite sensor includes two or more sensor elements. In some embodiments, signals are measured from a composite sensor in which the signals arise from one or more biosensors in the sensor element. For example, signals may be measured from a composite sensor in which the signals arise from a subset of the total number of biosensors in the sensor element. For example, signals may be measured from a composite sensor in which the signals arise from two of five biosensors in the sensor element.

In some embodiments, the panel is an array. In an array, each sensor element includes a single type of biosensor. An array comprises a plurality of individually and spatially localized sensor elements. Each sensor element includes a biosensor that is different than or the same as the biosensor of a different sensor element. In some embodiments, signals are measured from an array in which the signals arise separately from two or more selected biosensors in separate sensor elements. An array may comprise a plurality of sensor elements of a variety of sizes and configurations. An array may comprise a plurality of sensor elements arranged linearly. For example, an array may comprise a plurality of micrometer-sized sensor elements arranged in a single row. An array may comprise a plurality of sensor elements arranged in a grid. The grid may be two- or three-dimensional. In some embodiments, the grid is a spatially addressable grid. In some embodiments, the biosensors are incorporated into an array, such as a multichannel or multiplexed array.

The biosensors of the present disclosure can be used in any setting where lactate detection is required or desired, such a medical setting (e.g., determining the level of blood lactate in a subject), environmental setting (e.g., determining the level of lactate in an environmental sample), biological setting (e.g., determining the presence or amount of lactate in a reaction), or in process engineering, such as monitoring the amount of lactate in a fermentation reaction (e.g., a bacterial culture, a yeast culture, beer/wine production, etc.). Other examples include, but are not limited to, uses in the food industry (Suleiman et al., In: Biosensor Design and Application: Mathewson and Finley Eds: *American Chemical Society*, Washington, D C 1992, vol. 511); in clinical chemistry (Wilkins et al., 1996, Med. Eng. Phys. 1996, 18, 273-288; Pickup, Tr. Biotech. 1993, 11, 285-291; Meyerhoff et al., Endricon 1966, 6, 51-58; Riklin et al., Nature 1995, 376, 672-675); Willner et al., J. Am. Chem. Soc. 1996, 118, 10321-10322); as the basis for the construction of a fluorescent flow cell containing immobilized ligand binding protein-FAST conjugates (see, e.g., Wilkins et al., 1966, *Med. Eng. Phys.*, 18, 273-288; Pickup, Tr., 1993, *Biotech*, 11, 285-291; Meyerhoff et al., 1966, *Endricon.*, 6, 51; Group, 1993, *New Engl. J. Med.*, 329, 977-986; Gough et al., 1995, *Diabetes*, 44, 1005-1009); and in an implantable devices.

The biosensors as detailed herein may be administered in a variety of ways known by those of skill in the art, as appropriate for each application. Biosensors may be provided in a solution. The solution may be buffered. Biosensors may be provided in a solution and mixed directly with a sample. In some embodiments, a biosensor is immobilized onto a surface. Biosensors may be immobilized within a disposable cartridge into which a sample may be introduced or applied. Biosensors may be implanted or incorporated in a wearable device. The biosensor may be provided as an optode.

The biosensor may be attached to or incorporated in a wearable device. Wearable devices may include, for example, adhesive strips, patches, and contact lenses. The biosensor may be configured for placement in contact with a subject's skin or mucosal surface. In some embodiments, the biosensor is configured as an adhesive strip. In some embodiments, the biosensor is configured within or on the surface of a contact lens. In some embodiments, the contact lens is formed from a transparent substrate shaped to be worn directly over a subject's eye, as described in, for example, U.S. Pat. No. 8,608,310.

The biosensor may be implanted. The biosensor may be implanted in a subject's body. The biosensor may be implanted in a subject's blood vessel, vein, eye, natural or artificial pancreas, skin, or anywhere in the alimentary canal including the stomach, intestine and esophagus. The biosensor may be implanted in a subject with a microbead. In some embodiments, the biosensor is configured to be implanted in the skin. The biosensor may be implanted in a subject sub-dermally. The biosensor may generate the signal trans-dermally. In some embodiments, the biosensor may be implanted in a subject with transdermal microbeads, wherein the optical signals can be transmitted remotely between the biosensor and detecting device.

In some embodiments, the biosensor is administered as an optode. As used herein, "optode" refers to an optical fiber with a single biosensor, or a composite biosensor, immobilized at the surface or at the end. An "optode" may also be referred to as an "optrode." In some embodiments, the biosensor is implanted in a subject as an optode. The optode may be incorporated with or into a needle. The optode may be incorporated with a probe such as endoscopy or colonoscopy probes. The optode may be used in a tumor, near a tumor, or at the periphery of a tumor. In some embodiments, the biosensor may be implanted in a subject as an optode, wherein the optical signals can be transmitted between the biosensor and detecting device using physical links. In some embodiments, the biosensor is administered as an optode to a sample or reaction. The optode may be contacted with a sample or reaction. In some embodiments, an optode is used to continuously or episodically monitor a ligand in a sample or reaction.

Methods of Detecting the Presence of a Ligand

Provided herein is a method of detecting the presence of a ligand in a sample. The method may include contacting the biosensor with the sample; measuring a signal from the biosensor; and comparing the signal to a ligand-free control. A difference in signal indicates the presence of ligand in the sample.

Also provided herein is a method of detecting the presence of lactate in a sample. The method may include (a) providing a lactate biosensor disclosed herein in which the reporter group is attached the lactate-binding protein so that a signal transduced by the reporter group when the lactate-binding protein is bound to lactate differs from a signal transduced by the reporter group when the lactate-binding protein is not bound to lactate; (b) contacting the biosensor with the test sample under conditions such that the biosensor can bind to lactate present in the test sample; and (c) comparing the signal transduced by the reporter group when the biosensor is contacted with the test sample with the signal transduced by the reporter group when the biosensor is contacted with a lactate-free control sample, wherein a difference in the signal transduced by the reporter group when the biosensor is contacted with the test sample, as compared to when the biosensor is contacted with the control sample, indicates that the test sample contains lactate.

Methods of Determining the Concentration of a Ligand

Provided herein is a method of determining the concentration of a ligand in a sample. The method may include contacting the biosensor with the sample; measuring a signal from the biosensor; and comparing the signal to a standard hyperbolic ligand binding curve to determine the concentration of ligand in the test sample. The standard hyperbolic ligand binding curve may be prepared by measuring the signal transduced by the biosensor when contacted with control samples containing known concentrations of ligand.

Another aspect of the present disclosure provides a method of determining the concentration of lactate in a test sample comprising, consisting of, or consisting essentially of: (a) providing a lactate biosensor comprising a lactate biosensor as described herein in which the reporter group is attached the lactate-binding protein so that a signal transduced by the reporter group when the lactate-binding protein is bound to lactate differs from a signal transduced by the reporter group when the lactate-binding protein is not bound to lactate; (b) contacting the biosensor with the test sample under conditions such that the biosensor can bind to lactate present in the test sample; and (c) comparing the signal transduced by the reporter group when the biosensor is contacted with the test sample with a standard hyperbolic lactate binding curve prepared by measuring the signal transduced by the reporter group when the biosensor is contacted with control samples containing known quantities of lactate to determine the concentration of lactate in the test sample.

Methods of Monitoring the Presence of a Ligand

The present invention is directed to a method of episodically or continuously monitoring the presence of a ligand in a reaction. In certain embodiments, the biosensors may be used in the continuous monitoring of lactate in a reaction. In certain embodiments, the lactate sensors may be used in episodic monitoring of sample aliquots.

The method of episodically or continuously monitoring the presence of a ligand in a reaction may include contacting the biosensor with the reaction; maintaining the reaction under conditions such that the polypeptide is capable of binding ligand present in the reaction; and episodically or continuously monitoring the signal from the biosensor in the reaction.

The method of episodically or continuously monitoring the presence of a ligand in a reaction may include contacting the biosensor with the reaction; maintaining the reaction under conditions such that the polypeptide is capable of binding ligand present in the reaction; episodically or continuously monitoring the signal from the biosensor in the reaction; and comparing the signal to a standard hyperbolic ligand binding curve to determine the concentration of ligand in the test sample. The standard hyperbolic ligand binding curve may be prepared by measuring the signal transduced by the biosensor when contacted with control samples containing known concentrations of ligand.

In some embodiments, the method further includes comparing the signal to a ligand-free control, wherein a difference in signal indicates the presence of ligand in the reaction.

In some embodiments, the method further includes comparing the signal to a standard hyperbolic ligand binding curve to determine the concentration of ligand in the test sample. The standard hyperbolic ligand binding curve may be prepared by measuring the signal transduced by the biosensor when contacted with control samples containing known concentrations of ligand.

Another aspect of the present disclosure provides a method of continuously monitoring the presence of lactate in a reaction comprising, consisting of, or consisting essentially of: (a) providing a lactate biosensor as described herein in which the reporter group is attached the lactate-binding protein so that a signal transduced by the reporter group when the lactate-binding protein is bound to lactate differs from a signal transduced by the reporter group when the lactate-binding protein is not bound to lactate (b) maintaining the biosensor within the reaction and under conditions such that the biosensor can bind to lactate present in the reaction; (c) continuously monitoring the signal transduced by the reporter group when the biosensor is contacted with the lactate present in the reaction; and optionally (d) comparing the signal transduced by the reporter group when the biosensor is contacted with the lactate present in the reaction with the signal transduced by the reporter group when the biosensor is contacted with a lactate-free control sample, wherein a difference in the signal transduced by the reporter group when the biosensor is contacted with the lactate present in the reaction, as compared to when the biosensor is contacted with the control sample, indicates lactate is present in the reaction.

Yet another aspect of the present disclosure provides a method of continuously monitoring the concentration of lactate in a reaction comprising, consisting of, or consisting essentially of: (a) providing a lactate biosensor comprising a lactate biosensor as described herein in which the reporter group is attached the lactate so that a signal transduced by the reporter group when the lactate-binding protein is bound to ligand differs from a signal transduced by the reporter group when the lactate-binding protein is not bound to lactate; (b) maintaining the biosensor within the reaction under conditions such that the biosensor can bind to lactate present in the reaction; and (c) continuously monitoring the signal transduced by the reporter group when the biosensor is contacted with the lactate present in the reaction; and (d) comparing the signal transduced by the reporter group when the biosensor is contacted with the lactate present in the reaction with a standard hyperbolic lactate binding curve prepared by measuring the signal transduced by the reporter group when the biosensor is contacted with control samples containing known quantities of lactate to determine the concentration of lactate in the reaction.

General Definitions

Unless specifically defined otherwise, all technical and scientific terms used herein shall be taken to have the same meaning as commonly understood by one of ordinary skill in the art (e.g., in cell culture, molecular genetics, and biochemistry).

As used herein, the term "about" in the context of a numerical value or range means±10% of the numerical value or range recited or claimed, unless the context requires a more limited range.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together. A and C together, B and C together, or A and B and C together." In addition, use of the term "based on," above and in the claims is intended to mean, "based at least in part on," such that an unrecited feature or element is also permissible It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to and including 5.0 mg.

A small molecule is a compound that is less than 2000 daltons in mass. The molecular mass of the small molecule is preferably less than 1000 daltons, more preferably less than 600 daltons, e.g., the compound is less than 500 daltons, 400 daltons, 300 daltons, 200 daltons, or 100 daltons.

As used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes/nucleic acids or sequences/amino acids that flank it in its naturally-occurring state. Purified also defines a degree of sterility that is safe for administration to a human subject, e.g., lacking infectious or toxic agents.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

"Subject" as used herein refers to any organism from which a biological sample is obtained. For example, the sample is a biological fluid or tissue. For example, a subject is one who wants or is in need of detecting ligand or determining the concentration of ligand with the herein described biosensors. The subject may be a human or a non-human animal. The subject may be a mammal. The mammal may be a primate or a non-primate. The mammal can be a primate such as a human; a non-primate such as, for example, dog, cat, horse, cow, pig, mouse, rat, camel, llama, goat, rabbit, sheep, hamster, and guinea pig; or non-human primate such as, for example, monkey, chimpanzee, gorilla, orangutan, and gibbon. The subject may be of any age or stage of development, such as, for example, an adult, an adolescent, or an infant.

As used herein, an "expression vector" is a DNA or RNA vector that is capable of effecting expression of one or more polynucleotides. Preferably, the expression vector is also capable of replicating within the host cell. Expression vectors can be either prokaryotic or eukaryotic, and are typically include plasmids. Expression vectors of the present invention include any vectors that function (i.e., direct gene expression) in host cells of the present invention, including in one of the prokaryotic or eukaryotic cells described herein, e.g. gram-positive, gram-negative, pathogenic, non-pathogenic, commensal, cocci, *bacillus*, or spiral-shaped bacterial cells; archaeal cells; or protozoan, algal, fungi, yeast, plant, animal, vertebrate, invertebrate, arthropod, mammalian, rodent, primate, or human cells. Expression vectors of the present invention contain regulatory sequences such as transcription control sequences, translation control sequences, origins of replication, and other regulatory sequences that are compatible with the host cell and that control the expression of a polynucleotide. In particular, expression vectors of the present invention include transcription control sequences. Transcription control sequences are sequences which control the initiation, elongation, and termination of transcription. Particularly important transcription control sequences are those which control transcription initiation such as promoter, enhancer, operator and repressor sequences. Suitable transcription control sequences include any transcription control sequence that can function in at least one of the cells of the present invention. A variety of such transcription control sequences are known to those skilled in the art.

As used herein, the singular forms "a," "an," and "the" include the plural reference unless the context clearly dictates otherwise. Thus, for example, a reference to "a disease," "a disease state", or "a nucleic acid" is a reference to one or more such embodiments, and includes equivalents thereof known to those skilled in the art and so forth.

As used herein, "pharmaceutically acceptable" carrier or excipient refers to a carrier or excipient that is suitable for use with humans and/or animals without undue adverse side effects (such as toxicity, irritation, and allergic response) commensurate with a reasonable benefit/risk ratio. It can be, e.g., a pharmaceutically acceptable solvent, suspending agent or vehicle, for delivering the instant compounds to the subject.

The term "diagnosis" refers to a determination that a disease is present in the subject. Similarly, the term "prognosis" refers to a relative probability that a certain future outcome may occur in the subject. For example, in the context of the present disclosure, prognosis can refer to the likelihood that an individual will develop a disease, or the likely severity of the disease (e.g., severity of symptoms, rate of functional decline, survival, etc.).

Unless required otherwise by context, the terms "polypeptide" and "protein" are used interchangeably herein.

A polypeptide or class of polypeptides may be defined by the extent of identity (% identity) of its amino acid sequence to a reference amino acid sequence, or by having a greater % identity to one reference amino acid sequence than to another. A variant of any of genes or gene products disclosed herein may have. e.g., 50%, 55%, 60%, 65%, 70%, 75%, 80%, 85%, 90%, 95%, 96%, 97%, 98%, or 99%, sequence identity to the nucleic acid or amino acid sequences described herein. The term "% identity," in the context of two or more nucleic acid or polypeptide sequences, refers to two or more sequences or subsequences that are the same or have a specified percentage of amino acid residues or nucleotides that are the same, when compared and aligned for maximum correspondence, as measured using a sequence comparison algorithm or by visual inspection. For example, % identity is relative to the entire length of the coding regions of the sequences being compared, or the length of a particular fragment or functional domain thereof. Variants as disclosed herein also include homologs, orthologs, or paralogs of the genes or gene products described herein. In some embodiments, variants may demonstrate a percentage of homology or identity, for example, at least about 50%, 55%, 60%, 65%, 70%, 75%, 80%, 85%, 90%, 95%, 96%, 97%, 98%, or 99% identity conserved domains important for biological function, e.g., in a functional domain, e.g. a ligand-binding or catalytic domain.

For sequence comparison, one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Percent identity is determined using BLAST. For the BLAST searches, the following parameters were employed; (1) Expect threshold is 10; (2) Gap cost is Existence: 11 and Extension: 1; (3) The Matrix employed is BLOSUM62; (4) The filter for low complexity regions is "on."

The present invention also provides for functional fragments of the genes or gene products described herein. A fragment of a protein is characterized by a length (number of amino acids) that is less than the length of the full length mature form of the protein. A fragment, in the case of these sequences and all others provided herein, may be a part of the whole that is less than the whole. Moreover, a fragment ranges in size from a single nucleotide or amino acid within a polynucleotide or polypeptide sequence to one fewer nucleotide or amino acid than the entire polynucleotide or polypeptide sequence. Finally, a fragment is defined as any portion of a complete polynucleotide or polypeptide sequence that is intermediate between the extremes defined above.

For example, fragments of any of the proteins or enzymes disclosed herein or encoded by any of the genes disclosed herein can be 10 to 20 amino acids, 10 to 30 amino acids, 10 to 40 amino acids, 10 to 50 amino acids, 10 to 60 amino acids, 10 to 70 amino acids, 10 to 80 amino acids, 10 to 90 amino acids, 10 to 100 amino acids, 50 to 100 amino acids, 75 to 125 amino acids, 100 to 150 amino acids, 150 to 200 amino acids, 200 to 250 amino acids, 250 to 300 amino acids, 300 to 350, 350 to 375, or 350 to 400 amino acids. The fragments encompassed in the present subject matter comprise fragments that retain functional fragments. As such, the fragments preferably retain the binding domains that are required or are important for functional activity. Fragments can be determined or generated by using the sequence information herein, and the fragments can be tested for functional activity using standard methods known in the art.

For example, the encoded protein can be expressed by any recombinant technology known in the art and the binding activity of the protein can be determined.

As used herein a "biologically active" fragment is a portion of a polypeptide which maintains an activity of a full-length reference polypeptide. Biologically active fragments as used herein exclude the full-length polypeptide. Biologically active fragments can be any size as long as they maintain the defined activity. Preferably, the biologically active fragment maintains at least 10%, at least 50%, at least 75% or at least 90%, of the activity of the full length protein.

Amino acid sequence variants/mutants of the polypeptides of the defined herein can be prepared by introducing appropriate nucleotide changes into a nucleic acid defined herein, or by in vitro synthesis of the desired polypeptide. Such variants/mutants include, for example, deletions, insertions or substitutions of residues within the amino acid sequence. A combination of deletion, insertion and substitution can be made to arrive at the final construct, provided that the final peptide product possesses the desired activity and/or specificity.

Mutant (altered) peptides can be prepared using any technique known in the art. For example, a polynucleotide defined herein can be subjected to in vitro mutagenesis or DNA shuffling techniques as broadly described by Harayama (1998). Products derived from mutated/altered DNA can readily be screened using techniques described herein to determine if they possess, for example, lactate binding activity.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues. In some embodiments, a mutated or modified protein does not comprise any deletions or insertions. In various embodiments, a mutated or modified protein has less than about 10, 9, 8, 7, 6, 5, 4, 3, or 2 deleted or inserted amino acids.

Substitution mutants have at least one amino acid residue in the polypeptide molecule removed and a different residue inserted in its place. Sites may be substituted in a relatively conservative manner in order to maintain activity and/or specificity. Such conservative substitutions are shown in the table below under the heading of "exemplar) substitutions."

In certain embodiments, a mutant/variant polypeptide has only, or not more than, one or two or three or four conservative amino acid changes when compared to a naturally occurring polypeptide. Details of conservative amino acid changes are provided in the table below. As the skilled person would be aware, such minor changes can reasonably be predicted not to alter the activity of the polypeptide when expressed in a recombinant cell.

Exemplary Substitutions

| Original Residue | Exemplary Substitutions |
|---|---|
| Alanine (Ala) | Val; Leu; Ile; Gly |
| Arginine (Arg) | Lys |
| Asparagine (Asn) | Gln; His |
| Cysteine (Cys) | Ser |
| Glutamine (Gln) | Asn; His |
| Glutamic Acid (Glu) | Asp |
| Glycine (Gly) | Pro; Ala |
| Histidine (His) | Asn; Gln |
| Isoleucine (Ile) | Leu; Val; Ala |
| Leucine (Leu) | Ile; Val; Met; Ala; Phe |
| Lysine (Lys) | Arg |
| Methionine (Met) | Leu; Phe |
| Phenylalanine (Phe) | Leu; Val; Ala |
| Proline (Pro) | Gly |
| Serine (Ser) | Thr |
| Threonine (Thr) | Ser |
| Tryptophan (Trp) | Tyr |
| Tyrosine (Tyr) | Trp; Phe |
| Valine (Val) | Ile; Leu; Met; Phe; Ala |

Mutations can be introduced into a nucleic acid sequence such that the encoded amino acid sequence is altered by standard techniques, such as site-directed mutagenesis and PCR-mediated mutagenesis. Preferably, conservative amino acid substitutions are made at one or more predicted nonessential amino acid residues. A "conservative amino acid substitution" is one in which the amino acid residue is replaced with an amino acid residue having a similar side chain. Families of amino acid residues having similar side chains have been defined in the art. Certain amino acids have side chains with more than one classifiable characteristic. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, tryptophan, cysteine), nonpolar side chains (e.g., alanine, valine, leucine, isoleucine, proline, phenylalanine, methionine, tyrosine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a given polypeptide is replaced with another amino acid residue from the same side chain family. Alternatively, in another embodiment, mutations can be introduced randomly along all or part of a given coding sequence, such as by saturation mutagenesis, and the resultant mutants can be screened for given polypeptide biological activity to identify mutants that retain activity. Conversely, the invention also provides for variants with mutations that enhance or increase the endogenous biological activity. Following mutagenesis of the nucleic acid sequence, the encoded protein can be expressed by any recombinant technology known in the art and the activity/specificity of the protein can be determined. An increase, decrease, or elimination of a given biological activity of the variants disclosed herein can be readily measured by the ordinary person skilled in the art, i.e., by measuring the capability for binding a ligand and/or signal transduction.

In various embodiments, a polypeptide comprises mutations such that 1, 2, 3, 4, 5, 6, 7, 8, 9, or 10, or less than about 10, 9, 8, 7, 6, 5, 4, 3, or 2 amino acids is substituted with a cysteine and/or a lysine.

Polypeptides can be produced in a variety of ways, including production and recovery of natural polypeptides or recombinant polypeptides according to methods known in the art. In one embodiment, a recombinant polypeptide is produced by culturing a cell capable of expressing the polypeptide under conditions effective to produce the polypeptide, such as a host cell defined herein.

Key to the Sequence Listing

| SEQ ID NO | Sequence Name |
|---|---|
| 1 | ttLacBP1 [U.S. National Center for Biotechnology Information (NCBI) Accession No. YP_144032.1] |
| 2 | tsLacBP2 [U.S. National Center for Biotechnology Information (NCBI) Accession Nos. YP_004202714.1 and WP_015717434.1] |
| 3 | toLacBP3 [U.S. National Center for Biotechnology Information (NCBI) Accession Nos. YP_006972155.1 and WP_016329249.1] |
| 4 | tsLacBP4 [U.S. National Center for Biotechnology Information (NCBI) Accession Nos. YP_002514099.1 and WP_012638591.1] |
| 5 | rdLacBP5 [U.S. National Center for Biotechnology Information (NCBI) Accession Nos. YP_683924.1 and WP_011569849.1] |
| 6 | msLacBP6 [U.S. National Center for Biotechnology Information (NCBI) Accession Nos. YP_006556686.1 and WP_014869652.1] |
| 7 | tsLacBP7 [U.S. National Center for Biotechnology Information (NCBI) Accession Nos. YP_005654632.1 and WP_014515914.1] |
| 8 | maLacBP8 [U.S. National Center for Biotechnology Information (NCBI) Accession Nos. YP_005886720.1 and WP_003515468.1] |
| 9 | adLacBP9 [U.S. National Center for Biotechnology Information (NCBI) Accession No. YP_466099.1 and WP_011421944.1] |
| 10 | pgLacBP10 [U.S. National Center for Biotechnology Information (NCBI) Accession No. YP_004304976.1 and WP_013653981.1] |
| 11 | psLacBP11 [U.S. National Center for Biotechnology Information (NCBI) Accession No. YP_006522676.1 and WP_014851134.1] |
| 12 | rsLacBP12 [U.S. National Center for Biotechnology Information (NCBI) Accession No. RSP_3372] |
| 13 | fsLacBP13 [U.S. National Center for Biotechnology Information (NCBI) Accession Nos. YP_004603455.1 and WP_013886373.1] |
| 14 | taLacBP14 [U.S. National Center for Biotechnology Information (NCBI) Accession No. YP_003317968.1] |
| 15 | ttLacPB1 (with signal peptide replaced with M and a GGSHHHHHH at C-terminus) |
| 16 | tsLacBP2 (with signal peptide replaced with M and a GGSHHHHHH at C-terminus) |
| 17 | toLacBP3 (with signal peptide replaced with M and a GGSHHHHHH at C-terminus) |
| 18 | tsLacBP4 (with signal peptide replaced with M and a GGSHHHHHH at C-terminus) |
| 19 | rdLacBP5 (with signal peptide replaced with M and a GGSHHHHHH at C-terminus) |
| 20 | msLacBP6 (with signal peptide replaced with M and a GGSHHHHHH at C-terminus) |
| 21 | tsLacBP7 (with signal peptide replaced with M and a GGSHHHHHH at C-terminus) |
| 22 | maLacBP8 (with signal peptide replaced with M and a GGSHHHHHH at C-terminus) |
| 23 | adLacBP9 (with signal peptide replaced with M and a GGSHHHHHH at C-terminus) |
| 24 | pgLacBP10 (with signal peptide replaced with M and a GGSHHHHHH at C-terminus) |
| 25 | psLacBP11 (with signal peptide replaced with M and a GGSHHHHHH at C-terminus) |
| 26 | rsLacBP12 (with signal peptide replaced with M and a GGSHHHHHH at C-terminus) |
| 27 | fsLacBP13 (with signal peptide replaced with M and a GGSHHHHHH at C-terminus) |
| 28 | taLacBP14 (with signal peptide replaced with M and a GGSHHHHHH at C-terminus) |
| 29 | msLacBP6.10C (10C substitution mutant with signal peptide replaced with M and a GGSHHHHHH at C-terminus) |
| 30 | msLacBP6.12C (12C substitution mutant with signal peptide replaced with M and a GGSHHHHHH at C-terminus) |
| 31 | msLacBP6.43C (43C substitution mutant with signal peptide replaced with M and a GGSHHHHHH at C-terminus) |
| 32 | msLacBP6.49C (49C substitution mutant with signal peptide replaced with M and a GGSHHHHHH at C-terminus) |
| 33 | msLacBP6.50C (50C substitution mutant with signal peptide replaced with M and a GGSHHHHHH at C-terminus) |
| 34 | msLacBP6.68C (68C substitution mutant with signal peptide replaced with M and a GGSHHHHHH at C-terminus) |
| 35 | msLacBP6.169C (169C substitution mutant with signal peptide replaced with M and a GGSHHHHHH at C-terminus) |
| 36 | msLacBP6.170C (170C substitution mutant with signal peptide replaced with M and a GGSHHHHHH at C-terminus) |
| 37 | msLacBP6.171C (171C substitution mutant with signal peptide replaced with M and a GGSHHHHHH at C-terminus) |

-continued

| SEQ ID NO | Sequence Name |
|---|---|
| 38 | msLacBP6.187C (187C substitution mutant with signal peptide replaced with M and a GGSHHHHHH at C-terminus) |
| 39 | msLacBP6.188C (188C substitution mutant with signal peptide replaced with M and a GGSHHHHHH at C-terminus) |
| 40 | msLacBP6.192C (192C substitution mutant with signal peptide replaced with M and a GGSHHHHHH at C-terminus) |
| 41 | msLacBP6.196C (196C substitution mutant with signal peptide replaced with M and a GGSHHHHHH at C-terminus) |
| 42 | tsLacBP7.189C (189C substitution mutant with signal peptide replaced with M and a GGSHHHHHH at C-terminus) |
| 43 | maLacBP8.189C (189C substitution mutant with signal peptide replaced with M and a GGSHHHHHH at C-terminus) |
| 44 | adLacBP9.C191 (191C substitution mutant with signal peptide replaced with M and a GGSHHHHHH at C-terminus) |
| 45 | psLacBP11.195C (195C substitution mutant with signal peptide replaced with M and a GGSHHHHHH at C-terminus) |
| 46 | rsLacBP12.191C (191C substitution mutant with signal peptide replaced with M and a GGSHHHHHH at C-terminus) |
| 47 | fsLacBP13.188C (188C substitution mutant with signal peptide replaced with M and a GGSHHHHHH at C-terminus) |
| 48 | taLacBP14.186C (186C substitution mutant with signal peptide replaced with M and a GGSHHHHHH at C-terminus) |
| 49 | msLacBP6_187C_F68L (187C, 68L double substitution mutant with signal peptide replaced with M and a GGSHHHHHH at C-terminus) |
| 50 | msLacBP6_187C_F68M (187C, 68M double substitution mutant with signal peptide replaced with M and a GGSHHHHHH at C-terminus) |
| 51 | msLacBP6_187C_L70F (187C, 70F double substitution mutant with signal peptide replaced with M and a GGSHHHHHH at C-terminus) |
| 52 | msLacBP6_187C_L70I (187C, 70I double substitution mutant with signal peptide replaced with M and a GGSHHHHHH at C-terminus) |
| 53 | msLacBP6_187C_L70M (187C, 70M double substitution mutant with signal peptide replaced with M and a GGSHHHHHH at C-terminus) |
| 54 | msLacBP6_187C_P150A (187C, 150A double substitution mutant with signal peptide replaced with M and a GGSHHHHHH at C-terminus) |
| 55 | msLacBP6_187C_P150S (187C, 150S double substitution mutant with signal peptide replaced with M and a GGSHHHHHH at C-terminus) |
| 56 | msLacBP6_187C_D220E (187C, 220E double substitution mutant with signal peptide replaced with M and a GGSHHHHHH at C-terminus) |
| 57 | msLacBP6_187C_D220L (187C, 220L double substitution mutant with signal peptide replaced with M and a GGSHHHHHH at C-terminus) |
| 58 | msLacBP6_187C_D220N (187C, 220N double substitution mutant with signal peptide replaced with M and a GGSHHHHHH at C-terminus) |
| 59 | msLacBP6_187C_D220Q (187C, 220Q double substitution mutant with signal peptide replaced with M and a GGSHHHHHH at C-terminus) |
| 60 | msLacBP6_187C_D220S (187C, 220S double substitution mutant with signal peptide replaced with M and a GGSHHHHHH at C-terminus) |
| 61 | msLacBP6_187C_bZifC (187C substitution mutant, with bZif fusion, signal peptide replaced with M and a GGSHHHHHH at C-terminus) |
| 62 | msLacBP6_188C_bZifC (188C substitution mutant, with bZif fusion, signal peptide replaced with M and a GGSHHHHHH at C-terminus) |
| 63 | Exemplary ttLacBP1 expression sequence. |
| 64 | Exemplary tsLacBP2 expression sequence. |
| 65 | Exemplary toLacBP3 expression sequence. |
| 66 | Exemplary tsLacBP4 expression sequence. |
| 67 | Exemplary rdLacBP5 expression sequence. |
| 68 | Exemplary msLacBP6 expression sequence. |
| 69 | Exemplary tsLacBP7 expression sequence. |
| 70 | Exemplary maLacBP8 expression sequence. |
| 71 | Exemplary adLacBP9 expression sequence. |
| 72 | Exemplary pgLacBP10 expression sequence. |
| 73 | Exemplary psLacBP11 expression sequence. |

-continued

| SEQ ID NO | Sequence Name |
|---|---|
| 74 | Exemplary fsLacBP13 expression sequence. |
| 75 | Exemplary taLacBP14 expression sequence. |
| 76 | Exemplary msLacBP6.10C expression sequence. |
| 77 | Exemplary msLacBP6.12C expression sequence. |
| 78 | Exemplary msLacBP6.43C expression sequence. |
| 79 | Exemplary msLacBP6.49C expression sequence. |
| 80 | Exemplary msLacBP6.50C expression sequence. |
| 81 | Exemplary msLacBP6.68C expression sequence. |
| 82 | Exemplary msLacBP6.169C expression sequence. |
| 83 | Exemplary msLacBP6.170C expression sequence. |
| 84 | Exemplary msLacBP6.171C expression sequence. |
| 85 | Exemplary msLacBP6.187C expression sequence. |
| 86 | Exemplary msLacBP6.188C expression sequence. |
| 87 | Exemplary msLacBP6.192C expression sequence. |
| 88 | Exemplary msLacBP6.196C expression sequence. |
| 89 | Exemplary tsLacBP7.189C expression sequence. |
| 90 | Exemplary maLacBP8.189C expression sequence. |
| 91 | Exemplary adLacBP9.C191 expression sequence. |
| 92 | Exemplary psLacBP11.195C expression sequence. |
| 93 | Exemplary rsLacBP12.191C expression sequence. |
| 94 | Exemplary fsLacBP13.188C expression sequence. |
| 95 | Exemplary msLacBP6__187C__F68L expression sequence. |
| 96 | Exemplary msLacBP6__187C__F68M expression sequence. |
| 97 | Exemplary msLacBP6__187C__L70F expression sequence. |
| 98 | Exemplary msLacBP6__187C__L70I expression sequence. |
| 99 | Exemplary msLacBP6__187C__L70M expression sequence. |
| 100 | Exemplary msLacBP6__187C__P150A expression sequence. |
| 101 | Exemplary msLacBP6__187C__P150S expression sequence. |
| 102 | Exemplary msLacBP6__187C__D220E expression sequence. |
| 103 | Exemplary msLacBP6__187C__D220L expression sequence. |
| 104 | Exemplary msLacBP6__187C__D220N expression sequence. |
| 105 | Exemplary msLacBPb__187C__D220Q expression sequence. |
| 106 | Exemplary msLacBP6__187C__D220S expression sequence. |
| 107 | Exemplary msLacBP6__187C__bZifC expression sequence. |
| 108 | Exemplary msLacBP6__188C__bZifC expression sequence. |
| 109 | βZif |
| 110 | ZF-QNK |
| 111 | Hexahistidine Tag |
| 112 | Hexalysine Tag |
| 113 | GGSHHHHHH |
| 114 | *E. coli* GGBP (with signal peptide removed) |
| 115 | ttLacPB1 (with signal peptide replaced with M) |
| 116 | tsLacBP2 (with signal peptide replaced with M) |
| 117 | toLacBP3 (with signal peptide replaced with M) |
| 118 | tsLacBP4 (with signal peptide replaced with M) |
| 119 | rdLacBP5 (with signal peptide replaced with M) |
| 120 | msLacBP6 (with signal peptide replaced with M) |
| 121 | tsLacBP7 (with signal peptide replaced with M) |
| 122 | maLacBP8 (with signal peptide replaced with M) |
| 123 | adLacBP9 (with signal peptide replaced with M) |
| 124 | pgLacBP10 (with signal peptide replaced with M) |
| 125 | psLacBP11 (with signal peptide replaced with M) |
| 126 | rsLacBP12 (with signal peptide replaced with M) |
| 127 | fsLacBP13 (with signal peptide replaced with M) |
| 128 | taLacBP14 (with signal peptide replaced with M) |
| 129 | FTXYX (conserved sequence) |
| 130 | NXIHSK (conserved sequence) |
| 131 | RXPGG (conserved sequence) |
| 132 | LPGX (conserved sequence) |
| 133 | VGPAVN (conserved sequence) |
| 134 | QPVDL (conserved sequence) |
| 135 | Exemplary taLacBP14.186C expression sequence. |
| 136 | Exemplary rsLacBP12 expression sequence. |
| 137 | 2ZZV seed sequence (ttLacBP1) |
| 138 | ecTrx |
| 139 | Adaptor0 |
| 140 | Adaptor1.0 |
| 141 | Adaptor2.0a |
| 142 | Adaptor2.0b |
| 143 | Adaptor3.0 |
| 144 | Adaptor4.0 |
| 145 | Adaptor5.0 |
| 146 | Adaptor6.0 |
| 147 | Adaptor7 0 |
| 148 | Adaptor8.0 |
| 149 | Adaptor9.0 |
| 150 | Adaptor10.0 |
| 151 | Adaptor11.0 |
| 152 | Adaptor12.0 |
| 153 | Adaptor13.0 |
| 154 | Adaptor14.0 |
| 155 | Adaptor15.0 |
| 156 | Adaptor16.0 |

The terms "bZif" and "βZif" are used synonymously herein.

Exemplary amino acid sequences are listed below for convenience:

ttLacPB1

(SEQ ID NO: 15)

```
MFSPLAVAQARRYRWRIQTAWDAGTVGYSLFQKFTERVKELTDGQLEVQP

FPAGAVVGTFDMFDAVKTGVLDGMNPFTLYWAGRMPVTAFLSSYALGLDR

PDQWETWFYSLGGLDIARRAFAEQGLFYVGPVQHDLNIIHSKKPIRRFED

FKGVKLRVPGGMIAEVFAAAGASTVLLPGGEVYPALERGVIDAADFVGPA

VNYNLGFHQVAKYIIMGPPETPAIHQPVDLMDFTINLNRWRSLPKPLQER

FIAAVHEYSWIHYAGIQKANLEAWPKYRQAGVEVIRLSNEDVRKERRLAI

PIWFKWAKMDKYSREAFASQLEYMKGIGYVTDEELKGLSLGGSHHHHHH**
```

tsLacBP2

(SEQ ID NO: 16)

```
MFSPLAVAQAPRFRWRIQSAWDAGTVGYSLFQKFAERVKELTDGQIEIQT

FPAGAVVGTFDMFDAVKTGVLDGMHPFTLYWAGRMPVTAFLSSYPLGLDR

PDQWETWYYGLGGLELARKAYEEQGLFFVGPVQHDYNLIHSKKPIKSFED

FKGVKLRVPGGMIAEIFAAAGAATVLLPGGEVYPALERGVIDAADFVGPA

VNYNLGFHQVTKYIIMGPPETPAIHQPVDLADITININRWRALPRNLQER

FEAAVHEWSWIHYAGIQKANLETWPKYKAAGVQVIRLSTVDVRKFRRVAI

PIWFKWAKQDKYTREAFASQLEYMKALGYVTDADIRGLSLGGSHHHHHH**
```

tsLacBP3

(SEQ ID NO: 17)

```
MKSTRRQFLKKAAIGVAASSAFSPLAIAQAPRFRWRIQSAWDAGTVGYTL

FQRFAERVKELTDGQIEIQPFPAGAVVGTFDMFDAVKTGVLDGMHPFTLY

WAGRMPVTAFLSSYPLGLDRPDQWETWYYGLGGLELARKAYEEQGLAYIG

PVQHDYNLIHSKKPIKSFEEFKGVKLRVPGGMIAEIFAAAGAATVLLPGG

EVYPALERGVIDAADFVGPAVNYNLGFHQVTKYIIMGPPETPAIHQPVDL

ADITLNLNRWRAVPKNLQERFEAAVHEWSWVHYAGIQKANLEAWPKYRAA

GVQIIRLSTVDVRKFRRVAIPIWFKWAKQDKYAKEAFQSQLEYMKALGYV

TDVDLRGLSLGGSHHHHHH**
```

tsLacBP4

(SEQ ID NO: 18)

```
MTARGVRWRMQSAWQPGTIGYRTFETWARSIQELTSGELSIEPFPAGAVA

GTFEMADAVRSGVLDGMNWFTVYWPGKMPAGVFMSAYPMALSLPHHWDMM

FDSFGGRQIVDELYDRQGLVFLGHVQHDLNLIHSKVPLRSTDDFRGKRIR
```

-continued

FPGGIIAETFAKVGVRTTLLPGGDVYPALERGTIDAADFVGPAVNYDLGF
HQVADYIIMGPPSTPALHQPVDLMDISVNKRSWSRISEHTQKLMYKFVKA
YSAEHFAAIQKANHEAWPKYKEAGVEVIHLSEEDAARFREAAIPLWFEWA
NKDRDAARLFKVHLEVMQDPSVAVITPDDIKDYKLNFGGSHHHHHH** rdLacBP5

(SEQ ID NO: 19)
MAAGEGTTWKIQTSHTGGIGLATFKDWASSIEEKTGGELAFTAFGANDVV
GDFQLYDAVKNGVLDAVNPFTIYAQGIIPAATFLTSYPLGLRNPHEWDVF
FYSLGGLEIARELYAAQGMKFVGPVHHGPNIIHSKVPIRSIDDFAGLKMR
MPGGMVAEVFSEIGAETTVLPGSEIFPALEKGTIDAADFVGPAVNYALGF
SQVTNYISMGPAGFMSLYQPVDLMDITVGQTAWDALSPQMQQFVEMETHV
YSDMHHAAIQKADQEAWAKFEADGTEVTRLSQDDVELMTEVAVPIWFDYA
NRDKDAARVFKIQLDYMMSGSLGYVTPEQIEGLTLNLGGSHHHHHH** msLacBP6

(SEQ ID NO: 20)
MATTWKIQSVWDAGTVGYDLFKEWCDGMEEKTGGELKFTCFPAKAVAADN
NGLFDAVRNGVLQGMNPFTLYWSGKIPASVFLSSYPAGPDQPHQWDTMFY
SLGMLEKTREIYKKFGLFYVGPIQHDANIIHSKQPINSLDDLKGLKMRLP
GGMVAEVFAKFGVAAVSLPGSDIFPALEKGTIDAADYVGPAVNWELGFSQ
VTKYILMGPPGIMSVYQPVDLMDLTVNLRAWNALDPKLQQIVEDEVRIYS
QKHYLAIQKRNIEAMKKFEAAGTTVTRLSQEDLQEFRRAAIPIWYSWANK
DEDAREIFDMQLEYMMNDTVGYITEDDIKGMNGGSHHHHHH tsLacBP7

(SEQ ID NO: 21)
MQAPRFRWRIQSAWDAGTVGYTLFQRFAERVKELTDGQIEIQTFPAGAVV
GTFDMFDAVKTGVLDGMHPFTLYWAGRMPVTAFLSSYPLGLDRPDQWETW
YYALGGLDLARRAFEEQGLFYVGPVQHDYNLIHSKKPIKSFEDFKGVKLR
VPGGMIADVFSAAGAATVLLPGGEVYPALERGVIDAADFVGPAVNYNLGF
HQVTKYIIMGPPETPAIHQPVDLADITLNLSRWRAVPKNLQERFEAAVHE
WSWIHYAGIQKANLETWPKYKAAGVQIIRLTTVDVRKFRRVAIPIWFKWA
KQDKYAREAFASQLEYMKALGYVTDADVRGLSLGGSHHHHHH*** maLacBP8

(SEQ ID NO: 22)
MQAATTWKIQSTWDAGTVGYTLFEEWAKSIEAKSGGELKFQAPPAKAVAA
DNNALFDAVRNGVLQGMNPFTLYWAGKIPASVFLSSYPAGPDQPHQWDTM
FYSMGMLEKTREIYKKFGLFYVGPIQHDANIIHSKQPVNSLDDLKGMKIR
VPGGMVAEVFQQFGVSTVSLPGSDIFPALEKGTIDAADFVGPAVNYELGF
SQVTDYIIFGPPGVMSIYQPVDLMDLTVSLRAWNSISPELQQLVEDEVRI
YSQKHYLAIQARNIEAMEKFKADGDTVTRLSQEDLETWRKAAIPIWFNWA
NKNDDARAILDIQLKYMMNDTVGYITEEDIKGFGGSHHHHHH*** adLacBP9

(SEQ ID NO: 23)
MQAPITLRFQSTWPQKDIFHEFALDYAKKVNEMSGGRLKIEVLAAGSVVK
AFDLLDAVSKGTLDGGHGVVAYWYGKNTALALWGSGPAFGMDPNMVLAWH
HYGGGRQLLEEIYRSLNLDVVSLMYGPMPTQPLGWFKQKPIAKPDDMKGL
KFRTVGLSIDIFNGLGAAVNALPGAEIVPAMDRGLLDAAEFNNASSDRVL

-continued

GFPDVSKIAMLQSFHQASEQFEILFNGKRFQALPADLKSIISIAAQAASA
DMSWKAIDRYSSDYFEMRDKQGVKFYSTRPEILKRQLEIWDQVMEKRAAE
NPTFKKVLESQRRFAQRAARWQNDTNVDFKMAYNHFFGGKKKATGGSHHH
HHH** pgLacBP10

(SEQ ID NO: 24)
MQEAVEWRMQALWDAGTTPFEFEKKFVERVGELTEGRFKITLYSAGQIVP
ANQAFDAVRSGAFEMMKTFDGYEAGKIPAFAFTSTIPFGFPQSDQYEAWF
YELGGLDLAREAYAKGGLFYIAPTVYGEEPMHSTVKIESIADMAGKKGRF
VGLASAVMADLGVAVSPLATAEVYTALEKGLIDFADRGDLTANYEAGLGE
VAKFIILPGVHQPTTATSYVANQAAYQKLPDGFKAALAVAAREISGSLRQ
HILVQDMEVLTKYKDQGVEVVRLDAADIAAARAKAVESWEKATKGDELAT
RVLKGQVDFMTSLGLLGGSHHHHHH*** psLacBP11

(SEQ ID NO: 25)
MQQAAGEPAKTYHWKMVTAWPKNYPGLGTSAERLAERVNAMSGGRLTIKV
YAAGELVPALEVFDAVSRGTAELGHGASYYWKGKVPTAQFFTSVPFGLST
SEMNAWLSKGGGQAFWDEAYAPFGVKPLVIGNTGMQMGGWYNKEINSLTD
LKGLKIRMPGLGGEVLSRLGATTVNLPGGEVFTALQTGAIDATDWVSPYN
DLAFGLHKAARYYYYPGWQEPQAVLELLINQKAFDSLPADLQAIVTEASL
AASRDMHDDYVYNNALALEQLKQQGTELKRFPDEVLAAMREQSDLILGEL
AAQSELNGRIWASMKAFQAQVEPMHEISEKELYNWRGGSHHHHHH*** rsLacBP12

(SEQ ID NO: 26)
MQAPLVMKMQTSWPASDIWMDFAREYVTRVEEMSGGRIKVDLLPAGAVVG
AFQVMDAVHDGVIDASHSVSAYWYGKSKAASFFGTGPVFGGSATTMLGWF
YQGGGQDLYRELTQDILGMNIVGFYGFPMPAQPFGWFKTEVNGVADIQGF
KYRTVGLAADLLQAMGMSVAQLPGGEIVPAMERGVIDAFEFNNPSSDMRF
GAQDVAKNYYLSSYHQASESFEYTFNRDFYEDLDPDLQAILKYAVEAAST
SNTALALRQYSADLATLAAENGVAVHRTPKDILSGQLEAWDKLIVDLEAD
EFFKKVLDSQRAWVEQVSYYELMNAADLGLAYEHHFPGKLKLGGSHHHH
H*** fsLacBP13

(SEQ ID NO: 27)
MEKKIRWKLAMTWGPTLHPLSDTAEHMAEIVKELSDGNFVINIDASNVHK
APFGIFDMVKLGQYEMGHTASYYYKGKNIAFLPLTTMPFGMTAPEQYAWF
YYGGGLELMQEAYTKHGMLAFPGGNTGNQMGGWFTKEINSLDDLKGLKMR
IPGFAGQIMSKLGVTVTNIPPGELYTALERGTVDAVEWTGPGMDINMGFH
KIAKYYYTGWHEPGSEVEFLINEKEYNKLPEKYKKILKIAMKTAAYDMYI
QSYEMNAEAWQQMKEKYPDIKVKVFPEEVLKEMKTAYDNLVASYEKESPM
FKKIMESKRAYLDKVRDWTHISDYLYLKSTSESNLNGGSHHHHHH*** taLacBP14

(SEQ ID NO: 28)
MEEYKFKMATFYLKGDSAFDVIDHFRQLVWKKTGGKVRIDAFQAGELGFP
VTEILEATSRGVVEMSIFYPNYKAAQDPVMALAGGRPGPMFDLRDQKAQV

-continued

DATKDLLERSFGRFGVRYIAPMVYGEPEILVSRRPMSSLKDLKGRIFRAS

GMAAEFYTAIGAQAMMLPAGELYQALQLGTIDGLEWTDYTANYKLGFHEV

AKNVLEPTKGVNLHSEATVHAFLVVNPKVWEKLPKEHQKAIQEAADEAYK

WGADHLAKLNKTYKDKWIKAGAKVTQLPKEDQDKVIEVSAKILSGYSAKS

PDAKEYARRLVELWKKLGYTKWSDALAKQIKGGSHHHHHH*** msLacBP6 Cysteine Scans msLacBP6.10C (SEQ ID NO: 29)

MATTWKIQSCWDAGTVGYDLFKEWSDGMEEKTGGELKFTAFPAKAVAADN

NGLFDAVRNGVLQGMNPFTLYWSGKIPASVFLSSYPAGPDQPHQWDTMFY

SLGMLEKTREIYKKFGLFYVGPIQHDANIIHSKQPINSLDDLKGLKMRLP

GGMVAEVFAKFGVAAVSLPGSDIFPALEKGTIDAADYVGPAVNWELGFSQ

VTKYILMGPPGIMSVYQPVDLMDLTVNLRAWNALDPKLQQIVEDEVRIYS

QKHYLAIQKRNIEAMKKFEAAGTTVTRLSQEDLQEFRRAAIPIWYSWANK

DEDAREIFDMQLEYMMNDTVGYITEDDIKGMNGGSHHHHHH** msLacBP6.12C (SEQ ID NO: 30)

MATTWKIQSVWCAGTVGYDLFKEWSDGMEEKTGGELKFTAFPAKAVAADN

NGLFDAVRNGVLQGMNPFTLYWSGKIPASVFLSSYPAGPDQPHWQDTMFY

SLGMLEKTREIYKKFGLFYVGPIQHDANIIHSKQPINSLDDLKGLKMRLP

GGMVAEVFAKFGVAAVSLGSDIFPALEKGTIDAADYVGPAVNWELGLFSQ

VTKYILMGPPGIMSVYQPVDLMDLTVNLRAWNALDPKLQQIVEDEVRIYS

QKHYLAIQKRNIEAMKKFEAAGTTVTRLSQEDLQEFRRAAIPIWYSWANK

DEDAREIFDMQLEYMMNDTVGYITEDDIKGMNGGSHHHHHH** msLacBP6.43C (SEQ ID NO: 31)

MATTWKIQSVWDAGTVGYDLFKEWSDGMEEKTGGELKFTAFPCKAVAADN

NGLFDAVRNGVLQGMNPFTLYWSGKIPASVFLSSYPAGPDQPHQWDTMFY

SLGMLEKTREIYKKFGLFYVGPIQHDANIIHSKQPINSLDDLKGLKMRLP

GGMVAEVFAKFGVAAVSLPGSDIFPALEKGTIDAADYVGPAVNWELGFSQ

VTKYILMGPPGIMSVYQPVDLMDLTVNLRAWNALDPKLQQIVEDEVRIYS

QKHYLAIQKRNIEAMKKFEAAGTTVTRLSQEDLQEFRRAAIPIWYSWANK

DEDAREIFDMQLEYMMNDTVGYITEDDIKGMNGGSHHHHHH** msLacBP649C (SEQ ID NO: 32)

MATTWKIQSVWDAGTVGYDLFKEWSDGMEEKTGGELKFTAFPAKAVAACN

NGLFDAVRNGVLQGMNPFTLYWSGKIPASVFLSSYPAGPDQPHQWDTMFY

SLGMLEKTREIYKKFGLFYVGPIQHDANIIHSKQPINSLDDLKGLKMRLP

GGMVAEVFAKFGVAAVSLPGSDIFPALEKGTIDAADYVGPAVNWELGFSQ

VTKYILMGPPGIMSVYQPVDLMDLTVNLRAWNALDPKLQQIVEDEVRIYS

QKHYLAIQKRNIEAMKKFEAAGTTVTRLSQEDLQEFRRAAIPIWYSWANK

DEDAREIFDMQLEYMMNDTVGYITEDDIKGMNGGSHHHHHH** msLacBP6.50C (SEQ ID NO: 33)

MATTWKIQSVWDAGTVGYDLFKEWSDGMEEKTGGELKFTAFPAKAVAADC

NGLFDAVRNGVLQGMNPFTLYWSGKIPASVFLSSYPAGPDQPHQWDTMFY

-continued

SLGMLEKTREIYKKFGLFYVGPIQHDANIIHSKQPINSLDDLKGLKMRLP

GGMVAEVFAKFGVAAVSLPGSDIFPALEKGTIDAADYVGPAVNWELGFSQ

VTKYILMGPPGIMSVYQPVDLMDLTVNLRAWNALDPKLQQIVEDEVRIYS

QKHYLAIQKRNIEAMKKEEAAGTTVTRLSQEDLQEERRAAIPIWYSWANK

DEDAREIFDMQLEYMMNDTVGYITEDDIKGMNGGSHHHHHH** msLacBP6.68C (SEQ ID NO: 34)

MATTWKIQSVWDAGTVGYDLFKEWSDGMEEKTGGELKFTAFPAKAVAADN

NGLFDAVRNGVLQGMNPCTLYWSGKIPASVFLSSYPAGPDQPHQWDTMFY

SLGMLEKTREIYKKFGLFYVGPIQHDANIIHSKQPINSLDDLKGLKMRLP

GGMVAEVFAKFGVAAVSLPGSDIFPALEKGTIDAADYVGPAVNWELGESQ

VTKYILMGPPGIMSVYQPVDLMDLTVNLRAWNALDPKLQQIVEDEVRIYS

QKHYLAIQKRNIEAMKKFEAAGTTVTRLSQEDLQEFRRAAIPIWYSWANK

DEDAREIFDMQLEYMMNDTVGYITEDDIKGMNGGSHHHHHH** msLacBP6.169C (SEQ ID NO: 35)

MATTWKIQSVWDAGTVGYDLFKEWSDGMEEKTGGELKFTAFPAKAVAADN

NGLFDAVRNGVLQGMNPFTLYWSGKIPASVFLSSYPAGPDQPHQWDTMFY

SLGMLEKTREIYKKFGLFYVGPIQHDANIIHSKQPINSLDDLKGLKMRLP

GGMVAEVFAKFGVAAVSLCGSDIFPALEKGTIDAADYVGRAVNWELGESQ

VTKYILMGPPGIMSVYQRVDLMDLTVNLRAWNALDPKLQQIVEDEVRIYS

QKHYLAIQKRNIEAMKKFEAAGTTVTRLSQEDLQEFRRAAIPIWYSWANK

DEDAREIFDMQLEYMMNDTVGYITEDDIEKGMNGGSHHHHHH** msLacBP6.170C (SEQ ID NO: 36)

MATTWKIQSVWDAGTVGYDLFKEWSDGMEEKTGGELKFTAFPAKAVAADN

NGLFDAVRNGVLQGMNPFTLYWSGKIPASVFLSSYPAGPDQPHQWDTMFY

SLGMLEKTREIYKKFGLFYVGPIQHDANIIHSKQPINSLDDLKGLKMRLP

GGMVAEVFAKFGVAAVSLPCSDIFPALEKGTIDAADYVGPAVNWELGFSQ

VTKYILMGPPGIMSVYQPVDLMDLTVNLRAWNALDPKLQQIVEDEVRIYS

QKHYLAIQKRNIEAMKKFEAAGTTVTRLSQEDLQEFRRAAIPIWYSWANK

DEDAREIFDMQLEYMMNDTVGYITEDDIKGMNGGSHHHHHH** msLacBP6.171C (SEQ ID NO: 37)

MATTWKIQSVWDAGTVGYDLFKEWSDGMEEKTGGELKFTAFPAKAVAADN

NGLFDAVRNGVLQGMNPFTLYWSGKIPASVFLSSYPAGPDQPHQWDTMFY

SLGMLEKTREIYKKFGLFYVGPIQHDANIIHSKQPINSLDDLKGLKMRIT

GGMVAEVFAKFGVAAVSLPGCDIFPALEKGTIDAADYVGPAVNWELGFSQ

VTKYILMGPPGIMSVYQPVDLMDLTYNLRAWNALDPKLQQIVEDEVRIYS

QKHYLAIQKRNIEAMKKFEAAGTTVTRLSQEDLQEFRRAAIPIWYSWANK

DEDAREIFDMQLEYMMNDTVGYITEDDIKGMNGGSHHHHHH** msLacBP6.187C (SEQ ID NO: 38)

MNTTWKIQSVWDAGTVGYDLFKEWSDGMEEKTGGELKFTAFPAKAVAADN

NGLFDAVRNGVLQGMNPFTLYWSGKIPASVFLSSYPAGPDQPHQWDTMFY

SLGMLEKTREIYKKFGLFYVGPIQHDANIIHSKQPINSLDDLKGLKMRLP

GGMVAEVFAKFGVAAVSLPGSDIFPALEKGTIDAADCVGPAVNWELGFSQ

VTKYILMGPPGIMSVYQPVDLMDLTVNLRAWNALDPKLQQIVEDEVRIYS

QKHYLAIQKRNIEAMKKFEAAGTTVTRLSQEDLQEFRRAAIPIWYSWANK

DEDAREIFDMQLEYMMNDTVGYITEDDIKGMNGGSHHHHHH** msLacBP6.188C
(SEQ ID NO: 39)
MATTWKIQSVWDAGTVGYDLFKEWSDGMEEKTGGELKFTAFPAKAVAADN

NGLFDAVRNGVLQGMNPFTLYWSGKIPASVFLSSYPAGPDQPHQWDTMFY

SLGMLEKTREIYKKFGLFYVGPIQHDANIIHSKQPINSLDDLKGLKMRLP

GGMVAEVFAKFGVAAVSLPGSDIFPALEKGITDAADYCGPAVNWELGFSQ

VTKYILMGPPGIMSVYQPVDLMDLTVNLRAWNALDPKLQQIVEDEVRIYS

QKHYLAIQKRNIEAMKKFEAAGTTVTRLSQEDLQEFRRAAIPIWYSWANK

DEDAREIFDMQLEYMMNDTYITEDDIKGMNGGSHHHHHH** msLacBP6.192C
(SEQ ID NO: 40)
MATTWKIQSVWDAGTVGYDLFKEWSDGMEEKTGGELKFTAFPAKAVAADN

NGLFDAVRNGVLQGMNPFTLYWSGKIPASVFLSSYPAGPDQPHQWDTMFY

SLGMLEKTREIYKKFGLFYVGPIQHDANIIHSKQPINSLDDLKGLKMRLP

GGMVAEVFAKFGVAAVSLPGSDIFPALEKGTIDAADYVGPACNWELGFSQ

VTKYILMGPPGIMSVYQPVDLMDLTVNLRAWNALDPKLQQIVEDEVRIYS

QKHYLAIQKRNIEAMKKFEAAGTTVTRLSQEDLQEFRRAAIPIWYSWANK

DEDAREIFDMQLEYMMNDTVGYITEDDIKGMNGGSHHHHHH** msLacBP6.196C
(SEQ ID NO: 41)
MATTWKIQSVWDAGTVGYDLFKEWSDGMEEKTGGELKFTAFPAKAVAADN

NGLFDAVRNGVLQGMNPFTLYWSGKIPASVFLSSYPAGPDQPHQWDTMFY

SLGMLEKTREIYKKFGLFYVGPIQHDANIIHSKQPINSLDDLKGLKMRLP

GGMVAEVFAKFGVAAVSLPGSDIFPALEKGTIDAADYVGPAVNWECGFSQ

VTKYILMGPPGIMSVYQPVDLMDLTVNLRAWNALDPKLQQIVEDEVRIYS

QKHYLAIQKRNIEAMKKFEAAGTTVTRLSQEDLQEFRRAALPIWYSWANK

DEDAREIFDMQLEYMMNDTVGYITEDDIKGMNGGSHHHHHH**

Additional Cysteine Scans
tsLacBP7.189C
(SEQ ID NO: 42)
MQAPRFRWRIQSAWDAGTVGYTLFQRFAERVKELTDGQIEIQTFPAGAVV

GTFDMFDAVKTGVLDGMHPFTLYWAGRMPVTAFLSSYPLGLDRPDQWETW

YYALGGLDLARRAFEEQGLFYVGPVQHDYNLIHSKKPIKSFEDFKGVKLR

VPGGMIADVFSAAGAATVLLPGGEVYPALERGVIDAADCVGPAVNYNLGF

HQVTKYIIMGPPETPAIHQPVDLADITLNLSRWRAVPKNLQERFEAAVHE

WSWIHYAGIQKANLETWPKYKAAGVQIIRLTTVDVRKFRRVAIPIWFKWA

KQDKYAREAFASQLEYMKALGYVTDADVRGLSLGGSHHHHHH*** maLacBP81 89C
(SEQ ID NO: 43)
MQAATTWKIQSTWDAGTVGYTLFEEWAKSIEAKSGGELKFQAFPAKAVAA

DNNALFDAVRNGVLQGMNPFTLYWAGKIPASVFLSSYPAGPDQPHQWDTM

FYSMGMLEKTREIYKKFGLFYVGPIQHDANIIHSKQPVNSLDDLKGMKIR

VPGGMVAEVFQQFGVSTVSLPGSDIFPALEKGTIDAADCVGPAVNYELGF

SQVTDYIIFGPPGVMSIYQPVDLMDLTVSLRAWNSISPELQQLVEDEVRI

YSQKHYLAIQARNIEAMEKFKADGDTVTRLSQEDLETWRKAAIPIWFNWA

NKNDDARAILDIQLKYMMNDTVGYITEEDIKGFGGSHHHHHH*** adLacBP9.C191
(SEQ ID NO: 44)
MQAPITLRFQSTWPQKDIFHEFALDYAKKVNEMSGGRLKIEVLAAGSVVK

AFDLLDAVSKGTLDGGHGVVAYWYGKNTALALWGSGPAFGMDPNMVLAWH

HYGGGRQLLEEIYRSLNLDVVSLMYGPMPTQPLGWFKQKPIAKPDDMKGL

KFRTVGLSIDIFNGLGAAVNALPGAEIVPAMDRGLLDAAECNNASSDRVL

GFPDVSKIAMLQSFHQASEQFEILFNGKRFQALPADLKSIISIAAQAASA

DMSWKAIDRYSSDYFEMRDKQGVKFYSTRPEILKRQLEIWDQVMEKRAAE

NPTFKKVLESQRRFAQRAARWQNDTNVDFKMAYNHFFGGKKKATGGSHHH

HHH*** psLacBP11.195C
(SEQ ID NO: 45)
MQQAAGEPAKTYHWKMVTAWPKNYPGLGTSAERLAERVNAMSGGRLTIKV

YAAGELVPALEVFDAVSRGTAELGHGASYYWKGKVPTAQFFTSVPFGLST

SEMNAWLSKGGGQAFWDEAYAPFGVKPLVIGNTGMQMGGWYNKEINSLTD

LKGLKIRMPGLGGEVLSRLGATTVNLPGGEVFTALQTGAIDATDCVSPYN

DLAFGLHKAARYYYYPGWQEPQAVLELLINQKAFDSLPADLQAIVTEASL

AASRDMHDDYVYNNALALEQLKQQGTELKRFPDEVLAAMREQSDLILGEL

AAQSELNGRIWASMKAFQAQVEPMHEISEKELYNWRGGSHHHHHH*** rsLacBP12.1.91C
(SEQ ID NO: 46)
MQAPLVMKMQTSWPASDIWMDFAREYVTRVEEMSGGRIKVDLLPAGAVVG

AFQVMDAVHDGVIDASHSVSAYWYGKSKAASFFGTGPVFGGSATTMLGWF

YQGGGQDLYRELTQDILGMNIVGFYGFPMPAQPFGWFKTEVNGVADIQGF

KYRTVGLAADLLQAMGMSVAQLPGGEIVPAMERGVIDAFECNNPSSDMRF

GAQDVAKNYYLSSYHQASESFEYTFNRDFYEDLDPDLQAILKYAVEAAST

SNTALALRQYSADLATLAAENGVAVHRTPKDILSGQLEAWDKLIVDLEAD

EFFKKVLDSQRAWVEQVSYYELMNAADLGLAYEHHFPGKLKLGGSHHHHH

H*** fsLad3P13.188C
(SEQ ID NO: 47)
MEKKIRWKLAMTWGPTLHPLSDTAEHMAEIVKELSDGNFVINIDASNVHK

APFGIFDMVKLGQYEMGHTASYYYKGKNIAFLPLTTMPFGMTAPEQYAWF

YYGGGLELMQEAYTKHGMLAFPGGNTGNQMGGWFTKEINSLDDLKGLKMR

IPGFAGQIMSKLGNTVTNIPPGELYTALERGTVDAVECTGPGMDINMGFH

KIAKYYYTGWHEPGSEVEFLINEKEYNKLPEKYKKILKIAMKTAAYDMYI

QSYEMNAEAWQQMKEKYPDIKVKVFPEEVLKEMKTAYDNLVASYEKESPM

FKKIMESKRAYLDKVRDWTHISDYLYLKSTSESNLNGGSHHHHHH***

-continued taLacBP14.186C (SEQ ID NO: 48)

MEEYKFKMATFYLKGDSAFDVIDHFRQLVWKKTGGKVRIDAFQAGELGFP

VTEILEATSRGVVEMSIFYPNYKAAQDPVMALAGGRPGPMFDLRDQKAQV

DATKDLLERSFGRFGVRYIAPMVYGEPEILVSRRPMSSLKDLKGRIFRAS

GMAAEFYTAIGAQAMMLPAGELYQALQLGTIDGLECTDYTANYKLGFHEV

AKNVLEPTKGVNLHSEATVHAFLVVNPKVWEKLPKEHQKAIQEAADEAYK

WGADHLAKLNKTYKDKWIKAGAKVTQLPKEDQDKVIEVSAKILSGYSAKS

PDAKEYARRLVELWKKLGYTKWSDALAKQIIKGGSHHHHHH*** msLacBP6 187C Affinity-Tuning Mutations msLacE3P6_187C F68L (SEQ ID NO: 49)

MATTWKIQSVWDAGTVGYDLFKEWCDGMEEKTGGELKFTCFPAKAVNADN

NGLFDAVRNGVLQGMNPLTLYWSGKIPASVFLSSYPAGPDQPHQWDTMFY

SLGMLEKTREIYKKFGLFYVGPIQHDANIIHSKQPINSLDDLKGLKMRLP

GGMVAEVFAKFGVAAVSLPGSDIFPALEKGITDAADCVGPAVNWELGFSQ

VTKYILMGYPGIMSVYQPVDLMDLTVNLRAWNALDPKLQQIVEDEVRIYS

QKHYLAIQKRNIEAMKKFEAAGTTVTRLSQEDLQEFRRAAIPIWYSWANK

DEDAREIFDMQLEYMMNDTVGYITEDDIKGMNGGSHHHHHH** msLacBP6_187C_F68M (SEQ ID NO: 50)

MATTWKIQSVWDAGTVGYDLFKEWCDGMEEKTGGELKFTCFPAKAVAADN

NGLFDAVRNGVLQGMNPMTLYWSGKIPASVFLSSYPAGPDQPHQWDTMFY

SLGMLEKTREIYKKFGLFYVGPIQHDANIIHSKQPINSLDDLKGLKMRLP

GGMVAEVFAKFGVAAVSLPGSDIFPALEKGTIDAADCVGPAVNWELGFSQ

VTKYILMGPPGIMSVYQPVDLMDLTVNLRAWNALDPKLQQIVEDEVRIYS

QKHYLAIQKRNIEAMKKFEAAGTTVTRLSQEDLQEFRRAAIPIWYSWANK

DEDAREIFDMQLEYMMNDTVGYITEDDIKGMNGGSHHHHHH** msLacBP6_187C_L70F (SEQ ID NO: 51)

MATTWKIQSVWDAGTVGYDLFKEWCDGMEEKTGGELKFTCFPAKAVAADN

NGLFDAVRNGVLQGMNPFTFYWSGKIPASVFLSSYPAGPDQPHQWDTMFY

SLGMLEKTREIYKKFGLFYVGPIQHDANIIHSKQPINSLDDLKGLKMRLP

GGMVAEVFAKFGVAAVSLPGSDIFPALEKGTIDAADCVGPAVNWELGFSQ

VTKYILMGPPGIMSVYQPVDLMDLTVNLRAWNALDPKLQQIVEDEVRIYS

QKHYLAIQKRNIEAMKKFEAAGTTVTRLSQEDLQEFRRAAIPIWYSWANK

DEDAREIFDMQLEYMMNDTVGYITEDDIKGMNGGSHHHHHH** msLacBP6_187C_L70I (SEQ ID NO: 52)

MATTWKIQSVWDAGTVGYDLFKEWCDGMEEKTGGELKFTCFPAKAVAADN

NGLFDAVRNGVLQGMNPFTIYWSGKIPASVFLSSYPAGPDQPHQWDTMFY

SLGMLEKTREIYKKFGLFYVGPIQHDANIIHSKQPINSLDDLKGLKMRLP

GGMVAEVFAKFGVAAVSLPGSDIFPALEKGTIDAADCVGPAVNWELGFSQ

VTKYILMGPPGIMSVYQPVDLMDLTVNLRAWNALDPKLQQIVEDEVRIYS

QKHYLAIQKRNIEAMKKFEAAGTTVTRLSQEDLQEFRRAAIPIWYSWANK

DEDAREIFDMQLEYMMNDTVGYITEDDIKGMNGGSHHHHHH**

-continued msLacBP6_187C_L70M (SEQ ID NO: 53)

MATTWKIQSVWDAGTVGYDLFKEWCDGMEEKTGGELKFTCFPAKAVAADN

NGLFDAVRNGVLQGMNPFTMYWSGKIPASVFLSSYPAGPDQPHQWDTMFY

SLGMLEKTREIYKKFGLFYVGPIQHDANIIHSKQPINSLDDLKGLKMRLP

GGMVAEVFAKFGVAAVSLPGSDIFPALEKGTIDAADCVGPAVNWELGFSQ

VTKYILMGPPGIMSVYQPVDLMDLTVNLRAWNALDPKLQQIVEDEVRIYS

QKHYLAIQKRNIEAMKKFEAAGTTVTRLSQEDLQEFRRAAIPIWYSWANK

DEDAREIFDMQLEYMMNDTVGYITEDDIKGMNGGSHHHHHH** msLacBP6_187C_P150A (SEQ ID NO: 54)

MATTWKIQSVWDAGTVGYDLFKEWCDGMEEKTGGELKFTCFPAKAVAADN

NGLFDAVRNGVLQGMNPFTLYWSGKIPASVFLSSYPAGPDQPHQWDTMFY

SLGMLEKTREIYKKFGLFYVGPIQHDANIIHSKQPINSLDDLKGLKMRLA

GGMVAEVFAKEGVAAVSLPGSDIFPALEKGITDAADCVGPAVNWELGFSQ

VTKYILMGPPGIMSVYQPVDLMDLTVNLRAWNALDPKLQQIVEDEVRIYS

QKHYLAIQKRNIEAMKKFEAAGITVTRLSQEDLQEFRRAAIPIWYSWANK

DEDAREIFDMQLEYMMNDTVGYITEDDIKGMNGGSHHHHHH* msLacBP6_187C_P150S (SEQ ID NO: 55)

MATTWKIQSVWDAGTVGYDLFKEWCDGMEEKTGGELKFTCFPAKAVAADN

NGLFDAVRNGVLQGMNPFTLYWSGKIPASVFLSSYPAGPDQPHQWDTMFY

SLGMLEKTREIYKKFGLFYVGPIQHDANIIHSKQPINSLDDLKGLKMRLS

GGMVAEVFAKFGVAAVSLPGSDIFPALEKGTIDAADCVGPAVNWELGESQ

VTKYILMGPPGIMSVYQPVDLMDLTVNLRAWNALDPKLQQIVEDEVRIYS

QKHYLAIQKRNIEAMKKFEAAGTTVTRLSQEDLQEFRRAAIPIWYSWANK

DEDAREIFDMQLEYMMNDTVGYITEDDIKGMNGGSHHHHHH** msLacBP6_187C_D220E (SEQ ID NO: 56)

MATTWKIQSVWDAGTVGYDLFKEWCDGMEEKTGGELKFTCFPAKAVAADN

NGLEDAVRNGVLQGMNPFTLYWSGKIPASVFLSSYPAGPDQPHQWDTMFY

SLGMLEKTREIYKKFGLFYVGPIQHDANIIHSKQPINSLDDLKGLKMRLP

GGMVAEVFAKFGVAAVSLPGSDIFPALEKGTIDAADCVGPAVNWELGFSQ

VTKYILMGPPGIMSVYQPVELMDLTVNLRAWNALDPKLQQIVEDEVRIYS

QKHYLAIQKRNIEAMKKFEAAGTTVTRLSQEDLQEFRRAAIPIWYSWANK

DEDAREIFDMQLEYMMNDTVGYITEDDIKGMNGGSHHHHHH** msLacBP6_187C_D220L (SEQ ID NO: 57)

MATTWKIQSVWDAGTVGYDLFKEWCDGMEEKTGGELKFTCFPAKAVAADN

NGLEDAVRNGVLQGMNPFTLYWSGKIPASVFLSSYPAGPDQPHQWDTMFY

SLGMLEKTREIYKKFGLFYVGPIQHDANIIHSKQPINSLDDLKGLKMRLP

GGMVAEVFAKFGVAAVSLPGSDIFPALEKGTIDAADCVGPAVNWELGFSQ

VTKYILMGPPGIMSVYQPVLLMDLTVNLRAWNALDPKLQQIVEDEVRIYS

QKHYLAIQKRNIEAMKKFEAAGTTVTRLSQEDLQEFRRAAIPIWYSWANK

DEDAREIFDMQLEYMMNDTVGYITEDDIKGMNGGSHHHHHH**

-continued msLacBP6_187C_D220N (SEQ ID NO: 58)

MATTWKIQSVWDAGTVGYDLFKEWCDGMEEKTGGELKFTCFPAKAVAADN

NGLFDAVRNGVLQGMNPFTLYWSGKIPASVFLSSYPAGPDQPHQWDTMFY

SLGMLEKTREIYKKFGLFYVGPIQHDANIIHSKQPINSLDDLKGLKMRLP

GGMVAEVFAKFGVAAVSLPGSDIFPALEKGTIDAADCVGPAVNWELGFSQ

VTKYILMGPPGIMSVYQPVNLMDLTVNLRAWNALDPKLQQIVEDEVRIYS

QKHYLAIQKRNIEAMKKFEAAGTTVIRLSQEDLQEFRRAAIPIWYSWANK

DEDAREIFDIVIQLEYMNINDIVGYITEDDIKGNINGGSHHHHHH** msLacBP6 187C_D220Q (SEQ ID NO: 59)

MATTWKIQSVWDAGTVGYDLFKEWCDGMEEKIGGELKFTCFPAKAVAADN

NGITDAVRNGVIQGMNPFTLYWSGKIPASVELSSYPAGPDQPHQWDTMFY

SLGMLEKTREIYKKFGLFYVGPIQHDANIIHSKQPINSLDDLKGLKMRLP

GGMVAEVFAKFGVAAVSLPGSDIFPALEKGTIDAADCVGPAVNWELGFSQ

VTKYILMGPPGIMSVYQPVQLMDLTVNLRAWNALDPKLQQIVEDEVRIYS

QKHYLAIQKRNIEAMKKFEAAGTTVTRLSQEDLQEFRRAAIPIWYSWANK

DEDAREIEDMQLEYMMNDTVGYITEDDIKGMNGGSHHHHHH** msLacBP6_187C_D220S (SEQ ID NO: 60)

MATTWKIQSVWDAGTVGYDLFKEWCDGMEEKTGGELKFTCFPAKAVAADN

NGLFDAVRNGVLQGMNPFTLYWSGKIPASVFLSSYPAGPDQPHQWDTMFY

SLGMLEKTREIYKKFGLFYVGPIQHDANIIHSKQPINSLDDLKGLKMRLP

GGMVAEVFAKFGVAAVSLPGSDIFPALEKGTIDAADCVGPAVNWELGFSQ

VTKYILMGPPGIMSVYQPVSLMDLTVNLRAWNALDPKLQQIVEDEVRIYS

QKHYLAIQKRNIEAMKKFEAAGTTVTRLSQEDLQEFRRAAIPIWYSWANK

DEDAREIFDMQLEYMMNDTVGYITEDDIKGMNGGSHHHHHH** msLacBP6 bZif Fusions
msLacBP6_187C_bZifC (SEQ ID NO: 61)

MATTWKIQSVWDAGTVGYDLFKEWCDGMEEKTGGELKFTCFPAKAVAADN

NGLFDAVRNGVLQGMNPFTLYWSGKIPASVFISSYPAGPDQPHQWDTMFY

SLGMLEKTREIYKKFGLFYVGPIQHDANIIHSKQPINSLDDLKGLKMRLP

GGMVAEVFAKFGVAAVSLPGSDIFPALEKGTIDAADCVGPAVNWELGFSQ

VTKYILMGPPGIMSVYQPVDLMDLTVNLRAWNALDPKLQQIVEDEVRIYS

QKHYLAIQKRNIEAMKKFEAAGTTVTRLSQEDLQEFRRAAIPIWYSWANK

DEDAREIFDMQLEYMMNDTVGYITEDDIKGMNGGSTGEKPYKCPECGKSF

SRSGGSHHHHHH** msLacBP6_188C_bZiftC (SEQ ID NO: 62)

MATTWKIQSVWDAGTVGYDLFKEWCDGMEEKTGGELKFTCFPAKAVAADN

NGLFDAVRNGVLQGMNPFTLYWSGKIPASVFLSSYPAGPDQPHQWDTMFY

SLGMLEKTREIYIKKFGLFYVGPIQHDANIHSKQPINSLDDLKGLKMRLP

GGMVAEVFAKFGVAAVSLPGSDIFPALEKGTIDAADYCGPAVNWELGFSQ

VTKYILMGPPGIMSVYQPVDLMDLTVNLRAWNALDPKLQQIVEDEVRIYS

QKHYLAIQKRNIEAMKKFEAAGTTVTRLSQEDLQEFRRAAIPIWYSWANK

-continued

DEDAREIFDMQLEYMMNDTVGYITEDDIKGMNGGSTGEKPYKCPECGKSF

SRSGGSHHHHHH**

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1. Fluorescently Responsive Sensor Engineering Phases

The engineering of FRSs can be divided into five phases:

1. Binding protein discovery. A set of lactate-binding protein sequence homologs is identified. Accurate assignment of their ligand-binding function requires application of a prediction method that incorporates information encoded in the experimentally determined three-dimensional structure of known periplasmic lactate-binding proteins.
2. Experimental lead validation. Synthetic genes are constructed, which are optimized for heterologous expression in *Escherichia coli* of one or more predicted lactate-binding protein sequences. The lactate-binding properties and thermostabilities of the corresponding expressed, purified proteins are evaluated.
3. Engineering of fluorescent responses. Semisynthetic fluorescent conjugates of the experimentally validated leads are constructed by first attaching single fluorophores to single cysteine mutants. The effect of lactate binding on the fluorescence emission properties of those conjugates is evaluated. The spectral properties of a subset of responsive fluorophores is improved using a double-labeling strategy in which a second fluorophore is site-specifically attached to a small domain fused to the N- or C-terminus (e.g. the end or last amino acid of the C-terminus or the first or beginning amino acid of the N-terminus of the engineered ligand-binding protein) to establish ligand-modulated fluorescence resonance energy transfer. Those singly or doubly labeled conjugates that evince strong, ratiometric responses are selected as FRSs for use in sensing applications.
4. Affinity tuning. Single or multiple mutations are introduced by site-directed mutagenesis to alter the lactate-binding affinities of lactate-responsive FRSs. A set of FRS variants is selected that together cover the clinical lactate concentration range with high accuracy.
5. Device Integration. FRSs are immobilized in the sampling component of the analytical device in a manner that preserves their fluorescent response and lactate affinity. Long-term storage conditions are established.

Example 2. Sensor Engineering Phase 1: Identification of A Family of Periplasmic Lactate-Binding Proteins Homologs Using Structurally Assisted Function Evaluation As a first step in constructing robust lactate sensor candidates, we examined bacterial genomic sequences to identify periplasmic lactate-binding protein sequences in known thermophiles. Homologs from such organisms are likely to encode thermostable proteins. Analysis of enzyme families has shown that overall sequence identity below ~60% is a weak predictor of function conservation (Todd, 2001, *J. Mol. Biol.,* 307, 113-1143; Tian, 2003, *J. Mol. Biol.,* 333, 863-882). Furthermore, functional assignments based on sequence homology alone are known to be particularly problematic in the PBP superfamily. For instance, PBPs that by overall sequence identity are predicted to bind oligopeptides were found to bind oligosaccharides. Enzyme functional assignments are improved greatly if a sequence selection filter based on conservation of catalytic residues identified from protein structures is included. Such catalytic residues comprise a subset of all the residues that contact an enzyme substrate or inhibitor. In the case of the PBPs, functional selection filters need to take into account all the protein-ligand contacts that encode the ligand-binding function. Accordingly, we have developed a structurally assisted functional evaluation (SAFE) method to identify PBP sequence homologs with accurately predicted function. The SAFE homolog search method consists of five steps:

1. Sequence homolog set is collected using the BLAST sequence alignment tool (Altschul et al., 1990, *J Mol Biol,* 215, 403-10), starting with *Thermus thermophilus* periplasmic lactate-binding protein (ttLacBP1) sequence as a seed sequence. The following BLAST parameters: (1) Expect threshold is 10.0; (2) Gap cost is Existence: 11 and Extension: 1; (3) The Matrix employed is BLOSUM62; (4) The filter for low complexity regions is "on." Permissive settings are used, such that pairwise hits are required to have a minimum of only 20% sequence identity with the seed sequence. The lengths of the hit and seed are mutually constrained such that the alignment covers at least 70% within each partner. This set of sequences defines a universe of possible lactate-binding proteins without accurately assigning function.
2. Structure-based encoding of biological function. A primary complementary surface comprising the protein residues that form hydrogen bonds and van der Waals contacts with the bound lactate-$Ca^{2+}$ complex is defined using computer-assisted, visual inspection of the three-dimensional structure of the ttLacBP1-lactate complex (Akiyama, 2009, *J. Mol. Biol.,* 392, 559-565, incorporated herein by reference). This definition specifies residue positions and their permitted amino acid identity. Multiple amino acid identities are permitted at each position to encode functionally equivalent residues. This definition establishes a search filter for the accurate prediction of lactate-binding proteins within the universe of sequence homologs collected in Step (1).
3. Accurate sequence alignment. Tools such as ClustalW (Chenna et al., 2003. *Nucleic Acids Res,* 31, 3497-500) are used to construct an accurate alignment of all the sequence homologs. The ttLacBP1 seed sequence is included in this alignment. This multiple sequence alignment establishes the equivalent positions of the ttLacBP1 PCS in each sequence homolog.
4. Function evaluation. The lactate-binding properties of each of the aligned sequence homologs is determined by measuring their compliance with the PCS sequence filter. A "Hamming distance", H, is assigned for each homolog, which specifies the degree of sequence identity of all the residues at the aligned PCS positions. A value of H=0 indicates that the identities of all the residues at the aligned PCS positions match the amino acid(s) allowed in the PCS search filter; H>0, indicates that one or more aligned positions have disallowed residues. Sequences for which H=0 are predicted to encode lactate-binding proteins.
5. Selection of representative SAFE homologs. The sequence homologs are ordered by (a) identity with the seed PCS, as measured by the Hamming distance, (b) fractional overall sequence identity with the seed sequence. A subset for sequences with H=0, sampling the fractional overall sequence identity is selected for experimental verification.

These steps are encoded in the ProteinHunter software tool, which encodes the flow of execution, applies the PCS search filter, and visualizes the results, and handles organism annotations such as thermophilicity, and Gram stain status.

The ProteinHunter package always executes BLAST searches, with the following command "blastall -p blastp -m 8 -b 50000 -d % s -i<INPUT FILE>-o<OUTPUT FILE>"

where <INPUT FILE> and <OUTPUT FILE> specify the input and output files, respectively for a given calculation. This command executes the BLAST alignment program for protein sequences with default parameters, intrinsically set by the program. The BLAST program version is 2.2.24.

The ProteinHunter package always executes multiple sequence alignments with the following command "clustalw -infile=<INPUT FILE>-outfile=<OUTPUTFILE>-align -quiet" This command executes the CLUSTALW multi-sequence alignment program for protein sequences. There are no user-specified parameter settings that alter the alignment behavior of the program. The CLUSTALW program version is 2.1.

Annotated genomic and plasmid sequences of 5062 prokaryotes were obtained from the National Center of Biotechnology Information (ftp://ftp.ncbi.nih.gov/genomes/Bacteria/all.gbk.tar.gz). The protein sequence for the *Thermus thermophilus* (ttLacBP1) lactate-$Ca^{2+}$ complex (FIG. 3A) was extracted from the protein structure file 2zzv (Akiyama, 2009, *J. Mol. Biol.,* 392, 559-565), and used as the seed sequence for the BLAST search described above.

Figures 3A, 3B:
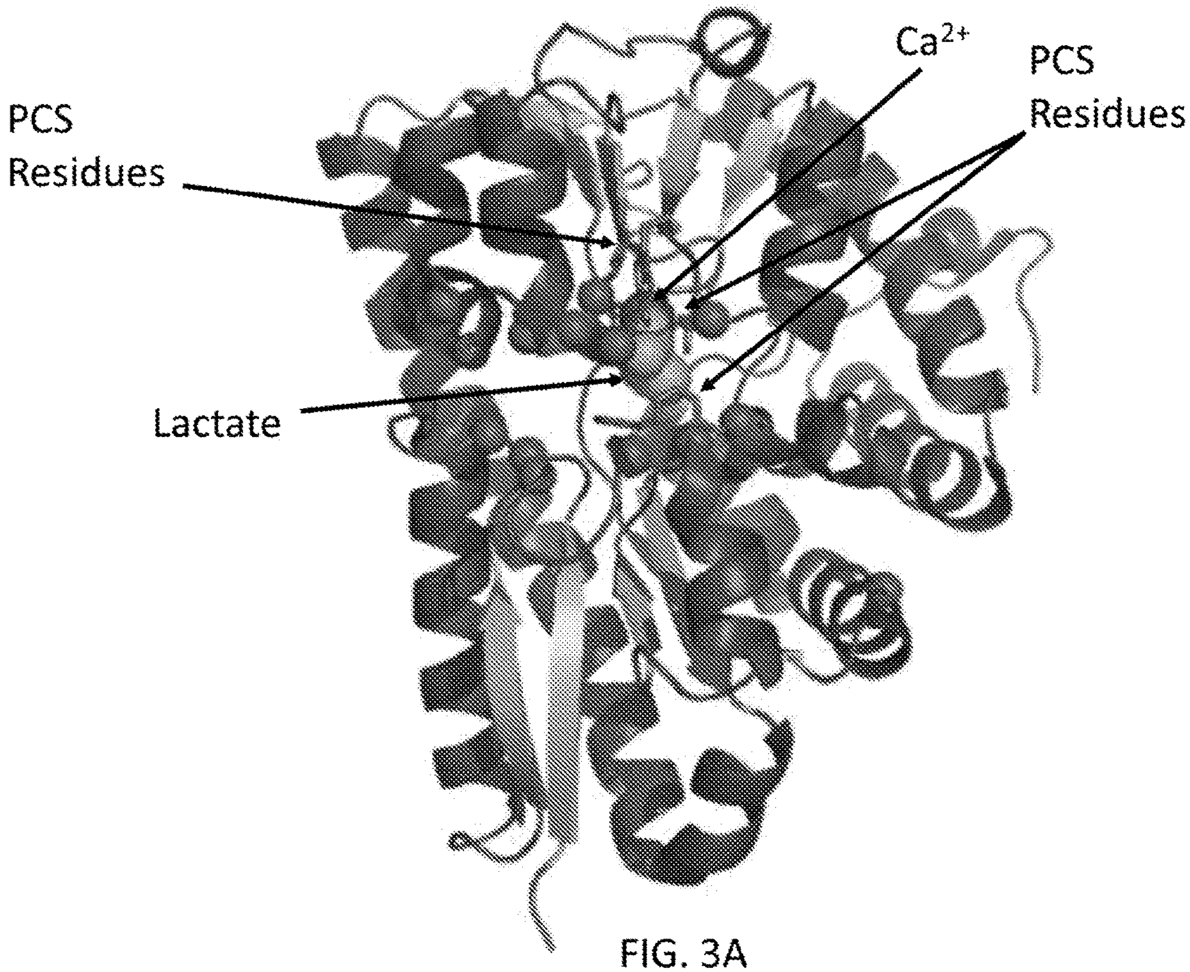
FIG. 3A shows the structure of the lactate-binding protein from *Thermus thermophilus* and FIG. 3B shows an exemplary PCS search filter for lactate-binding proteins.

In *Thermus thermophilus* (ttLacBP1), lactate binding is encoded by a PCS comprising eight residues (Table 1). Residues F98 and P180 form van der Waals contacts with lactate. The lactate carboxylate group forms hydrogen bonds with Y101 and R178 (bidentate). The lactate hydroxyl forms hydrogen bonds with N158 and D250. $Ca^{2+}$ is coordinated by N158, D216, Q247, and the lactate hydroxyl. A PCS filter specifying multiple amino acids at these eight positions was used to predict lactate-binding proteins (FIG. 3B). A total of 1855 sequence homologs from 777 genomes were identified, of which thirteen had PCS residues identical to that of ttLacBP1 (Table 2). The overall sequence identities of these homologs relative to the ttLacBP1 seed varied from 100% to 51%.

TABLE 1

Residues that comprise the primary complementary surface in ttLacBP1.

| Residue | Interaction |
|---|---|
| F98 | Van der Waals contact |
| Y101 | Hydrogen bond donor to lactate carboxylate |
| N158 | $Ca^{2+}$ coordination |
| R178 | Hydrogen bonds to carboxylate (bidentate) |
| P180 | Van der Waals contact |
| D216 | $Ca^{2+}$ coordination |
| Q247 | Hydrogen bonds to lactate carboxylate (donor) and hydroxyl (acceptor) |
| D250 | Hydrogen acceptor to lactate hydroxyl |

TABLE 2

| # | Accession code | PCS Position 98 | 101 | 158 | 178 | 180 | 216 | 247 | 250 | Identity | Thermophilicity | Gram | Organism |
|---|---|---|---|---|---|---|---|---|---|---|---|---|---|
| 1 | 2ZZV | F | Y | N | R | P | D | Q | D | | | | Seed sequence |
| 2 | NC_006461|YP_144032.1 | F | Y | N | R | P | D | Q | D | 1 | Thermophilic | − | *Thermus thermophilus* |
| 3 | NC_017587|YP_006058960.1 | F | Y | N | R | P | D | Q | D | 0.99 | Thermophilic | − | *Thermus thermophilus* |
| 4 | NC_005835|YP_004389.1 | F | Y | N | R | P | D | Q | D | 0.97 | Thermophilic | − | *Thermus thermophilus* |
| 5 | NC_014974|YP_004202714.1 | F | Y | N | R | P | D | Q | D | 0.85 | Thermophilic | − | *Thermus scotoductus* |
| 6 | NC_017278|YP_005654632.1 | F | Y | N | R | P | D | Q | D | 0.85 | Mesophilic | − | *Thermus* sp. |
| 7 | NC_019386|YP_006972155.1 | F | Y | N | R | P | D | Q | D | 0.84 | Mesophilic | − | *Thermus oshimai* |
| 8 | NC_011901|YP_002514099.1 | F | Y | N | R | P | D | Q | D | 0.55 | Mesophilic | + | *Thioalkalivibrio sulfidiphilus* |
| 9 | NC_018268|YP_006556686.1 | F | Y | N | R | P | D | Q | D | 0.55 | Mesophilic | + | *Marinobacter* sp. |
| 10 | NC_017067|YP_005431030.1 | F | Y | N | R | P | D | Q | D | 0.55 | Mesophilic | + | *Marinobacter hydrocarbonoclast* |
| 11 | NC_017506|YP_005886720.1 | F | Y | N | R | P | D | Q | D | 0.53 | ? | + | *Marinobacter adhaerens* |
| 12 | NC_008209|RD1_3770 | F | Y | N | R | P | D | Q | D | 0.51 | Mesophilic | − | *Roseobacter denitrificans* |
| 13 | NC_015730|YP_004689665.1 | F | Y | N | R | P | D | Q | D | 0.51 | Mesophilic | − | *Roseobacter litoralis* |
| 14 | NC_007760|YP_466099.1 | V | Y | Q | R | V | E | Q | E | 0.23 | Mesophilic | − | *Anaeromyxobacter dehalogenans* |
| 15 | NC_017957|YP_006373210.1 | F | Y | E | R | V | D | Q | T | 0.36 | Mesophilic | + | *Tistrella mobilis* |
| 16 | NC_015259|YP_004304976.1 | F | Y | E | R | V | D | Q | T | 0.35 | Mesophilic | − | *Polymorphum gilvum* |
| 17 | NC_010170|YP_001631949.1 | F | Y | E | R | V | D | Q | T | 0.35 | Mesophilic | − | *Bordetella petrii* |
| 18 | NC_013422|YP_003262724.1 | N | F | Q | R | P | E | E | N | 0.28 | Mesophilic | − | *Halothiobacillus neapolitanus* |
| 19 | NC_018177|YP_006522676.1 | A | Y | Q | R | P | D | E | A | 0.28 | Mesophilic | − | *Pseudomonas stutzeri* |
| 20 | NC_018012|YP_006415542.1 | A | Y | Q | R | P | E | E | T | 0.27 | Mesophilic | + | *Thiocystis violascens* |
| 21 | NC_007520|YP_391684.1 | N | Y | M | R | P | E | E | N | 0.27 | Mesophilic | − | *Thiomicrospira crunogena* |
| 22 | NC_017506|YP_005886939.1 | A | Y | Q | R | P | E | E | T | 0.27 | ? | + | *Marinobacter adhaerens* |
| 23 | NC_002505| NP_230142.1 | S | Y | Q | R | P | E | E | S | 0.26 | Mesophilic | − | *Vibrio cholerae* |
| 24 | NC_009439|YP_001189993.1 | T | Y | Q | R | P | D | E | A | 0.26 | Mesophilic | − | *Pseudomonas mendocina* |
| 25 | NC_007645|YP_432067.1 | A | Y | Q | R | P | E | E | T | 0.26 | Mesophilic | − | *Hahella chejuensis* |
| 26 | NC_007494|RSP_3372 | V | Y | F | R | V | E | Q | E | 0.26 | Mesophilic | − | *Rhodobacter sphaeroides* |
| 27 | NC_009429|YP_001170027.1 | V | Y | P | R | V | E | Q | E | 0.26 | Mesophilic | − | *Rhodobacter sphaeroides* |
| 28 | NC_009050|YP_001044890.1 | V | Y | P | R | V | F | Q | E | 0.25 | Mesophilic | − | *Rhodobacter sphaeroides* |
| 29 | NC_011726|YP_002373142.1 | A | Y | Q | R | P | E | E | P | 0.25 | Mesophilic | − | *Cyanothece* sp. |
| 30 | NC_011958|YP_002520469.1 | V | Y | P | R | V | E | Q | E | 0.25 | Mesophilic | − | *Rhodobacter sphaeroides* |
| 31 | NC_015458|YP_004415723.1 | V | Y | A | R | N | E | Q | E | 0.25 | ? | − | *Pusillimonas* sp. |
| 32 | NC_012850|YP_002977458.1 | T | Y | Q | R | A | E | E | P | 0.25 | Mesophilic | − | *Rhizobium leguminosarum* |
| 33 | NC_021291|YP_008046733.1 | V | Y | F | R | V | E | Q | E | 0.25 | Mesophilic | + | *Spiribacter salinus* |
| 34 | NC_017964|YP_006380679.1 | V | Y | A | R | N | E | Q | E | 0.25 | Mesophilic | + | *Advenella kashmirensis* |
| 35 | NC_022664|SPICUR_06625 | V | Y | F | R | V | E | Q | E | 0.25 | Mesophilic | + | *Spiribacter* sp. |
| 36 | NC_022247|VAPA_1c51320 | V | Y | P | R | V | E | Q | E | 0.25 | Mesophilic | − | *Variovorax paradoxus* |
| 37 | NC_008378|YP_765005.1 | V | Y | P | R | V | E | Q | E | 0.25 | Mesophilic | − | *Rhizobium leguminosarum* |
| 38 | NC_020514|YP_007546338.1 | A | Y | Q | R | P | E | E | T | 0.25 | Mesophilic | + | *Glaciecola psychrophila* |
| 39 | NC_017075|YP_005435121.1 | V | Y | L | R | V | E | Q | E | 0.24 | Mesophilic | + | *Rubrivivax gelatinosus* |
| 40 | NC_015276|YP_004311668.1 | A | Y | Q | R | P | E | E | T | 0.24 | Mesophilic | − | *Marinomonas mediterranea* |
| 41 | NC_022514|N234_24800 | V | Y | P | R | V | E | Q | E | 0.24 | Mesophilic | − | *Ralstonia pickettii* |
| 42 | NC_010530|YP_002007308.1 | V | Y | P | R | V | E | Q | E | 0.24 | Mesophilic | − | *Cupriavidus taiwanensis* |
| 43 | NC_018829|YP_006900354.1 | V | Y | F | R | V | E | Q | E | 0.24 | Mesophilic | − | *Bordetella bronchiseptica* |
| 44 | NC_008314|YP_728951.1 | V | Y | P | R | V | E | Q | E | 0.24 | Mesophilic | − | *Ralstonia eutropha* |
| 45 | NC_014931|YP_004157896.1 | V | Y | P | R | V | E | Q | E | 0.24 | Mesophilic | − | *Variovorax paradoxus* |
| 46 | NC_015677|YP_004618117.1 | V | Y | P | R | V | E | Q | E | 0.24 | Mesophilic | − | *Ramlibacter tataouinensis* |
| 47 | NC_007948|YP_550842.1 | V | Y | P | R | V | E | Q | E | 0.24 | Mesophilic | − | *Polaromonas* sp. |
| 48 | NC_015672|YP_004603455.1 | A | Y | Q | R | P | E | E | S | 0.24 | Thermophilic | − | *Flexistipes sinusarabici* |
| 49 | NC_002928|NP_885248.1 | V | Y | P | R | V | E | Q | E | 0.24 | Mesophilic | − | *Bordetella parapertussis* |

TABLE 2-continued

| # | Accession code | PCS Position 98 | 101 | 158 | 178 | 180 | 216 | 247 | 250 | Identity | Thermophilicity | Gram | Organism |
|---|---|---|---|---|---|---|---|---|---|---|---|---|---|
| 50 | NC_020528\|SM2011_c04289 | V | Y | L | R | V | E | Q | E | 0.24 | Mesophilic | – | *Sinorhizobium meliloti* |
| 51 | NC_012108\|YP_002602670.1 | S | Y | D | R | S | E | Q | T | 0.24 | Mesophilic | – | *Desulfobacterium autotrophicum* |
| 52 | NC_002929\|NP_880422.1 | V | Y | P | R | V | E | Q | E | 0.24 | Mesophilic | – | *Bordetella pertussis* |
| 53 | NC_010524\|YP_001793235.1 | V | Y | P | R | N | E | Q | E | 0.24 | Mesophilic | – | *Leptothrix cholodnii* |
| 54 | NC_002927\|NP_889568.1 | V | Y | P | R | V | E | Q | E | 0.24 | Mesophilic | – | *Bordetella bronchiseptica* |
| 55 | NC_002927\|NP_887256.1 | Y | Y | Q | R | S | E | E | G | 0.24 | Mesophilic | – | *Bordetella bronchiseptica* |
| 56 | NC_017223\|YP_005589816.1 | V | Y | P | R | V | E | Q | E | 0.24 | Mesophilic | – | *Bordetella pertussis* |
| 57 | NC_018518\|YP_006626729.1 | V | Y | P | R | V | E | Q | E | 0.23 | Mesophilic | – | *Bordetella pertussis* |
| 58 | NC_021285\|YP_008032986.1 | V | Y | P | R | V | E | Q | E | 0.23 | Mesophilic | – | *Achromobacter xylosoxidans* |
| 59 | NC_009636\|YP_001327610.1 | V | Y | P | R | V | E | Q | E | 0.23 | Mesophilic | – | *Sinorhizobium medicae* |
| 60 | NC_019382\|YP_006966915.1 | V | Y | P | R | V | E | Q | E | 0.23 | Mesophilic | – | *Bordetella bronchiseptica* |
| 61 | NC_008825\|YP_001022553.1 | V | Y | P | R | V | E | Q | E | 0.23 | Mesophilic | – | *Methylibium petroleiphilum* |
| 62 | NC_009715\|YP_001407794.1 | T | Y | Q | R | P | E | E | G | 0.23 | Mesophilic | – | *Campylobacter curvus* |
| 63 | NC_023061\|AX27061_4156 | V | Y | P | R | V | E | Q | E | 0.23 | Mesophilic | – | *Achromobacter xylosoxidans* |
| 64 | NC_011420\|YP_002297949.1 | V | Y | P | R | V | E | Q | E | 0.23 | Mesophilic | – | *Rhodospirillum centenum* |
| 65 | NC_017249\|YP_005606328.1 | V | Y | P | R | V | E | Q | E | 0.23 | Mesophilic | – | *Bradyrhizobium japonicum* |
| 66 | NC_010170\|YP_001631171.1 | V | Y | P | R | V | E | Q | E | 0.23 | Mesophilic | – | *Bordetella petrii* |
| 67 | NC_011992\|YP_002553916.1 | V | Y | P | R | V | E | Q | E | 0.23 | Mesophilic | – | *Acidovorax ebreus* |
| 68 | NC_015380\|YP_004357668.1 | V | Y | P | R | V | E | Q | E | 0.23 | Mesophilic | – | *Candidatus Pelagibacter* |
| 69 | NC_008782\|YP_987334.1 | V | Y | P | R | V | E | Q | E | 0.23 | Mesophilic | – | *Acidovorax* sp. |
| 70 | NC_018700\|YP_006840738.1 | V | Y | P | R | V | E | Q | E | 0.23 | Mesophilic | – | *Sinorhizobium meliloti* |
| 71 | NC_009714\|YP_001406989.1 | S | Y | Q | R | P | E | E | G | 0.23 | Mesophilic | – | *Campylobacter hominis* |
| 72 | NC_009675\|YP_001380108.1 | V | Y | P | R | V | E | Q | E | 0.23 | Mesophilic | – | *Anaeromyxobacter* sp. |
| 73 | NC_003047\|NP_386154.2 | V | Y | P | R | V | E | Q | E | 0.23 | Mesophilic | – | *Sinorhizobium meliloti* |
| 74 | NC_017249\|YP_005610987.1 | V | Y | Q | R | G | E | E | P | 0.23 | Mesophilic | – | *Bradyrhizobium japonicum* |
| 75 | NC_012791\|YP_002946820.1 | V | Y | P | R | V | E | Q | E | 0.23 | Mesophilic | – | *Variovorax paradoxus* |
| 76 | NC_009659\|YP_001351817.1 | V | Y | P | R | N | E | Q | E | 0.23 | Mesophilic | – | *Janthinobacterium* sp. |
| 77 | NC_016812\|YP_005189194.1 | V | Y | P | R | V | E | Q | E | 0.23 | Mesophilic | – | *Sinorhizobium fredii* |
| 78 | NC_014010\|YP_003552387.1 | V | Y | L | R | V | E | Q | E | 0.23 | Mesophilic | – | *Candidatus Puniceispirillum* |
| 79 | NC_014640\|YP_003979660.1 | V | Y | P | R | V | E | Q | E | 0.23 | Mesophilic | – | *Achromobacter xylosoxidans* |
| 80 | NC_019689\|YP_007080940.1 | F | Y | P | R | A | E | Q | E | 0.23 | Mesophilic | + | *Pleurocapsa* sp. |
| 81 | NC_019845\|C770_GR4Chr2100 | V | Y | P | R | V | E | Q | E | 0.23 | Mesophilic | – | *Sinorhizobium meliloti* |
| 82 | NC_009138\|YP_001098471.1 | V | Y | P | R | N | E | Q | E | 0.23 | Mesophilic | – | *Herminiimonas arsenicoxydans* |
| 83 | NC_017325\|YP_005719813.1 | V | Y | P | R | V | E | Q | E | 0.23 | Mesophilic | – | *Sinorhizobium meliloti* |
| 84 | NC_012587\|YP_002826460.1 | V | Y | P | R | V | E | Q | E | 0.22 | Mesophilic | – | *Sinorhizobium fredii* |
| 85 | NC_002927\|NP_890892.1 | V | Y | Q | R | A | E | E | P | 0.22 | Mesophilic | – | *Bordetella bronchiseptica* |
| 86 | NC_018000\|YP_006399658.1 | V | Y | P | R | V | E | Q | E | 0.22 | Mesophilic | – | *Sinorhizobium fredii* |
| 87 | NC_011891\|YP_002493485.1 | V | Y | P | R | V | E | Q | E | 0.22 | Mesophilic | – | *Anaeromyxobacter dehalogenans* |
| 88 | NC_013522\|YP_003317968.1 | V | Y | E | R | S | E | E | V | 0.22 | Thermophilic | – | *Thermanaerovibrio acidaminovor* |
| 89 | NC_015590\|YP_004549361.1 | V | Y | P | R | V | E | Q | E | 0.22 | Mesophilic | – | *Sinorhizobium meliloti* |
| 90 | NC_014217\|YP_003694031.1 | V | Y | P | R | V | E | Q | E | 0.22 | Mesophilic | – | *Starkeya novella* |
| 91 | NC_017322\|YP_005714018.1 | V | Y | P | R | V | E | Q | E | 0.22 | Mesophilic | – | *Sinorhizobium meliloti* |
| 92 | NC_023139\|Gal_04217 | T | Y | M | R | P | E | E | H | 0.22 | Mesophilic | + | *Phaeobacter gallaeciensis* |
| 93 | NC_013446\|CtCNB1_4165 | V | Y | P | R | V | E | Q | E | 0.22 | Mesophilic | – | *Comamonas testosteroni* |
| 94 | NC_014153\|YP_003643844.1 | A | Y | Q | R | G | E | E | L | 0.22 | Mesophilic | – | *Thiomonas intermedia* |
| 95 | NC_008254\|YP_675356.1 | A | Y | Q | R | P | E | E | L | 0.22 | Mesophilic | – | *Chelativorans* sp. |
| 96 | NC_015563\|YP_004489778.1 | A | Y | Q | R | N | E | E | P | 0.2 | Mesophilic | – | *Delftia* sp. |
| 97 | NC_011662\|YP_002355208.1 | A | Y | Q | R | G | E | E | T | 0.2 | Mesophilic | – | *Thauera* sp. |
| 98 | NC_016617\|YP_005030296.1 | S | N | E | R | V | E | Y | D | 0.19 | Mesophilic | + | *Azospirillum brasilense* |

TABLE 2-continued

| # | Accession code | PCS Position 98 | 101 | 158 | 178 | 180 | 216 | 247 | 250 | Iden-tity | Thermo-philicity | Gram | Organism |
|---|---|---|---|---|---|---|---|---|---|---|---|---|---|
| 99 | NC_014931\|YP_004153186.1 | S | N | E | R | V | E | Y | D | 0.18 | Mesophilic | − | *Variovorax paradoxus* |
| 100 | NC_013854\|YP_003449618.1 | S | N | E | R | V | E | Y | D | 0.18 | Mesophilic | + | *Azospirillum* sp. |
| 101 | NC_011992\|YP_002552063.1 | S | N | E | R | V | E | Y | D | 0.18 | Mesophilic | − | *Acidovorax ebreus* |
| 102 | NC_015726\|YP_004685150.1 | S | N | E | R | V | E | Y | D | 0.18 | Mesophilic | − | *Cupriavidus necator* |
| 103 | NC_016602\|YP_004993575.1 | S | K | Q | R | Q | E | G | D | 0.17 | Mesophilic | − | *Vibrio furnissii* |
| 104 | NC_021848\|M636_17130 | S | K | Q | R | Q | E | G | D | 0.17 | Mesophilic | − | *Vibrio parahaemolyticus* |
| 105 | NC_015138\|YP_004236450.1 | S | N | E | R | V | E | Y | D | 0.17 | Mesophilic | − | *Acidovorax avenae* |
| 106 | NC_015740\|YP_004712457.1 | S | K | Q | R | Q | E | G | D | 0.17 | Mesophilic | − | *Pseudomonas stutzeri* |
| 107 | NC_019955\|YP_007274546.1 | S | K | Q | R | Q | E | G | D | 0.17 | Mesophilic | − | *Vibrio parahaemolyticus* |
| 108 | NC_015677\|YP_004620070.1 | S | N | E | R | V | E | Y | D | 0.17 | Mesophilic | − | *Ramlibacter tataouinensis* |
| 109 | NC_021847\|M634_06555 | S | K | Q | R | Q | E | G | D | 0.17 | Mesophilic | − | *Vibrio parahaemolyticus* |
| 110 | NC_011894\|YP_002498655.1 | S | N | Q | R | P | E | H | D | 0.17 | Mesophilic | − | *Methylobacterium nodulans* |
| 111 | NC_014011\|YP_003554428.1 | S | N | E | R | V | E | Y | D | 0.17 | Mesophilic | − | *Aminobacterium colombiense* |
| 112 | NC_014965\|YP_004189356.1 | S | K | Q | R | Q | E | G | D | 0.16 | Mesophilic | − | *Vibrio vulnificus* |
| 113 | NC_022361\|M801_5209 | S | K | Q | R | Q | E | G | D | 0.16 | Mesophilic | − | *Pseudomonas aeruginosa* |
| 114 | NC_020912\|YP_007712269.1 | S | K | Q | R | Q | E | G | D | 0.16 | Mesophilic | − | *Pseudomonas aeruginosa* |
| 115 | NC_023019\|U769_28475 | S | K | Q | R | Q | E | G | D | 0.16 | Mesophilic | − | *Pseudomonas aeruginosa* |
| 116 | NC_023066\|T223_28430 | S | K | Q | R | Q | E | G | D | 0.16 | Mesophilic | − | *Pseudomonas aeruginosa* |
| 117 | NC_004459\|NP_759047.1 | S | K | Q | R | Q | E | G | D | 0.16 | Mesophilic | − | *Vibrio vulnificus* |
| 118 | NC_015556\|YP_004476114.1 | S | K | Q | R | Q | E | G | D | 0.16 | Mesophilic | − | *Pseudomonas fulva* |
| 119 | NC_017964\|YP_006378330.1 | S | N | Q | R | I | D | Y | E | 0.16 | Mesophilic | + | *Advenella kashmirensis* |
| 120 | NC_013851\|YP_003443034.1 | A | K | Q | R | M | E | G | D | 0.16 | Mesophilic | − | *Allochromatium vinosum* |
| 121 | NC_021285\|YP_008032454.1 | S | N | Q | R | V | E | Y | D | 0.16 | Mesophilic | − | *Achromobacter xylosoxidans* |
| 122 | NC_018828\|YP_006896115.1 | S | N | Q | R | V | E | Y | D | 0.15 | Mesophilic | − | *Bordetella parapertussis* |
| 123 | NC_018028\|YP_006456410.1 | S | K | Q | R | Q | E | G | D | 0.15 | Mesophilic | − | *Pseudomonas stutzeri* |
| 124 | NC_016584\|YP_004969840.1 | S | K | Q | R | Q | E | G | D | 0.15 | Mesophilic | + | *Desulfosporosinus orientis* |
| 125 | NC_009665\|YP_001367021.1 | S | K | Q | R | M | E | G | D | 0.15 | Mesophilic | − | *Shewanella baltica* |
| 126 | NC_021237\|YP_008000000.1 | S | K | Q | R | Q | E | G | D | 0.15 | Mesophilic | − | *Pseudomonas protegens* |
| 127 | NC_018177\|YP_006525655.1 | S | K | Q | R | Q | E | G | N | 0.14 | Mesophilic | − | *Pseudomonas stutzeri* |
| 128 | NC_009050\|YP_001045263.1 | N | N | Q | R | Q | E | N | P | 0.12 | Mesophilic | − | *Rhodobacter sphaeroides* |
| 129 | NC_011958\|YP_002520127.1 | N | N | Q | R | Q | E | N | P | 0.12 | Mesophilic | − | *Rhodobacter sphaeroides* |

Figure 4:
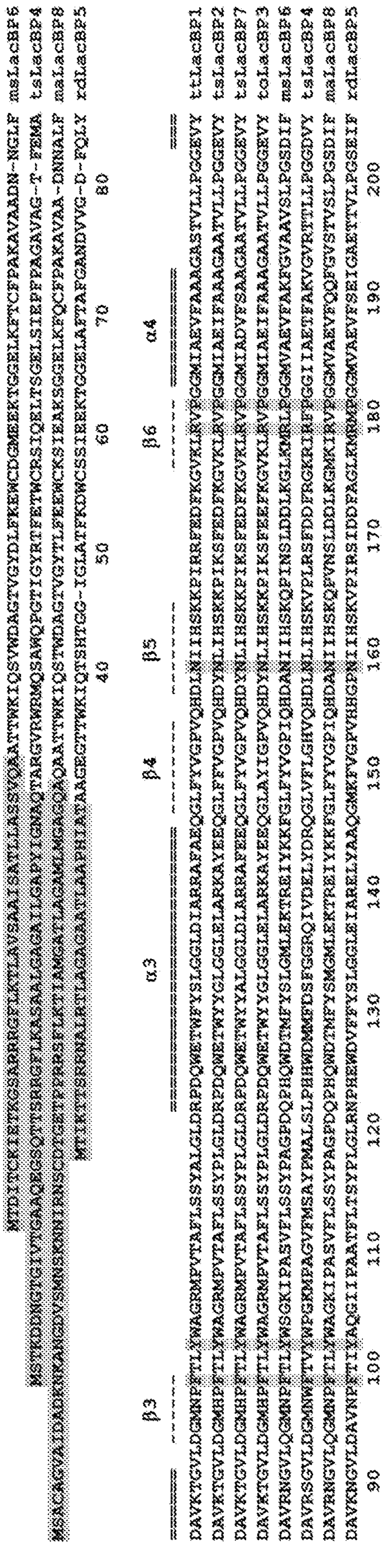
FIG. 4 shows an alignment of the homologs predicted to be lactate-binding proteins (alignment generated by ClustalW). Sequences taken from Table 2 (only H=0 homologs are shown). Numbering according to ttLacBP1. Leader peptides and primary complementary surface residues are show in gray. -, positions of insertions/deletions. Positions of the α helices ($\alpha_x$), and β sheets ($\beta_x$) observed in the ttLacBP1 structure are indicated. The leader peptide for toLacBP3 was deliberately left in place.

Example 3. Sensor Engineering Phase 2: Lead Protein Validation Using Ligand-Mediated Thermostability Shifts Eight homologs with PCS sequences that are identical to that of the ttLacBP1 seed sequence (i.e. H=0) were selected to probe different degrees of sequence identity with the seed (FIG. 4). We also selected an additional six proteins with one or more mutations in the PCS sequence to probe the necessary degree of conservation of this sequence (Table 3).

The lactate-binding properties of these proteins were determined experimentally (Table 3). These experiments comprise four successive steps:

1. Synthetic gene construction. The amino acid sequence of the homology leads are back translated into DNA sequences. These are optimized for directing heterologous cytoplasmic expression of the protein homologues in *E. coli*, using either the OrfOpt or OrfMorph programs. These programs predict mRNA sequences that direct high-level protein expression in *E. coli*. The predicted gene sequences are assembled de novo from synthetic oligonucleotides.
2. Heterologous protein expression of the homologues in *E. coli*. Plasmids carrying the synthetic expression constructs (see above) were transformed into KRX competent cells (Promega). Protein production was induced in bacterial cultures of these cultures.
3. Purification of successfully expressed protein using immobilized metal affinity chromatography.
4. Verification of lactate binding. Determination of the lactate-binding properties of the purified proteins using a thermal stability shift assay.

TABLE 3

Ligand-binding and thermostability properties of ttLacBP1 homologs.

| Name | Organism | NCBI Accession codes Genome | NCBI Accession codes Protein | Identity[a] | PCS sequence[b] | Gene Optimization[c] | Soluble Expression[d] | Thermostability[e] $^{apo}T_m$ (° C.) | Lactate Binding |
|---|---|---|---|---|---|---|---|---|---|
| ttLacBP1 | *Thermus thermophilus* | NC_006461 | YP_144032.1 | 1 | FYNRPDQD | OrfOpt | y, ppt | >100 | y[f] |
| tsLacBP2 | *Thermus scotoductus* | NC_014974 | YP_004202714.1 | 0.85 | FYNRPDQD | OrfOpt | n | | |
| toLacBP3 | *Thermus oshimai* | NC_019386 | YP_006972155.1 | 0.84 | FYNRPDQD | OrfOpt | n | | |
| tsLacBP4 | *Thioalkalivibrio sulfidophilus* | NC_011901 | YP_002514099.1 | 0.55 | FYNRPDQD | OrfOpt | n | | |
| rdLacBP5 | *Roseobacter denitrificans* | NC_008209 | YP_683924.1 | 0.51 | FYNRPDQD | OrfOpt | n | | |
| msLacBP6 | *Marinobacter* sp. | NC_018268 | YP_006556686.1 | 0.55 | FYNRPDQD | OrfOpt | y, sol | 70 | y[f,g] |
| lsLacBP7 | *Thermus* sp. | NC_017278 | YP_005654632.1 | 0.85 | FYNRPDQD | OrfMorph | y, ppt | >100 | y[f,g] |
| maLacBP8 | *Marinobacter adhaerens* | NC_017506 | YP_005886720.1 | 0.53 | FYNRPDQD | OrfMorph | y, sol | 75 | y[f,g] |
| adLacBP9 | *Anaeromyxobacter dehalogenans* | NC_007760 | YP_466099.1 | 0.23 | ***V*** Y ***Q*** R ***VE*** Q ***E*** | OrfMorph | y, ppt | 48 | weak[f,g] |
| pgLacBP10 | *Polymorphum gilvum* | NC_015259 | YP_004304976.1 | 0.35 | FY ***E*** R ***V*** DQ ***T*** | OrfMorph | y, sol | 49 | weak[f,g] |
| psLacBP11 | *Pseudomonas stutzeri* | NC_018177 | YP_006522676.1 | 0.28 | ***A*** Y ***Q*** RPD ***EA*** | OrfMorph | y, ppt | 60 | weak[f,g] |
| rsLacBP12 | *Rhodobacter sphaeroides* | NC_007494 | RSP_3372 | 0.26 | ***V*** Y ***F*** R ***VEQE*** | OrfMorph | y, sol | 48 | n[f,g] |
| fsLacBP13 | *Flexistipes sinusarabici* | NC_015672 | YP_004603455.1 | 0.24 | ***A*** Y ***Q*** RP ***E*** E ***S*** | OrfMorph | y, ppt | 46 | weak[f,g] |
| taLacBP14 | *Thermanaerovibrio acidaminovorans* | NC_013522 | YP_003317968.1 | 0.22 | ***Y*** Y ***E*** R ***SEEV*** | OrfMorph | y, ppt | 77 | n[f,g] |

[a]Number of identical residues shared with the probe sequence.
[b]Residue identity from the ClustalW alignment at positions 98, 101, 158, 178, 180, 216, 247, 250 (using ttLacBP1 as the reference sequence). Differences from the reference sequence are indicated in bold-italic.
[c]For gene optimization methods, see Materials and Methods.
[d]Judged by SDS gel electrophoresis of the soluble fraction of a total lysate: n, no expression; y, expression; sol, purified protein is soluble; ppt, purified protein precipitates over time.
[e]Determined in a Roche LightCycler, using SYPRO Orange to monitor the appearance of unfolded protein.
[f]Determined by monitoring dependence of protein thermostability on ligand concentration.
[g]Determined by monitoring a fluorescence response of a labeled conjugate.

Ten of the fourteen leads, produced soluble protein in a T7 expression system in sufficient quantity for functional analysis. Their lactate-binding properties of were tested using the thermal shift assay and using a fluorescent Acrylodan or Badan conjugate placed at the equivalent of position 187 in msLacBP6 (FIG. 3A). Lactate binding was observed with affinities comparable to ttLacBP1 only for proteins that have PCS sequences identical to the seed (Table 3). These results clearly establish that the SAFE method accurately identifies functional lactate-binding proteins, and that conservation of the seed PCS sequence is essential for function.

The homolog from *Marinobacter* species (msLacBP6) was produced at the highest level by heterologous expression in *E. coli*, and remained stably soluble in solution. It has a mid-point denaturation temperature of 70° C., and therefore has good thermostability for the uses described herein. This protein was selected as the candidate for constructing robust lactate sensors.

Example 4. Sensor Engineering Phase 3: Cysteine Mutant Scans and Fluorophore Screening to Identify Fluorescently Responsive Lactate Sensors Semi-synthetic FRSs can be engineered by site-specifically attaching thiol-reactive, environmentally sensitive fluorophores that respond to ligand-mediated conformational changes. Identification of FRS candidates that can be used for sensing applications comprises three steps:

1. Cysteine scan. Mutant lactate-binding proteins containing single cysteines are constructed for site-specific attachment of thiol-reactive fluorophores. General structural principles have been established to identify positions in PBPs where attached single fluorophores are likely to exhibit ligand-dependent responses (de Lorimier et al., 2002, *Protein Sci,* 11, 2655-75). Candidate positions fall into three classes: endosteric, replacing a residue that contacts the ligand directly; peristeric, located at the rim of the binding site; allosteric (Marvin et al., 1997, *Proc Natl Acad Sci USA,* 94, 4366-71; Marvin, 1998, *J Am Chem Soc,* 120, 7-11), located outside the binding site at sites that undergo local structural changes in concert with the hinge-bending motion.
2. Fluorophore screening. Thiol-reactive, environmentally sensitive fluorophores are attached to each cysteine mutant prepared in step 1.
3. Evaluation of the lactate-mediated change of all the fluorescent conjugates prepared in step 2. Responses to ligand binding in which there is both a change in fluorescence emission intensity and spectral shape are essential for chemometric applications, because such changes enable ratiometric measurements. Changes in spectral shape typically are accompanied by a shift in the wavelength of the emission intensity maxima. Three classes of fluorescent responses are possible:
   i. No response.
   ii. Monochromatic response (emission intensity increases or decreases without a change in spectral shape)
   iii. Dichromatic response (both intensity and spectral shape changes) which can be classified into two sub-classes:
      i. Hypsochromatic: emission intensity shifts to shorter wavelengths upon binding ligand (“blue shift”).
      ii. Bathochromatic: emission intensity shifts to longer wavelengths upon binding ligand (“red shift”).
4. Double labeling strategies to convert monochromatic responses into dichromatic signals, or to improve upon weak dichromatic responses.

Cysteine and Fluorophore Scans in msLacBP6.

The naphthalene derivatives Acrylodan and Badan have been particularly effective in establishing dichromatic responses in singly labeled proteins, because ligand-mediated protein conformational changes can be coupled to an exchange between two different fluorophore conformations (twists) that emit at different wavelengths. We therefore tested the lactate responses of Acrylodan and Badan conjugates attached to cysteine mutations at allosteric, endosteric, and peristeric positions (FIG. 3A). We constructed seventeen single cysteine mutants in msLacBP6, exploring one endosteric, fourteen peristeric, and two allosteric positions. Two dominant electronic transitions give rise to fluorescence emission in these fluorophores with maxima in the blue (<500 nm) and green (>500 nm) regions, respectively. Dichromatic responses occur when ligand binding shifts the population distribution of these two transitions in the ligand-free and ligand-bound protein. Of the 34 conjugates tested at these 17 sites, seven exhibited sufficiently large responses for chemometrics (Table 4); of these, four were dichromatic.

TABLE 4

Lactate response of Acrylodan and Badan conjugates in a cysteine scan of endo, peristeric and allosteric sites in the msLacBP6 scaffold.

| Position[a] | | | Response | | | | | |
|---|---|---|---|---|---|---|---|---|
| | | | Acrylodan | | | Badan | | |
| msLacBP6 | ttLacBP1 | Class[b] | Shape[c] | Intensity[d] | Excited states[e] | Shape[c] | Intensity[d] | Excited states[e] |
| V10C | A41 | p | 0 | | b/g | m | – | b/g |
| W11C | 42 | p | d[f] | – | b | 0 | | g |
| D12C | 43 | p | m | – | g | m | – | g |
| A43C | 74 | p | 0 | | b | 0 | | b |
| D49C | T80 | p | 0 | | b/g | 0 | | g |
| N50C | F81 | p | 0 | | b | 0 | | b |
| F68C | 98 | e | 0 | | b | 0 | | b |
| L70C | 100 | p | m | + | b | 0 | | b/g |
| Y71C | 101 | p | m | – | g | m | – | g |
| P150C | 180 | p | m | + | g | m | + | g |
| P169C | 199 | p | m | + | b | 0 | | g |
| G170C | 200 | p | d[f] | – | g | m[f] | – | g |
| S171C | G201 | p | 0 | | g | 0 | | g |
| Y187C | F217 | p | d[f] | + | b | d[f] | 0 | g |
| V188C | 218 | p | 0 | | b/g | m[f] | + | g |
| V192C | 222 | a | m[f] | + | g | m | + | g |
| L196C | 226 | a | 0 | | b/g | m | + | b/g |

[a]Aligned position in the ttLacBP1 numbering of the 2zzv PDB file is given.
[b]a, allosteric; e, endosteric; p, peristeric.
[c]m, monochromatic; d, dichromatic (i.e. spectral shape changes); 0, no change.
[d]+, increases in response to lactate; –, decreases; 0, no change.
[e]The dominant population of the excited states in the absence of lactate is determined from the emission bands intensities: b, blue (maxima < 500 nm); g, green (maxima > 500 nm); b/g, mixed population of blue and green.
[f]Chemometric lead.

Figure 5A:
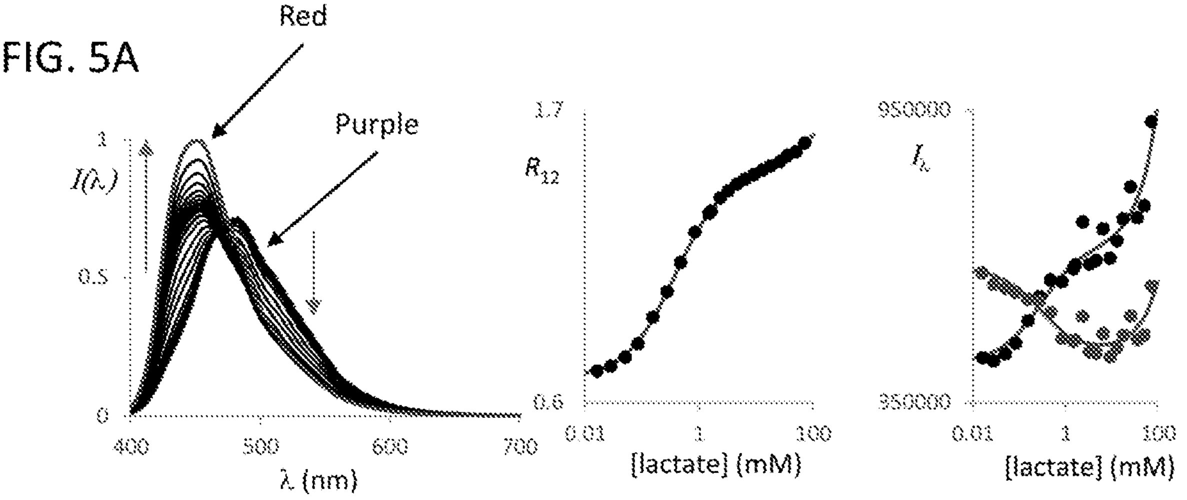
FIGS. 5A and B are sets of graphs showing the fluorescent response of Acrylodan and Badan conjugates of msLacBP6 187C. Left column, corrected emission spectra (purple line, no lactate; red line, 100 mM lactate; black lines, intermediate lactate concentrations). Middle column, ratiometric signals (black circles, experimental data points; gray lines, fit to binding isotherm to yield $^{app}K_d$). Right column, monochromatic signals (lines: fits to binding isotherm to yield $^{app}K_d$; circles: experimental data points at two different wavelengths).
Figure 5B:
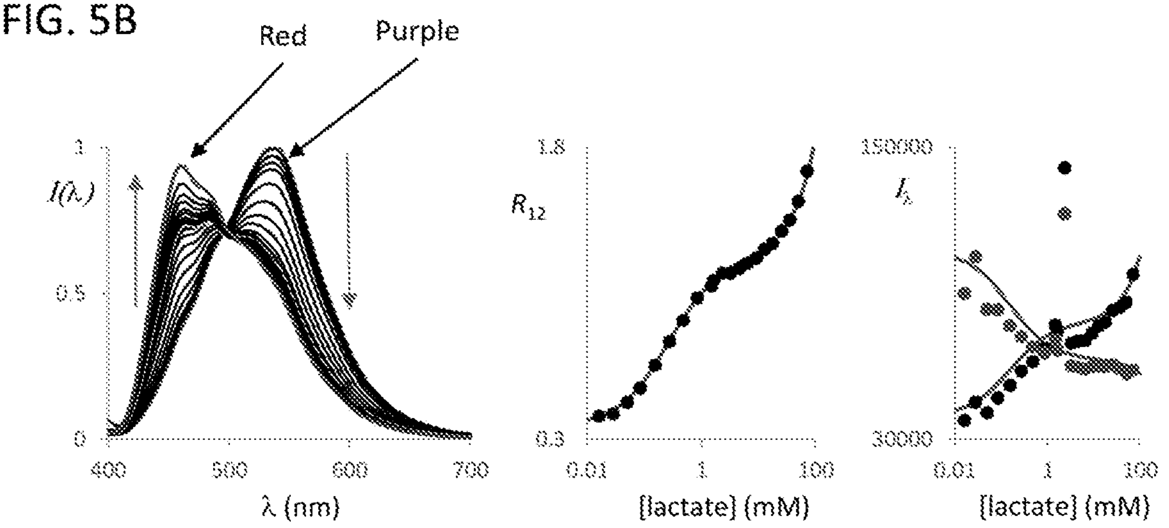
FIG. 5B: msLacBP6 187C-Badan ($\lambda_1$=460 nm, $\lambda_2$=537 nm; $^{app}K_d$=0.3 mM; $^{true}K_d$=0.2 mM).
Figure 6A:
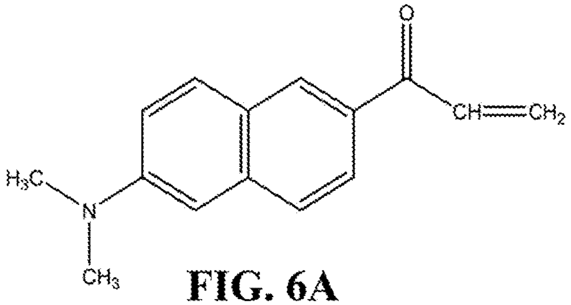
FIGS. 6A-E show the structures of exemplary fluorophores. Naphthalene family (arrows indicate known or potential internal twists)
Figure 6B:
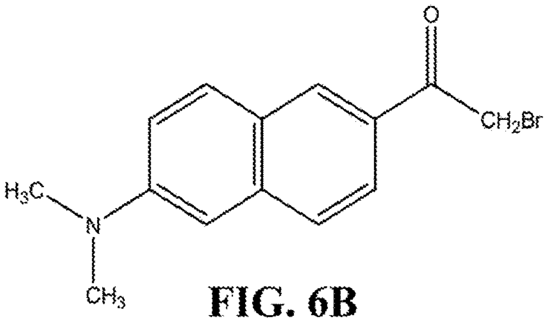
Figure 6C:
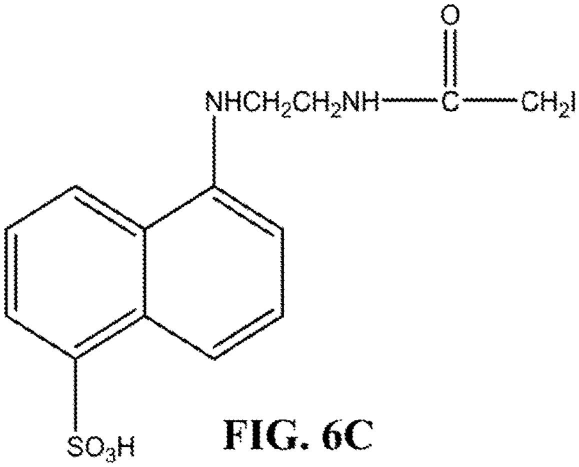
Figure 6D:
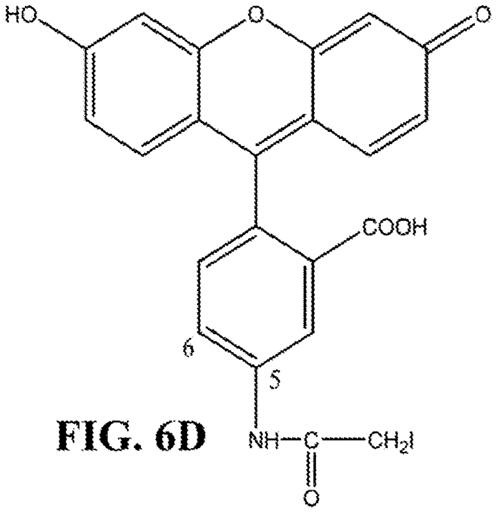
Figure 6E:
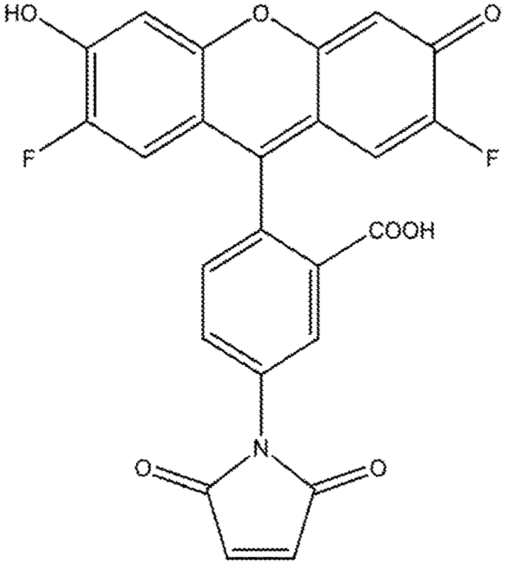
Figure 6F:
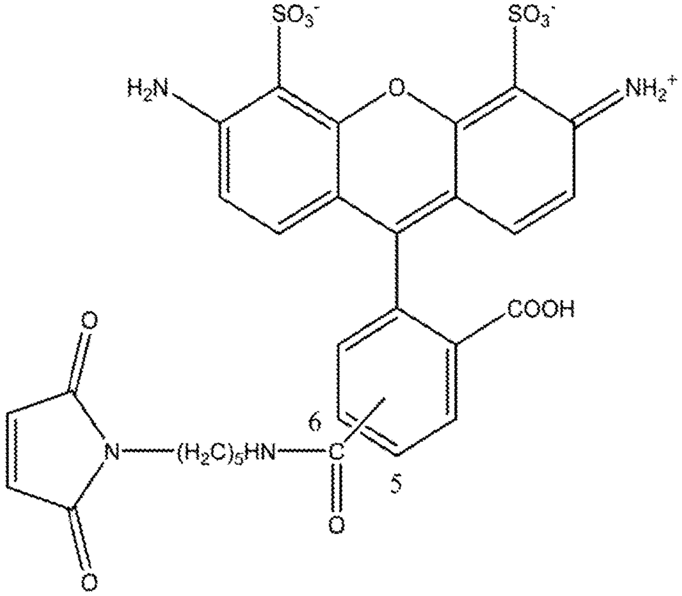
FIG. 6F shows Alexa 432.
Figure 6G:
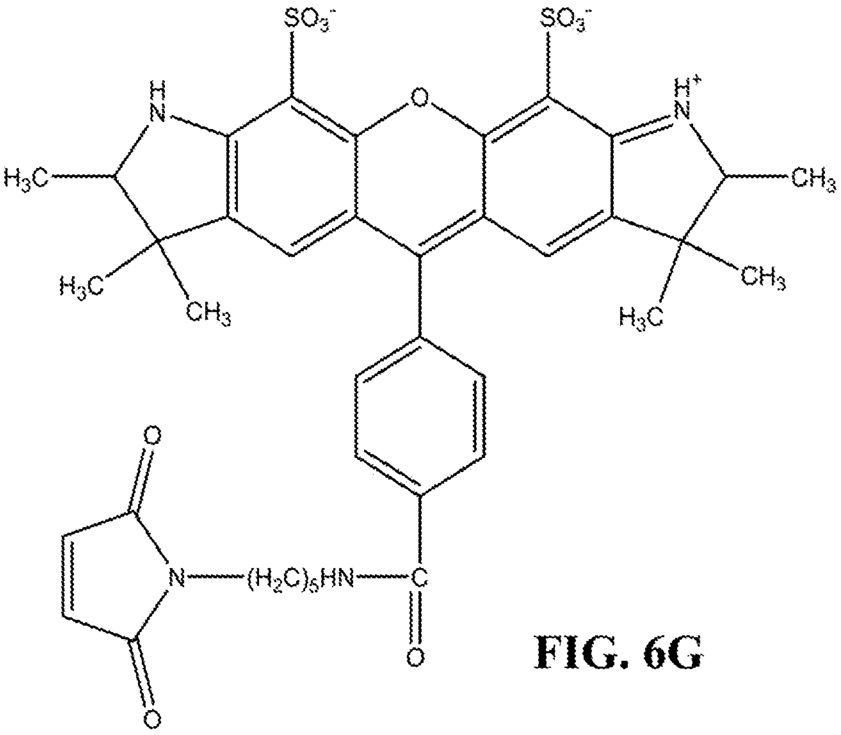
FIG. 6G shows Alexa532.
Figure 6H:
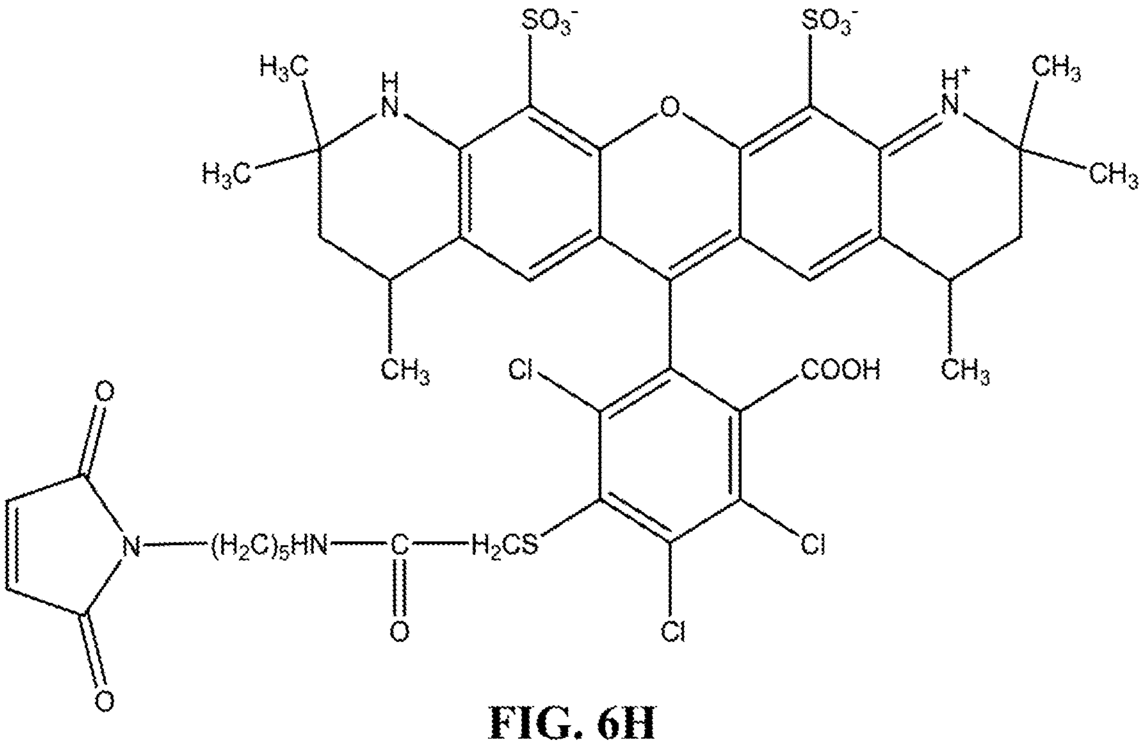
FIG. 6H shows Alexa 546.
Figure 6I:
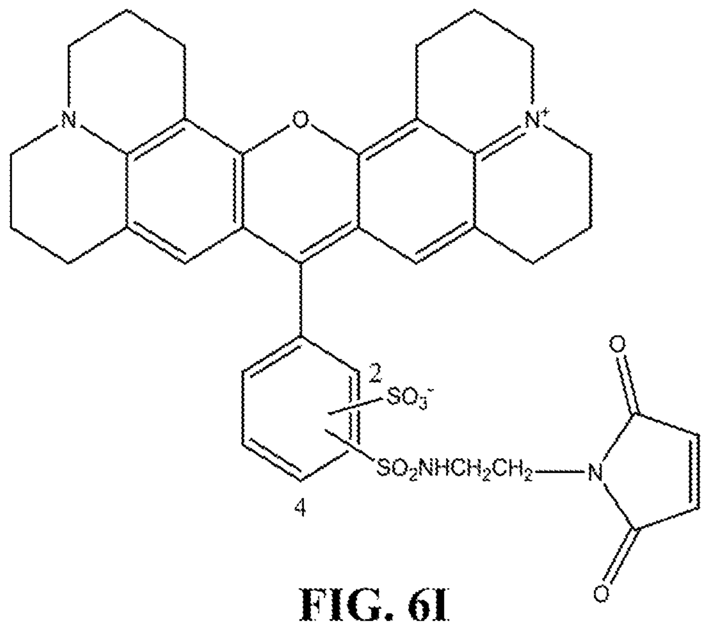
FIG. 6I shows Texas Red. Coumarin family.
Figure 6J:
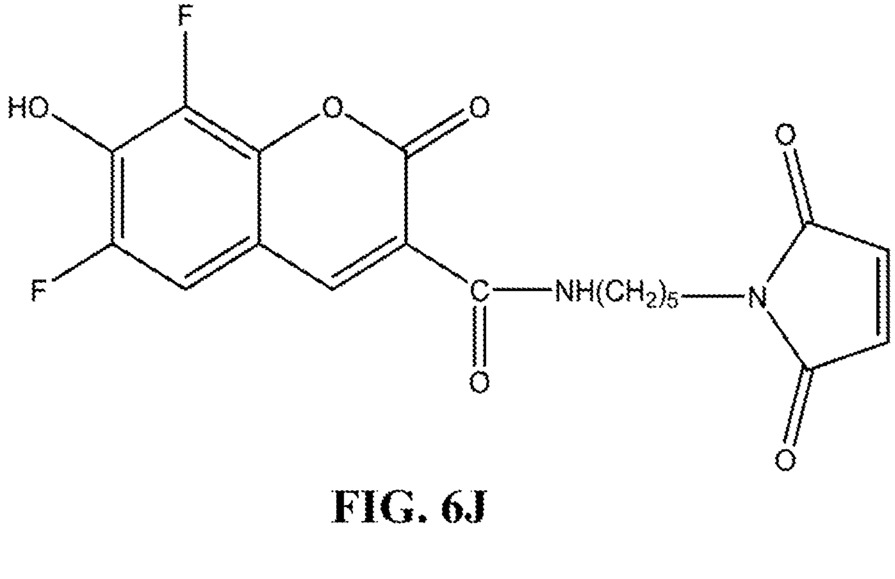
FIG. 6J shows Pacific Blue.
Figure 6K:
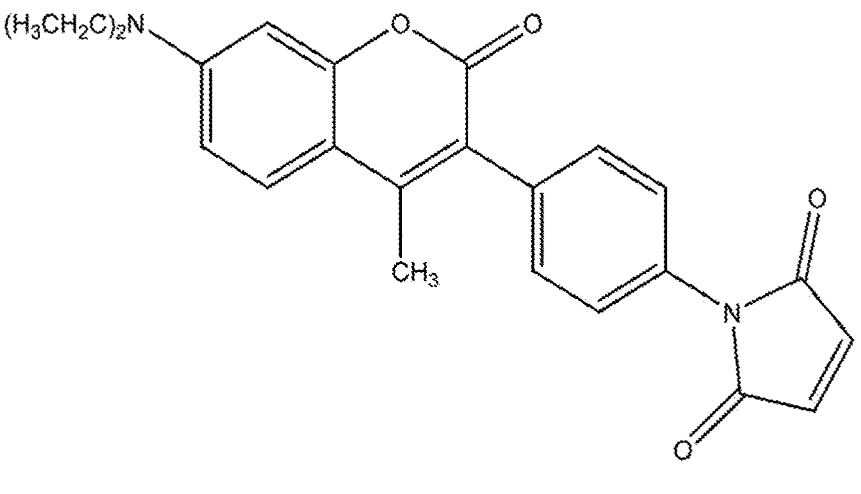
FIG. 6K shows CPM. Benzoxadiazole family.
Figure 6L:
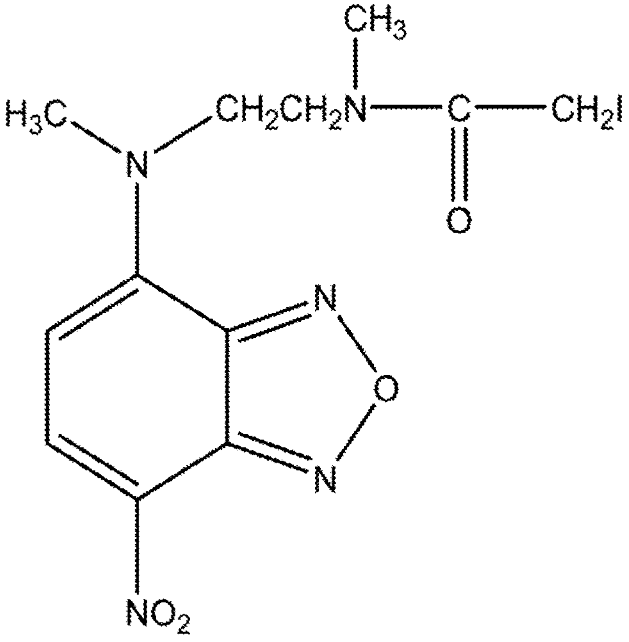
FIG. 6L shows IANBD. Boradiazaindacine (BODIPY) family.
Figure 6M:
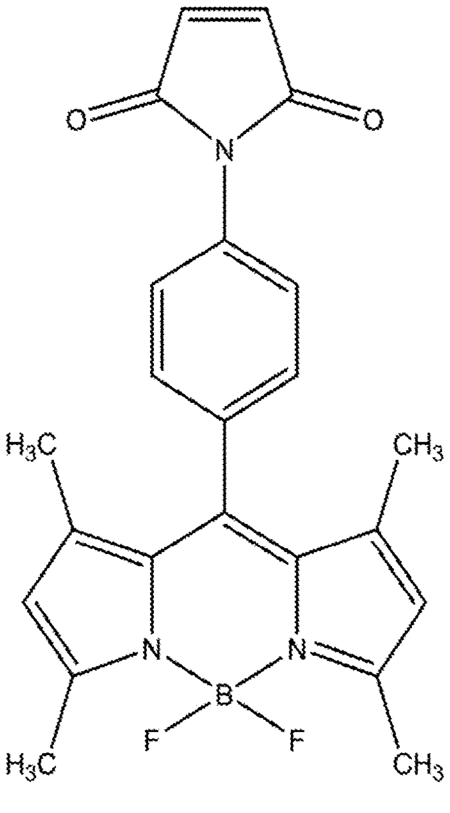
FIG. 6M shows BODIPY 499/508.
Figure 6N:
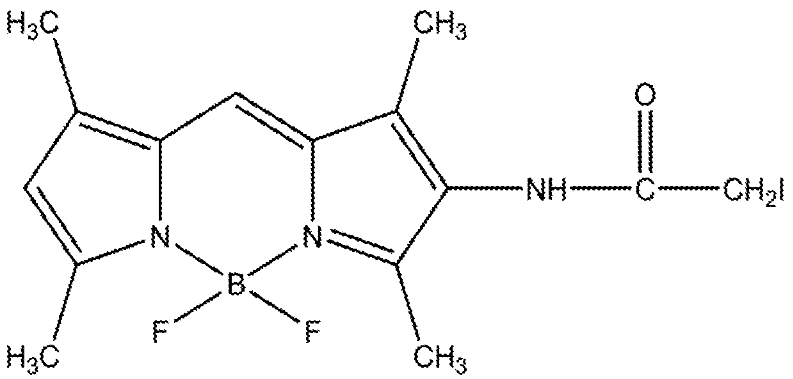
FIG. 6N shows BODIPY 507/545. Cyanine family.
Figure 6O:
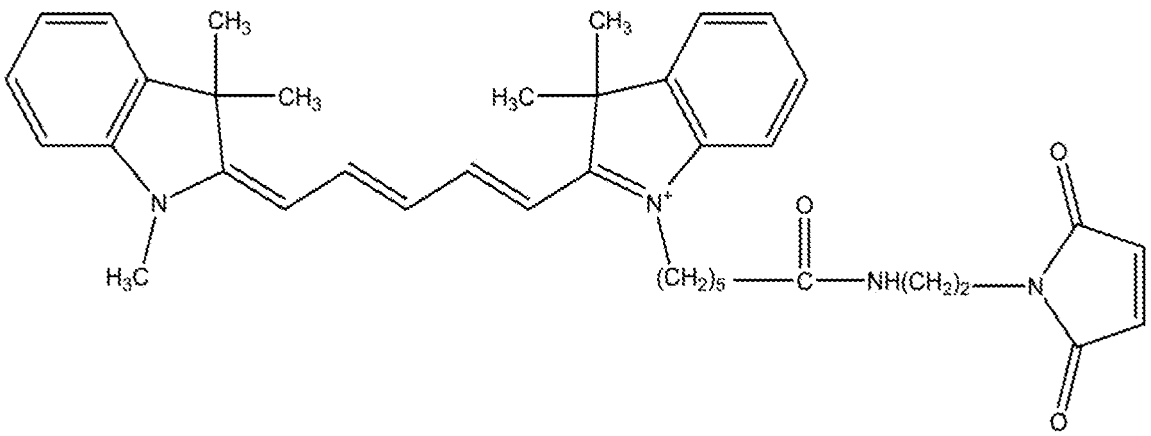
FIG. 6O shows Cy5. Miscellaneous.
Figure 6P:
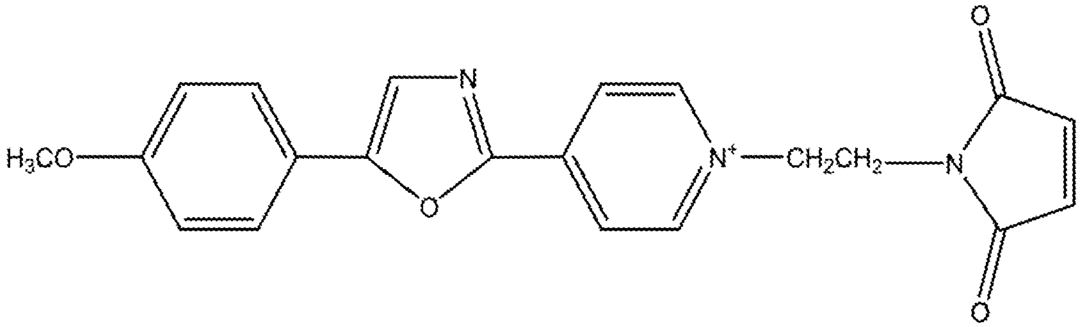
FIG. 6P shows PyMPO.

The lactate affinities range from 5 μM to 0.4 mM (Table 5), with 5-10 fold discrimination against pyruvate (where measured) and no binding to L-alanine. The most pronounced dichromatic responses were observed for the Acrylodan and Badan conjugates at msLacBP6 187C (FIGS. 5A and B). The ${}^{app}K_d$ values for these sensors were ~0.4 mM. Furthermore, their response continues beyond saturation of the first binding site well into the high millimolar lactate concentrations. This effect may reflect the presence of a second, weaker lactate-binding site. These conjugates are therefore well suited for the construction of lactate clinical biosensors.

TABLE 5

Lactate and pyruvate affinities for various msLacBP6 conjugates[a].

| | | Wavelengths (nm) | | Affinity (mM) | | | |
|---|---|---|---|---|---|---|---|
| | | | | Lactate | | Pyruvate | |
| Conjugate | Signal | $\lambda_1$ | $\lambda_2$ | ${}^{true}K_d$ | ${}^{app}K_d$ | ${}^{true}K_d$ | ${}^{app}K_d$ |
| W11C•Acrylodan | d | 473 | 520 | 0.4 | 0.4 | 2.8 | 2.6 |
| G170C•Acrylodan | d | 518 | 490 | 0.005 | 0.01 | | |
| G170C•Badan | m | 520 | n/a | 0.02 | n/a | | |
| Y187C•Acrylodan | d | 452 | 482 | 0.3 | 0.4 | | |
| Y187C•Acrylodan, βZif 5IAF | ngmFRET | 452 | 520 | 0.3 | 0.3 | 11 | 8.2 |
| Y187C•Acrylodan, βZif Alexa532 | ngmFRET | 452 | 550 | 0.3 | 0.4 | 8.5 | 8.2 |

TABLE 5-continued

Lactate and pyruvate affinities for various msLacBP6 conjugates[a].

| Conjugate | Signal | Wavelengths (nm) $\lambda_1$ | $\lambda_2$ | Affinity (mM) Lactate ${}^{true}K_d$ | ${}^{app}K_d$ | Pyruvate ${}^{true}K_d$ | ${}^{app}K_d$ |
|---|---|---|---|---|---|---|---|
| Y187C•Badan | d | 460 | 537 | 0.2 | 0.3 | | |
| V188C•Badan | m | 513 | n/a | 0.4 | n/a | | |
| V192C•Acrylodan | m | 500 | n/a | 0.02 | n/a | | |

[a]Determined by fitting the ratiometric signal of the intensities measured at λ1 and λ2 to equations 1-5.

In the msLacBP6 187C mutant, we further tested the lactate responses of the fluorescent conjugates, Pacific Blue and Oregon Green (FIG. 6). These two conjugates exhibited large monochromatic intensity changes.

Conservation of Signaling in Lactate-Binding Protein Homologs.

The equivalent of the 187C mutation identified in msLacBP6 (see above) was installed in the two expressed homologs that share the same PCS, tsLacBP7 and maLacBP8. The Acrylodan and Badan conjugates of these two proteins were tested for lactate binding (Table 6). As with msLacBP6, strong dichromatic responses were identified in both proteins, indicating that dichromatic signaling for cognate ligands is conserved among homologs. Identification of such a site in one homolog therefore is predictive for other family members identified by the SAFE search method.

TABLE 6

Lactate response of Acrylodan and Badan conjugates of ttLacBP1 homologs.

| Protein | Cysteine mutation[a] | Conjugate[b] | Shape[c] | Emission wavelength (nm) λ1 | λ2 | $K_d^{d-f}$ (mM) ${}^{app}K_d$ | ${}^{true}K_d$ |
|---|---|---|---|---|---|---|---|
| msLacBP6 | Y187C | A | d | 483 | 451 | 0.23 | 0.35 |
| | | B | d | 539 | 459 | 0.11 | 0.25 |
| tsLacBP7 | F189C | A | d | 487 | 457 | 1.8 | 1.7 |
| | | B | d | 463 | 493 | 0.5 | 0.5 |
| maLacBP8 | F189C | A | d | 483 | 458 | 1.5 | 1.5 |
| | | B | d | 527 | 462 | 0.4 | 0.6 |
| adLacBP9 | F191C | A | 0 | | | nb | nb |
| | | B | 0 | | | nb | nb |
| pgLacBP10 | | | | | | nb[f] | nb[f] |
| psLacBP11 | W195C | A | m/d | 487 | 466 | >100 | >100 |
| | | B | 0 | | | nb | nb |
| rsLacBP12 | F191C | A | 0 | | | nb | nb |
| | | B | 0 | | | nb | nb |
| fsLacBP13 | W188C | A | m | 482 | 450 | >100 | >100 |
| | | B | m | 483 | 466 | >100 | >100 |
| taLacBP14 | W186C | A | m | | | nb | nb |
| | | B | m | 515 | 491 | nb | nb |

[a]corresponds so Y187C in msLacBP6.

[b]A, Acrylodan; B, Badan.

[c]m, monochromatic; d, dichromatic (i.e. spectral shape change); 0, no or very small change.

[d]Determined by fitting the ratiometric signal of the intensities measured at λ1 and λ2 to equations 1-5 (see materials and methods).

[e]nb; no binding.

[f]Determinded in a Roche LightCycler, using SYPRO Orange to monitor the appearance of unfolded protein (see materials and methods).

We also the equivalent cysteine mutation in the other candidates that do not conserve the canonical lactate-binding PCS sequence (Table 3). Although several Acrylodan or Badan conjugates responded to lactate (Table 6), they did so with weak affinities, consistent with lactate not being their cognate ligand (Table 3).

Improving the Fluorescence Response to Lactate in Doubly Labeled Proteins.

We tested whether non-geometrically modulated fluorescence energy transfer (ngmFRET) effects in doubly labeled proteins could improve ratiometric signaling. To this end, we fused a small, disulfide-containing domain, βZif (Smith et al., 2005, *Protein Sci,* 14, 64-73) to the C-terminus of msLacBP6 187C (Table 5). This arrangement enables independent, site-specific labeling with two different, thiol-reactive fluorophores by first reacting at the unprotected thiol in the msLacBP6, followed by a reduction of the P3Zif disulfide to deprotect and label this second site with a second fluorophore. The first fluorophore, attached to msLacBP6 responds directly to lactate binding (directly responsive partner), whereas the second one, attached to the βZif fusion, does not (indirectly responsive partner). Indirectly responsive partners are selected according to their excitation and emission characteristics such that energy transfer is established between the two fluorophores. Under favorable circumstances, monochromatic responses of the directly responsive partner or weak dichromatic responses can be converted in to strong ratiometric signals, by exploiting ligand-induced modulation of non-geometrical factors affecting energy transfer such as changes in spectral overlap between the two partnered fluorophores, and alteration of non-radiative decay rates in the directly responsive partner. Mechanisms for non-geometrically modulated FRET (ngmFRET) effects are detailed in Materials and Methods and PCT International Patent Application No. PCT/US 16/62958, filed Nov. 19, 2016, the entire content of which is incorporated herein by reference.

Figure 7A:
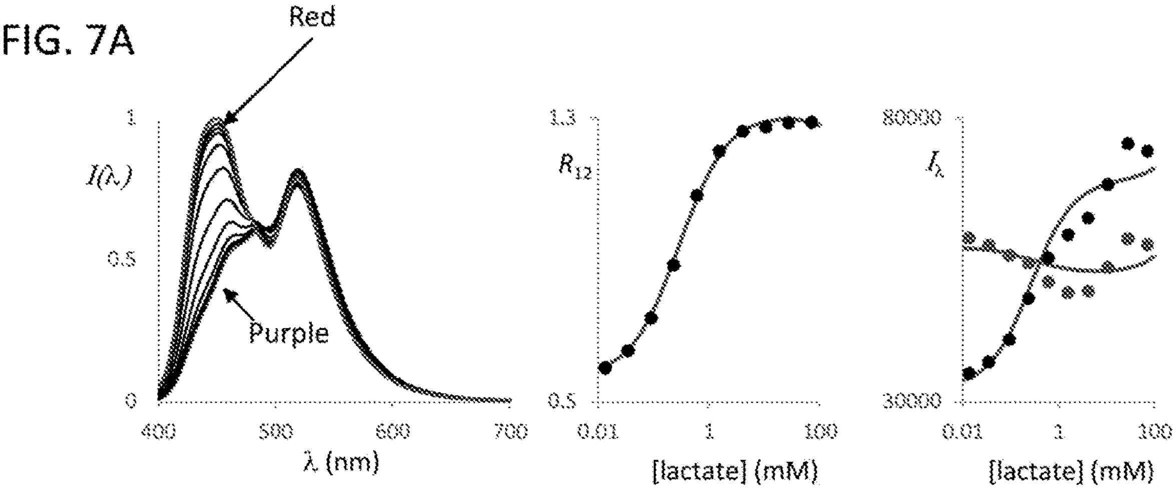
FIGS. 7A and B are sets of graphs showing the fluorescent responses of dually labeled msLacBP6 187C•Acrylodan. P3Zif conjugates. Left column, corrected emission spectra (purple line, no lactate; red line, 100 mM lactate; black lines, intermediate lactate concentrations). Middle column, ratiometric signals (black circles, experimental data points; gray lines, fit to binding isotherm to yield $^{app}K_d$). Right column, monochromatic signals (lines: fits to binding isotherm to yield $^{app}K_d$; circles: experimental data points at two different wavelengths).
Figure 7B:
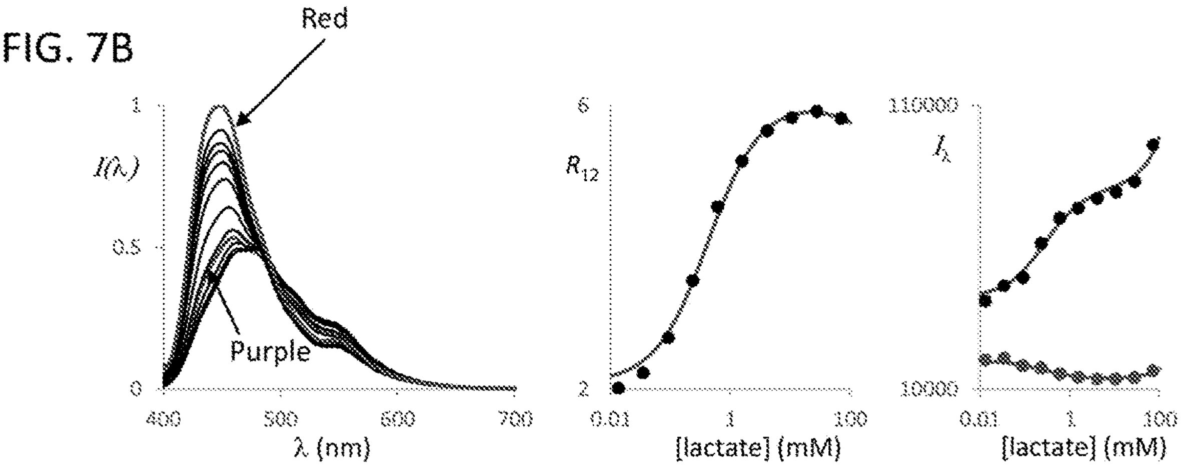
FIG. 7B: msLacBP6 187C•Acrylodan, βZif•Alexax532 ($\lambda_1$=452 nm, $\lambda_2$=550 nm; $^{app}K_d$=0.4 mM; $^{true}K_d$=0.3 mM).

These fusion proteins were doubly labeled with Acrylodan or Badan as the ngmFRET donor in the binding site and the Fluorescein derivatives 5-IAF or Alexa532 as the ngmFRET acceptor at the C-terminal βZif. In the Badan conjugates, the ngmFRET coupling was so strong that all the donor excited state energy was transferred to the acceptor, and the signal was converted from a dichromatic to a monochromatic response. In the Acrylodan conjugates, an improvement in the dichromatic signal was observed (FIG. 7).

Example 5. Sensor Engineering Phase 4: Affinity Tuning

Physiological blood lactate levels for a healthy individual under resting conditions are typically between 0.5 mM to 2.5 mM but during vigorous physical activity the concentration can rise up to 20-30 mM (Warrel, 2010, Oxford Textbook of Medicine. Oxford University Press; Burtis, 2012, Tietz Textbook of Clinical Chemistry and Molecular Diagnostics. Elsevier; Romero, 2010, *Anal. Chem.*, 82, 5568-5572; Suman, 2005, *Sens Actuators B Chem*, 107, 768-772). Hyperlactatemia is a persistent, mild to moderate (2.5-4 mM) increase in blood lactate concentration without metabolic acidosis, whereas lactic acidosis is characterized by persistently increased blood lactate levels (usually >5 mM) in association with metabolic acidosis. Measurements using reagentless sensors are most sensitive at analyte concentrations that match the dissociation constant (de Lorimier et al., 2002, *Protein Sci*, 11, 2655-75. Marvin et al., 1997, *Proc Natl Acad Sci USA*, 94, 4366-71). The lactate affinity of msLacBP6 187C•Acrylodan and msLacBP6 187C•Badan is slightly too high and must therefore be "tuned" by raising the $K_d$ value.

The mutations that alter lactate affinities fall into two classes:

1. Alteration of direct interactions in the PCS between the protein and the bound lactate.
2. Manipulation of the equilibrium between the open and closed states.

Representatives of mutant classes one and two were constructed in the msLacBP6 187C background, using Acrylodan and Badan conjugates to evaluate their effects on lactate binding (Table 7). In the PCS we mutated F68 (F98 in ttLacBP1) and D220 (D250 in ttLacBP1). The aromatic ring of F68 forms extensive van der Waals contacts with the bound lactate. The carboxylate of D220 forms an acceptor hydrogen bond to the lactate hydroxyl. P150 is located in the C-terminal domain, peripheral to the binding site and does not reach across the inter-domain interface. It could therefore be considered part of a secondary complementary surface layer (SCS). In the interface we mutated L70 (L100 in ttLacBP1), which is located at the periphery of the lactate-binding site, and forms a contact from the N- to the C-terminal domain across the inter-domain interface.

Both PCS and SCS mutations perturbed the spectral shapes of the lactate-mediated responses. The F68 mutations did not greatly affect lactate affinity, but at D220 and P150 10- to 100-fold decreases were observed. These mutants therefore extend the sensor range to high lactate concentrations. The interfacial L70F mutant destroyed ligand-mediated responses, but L70M subtly increased the response to the mid-point of the clinical reference range without perturbing the spectral shape of the response. None of the mutants bound L-alanine; all discriminated at least 10-fold against pyruvate. These affinity-tuned sensors therefore provide a suitable set for clinical chemistry applications.

TABLE 7

Lactate affinities of msLacBP6 187C mutants[a].

| | | Response | | | Emission wavelength (mn) | | Affinities (mM)[e] Lactate | | Pyruvate | Alanine |
|---|---|---|---|---|---|---|---|---|---|---|
| Mutation | Fluorophore | Shape[b] | Excited states[c] | Intensity[s] | $\lambda_1$ | $\lambda_2$ | $^{app}K_d$ | $^{true}K_d$ | $^{app}K_d$ | $^{app}K_d$ |
| | Acrylodan | d | b | + | 452 | 582 | 0.4 | 0.3 | | |
| | Badan | d | g | 0 | 460 | 537 | 0.3 | 0.2 | | |
| F68M | Acrylodan | d | b/g | + | 459 | 516 | 0.7 | 0.5 | 9.2 | n/b |
| | Badan | d[f] | g | − | 464 | 527 | 0.5 | 0.6 | 11[g] | n/b |
| F68L | Acrylodan | d | b/g | + | 459 | 516 | 0.6 | 0.5 | 13 | n/b |
| | Badan | d[f] | g | 0 | 463 | 535 | 0.4 | 0.4 | n/b | n/b |
| L70I | Acrylodan | d | b | + | 452 | 582 | 0.4 | 0.3 | 5.5[g] | n/b |
| | Badan | d | g | 0 | 460 | 537 | 0.3 | 0.2 | 16.2[g] | n/b |
| L70M | Acrylodan | d | b | 0 | 455 | 479 | 1.6 | 1.2 | | |
| | Badan | d | g | − | 459 | 539 | 1.1 | 0.7 | | |
| L70F | Acrylodan | 0 | b | | | | | | | |
| | Badan | 0 | g | | | | | | | |
| P150A | Acrylodan | m | b | − | 463 | | | 6.8 | | |
| | Badan | m | g | + | 527 | | | 2.4 | | |
| P150S | Acrylodan | m | b | − | 463 | | | 24 | | |
| | Badan | m | b/g | | 528 | | | 14.4 | | |
| D220N | Acrylodan | 0 | b/g | | | | | | | |
| | Badan | 0 | g | | | | | | | |
| D220S | Acrylodan | 0 | b/g | | | | | | | |
| | Badan | 0 | g | | | | | | | |
| D220Q | Acrylodan | 0 | b/g | | | | | | | |
| | Badan | 0 | g | | | | | | | |

TABLE 7-continued

Lactate affinities of msLacBP6 187C mutants[a].

| | | Response | | | Emission | | Affinities (mM)[e] | | | |
|---|---|---|---|---|---|---|---|---|---|---|
| | | | Excited | | wavelength (mn) | | Lactate | | Pyruvate | Alanine |
| Mutation | Fluorophore | Shape[b] | states[c] | Intensity[s] | $\lambda_1$ | $\lambda_2$ | $^{app}K_d$ | $^{true}K_d$ | $^{app}K_d$ | $^{app}K_d$ |
| D220E | Acrylodan | d[f] | b/g | + | 483 | 510 | 5.1 | 4.0 | 32[g] | n/b |
| | Badan | m | g | + | 532 | | | 3.1 | 29 | n/b |
| D220L | Acrylodan | 0 | b/g | | | | | | | |
| | Badan | 0 | g | | | | | | | |

[a]Determined by fitting the ratiometric signal of the intensities measured at λ1 and λ2 to equations 1-5.
[b]m, monochromatic; d, dichromatic (i.e. spectral shape changes); 0, no change.
[c]The dominant population of the excited states in the absence of lactate is determined from the emission bands intensities: b, blue (maxima ≤ 500 nm); g, green (maxima > 500 nm); b/g, mixed population of blue and green.
[d]+, increases in response to lactate; –, decreases; 0, no change.
[e]Blank entries, no measurements; n/b, no binding.
[f]Significant change in dichromatic spectral shape compared to wild-type 187 conjugate.
[g]Changes from a dichromatic to a monochromatic response.

Example 6. Sensor Arrays for Detecting a Wide Range of Lactate Concentrations The precision (reciprocal of the error) of individual sensor precision is maximal at the $K_d$ value, and decreases at lower or higher lactate concentrations (Marvin et al., 1997, *Proc Natl Acad Sci USA,* 94, 4366-71). Construction of a high-precision sensor capable of spanning the entire clinical concentration range from 0.5 mM to 2.5 mM and as well as high physical activity lactate levels (20-30 mM) therefore requires combining several sensors together to maintain a high precision level. The singly labeled conjugates msLacBP6 187C•Acrylodan, msLacBP6 187C-Badan, msLacBP6 187C 70M•Acrylodan, msLacBP6 187C 70M•Badan and their doubly-labeled βZif counterparts cover the clinical lactate concentration range.

Example 7. Sensor Engineering Phase 5: Device Integration

Protein immobilization on solid surfaces is an important step for incorporating biosensors into devices (Kim, 2013, *Biomicrofluidics,* 7, 041501; Borisov and Wolfbeis, 2008, *Chem Rev,* 108, 423-61; McDonagh, 2008, *Chem Rev,* 108, 400-422). Immobilization enables (i) spatial localization, (ii) control over the presentation of the sensors to the reader (e.g. by encoding geometries for optical readouts), (iii) selective retention in sample separation procedures. It is advantageous to control the geometry of the protein attachment to the solid surface, in order to minimize perturbation of the fluorescence sensing mechanism. Such constructs fuse an N- or C-terminal protein domain that mediate site-specific attachment to an appropriately chemically activated surface. For instance, hexa-histidine peptide for metal-mediated immobilization, or a disulfide-containing truncated zinc finger (βZif) (Smith et al., 2005, *Protein Sci,* 14, 64-73) at N- or C-termini of the FRS to thiol-reactive groups. Here we show that site-specific attachment of a robust lactate sensor to suitably derivatized agarose beads conserves its emission fluorescence spectral response, binding affinity, and thermostability.

Figure 8A:
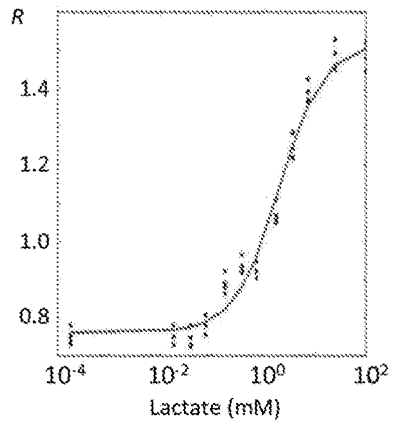
FIGS. 8A-D are graphs showing that immobilization of msLacBP6 187C, 70M-Acrvlodan conserves its thermostability and its binding affinity to lactate.
Figure 8B:
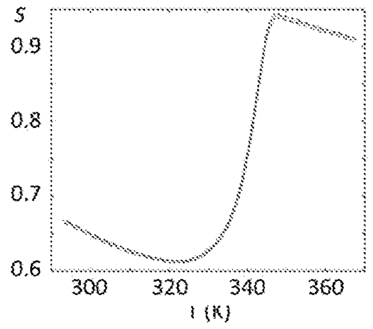
Figure 8C:
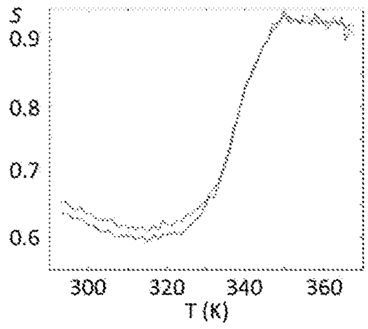
Figure 8D:
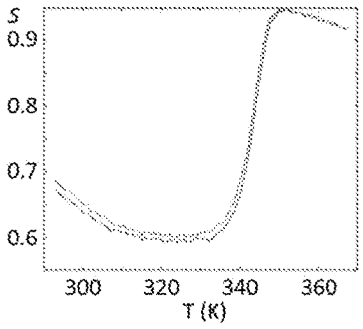

The msLacBP6 187C-Acrylodan L70M and msLacBP6 187C-Badan L70M proteins were site-specifically immobilized through its C-terminal hexa-histidine tag on commercially available magnetic beads coated with nickel-nitrilotriacetic acid (Ni-NTA). The use of magnetic beads affords a straightforward means for holding the beads in place within their respective sensor patches in the sampling cartridge with a magnetic field. Site-specific immobilization is intended to minimize perturbation of the sensing mechanism. The immobilized proteins exhibited a lactate titration curve similar to that measured in solution (FIG. 8A), indicating that immobilization interferes neither with ligand binding nor with the fluorescent signaling mechanism. Furthermore, comparison of protein thermostabilities determined in solution and on beads showed that protein stability is not perturbed significantly by immobilization (FIG. 8B-D).

The lactate-responsive magnetic beads were dried by incubation at 50° C. for 20 minutes, using an aqueous ammonium bicarbonate buffer. The stability properties of the sensor are recovered upon rehydration. The dried beads were aged in situ inside fully assembled sample-handling cartridges by incubation for 1 day at 25° C. and 50° C. in the dark. Fluorescence and lactate-responsive properties were tested in cartridges stored for one day. At all temperatures, the fluorescence ratio in the absence of lactate, and the lactate affinities were conserved. The msLacBP6 187C-based FRSs therefore are sufficiently robust to be handled at ambient temperatures in a desiccated state, greatly simplifying manufacturing, distribution, and long-term storage conditions.

Example 8. Materials and Methods

Bioinformatic Searches.

Annotated genomic and plasmid sequences of 5062 prokaryotes were obtained from the National Center of Biotechnology Information (ftp://ftp.ncbi.nih.gov/genomes/Bacteria/all.gbk.tar.gz), together with annotations recording prokaryotic lifestyles (ftp:/ftp.ncbi.nih.gov/genomes/Bacteria/ProkaryotesOrganismInfo.txt). The Protein Databank (PDB) was downloaded from www.rcsb.org. The downloaded genomic and structural data files were organized into pre-processed two databases (PG, prokaryotic genomes; PDB). The 'ProteinHunter' program provides an interface and methods for organizing, querying, and analyzing these databases. ProteinHunter comprises a graphical user interface, set of computer scripts, and a parallel computing environment. Together these set up the calculations, manage the flow of information and execution in each of the calculation phases, control other programs that carry out specific calculations such as BLAST (Altschul et al., 1990, *J Mol Biol,* 215, 403-10) and ClustalW (Chenna et al., 2003. *Nucleic Acids Res,* 31, 3497-500), and visualize the results.

To construct homolog sequence sets, single sequence seeds were extracted from either preprocessed PDB or PG databases. Homolog sets were then identified in the PDB or PG by using a seed sequence for a uni-directional BLAST search with the following parameters: expect threshold, 10.0; gap costs for existence, 11, and extension, 1; BLOSUM matrix; low complexity filter is on (the ProteinHunter package always executes BLAST searches with the following command "blastall -p blastp -m 8 -b 50000 -d<database file>-i<input file>-o<output file>, where <database file> specifies the name of the prebuilt search sequence file and <input file> and <output file> the seed sequence input and hit output files respectively. A pairwise BLAST alignment was scored in ProteinHunter as a homolog hit if it exceeded a minimum fraction of identical residues and if the alignment covered at least 70% of the probe and target sequences.

Function was inferred using the sequence of PCS residues. A eight-residue, non-contiguous sequence comprising the PCS between the protein and the bound lactate in the ttLacBP1 structure (PDB entry 2zzv) was identified using ProteinHunter (FIGS. 3A and B and Table 1). PCS residues were selected as members of the PCS if the calculated distance between any of their atoms and any lactate atom was less than 5 Å, and the distances between their backbone $C_\alpha$ and any atom in lactate-$Ca^{2+}$ complex was greater than that of their $C_\beta$ atom and any atom in the ligand complex. Secondary shell residues that do not form hydrogen bonds or van der Waals contacts were removed by inspection from the resulting set. To determine the PCS sequence of members in the ttLacBP1 homolog set identified in ProteinHunter, their sequences were aligned using ClustalW (Chenna et al., 2003, *Nucleic Acids Res,* 31, 3497-500). This alignment identifies the positions of the PCS residues in each homolog, from which the corresponding PCS sequence in that homology is then read. For each homolog, the number of PCS mutations relative to the lactate-binding PCS (Hamming distance, $H_{PCS}$) was counted. Homologs with $H_{PCS}$=0 were inferred to be lactate-binding proteins. The PCS sequences were displayed sorted by their $H_{PCS}$ values, and within each $H_{PCS}$ value sorted by their fraction identical residues, indicating the replicon within which they reside (chromosome or plasmid), whether this replicon contains paralogs, and the temperature tolerance (hyperthermophile, thermophile, mesophile, psychrophile, unknown), their Gram stain classification (if known), and the percentage genomic AT content. Duplicate hits were removed automatically from this list if the organism name (genus and species), fractional identity and paralogs were the same. From this list representative, unique ttLacBP1 homologs with $H_{PCS}$=0 were chosen by inspection (Table 2).

Gene Synthesis and Mutaeenesis.

The amino acid sequences for the predicted LacBP homologs identified in the bioinformatic search (see above) were extracted from the PG database. The putative leader peptide that mediates anchoring of the periplasmic-binding protein on the outside of the membrane (Gram positive bacteria) or directs secretion into the periplasm (Gram negative bacteria) was deleted by examining the multiple sequence alignment and removing the sequences N-terminal to the start of the mature LacBP amino acid sequence. Endogenous cysteines were changed to alanine. A hexahistidine tag was placed behind a GGS linker at the C-terminus of the mature protein to enable metal-mediated affinity purification (Hengen, 1995, *Adv Healthc Mater,* 2, 43-56). The final amino acid sequences were back-translated into a DNA sequence encoding the open reading frame (ORF), which was placed in a construct behind an efficient Shine-Dalgarno ribosome-binding site, and flanked by a T7 promoter and terminator at the 5' and 3' ends respectively, using the GeneFab program (Cox et al., 2007, *Protein Sci,* 16, 379-90). The resulting ORF sequences were optimized in context by OrfOpt or OrfMorph programs designed to predict highly expressed mRNA sequences in *E. coli* (see below). The resulting DNA sequences were synthesized by oligonucleotide assembly and cloned into pUC57 by GeneWiz, Inc. (South Plainfield, N.J.).

Subsequent single and multiple point mutations were designed by preparing mutant sequences of the synthetic ORF sequences using the GfMutagenesis program that introduces point mutations into an ORF using the most prevalent codon in *E. coli* for an amino acid. Constructs for site-specific double labeling were designed by inserting the (3Zif domain sequence (Smith et al., 2005, *Protein Sci,* 14, 64-73) before the hexa-histidine C-terminal purification tag. All variants also were constructed by total gene synthesis.

Synthetic Gene Optimization.

The OrfOpt program (U.S. Patent Publication No. 2011/0171737, incorporated by reference) uses stochastic optimization algorithms that choose different codons within an ORF without altering the amino acid sequence to optimize a target function designed to identify mRNA sequences that express proteins at high levels in *E. coli.* The OrfOpt simultaneously imposes AU-rich nucleotide composition at the 5' and 3' ends of the ORF, low RNA secondary structure content and favorable codon usage (Allert et al., 2010, *J Mol Biol.* 402, 905-18). The OrfMorph program reproduces the pattern of codon usage and RNA secondary structure observed in the parent genome of a protein, but using *E. coli* codon preferences and nucleotide composition.

Codon usage is calculated using the codon adaptation index (CAI), as described for OrfOpt, using codon frequency tables calculated for the genome under examination. The mean CAI value for a genome, $\mu_c$, and its standard deviation, $\sigma_c$, are calculated over all the codons in a genome. A codon usage score, c, is calculated for each codon in an open reading frame (ORF) by averaging the CAI over a 9-codon window, centered on the codon for which this score is calculated. A normalized codon usage score, $z_c$, is calculated for each codon as Z-score: $z_c=(c-\mu_c)/\sigma_c$. A plot of $z_c$ along an ORF establishes the codon usage pattern of that ORF. Rare codons ($z_c<0$) are hypothesized to slow down the elongation rate of ribosome translation, introducing "pause" sites at extreme values. Such pause sites are hypothesized to direct kinetics of co-translational folding, allowing a newly synthesized segment to fold before more protein is made. An RNA secondary structure score, s, is determined for each nucleotide by summing its participation in all possible hairpins that can form in its vicinity (settings: minimum duplex length 4 basepairs; maximum loop length, 30 bases; vicinity length, 100 bases), as described for OrfOpt. The average secondary structure energy, $\mu_s$, and its standard deviations, $\sigma_s$, are calculated over all the nucleotides in a genome. A normalized secondary structure energy score, $z_s$, is calculated for codon as the Z-score: $z_s=(c-\mu_s)/\sigma_s$. A plot of $z_s$ along an ORF establishes the secondary structure pattern of that ORF. Regions of above-average secondary structure ($z_s>0$) are hypothesized to slow down the elongation rate of ribose translation, introducing "pause" sites at extremes. As with CAI-mediated pause sites, secondary structure-driven pause sites are hypothesized to direct the kinetics of co-translational folding.

To mimic these patterns for heterologous expression of an ORF in *E. coli*, first the $z_c$ and $z_s$ scores are calculated using the parent organism codon table, $\mu_c$, $\sigma_c$, $\mu_s$, and $\sigma_s$ values. Second, a stochastic search algorithm is used that randomly chooses between degenerate codons to construct trial mRNA nucleotide sequences, calculating $z_c$ and $z_s$ scores for each trial sequence, but using the *E. coli* codon table, and *E. coli* $\mu_c$, $\sigma_c$, $\mu_s$, and $\sigma_s$ values. For each trial, the absolute differences between the *E. coli* trial scores, and the wild-type scores are summed over the entire ORF. The OrfMorph program searches for a minimum of these differences. The stochastic search algorithm operates by first choosing a codon position, second choosing a degenerate codon within the allowed codons at that position. If the choice results in an improved score, the sequence is kept, otherwise it is rejected. After a position has been selected, it is removed from the pool of allowed positions, and the next is chosen from the remainder. The algorithm terminates when two successive sweeps do not yield further improvements in the score. The resulting RNA nucleotide sequence that has codon usage patterns and secondary structure patterns that closely match those of the wild-type mRNA sequence in its parental genomic context. The strategy is that such matching improves production of soluble protein by mimicking co-translational folding contributions that minimize mis-folded protein intermediate aggregation.

Protein Expression Purification, and Fluorescent Conjugate Preparation.

Plasmids carrying the expression constructs (see above) were transformed into KRX competent cells (Promega), and grown overnight at 37° C. on LB agar plates (100 mg/mL ampicillin). A single colony was picked and grown overnight at 37° C. in Terrific Broth (TB: Research Products International). The overnight cultures were diluted 1:20 in 500 mL TB (100 mg/mL ampicillin, 1 mM $CaCl_2$), grown to an optical density of $A_{600}$=0.5 at 37° C. in vigorously aerated shaker flasks, induced by the addition of 2.5 mL rhamnose (20% w/v), and grown for a further 3-4 hrs. The cells were harvested by centrifugation (5,000 rpm, 10 min). After decanting the supernatant, the cell pellets were stored −80° C. The cell pellets were thawed, resuspended in 8 mL binding buffer (10 mM imadozole, 20 mM MOPS, 500 mM NaCl, 1 mM $CaCl_2$, pH 7.8). Following resuspension, 3 mL of BugBuster HT (EMD Millipore) was added. After incubation (20 mins, 25° C.), the cells were lysed on ice by sonication (2 minutes of one-second on/off pulses, 20-30% power). A clarified lysate was prepared by centrifugation (15,000 rpm, 20 min, 4° C.) from which recombinant protein was purified by batch immobilized metal affinity chromatography (IMAC). Resuspended IMAC agarose beads (5 mL; Sigma-Aldrich, P6611) were added to the lysate. After incubation at 4° C. in a Mini LabRoller (Labnet International) for 1 hr. the beads were washed at least five times with binding buffer. The immobilized protein beads were resuspended in labeling buffer (20 mM MOPS, 100 mM NaCl, 1 mM $CaCl_2$, pH 6.9) and labeled overnight (4° C., rotating end-over-end) with a thiol-reactive fluorophore (5-fold stoichiometric excess over protein). Following two rinses with labeling buffer to remove unincorporated label. For double labeling of βZif fusions, a second thiol-reactive label was added following reduction of the disulfide with 5 mM TCEP. To elute labeled protein from the IMAC beads, 6 mL of elution buffer (400 mM imidazole, 500 mM NaCl, 20 mM MOPS, 1 mM $CaCl_2$, pH 7.8) was added, incubated for 30 min (4° C., rotating end-over-end), and the beads removed by centrifugation. Following dialysis of the eluate against three changes of assay buffer (20 mM MOPS, 20 mM KCl, 1 mM $CaCl_2$, pH 7.4), using 10 kDa semi-perimeable membrane (Snakeskin tubing, Thermo Scientific), the fluorescent conjugates were concentrated in a 10 kDa cutoff spin concentrator (Vivaspin, GE Healthcare). Protein purity was assessed by SDS/PAGE. Protein concentrations were determined by (Nanodrop1000) at 280 nm (using extinction coefficients calculated from their sequence (Gill and von Hippel, 1989, *Anal Biochem,* 182, 319-26: Artimo et al. 2012, *Nucleic Acids Res,* 40, W597-603), or at the fluorophore absorbance peak (Acrylodan, 391 nm and Badan, 387 nm).

Determination of Temperature- and Ligand-Dependent Fluorescence Landscapes.

12-, 24-, or 48-point logarithmic titration series were prepared on a Tecan Freedom liquid-handling robot, using an in-house program, 'TitrationPlate', that compiles an abstract description of a multi-component titration series into machine instructions for operating the robot. Temperature-dependent fluorescence emission intensities of 20 μL aliquots, each containing 10 μM protein, were measured in 384-well microtiter plates in a LightCycler 480 II (Roche) using excitation and emission wavelengths available for this instrument that most closely matched the optical characteristics of the fluorescent conjugate. Temperatures were advanced in 1K steps. At each temperature, data was collected at 1-second intervals for 60 seconds at which point the signal had relaxed to a steady value associated with the new temperature. Under these experimental photobleaching was not observed. The in-house program 'TitrationMeltPlate' was used to convert these observations into time-independent datasets that record fluorescence as a function of temperature for each well and associate wells with their concentration of titrant and additive. Management tools were developed to maintain a database of titrations and their analyses.

Determination of Emission Intensity Spectra.

Ligand- and wavelength-dependent emission intensities were recorded on a Nanodrop3300 (Thermo Scientific) at room temperature. Using the LED closest to the optimal excitation wavelength of the fluorophore (UV, 365 nm; blue, 470 nm; 'white', 460-550 nm).

Ratiometric Analysis of Lactate Binding.

Isothermal lactate titrations were extracted from the fluorescent landscape or emission spectra datasets obtained as described above. Monochromatic emission intensities $I_\lambda$ (these intensities correspond to a bandpass intensity, recorded either with a physical filter in the case of the Roche LightCycler, or by integrating in the interval λ−δ, λ+δ in the case of an emission spectrum), were fit to $$I_\lambda = {}^{apo}\beta_\lambda(1-\bar{y}_{true}) + {}^{sat}\beta_\lambda \bar{y}_{true} \quad 1$$

where ${}^{apo}\beta_\lambda$ and ${}^{sat}\beta_\lambda$ are the fluorescence baselines associated with the ligand-free and ligand-bound states of the protein, respectively, and $\bar{y}_{true}$ the fractional saturation of the protein (Layton and Hellinga, 2010, *Biochemistry,* 49, 10831-41). Baseline functions can be constant, linear, or a second-order polynomial. For the ligand- and temperature-dependent fluorescence landscapes, we use a constant value for ${}^{apo}\beta_x$, but ${}^{sat}\beta_x$ is described by a linear dependence on lactate concentration, [L]:

$$ {}^{sat}\beta_x = a_x + b_x[L] \quad 2$$

For a single lactate-binding site, the fractional saturation is given by $$\bar{y} = \frac{[L]}{[L] + K_d} \quad (3)$$

where [L] is the ligand (lactate) concentration and $K_d$ the dissociation constant, ${}^{true}K_d$ for $\bar{y}_{true}$.

A ratiometric signal at a given point in a titration series, $R_{12}(t)$, is given by the ratio of intensities at two wavelengths, ${}^{obs}I(\lambda 1,t)$, ${}^{obs}I(\lambda_2,t)$ in the emission spectrum measured at that point:

$$R_{12}(t) = \frac{a_t^{obs} I(\lambda_1, t)}{a_t^{obs} I(\lambda_2, t)} \quad (4)$$

where $a_t$ is an attenuation factor that describes the effect of variations in sample size (i.e. the amount of observable fluorophore) in the $t^{th}$ sample on the wavelength-independent intensity of the entire emission spectrum. This signal removes wavelength-independent emission intensity attenuation effects due to variations in conjugate concentration, photobleaching, fluctuations in excitation source intensities, and detection efficiency (Demchenko, 2010, *J Fluoresc,* 20, 1099-128; Demchenko, 2014, *Journal of Molecular Structure,* 1077, 51-67). It is a key aspect for high-precision sensing using the reagentless fluorescently-responsive sensors described here. The ratiometric signal also can be fit to a binding isotherm:

$$R_{1,2} = {}^{apo}\beta_R(1-\bar{y}_R) + {}^{sat}\beta_R\bar{y}_R \quad (5)$$

where ${}^{apo}\beta_R$ and ${}^{sat}\beta_R$ are the baselines, and $\bar{y}_R$ the apparent fractional saturation of the protein (with ${}^{app}K_d$). In general, ${}^{true}K_d \neq {}^{app}K_d$; if both baselines are constant, a simple relationship can be derived relating ${}^{app}K_d$ to ${}^{true}K_d$ (Grimley et al., 2013, *J Neurosci,* 33, 16297-309):

$${}^{app}K_d = {}^{true}K_d \frac{{}^{apo}I_{\lambda 2}}{{}^{sat}I_{\lambda 2}} \quad (6)$$

where ${}^{apo}I_{\lambda 2}$ and ${}^{sat}I_{\lambda 2}$ are the emission intensities of the monochromatic signal at wavelength $\lambda_2$ of the ligand-free and ligand-bound protein, respectively.

Following a fit of the titration series using equations 4 and 5, $a_t$ values can be recovered by taking the average comparison of the observed and calculated intensities at the two wavelengths:

$$a_t = \frac{1}{2}\left(\frac{{}^{calc}I(\lambda_1, t)}{{}^{obs}I(\lambda_1, t)} + \frac{{}^{calc}I(\lambda_2, t)}{{}^{obs}I(\lambda_2, t)}\right) \quad (7)$$

The $a_t$ value can then be applied to all wavelengths to obtain an emission spectrum or integrated intensity of the $t^{th}$ titration point corrected for variations in sample size:

$${}^{corr}I(\lambda) = a_t{}^{obs}I(\lambda) \quad (8)$$

where ${}^{corr}I(\lambda)$ and ${}^{obs}I(\lambda)$ are the wavelength-dependent intensities of the corrected and observed emission spectra, respectively.

The fractional error in the chemometric concentration measurement, depends on the first derivative of the binding isotherm as follows (Marvin et al., 1997, *Proc Natl Acad Sci USA,* 94, 4366-71):

$$\frac{\partial S}{S} = \frac{\varepsilon_{1,2}}{S} \times \left(\frac{dR_{1,2}}{dS}\right)^{-1} \quad (9)$$

Where $R_{1,2}$ is the ratiometric signal (equation 5), $\varepsilon_{1,2}$ its experimental error, and $\delta S$ is the resulting chemometric error in the concentration. We can then define a relative precision function $$P(S) = \frac{S}{\delta S} \times \frac{1}{P_{max}} \quad (10)$$

where P(S) is the relative precision at concentration S, which reaches a maximum value (i.e. lowest error), $P_{max}$, at the $K_d$.

For a given isothermal titration, values for ${}^{app}K_d$ and ${}^{true}K_d$ were obtained using a non-linear fitting algorithm in which these two parameters were simultaneously fit to the three experimental binding isotherms using equations 1 and 5, with the two monochromatic isotherms sharing the same ${}^{true}K_d$ value. Three separate pairs of ${}^{apo}\beta$ and ${}^{sat}\beta$ were fit in this procedure, corresponding to the two monochromatic and the ratiometric signals, respectively. Two distinct ratiometric response models can be used: coupled (both wavelengths respond to ligand); uncoupled (the second wavelength is non-responsive; i.e. remains constant). Optionally, an attenuation vector, a(t) containing a, values for each titration point (equation 7), can be refined by iterative fit cycles in which the a(t) vector of a previous cycle is used to adjust the integrated intensities of the next cycle. Programs 'Nanodrop3300' and 'TitrationMeltAnalysis' were developed to analyze wavelength- or temperature-dependent ligand-binding datasets respectively.

Analysis of Lactate-Binding Properties Using Thermal Melts.

The thermal stability of purified LacBP candidate proteins was determined by measuring the temperature-dependence of the fluorescence signal of an extrinsically added dye, SYPRO, using a Roche LightCycler (Layton and Hellinga, 2010, *Biochemistry,* 49, 10831-41). The total fluorescence intensity, S, is given by $$S = \beta_F f_F + \beta_U f_U \quad (11)$$

where $f_F$ and $f_U$ are the fractions of protein in the folded and unfolded states, respectively, and $\beta_F$ and $\beta_U$the fluorescence baselines of these two states. To get the fractions of the two states, we have $$f_N = \frac{1}{1 + K_U(T)} \text{ and } f_U = 1 - f_N \quad (12)$$

where $K_U(T)$ is the temperature-dependent unfolding equilibrium constant, which by the van't $\Delta H_U$ approximation is given by $$K_U = e^{-\Delta H_U\left(\frac{1}{T} - \frac{1}{T_m}\right)/R} \quad (13)$$

Where T is the temperature, $T_m$, the unfolding reaction transition mid-point temperature, and $\Delta H_U$ the enthalpy of unfolding.

To obtain the temperature dependence of the binding reaction, the $K_d$ values of all the individually determined isotherms were fit the Gibbs-Hemholtz equation (Layton and Hellinga, 2010, *Biochemistry,* 49, 10831-41):

$$\Delta G_b^*(T) = \Delta^{ref} H_b^* + \Delta C_{p,b}(T - T_{ref}) - T\left(\Delta^{ref} S_b^* + \Delta C_{p,b}\ln\frac{T}{T_{ref}}\right) \quad 14$$

where $\Delta G_b^*(T)$ is the standard free energy of binding at 1 M ligand at temperature T, $P_G$ $$\Delta G_b^*(T) = -RT\ln\left(1 + \frac{1}{K_d(T)}\right) \quad 15$$

$\Delta_{ref} H_b^*$ and $\Delta^{ref} S_b^*$ the molar enthalpy and entropy of binding, respectively, at the reference temperature, $T_{ref}$, and $\Delta C_{p,b}$ the heat capacity of the binding reaction. This data analysis was carried out using 'TitrationMeltAnalysis'.

Mechanism for Chemical Sensing Based on Non-Geometric Modulation of FRET (ngmFRET).

The subject matter disclosed herein is not limited to or bound by any particular scientific theory. However, discussions regarding ngmFRET are provided to facilitate the understanding of possible mechanisms involved with ngmFRET signaling in various embodiments described herein. Equations for calculating various values mentioned herein are also provided.

The total signal, S, of a fluorescent sensor (either single-wavelength emission intensities, $I_\lambda$, or ratios of intensities at two wavelengths, $R_{12}$) is the sum of the fluorescence due to the ligand-free (apo) and ligand-bound states:

$$S=\alpha(1-\bar{y})+\beta\bar{y} \quad 16$$

where α and β are the fluorescent baselines in the ligand-free and -bound states, respectively, and $\bar{y}$ is the fractional occupancy of the binding sites (equation 3).

Fluorescence quantum yields are the fractions of photons emitted by the excited state relative to the total absorbed, and correspond to the ratio of the radiative decay rate relative to the sum of the rates of all possible decay pathways (FIG. 9A-D). For a single fluorophore:

$$Q = \frac{k_r}{k_r + k_{nr}} \quad 17$$

where $k_r$ and $k_{nr}$ are the radiative and non-radiative decay rates of the excited state, respectively. If we define q as the ratio between the radiative and non-radiative decay rates, $$q = \frac{k_{nr}}{k_r} \quad 18$$

then the quantum yield can be written as $$Q = \frac{1}{q+1} \quad 19$$

Chemical sensors exploit the ligand-mediated shift of a fluorescent system between the ligand-free and ligand-bound states which each exhibit distinct quantum yields:

$$Q_{obs}=Q_{apo}(1-\bar{y})+Q_{sat}\bar{y} \quad 20$$

where $Q_{obs}$, $Q_{apo}$ and $Q_{sat}$ are the quantum yield of the total system, the apo-protein, and the ligand-bound complex, respectively. In a system involving ngmFRET between a donor and acceptor fluorophore, the $Q_{apo}$ and $Q_{sat}$ quantum yields each are combinations of their respective donor and acceptor quantum yields:

$$Q_{apo}={}^{D}Q_{apo}+{}^{A}Q_{apo} \text{ and } Q_{sat}={}^{D}Q_{sat}+{}^{A}Q_{sat} \quad 21$$

where the superscripts D and A indicate donor and acceptor fluorophores respectively. To understand ngmFRET-based sensors, we therefore need to examine the factors that affect each of these four quantum yields.

Figure 9A:
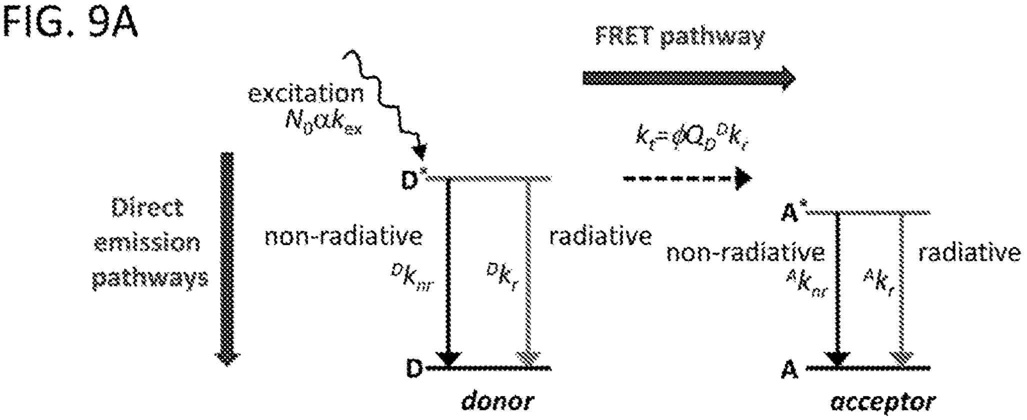
FIGS. 9A-C are diagrams showing three dominant factors that affect ngmFRET between donor and acceptors in which one partner responds to ligand binding.
Figure 9B:
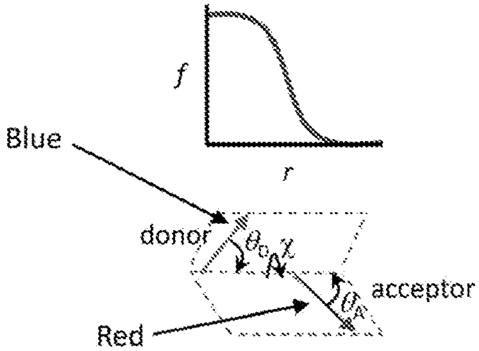
Figure 9C:
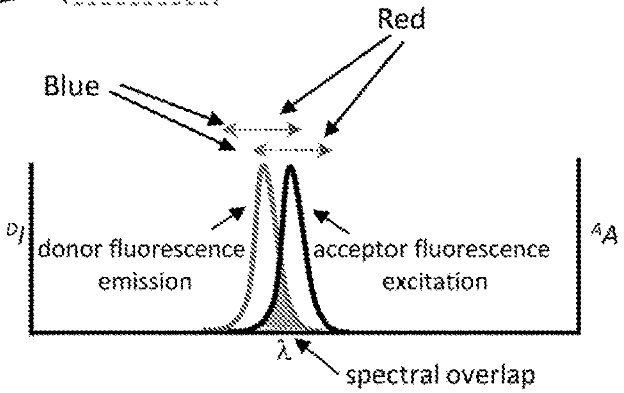
Figure 9D:
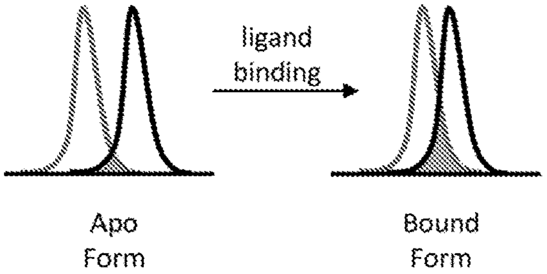

The intensity of the light emitted by a donor or its acceptor is determined by the rate of photon emission from their respective excited states (FIG. 9A). The excited state of a donor is formed by the incident light from the excitation source, and there are three pathways by which this state decays: radiative and non-radiative decay and resonance transfer (by itself and regardless of the presence of any other fluorophore/parter). By contrast, the rate of formation of the acceptor excited state is determined by the resonance transfer rate from the donor, and there are only two processes that determine its decay rate: the radiative and non-radiative pathways (by itself and regardless of the presence of any other fluorophore/parter). In an ngmFRET system, the patterns of ligand-mediated fluorescence intensity changes therefore depend on whether the fluorophore that responds directly to ligand binding functions as a donor or acceptor. To understand these relationships, we analyze the factors that determine the rates of formation and decay of the donor and acceptor excited states.

The rate of resonance energy transfer, $k_t$, along a non-radiative pathway between donor and acceptor (FIG. 9A) is a fraction of the donor radiative emission pathway rate (by itself and regardless of the presence of any other fluorophore/parter), ${}^{D}k_r$ (the emission rate in the absence of an acceptor) multiplied by the energy transfer coupling factor, ϕ, (Lakowicz, 2006, Principles of fluorescence spectroscopy. Springer, New York; Valeur, 2012, Molecular Fluorescence. Principles and Applications. Weinheim: Wiley):

$$k_t=\varphi Q_D {}^{D}k_r \quad 22$$

where $Q_D$ is the donor quantum yield in the absence of an acceptor.

According to the Förster model of weakly coupled oscillators (Lakowicz 2006 Principles of fluorescence spectroscopy. Springer, New York; Valeur 2012 Molecular Fluorescence. Principles and Applications. Weinheim: Wiley), the energy gransfer coupling factor is dependent on the spectral overlap, J, of the donor emission, ${}^{D}\lambda_{em}$, and acceptor excitation spectrum, ${}^{A}\lambda_{ex}$, and the variation of the geometry, G, between the donor and acceptor excited state transition dipoles with distance, r, and orientation factor, κ:

$$\varphi = G(r, \kappa)J({}^{D}\lambda_{em}, {}^{A}\lambda_{ex})\frac{9000\ln 10}{128\pi^5 N_A n^4} \quad 23$$

where $$G(r, \kappa) = \frac{\kappa^2}{r^6} \quad 24$$

and $$J({}^{D}\lambda_{em}, {}^{A}\lambda_{ex}) = \int F({}^{D}\lambda_{em})\varepsilon({}^{A}\lambda_{ex})\lambda^4 d\lambda \quad 25$$

with n the refractive index of medium, $N_A$ Avogrado's number, $F({}^{D}\lambda_{em})$ the normalized donor emission spectrum, and $\varepsilon(^A\lambda_{ex})$ the absorption coefficient of the acceptor excitation spectrum [this analysis is a re-arrangement of the traditional presentation of the equations describing traditional geometrically-modulated FRET (tgmFRET), separating the different contributions (geometry, spectral overlap, quenching)]. Ligand-mediated modulation of r, K and J therefore affects $k_t$ (FIG. 9B-D), leading to changes in donor and acceptor emission intensities (see below).

At steady state, the concentration of the donor excited state, [D*], is given by the following rate balance equation (see FIG. 9A):

$$N_0\alpha k_{ex}-[D^*](^Dk_{nr}+^Dk_r+k_t)=0 \quad 26$$

where $N_0$ is the population of ground state fluorophores, $k_{ex}$ the rate of excitation photon absorption, $\alpha$ the effective illumination, $k_k$, the resonance energy transfer rate, $^Dk_{nr}$ and $^Dk_r$ the radiative and non-radiative decay rates of the donor (by itself and regardless of the presence of any other fluorophore/parter) in the absence of acceptor, respectively. Substituting $^Dk_r(d+1)$ for $_Dk_r+^Dk_{nr}$ (using equation 18, with d ≡q, the ratio of non-radiative to radiative decay rates in the donor), and replacing $k_t$ with equation 22 (with $Q_D=1/(1+d)$, according to equation 23), we obtain $$N_0\alpha k_{ex}-[D^*]^Dk_r\left(1+d+\frac{\varphi}{1+d}\right)=0 \quad 27$$

Hence $$[D^*]=\frac{N_0\alpha k_{es}}{^Dk_r\left(1+d+\frac{\varphi}{1+d}\right)} \quad 28$$

The intensity of the emitted donor light, $I_D$, is $$I_D=[D^*]^Dk_r=\frac{N_0\alpha k_{es}}{\left(1+d+\frac{\varphi}{1+d}\right)} \quad 29$$

The donor quantum yield, $Q_D$, is this emission intensity relative to the intensity of the excitation, $k_{ex}\alpha N_0$ $$Q_D=\frac{1}{\left(1+d+\frac{\varphi}{1+d}\right)} \quad 30$$

The rate balance equation for the acceptor excited state concentration, [A*], is given by $$[D^*]k_t-[A^*](^Ak_r+^Ak_{nr}) \quad 31$$

Consequently, by applying equations 19, 22 and 30, the acceptor quantum yield, $Q_A$, is $$Q_A=\frac{\varphi}{(1+a)(1+d)\left(1+d+\frac{\varphi}{1+d}\right)} \quad 32$$

where a is the ratio of the radiative and non-radiative pathways in the acceptor.

The ratio of the acceptor and donor quantum yields therefore is $$\frac{Q_A}{Q_B}=\frac{\varphi}{(1+d)(1+a)} \quad 33$$

This equation clearly shows that any ligand-mediated change in energy transfer (ϕ) or change in the ratio of radiative to non-radiative emission rates of either the donor (d) or acceptor (a) leads to a change in the ratio of donor and acceptor emission intensities, thereby enabling ratiometry.

Classical ligand-mediated modulation of tgmFRET is concerned only with ligand-mediated changes in the distance between the donor and acceptor (Clegg, 1995, *Curr. Opin. Biotechnol.*, 6, 103-110; Cheung, 1991, *Topics in Fluorescence Spectroscopy*, 2, 127-176), and does not take advantage of effects that alter the photophysics of individual chromophores. By contrast, in ngmFRET systems, the directly responsive partner (DRP) responds to ligand binding through ligand mediated changes that alter the ratio of its radiative and non-radiative pathways (quenching, d or a) or its spectral properties (J), whereas the indirectly responsive partner (IRP) changes only as a consequence of the effect that such change have on the resonance energy transfer rate ($k_t$). It is important to realize that the DRP can function either as a ngmFRET donor an acceptor, depending on how the spectral overlap is set up with the IRP. Regardless of whether the DRP is a donor or acceptor, ligand-mediated alteration of its non-radiative to radiative decay rate ratio (parameter d for a DRP donor; a for an acceptor; by itself and regardless of the presence of any other fluorophore/parter) changes its emission intensity. In DRP donors quenching also alters the ngmFRET transfer rate (see equations 22 and 27), thereby changing the emission intensities of not only itself but also its IRP. By contrast, in DPR acceptors quenching does not alter ngmFRET, and hence do not affect its IRP donor intensity. A DRP acceptor therefore can alter intensities of its donor IRP only if ligand binding changes ϕ. If the DRP is a donor, then manipulation of the ngmFRET coupling factor, ϕ, changes the rate of excited state decay; if it is an acceptor, the rate of excited state formation is altered.

Regardless of whether the DRP is a donor or acceptor, a change in any of the two parameters (ϕ and d or a) alters the ratio of the donor and acceptor quantum yields (equation 33), thereby enabling ratiometry. Ligand-mediated donor DRP quenching affects the quantum yields of both the donor, $Q_D$, and acceptor, $Q_A$, quantum yields (equations 30, 32). Quenching of an acceptor DRP alters only $Q_A$ (equation 30). Changes in ϕ affect quantum yields of both fluorophores, regardless whether the DRP functions as the donor or acceptor (equations 23-25, 30, 32). For systems in which there is no ligand-mediated change in the (average) distance between the two fluorophores, 0 changes only if the DRP switches between two different excited state populations ("dipole switching") in response to ligand binding and if the two excited states differ in their spectral properties (emission for donor DRPs; absorption for acceptor DRPs). Excited state dipoles usually also differ in their dipole orientations, so it is likely that changes in spectral overlap involve (re-)orientation effects. They are also likely to differ in the relative rates of their radiative and non-radiative decay rates. Dipole switching therefore is likely to involve a combination of changes in ngmFRET and quenching effects.

There are eight possible combinations of ligand-mediated changes in quenching and ngmFRET parameters, which have different outcomes on the two emission intensities and their ratio, depending on whether the DRP is the donor or acceptor. The qualitative behavior of the resulting sixteen possibilities in ngmFRET systems are shown in Table 8. Twelve of these have a predictable outcome on the direction of change in the ratio of the two emission intensities. The effect on the direction of change for both donor and acceptor emission intensities can be predicted for seven models. For the other models, the direction of change of one or both peaks depends on the size of the change in the underlying parameters. Purely geometric effects (changes in inter-dipole distance or orientation) always result in anti-correlated changes in emission intensity changes (i.e. one increases and the other decreases, or vice versa). Correlated (i.e both intensities increase or decrease) or uncorrelated (one changes, the other remains constant) intensity changes therefore are prima face evidence for an ngmFRET effect.

TABLE 8

Qualitative analysis of the patterns of donor and acceptor emission intensity changes in ngmFRET[a]

| Directly responsive partner | Model | $Q_A/Q_D$ | $Q_D$ | $Q_A$ |
|---|---|---|---|---|
| Donor | $d^0\ \phi^+$ | ↑ | ↓ | ↑ |
| | $d^0\ \phi^-$ | ↓ | ↑ | ↓ |
| | $d^+\ \phi^0$ | ↓ | ↓ | ↓ |
| | $d^+\ \phi^+$ | * | ↓ | * |
| | $d^+\ \phi^-$ | ↓ | * | ↓ |
| | $d^-\ \phi^0$ | ↑ | ↑ | ↑ |
| | $d^-\ \phi^+$ | ↑ | * | ↑ |
| | $d^-\ \phi^-$ | * | ↑ | * |
| Acceptor | $a^0\ \phi^+$ | ↑ | ↓ | * |
| | $a^0\ \phi^-$ | ↓ | ↑ | * |
| | $a^+\ \phi^0$ | ↓ | 0 | ↓ |
| | $a^+\ \phi^+$ | * | ↓ | * |
| | $a^+\ \phi^-$ | ↓ | ↑ | * |
| | $a^-\ \phi^0$ | ↑ | 0 | ↑ |
| | $a^-\ \phi^+$ | ↑ | ↓ | ↑ |
| | $a^-\ \phi^-$ | * | ↑ | * |

[a]The effects of increasing or decreasing quenching in the directly responsive ngmFRET partner (d for donors, a for acceptors) or the energy transfer coupling ($\phi$) between the donor and acceptor are tabulated. The consequences of using a directly responsive donor or acceptor are examined. The models examine the effects of changing quenching (no change, $d^0$ or $a^0$; increase $d^+$ or $a^+$; decrease, $d^-$ or $a^-$) and energy transfer coupling factor (no change, $\phi^0$; increase, $\phi^+$; decrease, $\phi^-$). Changes in quenching and energy transfer coupling parameters can occur singly or in combination, leading to 16 possible models. The consequences of these models on the direction of change in the magnitude (↑, increase; ↓, decrease; 0, no change; *, unpredictable) are tabulated for donor, $Q_D$ (equation 30), and acceptor quantum yields, $Q_A$ (equation 32), and their ratio, $Q_A/Q_D$ (equation 33).

Example 9. Lactate Biosensors and Uses Thereof

We report the construction of a robust, thermostable, reagentless, fluorescently responsive lactate biosensor and its variants derived from *Marinobacter* species (msLacBP). These proteins potentially can be used for high-precision chemometric measurements that span the entire clinical lactate concentration range, using fluorescence ratiometry measured with straightforward, inexpensive instrumentation.

Thermostable homologs of the *Termus thermophilus* lactate-binding protein (ttLacBP1) were identified using a bioinformatics search strategy that applied a structure-based sequence filter to identify the subset of sequences that retain the original function within the larger collection of aligned sequence homologs. The homologs tested appeared at sequence identities from 100% to 51% of the ttLacBP1 probe. At levels below 60%, overall identities are weak predictors of biological function (Todd, 2001, *J. Mol. Biol.,* 307, 1113-1143; Tian, 2003. *J. Mol. Biol.,* 333, 863-882; George, 2005, *Proc Natl Acad Sci USA,* 102, 12299-12304), application of the structure-based filter therefore was essential for accurate identification. The lactate-binding properties of the predicted hits were tested experimentally by constructing synthetic genes optimized for heterologous protein expression in *E. coli* (Allert, Cox and Hellinga, 2010, *J Mol Biol,* 402, 905-18) and determining the lactate-binding properties of the expressed proteins. This search resulted in the identification of a homolog from *Marinobacter* species (msLacBP) as a suitable candidate for lactate sensor engineering.

Peristerically placed Acrylodan and Badan fluorescent conjugates were found to be highly effective ratiometric lactate sensors in msLacBP6. A series of additional mutations were introduced to manipulate lactate affinities. Variants spanning three orders of magnitude (0.2-24 mM) were identified. Within these, a subset of mutants covers the entire pathophysiological lactate concentration range.

Installation of the most effective signaling mutant identified in msLacBP6, 187C, into its equivalent positions in two other homologs demonstrated that the properties of signaling mutants are conserved across a homology family. Furthermore, we showed that lactate binding is present only in homologs that conserve the canonical PCS sequence identified in ttLacBP1.

The msLacBP6-based FRSs can be immobilized site-specifically on magnetic beads without affecting protein stability, fluorescence responses, or lactate affinities. They can be dried, and aged without adversely affecting sensing performance.

Reagentless, fluorescently responsive sensors present a number of advantages over enzyme-based biosensors, including self-calibration, elimination of chemical transformations and multiple substrates, which together lead to simple sample-handling fluidic circuitry and rapid response times. FRSs can be used for one-time, episodic, and continuous monitoring measurements. Additionally, the use of robust engineered lactate sensors based on thermophilic proteins is likely to simplify manufacturing and distribution processes. Combination of mutant lactate sensors reported here into multiplexed arrays or composites can determine lactate concentration samples from 0.5 mM to 2.5 mM and also capture the lactate levels at high physical activity (20-30 mM) with high precision in one measurement. Such systems have significant potential for the development of next-generation high-accuracy, wide dynamic range sensing applications in continuous monitoring, point-of-care, or wearable systems for clinical chemistry, sports medicine, and the food and beverage industry.

The lactate sensors can be incorporated into point-of-care clinical devices to measure lactate concentrations accurately, and rapidly at the patient bedside. In such a device, a small blood sample (<10 μL) is obtained by means of a finger stick using a lancet. This sample droplet is then placed on the aperture of a disposable cartridge containing desiccated, immobilized lactate sensors inside a small measurement chamber. The sample enters the chamber by virtue of passive capillary action, wetting the sensors upon contact. As soon as the sensors have been wetted, they bind lactate, and report on its concentration by virtue of the engineered fluorescent sensor mechanism. The cartridge is placed inside a small reader (handheld or on a desktop), and their fluorescence signal is measured by the (inexpensive) optoelectronic components of the reader. Excitation light is provided by a light-emitting diode (LED). In the case of Acrylodan or Badan, a commercially available 400 nm blue LED is used, and the emitted light is measured through two bandpass filters. Cartridges can contain multiple sensors, spanning the entire clinical range of possible lactate concentrations. Each sensor is immobilized at a particular, known location inside the cartridge, providing "spatial addressability". The intensity at a particular wavelength is then recorded by imagining these sensors using an inexpensive camera, such as a Complementary metal-oxide semiconductor (CMOS) device commonly found in consumer electronics such as cell phones. Each pixel in the camera records the emitted light on a gray scale. Integration of that signal imaged through the two signals, is analyzed by an on-board computer to calculate the ratiometric signal for each immobilized sensor. Pre-recorded hyperbolic binding curves are then used to calculate the lactate concentration in the sample. Recording through multiple sensors, tuned for accurate detection at different lactate concentrations provides a high-accuracy reading. This process is completed in less than a minute.

Similar instrumentation can be used for any type of episodic measurements, for instance, using other bodily fluids, or samples obtained from animals, or non-biological samples such as foods and beverages.

The FRS lactate sensors also can be used to monitor lactate levels continuously. For instance, sensors can be immobilized at the tip of a thin optical fiber to construct a lactate-responsive optode. Such an optode can be introduced into the body subcutaneously, using a small needle. Excitation and emission light are passed to and from the immobilized sensor, respectively. The sensor is in continuous contact with the sample. Fluctuations in the lactate sample alter the dynamic equilibrium between the open and closed states of the lactate-binding protein, which is transduced into fluctuations of the fluorescent emission signal, by virtue of the sensing mechanism of the conjugated fluorophore. The emitted light intensities are read through filters by a reader connected to the optode. This reader continuously displays the change in signal, and the corresponding calculated lactate concentrations. Continuous lactate monitoring accomplished using a device containing the immobilized lactate biosensor(s), e.g., a fiber optic biosensor, introduced into the subject intradermally or subcutaneously (Judge et al., 2011, Diabetes Technology & Therapeutics 13 (3):309-317; Weidemaier et al., 2011, Biosensors and Bioelectronics 26:4117-4123; hereby incorporated by reference). Biosensors provided herein may also be included in sports training aid devices such as patches. When a subject sweats and perspiration contacts the biosensors, the presence and/or level of lactate is detected.

As was discussed above, the features that distinguish the described constructs, devices, and methods from earlier lactate assay systems include:

Self-calibration
Rapid response time
Simple sample-handling fluidic circuitry
No additional components/substrates ("reagentless")
No incubation time to develop signal. Reading is near-instantaneous and continuous
Stability (simplifies manufacturing, distribution, storage)
Small sample volume (<10 μL).
Capable of precise measurements over extended lactate concentration range (from the low range to the normal range to the hyperlactatemia range)
Multiple sensors also provides redundancy, lowering error
Large scope of uses: episodic, continuous, ex vivo, in vivo, optodes, implants, dermal patches.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A biosensor for lactate, comprising a lactate-binding protein and a reporter group that transduces a detectable signal, wherein the reporter group is attached to the lactate-binding protein so that a signal transduced by the reporter group when the lactate-binding protein is bound to lactate differs from a signal transduced by the reporter group when the lactate-binding protein is not bound to lactate, wherein the lactate-binding protein does not comprise an enzyme, wherein the lactate-binding protein comprises a mutant of a *Marinobacter* sp. lactate-binding protein, wherein the lactate-binding protein comprises an amino acid sequence having at least 95% identity to the amino acid sequence of SEQ ID NO: 120 and a Y187X mutation to SEQ ID NO: 120, wherein X is any amino acid, a conservative substitution, or a cysteine.

2. The biosensor of claim 1, wherein the lactate-binding protein comprises the amino acid sequence of SEQ ID NO: 53, and wherein Acrylodan or Badan is attached to a cysteine of said lactate-binding protein.

3. The biosensor of claim 1, wherein the lactate-binding protein comprises a Y187C mutation to the amino acid sequence of SEQ ID NO: 120.

4. The biosensor of claim 1, wherein the lactate-binding protein further comprises a mutation compared to a naturally occurring *Marinobacter* sp. lactate-binding protein, wherein the lactate binding protein comprises no deletions or insertions compared to the naturally occurring *Marinobacter* sp. lactate binding protein.

5. The biosensor of claim 1, wherein the lactate-binding protein further comprises a mutation compared to a naturally occurring *Marinobacter* sp. lactate-binding protein, wherein the lactate-binding protein comprises (i) less than 5, 4, 3, 2, or 1 inserted amino acids, and/or (ii) less than 5, 4, 3, 2, or 1 deleted amino acids compared to the naturally occurring *Marinobacter* sp. lactate-binding protein.

6. The biosensor of claim 1, wherein the Y187X mutation alters the lactate-binding protein's affinity and/or specificity for lactate as compared to the naturally occurring *Marinobacter* sp. lactate-binding protein.

7. The biosensor of claim 1, wherein the lactate-binding protein comprises, from the N-terminus to the C-terminus: a first β-strand (β1), followed by a first α-helix (α1), followed by a second β-strand (β2), followed by a second α-helix (α2), followed by a third β-strand (β3), followed by a third α-helix (α3), followed by a fourth β-strand (β4), followed by a fifth β-strand (β5), followed by a sixth β-strand (β6), followed by a fourth α-helix (α4), followed by a fifth α-helix (a5), followed by a seventh β-strand (α7), followed by a sixth α-helix (a6), followed by an eighth β-strand (β8), followed by a ninth β-strand (β9), followed by a seventh α-helix (a7), followed by a tenth β-strand (β10), and followed by an eighth α-helix (a8).

8. The biosensor of claim 7, wherein the lactate-binding protein further comprises (i) 1, 2, or 3 amino acid substitutions between β1 and α1; (ii) 1, 2, or 3 amino acid substitutions between β2 and α2; (iii) 1, 2, or 3 amino acid substitutions between β3 and α3; (iv) $_{1,\ 2}$, or 3 amino acid substitutions between β4 and β5, (v) 1, 2, or 3 amino acid substitutions between β5 and β6, (vi) 1, 2, or 3 amino acid substitutions between β6 and α4, (vii) 1, 2, or 3 amino acid substitutions between α4 and α5, (viii) 1, 2, or 3 amino acid substitutions between α5 and α7, (ix) 1, 2, or 3 amino acid substitutions between β7 and α6, (x) 1, 2, or 3 amino acid substitutions between α6 and β8, (xi) 1, 2, or 3 amino acid substitutions between β8 and β9, (xi) 1, 2, or 3 amino acid substitutions between β9 and α7, (xiii) 1, 2, or 3 amino acid substitutions between α7 and β10, (xiv) 1, 2, or 3 amino acid substitutions between β10 and α8, (xv) 1, 2, or 3 amino acid substitutions in any one of or any combination of α1, α2, α3, α4, α5, α6, α7, and/or α8, or (xv) 1, 2, or 3 amino acid substitutions in any one of or any combination of β1, β2, β3, β4, β5, β6, β7, β8, β9, and/or β10.

9. The biosensor of claim 1, wherein the $C_{\alpha}$, root-mean-square deviation (RMSD) between the backbone of the lactate-binding protein and the naturally occurring *Marinobacter* sp. lactate-binding protein (msLacBP6), is between 0-3 Å, 0-1 Å, 0-1.5 Å, 0-2 Å, 0.1-3 Å, 0.5-1 Å, 0.5-1.5 Å, or 0.5-2 Å, or less than 0.1 Å, 0.2 Å, 0.3 Å, 0.4 Å, 0.5 Å, 0.6 Å, 0.7 Å, 0.8 Å, 0.9 Å, 1.0 Å, 1.5 Å, 1.6 Å, 1.7 Å, 1.8 Å, 1.9 Å, 2.0 Å, 2.5 Å, or 3 Å.

10. The biosensor of claim 1, wherein the reporter group is covalently attached to the lactate-binding protein.

11. The biosensor of claim 1, wherein the reporter group is conjugated to a cysteine of the lactate-binding protein.

12. The biosensor of claim 1, wherein the reporter group comprises a fluorophore.

13. A method of detecting the presence or concentration of lactate in a sample, the method comprising:

(a) contacting the biosensor of claim 1 with the sample;

(b) measuring a signal from the biosensor; and (c) comparing the signal to a lactate control value, wherein a difference in signal indicates the presence of lactate in the sample.

14. A method for monitoring the level of lactate in a subject, comprising:

(a) administering the biosensor of claim 1 or a device comprising the biosensor of claim 1 to the subject, wherein after administration the biosensor is in contact with a bodily fluid or surface of the subject, and (b) detecting (i) a signal produced by the reporter group of the biosensor continuously or repeatedly at intervals less than 30 minutes apart, and/or (ii) whether a signal is produced by the reporter group of the biosensor continuously or repeatedly at interval less than 30 minutes apart.

15. The biosensor of claim 1, wherein the lactate binding protein further comprises a L70X mutation to SEQ ID NO: 120, wherein X is any amino acid, conservative substitution, or a cysteine.

16. The biosensor of claim 15, wherein the lactate binding protein comprises a L70M mutation to SEQ ID NO: 120.

17. The biosensor of claim 1, wherein the lactate binding protein further comprises a mutation selected from the group consisting of V10C, W11C, D12C, A43C, D49C, N50C, F68C, F68M, F68L, L70C, L701, L70M, L70F, Y71C, P150C, P150A, P150S, P169C, G170C, S171C, V188C, V192C, L196C, D220N, D220S, D220Q, D220E, and D220.

* * * * *